US012703733B2

(12) United States Patent
Yee et al.

(10) Patent No.: US 12,703,733 B2
(45) Date of Patent: Aug. 11, 2026

(54) PROCESS FOR PRODUCING DONOR-BATCHED CELLS EXPRESSING A RECOMBINANT RECEPTOR

(71) Applicant: Juno Therapeutics, Inc., Seattle, WA (US)

(72) Inventors: Nathan Yee, Seattle, WA (US); Ryan Larson, Seattle, WA (US); Calvin Chan, Seattle, WA (US); Sara Cooper, Seattle, WA (US); Jeffrey Teoh, Seattle, WA (US); Daniel Cossette, Seattle, WA (US); Kohana Leuba, Seattle, WA (US)

(73) Assignee: Juno Therapeutics, Inc., Seattle, WA (US)

( * ) Notice: Subject to any disclaimer, the term of this patent is extended or adjusted under 35 U.S.C. 154(b) by 746 days.

(21) Appl. No.: 17/924,635

(22) PCT Filed: May 12, 2021

(86) PCT No.: PCT/US2021/032108

§ 371 (c)(1),
(2) Date: Nov. 10, 2022

(87) PCT Pub. No.: WO2021/231661

PCT Pub. Date: Nov. 18, 2021

(65) Prior Publication Data

US 2023/0181641 A1 Jun. 15, 2023

Related U.S. Application Data

(60) Provisional application No. 63/024,505, filed on May 13, 2020.

(51) Int. Cl.

| | |
|---|---|
| ***C07K 14/725*** | (2006.01) |
| ***A61K 38/17*** | (2006.01) |
| ***A61K 40/11*** | (2025.01) |
| ***A61K 40/31*** | (2025.01) |
| ***A61K 40/32*** | (2025.01) |
| ***A61K 40/42*** | (2025.01) |
| ***A61P 35/00*** | (2006.01) |
| ***C07K 14/705*** | (2006.01) |

(Continued)

(52) U.S. Cl.

CPC ...... *C07K 14/7051* (2013.01); *A61K 38/1774* (2013.01); *A61K 40/11* (2025.01); *A61K 40/31* (2025.01); *A61K 40/32* (2025.01); *A61K 40/4211* (2025.01); *A61K 40/4215* (2025.01); *A61P 35/00* (2018.01); *C07K 14/70521* (2013.01); *C07K 14/7151* (2013.01); *C12N 5/0636* (2013.01); *A61K 2239/31* (2023.05); *A61K 2239/38* (2023.05); *A61K 2239/48* (2023.05); *C12N 2500/32* (2013.01); *C12N 2501/2302* (2013.01); *C12N 2501/2307* (2013.01); *C12N 2501/2315* (2013.01); *C12N 2501/51* (2013.01); *C12N 2501/515* (2013.01)

(58) Field of Classification Search

CPC .......... C07K 14/7051; C07K 14/70521; C07K 14/7151; A61K 40/11; A61K 40/31; A61K 40/32; A61K 40/4215; A61K 2239/31; A61K 2239/48; A61K 2121/00; A61K 40/15; A61P 35/00; C12N 5/0636; C12N 2501/2302; C12N 2501/2307; C12N 2501/2315; C12N 2501/515; C12N 2510/00; C12N 2310/20

See application file for complete search history.

(56) References Cited

U.S. PATENT DOCUMENTS

| | | | |
|---|---|---|---|
| 4,361,549 | A | 11/1982 | Kung et al. |
| 4,452,773 | A | 6/1984 | Molday |

(Continued)

FOREIGN PATENT DOCUMENTS

| | | | |
|---|---|---|---|
| CN | 108 118 029 | A | 6/2018 |
| DE | 19641876 | | 4/1998 |

(Continued)

OTHER PUBLICATIONS

Hoji, A., Connolly, N.C., Buchanan, W.G. and Rinaldo Jr, C.R., 2007. CD27 and CD57 expression reveals atypical differentiation of human immunodeficiency virus type 1-specific memory CD8+ T cells. Clinical and Vaccine Immunology, 14(1), pp. 74-80. (Year: 2007).*

(Continued)

*Primary Examiner* — Jeremy C Flinders
*Assistant Examiner* — Masudur Rahman
(74) *Attorney, Agent, or Firm* — Morrison & Foerster LLP

(57) ABSTRACT

Provided herein are methods of producing engineered T cell compositions enriched for CD57 negative and/or CD27 positive T cells, such as from a plurality of donors. In some embodiments, the T cells are engineered with a recombinant receptor, such as a chimeric antigen receptor (CAR). Also provided herein are engineered T cell compositions containing T cells enriched for CD57 negative and/or CD27 positive T cells derived from a plurality of different donors, including compositions in which the T cells are engineered with or express a recombinant receptor (e.g. CAR). Also provided are methods of using the engineered T cell compositions in adoptive therapy, including in connection for cancer immunotherapy, such as for allogeneic therapies or for administration to one or more subjects in which the T cells are not derived from the subject(s) to whom the compositions are administered.

24 Claims, 62 Drawing Sheets

Specification includes a Sequence Listing.

(51) Int. Cl.
*C07K 14/715* (2006.01)
*C12N 5/0783* (2010.01)

(56) References Cited

U.S. PATENT DOCUMENTS

| | | | |
|---|---|---|---|
| 4,690,915 | A | 9/1987 | Rosenberg |
| 4,795,698 | A | 1/1989 | Owen |
| 5,033,252 | A | 7/1991 | Carter |
| 5,052,558 | A | 10/1991 | Carter |
| 5,087,616 | A | 2/1992 | Myers |
| 5,168,049 | A | 12/1992 | Meade et al. |
| 5,200,084 | A | 4/1993 | Liberti |
| 5,219,740 | A | 6/1993 | Miller |
| 5,323,907 | A | 6/1994 | Kalvelage |
| 5,356,802 | A | 10/1994 | Chandrasegaran |
| 5,436,150 | A | 7/1995 | Chandrasegaran |
| 5,487,994 | A | 1/1996 | Chandrasegaran |
| 5,506,121 | A | 4/1996 | Skerra |
| 5,538,848 | A | 7/1996 | Livak et al. |
| 5,789,538 | A | 8/1998 | Rebar et al. |
| 5,925,517 | A | 7/1999 | Tyagi et al. |
| 5,925,523 | A | 7/1999 | Dove et al. |
| 6,007,988 | A | 12/1999 | Choo et al. |
| 6,013,453 | A | 1/2000 | Choo et al. |
| 6,022,951 | A | 2/2000 | Sano et al. |
| 6,040,177 | A | 3/2000 | Riddell et al. |
| 6,060,273 | A | 5/2000 | Dirks et al. |
| 6,103,493 | A | 8/2000 | Skerra |
| 6,123,655 | A | 9/2000 | Fell |
| 6,140,081 | A | 10/2000 | Barbas |
| 6,156,493 | A | 12/2000 | Stayton |
| 6,165,750 | A | 12/2000 | Stayton |
| 6,174,670 | B1 | 1/2001 | Wittwer et al. |
| 6,200,759 | B1 | 3/2001 | Dove et al. |
| 6,207,453 | B1 | 3/2001 | Maass |
| 6,303,121 | B1 | 10/2001 | Kwon |
| 6,326,145 | B1 | 12/2001 | Whitcombe et al. |
| 6,329,144 | B1 | 12/2001 | Kubista et al. |
| 6,368,813 | B1 | 4/2002 | Reznik et al. |
| 6,410,319 | B1 | 6/2002 | Raubitschek |
| 6,451,995 | B1 | 9/2002 | Cheung |
| 6,453,242 | B1 | 9/2002 | Eisenberg et al. |
| 6,503,717 | B2 | 1/2003 | Case et al. |
| 6,534,261 | B1 | 3/2003 | Cox, III et al. |
| 6,569,997 | B1 | 5/2003 | Kwon |
| 6,599,692 | B1 | 7/2003 | Case et al. |
| 6,635,427 | B2 | 10/2003 | Wittwer et al. |
| 6,689,558 | B2 | 2/2004 | Case |
| 6,733,433 | B1 | 5/2004 | Fell |
| 7,067,317 | B2 | 6/2006 | Rebar et al. |
| 7,070,995 | B2 | 7/2006 | Jensen |
| 7,262,054 | B2 | 8/2007 | Jamieson et al. |
| 7,265,209 | B2 | 9/2007 | Jensen |
| 7,354,762 | B2 | 4/2008 | Jensen |
| 7,446,179 | B2 | 11/2008 | Jensen |
| 7,446,190 | B2 | 11/2008 | Sadelain |
| 7,446,191 | B2 | 11/2008 | Jensen |
| 7,482,000 | B2 | 1/2009 | DeVaux |
| 7,510,687 | B2 | 3/2009 | Mazzeo et al. |
| 7,547,438 | B2 | 6/2009 | Thomas et al. |
| 7,776,562 | B2 | 8/2010 | Busch et al. |
| 7,888,121 | B2 | 2/2011 | Urnov et al. |
| 7,914,796 | B2 | 3/2011 | Miller et al. |
| 7,951,925 | B2 | 5/2011 | Ando et al. |
| 7,972,854 | B2 | 7/2011 | Miller et al. |
| 7,981,632 | B2 | 7/2011 | Schmidt |
| 8,110,379 | B2 | 2/2012 | DeKelver et al. |
| 8,298,782 | B2 | 10/2012 | Busch et al. |
| 8,324,353 | B2 | 12/2012 | Jensen |
| 8,339,645 | B2 | 12/2012 | Nakawaki |
| 8,389,282 | B2 | 3/2013 | Sadelain et al. |
| 8,409,861 | B2 | 4/2013 | Guschin et al. |
| 8,479,118 | B2 | 7/2013 | Lyndersay et al. |
| 8,586,526 | B2 | 11/2013 | Gregory et al. |
| 8,703,489 | B2 | 4/2014 | Wang |
| 8,735,540 | B2 | 5/2014 | Schmidt |
| 8,802,374 | B2 | 8/2014 | Jensen |
| 8,822,647 | B2 | 9/2014 | Jensen |
| 8,911,993 | B2 | 12/2014 | June et al. |
| 8,945,868 | B2 | 2/2015 | Collingwood et al. |
| 8,956,828 | B2 | 2/2015 | Bonini et al. |
| 9,005,973 | B2 | 4/2015 | Cost et al. |
| 9,023,604 | B2 | 5/2015 | Schmidt et al. |
| 9,045,763 | B2 | 6/2015 | DeKelver et al. |
| 9,150,847 | B2 | 10/2015 | Rebar |
| 9,200,266 | B2 | 12/2015 | Wang |
| 9,255,250 | B2 | 2/2016 | Gregory et al. |
| 9,458,205 | B2 | 10/2016 | Gregory et al. |
| 2001/0026932 | A1 | 10/2001 | Thomas et al. |
| 2002/0131960 | A1 | 9/2002 | Sadelain |
| 2003/0170238 | A1 | 9/2003 | Gruenberg |
| 2003/0232410 | A1 | 12/2003 | Liljedahl et al. |
| 2005/0026157 | A1 | 2/2005 | Baltimore et al. |
| 2005/0064474 | A1 | 3/2005 | Urnov et al. |
| 2005/0208489 | A1 | 9/2005 | Carroll et al. |
| 2006/0063231 | A1 | 3/2006 | Li et al. |
| 2007/0116690 | A1 | 5/2007 | Yang et al. |
| 2008/0159996 | A1 | 7/2008 | Ando et al. |
| 2008/0171951 | A1 | 7/2008 | Fell |
| 2008/0279851 | A1 | 11/2008 | Coyle et al. |
| 2010/0218264 | A1 | 8/2010 | Cui et al. |
| 2011/0003380 | A1 | 1/2011 | Miltenyi |
| 2011/0265198 | A1 | 10/2011 | Gregory et al. |
| 2011/0301073 | A1 | 12/2011 | Gregory et al. |
| 2012/0017290 | A1 | 1/2012 | Cui et al. |
| 2013/0122591 | A1 | 5/2013 | Cost et al. |
| 2013/0137104 | A1 | 5/2013 | Cost et al. |
| 2013/0149337 | A1 | 6/2013 | Cooper et al. |
| 2013/0177983 | A1 | 7/2013 | Rebar |
| 2013/0196373 | A1 | 8/2013 | Gregory et al. |
| 2013/0287748 | A1 | 10/2013 | June |
| 2014/0120622 | A1 | 5/2014 | Gregory et al. |
| 2014/0271635 | A1 | 9/2014 | Brogdon et al. |
| 2014/0295458 | A1 | 10/2014 | Schmidt et al. |
| 2015/0056705 | A1 | 2/2015 | Conway et al. |
| 2015/0335708 | A1 | 11/2015 | Froelich et al. |
| 2016/0024474 | A1 | 1/2016 | Conway et al. |
| 2016/0030477 | A1 | 2/2016 | Conway et al. |
| 2016/0152723 | A1 | 6/2016 | Chen et al. |
| 2016/0272999 | A1 | 9/2016 | Duchateau et al. |
| 2017/0016027 | A1 | 1/2017 | Lee et al. |
| 2017/0037369 | A1 | 2/2017 | Ramsborg et al. |
| 2017/0051035 | A1 | 2/2017 | Payne et al. |
| 2017/0211075 | A1 | 7/2017 | Lee et al. |
| 2017/0281766 | A1 | 10/2017 | Wiltzius |
| 2021/0393691 | A1 | 12/2021 | Cooper et al. |

FOREIGN PATENT DOCUMENTS

| | | |
|---|---|---|
| EP | 0452342 | 10/1991 |
| EP | 2537416 | 12/2012 |
| WO | WO 1986/002077 | 4/1986 |
| WO | WO 1992/008796 | 5/1992 |
| WO | WO 1994/028143 | 12/1994 |
| WO | WO 1995/019431 | 7/1995 |
| WO | WO 1996/006166 | 2/1996 |
| WO | WO 1996/013593 | 5/1996 |
| WO | WO 1996/018105 | 6/1996 |
| WO | WO 1996/024606 | 8/1996 |
| WO | WO 1998/040396 | 9/1998 |
| WO | WO 1998/053057 | 11/1998 |
| WO | WO 1998/053058 | 11/1998 |
| WO | WO 1998/053059 | 11/1998 |
| WO | WO 1998/053060 | 11/1998 |
| WO | WO 1998/054311 | 12/1998 |
| WO | WO 1999/018129 | 4/1999 |
| WO | WO 1999/060120 | 11/1999 |
| WO | WO 1999/061065 | 12/1999 |
| WO | WO 2000/014257 | 3/2000 |
| WO | WO 2000/027878 | 5/2000 |
| WO | WO 2000/038762 | 7/2000 |
| WO | WO 2001/056603 | 8/2001 |
| WO | WO 2001/060970 | 8/2001 |
| WO | WO 2001/088197 | 11/2001 |

(56) References Cited

FOREIGN PATENT DOCUMENTS

| | | |
|---|---|---|
| WO | WO 2002/016536 | 2/2002 |
| WO | WO 2002/054065 | 7/2002 |
| WO | WO 2002/077018 | 10/2002 |
| WO | WO 2002/099084 | 12/2002 |
| WO | WO 2003/016496 | 2/2003 |
| WO | WO 2003/020763 | 3/2003 |
| WO | WO 2004/033685 | 4/2004 |
| WO | WO 2007/001459 | 11/2005 |
| WO | WO 2006/000830 | 1/2006 |
| WO | WO 2006/054961 | 5/2006 |
| WO | WO 2006/056061 | 6/2006 |
| WO | WO 2008/051424 | 5/2008 |
| WO | WO 2009/072003 | 6/2009 |
| WO | WO 2010/033140 | 3/2010 |
| WO | WO 2011/044186 | 4/2011 |
| WO | WO 2012/012695 | 1/2012 |
| WO | WO 2012/129514 | 9/2012 |
| WO | WO 2012/138927 | 10/2012 |
| WO | WO 2013/011011 | 1/2013 |
| WO | WO 2013/038191 | 3/2013 |
| WO | WO 2013/071154 | 5/2013 |
| WO | WO 2013/123061 | 8/2013 |
| WO | WO 2013/124474 | 8/2013 |
| WO | WO 2013/126726 | 8/2013 |
| WO | WO 2013/166321 | 11/2013 |
| WO | WO 2014/031687 | 2/2014 |
| WO | WO 2014/055668 | 4/2014 |
| WO | WO 2014/076277 | 5/2014 |
| WO | WO 2015/075175 | 5/2015 |
| WO | WO 2015/161276 | 10/2015 |
| WO | WO 2015/164675 | 10/2015 |
| WO | WO 2016/073602 | 5/2016 |
| WO | WO 2016/187216 | 11/2016 |
| WO | WO 2018/170188 | 9/2018 |
| WO | WO 2018/197949 | 11/2018 |
| WO | WO 2019/113556 | 6/2019 |
| WO | WO 2019/113559 | 6/2019 |
| WO | WO 2020/097132 | 5/2020 |
| WO | WO 2021/231661 | 11/2021 |

OTHER PUBLICATIONS

Zhao, L. and Cao, Y.J., 2019. Engineered T cell therapy for cancer in the clinic. Frontiers in immunology, 10, p. 2250. (Year: 2019).*

Raskov, H., Orhan, A., Christensen, J.P. and Gögenur, I., 2021. Cytotoxic CD8+ T cells in cancer and cancer immunotherapy. British journal of cancer, 124(2), pp. 359-367. (Year: 2021).*

Ohkawa, T., Seki, S., Dobashi, H., Koike, Y., Habu, Y., Ami, K., Hiraide, H. and Sekine, I., 2001. Systematic characterization of human CD8+ T cells with natural killer cell markers in comparison with natural killer cells and normal CD8+ T cells. Immunology, 103(3), pp. 281-290. (Year: 2001).*

Alonso-Camino et al., "CARbodies: Human Antibodies Against Cell Surface Tumor Antigens Selected From Repertoires Displayed on T Cell Chimeric Antigen Receptors," Mol Ther Nucl Acids (2013) 2: e93, 11 pages.

Alvarez-Fernandez et al., "A short CD3/CD28 costimulation combined with IL-21 enhance the generation of human memory stem T cells for adoptive immunotherapy," J Transl Med. (Jul. 2016) 14(1):214, 10 pages.

Arakawa et al. "Cloning and sequencing of the VH and V kappa genes of an anti-CD3 monoclonal antibody, and construction of a mouse/human chimeric antibody," J Biochem. (1996) 120(3): 657-662.

Argarana et al. "Molecular cloning and nucleotide sequence of the streptavidin gene," Nucleic Acids Res. (1986) 14(4): 1871-1882.

Barrett et al., "Chimeric Antigen Receptor Therapy for Cancer," Annual Review of Medicine (2014) 65:333-347.

Baum et al., "Retrovirus vectors: toward the plentivirus?," Molecular Therapy: The Journal of the American Society of Gene Therapy (2006) 13:1050-1063.

Bes et al., "Mapping the paratope of anti-CD4 recombinant Fab 13B8.2 by combining parallel peptide synthesis and site-directed mutagenesis," J. Biol. Chem. (2003) 278:14265-14273.

Blair et al., "CD40 ligand (CD154) triggers a short-term CD4(+) T cell activation response that results in secretion of immunomodulatory cytokines and apoptosis," J Exp Med (Feb. 21, 2000) 191(4):651-60.

Boch et al., "Breaking the code of DNA binding specificity of TAL-type III effectors," Science (Dec. 11, 2009) 326(5959):1509-12.

Boris-Lawrie et al., "Recent advances in retrovirus vector technology," Cur. Opin. Genet. Develop. (1993) 3:102-109.

Brash et al., "Strontium phosphate transfection of human cells in primary culture: stable expression of the simian virus 40 large-T-antigen gene in primary human bronchial epithelial cells," Mol. Cell Biol. (1987) 7: 2031-2034.

Brentjens et al., "CD19-targeted T cells rapidly induce molecular remissions in adults with chemotherapy-refractory acute lymphoblastic leukemia," Sci Transl Med. (2013) 5(177):177ra38, 19 pages.

Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA (1993) 90:8033-8037.

Carlens et al., "Ex vivo T lymphocyte expansion for retroviral transduction: influence of serum-free media on variations in cell expansion rates and lymphocyte subset distribution," Exp Hematol (2000) 28(10): 1137-1146.

Carrillo et al., "The Multiple Sequence Alignment Problem in Biology," SIAM Journal on Applied Mathematics (1988) 48(5):1073-1082.

Casati et al., "Clinical-scale selection and viral transduction of human naïve and central memory CD8+ T cells for adoptive cell therapy of cancer patients," Cancer Immunology (2013) 62(10): 1563-1573.

Cavalieri et al., "Human T lymphocytes transduced by lentiviral vectors in the absence of TCR activation maintain an intact immune competence," Blood (2003) 102(2): 497-505.

Challita et al., "Multiple Modifications in Cis Elements of the Long Terminal Repeat of Retroviral Vectors Lead to Increased Expression and Decreased DNA Methylation in Embryonic Carcinoma Cells," J Virol (1995) 69(2): 748-55.

Cheadle et al., "Chimeric antigen receptors for T-cell based therapy," Methods Mol Biol (2012) 907:645-666.

Chervin et al., "Engineering higher affinity T cell receptors using a T cell display system," J Immunol Methods. (2008) 339(2): 175-84.

Chicaybam et al., "An efficient low cost method for gene transfer to T lymphocytes," PLoS ONE (2013) 8(3): e60298, 11 pages.

Cho et al., "Human mammalian cell sorting using a highly integrated micro-fabricated fluorescence-activated cell sorter (microFACS)," Lab Chip (2010) 10: 1567-1573.

Chothia et al., "The outline structure of the T-cell alpha beta receptor," EMBO J. (1988) 7(12): 3745-55.

Christian et al., "Targeting DNA double-strand breaks with TAL effector nucleases," Genetics (Oct. 2010) 186(2):757-61.

Cooper et al., "T-cell clones can be rendered specific for CD19: toward the selective augmentation of the graft-versus-B-lineage leukemia effect," Blood. (2003) 101:1637-1644.

Davila et al., "CD19 CAR-targeted T cells induce long-term remission and B Cell Aplasia in an immunocompetent mouse model of B cell acute lymphoblastic leukemia," PLoS ONE (2013) 8(4): e61338, 14 pages.

De Felipe et al., "Targeting of proteins derived from self-processing polyproteins containing multiple signal sequences," Trafic (2004) 5(8):616-626.

De Felipe, "Skipping the co-expression problem: the new 2A "CHYSEL" technology," Genetics Vaccines and Therapy (2004) 2:13, 6 pages.

Deng et al., "An agonist human ICOS monoclonal antibody that induces T cell activation and inhibits proliferation of a myeloma cell line", Hybrid Hybridomics. (2004) 23(3):176-182.

(56) References Cited

OTHER PUBLICATIONS

Entschladen et al., "Differential requirement of protein tyrosine kinases and protein kinase C in the regulation of T cell locomotion in three-dimensional collagen matrices," J Immunol. (1997) 159(7): 3203-3210.
Fairhead et al., "Plug-and-play pairing via defined divalent streptavidins," J Mol Biol. (2014, E-pub. Sep. 19, 2013) 426(1):199-214.
Fedorov et al., "PD-1- and CTLA-4-Based Inhibitory Chimeric Antigen Receptors (iCARs) Divert Off-Target Immunotherapy Responses," Sci Transl Medicine (2013) 5(215):215ra172, 25 pages.
Fraietta et al., "Determinants of response and resistance to CD19 chimeric antigen receptor (CAR) T cell therapy of chronic lymphocytic leukemia," Nat Med. (2018) 24(5):563-571.
Frecha et al., "Advances in the field of lentivector-based transduction of T and B lymphocytes for gene therapy," Molecular Therapy: The Journal of the American Society of Gene Therapy (2010) 18:1748-1757.
Friedl et al., "T lymphocyte locomotion in a three-dimensional collagen matrix: Expression and function of cell adhesion molecules," J Immunol. (1995) 154: 4973-4985.
Gaj et al., "ZFN, TALEN, and CRISPR/Cas-based methods for genome engineering," Trends Biotechnol (Jul. 2013) 31(7):397-405.
Gattinoni et al., "T memory stem cells in health and disease," Nat Med. (Jan. 2017) 23(1):18-27.
Gee et al., "GMP CAR-T cell production," Best Pract Res Clin Haematol (Jun. 2018) 31(2):126-134.
Gearing et al., "The international standard for human interleukin-2. Calibration by international collaborative study," J Immunol Methods. (1988) 114(1-2): 3-9.
GenBank Accession No. AF451974.1, "Synthetic construct single chain Fv anti-human CD28 antibody scFv28.3 mRNA, partial cds," (Jul. 26, 2016), Downloaded on Sep. 30, 2024, 2 pages.
Godin et al., "Microfluidics and photonics for Bio-System-on-a-Chip: a review of advancements in technology towards a microfluidic flow cytometry chip," J Biophoton. (2008) 1(5):355-376.
Hackett et al., "A transposon and transposase system for human application," Molecular Therapy: The Journal of the American Society of Gene Therapy (2010) 18:674-683.
Hermans et al., "The VITAL assay: a versatile fluorometric technique for assessing CTL- and NKT-mediated cytotoxicity against multiple targets in vitro and in vivo," J. Immunological Methods (2004) 285(1): 25-40.
Hinrichs et al., "Human effector CD8+ T cells derived from naïve rather than memory subsets possess superior traits for adoptive immunotherapy," Blood (2011) 117(3): 808-814.
Holler et al., "In vitro evolution of a T cell receptor with high affinity for peptide/MHC," Proc Natl Acad Sci U S A. (2000) 97(10): 5387-5392.
Holler et al., "TCRs with high affinity for foreign pMHC show self-reactivity," Nat Immunol. Jan. 2003;4(1):55-62.
Holliger et al., "'Diabodies': Small Bivalent and Bispecific Antibody Fragments," Proc. Natl. Acad. Sci. USA (1993) 90:6444-6448.
Holt et al., "Domain Antibodies: Proteins For Therapy," Trends in Biotechnology (2003) 21(11): 484-490.
Howarth et al., "A monovalent streptavidin with a single femtomolar biotin binding site," Nat Methods. (2006) 3(4): 267-273.
Huang et al., "DNA transposons for modification of human primary T lymphocytes," Methods Mol Biol (2009) 506: 115-126.
Hudecek et al., "Receptor affinity and extracellular domain modifications affect tumor recognition by ROR1-specific chimeric antigen receptor T cells," Clin Cancer Res (2013) 19(12):3153-3164.
Hutten et al., "New magnetic nanoparticles for biotechnology," J Biotechnol. (2004) 112(1-2): 47-63.
Iliades et al., "Triabodies: single chain Fv fragments without a linker form trivalent trimers," FEBS Lett. (1997) 409(3): 437-441.
Ill et al., "Design and construction of a hybrid immunoglobulin domain with properties of both heavy and light chain variable regions," Protein Eng. (1997) 10(8): 949-957.
Janeway et al., Immunobiology: The Immune System in Health and Disease, 3rd Ed., Current Biology Publications (1997), p. 4:33.
Johnston, et al., "Biolistic transformation: microbes to mice," Nature (1990) 346: 776-777.
Jores et al., "Resolution of hypervariable regions in T-cell receptor beta chains by a modified Wu-Kabat index of amino acid diversity.," PNAS (1990) 87(23):9138-9142.
Kared et al., "CD57 in human natural killer cells and T-lymphocytes," Cancer Immunol Immunother (2016) 65(4):441-52.
Kim et al., "Chimeric restriction endonuclease." Proc Natl Acad Sci USA (Feb. 1, 1994) 91(3):883-7.
Kim et al., "Insertion and deletion mutants of Fokl restriction endonuclease.," J. Biol. Chem. (1994) 269(50):31978-31982.
Klebanoff et al., "Sorting through subsets: which T-cell populations mediate highly effective adoptive immunotherapy?," J Immunother. (2012) 35(9): 651-660.
Kochenderfer et al., "Construction and preclinical evaluation of an anti-CD19 chimeric antigen receptor," J. Immunotherapy (2009) 32(7): 689-702.
Kochenderfer et al., "Treating B-cell cancer with T cells expressing anti-CD19 chimeric antigen receptors," Nature Reviews Clinical Oncology (2013) 10:267-276.
Kollmannsperger et al., "Live-cell protein labelling with nanometre precision by cell squeezing," Nat Commun (Jan. 29, 2016) 7:10372, 7 pages.
Koste et al., "T-cell receptor transfer into human T cells with ecotropic retroviral vectors," Gene Therapy (2014) 21: 533-538.
Kotb, "Bacterial pyrogenic exotoxins as superantigens," Clin Microbiol Rev. (1995) 8(3):411-426.
Kurucz et al., "A bacterially expressed single-chain Fv construct from the 2B4 T-cell receptor," Proc Natl Acad Sci U S A. (1993) 90(9): 3830-3834.
Larson et al., "Defined cell composition and precise control over JCAR017 dose enables identification of relationships between chimeric antigen receptor T cell product attributes, pharmacokinetics, and clinical endpoints in NHL," Cancer Res. (2018) 78(13 Suppl): Abstract nr 960, 4 pages.
Lee et al., "Nonendocytic delivery of functional engineered nanoparticles into the cytoplasm of live cells using a novel, high-throughput microfluidic device," Nano Lett (Dec. 12, 2012) 12(12):6322-7, 12 pages.
Lefranc et al., "IMGT unique numbering for immunoglobulin and T cell receptor variable domains and Ig superfamily V-like domains," Dev Comp Immunol (2003) 27(1):55-77.
Li et al., "Alteration of the cleavage distance of Fok l restriction endonuclease by insertion mutagenesis," Proc. Natl. Acad. Sci. USA (1993) 90 (7):2764-2768.
Li et al., "Directed evolution of human T-cell receptors with picomolar affinities by phage display," Nat Biotechnol. (2005) 23:349-354.
Li et al., "Functional domains in Fok l restriction endonuclease," Proc. Natl. Acad. Sci. USA (1992) 89 (10):4275-4279.
Li et al., "TAL nucleases (TALNs): hybrid proteins composed of TAL effectors and Fokl DNA-cleavage domain," Nucleic Acids Research (2011, e-pub. Aug. 10, 2010):39(1):359-372.
Lier et al., "Tissue distribution and biochemical and functional properties of Tp55 (CD27), a novel T cell differentiation antigen," J Immunol (Sep. 1, 1987) 139(5):1589-96.
Lim et al. "Engineered Streptavidin Monomer and Dimer with Improved Stability and Function," Biochemistry (2010), 50: 8682-91.
Ling et al., "B-cell and plasma cell antigens: new and previously defined clusters," Leucocyte typing III. (1987) 302-355.
Liu et al., "Inclusion of Strep-tag II in design of antigen receptors for T-cell immunotherapy," Nature Biotechnology (Apr. 2016) 34(4):430-434.
Lloyd et al., "Beyond the antigen receptor: editing the genome of T-cells for cancer adoptive cellular therapies," Front Immunol (2013) 4:221, 7 pages.
Lupton et al., "Dominant positive and negative selection using a hygromycin phosphotransferase-thymidine kinase fusion gene," Mol. and Cell Biol. (1991) 11:6: 3374-3378.
Manuri et al., "piggyBac transposon/transposase system to generate CD19-specific T cells for the treatment of B-lineage malignancies," Hum Gene Ther (2010) 21(4): 427-437.

(56) References Cited

OTHER PUBLICATIONS

Martin et al., "The affinity-selection of a minibody polypeptide inhibitor of human interleukin-6," EMBO J. (1994) 13(22): 5303-5309.
Melero et al., "Agonist antibodies to TNFR molecules that costimulate T and NK cells," Clin Cancer Res (2013) 19(5):1044-1053.
Methods in Molecular Medicine, vol. 58: Metastasis Research Protocols, vol. 2: Cell Behavior In Vitro and In Vivo, p. 17-23 Edited by: S. A. Brooks and U. Schumacher © Humana Press Inc., Totowa, NJ.
Miller et al., "Improved retroviral vectors for gene transfer and expression," BioTechniques (1989) 7:980-990.
Miller et al., "Retrovirus packaging cells," Human Gene Therapy (1990) 1:5-14.
Mittler et al., "Anti-CD137 antibodies in the treatment of autoimmune disease and cancer", Immunol. Res. (2004) 29(1-3): 197-208.
Moscou et al., "A simple cipher governs DNA recognition by TAL effectors," Science (Dec. 11, 2009) 326(5959):1501.
Naldini, "Lentiviruses as gene transfer agents for delivery to non-dividing cells", Curr Opin Biotechnol., Oct. 9, 1998; 5:457-63.
Nowrousian, "Next-generation Sequencing Techniques for Eukaryotic Microorganisms: Sequencing-Based Solutions to Biological Problems," Eukaryot Cell (2010) 9(9): 1300-1310.
Ohkawa et al., "Systematic characterization of human CD8+ T cells with natural killer cell markers in comparison with natural killer cells and normal CD8+ T cells," Immunology (2001) 103(3); 281-290.
Park et al., "Treating cancer with genetically engineered T cells," Trends Biotechnol. (2011) 29(11): 550-557.
Park. et al. "Expression of anti-HVEM single-chain antibody on tumor cells induces tumor-specific immunity with long-term memory", (2012) Cancer Immunol Immunother 61(2):203-214.
Paulsen et al., "Modulation of CD4+ T-cell activation by CD95 co-stimulation", Cell Death Differ. (2011) 18(4): 619-631.
Riddell et al., "Phase I study of cellular adoptive immunotherapy using genetically modified CD8+ HIV-specific T cells for HIV seropositive patients undergoing allogeneic bone marrow transplant," Human Gene Therapy (1992) 3:319-338.
Rosenberg, et al., "Cell transfer immunotherapy for metastatic solid cancer—what clinicians need to know," Nat Rev Clin Oncol. (2011) 8(10):577-85.
Sabatino et al., "Generation of clinical-grade CD19-specific CAR-modified CD8+ memory stem cells for the treatment of human B-cell malignancies," Blood. (Jul. 2016) 128(4): 519-528.
Sadelain et al., "The basic principles of chimeric antigen receptor design," Cancer Discov. (2013) 3(4): 388-398.
Sanjana et al., "Improved vectors and genome-wide libraries for CRISPR screening," Nat Methods (Aug. 2014) 11(8):783-784.
Scarpa et al., "Characterization of recombinant helper retroviruses from Moloney-based vectors in ecotropic and amphotropic packaging cell lines," Virology (1991) 180:849-852.
Schlueter et al., "Specificity and binding properties of a single-chain T cell receptor," J Mol Biol. (1996) 256(5): 859-69.
Schuler et al., SYFPEITHI, Database for Searching and T-Cell Epitope Prediction. in Immunoinformatics Methods in Molecular Biology, (2007) 409(1): 75-93.
Sharma et al., "Efficient sleeping beauty DNA transposition from DNA minicircles," Molec Ther Nucl Acids (2013) 2, e74, 10 pages.
Shendure et al., "Advanced Sequencing Technologies: Methods and Goals," Nat Rev Genet (2004) 5(5): 335-344.
Sheng et al., "Structure-based cleavage mechanism of Thermus thermophilus Argonaute DNA guide strand-mediated DNA target cleavage," Proc. Natl. Acad. Sci. USA (2014, e-pub. Dec. 27, 2013) 111(2):652-657.
Singh et al., "Early memory phenotypes drive T cell proliferation in patients with pediatric malignancies," Sci Trans Med. (2016) 8(320):320ra3, 9 pages.
Singh et al., "ProPred: prediction of HLA-DR binding sites," Bioinformatics. (2001) 17(12): 1236-1237.
Smith et al., "Ex vivo expansion of human T cells for adoptive immunotherapy using the novel Xeno-free CTS Immune Cell Serum Replacement," Clinical & Translational Immunology (2015) 4:e31, 10 pages.
Soman et al., "MTS dye based colorimetric CTLL-2 cell proliferation assay for product release and stability monitoring of interleukin-15: assay qualification, standardization and statistical analysis," J Immunol Methods. (2009) 348(1-2): 83-94.
Soo Hoo et al., "Characterization of a single-chain T-cell receptor expressed in *Escherichia coli,*" Proc Natl Acad Sci U S A. (1992) 89(10): 4759-4763.
Stemberger et al., "Novel Serial Positive Enrichment Technology Enables Clinical Multiparameter Cell Sorting," PLoS One (2012) 7(4): e35798, 11 pages.
Stone et al., "The assembly of single domain antibodies into bispecific decavalent molecules," J Immunol Methods. (2007) 318(1-2): 88-94.
Strioga et al., "CD8+ CD28- and CD8+ CD57+ T cells and their role in health and disease," Immunology (2011) 134: 17-32.
Swarts et al., "DNA-guided DNA interference by a prokaryotic Argonaute," Nature (2014) 507(7491):258-261, 32 pages.
Terakura et al., "Generation of CD19-chimeric antigen receptor modified CD8+ T cells derived from virus-specific central memory T cells," Blood (2012) 1:72-82.
Themeli et al., "Generation of tumor-targeted human T lymphocytes from induced pluripotent stem cells for cancer therapy," Nat Biotechnol. (2013) 31(10): 928-933.
Tiercy, "How to select the best available related or unrelated donor of hematopoietic stem cells?," Haematologica (2016) 101(6):680-7.
Traunecker et al., "Bispecific single chain molecules (Janusins) target cytotoxic lymphocytes on HIV infected cells," EMBO j. (1991) 10(12):3655-3659.
Traunecker et al., "Janusin: new molecular design for bispecific reagents," Int J Cancer Suppl. (1992) 7:51-52.
Tsukahara et al., "CD19 target-engineered T-cells accumulate at tumor lesions in human B-cell lymphoma xenograft mouse models," Biochem Biophys Res Commun (2013) 438(1): 84-89.
Turtle et al., "Engineered T cells for anti-cancer therapy," Curr. Opin. Immunol. (2012) 24(5): 633-39.
UniProt Accesion No. P20963.2 "CD3Z_HUMAN. T-cell surface glycoprotein CD3 zeta chain," Last updated Oct. 10, 2002, Downloaded on Sep. 27, 2024, 16 pages.
UniProt Accesion No. Q07011.1 "TNR9_HUMAN. Tumor necrosis factor receptor superfamily member 9," Last updated Feb. 1, 1995, Downloaded on Sep. 27, 2024, 13 pages.
Van Tendeloo et al., "High-level transgene expression in primary human T lymphocytes and adult bone marrow CD34+ cells via electroporation-mediated gene delivery," Gene Therapy (2000) 7(16): 1431-1437.
Vanhove et al., "Selective blockade of CD28 and not CTLA-4 with a single-chain Fv-alpha1-antitrypsin fusion antibody," Blood. (2003) 102(2): 564-570.
Verhoeyen et al., "Lentiviral vector gene transfer into human T cells," Methods Mol Biol. (2009) 506: 97-114.
Voss et al. "Mutagenesis of a flexible loop in Streptavidin Leads to Higher Affinity for the Strep-tag II Peptide and Improved Performance in Recombinant Protein Purification", Protein Engineering (1997) 10(8): 975-982.
Wadhwa et al., "Receptor mediated glycotargeting," J. Drug Targeting (1995) 3: 111-127.
Wadhwa et al., "The 2nd International Standard for Interleukin-2 (IL-2). Report of a collaborative study." J Immunol Methods. (2013) 397(1-2):1-7.
Wang et al., "Clinical manufacturing of CAR T cells: foundation of a promising therapy," Molecular Therapy—Oncolytics (Jun. 2016) 3:16015, 7 pages.
Wang et al., "Phenotypic and functional attributes of lentivirus-modified CD19-specific human CD8+ central memory T cells manufactured at clinical scale," J Immunother. (2012) 35(9):689-701.
Wang et al., "Genetic Screens in Human Cells Using the CRISPR-Cas9 System," Science (2014, e-pub. Dec. 12, 2013) 343(6166):80-84, 12 pages.

(56) References Cited

OTHER PUBLICATIONS

Wolfl et al., "Antigen specific activation and cytokine-facilitated expansion of naïve, human Cd8+ T cells," Nature Protocols (2014) 9(4): 950-966.
Worel et al., "Influence of CD27- CD28- T-Cells on the Therapeutic Outcome in Adult Patients with Relapsed or Refractory Diffuse Large B-Cell Lymphoma after CART-Infusion," Blood (Nov. 13, 2019) 134(Supplement 1):1935, 3 pages.
Wu et al., "Adoptive T-cell therapy using autologous tumor-infiltrating lymphocytes for metastatic melanoma: current status and future outlook," Cancer (2012) 18(2): 160-175.
Wu et al., "Engineering soluble monomeric streptavidin with reversible biotin binding capability", J. Biol. Chem. (2005) 280(24): 23225-23231.
Wulfing et al., "Correctly folded T-cell receptor fragments in the periplasm of *Escherichia coli*. Influence of folding catalysts," J Mol Biol. (1994) 242(5): 655-669.
Zhang et al., "A novel approach to make homogeneous protease-stable monovalent streptavidin," Biochem Biophys Res Commun. (2015) 463(4): 1059-63.
Zhu et al., "Patient-derived glioblastoma stem cells are killed by CD133-specific CAR T cells but induce the T cell aging marker CD57," Oncotarget. (2015) 6(1): 171-84.
D'Angeac et al., "CD57+ T lymphocytes are derived from CD57- precursors by differentiation occurring in late immune responses," Eur J Immunol (Jul. 1994) 24(7):1503-1511.
Taraban et al., "Expression and costimulatory effects of the TNF receptor superfamily members CD134 (OX40) and CD137 (4-1BB), and their role in the generation of anti-tumor immune responses", Eur J Immunol. (Dec. 2002, e-pub. Nov. 28, 2002) 32(12):3617-3627.

* cited by examiner

SEQUENCE LISTING

<160> NUMBER OF SEQ ID NOS: 98

<210> SEQ ID NO 1
<211> LENGTH: 12
<212> TYPE: PRT
<213> ORGANISM: Artificial Sequence
<220> FEATURE:
<223> OTHER INFORMATION: spacer (IgG4hinge)

<400> SEQUENCE: 1

Glu Ser Lys Tyr Gly Pro Pro Cys Pro Pro Cys Pro
1               5                   10

<210> SEQ ID NO 2
<211> LENGTH: 36
<212> TYPE: DNA
<213> ORGANISM: Artificial Sequence
<220> FEATURE:
<223> OTHER INFORMATION: spacer (IgG4hinge)

<400> SEQUENCE: 2
gaatctaagt acggaccgcc ctgcccccct tgccct                              36

<210> SEQ ID NO 3
<211> LENGTH: 119
<212> TYPE: PRT

-continued

```
<213> ORGANISM: Artificial Sequence
<220> FEATURE:
<223> OTHER INFORMATION: Hinge-CH3 spacer

<400> SEQUENCE: 3

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
                85                  90                  95

Cys Ser Val Met His Glu Ala Leu His Asn His Tyr Thr Gln Lys Ser
            100                 105                 110

Leu Ser Leu Ser Leu Gly Lys
        115


<210> SEQ ID NO 4
<211> LENGTH: 229
<212> TYPE: PRT
<213> ORGANISM: Artificial Sequence
<220> FEATURE:
<223> OTHER INFORMATION: Hinge-CH2-CH3 spacer

<400> SEQUENCE: 4

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205
```

-continued

```
Val Met His Glu Ala Leu His Asn His Tyr Thr Gln Lys Ser Leu Ser
    210                 215                 220

Leu Ser Leu Gly Lys
225


<210> SEQ ID NO 5
<211> LENGTH: 282
<212> TYPE: PRT
<213> ORGANISM: Artificial Sequence
<220> FEATURE:
<223> OTHER INFORMATION: IgD-hinge-Fc

<400> SEQUENCE: 5

Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
            20                  25                  30

Thr Thr Arg Asn Thr Gly Arg Gly Gly Glu Glu Lys Lys Lys Glu Lys
        35                  40                  45

Glu Lys Glu Glu Gln Glu Glu Arg Glu Thr Lys Thr Pro Glu Cys Pro
    50                  55                  60

Ser His Thr Gln Pro Leu Gly Val Tyr Leu Leu Thr Pro Ala Val Gln
65                  70                  75                  80

Asp Leu Trp Leu Arg Asp Lys Ala Thr Phe Thr Cys Phe Val Val Gly
                85                  90                  95

Ser Asp Leu Lys Asp Ala His Leu Thr Trp Glu Val Ala Gly Lys Val
            100                 105                 110

Pro Thr Gly Gly Val Glu Glu Gly Leu Leu Glu Arg His Ser Asn Gly
        115                 120                 125

Ser Gln Ser Gln His Ser Arg Leu Thr Leu Pro Arg Ser Leu Trp Asn
    130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175

Leu Ser Leu Asn Leu Leu Ala Ser Ser Asp Pro Pro Glu Ala Ala Ser
            180                 185                 190

Trp Leu Leu Cys Glu Val Ser Gly Phe Ser Pro Pro Asn Ile Leu Leu
        195                 200                 205

Met Trp Leu Glu Asp Gln Arg Glu Val Asn Thr Ser Gly Phe Ala Pro
    210                 215                 220

Ala Arg Pro Pro Pro Gln Pro Gly Ser Thr Thr Phe Trp Ala Trp Ser
225                 230                 235                 240

Val Leu Arg Val Pro Ala Pro Pro Ser Pro Gln Pro Ala Thr Tyr Thr
                245                 250                 255

Cys Val Val Ser His Glu Asp Ser Arg Thr Leu Leu Asn Ala Ser Arg
            260                 265                 270

Ser Leu Glu Val Ser Tyr Val Thr Asp His
        275                 280


<210> SEQ ID NO 6
<211> LENGTH: 24
<212> TYPE: PRT
<213> ORGANISM: Artificial Sequence
<220> FEATURE:
<223> OTHER INFORMATION: T2A

<400> SEQUENCE: 6
```

```
Leu Glu Gly Gly Gly Glu Gly Arg Gly Ser Leu Leu Thr Cys Gly Asp
1               5                   10                  15

Val Glu Glu Asn Pro Gly Pro Arg
            20


<210> SEQ ID NO 7
<211> LENGTH: 357
<212> TYPE: PRT
<213> ORGANISM: Artificial Sequence
<220> FEATURE:
<223> OTHER INFORMATION: tEGFR

<400> SEQUENCE: 7

Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
    210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335
```

```
Thr Gly Met Val Gly Ala Leu Leu Leu Leu Leu Val Val Ala Leu Gly
            340                 345                 350

Ile Gly Leu Phe Met
        355


<210> SEQ ID NO 8
<211> LENGTH: 27
<212> TYPE: PRT
<213> ORGANISM: Artificial Sequence
<220> FEATURE:
<223> OTHER INFORMATION: CD28 (amino acids 153-179 of Accession No.
      P10747)

<400> SEQUENCE: 8

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25


<210> SEQ ID NO 9
<211> LENGTH: 66
<212> TYPE: PRT
<213> ORGANISM: Artificial Sequence
<220> FEATURE:
<223> OTHER INFORMATION: CD28 (amino acids 114-179 of Accession No.
      P10747)

<400> SEQUENCE: 9

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val
65


<210> SEQ ID NO 10
<211> LENGTH: 41
<212> TYPE: PRT
<213> ORGANISM: Artificial Sequence
<220> FEATURE:
<223> OTHER INFORMATION: CD28 (amino acids 180-220 of P10747)

<400> SEQUENCE: 10

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40


<210> SEQ ID NO 11
<211> LENGTH: 41
<212> TYPE: PRT
<213> ORGANISM: Artificial Sequence
<220> FEATURE:
<223> OTHER INFORMATION: CD28 (LL to GG)

<400> SEQUENCE: 11
```

```
Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40


<210> SEQ ID NO 12
<211> LENGTH: 42
<212> TYPE: PRT
<213> ORGANISM: Artificial Sequence
<220> FEATURE:
<223> OTHER INFORMATION: 4-1BB (amino acids 214-255 of Q07011.1)

<400> SEQUENCE: 12

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40


<210> SEQ ID NO 13
<211> LENGTH: 112
<212> TYPE: PRT
<213> ORGANISM: Artificial Sequence
<220> FEATURE:
<223> OTHER INFORMATION: CD3 zeta

<400> SEQUENCE: 13

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 14
<211> LENGTH: 112
<212> TYPE: PRT
<213> ORGANISM: Artificial Sequence
<220> FEATURE:
<223> OTHER INFORMATION: CD3 zeta

<400> SEQUENCE: 14

Arg Val Lys Phe Ser Arg Ser Ala Glu Pro Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
```

```
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 15
<211> LENGTH: 112
<212> TYPE: PRT
<213> ORGANISM: Artificial Sequence
<220> FEATURE:
<223> OTHER INFORMATION: CD3 zeta

<400> SEQUENCE: 15

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 16
<211> LENGTH: 335
<212> TYPE: PRT
<213> ORGANISM: Artificial Sequence
<220> FEATURE:
<223> OTHER INFORMATION: tEGFR

<400> SEQUENCE: 16

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140
```

```
Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
        275                 280                 285

Pro Asn Cys Thr Tyr Gly Cys Thr Gly Pro Gly Leu Glu Gly Cys Pro
    290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335


<210> SEQ ID NO 17
<211> LENGTH: 18
<212> TYPE: PRT
<213> ORGANISM: Artificial Sequence
<220> FEATURE:
<223> OTHER INFORMATION: T2A

<400> SEQUENCE: 17

Glu Gly Arg Gly Ser Leu Leu Thr Cys Gly Asp Val Glu Glu Asn Pro
1               5                   10                  15

Gly Pro


<210> SEQ ID NO 18
<211> LENGTH: 22
<212> TYPE: PRT
<213> ORGANISM: Artificial Sequence
<220> FEATURE:
<223> OTHER INFORMATION: P2A

<400> SEQUENCE: 18

Gly Ser Gly Ala Thr Asn Phe Ser Leu Leu Lys Gln Ala Gly Asp Val
1               5                   10                  15

Glu Glu Asn Pro Gly Pro
            20


<210> SEQ ID NO 19
<211> LENGTH: 19
<212> TYPE: PRT
<213> ORGANISM: Artificial Sequence
<220> FEATURE:
<223> OTHER INFORMATION: P2A

<400> SEQUENCE: 19

Ala Thr Asn Phe Ser Leu Leu Lys Gln Ala Gly Asp Val Glu Glu Asn
1               5                   10                  15
```

Pro Gly Pro

<210> SEQ ID NO 20
<211> LENGTH: 20
<212> TYPE: PRT
<213> ORGANISM: Artificial Sequence
<220> FEATURE:
<223> OTHER INFORMATION: E2A

<400> SEQUENCE: 20

Gln Cys Thr Asn Tyr Ala Leu Leu Lys Leu Ala Gly Asp Val Glu Ser
1 5 10 15

Asn Pro Gly Pro
20

<210> SEQ ID NO 21
<211> LENGTH: 22
<212> TYPE: PRT
<213> ORGANISM: Artificial Sequence
<220> FEATURE:
<223> OTHER INFORMATION: F2A

<400> SEQUENCE: 21

Val Lys Gln Thr Leu Asn Phe Asp Leu Leu Lys Leu Ala Gly Asp Val
1 5 10 15

Glu Ser Asn Pro Gly Pro
20

<210> SEQ ID NO 22
<211> LENGTH: 30
<212> TYPE: PRT
<213> ORGANISM: Artificial Sequence
<220> FEATURE:
<223> OTHER INFORMATION: Linker

<400> SEQUENCE: 22

Pro Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Pro
20 25 30

<210> SEQ ID NO 23
<211> LENGTH: 17
<212> TYPE: PRT
<213> ORGANISM: Artificial Sequence
<220> FEATURE:
<223> OTHER INFORMATION: Linker

<400> SEQUENCE: 23

Gly Ser Ala Asp Asp Ala Lys Lys Asp Ala Ala Lys Lys Asp Gly Lys
1 5 10 15

Ser

<210> SEQ ID NO 24
<211> LENGTH: 66
<212> TYPE: DNA
<213> ORGANISM: Artificial Sequence
<220> FEATURE:
<223> OTHER INFORMATION: GMCSFR alpha chain signal sequence

<400> SEQUENCE: 24
atgcttctcc tggtgacaag ccttctgctc tgtgagttac cacacccagc attcctcctg 60
atccca 66

<210> SEQ ID NO 25
<211> LENGTH: 22
<212> TYPE: PRT
<213> ORGANISM: Artificial Sequence
<220> FEATURE:
<223> OTHER INFORMATION: GMCSFR alpha chain signal sequence

<400> SEQUENCE: 25

```
Met Leu Leu Leu Val Thr Ser Leu Leu Leu Cys Glu Leu Pro His Pro
1               5                   10                  15

Ala Phe Leu Leu Ile Pro
            20
```

<210> SEQ ID NO 26
<211> LENGTH: 18
<212> TYPE: PRT
<213> ORGANISM: Artificial Sequence
<220> FEATURE:
<223> OTHER INFORMATION: CD8 alpha signal peptide

<400> SEQUENCE: 26

```
Met Ala Leu Pro Val Thr Ala Leu Leu Leu Pro Leu Ala Leu Leu Leu
1               5                   10                  15

His Ala
```

<210> SEQ ID NO 27
<211> LENGTH: 15
<212> TYPE: PRT
<213> ORGANISM: Artificial Sequence
<220> FEATURE:
<223> OTHER INFORMATION: Hinge

<400> SEQUENCE: 27

```
Glu Pro Lys Ser Cys Asp Lys Thr His Thr Cys Pro Pro Cys Pro
1               5                   10                  15
```

<210> SEQ ID NO 28
<211> LENGTH: 12
<212> TYPE: PRT
<213> ORGANISM: Artificial Sequence
<220> FEATURE:
<223> OTHER INFORMATION: Hinge

<400> SEQUENCE: 28

```
Glu Arg Lys Cys Cys Val Glu Cys Pro Pro Cys Pro
1               5                   10
```

<210> SEQ ID NO 29
<211> LENGTH: 61
<212> TYPE: PRT
<213> ORGANISM: Artificial Sequence
<220> FEATURE:
<223> OTHER INFORMATION: Hinge

<400> SEQUENCE: 29

```
Glu Leu Lys Thr Pro Leu Gly Asp Thr His Thr Cys Pro Arg Cys Pro
1               5                   10                  15

Glu Pro Lys Ser Cys Asp Thr Pro Pro Pro Cys Pro Arg Cys Pro Glu
            20                  25                  30

Pro Lys Ser Cys Asp Thr Pro Pro Pro Cys Pro Arg Cys Pro Glu Pro
        35                  40                  45

Lys Ser Cys Asp Thr Pro Pro Pro Cys Pro Arg Cys Pro
    50                  55                  60
```

<210> SEQ ID NO 30
<211> LENGTH: 12
<212> TYPE: PRT
<213> ORGANISM: Artificial Sequence
<220> FEATURE:
<223> OTHER INFORMATION: Hinge

<400> SEQUENCE: 30

Glu Ser Lys Tyr Gly Pro Pro Cys Pro Ser Cys Pro
1               5                   10

<210> SEQ ID NO 31
<211> LENGTH: 5
<212> TYPE: PRT
<213> ORGANISM: Artificial Sequence
<220> FEATURE:
<221> NAME/KEY: VARIANT
<222> LOCATION: (1)...(1)
<223> OTHER INFORMATION: Xaa is glycine, cysteine or arginine
<220> FEATURE:
<221> NAME/KEY: VARIANT
<222> LOCATION: (4)...(4)
<223> OTHER INFORMATION: Xaa is cysteine or threonine
<220> FEATURE:
<223> OTHER INFORMATION: Hinge

<400> SEQUENCE: 31

Xaa Pro Pro Xaa Pro
1               5

<210> SEQ ID NO 32
<211> LENGTH: 9
<212> TYPE: PRT
<213> ORGANISM: Artificial Sequence
<220> FEATURE:
<223> OTHER INFORMATION: Hinge

<400> SEQUENCE: 32

Tyr Gly Pro Pro Cys Pro Pro Cys Pro
1               5

<210> SEQ ID NO 33
<211> LENGTH: 10
<212> TYPE: PRT
<213> ORGANISM: Artificial Sequence
<220> FEATURE:
<223> OTHER INFORMATION: Hinge

<400> SEQUENCE: 33

Lys Tyr Gly Pro Pro Cys Pro Pro Cys Pro
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Hinge

<400> SEQUENCE: 34

Glu Val Val Val Lys Tyr Gly Pro Pro Cys Pro Pro Cys Pro
1               5                   10

<210> SEQ ID NO 35
<211> LENGTH: 11
<212> TYPE: PRT
<213> ORGANISM: Artificial Sequence

```
<220> FEATURE:
<223> OTHER INFORMATION: CDR L1

<400> SEQUENCE: 35

Arg Ala Ser Gln Asp Ile Ser Lys Tyr Leu Asn
1               5                   10


<210> SEQ ID NO 36
<211> LENGTH: 7
<212> TYPE: PRT
<213> ORGANISM: Artificial Sequence
<220> FEATURE:
<223> OTHER INFORMATION: CDR L2

<400> SEQUENCE: 36

Ser Arg Leu His Ser Gly Val
1               5


<210> SEQ ID NO 37
<211> LENGTH: 9
<212> TYPE: PRT
<213> ORGANISM: Artificial Sequence
<220> FEATURE:
<223> OTHER INFORMATION: CDR L3

<400> SEQUENCE: 37

Gly Asn Thr Leu Pro Tyr Thr Phe Gly
1               5


<210> SEQ ID NO 38
<211> LENGTH: 5
<212> TYPE: PRT
<213> ORGANISM: Artificial Sequence
<220> FEATURE:
<223> OTHER INFORMATION: CDR H1

<400> SEQUENCE: 38

Asp Tyr Gly Val Ser
1               5


<210> SEQ ID NO 39
<211> LENGTH: 16
<212> TYPE: PRT
<213> ORGANISM: Artificial Sequence
<220> FEATURE:
<223> OTHER INFORMATION: CDR H2

<400> SEQUENCE: 39

Val Ile Trp Gly Ser Glu Thr Thr Tyr Tyr Asn Ser Ala Leu Lys Ser
1               5                   10                  15


<210> SEQ ID NO 40
<211> LENGTH: 7
<212> TYPE: PRT
<213> ORGANISM: Artificial Sequence
<220> FEATURE:
<223> OTHER INFORMATION: CDR H3

<400> SEQUENCE: 40

Tyr Ala Met Asp Tyr Trp Gly
1               5


<210> SEQ ID NO 41
<211> LENGTH: 120
<212> TYPE: PRT
<213> ORGANISM: Artificial Sequence
<220> FEATURE:
```

<223> OTHER INFORMATION: VH

<400> SEQUENCE: 41

```
Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120
```

<210> SEQ ID NO 42
<211> LENGTH: 107
<212> TYPE: PRT
<213> ORGANISM: Artificial Sequence
<220> FEATURE:
<223> OTHER INFORMATION: VL

<400> SEQUENCE: 42

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105
```

<210> SEQ ID NO 43
<211> LENGTH: 245
<212> TYPE: PRT
<213> ORGANISM: Artificial Sequence
<220> FEATURE:
<223> OTHER INFORMATION: scFv

<400> SEQUENCE: 43

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
```

```
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser
                245


<210> SEQ ID NO 44
<211> LENGTH: 11
<212> TYPE: PRT
<213> ORGANISM: Artificial Sequence
<220> FEATURE:
<223> OTHER INFORMATION: CDR L1

<400> SEQUENCE: 44

Lys Ala Ser Gln Asn Val Gly Thr Asn Val Ala
1               5                   10


<210> SEQ ID NO 45
<211> LENGTH: 7
<212> TYPE: PRT
<213> ORGANISM: Artificial Sequence
<220> FEATURE:
<223> OTHER INFORMATION: CDR L2

<400> SEQUENCE: 45

Ser Ala Thr Tyr Arg Asn Ser
1               5


<210> SEQ ID NO 46
<211> LENGTH: 9
<212> TYPE: PRT
<213> ORGANISM: Artificial Sequence
<220> FEATURE:
<223> OTHER INFORMATION: CDR L3

<400> SEQUENCE: 46

Gln Gln Tyr Asn Arg Tyr Pro Tyr Thr
1               5


<210> SEQ ID NO 47
```

<211> LENGTH: 5
<212> TYPE: PRT
<213> ORGANISM: Artificial Sequence
<220> FEATURE:
<223> OTHER INFORMATION: CDR H1

<400> SEQUENCE: 47

```
Ser Tyr Trp Met Asn
1               5
```

<210> SEQ ID NO 48
<211> LENGTH: 17
<212> TYPE: PRT
<213> ORGANISM: Artificial Sequence
<220> FEATURE:
<223> OTHER INFORMATION: CDR H2

<400> SEQUENCE: 48

```
Gln Ile Tyr Pro Gly Asp Gly Asp Thr Asn Tyr Asn Gly Lys Phe Lys
1               5                   10                  15

Gly
```

<210> SEQ ID NO 49
<211> LENGTH: 13
<212> TYPE: PRT
<213> ORGANISM: Artificial Sequence
<220> FEATURE:
<223> OTHER INFORMATION: CDR H3

<400> SEQUENCE: 49

```
Lys Thr Ile Ser Ser Val Val Asp Phe Tyr Phe Asp Tyr
1               5                   10
```

<210> SEQ ID NO 50
<211> LENGTH: 122
<212> TYPE: PRT
<213> ORGANISM: Artificial Sequence
<220> FEATURE:
<223> OTHER INFORMATION: VH

<400> SEQUENCE: 50

```
Glu Val Lys Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Gln Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Phe Cys
                85                  90                  95

Ala Arg Lys Thr Ile Ser Ser Val Val Asp Phe Tyr Phe Asp Tyr Trp
            100                 105                 110

Gly Gln Gly Thr Thr Val Thr Val Ser Ser
        115                 120
```

<210> SEQ ID NO 51
<211> LENGTH: 108
<212> TYPE: PRT
<213> ORGANISM: Artificial Sequence
<220> FEATURE:

<223> OTHER INFORMATION: VL

<400> SEQUENCE: 51

Asp Ile Glu Leu Thr Gln Ser Pro Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Pro Leu Ile
        35                  40                  45

Tyr Ser Ala Thr Tyr Arg Asn Ser Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Lys Asp Leu Ala Asp Tyr Phe Cys Gln Gln Tyr Asn Arg Tyr Pro Tyr
                85                  90                  95

Thr Ser Gly Gly Gly Thr Lys Leu Glu Ile Lys Arg
            100                 105

<210> SEQ ID NO 52
<211> LENGTH: 15
<212> TYPE: PRT
<213> ORGANISM: Artificial Sequence
<220> FEATURE:
<223> OTHER INFORMATION: Linker

<400> SEQUENCE: 52

Gly Gly Gly Gly Ser Gly Gly Gly Gly Ser Gly Gly Gly Gly Ser
1               5                   10                  15

<210> SEQ ID NO 53
<211> LENGTH: 245
<212> TYPE: PRT
<213> ORGANISM: Artificial Sequence
<220> FEATURE:
<223> OTHER INFORMATION: scFv

<400> SEQUENCE: 53

Glu Val Lys Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Gln Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Phe Cys
                85                  90                  95

Ala Arg Lys Thr Ile Ser Ser Val Val Asp Phe Tyr Phe Asp Tyr Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Gly Ser Asp Ile Glu Leu Thr Gln Ser
    130                 135                 140

Pro Lys Phe Met Ser Thr Ser Val Gly Asp Arg Val Ser Val Thr Cys
145                 150                 155                 160

Lys Ala Ser Gln Asn Val Gly Thr Asn Val Ala Trp Tyr Gln Gln Lys

```
                165                 170                 175

Pro Gly Gln Ser Pro Lys Pro Leu Ile Tyr Ser Ala Thr Tyr Arg Asn
            180                 185                 190

Ser Gly Val Pro Asp Arg Phe Thr Gly Ser Gly Ser Gly Thr Asp Phe
        195                 200                 205

Thr Leu Thr Ile Thr Asn Val Gln Ser Lys Asp Leu Ala Asp Tyr Phe
    210                 215                 220

Cys Gln Gln Tyr Asn Arg Tyr Pro Tyr Thr Ser Gly Gly Gly Thr Lys
225                 230                 235                 240

Leu Glu Ile Lys Arg
                245


<210> SEQ ID NO 54
<211> LENGTH: 12
<212> TYPE: PRT
<213> ORGANISM: Artificial Sequence
<220> FEATURE:
<223> OTHER INFORMATION: HC-CDR3

<400> SEQUENCE: 54

His Tyr Tyr Tyr Gly Gly Ser Tyr Ala Met Asp Tyr
1               5                   10


<210> SEQ ID NO 55
<211> LENGTH: 7
<212> TYPE: PRT
<213> ORGANISM: Artificial Sequence
<220> FEATURE:
<223> OTHER INFORMATION: LC-CDR2

<400> SEQUENCE: 55

His Thr Ser Arg Leu His Ser
1               5


<210> SEQ ID NO 56
<211> LENGTH: 9
<212> TYPE: PRT
<213> ORGANISM: Artificial Sequence
<220> FEATURE:
<223> OTHER INFORMATION: LC-CDR3

<400> SEQUENCE: 56

Gln Gln Gly Asn Thr Leu Pro Tyr Thr
1               5


<210> SEQ ID NO 57
<211> LENGTH: 735
<212> TYPE: DNA
<213> ORGANISM: Artificial Sequence
<220> FEATURE:
<223> OTHER INFORMATION: Sequence encoding scFv

<400> SEQUENCE: 57

gacatccaga tgacccagac cacctccagc ctgagcgcca gcctgggcga ccgggtgacc      60

atcagctgcc gggccagcca ggacatcagc aagtacctga actggtatca gcagaagccc     120

gacggcaccg tcaagctgct gatctaccac accagccggc tgcacagcgg cgtgcccagc     180

cggtttagcg gcagcggctc cggcaccgac tacagcctga ccatctccaa cctggaacag     240

gaagatatcg ccacctactt ttgccagcag ggcaacacac tgccctacac ctttggcggc     300

ggaacaaagc tggaaatcac cggcagcacc tccggcagcg gcaagcctgg cagcggcgag     360

ggcagcacca agggcgaggt gaagctgcag gaaagcggcc ctggcctggt ggcccccagc     420
```

```
cagagcctga gcgtgacctg caccgtgagc ggcgtgagcc tgcccgacta cggcgtgagc    480

tggatccggc agcccccag gaagggcctg gaatggctgg gcgtgatctg ggcagcgag     540

accacctact acaacagcgc cctgaagagc cggctgacca tcatcaagga caacagcaag    600

agccaggtgt tcctgaagat gaacagcctg cagaccgacg acaccgccat ctactactgc    660

gccaagcact actactacgg cggcagctac gccatggact actggggcca gggcaccagc    720

gtgaccgtga gcagc                                                      735


<210> SEQ ID NO 58
<211> LENGTH: 18
<212> TYPE: PRT
<213> ORGANISM: Artificial Sequence
<220> FEATURE:
<223> OTHER INFORMATION: Linker

<400> SEQUENCE: 58

Gly Ser Thr Ser Gly Ser Gly Lys Pro Gly Ser Gly Glu Gly Ser Thr
1               5                   10                  15

Lys Gly


<210> SEQ ID NO 59
<211> LENGTH: 326
<212> TYPE: PRT
<213> ORGANISM: Artificial Sequence
<220> FEATURE:
<223> OTHER INFORMATION: Human IgG2 Fc (Uniprot P01859)

<400> SEQUENCE: 59

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220
```

```
Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 60
<211> LENGTH: 327
<212> TYPE: PRT
<213> ORGANISM: Artificial Sequence
<220> FEATURE:
<223> OTHER INFORMATION: Human IgG4 Fc (Uniprot P01861)

<400> SEQUENCE: 60

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255
```

```
Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 61
<211> LENGTH: 107
<212> TYPE: PRT
<213> ORGANISM: Artificial Sequence
<220> FEATURE:
<223> OTHER INFORMATION: FKBP

<400> SEQUENCE: 61

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Met Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105


<210> SEQ ID NO 62
<211> LENGTH: 107
<212> TYPE: PRT
<213> ORGANISM: Artificial Sequence
<220> FEATURE:
<223> OTHER INFORMATION: FKBP12v36

<400> SEQUENCE: 62

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105
```

<210> SEQ ID NO 63
<211> LENGTH: 16
<212> TYPE: PRT
<213> ORGANISM: Artificial Sequence
<220> FEATURE:
<223> OTHER INFORMATION: acylation motif

<400> SEQUENCE: 63

Met Gly Ser Asn Lys Ser Lys Pro Lys Asp Ala Ser Gln Arg Arg Arg
1               5                   10                  15

<210> SEQ ID NO 64
<211> LENGTH: 5
<212> TYPE: PRT
<213> ORGANISM: Artificial Sequence
<220> FEATURE:
<221> NAME/KEY: VARIANT
<222> LOCATION: (4)...(4)
<223> OTHER INFORMATION: Xaa can be any amino acid
<220> FEATURE:
<223> OTHER INFORMATION: dual acylation region

<400> SEQUENCE: 64

Met Gly Cys Xaa Cys
1               5

<210> SEQ ID NO 65
<211> LENGTH: 4
<212> TYPE: PRT
<213> ORGANISM: Artificial Sequence
<220> FEATURE:
<221> NAME/KEY: VARIANT
<222> LOCATION: (4)...(4)
<223> OTHER INFORMATION: Xaa can be any amino acid
<220> FEATURE:
<223> OTHER INFORMATION: CAAX box

<400> SEQUENCE: 65

Cys Ala Ala Xaa
1

<210> SEQ ID NO 66
<211> LENGTH: 159
<212> TYPE: PRT
<213> ORGANISM: Streptomyces avidinii
<220> FEATURE:
<223> OTHER INFORMATION: UniProt No. P22629

<400> SEQUENCE: 66

Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Glu Ser Ala Val Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

```
Thr Phe Thr Lys Val Lys Pro Ser Ala Ala Ser Ile Asp Ala Ala Lys
    130                 135                 140

Lys Ala Gly Val Asn Asn Gly Asn Pro Leu Asp Ala Val Gln Gln
145                 150                 155


<210> SEQ ID NO 67
<211> LENGTH: 126
<212> TYPE: PRT
<213> ORGANISM: Streptomyces avidinii
<220> FEATURE:
<223> OTHER INFORMATION: Minimal streptavidin
      i

<400> SEQUENCE: 67

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Glu Ser
            20                  25                  30

Ala Val Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Asn Ala Trp Lys Ser Thr Leu Val
            100                 105                 110

Gly His Asp Thr Phe Thr Lys Val Lys Pro Ser Ala Ala Ser
        115                 120                 125


<210> SEQ ID NO 68
<211> LENGTH: 126
<212> TYPE: PRT
<213> ORGANISM: Streptomyces avidinii
<220> FEATURE:
<223> OTHER INFORMATION: Minimal mutein Streptavidin
      Ile44-Gly45-Ala46-Arg47

<400> SEQUENCE: 68

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Ile Gly
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Asn Ala Trp Lys Ser Thr Leu Val
            100                 105                 110

Gly His Asp Thr Phe Thr Lys Val Lys Pro Ser Ala Ala Ser
        115                 120                 125


<210> SEQ ID NO 69
```

```
<211> LENGTH: 8
<212> TYPE: PRT
<213> ORGANISM: Artificial Sequence
<220> FEATURE:
<223> OTHER INFORMATION: Strep-tag II

<400> SEQUENCE: 69

Trp Ser His Pro Gln Phe Glu Lys
1               5


<210> SEQ ID NO 70
<211> LENGTH: 28
<212> TYPE: PRT
<213> ORGANISM: Artificial Sequence
<220> FEATURE:
<223> OTHER INFORMATION: Twin-Strep-tag

<400> SEQUENCE: 70

Trp Ser His Pro Gln Phe Glu Lys Gly Gly Gly Ser Gly Gly Gly Ser
1               5                   10                  15

Gly Gly Gly Ser Trp Ser His Pro Gln Phe Glu Lys
            20                  25


<210> SEQ ID NO 71
<211> LENGTH: 24
<212> TYPE: PRT
<213> ORGANISM: Artificial Sequence
<220> FEATURE:
<223> OTHER INFORMATION: Twin-Strep-tag

<400> SEQUENCE: 71

Trp Ser His Pro Gln Phe Glu Lys Gly Gly Gly Ser Gly Gly Gly Ser
1               5                   10                  15

Trp Ser His Pro Gln Phe Glu Lys
            20


<210> SEQ ID NO 72
<211> LENGTH: 28
<212> TYPE: PRT
<213> ORGANISM: Artificial Sequence
<220> FEATURE:
<223> OTHER INFORMATION: Twin-Strep-tag

<400> SEQUENCE: 72

Trp Ser His Pro Gln Phe Glu Lys Gly Gly Gly Ser Gly Gly Gly Ser
1               5                   10                  15

Gly Gly Ser Ala Trp Ser His Pro Gln Phe Glu Lys
            20                  25


<210> SEQ ID NO 73
<211> LENGTH: 127
<212> TYPE: PRT
<213> ORGANISM: Streptomyces avidinii
<220> FEATURE:
<223> OTHER INFORMATION: Minimal mutein Streptavidin
      Ile44-Gly45-Ala46-Arg47

<400> SEQUENCE: 73

Met Glu Ala Gly Ile Thr Gly Thr Trp Tyr Asn Gln Leu Gly Ser Thr
1               5                   10                  15

Phe Ile Val Thr Ala Gly Ala Asp Gly Ala Leu Thr Gly Thr Tyr Ile
            20                  25                  30

Gly Ala Arg Gly Asn Ala Glu Ser Arg Tyr Val Leu Thr Gly Arg Tyr
        35                  40                  45
```

```
Asp Ser Ala Pro Ala Thr Asp Gly Ser Gly Thr Ala Leu Gly Trp Thr
    50                  55                  60

Val Ala Trp Lys Asn Asn Tyr Arg Asn Ala His Ser Ala Thr Thr Trp
65                  70                  75                  80

Ser Gly Gln Tyr Val Gly Gly Ala Glu Ala Arg Ile Asn Thr Gln Trp
                85                  90                  95

Leu Leu Thr Ser Gly Thr Thr Glu Ala Asn Ala Trp Lys Ser Thr Leu
            100                 105                 110

Val Gly His Asp Thr Phe Thr Lys Val Lys Pro Ser Ala Ala Ser
        115                 120                 125


<210> SEQ ID NO 74
<211> LENGTH: 8
<212> TYPE: PRT
<213> ORGANISM: Artificial Sequence
<220> FEATURE:
<221> NAME/KEY: VARIANT
<222> LOCATION: (2)...(2)
<223> OTHER INFORMATION: Xaa is any amino acid
<220> FEATURE:
<221> NAME/KEY: VARIANT
<222> LOCATION: (7)...(7)
<223> OTHER INFORMATION: Xaa is Gly or Glu
<220> FEATURE:
<221> NAME/KEY: VARIANT
<222> LOCATION: (8)...(8)
<223> OTHER INFORMATION: Xaa is Gly, Lys or Arg
<220> FEATURE:
<223> OTHER INFORMATION: Streptavidin-binding peptide

<400> SEQUENCE: 74

Trp Xaa His Pro Gln Phe Xaa Xaa
1               5


<210> SEQ ID NO 75
<211> LENGTH: 8
<212> TYPE: PRT
<213> ORGANISM: Artificial Sequence
<220> FEATURE:
<223> OTHER INFORMATION: Streptavidin binding peptide, Strep-tag

<400> SEQUENCE: 75

Trp Arg His Pro Gln Phe Gly Gly
1               5


<210> SEQ ID NO 76
<211> LENGTH: 17
<212> TYPE: PRT
<213> ORGANISM: Artificial Sequence
<220> FEATURE:
<221> NAME/KEY: VARIANT
<222> LOCATION: (9)...(9)
<223> OTHER INFORMATION: Xaa is any amino acid
<220> FEATURE:
<221> NAME/KEY: REPEAT
<222> LOCATION: (9)...(9)
<223> OTHER INFORMATION: Repeat either 8 or 12 times
<220> FEATURE:
<223> OTHER INFORMATION: Sequential modules of streptavidin-binding
      peptide

<400> SEQUENCE: 76

Trp Ser His Pro Gln Phe Glu Lys Xaa Trp Ser His Pro Gln Phe Glu
1               5                   10                  15

Lys


<210> SEQ ID NO 77
```

```
<211> LENGTH: 20
<212> TYPE: PRT
<213> ORGANISM: Artificial Sequence
<220> FEATURE:
<221> NAME/KEY: REPEAT
<222> LOCATION: (9)...(12)
<223> OTHER INFORMATION: Repeat either 2 or 3 times
<220> FEATURE:
<223> OTHER INFORMATION: Sequential modules of streptavidin-binding
      peptide

<400> SEQUENCE: 77

Trp Ser His Pro Gln Phe Glu Lys Gly Gly Gly Ser Trp Ser His Pro
1               5                   10                  15

Gln Phe Glu Lys
            20


<210> SEQ ID NO 78
<211> LENGTH: 30
<212> TYPE: PRT
<213> ORGANISM: Artificial Sequence
<220> FEATURE:
<223> OTHER INFORMATION: Twin-Strep-tag

<400> SEQUENCE: 78

Ser Ala Trp Ser His Pro Gln Phe Glu Lys Gly Gly Gly Ser Gly Gly
1               5                   10                  15

Gly Ser Gly Gly Gly Ser Trp Ser His Pro Gln Phe Glu Lys
            20                  25                  30


<210> SEQ ID NO 79
<211> LENGTH: 30
<212> TYPE: PRT
<213> ORGANISM: Artificial Sequence
<220> FEATURE:
<223> OTHER INFORMATION: Twin-Strep-tag

<400> SEQUENCE: 79

Ser Ala Trp Ser His Pro Gln Phe Glu Lys Gly Gly Gly Ser Gly Gly
1               5                   10                  15

Gly Ser Gly Gly Ser Ala Trp Ser His Pro Gln Phe Glu Lys
            20                  25                  30


<210> SEQ ID NO 80
<211> LENGTH: 159
<212> TYPE: PRT
<213> ORGANISM: Streptomyces avidinii
<220> FEATURE:
<223> OTHER INFORMATION: Mutein Streptavidin Val44-Thr45-Ala46-Arg47

<400> SEQUENCE: 80

Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Val Thr Ala Arg Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95
```

```
Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ala Ser Ile Asp Ala Ala Lys
    130                 135                 140

Lys Ala Gly Val Asn Asn Gly Asn Pro Leu Asp Ala Val Gln Gln
145                 150                 155


<210> SEQ ID NO 81
<211> LENGTH: 126
<212> TYPE: PRT
<213> ORGANISM: Streptomyces avidinii
<220> FEATURE:
<223> OTHER INFORMATION: Minimal mutein Streptavidin
      Val44-Thr45-Ala46-Arg47

<400> SEQUENCE: 81

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Asn Ala Trp Lys Ser Thr Leu Val
            100                 105                 110

Gly His Asp Thr Phe Thr Lys Val Lys Pro Ser Ala Ala Ser
        115                 120                 125


<210> SEQ ID NO 82
<211> LENGTH: 127
<212> TYPE: PRT
<213> ORGANISM: Streptomyces avidinii
<220> FEATURE:
<223> OTHER INFORMATION: Minimal mutein Streptavidin
      Val44-Thr45-Ala46-Arg47

<400> SEQUENCE: 82

Met Glu Ala Gly Ile Thr Gly Thr Trp Tyr Asn Gln Leu Gly Ser Thr
1               5                   10                  15

Phe Ile Val Thr Ala Gly Ala Asp Gly Ala Leu Thr Gly Thr Tyr Val
            20                  25                  30

Thr Ala Arg Gly Asn Ala Glu Ser Arg Tyr Val Leu Thr Gly Arg Tyr
        35                  40                  45

Asp Ser Ala Pro Ala Thr Asp Gly Ser Gly Thr Ala Leu Gly Trp Thr
    50                  55                  60

Val Ala Trp Lys Asn Asn Tyr Arg Asn Ala His Ser Ala Thr Thr Trp
65                  70                  75                  80

Ser Gly Gln Tyr Val Gly Gly Ala Glu Ala Arg Ile Asn Thr Gln Trp
                85                  90                  95

Leu Leu Thr Ser Gly Thr Thr Glu Ala Asn Ala Trp Lys Ser Thr Leu
            100                 105                 110
```

```
Val Gly His Asp Thr Phe Thr Lys Val Lys Pro Ser Ala Ala Ser
        115                 120                 125


<210> SEQ ID NO 83
<211> LENGTH: 4
<212> TYPE: PRT
<213> ORGANISM: Artificial Sequence
<220> FEATURE:
<223> OTHER INFORMATION: Streptavidin-binding peptide

<400> SEQUENCE: 83

His Pro Gln Phe
1


<210> SEQ ID NO 84
<211> LENGTH: 8
<212> TYPE: PRT
<213> ORGANISM: Artificial Sequence
<220> FEATURE:
<221> NAME/KEY: VARIANT
<222> LOCATION: (1)...(1)
<223> OTHER INFORMATION: Xaa is Trp, Lys or Arg
<220> FEATURE:
<221> NAME/KEY: VARIANT
<222> LOCATION: (2)...(2)
<223> OTHER INFORMATION: Xaa is any amino acid
<220> FEATURE:
<221> NAME/KEY: VARIANT
<222> LOCATION: (7)...(7)
<223> OTHER INFORMATION: Xaa is Gly or Glu
<220> FEATURE:
<221> NAME/KEY: VARIANT
<222> LOCATION: (8)...(8)
<223> OTHER INFORMATION: Xaa is Gly, Lys or Arg
<220> FEATURE:
<223> OTHER INFORMATION: Streptavidin-binding peptide

<400> SEQUENCE: 84

Xaa Xaa His Pro Gln Phe Xaa Xaa
1               5


<210> SEQ ID NO 85
<211> LENGTH: 159
<212> TYPE: PRT
<213> ORGANISM: Streptomyces avidinii
<220> FEATURE:
<223> OTHER INFORMATION: Mutein Streptavidin Ile44-Gly45-Ala-46-Arg47

<400> SEQUENCE: 85

Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Ile Gly Ala Arg Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125
```

```
Thr Phe Thr Lys Val Lys Pro Ser Ala Ala Ser Ile Asp Ala Ala Lys
    130                 135                 140

Lys Ala Gly Val Asn Asn Gly Asn Pro Leu Asp Ala Val Gln Gln
145                 150                 155


<210> SEQ ID NO 86
<211> LENGTH: 126
<212> TYPE: PRT
<213> ORGANISM: Streptomyces avidinii
<220> FEATURE:
<223> OTHER INFORMATION: Minimal mutein Streptavidin
      Val44-Thr45-Ala46-Arg47 and Glu117, Gly120, Tyr121
      (mutein m1-9)

<400> SEQUENCE: 86

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Glu Asn Ala Gly Tyr Ser Thr Leu Val
            100                 105                 110

Gly His Asp Thr Phe Thr Lys Val Lys Pro Ser Ala Ala Ser
        115                 120                 125


<210> SEQ ID NO 87
<211> LENGTH: 139
<212> TYPE: PRT
<213> ORGANISM: Streptomyces avidinii
<220> FEATURE:
<223> OTHER INFORMATION: Mutein Streptavidin Val44-Thr45-Ala-46-Arg47
      and Glu117, Gly120, Tyr121 (mutein m1-9)

<400> SEQUENCE: 87

Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Val Thr Ala Arg Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Glu Asn Ala Gly Tyr Ser Thr Leu Val Gly His Asp
        115                 120                 125

Thr Phe Thr Lys Val Lys Pro Ser Ala Ala Ser
    130                 135
```

<210> SEQ ID NO 88
<211> LENGTH: 127
<212> TYPE: PRT
<213> ORGANISM: Streptomyces avidinii
<220> FEATURE:
<223> OTHER INFORMATION: Minimal streptavidin

<400> SEQUENCE: 88

```
Met Glu Ala Gly Ile Thr Gly Thr Trp Tyr Asn Gln Leu Gly Ser Thr
1               5                   10                  15

Phe Ile Val Thr Ala Gly Ala Asp Gly Ala Leu Thr Gly Thr Tyr Glu
            20                  25                  30

Ser Ala Val Gly Asn Ala Glu Ser Arg Tyr Val Leu Thr Gly Arg Tyr
        35                  40                  45

Asp Ser Ala Pro Ala Thr Asp Gly Ser Gly Thr Ala Leu Gly Trp Thr
    50                  55                  60

Val Ala Trp Lys Asn Asn Tyr Arg Asn Ala His Ser Ala Thr Thr Trp
65                  70                  75                  80

Ser Gly Gln Tyr Val Gly Gly Ala Glu Ala Arg Ile Asn Thr Gln Trp
                85                  90                  95

Leu Leu Thr Ser Gly Thr Thr Glu Ala Asn Ala Trp Lys Ser Thr Leu
            100                 105                 110

Val Gly His Asp Thr Phe Thr Lys Val Lys Pro Ser Ala Ala Ser
        115                 120                 125
```

<210> SEQ ID NO 89
<211> LENGTH: 28
<212> TYPE: PRT
<213> ORGANISM: Artificial Sequence
<220> FEATURE:
<223> OTHER INFORMATION: Mutein Streptavidin

<400> SEQUENCE: 89

```
Trp Ser His Pro Gln Phe Glu Lys Gly Gly Gly Ser Gly Gly Gly Ser
1               5                   10                  15

Gly Gly Ser Ala Trp Ser His Pro Gln Phe Glu Lys
            20                  25
```

<210> SEQ ID NO 90
<211> LENGTH: 9
<212> TYPE: PRT
<213> ORGANISM: Artificial Sequence
<220> FEATURE:
<223> OTHER INFORMATION: Strep-tag

<400> SEQUENCE: 90

```
Ala Trp Arg His Pro Gln Phe Gly Gly
1               5
```

<210> SEQ ID NO 91
<211> LENGTH: 116
<212> TYPE: PRT
<213> ORGANISM: Artificial Sequence
<220> FEATURE:
<223> OTHER INFORMATION: VH anti-CD28 antibody CD28.3

<400> SEQUENCE: 91

```
Leu Gln Gln Ser Gly Ala Glu Leu Val Lys Pro Gly Ala Ser Val Arg
1               5                   10                  15

Leu Ser Cys Lys Ala Ser Gly Tyr Thr Phe Thr Glu Tyr Ile Ile His
            20                  25                  30
```

```
Trp Ile Lys Leu Arg Ser Gly Gln Gly Leu Glu Trp Ile Gly Trp Phe
        35                  40                  45

Tyr Pro Gly Ser Asn Asp Ile Gln Tyr Asn Ala Lys Phe Lys Gly Lys
    50                  55                  60

Ala Thr Leu Thr Ala Asp Lys Ser Ser Ser Thr Val Tyr Met Glu Leu
65                  70                  75                  80

Thr Gly Leu Thr Ser Glu Asp Ser Ala Val Tyr Phe Cys Ala Arg Arg
                85                  90                  95

Asp Asp Phe Ser Gly Tyr Asp Ala Leu Pro Tyr Trp Gly Gln Gly Thr
            100                 105                 110

Met Val Thr Val
        115


<210> SEQ ID NO 92
<211> LENGTH: 108
<212> TYPE: PRT
<213> ORGANISM: Artificial Sequence
<220> FEATURE:
<223> OTHER INFORMATION: VL anti-CD28 antibody CD28.3

<400> SEQUENCE: 92

Asp Ile Gln Met Thr Gln Ser Pro Ala Ser Leu Ser Val Ser Val Gly
1               5                   10                  15

Glu Thr Val Thr Ile Thr Cys Arg Thr Asn Glu Asn Ile Tyr Ser Asn
            20                  25                  30

Leu Ala Trp Tyr Gln Gln Lys Gln Gly Lys Ser Pro Gln Leu Leu Ile
        35                  40                  45

Tyr Ala Ala Thr His Leu Val Glu Gly Val Pro Ser Arg Phe Ser Gly
    50                  55                  60

Ser Gly Ser Gly Thr Gln Tyr Ser Leu Lys Ile Thr Ser Leu Gln Ser
65                  70                  75                  80

Glu Asp Phe Gly Asn Tyr Tyr Cys Gln His Phe Trp Gly Thr Pro Cys
                85                  90                  95

Thr Phe Gly Gly Gly Thr Lys Leu Glu Ile Lys Arg
            100                 105


<210> SEQ ID NO 93
<211> LENGTH: 119
<212> TYPE: PRT
<213> ORGANISM: Artificial Sequence
<220> FEATURE:
<223> OTHER INFORMATION: VH anti-CD3 antibody OKT3

<400> SEQUENCE: 93

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
```

```
            100                 105                 110

Thr Thr Leu Thr Val Ser Ser
        115


<210> SEQ ID NO 94
<211> LENGTH: 106
<212> TYPE: PRT
<213> ORGANISM: Artificial Sequence
<220> FEATURE:
<223> OTHER INFORMATION: VL anti-CD3 antibody OKT3

<400> SEQUENCE: 94

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn
            100                 105


<210> SEQ ID NO 95
<211> LENGTH: 248
<212> TYPE: PRT
<213> ORGANISM: Artificial Sequence
<220> FEATURE:
<223> OTHER INFORMATION: Variable Heavy chain of Fab fragment m13B8.2

<400> SEQUENCE: 95

Ala Met Gln Val Gln Leu Lys Gln Ser Gly Pro Gly Leu Val Gln Pro
1               5                   10                  15

Ser Gln Ser Leu Ser Ile Thr Cys Thr Val Ser Gly Phe Ser Leu Thr
            20                  25                  30

Thr Phe Gly Val His Trp Val Arg Gln Ser Pro Gly Lys Gly Leu Glu
        35                  40                  45

Trp Leu Gly Val Ile Trp Ala Ser Gly Ile Thr Asp Tyr Asn Val Pro
    50                  55                  60

Phe Met Ser Arg Leu Ser Ile Thr Lys Asp Asn Ser Lys Ser Gln Val
65                  70                  75                  80

Phe Phe Lys Leu Asn Ser Leu Gln Pro Asp Asp Thr Ala Ile Tyr Tyr
                85                  90                  95

Cys Ala Lys Asn Asp Pro Gly Thr Gly Phe Ala Tyr Trp Gln Gly Thr
            100                 105                 110

Leu Val Thr Val Ser Ser Thr Lys Gly Pro Ser Val Phe Pro Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Leu
                165                 170                 175
```

```
Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Gly Ser Ala Trp Ser His Pro
    210                 215                 220

Gln Phe Glu Lys Gly Gly Gly Ser Gly Gly Gly Ser Gly Gly Ser Ala
225                 230                 235                 240

Trp Ser His Pro Gln Phe Glu Lys
                245


<210> SEQ ID NO 96
<211> LENGTH: 218
<212> TYPE: PRT
<213> ORGANISM: Artificial Sequence
<220> FEATURE:
<223> OTHER INFORMATION: Variable Light chain of Fab Fragment m13B8.2

<400> SEQUENCE: 96

Ala Met Asp Ile Gln Met Thr Gln Ser Pro Ala Ser Leu Ser Ala Ser
1               5                   10                  15

Val Gly Glu Thr Val Thr Phe Thr Cys Arg Ala Ser Glu Met Ile Tyr
            20                  25                  30

Ser Tyr Leu Ala Trp Tyr Gln Gln Lys Gln Gly Lys Ser Pro Gln Leu
        35                  40                  45

Leu Val His Asp Ala Lys Thr Leu Ala Glu Gly Val Pro Ser Arg Phe
    50                  55                  60

Ser Gly Gly Gly Ser Gly Thr Gln Phe Ser Leu Lys Ile Asn Thr Leu
65                  70                  75                  80

Gln Pro Glu Asp Phe Gly Thr Tyr Tyr Cys Gln Ala His Tyr Gly Asn
                85                  90                  95

Pro Pro Thr Phe Gly Gly Gly Thr Lys Leu Glu Ile Lys Arg Gly Ile
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys Gly Ser
    210                 215


<210> SEQ ID NO 97
<211> LENGTH: 118
<212> TYPE: PRT
<213> ORGANISM: Artificial Sequence
<220> FEATURE:
<223> OTHER INFORMATION: Variable Heavy chain of huOKT8

<400> SEQUENCE: 97

Gln Val Gln Leu Val Gln Ser Gly Ala Glu Val Lys Lys Pro Gly Ala
1               5                   10                  15
```

-continued

```
Thr Val Lys Ile Ser Cys Lys Val Ser Gly Phe Asn Ile Lys Asp Thr
            20                  25                  30

Tyr Ile His Trp Val Gln Gln Ala Pro Gly Lys Gly Leu Glu Trp Met
        35                  40                  45

Gly Arg Ile Asp Pro Ala Asn Asp Asn Thr Leu Tyr Ala Ser Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Gly Tyr Tyr Val Phe Asp His Trp Gly Gln Gly Thr
            100                 105                 110

Leu Val Thr Val Ser Ser
        115


<210> SEQ ID NO 98
<211> LENGTH: 107
<212> TYPE: PRT
<213> ORGANISM: Artificial Sequence
<220> FEATURE:
<223> OTHER INFORMATION: Variable Light chain of huOKT8

<400> SEQUENCE: 98

Asp Val Gln Ile Thr Gln Ser Pro Ser Ser Leu Ser Ala Ser Val Gly
1               5                   10                  15

Asp Arg Val Thr Ile Thr Cys Arg Thr Ser Arg Ser Ile Ser Gln Tyr
            20                  25                  30

Leu Ala Trp Tyr Gln Gln Lys Pro Gly Lys Val Pro Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln His Asn Glu Asn Pro Leu
                85                  90                  95

Thr Phe Gly Gly Gly Thr Lys Val Glu Ile Lys
            100                 105
```

PROCESS FOR PRODUCING DONOR-BATCHED CELLS EXPRESSING A RECOMBINANT RECEPTOR

CROSS-REFERENCE TO RELATED APPLICATIONS

This application is a National Stage application under 35 U.S.C. § 371 of International Application No. PCT/US2021/032108, filed on May 12, 2021, which claims priority to U.S. provisional application 63/024,505, filed May 13, 2020, entitled "PROCESS FOR PRODUCING DONOR-BATCHED CELLS EXPRESSING A RECOMBINANT RECEPTOR," the contents of which are incorporated by reference in their entirety for all purposes.

INCORPORATION BY REFERENCE OF SEQUENCE LISTING

The present application is being filed along with a Sequence Listing in electronic format. The Sequence Listing is provided as a file entitled 735042023800SeqList.TXT, created Nov. 9, 2022, which is 72,263 bytes in size. The information in the electronic format of the Sequence Listing is incorporated by reference in its entirety.

FIELD

The present disclosure relates in some aspects to methods of producing engineered T cell compositions enriched for CD57 negative and/or CD27 positive T cells, such as from a plurality of donors. In some embodiments, the T cells are engineered with a recombinant receptor, such as a chimeric antigen receptor (CAR). Also included in the present disclosure are engineered T cell compositions containing T cells enriched for CD57 negative and/or CD27 positive T cells, derived from a plurality of different donors, including compositions in which the T cells are engineered with or express a recombinant receptor (e.g. CAR). Also provided are methods of using the engineered T cell compositions in adoptive therapy, including in connection with cancer immunotherapy, such as for allogeneic therapies or for administration to one or more subject in which the T cells are not derived from the subject(s) to whom the compositions are administered.

BACKGROUND

Various cell therapy methods are available for treating diseases and conditions. Among cell therapy methods are methods involving immune cells, such as T cells, genetically engineered with a recombinant receptor, such as a chimeric antigen receptors. However, in some cases, some of the existing processes may result in a cell population with low consistency, potency or persistence in vivo. Improved methods for manufacturing and/or engineering such cell compositions are needed, including in connection with administration as a cell therapy to diseased subjects.

SUMMARY

Provided herein is a method of preparing a T cell composition from a donor pool, wherein the method is or includes (A) obtaining a plurality of engineered T cell compositions from a plurality of different donors, each engineered T cell composition including T cells enriched for T cells surface negative for CD57 (CD57−) from a donor sample from an individual donor of the plurality of different donors, wherein the T cells include T cells genetically engineered with a recombinant receptor; and (B) combining the plurality of engineered T cell compositions to produce a donor pooled engineered T cell composition.

In some embodiments, each of the plurality of T cell compositions is generated by a process that is or includes (a) selecting T cells enriched for T cells surface negative for CD57 (CD57−) from a donor sample from the individual donor, thereby generating a CD57 depleted T cell population; and (b) introducing a heterologous nucleic acid encoding the recombinant receptor into the CD57 depleted cell population, thereby generating the engineered T cell composition. In some embodiments, prior to step (b) the method includes stimulating the CD57 depleted T cell population under conditions to activate T cells in the population.

Also provided herein is a method of preparing a T cell composition from a donor pool, wherein the method is or includes (A) obtaining a plurality of engineered T cell compositions from a plurality of different donors, each engineered T cell composition including T cells enriched for T cells surface positive for CD27 (CD27+) from a donor sample from an individual donor of the plurality of different donors, wherein the T cells include T cells genetically engineered with a recombinant receptor; and (B) combining the plurality of engineered T cell compositions to produce a donor pooled engineered T cell composition.

In some embodiments, each of the plurality of T cell compositions is generated by a process that is or includes (a) selecting T cells enriched for T cells surface positive for CD27 (CD27+) from a donor sample from the individual donor, thereby generating a CD27 enriched T cell population; and (b) introducing a heterologous nucleic acid encoding the recombinant receptor into the CD27 enriched cell population, thereby generating the engineered T cell composition. In some embodiments, prior to step (b) the method includes stimulating the CD27 enriched T cell population under conditions to activate T cells in the population.

In some embodiments, the method further includes (c) incubating the engineered cells for up to 96 hours subsequent to the introducing. In some embodiments the incubating is carried out at a temperature of at or about 37°±2° C. In some embodiments, the incubating is carried out under conditions in which the cells are not expanded or not substantially expanded compared to the number of cells at the initiation of the incubating. In some embodiments, the method further includes (c) cultivating the engineered T cell composition under conditions for expansion of T cells in the composition.

In some embodiments, the selecting T cells enriched for T cells surface negative for CD57 (CD57−) includes (i) selecting one of (a) cells surface positive for a T cell marker(s) and (b) cells surface negative for CD57 (CD57−) from a donor sample from an individual donor, thereby generating an enriched population of cells; and (ii) selecting, from the enriched population of cells, for the other of (a) cells surface positive for the T cell marker(s) and (b) CD57− cells, thereby generating a CD57 depleted T cell population. In some embodiments, the selecting T cells enriched for T cells surface positive for CD27 (CD27+) includes (i) selecting one of (a) cells surface positive for a T cell marker(s) and (b) cells surface positive for CD27 (CD27+) from a donor sample from an individual donor, thereby generating an enriched population of cells; and (ii) selecting, from the enriched population of cells, for the other of (a) cells surface positive for the T cell marker(s) and (b) CD27+ cells, thereby generating a CD27 enriched T cell population. In some embodiments, the T cell marker(s) is CD3. In some embodiments, the T cell marker(s) is CD4. In some embodiments, the T cell marker(s) is CD8. In some embodiments, the T cell surface marker(s) is CD4 and CD8.

In some embodiments, the method further includes knocking out expression of (i) an endogenous major histocompatibility complex (MHC) or a component thereof, optionally beta-2-microglobulin (β2M); and/or (ii) an endogenous T cell receptor (TCR) or a component thereof, optionally TRAC, in T cells prior to or during one or more of the steps of any of the methods provided herein. In some embodiments, the method further includes knocking out expression of an endogenous major histocompatibility complex (MHC) or a component thereof, prior to or during one or more of the steps of any of the methods provided herein. In some embodiments, the method further includes knocking out expression of an endogenous T cell receptor (TCR) or a component thereof, prior to or during one or more of the steps of any of the methods provided herein. In some embodiments, the engineered T cell compositions are knocked out (KO) for expression of (i) an endogenous major histocompatibility complex (MHC) or a component thereof, optionally beta-2-microglobulin (132M) and/or (ii) an endogenous T cell receptor (TCR) or a component thereof, optionally T cell receptor alpha constant (TRAC). In some embodiments, the engineered T cell compositions are knocked out (KO) for expression of an endogenous major histocompatibility complex (MHC) or a component thereof. In some embodiments, the engineered T cell compositions are knocked out (KO) for expression of an endogenous T cell receptor (TCR) or a component thereof. In some embodiments, the engineered T cell compositions are knocked out (KO) for expression of (i) an endogenous major histocompatibility complex (MHC) or a component thereof; and (ii) an endogenous T cell receptor (TCR) or a component thereof. In some embodiments, the MHC or a component thereof is beta-2-microglobulin (β2M). In some embodiments, the engodenous TCR is T cell receptor alpha constant (TRAC).

In some embodiments, the method further includes selecting cells of the engineered T cell composition that are surface negative for CD3 (CD3−). In some embodiments, selecting cells of the engineered T cell composition that are CD3− includes contacting the cells with an antibody capable of specifically binding to CD3 and recovering cells not bound to the antibody, thereby effecting negative selection. In some embodiments, the cells of the engineered T cell composition are selected for cells that are surface negative for CD3 (CD3−). In some embodiments, the cells of the engineered T cell composition are surface negative for CD3−.

In some of any of the embodiments, provided herein is a method of preparing a T cell composition from a donor pool that is or includes: (a) selecting T cells enriched for T cells surface negative for CD57 (CD57−) from a donor sample from an individual donor, thereby generating a CD57 depleted T cell population; (b) genetically engineering the CD57 depleted T cell population, thereby producing an engineered T cell composition, the genetic engineering comprising: (1) knocking out expression of (i) an endogenous major histocompatibility complex (MHC) or a component thereof, optionally beta-2-microglobulin (β2M); and/or (ii) an endogenous T cell receptor (TCR) or a component thereof, optionally TRAC, in cells of the CD57 depleted T cell population; and (2) introducing a heterologous nucleic acid encoding the recombinant receptor into the cells of the CD57 depleted T cell population, optionally wherein the heterologous nucleic acid is inserted into a locus of a gene encoding for the endogenous MHC and/or the endogenous TCR; wherein the knocking out in (1) and the introducing in (2) can be carried out concurrently or successively in either order; (c) repeating steps (a) and (b) for a plurality of different donors to produce a plurality of donor engineered T cell compositions, wherein each donor engineered T cell composition is generated from cells from an individual donor of the plurality of different donors; and (d) combining the plurality of donor engineered T cell compositions from the plurality of different individual donors. In some of any of the embodiments, provided herein is a method of preparing a T cell composition from a donor pool that is or includes: (a) selecting T cells enriched for T cells surface negative for CD57 (CD57−) from a donor sample from an individual donor, thereby generating a CD57 depleted T cell population; (b) genetically engineering the CD57 depleted T cell population, thereby producing an engineered T cell composition, the genetic engineering comprising: (1) knocking out expression of (i) an endogenous major histocompatibility complex (MHC) or a component thereof; and/or (ii) an endogenous T cell receptor (TCR) or a component thereof, in cells of the CD57 depleted T cell population; and (2) introducing a heterologous nucleic acid encoding the recombinant receptor into the cells of the CD57 depleted T cell population; wherein the knocking out in (1) and the introducing in (2) can be carried out concurrently or successively in either order; (c) repeating steps (a) and (b) for a plurality of different donors to produce a plurality of donor engineered T cell compositions, wherein each donor engineered T cell composition is generated from cells from an individual donor of the plurality of different donors; and (d) combining the plurality of donor engineered T cell compositions from the plurality of different individual donors. In some embodiments, the MHC or a component thereof is beta-2-microglobulin (β2M). In some embodiments, the engodenous TCR is T cell receptor alpha constant (TRAC). In some embodiments, the heterologous nucleic acid is inserted into a locus of a gene encoding for the endogenous MHC and/or the endogenous TCR. In some embodiments, the heterologous nucleic acid is inserted into a locus of a gene encoding for the endogenous MHC. In some embodiments, the heterologous nucleic acid is inserted into a locus of a gene encoding for the endogenous TCR.

In some of any of the embodiments, provided herein is a method of preparing a T cell composition from a donor pool that is or includes: (a) selecting T cells enriched for T cells surface positive for CD27 (CD27+) from a donor sample from an individual donor, thereby generating a CD27 enriched T cell population; (b) genetically engineering the CD27 enriched T cell population, thereby producing an engineered T cell composition, the genetic engineering comprising: (1) knocking out expression of (i) an endogenous major histocompatibility complex (MHC) or a component thereof; and/or (ii) an endogenous T cell receptor (TCR) or a component thereof, in cells of the CD27 enriched T cell population; and (2) introducing a heterologous nucleic acid encoding the recombinant receptor into the cells of the CD27 enriched T cell population; wherein the knocking out in (1) and the introducing in (2) can be carried out concurrently or successively in either order; (c) repeating steps (a) and (b) for a plurality of different donors to produce a plurality of donor engineered T cell compositions, wherein each donor engineered T cell composition is generated from cells from an individual donor of the plurality of different donors; and (d) combining the plurality of donor engineered T cell compositions from the plurality of different individual donors. In some embodiments, the MHC or a component thereof is beta-2-microglobulin (β2M). In some embodiments, the engodenous TCR is T cell receptor alpha constant (TRAC). In some embodiments, the heterologous nucleic acid is inserted into a locus of a gene encoding for the endogenous MHC and/or the endogenous TCR. In some embodiments, the heterologous nucleic acid is inserted into a locus of a gene encoding for the endogenous MHC. In some embodiments, the heterologous nucleic acid is inserted into a locus of a gene encoding for the endogenous TCR.

In some embodiments, the method is repeated for each of the individual donors of the plurality of different donors.

In some embodiments, the method further includes selecting cells of the engineered T cell composition that are surface negative for CD3 (CD3−). In some embodiments, selecting cells of the engineered T cell composition that are CD3− includes contacting the cells with an antibody capable of specifically binding to CD3 and recovering cells not bound to the antibody, thereby effecting negative selection. In some embodiments, the cells of the engineered T cell composition are selected for cells that are surface negative for CD3 (CD3−). In some embodiments, the cells of the engineered T cell composition are surface negative for CD3−.

In some embodiments, each of the plurality of engineered T cell compositions has been cryopreserved and thawed prior to the combining.

In some embodiments, each of the plurality of engineered T cell compositions independently contains greater than or greater than at or about 75% CD3+/CD57− cells, greater than at or about 80% CD3+/CD57− cells, greater than at or about 85% CD3+/CD57− cells, greater than at or about 90% CD3+/CD57− cells, or greater than at or about 95% CD3+/CD57− cells. In some embodiments, each of the plurality of engineered T cell compositions independently contains greater than or greater than at or about 75% CD57− cells. In some embodiments, each of the plurality of engineered T cell compositions independently contains greater than or greater than at or about 80% CD57− cells. In some embodiments, each of the plurality of engineered T cell compositions independently contains greater than at or about 85% CD57− cells. In some embodiments, each of the plurality of engineered T cell compositions independently contains greater than at or about 90% CD57− cells. In some embodiments, each of the plurality of engineered T cell compositions independently contains greater than at or about 95% CD57− cells. In some embodiments, each of the plurality of engineered T cell compositions independently contains greater than or greater than at or about 40% CD3+/CD57−/recombinant receptor+ cells, greater than at or about 45% CD3+/CD57−/recombinant receptor+ cells, greater than at or about 50% CD3+/CD57−/recombinant receptor+ cells, greater than at or about 55% CD3+/CD57−/recombinant receptor+ cells, greater than at or about 60% CD3+/CD57−/recombinant receptor+ cells, greater than at or about 65% CD3+/CD57−/recombinant receptor+ cells or greater than at or about 70% CD3+/CD57−/recombinant receptor+ cells. In some embodiments, each of the plurality of engineered T cell compositions independently contains greater than or greater than at or about 40% CD57−/recombinant receptor+ cells. In some embodiments, each of the plurality of engineered T cell compositions independently contains greater than at or about 45% CD57−/recombinant receptor+ cells. In some embodiments, each of the plurality of engineered T cell compositions independently contains greater than at or about 50% CD57−/recombinant receptor+ cells. In some embodiments, each of the plurality of engineered T cell compositions independently contains greater than at or about 55% CD57−/recombinant receptor+ cells. In some embodiments, each of the plurality of engineered T cell compositions independently contains greater than at or about 60% CD57−/recombinant receptor+ cells. In some embodiments, each of the plurality of engineered T cell compositions independently contains greater than at or about 65% CD57−/recombinant receptor+ cells. In some embodiments, each of the plurality of engineered T cell compositions independently contains greater than at or about 70% CD57−/recombinant receptor+ cells. In some embodiments, each of the plurality of engineered T cell compositions independently contains greater than at or about 75% CD57−/recombinant receptor+ cells. In some embodiments, each of the plurality of engineered T cell compositions independently contains greater than at or about 80% CD57−/recombinant receptor+ cells.

In some embodiments, each of the plurality of engineered T cell compositions independently contains greater than or greater than at or about 75% CD27+ cells. In some embodiments, each of the plurality of engineered T cell compositions independently contains greater than or greater than at or about 80% CD27+ cells. In some embodiments, each of the plurality of engineered T cell compositions independently contains greater than at or about 85% CD27+ cells. In some embodiments, each of the plurality of engineered T cell compositions independently contains greater than at or about 90% CD27+ cells. In some embodiments, each of the plurality of engineered T cell compositions independently contains greater than at or about 95% CD27+ cells. In some embodiments, each of the plurality of engineered T cell compositions independently contains greater than or greater than at or about 40% CD27+/recombinant receptor+ cells. In some embodiments, each of the plurality of engineered T cell compositions independently contains greater than at or about 45% CD27+/recombinant receptor+ cells. In some embodiments, each of the plurality of engineered T cell compositions independently contains greater than at or about 50% CD27+/recombinant receptor+ cells. In some embodiments, each of the plurality of engineered T cell compositions independently contains greater than at or about 55% CD27+/recombinant receptor+ cells. In some embodiments, each of the plurality of engineered T cell compositions independently contains greater than at or about 60% CD57−/recombinant receptor+ cells. In some embodiments, each of the plurality of engineered T cell compositions independently contains greater than at or about 65% CD27+/recombinant receptor+ cells. In some embodiments, each of the plurality of engineered T cell compositions independently contains greater than at or about 70% CD27+/recombinant receptor+ cells. In some embodiments, each of the plurality of engineered T cell compositions independently contains greater than at or about 75% CD27+/recombinant receptor+ cells. In some embodiments, each of the plurality of engineered T cell compositions independently contains greater than at or about 80% CD27+/recombinant receptor+ cells.

In some embodiments, each of the plurality of engineered T cell compositions contains CD4+ and CD8+ T cells. In some embodiments, each of the plurality of engineered T cell compositions contains a ratio of CD4+ to CD8+ T cells of between at or about 1:5 and at or about 5:1. In some embodiments, each of the plurality of engineered T cell compositions contains a ratio of CD4+ to CD8+ T cells of between at or about 1:3 and at or about 3:1. In some embodiments, each of the plurality of engineered T cell compositions contains a ratio of CD4+ to CD8+ T cells of between at or about 1:2 and at or about 2:1. In some embodiments, each of the plurality of engineered T cell compositions contains a ratio of CD4+ to CD8+ T cells of about 1:1.

In some embodiments, the method further includes, prior to the knocking out, stimulating the CD57 depleted T cell population under conditions to activate T cells in the population. In some embodiments, the method further includes, prior to the knocking out, stimulating the CD27 enriched T cell population under conditions to activate T cells in the population. In some embodiments, the knocking out and the introducing the heterologous nucleic acid are carried out concurrently. In some embodiments, the knocking out and the introducing the heterologous nucleic acid are carried out successively in either order.

In some of any of the embodiments, provided herein is a method of preparing a T cell composition from a donor pool that is or includes (a) selecting for one of (i) cells surface positive for a T cell marker(s) and (ii) cells surface negative for CD57 (CD57−) from a donor sample from a plurality of different donors, thereby generating an enriched population of cells; and (b) selecting, from the enriched population of cells, the other of (i) cells surface positive for the T cell marker(s) and (ii) CD57− cells, thereby generating a CD57 depleted T cell population.

In some of any of the embodiments, provided herein is a method of preparing a T cell composition from a donor pool that is or includes (a) selecting for one of (i) cells surface positive for a T cell marker(s) and (ii) cells surface positive for CD27 (CD27+) from a donor sample from a plurality of different donors, thereby generating an enriched population of cells; and (b) selecting, from the enriched population of cells, the other of (i) cells surface positive for the T cell marker(s) and (ii) CD27+ cells, thereby generating a CD27 enriched T cell population.

In some embodiments, the T cell marker(s) is CD3. In some embodiments, the T cell marker(s) is CD4. In some embodiments, the T cell marker(s) is CD8. In some embodiments, the T cell surface marker(s) is CD4 and CD8.

In some embodiments, the donor sample is a pooled sample comprising cells from the plurality of different donors, whereby the method produces a pooled CD57 depleted T cell population. In some embodiments, the donor sample is a sample from an individual donor, and steps (i) and (ii) are repeated separately for each donor sample from the plurality of different donors, whereby the method produces a CD57 depleted T cell population for each individual donor. In some embodiments, the method further includes combining the CD57 depleted T cell populations for each individual donor together to produce a pooled CD57 depleted T cell population.

In some embodiments, the donor sample is a pooled sample comprising cells from the plurality of different donors, whereby the method produces a pooled CD27 enriched T cell population. In some embodiments, the donor sample is a sample from an individual donor, and steps (i) and (ii) are repeated separately for each donor sample from the plurality of different donors, whereby the method produces a CD27 enriched T cell population for each individual donor. In some embodiments, the method further includes combining the CD27 enriched T cell populations for each individual donor together to produce a pooled CD27 enriched T cell population.

In some embodiments, the T cell marker(s) is CD3. In some embodiments, the T cell marker(s) is CD4. In some embodiments, the T cell marker(s) is CD8. In some embodiments, the T cell surface marker(s) is CD4 and CD8.

In some of any of the provided embodiments, provided herein is a method of preparing a T cell composition from a donor pool that is or includes selecting for T cells that are surface negative for CD57 (CD57−) from a donor sample, wherein the donor sample is a pooled cell population enriched for human T cells from a plurality of different donors, thereby generating a pooled CD57 depleted T cell population.

In some of any of the provided embodiments, provided herein is a method of preparing a T cell composition from a donor pool that is or includes (a) selecting for T cells that are surface negative for CD57 (CD57−) from a donor sample, wherein the donor sample is enriched for human T cells from an individual donor, thereby generating a CD57 depleted T cell population; (b) repeating step (a) for a plurality of different individual donors; and (c) combining each of the CD57 depleted T cell populations from each of the individual donors, thereby generating a pooled CD57 depleted T cell population.

In some of any of the provided embodiments, provided herein is a method of preparing a T cell composition from a donor pool that is or includes selecting for T cells from a donor sample, wherein the donor sample is a pooled cell population enriched for human T cells that are surface negative for CD57 (CD57−) from a plurality of different donors, thereby generating a pooled CD57 depleted T cell population.

In some of any of the provided embodiments, provided herein is a method of preparing a T cell composition from a donor pool that is or includes (a) selecting for T cells from a donor sample, wherein the sample is enriched for human T cells that are surface negative for CD57 (CD57−) from an individual donor, thereby generating a CD57 depleted T cell population; (b) repeating step (a) for a plurality of different donors; and (c) combining each of the CD57 depleted T cell populations from each of the individual donors, thereby generating a pooled CD57 depleted T cell population.

In some of any of the provided embodiments, provided herein is a method of preparing a T cell composition from a donor pool that is or includes selecting for T cells that are surface positive for CD27 (CD27+) from a donor sample, wherein the donor sample is a pooled cell population enriched for human T cells from a plurality of different donors, thereby generating a pooled CD27 enriched T cell population.

In some of any of the provided embodiments, provided herein is a method of preparing a T cell composition from a donor pool that is or includes (a) selecting for T cells that are surface positive for CD27 (CD27+) from a donor sample, wherein the donor sample is enriched for human T cells from an individual donor, thereby generating a CD27 enriched T cell population; (b) repeating step (a) for a plurality of different individual donors; and (c) combining each of the CD27 enriched T cell populations from each of the individual donors, thereby generating a pooled CD27 enriched T cell population.

In some of any of the provided embodiments, provided herein is a method of preparing a T cell composition from a donor pool that is or includes selecting for T cells from a donor sample, wherein the donor sample is a pooled cell population enriched for human T cells that are surface positive for CD27 (CD27+) from a plurality of different donors, thereby generating a pooled CD27 enriched T cell population.

In some of any of the provided embodiments, provided herein is a method of preparing a T cell composition from a donor pool that is or includes (a) selecting for T cells from a donor sample, wherein the sample is enriched for human T cells that are surface positive for CD27 (CD27+) from an individual donor, thereby generating a CD27 enriched T cell population; (b) repeating step (a) for a plurality of different donors; and (c) combining each of the CD27 enriched T cell populations from each of the individual donors, thereby generating a pooled CD27 enriched T cell population.

In some embodiments, the donor sample enriched for human T cells is obtained by selecting for CD3+ T cells. In some embodiments, the donor sample enriched for human T cells is obtained by selecting for CD4+ T cells and/or CD8+ T cells. In some embodiments, the donor sample enriched for human T cells is obtained by selecting for CD4+ T cells. In some embodiments, the donor sample enriched for human T cells is obtained by selecting for CD8+ T cells. In some embodiments, the donor sample enriched for human T cells contains greater than at or about 85% CD3+ T cells. In some embodiments, the donor sample enriched for human T cells contains greater than at or about 90% CD3+ T cells. In some embodiments, the donor sample enriched for human T cells contains greater than at or about 95% CD3+ T cells. In some embodiments, the donor sample enriched for human T cells contains CD4+ and CD8+ T cells. In some embodiments, the donor sample enriched for human T cells contains a ratio of CD4+ to CD8+ T cells of between at or about 1:5 and at or about 5:1. In some embodiments, the donor sample enriched for human T cells contains a ratio of CD4+ to CD8+ T cells of between at or about 1:3 and at or about 3:1. In some embodiments, the donor sample enriched for human T cells contains a ratio of CD4+ to CD8+ T cells of between at or about 1:2 and at or about 2:1. In some embodiments, the donor sample enriched for human T cells contains a ratio of CD4+ to CD8+ T cells of about 1:1. In some embodiments, the selecting for T cells is or includes selecting for CD3+ T cells. In some embodiments, the selecting for T cells is or includes selecting for CD4+ and/or CD8+ T cells. In some embodiments, the donor sample enriched for CD57− human T cells is obtained by selecting for CD57− T cells.

In some embodiments, (a) cells of the CD57 depleted T cell population are knocked out (KO) for expression of (i) an endogenous major histocompatibility complex (MHC) or a component thereof, optionally beta-2-microglobulin (β2M); and/or (ii) an endogenous T cell receptor (TCR) or a component thereof, optionally T cell receptor alpha constant (TRAC); and/or (b) the method further includes knocking out expression of (i) an endogenous major histocompatibility complex (MHC) or a component thereof, optionally beta-2-microglobulin (02M); and/or (ii) an endogenous T cell receptor (TCR) or a component thereof, optionally TRAC, in cells of the CD57 depleted T cell population. In some embodiments, cells of the CD57 depleted T cell population are knocked out (KO) for expression of (i) an endogenous major histocompatibility complex (MHC) or a component thereof; and/or (ii) an endogenous T cell receptor (TCR) or a component thereof. In some embodiments, the method further includes knocking out expression of (i) an endogenous major histocompatibility complex (MHC) or a component thereof; and/or (ii) an endogenous T cell receptor (TCR) or a component thereof, in cells of the CD57 depleted T cell population. In some embodiments, (a) cells of the pooled CD57 depleted T cell population are knocked out (KO) for expression of (i) an endogenous major histocompatibility complex (MHC) or a component thereof, optionally beta-2-microglobulin (β2M); and/or (ii) an endogenous T cell receptor (TCR) or a component thereof, optionally T cell receptor alpha constant (TRAC); and/or (b) the method further includes knocking out expression of (i) an endogenous major histocompatibility complex (MHC) or a component thereof, optionally beta-2-microglobulin (132M); and/or (ii) an endogenous T cell receptor (TCR) or a component thereof, optionally T cell receptor alpha constant (TRAC), in cells of the pooled CD57 depleted T cell population. In some embodiments, cells of the pooled CD57 depleted T cell population are knocked out (KO) for expression of (i) an endogenous major histocompatibility complex (MHC) or a component thereof; and/or (ii) an endogenous T cell receptor (TCR) or a component thereof. In some embodiments, the method further includes knocking out expression of (i) an endogenous major histocompatibility complex (MHC) or a component thereof; and/or (ii) an endogenous T cell receptor (TCR) or a component thereof, in cells of the pooled CD57 depleted T cell population.

In some embodiments, cells of the CD27 enriched T cell population are knocked out (KO) for expression of (i) an endogenous major histocompatibility complex (MHC) or a component thereof; and/or (ii) an endogenous T cell receptor (TCR) or a component thereof. In some embodiments, the method further includes knocking out expression of (i) an endogenous major histocompatibility complex (MHC) or a component thereof; and/or (ii) an endogenous T cell receptor (TCR) or a component thereof, in cells of the CD27 enriched T cell population. In some embodiments, cells of the pooled CD27 enriched T cell population are knocked out (KO) for expression of (i) an endogenous major histocompatibility complex (MHC) or a component thereof; and/or (ii) an endogenous T cell receptor (TCR) or a component thereof. In some embodiments, the method further includes knocking out expression of (i) an endogenous major histocompatibility complex (MHC) or a component thereof; and/or (ii) an endogenous T cell receptor (TCR) or a component thereof, in cells of the pooled CD27 enriched T cell population.

In some embodiments, the endogenous MHC or component thereof is β2M. In some embodiments, the endogenous TCR is TRAC.

In some embodiments, the method further includes selecting knocked out cells that are surface negative for CD3 (CD3−). In some embodiments, selecting knocked out cells that are CD3-includes contacting the cells with an antibody capable of specifically binding to CD3 and recovering cells not bound to the antibody, thereby effecting negative selection. In some embodiments, the knocked out cells are selected for cells that are surface negative for CD3 (CD3−). In some embodiments, the knocked out cells are surface negative for CD3−.

In some embodiments, (a) a heterologous polynucleotide encoding a recombinant receptor is introduced into cells of the CD57 depleted T cell population; and/or (b) the method further includes introducing into cells of the CD57 depleted T cell population a heterologous polynucleotide encoding a recombinant receptor, the method thereby generating an engineered T cell composition. In some embodiments, a heterologous polynucleotide encoding a recombinant receptor is introduced into cells of the CD57 depleted T cell population, thereby generating an engineered T cell composition. In some embodiments, the method further includes introducing into cells of the CD57 depleted T cell population a heterologous polynucleotide encoding a recombinant receptor, thereby generating an engineered T cell composition. In some embodiments, (a) a heterologous polynucleotide encoding a recombinant receptor is introduced into cells of the pooled CD57 depleted T cell population; and/or (b) the method further includes introducing into cells of the pooled CD57 depleted T cell population a heterologous polynucleotide encoding a recombinant receptor, the method thereby generating an engineered T cell composition. In some embodiments, a heterologous polynucleotide encoding a recombinant receptor is introduced into cells of the pooled CD57 depleted T cell population, thereby generating an engineered T cell composition. In some embodiments, the method further includes introducing into cells of the pooled CD57 depleted T cell population a heterologous polynucleotide encoding a recombinant receptor, thereby generating an engineered T cell composition.

In some embodiments, the knocking out and the introducing the heterologous nucleic acid are carried out concurrently. In some embodiments, the knocking out and the introducing the heterologous nucleic acid are carried out successively in either order. In some embodiments, the combining is performed prior to the cells of the CD57 depleted T cell population being knocked out and/or introduced to the heterologous nucleic acid. In some embodiments, the combining is performed prior to the cells of the CD57 depleted T cell population being knocked out. In some embodiments, the combining is performed prior to the cells of the CD57 depleted T cell population being introduced to the heterologous nucleic acid. In some embodiments, the combining is performed prior to the cells of the CD57 depleted T cell population being knocked out and introduced to the heterologous nucleic acid. In some embodiments, the combining is performed after the cells of the CD57 depleted T cell are knocked out and/or introduced to the heterologous nucleic acid. In some embodiments, the combining is performed after the cells of the CD57 depleted T cell population are knocked out. In some embodiments, the combining is performed after the cells of the CD57 depleted T cell population are introduced to the heterologous nucleic acid. In some embodiments, the combining is performed after the cells of the CD57 depleted T cell population are knocked out and introduced to the heterologous nucleic acid.

In some embodiments, a heterologous polynucleotide encoding a recombinant receptor is introduced into cells of the CD27 enriched T cell population, thereby generating an engineered T cell composition. In some embodiments, the method further includes introducing into cells of the CD27 enriched T cell population a heterologous polynucleotide encoding a recombinant receptor, the method thereby generating an engineered T cell composition. In some embodiments, (a) a heterologous polynucleotide encoding a recombinant receptor is introduced into cells of the pooled CD27 enriched T cell population; and (b) the method further includes introducing into cells of the pooled CD27 enriched T cell population a heterologous polynucleotide encoding a recombinant receptor, the method thereby generating an engineered T cell composition.

In some embodiments, the knocking out and the introducing the heterologous nucleic acid are carried out concurrently. In some embodiments, the knocking out and the introducing the heterologous nucleic acid are carried out successively in either order. In some embodiments, the combining is performed prior to the cells of the CD27 enriched T cell population being knocked out and/or introduced to the heterologous nucleic acid. In some embodiments, the combining is performed prior to the cells of the CD27 enriched T cell population being knocked out. In some embodiments, the combining is performed prior to the cells of the CD27 enriched T cell population being introduced to the heterologous nucleic acid. In some embodiments, the combining is performed prior to the cells of the CD27 enriched T cell population being knocked out and introduced to the heterologous nucleic acid. In some embodiments, the combining is performed after the cells of the CD27 enriched T cell population are knocked out and/or introduced to the heterologous nucleic acid. In some embodiments, the combining is performed after the cells of the CD27 enriched T cell population are knocked out. In some embodiments, the combining is performed after the cells of the CD27 enriched T cell population are introduced to the heterologous nucleic acid. In some embodiments, the combining is performed after the cells of the CD27 enriched T cell population are knocked out and introduced to the heterologous nucleic acid.

Also provided herein is a method of preparing a T cell composition from a donor pool that is or includes (i) selecting for one of (a) cells surface positive for CD3 (CD3+), or surface positive for CD4 (CD4+) and/or CD8 (CD8+) and (b) cells surface negative for CD57 (CD57−) from a donor sample, thereby generating an enriched population of cells; (ii) selecting, from the enriched population of cells, the other of (a) CD3+, or CD4+ and/or CD8+ cells and (b) CD57− cells, thereby generating a CD57 depleted T cell population; (iii) stimulating cells of the CD57 depleted T cell population under conditions to activate T cells in the population; (iv) genetically engineering the stimulated cells, thereby producing an engineered T cell composition, the genetic engineering including: (1) knocking out expression of (a) an endogenous major histocompatibility complex (MHC) or a component thereof, optionally beta-2-microglobulin (β2M); and/or (b) an endogenous T cell receptor (TCR) or a component thereof, optionally T cell receptor alpha constant (TRAC), in the stimulated cells; and (2) introducing a heterologous polynucleotide encoding a recombinant receptor into the stimulated cells, optionally into a locus of a gene encoding for TRAC; wherein the knocking out in (1) and the introducing in (2) can be carried out concurrently or successively in either order; (v) incubating the engineered T cell composition for up to 96 hours, optionally at a temperature of at or about 37°±2° C., optionally wherein the incubating further includes cultivating the cells under conditions to promote proliferation or expansion; (vi) repeating steps (i) through (v) for a plurality of different donors to produce a plurality of donor engineered T cell compositions, wherein each donor engineered T cell composition is generated from cells from an individual donor of the plurality of different donors; and (vii) combining the plurality of donor engineered T cell compositions from the plurality of different donors.

In some embodiments, the frequency of CD57+ T cells in the CD57 depleted T cell population and/or the pooled CD57 depleted T cell population is less than about or about 35%, 30%, 20%, 10%, 5%, 1% or 0.1% of the frequency of CD57+ T cells in the donor sample. In some embodiments, the frequency of CD57+ T cells in the CD57 depleted T cell population and/or the pooled CD57 depleted T cell population is less than about 35% of the frequency of CD57+ T cells in the donor sample. In some embodiments, the frequency of CD57+ T cells in the CD57 depleted T cell population and/or the pooled CD57 depleted T cell population is less than about 30% of the frequency of CD57+ T cells in the donor sample. In some embodiments, the frequency of CD57+ T cells in the CD57 depleted T cell population and/or the pooled CD57 depleted T cell population is less than about 25% of the frequency of CD57+ T cells in the donor sample. In some embodiments, the frequency of CD57+ T cells in the CD57 depleted T cell population and/or the pooled CD57 depleted T cell population is less than about 20% of the frequency of CD57+ T cells in the donor sample. In some embodiments, the frequency of CD57+ T cells in the CD57 depleted T cell population and/or the pooled CD57 depleted T cell population is less than about 10% of the frequency of CD57+ T cells in the donor sample. In some embodiments, the frequency of CD57+ T cells in the CD57 depleted T cell population and/or the pooled CD57 depleted T cell population is less than about 50% of the frequency of CD5+ T cells in the donor sample. In some embodiments, the frequency of CD57+ T cells in the CD57 depleted T cell population and/or the pooled CD57 depleted T cell population is less than about 1% of the frequency of CD5+ T cells in the donor sample.

In some embodiments, the CD57 depleted T cell population and/or the pooled CD57 depleted T cell population contains less than about 20% CD57+ T cells, less than about 15% CD57+ T cells, less than about 10% CD57+ T cells, less than about 5% CD57+ T cells, less than about 1% CD57+ T cells, or less than about 0.1% CD57+ T cells. In some embodiments, the CD57 depleted T cell population contains less than about 20% CD57+ T cells, less than about 15% CD57+ T cells, less than about 10% CD57+ T cells, less than about 5% CD57+ T cells, less than about 1% CD57+ T cells, or less than about 0.1% CD57+ T cells. In some embodiments, the pooled CD57 depleted T cell population contains less than about 20% CD57+ T cells, less than about 15% CD57+ T cells, less than about 10% CD57+ T cells, less than about 5% CD57+ T cells, less than about 1% CD57+ T cells, or less than about 0.1% CD57+ T cells. In some embodiments, the CD57 depleted T cell population and/or the pooled CD57 depleted T cell population contains less than about 5% CD57+ T cells. In some embodiments, the pooled CD57 depleted T cell population contains less than about 5% CD57+ T cells. In some embodiments, the CD57 depleted T cell population and/or the pooled CD57 depleted T cell population is free or is essentially free of CD57+ T cells. In some embodiments, the CD57 depleted T cell population is free or is essentially free of CD57+ T cells. In some embodiments, the pooled CD57 depleted T cell population is free or is essentially free of CD57+ T cells.

Also provided herein is a method of preparing a T cell composition from a donor pool that is or includes (i) selecting for one of (a) cells surface positive for CD3 (CD3+), or surface positive for CD4 (CD4+) and/or CD8 (CD8+) and (b) cells surface positive for CD27 (CD27+) from a donor sample, thereby generating an enriched population of cells; (ii) selecting, from the enriched population of cells, the other of (a) CD3+, or CD4+ and/or CD8+ cells and (b) CD27+ cells, thereby generating a CD27 enriched T cell population; (iii) stimulating cells of the CD27 enriched T cell population under conditions to activate T cells in the population; (iv) genetically engineering the stimulated cells, thereby producing an engineered T cell composition, the genetic engineering including: (1) knocking out expression of (a) an endogenous major histocompatibility complex (MHC) or a component thereof; and/or (b) an endogenous T cell receptor (TCR) or a component thereof, in the stimulated cells; and (2) introducing a heterologous polynucleotide encoding a recombinant receptor into the stimulated cells; wherein the knocking out in (1) and the introducing in (2) can be carried out concurrently or successively in either order; (v) incubating the engineered T cell composition for up to 96 hours; (vi) repeating steps (i) through (v) for a plurality of different donors to produce a plurality of donor engineered T cell compositions, wherein each donor engineered T cell composition is generated from cells from an individual donor of the plurality of different donors; and (vii) combining the plurality of donor engineered T cell compositions from the plurality of different donors.

In some embodiments, the frequency of CD27− T cells in the CD27 enriched T cell population and/or the pooled CD27 enriched T cell population is less than about or about 35%, 30%, 20%, 10%, 5%, 1% or 0.1% of the frequency of CD27− T cells in the donor sample. In some embodiments, the frequency of CD27− T cells in the CD27 enriched T cell population and/or the pooled CD27 enriched T cell population is less than about 35% of the frequency of CD27− T cells in the donor sample. In some embodiments, the frequency of CD27− T cells in the CD27 enriched T cell population and/or the pooled CD27 enriched T cell population is less than about 30% of the frequency of CD27− T cells in the donor sample. In some embodiments, the frequency of CD27− T cells in the CD27 enriched T cell population and/or the pooled CD27 enriched T cell population is less than about 25% of the frequency of CD27− T cells in the donor sample. In some embodiments, the frequency of CD27− T cells in the CD27 enriched T cell population and/or the pooled CD27 enriched T cell population is less than about 20% of the frequency of CD27− T cells in the donor sample. In some embodiments, the frequency of CD27− T cells in the CD27 enriched T cell population and/or the pooled CD27 enriched T cell population is less than about 10% of the frequency of CD27− T cells in the donor sample. In some embodiments, the frequency of CD27− T cells in the CD27 enriched T cell population and/or the pooled CD27 enriched T cell population is less than about 50% of the frequency of CD5+ T cells in the donor sample. In some embodiments, the frequency of CD27− T cells in the CD27 enriched T cell population and/or the pooled CD27 enriched T cell population is less than about 1% of the frequency of CD27− T cells in the donor sample.

In some embodiments, the CD27 enriched T cell population and/or the pooled CD27 enriched T cell population contains less than about 20% CD27− T cells, less than about 15% CD27− T cells, less than about 10% CD27− T cells, less than about 5% CD27− T cells, less than about 1% CD27− T cells, or less than about 0.1% CD27− T cells. In some embodiments, the CD27 enriched T cell population contains less than about 20% CD27− T cells, less than about 15% CD27− T cells, less than about 10% CD27− T cells, less than about 5% CD27− T cells, less than about 1% CD27− T cells, or less than about 0.1% CD27− T cells. In some embodiments, the pooled CD27 enriched T cell population contains less than about 20% CD27− T cells, less than about 15% CD27− T cells, less than about 10% CD27− T cells, less than about 5% CD27− T cells, less than about 1% CD27− T cells, or less than about 0.1% CD27− T cells. In some embodiments, the CD27 enriched T cell population and/or the pooled CD27 enriched T cell population contains less than about 5% CD27− T cells. In some embodiments, the CD27 enriched T cell population contains less than about 5% CD27− T cells. In some embodiments, the pooled CD27 enriched T cell population contains less than about 5% CD27− T cells. In some embodiments, the CD27 enriched T cell population and/or the pooled CD27 enriched T cell population is free or is essentially free of CD27− T cells. In some embodiments, the CD27 enriched T cell population is free or is essentially free of CD27− T cells. In some embodiments, the pooled CD27 enriched T cell population is free or is essentially free of CD27− T cells.

In some embodiments, the cells of the CD57 depleted T cell population and/or the pooled CD57 depleted T cell population exhibit a lower coefficient of variation (CV) in expression of one or more molecules, compared to that of the cells of the donor sample. In some embodiments, the cells of the CD57 depleted T cell population exhibit a lower coefficient of variation (CV) in expression of one or more molecules, compared to that of the cells of the donor sample. In some embodiments, the cells of the pooled CD57 depleted T cell population exhibit a lower coefficient of variation (CV) in expression of one or more molecules, compared to that of the cells of the donor sample. In some embodiments, the one or more molecules includes a marker of naïve T cells. In some embodiments, the one or more molecules is or includes CD27, Ki67, CD25, CD28, CCR7, and/or CD45RA. In some embodiments, the cells of the CD57 depleted T cell population and/or the pooled CD57 depleted T cell population exhibit a lower CV in expression of CD27 and/or Ki67, compared to that of the cells of the donor sample. In some embodiments, the cells of the CD57 depleted T cell population exhibit a lower CV in expression of CD27, compared to that of the cells of the donor sample. In some embodiments, the cells of the CD57 depleted T cell population exhibit a lower CV in expression of Ki67, compared to that of the cells of the donor sample. In some embodiments, the cells of the pooled CD57 depleted T cell population exhibit a lower CV in expression of CD27, compared to that of the cells of the donor sample. In some embodiments, the cells of the pooled CD57 depleted T cell population exhibit a lower CV in expression of Ki67, compared to that of the cells of the donor sample.

In some embodiments, the cells of the CD27 enriched T cell population exhibit a lower coefficient of variation (CV) in expression of one or more molecules, compared to that of the cells of the donor sample. In some embodiments, the cells of the pooled CD27 enriched T cell population exhibit a lower coefficient of variation (CV) in expression of one or more molecules, compared to that of the cells of the donor sample. In some embodiments, the one or more molecules includes a marker of naïve T cells. In some embodiments, the one or more molecules is or includes Ki67, CD25, CD28, CCR7, and/or CD45RA. In some embodiments, the one or more molecules is or includes Ki67. In some embodiments, the one or more molecules is or includes CCR7. In some embodiments, the one or more molecules is or includes CD45RA. In some embodiments, the one or more molecules is or includes CD28.

In some embodiments, the donor sample is or includes an apheresis product or a leukapheresis product.

In some embodiments, the plurality of different donors includes at least about or about 2 different donors, at least about or about 5 different donors, at least about or about 10 different donors, at least about or about 15 different donors, at least about or about 20 different donors, at least about or about 25 different donors, at least about or about 50 different donors, or at least about or about 100 different donors, or any range between any of the foregoing. In some embodiments, the plurality of different donors includes between 5 and 25 donors. In some embodiments, the plurality of different donors includes between 25 and 50 donors. In some embodiments, the plurality of different donors includes between 50 and 100 donors. In some embodiments, the plurality of different donors includes two or more donors that are less than 100% human leukocyte antigen (HLA) matched, less than about 90% HLA matched, less than about 80% HLA matched, less than about 70% HLA matched, less than about 60% HLA matched, or less than about 50% HLA matched. In some embodiments, the plurality of different donors includes at least two donors that are not 100% HLA matched. In some embodiments, the individual donor is healthy or is not suspected of having a disease or condition at the time the donor sample is obtained from the individual donor. In some embodiments, the individual donor has a disease or condition at the time the donor sample is obtained from the individual donor. In some embodiments, the plurality of different donors includes at least one donor that is healthy or is not suspected of having a disease or condition at the time the donor sample is obtained from the at least one donor. In some embodiments, the plurality of different donors includes at least one donor that has a disease or condition at the time the donor sample is obtained from the at least one donor. In some embodiments, each of the donors of the plurality of different donors is healthy or is not suspected of having a disease or condition at the time the donor sample is obtained from each of the different donors.

In some embodiments, the selecting is or includes immunoaffinity-based selection. In some embodiments, the immununoaffinity-based selection includes contacting T cells with an antibody capable of specifically binding to CD57 and recovering cells not bound to the antibody, thereby effecting negative selection. In some embodiments, the selecting is or includes immunoaffinity-based selection. In some embodiments, the immunuunoaffinity-based selection includes contacting T cells with an antibody capable of specifically binding to CD27 and recovering cells bound to the antibody, thereby effecting positive selection. In some embodiments, the immunuunoaffinity-based selection includes contacting T cells with an antibody capable of specifically binding to CD3, CD4, or CD8, and recovering cells bound to the antibody, thereby effecting positive selection. In some embodiments, the immunuunoaffinity-based selection includes contacting T cells with an antibody capable of specifically binding to CD3 and recovering cells bound to the antibody, thereby effecting positive selection. In some embodiments, the immunuunoaffinity-based selection includes contacting T cells with an antibody capable of specifically binding to CD4 and recovering cells bound to the antibody, thereby effecting positive selection. In some embodiments, the immunuunoaffinity-based selection includes contacting T cells with an antibody capable of specifically binding to CD8 and recovering cells bound to the antibody, thereby effecting positive selection. In some embodiments, the antibody is immobilized on a solid surface. In some embodiments, the solid surface is a magnetic particle. In some embodiments, the antibody is immobilized on or attached to an affinity chromatography matrix. In some embodiments, the antibody further includes one or more binding partners capable of forming a reversible bond with a binding reagent immobilized on the matrix, whereby the antibody is reversibly bound to said chromatography matrix during said contacting. In some embodiments, the binding reagent is a streptavidin mutein that reversibly binds to the binding partner.

In some embodiments, (a) the method further includes cryopreserving the CD57 depleted T cell population and/or the pooled CD57 depleted T cell population; and/or (b) the CD57 depleted T cell population and/or the pooled CD57 depleted T cell population is formulated with a cryoprotectant. In some embodiments, the method further includes cryopreserving the CD57 depleted T cell population. In some embodiments, the method further includes cryopreserving the pooled CD57 depleted T cell population. In some embodiments, the CD57 depleted T cell population is formulated with a cryoprotectant. In some embodiments, the pooled CD57 depleted T cell population is formulated with a cryoprotectant. In some embodiments, the CD57 depleted T cell population and/or the pooled CD57 depleted T cell population is thawed before the subsequent step. In some embodiments, the CD57 depleted T cell population is thawed before the subsequent step. In some embodiments, the pooled CD57 depleted T cell population is thawed before the subsequent step.

In some embodiments, the method further includes cryopreserving the CD27 enriched T cell population. In some embodiments, the method further includes cryopreserving the pooled CD27 enriched T cell population. In some embodiments, the CD27 enriched T cell population is formulated with a cryoprotectant. In some embodiments, the pooled CD27 enriched T cell population is formulated with a cryoprotectant. In some embodiments, the CD27 enriched T cell population is thawed before the subsequent step. In some embodiments, the pooled CD27 enriched T cell population is thawed before the subsequent step.

In some embodiments, the endogenous MHC or a component thereof is or includes MHC class I protein or a component thereof. In some embodiments, the endogenous MHC or a component thereof includes β2M. In some embodiments, the endogenous TCR or a component thereof includes TRAC and/or T cell receptor beta constant (TRBC). In some embodiments, the endogenous TCR or a component thereof includes TRAC. In some embodiments, the endogenous TCR or a component thereof includes TRBC. In some embodiments, the knocking out includes introducing into the cells an agent that reduces expression of a product encoded by, or disrupts, the endogenous β2M gene and/or the endogenous TRAC gene. In some embodiments, the knocking out includes introducing into the cells an agent that reduces expression of a product encoded by, or disrupts, the endogenous β2M gene. In some embodiments, the knocking out includes introducing into the cells an agent that reduces expression of a product encoded by, or disrupts, the endogenous TRAC gene. In some embodiments, the knocking out includes introducing into the cells an agent that reduces expression and/or activity of β2M and/or TRAC. In some embodiments, the knocking out includes introducing into the cells an agent that reduces expression and/or activity of β2M. In some embodiments, the knocking out includes introducing into the cells an agent that reduces expression and/or activity of TRAC. In some embodiments, the knocking out includes introducing into the cells a zinc finger nuclease (ZFN), a TAL-effector nuclease (TALEN), or a CRISPR-Cas9 combination. In some embodiments, the knocking out includes introducing into the cells a zinc finger nuclease (ZFN). In some embodiments, the knocking out includes introducing into the cells a TAL-effector nuclease (TALEN). In some embodiments, the knocking out includes introducing into the cells a CRISPR-Cas combination.

In some of any of the provided embodiments, provided herein is a method of genetically engineering a CD57 depleted T cell population, further including introducing a heterologous polynucleotide encoding a recombinant receptor into the cells produced by any of the methods, thereby generating an engineered T cell composition. In some embodiments, the genetic engineering is performed prior to one or more of the steps of selecting the cells. In some embodiments, the engineered T cells exhibit a lower CV in the expression of the recombinant receptor, compared to a method in which the engineered T cells are not depleted for CD57+ T cells.

In some of any of the provided embodiments, provided herein is a method of genetically engineering a CD27 enriched T cell population, further including introducing a heterologous polynucleotide encoding a recombinant receptor into the cells produced by any of the methods, thereby generating an engineered T cell composition. In some embodiments, the genetic engineering is performed prior to one or more of the steps of selecting the cells. In some embodiments, the engineered T cells exhibit a lower CV in the expression of the recombinant receptor, compared to a method in which the engineered T cells are not depleted for CD27− T cells.

In some embodiments, the introducing includes targeted insertion of the heterologous polynucleotide with a viral vector comprising the heterologous polynucleotide. In some embodiments, the viral vector is an adeno-associated viral (AAV) vector. In some embodiments, the heterologous polynucleotide is inserted into the genetic locus of the β2M gene or the TRAC gene. In some embodiments, the heterologous polynucleotide is inserted into the genetic locus of the β2M gene. In some embodiments, the heterologous polynucleotide is inserted into the genetic locus of the TRAC gene.

In some embodiments, the method further includes incubating the engineered cells for up to 96 hours subsequent to the introducing. In some embodiments, the incubating is carried out at a temperature of at or about 37°±2° C. In some embodiments, the incubating is carried out for up to 72 hours subsequent to the introducing. In some embodiments, the incubating is carried out for up to 48 hours subsequent to the introducing. In some embodiments, the incubating is carried out for up to 24 hours subsequent to the introducing. In some embodiments, the incubating results in integration of the viral vector into the genome of the CD57 depleted T cells and/or the pooled CD57 depleted T cells. In some embodiments, the incubating results in integration of the viral vector into the genome of the CD57 depleted T cells. In some embodiments, the incubating results in integration of the viral vector into the genome of the pooled CD57 depleted T cells. In some embodiments, the incubating results in integration of the viral vector into the genome of the CD27 enriched T cells. In some embodiments, the incubating results in integration of the viral vector into the genome of the pooled CD27 enriched T cells.

In some embodiments, the method further includes cultivating the cells under conditions to promote proliferation or expansion. In some embodiments, the cultivating is carried out in the presence of one or more recombinant cytokines. In some embodiments, the one or more recombinant cytokines is one or more of IL-2, IL-7 and IL-15.

In some embodiments, the method further includes harvesting or collecting cells produced by the method. In some embodiments, the harvesting or collecting is carried out at a time when the a threshold number of cells have been produced by the method. In some embodiments, the time to reach the threshold number is less time than a method that does not include depleting CD57+ T cells. In some embodiments, the time to reach the threshold number is less time than a method that does not include depleting CD27− T cells. In some embodiments, (a) the method further includes formulating the harvested or collected cells for cryopreservation in the presence of a cryoprotectant; and/or (b) the harvested or collected cells are formulated in the presence of a pharmaceutically acceptable excipient. In some embodiments, the method further includes formulating the harvested or collected cells for cryopreservation in the presence of a cryoprotectant. In some embodiments, the harvested or collected cells are formulated in the presence of a pharmaceutically acceptable excipient.

In some embodiments, the recombinant receptor is capable of binding to a target antigen that is associated with, specific to and/or expressed on a cell or tissue of a disease or a condition. In some embodiments, the disease or the condition is an infectious disease or disorder, an autoimmune disease, an inflammatory disease or a tumor or a cancer. In some embodiments, the disease or the condition is a tumor or a cancer. In some embodiments, the target antigen is a tumor antigen. In some embodiments, the target antigen is selected from among αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrin receptor A2 (EPHa2), estrogen receptor, Fc receptor like 5 (FCRLS; also known as Fc receptor homolog 5 or FCRHS), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha(IL-22Rα), IL-13 receptor alpha 2 (IL-13Rα2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen or an antigen associated with a universal tag and/or biotinylated molecules and/or molecules expressed by HIV, HCV, HBV or other pathogens. In some embodiments, the recombinant receptor is or contains a functional non-TCR antigen receptor or a TCR or antigen-binding fragment thereof. In some embodiments, the recombinant receptor is a chimeric antigen receptor (CAR). In some embodiments, the recombinant receptor includes an extracellular domain comprising an antigen-binding domain, a spacer and/or a hinge region, a transmembrane domain and an intracellular signaling domain comprising a costimulatory signaling region. In some embodiments, the extracellular domain includes an antigen-binding domain comprising an scFv. In some embodiments, the intracellular signaling domain is or includes a primary signaling domain, a signaling domain that is capable of inducing a primary activation signal in a T cell, a signaling domain of a T cell receptor (TCR) component and/or a signaling domain comprising an immunoreceptor tyrosine-based activation motif (ITAM). In some embodiments, the intracellular signaling domain is or includes an intracellular signaling domain of a CD3 chain. In some embodiments, the intracellular signaling domain is or includes a CD3-zeta (CD3ζ) chain or a signaling portion thereof. In some embodiments, the costimulatory signaling region includes an intracellular signaling domain of a CD28, a 4-1BB or an ICOS or a signaling portion thereof. In some embodiments, the costimulatory signaling region includes an intracellular signaling domain of a CD28 or a signaling portion thereof. In some embodiments, the costimulatory signaling region includes an intracellular signaling domain of a 4-1BB or a signaling portion thereof. In some embodiments, the costimulatory signaling region includes an intracellular signaling domain of an ICOS or a signaling portion thereof.

In some embodiments, the T cells produced by the method are for administration to at least one subject having a disease or condition. In some embodiments, at least a portion of the T cells are allogeneic to the at least one subject. In some embodiments, the disease or condition is an infectious disease or disorder, an autoimmune disease, an inflammatory disease or a tumor or a cancer. In some embodiments, the disease or condition is a tumor or a cancer. In some embodiments, the T cells produced by the method are formulated for administration as one or more unit doses and the cells contain at least about 100 unit doses of the cells, at least about 200 unit doses of the cells, at least about 300 unit doses of the cells, at least about 400 unit doses of the cells, at least about 500 unit doses of the cells, at least about 600 unit doses, at least about or at least about 1,000 unit doses of the cells. In some embodiments, the T cells produced by the method are formulated for administration as one or more unit doses and the cells contain between about 100 unit doses and about 1000 use doses, between about 100 unit doses and about 500 unit doses, between about 100 unit doses and about 200 unit doses, between about 250 unit doses and about 500 unit doses, or between about 500 unit doses and 1000 unit doses. In some embodiments, the T cells produced by the method are for administration to at least 2 subjects, at least 5 subjects, at least 10 subjects, at least 25 subjects, at least 50 subjects, at least 100 subjects, at least 200 subjects, at least 500 subjects, or at least 1,000 subjects. In some embodiments, the T cells produced by the method are for administration to between about 2 subjects and 1000 subjects, between about 5 subjects and 500 subjects, between about 10 subjects and about 200 subjects, between about 20 subjects and about 150 subjects, or between about 25 subjects and about 50 subjects. In some embodiments, the unit dose contains between about 10 and 75 million cells per milliliter number of cells/concentration of cells. In some embodiments, the unit dose contains between and between about $5.0\times10^6$ and $1\times10^9$, $5.0\times10^6$ and $5.0\times10^8$, $5.0\times10^6$ and $2.5\times10^8$, $5.0\times10^6$ and $1.0\times10^8$, $5.0\times10^6$ and $7.5\times10^7$, $1\times10^7$ and $1\times10^9$, $1\times10^7$ and $5.0\times10^8$, $1\times10^7$ and $2.5\times10^8$, $1\times10^7$ and $1.0\times10^8$, $1.0\times10^7$ and $7.5\times10^7$, $1.0\times10^7$ and $5.0\times10^7$, $1.0\times10^7$ and $2.5\times10^7$, $1.5\times10^7$ and $2.25\times10^7$, $2.5\times10^7$ and $1.0\times10^9$, or $2.5\times10^7$ and $7.5\times10^8$ cells. In some embodiments, the unit dose contains between and between about $5.0\times10^6$ and $1\times10^9$, $1.0\times10^7$ and $1.0\times10^9$, $2.5\times10^7$ and $1\times10^9$, $5.0\times10^7$ and $1.0\times10^9$, $7.5\times10^7$ and $1.0\times10^9$, $1.0\times10^8$ and $1.0\times10^9$, $5.0\times10^7$ and $7.5\times10^8$, $5\times10^7$ and $5.0\times10^8$, $5\times10^7$ and $2.5\times10^8$, $5.0\times10^7$ and $1.0\times10^8$, or $5.0\times10^7$ and $7.5\times10^7$ recombinant receptor-expressing cells. In some embodiments, the unit dose contains about $5.0\times10^6$ recombinant receptor-expressing cells. In some embodiments, the unit dose contains about $1.0\times10^7$ recombinant receptor-expressing cells. In some embodiments, the unit dose contains about $1.5\times10^7$ recombinant receptor-expressing cells. In some embodiments, the unit dose contains about $3.0\times10^7$ recombinant receptor-expressing cells. In some embodiments, the unit dose contains about $4.5\times10^7$ recombinant receptor-expressing cells. In some embodiments, the unit dose contains about $6.0\times10^7$ recombinant receptor-expressing cells. In some embodiments, the unit dose contains about $8.0\times10^7$ recombinant receptor-expressing cells. In some embodiments, the unit dose contains about $1.0\times10^8$ recombinant receptor-expressing cells. In some embodiments, the unit dose contains about $1.5\times10^8$ recombinant receptor-expressing cells. In some embodiments, the unit dose contains about $3.0\times10^8$ recombinant receptor-expressing cells. In some embodiments, the unit dose contains about $4.5\times10^8$ recombinant receptor-expressing cells. In some embodiments, the unit dose contains about $6.0\times10^8$ recombinant receptor-expressing cells. In some embodiments, the unit dose contains about $8.0\times10^8$ recombinant receptor-expressing cells. In some embodiments, the unit dose contains about $1.0\times10^9$ recombinant receptor-expressing cells.

In some embodiments, the method further includes stimulating cells of the CD57 depleted T cell population and/or the pooled CD57 depleted T cell population under conditions to activate T cells in the population, thereby generating a stimulated T cell population. In some embodiments, the method further includes stimulating cells of the CD57 depleted T cell population under conditions to activate T cells in the population, thereby generating a stimulated T cell population. In some embodiments, the method further includes stimulating cells of the pooled CD57 depleted T cell population under conditions to activate T cells in the population, thereby generating a stimulated T cell population. In some embodiments, the method further includes stimulating cells of the CD27 enriched T cell population under conditions to activate T cells in the population, thereby generating a stimulated T cell population. In some embodiments, the method further includes stimulating cells of the pooled CD27 enriched T cell population under conditions to activate T cells in the population, thereby generating a stimulated T cell population.

In some embodiments, the stimulating conditions include the presence of a stimulatory reagent, said stimulatory reagent being capable of activating one or more intracellular signaling domains of one or more components of a TCR complex and one or more intracellular signaling domains of one or more costimulatory molecules. In some embodiments, the stimulatory reagent contains (i) a primary agent that specifically binds to a member of a TCR complex, optionally that specifically binds to CD3 and (ii) a secondary agent that specifically binds to a T cell costimulatory molecule, optionally wherein the costimulatory molecule is selected from CD28, CD137 (4-1-BB), OX40 or ICOS. In some embodiments, at least one of the primary and secondary agents is or includes an antibody or an antigen-binding fragment thereof. In some embodiments, the primary agent is an anti-CD3 antibody or an antigen-binding fragment thereof and the secondary agent is an anti-CD28 antibody or an antigen-binding fragment thereof. In some embodiments, the antigen binding fragment is a monovalent antibody fragment selected from the group consisting of a Fab fragment, an Fv fragment, and a single-chain Fv fragment (scFv). In some embodiments, the antigen binding fragment is a Fab. In some embodiments, the antigen binding fragment is a scFv. In some embodiments, the primary agent and the secondary agent are reversibly bound on the surface of an oligomeric particle reagent comprising a plurality of streptavidin molecules or streptavidin mutein molecules. In some embodiments, the streptavidin molecules or the streptavidin mutein molecules bind to or are capable of binding to biotin, avidin, a biotin analog or a biotin mutein, an avidin analog or an avidin mutein and/or a biologically active fragment thereof. In some embodiments, the primary agent contains an anti-CD3 Fab. In some embodiments, the secondary agent contains an anti-CD28 Fab. In some embodiments, the primary agent contains an anti-CD3 Fab and the secondary agent contains an anti-CD28 Fab.

In some embodiments, the method further includes separating the stimulatory reagent from the T cells, said separating comprising contacting the T cells with a substance, said substance being capable of reversing bonds between the primary and secondary agents and the oligomeric particle reagent. In some embodiments, the substance is a free binding partner and/or is a competition agent. In some embodiments, the substance is or includes a streptavidin-binding peptide, biotin or a biologically active fragment thereof, or a biotin analog or biologically active fragment thereof. In some embodiments, the substance is or includes biotin or a biotin analog. In some embodiments, the stimulating conditions include the presence of one or more recombinant cytokines. In some embodiments, the stimulating conditions includes the presence of one or more of recombinant IL-2, IL-7 and IL-15. In some embodiments, (a) the method further includes formulating the stimulated T cells for cryopreservation in the presence of a cryoprotectant; and/or (b) the stimulated T cells are formulated in the presence of a cryoprotectant. In some embodiments, the method further includes formulating the stimulated T cells for cryopreservation in the presence of a cryoprotectant. In some embodiments, the stimulated T cells are formulated in the presence of a cryoprotectant.

Provided herein is a composition containing the T cell population produced by any of the methods provided herein.

Provided herein is a composition containing T cells from a donor pool, containing a population of T cells enriched in human T cells that are surface negative for CD57 (CD57−), wherein the population of cells is from a plurality of different donors, and wherein the plurality of different donors include at least two donors that are not 100% human leukocyte antigen (HLA) matched.

In some embodiments, the T cells include T cells genetically engineered with a recombinant receptor. In some embodiments, the frequency of CD57+ T cells in the composition is less than about or about 35%, 30%, 20%, 10%, 5%, 1% or 0.1% of the total T cells in the composition. In some embodiments, the frequency of CD57+ T cells in the composition is less than about 20% of the total T cells in the composition. In some embodiments, the composition contains less than about 20% CD57+ T cells, less than about 15% CD57+ T cells, less than about 10% CD57+ T cells, less than about 5% CD57+ T cells, less than about 1% CD57+ T cells, or less than about 0.1% CD57+ T cells. In some embodiments, the composition contains less than about 15% CD57+ T cells. In some embodiments, the composition contains less than about 10% CD57+ T cells. In some embodiments, the composition contains less than about 5% CD57+ T cells. In some embodiments, the composition contains less than about 1% CD57+ T cells. In some embodiments, the composition contains less than about 0.1% CD57+ T cells. In some embodiments, the composition is free or is essentially free of CD57+ T cells. In some embodiments, the composition contains greater than or greater than at or about 75% CD3+/CD57− cells. In some embodiments, the composition contains greater than at or about 80% CD3+/CD57− cells. In some embodiments, the composition contains greater than at or about 85% CD3+/CD57− cells. In some embodiments, the composition contains greater than at or about 90% CD3+/CD57− cells. In some embodiments, the composition contains greater than at or about 95% CD3+/CD57− cells. In some embodiments, the composition contains greater than or greater than at or about 40% CD3+/CD57−/recombinant receptor+ cells. In some embodiments, the composition contains greater than at or about 45% CD3+/CD57−/recombinant receptor+ cells. In some embodiments, the composition contains greater than at or about 50% CD3+/CD57−/recombinant receptor+ cells. In some embodiments, the composition contains greater than at or about 55% CD3+/CD57−/recombinant receptor+ cells. In some embodiments, the composition contains greater than at or about 60% CD3+/CD57−/recombinant receptor+ cells. In some embodiments, the composition contains greater than at or about 65% CD3+/CD57−/recombinant receptor+ cells. In some embodiments, the composition contains greater than at or about 70% CD3+/CD57−/recombinant receptor+ cells.

In some embodiments, the composition contains greater than or greater than at or about 40% CD57−/recombinant receptor+ cells. In some embodiments, the composition contains greater than at or about 45% CD57−/recombinant receptor+ cells. In some embodiments, the composition contains greater than at or about 50% CD57−/recombinant receptor+ cells. In some embodiments, the composition contains greater than at or about 55% CD57−/recombinant receptor+ cells. In some embodiments, the composition contains greater than at or about 60% CD57−/recombinant receptor+ cells. In some embodiments, the composition contains greater than at or about 65% CD57−/recombinant receptor+ cells. In some embodiments, the composition contains greater than at or about 70% CD57−/recombinant receptor+ cells. In some embodiments, the composition contains greater than at or about 75% CD57−/recombinant receptor+ cells.

Also provided herein is a composition containing T cells from a donor pool, containing a population of T cells enriched in human T cells that are surface positive for CD27 (CD27+), wherein the population of cells is from a plurality of different donors, and wherein the plurality of different donors include at least two donors that are not 100% human leukocyte antigen (HLA) matched.

In some embodiments, the T cells include T cells genetically engineered with a recombinant receptor. In some embodiments, the frequency of CD27− T cells in the composition is less than about or about 35%, 30%, 20%, 10%, 5%, 1% or 0.1% of the total T cells in the composition. In some embodiments, the composition contains less than about 15% CD27− T cells. In some embodiments, the composition contains less than about 10% CD27− T cells. In some embodiments, the composition contains less than about 5% CD27− T cells. In some embodiments, the composition contains less than about 1% CD27− cells. In some embodiments, the composition contains less than about 0.1% CD27− T cells. In some embodiments, the composition is free or is essentially free of CD27− T cells. In some embodiments, the composition contains greater than or greater than at or about 75% CD27+ cells. In some embodiments, the composition contains greater than at or about 80% CD27+ cells. In some embodiments, the composition contains greater than at or about 85% CD27+ cells. In some embodiments, the composition contains greater than at or about 90% CD27+ cells. In some embodiments, the composition contains greater than at or about 95% CD27+ cells. In some embodiments, the composition contains greater than or greater than at or about 40% CD27+/recombinant receptor+ cells. In some embodiments, the composition contains greater than at or about 45% CD27+/recombinant receptor+ cells. In some embodiments, the composition contains greater than at or about 50% CD27+/recombinant receptor+ cells. In some embodiments, the composition contains greater than at or about 55% CD27+/recombinant receptor+ cells. In some embodiments, the composition contains greater than at or about 60% CD27+/recombinant receptor+ cells. In some embodiments, the composition contains greater than at or about 65% CD27+/recombinant receptor+ cells. In some embodiments, the composition contains greater than at or about 70% CD27+/recombinant receptor+ cells.

In some embodiments, each of the plurality of engineered T cell compositions contains CD4+ and CD8+ T cells. In some embodiments, each of the plurality of engineered T cell compositions contains a ratio of CD4+ to CD8+ T cells of between at or about 1:5 and at or about 5:1. In some embodiments, each of the plurality of engineered T cell compositions contains a ratio of CD4+ to CD8+ T cells of between at or about 1:3 and at or about 3:1. In some embodiments, each of the plurality of engineered T cell compositions contains a ratio of CD4+ to CD8+ T cells of between at or about 1:2 and at or about 2:1. In some embodiments, each of the plurality of engineered T cell compositions contains a ratio of CD4+ to CD8+ T cells of about 1:1.

In some embodiments, the cells of the composition exhibit a lower coefficient of variation (CV) in expression of one or more molecules, compared to that of a population of cells not enriched in human T cells that are surface negative for CD57 (CD57−). In some embodiments, the coefficient of variation (CV) of the cells of the composition is at least 20% lower, at least 40% lower, at least 60% lower, or at least 80% lower than that of a population of cells not enriched in human T cells that are surface negative for CD57 (CD57−). In some embodiments, the one or more molecules is or includes a marker of naïve T cells. In some embodiments, the one or more molecules is CD27, Ki67, CD25, CD28, CCR7, and/or CD45RA. In some embodiments, the cells of the composition exhibit a lower coefficient of variation (CV) in expression of CD27 and/or Ki67, compared to that of a population of cells not enriched in human T cells that are surface negative for CD57 (CD57−). In some embodiments, the cells of the composition exhibit a lower coefficient of variation (CV) in expression of CD27, compared to that of a population of cells not enriched in human T cells that are surface negative for CD57 (CD57−). In some embodiments, the cells of the composition exhibit a lower coefficient of variation (CV) in expression of Ki67, compared to that of a population of cells not enriched in human T cells that are surface negative for CD57 (CD57−). In some embodiments, the cells of the composition exhibit a lower coefficient of variation (CV) in expression of CD27 and Ki67, compared to that of a population of cells not enriched in human T cells that are surface negative for CD57 (CD57−). In some embodiments, the coefficient of variation (CV) of the cells of the composition is at least 20% lower, at least 40% lower, at least 60% lower, or at least 80% lower than that of a population of cells not enriched in human T cells that are surface negative for CD57 (CD57−). In some embodiments, the coefficient of variation (CV) of the cells of the composition is at least 20% lower than that of a population of cells not enriched in human T cells that are surface negative for CD57 (CD57−). In some embodiments, the coefficient of variation (CV) of the cells of the composition is at least 40% lower than that of a population of cells not enriched in human T cells that are surface negative for CD57 (CD57−). In some embodiments, the coefficient of variation (CV) of the cells of the composition is at least 60% lower than that of a population of cells not enriched in human T cells that are surface negative for CD57 (CD57−). In some embodiments, the coefficient of variation (CV) of the cells of the composition is at least 80% lower than that of a population of cells not enriched in human T cells that are surface negative for CD57 (CD57−).

In some embodiments, the cells of the composition exhibit a lower coefficient of variation (CV) in expression of one or more molecules, compared to that of a population of cells not enriched in human T cells that are surface positive for CD27 (CD27+). In some embodiments, the coefficient of variation (CV) of the cells of the composition is at least 20% lower, at least 40% lower, at least 60% lower, or at least 80% lower than that of a population of cells not enriched in human T cells that are surface positive for CD27 (CD27+). In some embodiments, the one or more molecules is or includes a marker of naïve T cells. In some embodiments, the one or more molecules is Ki67, CD25, CD28, CCR7, and/or CD45RA. In some embodiments, the cells of the composition exhibit a lower coefficient of variation (CV) in expression of Ki67, compared to that of a population of cells not enriched in human T cells that are surface positive for CD27 (CD27+). In some embodiments, the coefficient of variation (CV) of the cells of the composition is at least 20% lower, at least 40% lower, at least 60% lower, or at least 80% lower than that of a population of cells not enriched in human T cells that are surface positive for CD27 (CD27+). In some embodiments, the coefficient of variation (CV) of the cells of the composition is at least 20% lower than that of a population of cells not enriched in human T cells that are surface positive for CD27 (CD27+). In some embodiments, the coefficient of variation (CV) of the cells of the composition is at least 40% lower than that of a population of cells not enriched in human T cells that are surface positive for CD27 (CD27+). In some embodiments, the coefficient of variation (CV) of the cells of the composition is at least 60% lower than that of a population of cells not enriched in human T cells that are surface positive for CD27 (CD27+). In some embodiments, the coefficient of variation (CV) of the cells of the composition is at least 80% lower than that of a population of cells not enriched in human T cells that are surface positive for CD27 (CD27+).

In some embodiments, the plurality of different donors includes at least about or about 2 different donors, at least about or about 5 different donors, at least about or about 10 different donors, at least about or about 15 different donors, at least about or about 20 different donors, at least about or about 25 different donors, at least about or about 50 different donors, or at least about or about 100 different donors. In some embodiments, the plurality of different donors includes about 2 different donors, about 5 different donors, about 10 different donors, about 15 different donors, about 20 different donors, about 25 different donors, about 50 different donors, or about 100 different donors. In some embodiments, the plurality of different donors includes about 2 different donors. In some embodiments, the plurality of different donors includes about 5 different donors. In some embodiments, the plurality of different donors includes about 10 different donors. In some embodiments, the plurality of different donors includes about 20 different donors. In some embodiments, the plurality of different donors includes about 25 different donors. In some embodiments, the plurality of different donors includes about 50 different donors. In some embodiments, the plurality of different donors includes about 100 different donors. In some embodiments, the plurality of different donors includes fewer than or fewer than about 25 donors. In some embodiments, the plurality of different donors includes two or more donors that are less than 100% human leukocyte antigen (HLA) matched, less than about 90% HLA matched, less than about 80% HLA matched, less than about 70% HLA matched, less than about 60% HLA matched, or less than about 50% HLA matched. In some embodiments, the plurality of different donors includes at least two donors that are not 100% HLA matched. In some embodiments, the plurality of different donors includes at least one donor that is healthy or is not suspected of having a disease or condition at the time the cells are obtained from the at least one donor. In some embodiments, the plurality of different donors includes at least one donor that has a disease or condition at the time the cells are obtained from the at least one donor. In some embodiments, each of the donors of the plurality of different donors is healthy or is not suspected of having a disease or condition at the time the cells are obtained from each of the different donors.

In some embodiments, the T cells include T cells knocked out for expression of (i) an endogenous major histocompatibility complex (MHC) or a component thereof, optionally beta-2-microglobulin (β2M); and/or (ii) an endogenous T cell receptor (TCR) or a component thereof, optionally T cell receptor alpha constant (TRAC). In some embodiments, the T cells include T cells knocked out for expression of an endogenous major histocompatibility complex (MHC) or a component thereof. In some embodiments, the T cells include T cells knocked out for expression an endogenous T cell receptor (TCR) or a component thereof. In some embodiments, the T cells include T cells knocked out for expression of (i) an endogenous major histocompatibility complex (MHC) or a component thereof; and (ii) an endogenous T cell receptor (TCR) or a component thereof. In some embodiments, the endogenous MHC is or includes MHC class I protein or a component thereof. In some embodiments, the endogenous MHC is or includes beta-2-microglobulin (132M). In some embodiments, the endogenous TCR or a component thereof is or includes T cell receptor alpha constant (TRAC) and/or T cell receptor beta constant (TRBC). In some embodiments, the endogenous TCR or a component thereof is or includes T-cell receptor alpha constant (TRAC). In some embodiments, the heterologous polynucleotide is inserted into the genetic locus of the β2M gene or the TRAC gene. In some embodiments, the heterologous polynucleotide is inserted into the genetic locus of the TRAC gene.

In some embodiments, the method further includes selecting knocked out T cells that are surface negative for CD3 (CD3−). In some embodiments, selecting knocked out T cells that are CD3-includes contacting the cells with an antibody capable of specifically binding to CD3 and recovering cells not bound to the antibody, thereby effecting negative selection. In some embodiments, the knocked out T cells are selected for cells that are surface negative for CD3 (CD3−). In some embodiments, the knocked out T cells are surface negative for CD3−.

In some embodiments, the composition contains a cryprotectant. In some embodiments, the composition contains a pharmaceutically acceptable excipient.

In some embodiments, the recombinant receptor is capable of binding to a target antigen that is associated with, specific to and/or expressed on a cell or tissue of a disease or a condition. In some embodiments, the disease or the condition is an infectious disease or disorder, an autoimmune disease, an inflammatory disease or a tumor or a cancer. In some embodiments, the target antigen is a tumor antigen. In some embodiments, the target antigen is selected from among αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrin receptor A2 (EPHa2), estrogen receptor, Fc receptor like 5 (FCRLS; also known as Fc receptor homolog 5 or FCRHS), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha(IL-22Rα), IL-13 receptor alpha 2 (IL-13Rα2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen or an antigen associated with a universal tag and/or biotinylated molecules and/or molecules expressed by HIV, HCV, HBV or other pathogens. In some embodiments, the target antigen is CD19.

In some embodiments, the recombinant receptor is or includes a functional non-TCR antigen receptor or a TCR or antigen-binding fragment thereof. In some embodiments, the recombinant receptor is a chimeric antigen receptor (CAR). In some embodiments, the recombinant receptor contains an extracellular domain comprising an antigen-binding domain, a spacer and/or a hinge region, a transmembrane domain and an intracellular signaling domain comprising a costimulatory signaling region. In some embodiments, the extracellular domain contains an antigen-binding domain comprising an scFv. In some embodiments, the extracellular domain contains an antigen-binding domain is an scFv. In some embodiments, the intracellular signaling domain is or contains a primary signaling domain, a signaling domain that is capable of inducing a primary activation signal in a T cell, a signaling domain of a T cell receptor (TCR) component and/or a signaling domain comprising an immunoreceptor tyrosine-based activation motif (ITAM). In some embodiments, the intracellular signaling domain is or contains an intracellular signaling domain of a CD3 chain. In some embodiments, the intracellular signaling domain is or contains a CD3-zeta (CD3ζ) chain or a signaling portion thereof. In some embodiments, the costimulatory signaling region contains an intracellular signaling domain of a CD28, a 4-1BB or an ICOS or a signaling portion thereof.

In some embodiments, the composition is for treatment of a subject having a disease or condition. In some embodiments, the disease or condition is a cancer or a tumor. In some embodiments, the cells of the composition are formulated for administration as one or more unit doses and the cells contains at least about 100 unit doses of the cells, at least about 200 unit doses of the cells, at least about 300 unit doses of the cells, at least about 400 unit doses of the cells, at least about 500 unit doses of the cells, at least about 600 unit doses, at least about or at least about 1,000 unit doses of the cells. In some embodiments, the T cells produced by the method are formulated for administration as one or more unit doses and the cells contain between about 100 unit doses and about 1000 use doses, between about 100 unit doses and about 500 unit doses, between about 100 unit doses and about 200 unit doses, between about 250 unit doses and about 500 unit doses, or between about 500 unit doses and 1000 unit doses. In some embodiments, the cells of the composition are for administration to at least 2 subjects, at least 5 subjects, at least 10 subjects, at least 25 subjects, at least 50 subjects, at least 100 subjects, at least 200 subjects, at least 500 subjects, or at least 1,000 subjects. In some embodiments, the T cells produced by the method are for administration to between about 2 subjects and 1000 subjects, between about 5 subjects and 500 subjects, between about 10 subjects and about 200 subjects, between about 20 subjects and about 150 subjects, or between about 25 subjects and about 50 subjects.

In some embodiments, the unit dose contains between about 10 and 75 million cells per milliliter. In some embodiments, the unit dose contains between and between about $5.0\times10^6$ and $1\times10^9$, $5.0\times10^6$ and $5.0\times10^8$, $5.0\times10^6$ and $2.5\times10^8$, $5.0\times10^6$ and $1.0\times10^8$, $5.0\times10^6$ and $7.5\times10^7$, $1\times10^7$ and $1\times10^9$, $1\times10^7$ and $5.0\times10^8$, $1\times10^7$ and $2.5\times10^8$, $1\times10^7$ and $1.0\times10^8$, $1.0\times10^7$ and $7.5\times10^7$, $1.0\times10^7$ and $5.0\times10^7$, $1.0\times10^7$ and $2.5\times10^7$, $1.5\times10^7$ and $2.25\times10^7$, $2.5\times10^7$ and $1.0\times10^9$, or $2.5\times10^7$ and $7.5\times10^8$ cells. In some embodiments, the unit dose contains between and between about $5.0\times10^6$ and $1\times10^9$, $1.0\times10^7$ and $1.0\times10^9$, $2.5\times10^7$ and $1\times10^9$, $5.0\times10^7$ and $1.0\times10^9$, $7.5\times10^7$ and $1.0\times10^9$, $1.0\times10^8$ and $1.0\times10^9$, $5.0\times10^7$ and $7.5\times10^8$, $5\times10^7$ and $5.0\times10^8$, $5\times10^7$ and $2.5\times10^8$, $5.0\times10^7$ and $1.0\times10^8$, or $5.0\times10^7$ and $7.5\times10^7$ recombinant receptor-expressing cells. In some embodiments, the unit dose contains about $5.0\times10^6$ recombinant receptor-expressing cells. In some embodiments, the unit dose contains about $1.0\times10^7$ recombinant receptor-expressing cells. In some embodiments, the unit dose contains about $5.0\times10^7$ recombinant receptor-expressing cells. In some embodiments, the unit dose contains about $1.0\times10^8$ recombinant receptor-expressing cells. In some embodiments, the unit dose contains about $5.0\times10^8$ recombinant receptor-expressing cells. In some embodiments, the unit dose contains about $1.0\times10^9$ recombinant receptor-expressing cells.

Provided herein is a container containing any of the compositions provide herein. In some embodiments, the container is a bag. In some embodiments, the container is a freezing bag. In some embodiments, the container is filled with the composition to a volume that is: between or between about 15 mL and 150 mL, 20 mL and 100 mL, 20 mL and 80 mL, 20 mL and 60 mL, 20 mL and 40 mL, 40 mL and 100 mL, 40 mL and 80 mL, 40 mL and 60 mL, 60 mL and 100 mL, 60 mL and 80 mL or 80 mL and 100 mL, each inclusive; or at least or at least about 15 mL, at least or at least about 20 mL, at least or at least about 30 mL, at least or at least about 40 mL, at least or at least about 50 mL, at least or at least about 60 mL, at least or at least about 70 mL, at least or at least about 80 mL or at least or at least about 90 mL; and/or no more than 100 mL. In some embodiments, the container is filled with the composition to a volume that is between or between about 1 mL and 10 mL, or between about 2 ml and 5 ml. In some embodiments, the container is filled with the composition to a surface area to volume ratio that: is between or between about 0.1 $cm^{-1}$ and 100 $cm^{-1}$; 1 $cm^{-1}$ and 50 $cm^{-1}$, 1 $cm^{-1}$ and 20 $cm^{-1}$, 1 $cm^{-1}$ and 10 $cm^{-1}$, 1 $cm^{-1}$ and 7 $cm^{-1}$, 1 $cm^{-1}$ and 6 $cm^{-1}$, 1 $cm^{-1}$ and 3 $cm^{-1}$, 1 $cm^{-1}$ and 2 $cm^{-1}$, 2 $cm^{-1}$ and 20 $cm^{-1}$, 2 $cm^{-1}$ and 10 $cm^{-1}$, 2 $cm^{-1}$ and 7 $cm^{-1}$, 2 $cm^{-1}$ and 6 $cm^{-1}$, 2 $cm^{-1}$ and 3 $cm^{-1}$, 3 $cm^{-1}$ and 20 $cm^{-1}$, 3 $cm^{-1}$ and 10 $cm^{-1}$, 3 $cm^{-1}$ and 7 $cm^{-1}$, 3 $cm^{-1}$ and 6 $cm^{-1}$, 6 $cm^{-1}$ and 20 $cm^{-1}$, 6 $cm^{-1}$ and 10 $cm^{-1}$, 6 $cm^{-1}$ and 7 $cm^{-1}$, 7 $cm^{-1}$ and 20 $cm^{-1}$, 7 $cm^{-1}$ and 10 $cm^{-1}$, or 7 $cm^{-1}$ and 20 $cm^{-1}$, each inclusive; or is, is about, or is at least 3 $cm^{-1}$, 4 $cm^{-1}$, 5 $cm^{-1}$, 6 $cm^{-1}$, 7 $cm^{-1}$, 10 $cm^{-1}$, 15 $cm^{-1}$, or 20 $cm^{-1}$.

Provided herein is a method of treatment that is or includes administering any of the compositions provided herein to a subject having or suspected of having a disease or a condition, wherein the T cells of the composition are not derived from the subject.

Also provided herein is a method of treatment that is or includes administering any of the compositions provided herein to a subject having or suspected of having a disease or a condition, wherein at least a portion of the T cells of the composition are not derived from the subject.

In some embodiments, less than 100% of the T cells of the composition are HLA-identical to the T cells of the subject. In some embodiments, the disease or condition is an infectious disease or disorder, an autoimmune disease, an inflammatory disease or a tumor or a cancer. In some embodiments, the disease or condition is a cancer.

Also provided herein is a use of any of the compositions provided herein for treating a disease or disorder. In some embodiments, the disease or condition is an infectious disease or disorder, an autoimmune disease, an inflammatory disease or a tumor or a cancer. In some embodiments, the disease or condition is a cancer or a tumor.

BRIEF DESCRIPTION OF THE DRAWINGS

FIG. 1D) among CD8+ T cells obtained from seven different donors (Donors A-G), over approximately 240 hours after the start of stimulation in an exemplary manufacturing process for primary human T cells, or a similar process without transduction of the cells.

DETAILED DESCRIPTION

Figure 1A:
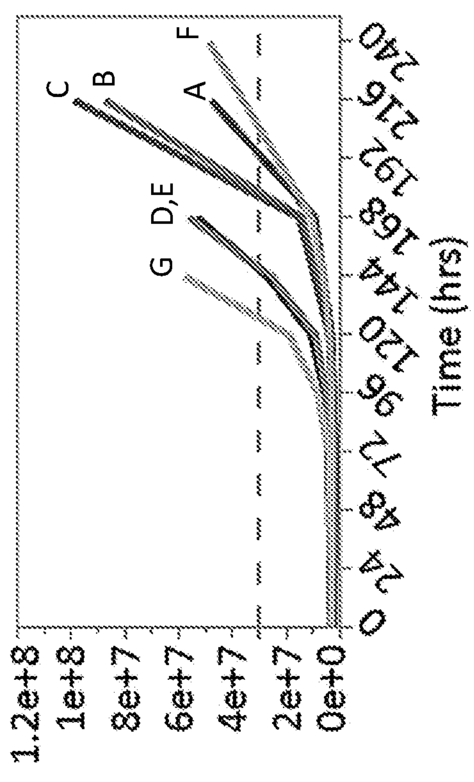
FIGS. 1A-1D show the total cell number (FIG. 1A), fold expansion (FIG. 1B), percent viability (FIG. 1C) and percent Ki67+ cells (marker associated with cell cycle entry.
Figure 1B:
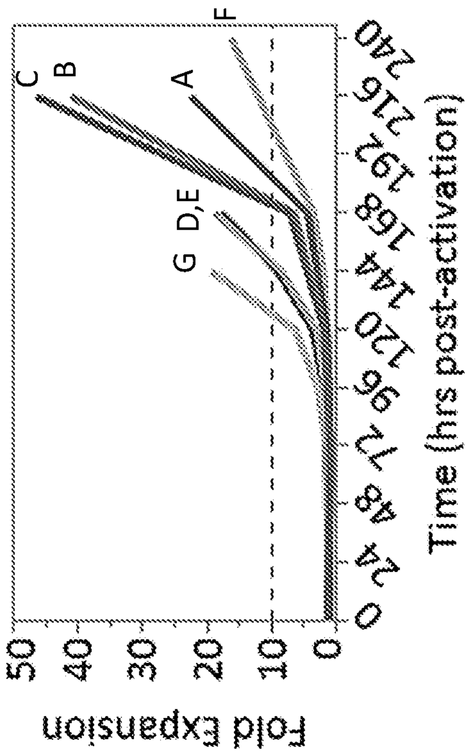
Figure 1C:
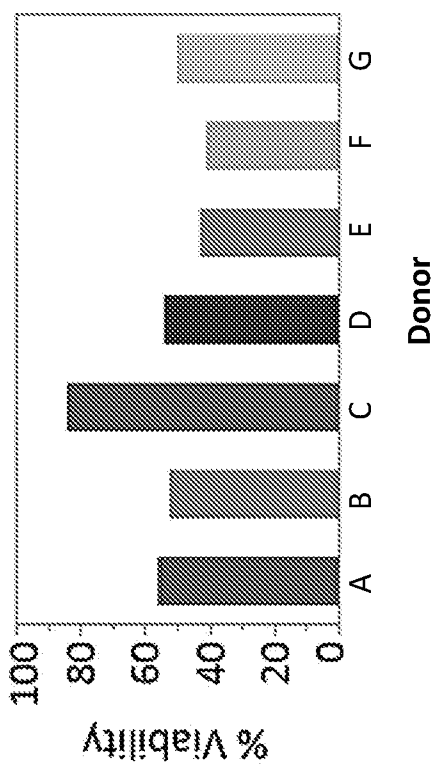

Provided herein are methods for preparing engineered T cell compositions enriched for CD57 negative (CD57−) T cells from a plurality of different donors (or donor pool). Also provided are compositions containing engineered T cells enriched in CD57− cells in which the T cells are from a plurality of different donors, including compositions produced by the provided methods. Also provided herein are methods for preparing engineered T cell compositions enriched for CD27 positive (CD27+) T cells from a plurality of different donors (or donor pool). Also provided are compositions containing engineered T cells enriched in CD27+ cells in which the T cells are from a plurality of different donors, including compositions produced by the provided methods. In some embodiments the engineered T cells are genetically engineered to express a recombinant receptor, such as a chimeric antigen receptor (CAR). In some aspects, the methods provided herein include, selecting, isolating, enriching, stimulating, activating, genetically engineering (e.g. engineering the cells with a recombinant receptor and/or knocking out an immune gene), and/or incubating or expanding cells to produce a composition having a reduced frequency of CD57+ T cells, such as compared to a starting donor sample, e.g. a leukapheresis or apheresis sample. In some aspects, the methods provided herein include, selecting, isolating, enriching, stimulating, activating, genetically engineering (e.g. engineering the cells with a recombinant receptor and/or knocking out an immune gene), and/or incubating or expanding cells to produce a composition having a reduced frequency of CD27− T cells, such as compared to a starting donor sample, e.g. a leukapheresis or apheresis sample.

In some embodiments, the provided methods can include separately preparing or producing a composition of T cells enriched in CD57− cells that are engineered with a expressing a recombinant receptor (e.g. a CAR) from a plurality of individual donors. The separate methods can include selecting T cells enriched in CD57− T cells, stimulating or activating the T cells, genetically engineering (e.g. engineering the cells with a recombinant receptor and/or knocking out an immune gene), and/or incubating or expanding cells to produce a composition containing CD57− T cells expressing a recombinant receptor (e.g. CAR) from each of the individual donors. In some embodiments, the provided methods can include separately preparing or producing a composition of T cells enriched in CD27+ cells that are engineered with a expressing a recombinant receptor (e.g. a CAR) from a plurality of individual donors. The separate methods can include selecting T cells enriched in CD27+ T cells, stimulating or activating the T cells, genetically engineering (e.g. engineering the cells with a recombinant receptor and/or knocking out an immune gene), and/or incubating or expanding cells to produce a composition containing CD27+ T cells expressing a recombinant receptor (e.g. CAR) from each of the individual donors. In some aspects, the engineered compositions are generated from a sample, population, or composition of cells from an individual donor. In some aspects, an engineered composition from an individual donor is combined with an engineered composition from one or more other individual donors to produce a pooled engineered composition from a plurality of different donors. Samples, populations, or compositions of cells from a plurality of individual donors may be combined at any time after the engineering to create the pooled engineered composition.

In some embodiments, the provided methods can include pooling or combining cells from a plurality of donors into a single composition in connection with any one or more steps of producing the engineered cell composition. In some embodiments, the methods can include selecting T cells enriched in CD57− T cells, stimulating or activating the T cells, genetically engineering (e.g. engineering the cells with a recombinant receptor and/or knocking out an immune gene), and/or incubating or expanding cells to produce a pooled composition containing CD57− T cells expressing a recombinant receptor (e.g. CAR) from the plurality of donors. In the methods, prior to or at any one or more of the steps of selecting T cells enriched in CD57− T cells, stimulating or activating the T cells, genetically engineering (e.g. engineering the cells with a recombinant receptor and/or knocking out an immune gene), and/or incubating or expanding cells, the cells can be combined from the plurality of donors for subsequent steps in the process. In some embodiments, the methods can include selecting T cells enriched in CD27+ T cells, stimulating or activating the T cells, genetically engineering (e.g. engineering the cells with a recombinant receptor and/or knocking out an immune gene), and/or incubating or expanding cells to produce a pooled composition containing CD27+ T cells expressing a recombinant receptor (e.g. CAR) from the plurality of donors. In the methods, prior to or at any one or more of the steps of selecting T cells enriched in CD27+ T cells, stimulating or activating the T cells, genetically engineering (e.g. engineering the cells with a recombinant receptor and/or knocking out an immune gene), and/or incubating or expanding cells, the cells can be combined from the plurality of donors for subsequent steps in the process. In some aspects, the engineered compositions are generated from a sample, population, or composition of cells from a plurality of different individual donors, thereby generating a pooled engineered composition. Samples, populations, or compositions of cells from a plurality of different individual donors may be combined at any time prior to, during, or after the genetic engineering. In some aspects samples, populations, or compositions of cells from a plurality of different individual donors are combined prior to or during the genetic engineering.

Particular embodiments contemplate that existing methods for generating engineered T cells, e.g., engineered T cells expressing chimeric antigen receptors (CARs), such as from a plurality of donors, may include steps, stages, or phases where populations or compositions of T cells proliferate or expand. However, in some cases, a portion of populations or compositions may not display any proliferation or expansion, or, in some cases, may expand slowly are thus require extra days to complete the engineering process.

Further, in some cases, populations or compositions from particular donors may not display any proliferation or expansion, or, in some cases, may expand more slowly than those derived from another donor, and thus require extra days to complete the engineering process. In some aspects, this can result in compositions of engineered T cells (e.g. CART cells) that exhibit substantial variability among different individual donor subjects from which they are produced.

In some aspects, existing methods or processes for generating or manufacturing engineered cell compositions, including existing methods or processes for generating or manufacturing engineered cell compositions derived from a plurality of donors, can result in heterogeneity in the manufacturing process. In some aspects, phenotypes associated with memory T cells can affect clinical outcome (see, e.g., Fraietta et al., Nat Med. 2018; 24(5):563-571; and Larson et al., Cancer Res. 2018; 78(13 Suppl):Abstract nr 960). In some cases, enrichment for cells exhibiting early memory T cell phenotypes can improve the manufacturing of engineered cell compositions (see, e.g., Singh et al., Sci Trans Med. 2016; 8(320):320ra3).

The provided methods and compositions address these issues. The provided methods and compositions are directed, at least in part, to engineered T cell compositions enriched for CD57− T cells, generated from enriched CD57− T cells from a plurality of donors. In some aspects, the enriched CD57-T cell compositions used to produce the engineered T cell compositions exhibit more consistent features among different T cell compositions, including a more consistent ability to undergo proliferation and expansion, such as during processes for stimulating or engineering T cells. The provided methods and compositions are also directed, at least in part, to engineered T cell compositions enriched for CD27+ T cells, generated from enriched CD27+ T cells from a plurality of donors. In some aspects, the enriched CD27+ T cell compositions used to produce the engineered T cell compositions exhibit more consistent features among different T cell compositions, including a more consistent ability to undergo proliferation and expansion, such as during processes for stimulating or engineering T cells. CD57 (which is also known as HNK1 and LEU7) is a beta-1,3-glucuronyltransferase that may be expressed on the surface of T and NK lymphocytes. In some aspects, CD57 expression, e.g., surface expression, is associated with mature, effector-differentiated sub-populations of T and NK cells. In some aspects, CD57 expression corresponds with T cells or T cell populations that lack expression of co-stimulatory receptors CD28 and CD27, which, in certain aspects, can affect sustained proliferation and cell survival. In particular aspects, CD57 expression may also identify cells with less or reduced proliferative capacity. In some aspects, CD57+ CD28− cell populations may demonstrate shortened telomere length and reduced proliferative capacity as compared to CD57− cell populations (Reviewed in Strioga, Pasukoniene, & Characiejus, Immunol. (2011)). By contrast, CD27 (also known as TNFRSF7) CD27 tends to be more strongly expressed in younger and healthier donors (van Lier et al., J. Immunol. (1987) 139(5):1589-96), and higher content of $CD27^+$ T cells is correlated with better outcome of immunotherapy in treated patients (Worel et al., Blood (2019) 134 (Suppl. 1):1935). CD27 also has an inversely proportional relation to CD57 marker (Kared et al., Cancer Immunol. Immunother. (2016) 65(4):441-52). Thus, it is contemplated herein that enriching for CD27+ cells in a cellular composition may result in a reduced or substantially reduced frequency of CD57+ cells in the composition.

Particular embodiments contemplate that a reduction in the frequency of CD57+ T cells from starting cellular material (e.g. a donor sample), or from cells produced by any other step described in the manufacturing process described herein, used in genetic engineering processes will enrich for cells with greater proliferative capacity. In some aspects, negative selection of CD57+ T cells improves manufacturing success and drug product consistency by pre-enriching for cells that are better poised to expand. For example, negative selection of CD57+ cells may pre-enrich for CD27+ cells, while positive selection of CD27+ cells may pre-enrich for CD57− cells. Additionally, in some embodiments, enriching the populations or compositions of cells with cells exhibiting increased proliferative capacity may reduce the extent of effector cell differentiation, which should aid in improved target product profile consistency across subjects in an autologous setting or across batches in an allogeneic setting (CD27+, CCR7+ T cells).

In some embodiments, the methods are used in connection with a process that generates or produces genetically engineered T cell compositions that are suitable for cell therapy, including allogeneic cell therapy, in a manner that may be faster and more efficient than alternative processes. In certain embodiments, the methods provided herein have a high rate of success for generating or producing compositions of engineered T cells from a broader population of subjects than what may be possible from alternative processes. Thus, in some aspects, the speed and efficiency of the provided methods for generating engineered T cell compositions for cell therapy allow for easier planning and coordination of cell therapy treatments, such as autologous therapy, to a broader population of subjects than what may be possible by some alternative methods. In some aspects, it is contemplated that depletion of CD57+ cells (e.g. CD57+ T cells) is advantageous, such as by improving the consistency of the cell populations in downstream processes. Similarly, it is contemplated that selection of CD27+ cells (e.g. CD27+ T cells) is also advantageous, such as by reduced the frequency of CD57+ cells and/or improving the consistency of the cell populations in downstream processes. For example, it is observed herein that depleting CD57+ cells may deplete cells with less or reduced proliferative capacity, such that depleted compositions exhibited improved consistency in cell proliferation rates. As another example, enrichment of CD27+ cells may enrich for cells with more or increased proliferative capacity, such that enriched compositions exhibited improved consistency in cell proliferation rates. Relatedly, improving consistency in cell proliferation rates may improve consistency in the duration required for cell populations to reach a harvest criterion. It is additionally observed herein that depleting CD57+ cells prior to transducing the cell population with a vector encoding a chimeric antigen receptor (CAR) may improve consistency in the CAR expression of the transduced cells.

In some aspects, pre-selecting incoming donor cells with improved proliferative capacity, e.g., by removing CD57+ T cells or screening for low amounts of CD57+ T cells, can offer improved process control over the number of cells used in a process to generate a cell therapy. In certain embodiments, expression of CD57 may serve as a biomarker indicating cells that exhibit delayed or poor growth. Conversely, expression of CD27 may serve as a biomarker indicating cells that exhibit improved or increased growth. Thus, some of the provided embodiments are directed to methods that utilize one or more selection reagents or process steps to selectively remove CD57+ cells prior to a process for stimulating, genetically engineering, or expanding cells. In some aspects, CD57+ cells may be removed or reduced by virtue of selecting for CD27+ cells. In some aspects, such reagents and process steps may be used in conjunction with CD8+ and CD4+ selection strategies. For example, in some embodiments, selection of CD57+ cells is employed to remove or deplete CD57+ cells from a sample, composition, or population of cells prior to any steps for CD8+ or CD4+ selection. Selection of CD27+ cells may be employed to enrich for CD27+ cells and/or reduce the frequency of CD57+ cells in a sample, composition, or population of cells prior to any steps for CD8+ or CD4+ selection. For example, in some embodiments, selection of CD57+ T cells is employed to remove or deplete CD57+ T cells from a sample, composition, or population of cells prior to any steps for CD8+ or CD4+ selection, thereby generating a CD57-depleted population. In some aspects, it may be advantageous to deplete CD57+ cells by negative selection (as opposed to positive selection), such as prior to any steps for CD8+ or CD4+ selection. In some aspects, depleting CD57+ cells by negative selection, such as prior to any steps for CD8+ or CD4+ selection, reduces the likelihood of the CD57-depleted population being contaminated by one or more reagents or solutions used in the CD57 selection step. In some aspects, such reagents and process steps may be used in conjunction with CD3+ selection strategies. For example, in some embodiments, selection of CD57+ cells is employed to remove or deplete CD57+ cells from a sample, composition, or population of cells prior to any steps for CD3+ selection. Selection of CD27+ cells may be employed to enrich for CD27+ cells and/or reduce the frequency of CD57+ cells in a sample, composition, or population of cells prior to any steps for CD3+ selection. For example, in some embodiments, selection of CD57+ T cells is employed to remove or deplete CD57+ T cells from a sample, composition, or population of cells prior to any steps for CD3+ selection, thereby generating a CD57-depleting population. In some aspects, it may be advantageous to deplete CD57+ cells by negative selection (as opposed to positive selection), such as prior to any steps for CD3+ selection. In some aspects, depleting CD57+ cells by negative selection, such as prior to any steps for CD3+ selection, reduces the likelihood of the CD57-depleted population being contaminated by one or more reagents or solutions used in the CD57 selection step.

For example, in some embodiments, depletion of CD3+ cells is employed to remove or deplete CD3+ cells following genetic engineering of a cell composition that was previously depleted for CD27+ cells and/or enriched for CD27+ cells (e.g. a CD27 enriched T cell population and/or a CD57 depleted T cell population). In particular embodiments, CD27 enriched and/or CD57 depleted T cell populations are subjected to genetic engineering to disrupt one or more genes encoding for a T-cell receptor (TCR) or a component thereof, such as described in Section E.2. In some embodiments, the T cell receptor alpha constant TRAC region is knocked out to disrupt TCR complex formation and CD3 cell-surface expression, such that cells successfully knocked out for TRAC do not exhibit cell surface expression of CD3. Thus, depletion of CD3+ cells in CD57 depleted and/or CD27 enriched compositions subjected to TRAC knockout will ensure the removal of non-edited cells still expressing CD3.

In some embodiments, selection of CD57+ T cells is employed to remove or deplete CD57+ T cells from a sample, composition, or population of cells following any steps for CD8+ or CD4+ selection. Similarly, in some embodiments, selection of CD27+ T cells is employed to enrich for CD27+ cells and/or reduce the frequency of CD57+ T cells from a sample, composition, or population of cells following any steps for CD8+ or CD4+ selection. In some aspects, such reagents and process steps may be used in conjunction with CD3+ selection strategies. For example, in some embodiments, selection of CD57+ T cells is employed to remove or deplete CD57+ T cells from a sample, composition, or population of cells prior to any steps for CD3+ selection. In some embodiments, selection of CD57+ T cells is employed to remove or deplete CD57+ T cells from a sample, composition, or population of cells following any steps for CD3+ selection. In some embodiments, CD57+ cells are selected or removed with CD57-directed magnetic beads that bind CD57+ cells, such as in a column, and the column flow-through (unbound fractions) would then contain a CD57+ depleted cell source, e.g., a population of cells enriched for CD57− T cells. In some embodiments, CD57+ T cells are selected or removed with CD57− directed magnetic beads that bind CD57+ T cells, such as in a column, and the column flow-through (unbound fractions) would then contain a CD57+ depleted cell source, e.g., a population of cells enriched for CD57− T cells. In some embodiments, CD27+ T cells are selected or enriched with CD27-directed magnetic beads or other reagents that bind CD27+ T cells, such as in a column, and the column flow-through (unbound fractions) would then contain a CD27− cell population, which may be discarded prior to elution of the CD27+ enriched cell population In some embodiments, selection of CD57+ T cells is employed to remove or deplete CD57+ T cells from a sample, composition, or population of cells following any steps for CD3+ selection. Similarly, in some embodiments, selection of CD27+ T cells is employed to enrich for CD27+ cells and/or reduce the frequency of CD57+ T cells from a sample, composition, or population of cells following any steps for CD3+ selection. In some aspects, such reagents and process steps may be used in conjunction with CD3+ selection strategies. For example, in some embodiments, selection of CD57+ T cells is employed to remove or deplete CD57+ T cells from a sample, composition, or population of cells prior to any steps for CD3+ selection. In some embodiments, selection of CD57+ T cells is employed to remove or deplete CD57+ T cells from a sample, composition, or population of cells following any steps for CD3+ selection. In some embodiments, CD57+ cells are selected or removed with CD57-directed magnetic beads that bind CD57+ cells, such as in a column, and the column flow-through (unbound fractions) would then contain a CD57+ depleted cell source, e.g., a population of cells enriched for CD57− T cells. In some embodiments, CD57+ T cells are selected or removed with CD57-directed magnetic beads that bind CD57+ T cells, such as in a column, and the column flow-through (unbound fractions) would then contain a CD57+ depleted cell source, e.g., a population of cells enriched for CD57− T cells. In some embodiments, CD27+ T cells are selected or enriched with CD27-directed magnetic beads or other reagents that bind CD27+ T cells, such as in a column, and the column flow-through (unbound fractions) would then contain a CD27− cell population, which may be discarded prior to elution of the CD27+ enriched cell population.

Particular embodiments contemplate that some existing ex vivo T-cell activation or expansion protocols are likely to reduce the presence of CD57+ T cell after an amount of time, such as after the first 48 hours of the process, since CD57+ T cells are less likely to proliferate. In some aspects, the CD57+ cells (e.g. CD57+ T cells) either die during such processes or their frequency is diminished by subsets of cells that are capable of robust expansion. The same processes may enhance the frequency of subsets of cells that are capable of robust expansion, such as CD27+ cells. However, while a natural reduction of CD57+ T cells may occur during such processes, the natural reduction does not control for the quantity of cells entering process that exhibit high proliferative capacity (e.g., CD57− cells). Thus, in some aspects, since CD57+ cells (e.g. CD57+ T cells) are viable but less proliferative cells, they contribute to the overall starting cell number input to the process. Thus, in some embodiments, an advantage of removing CD57+ T cells or verifying low CD57+ T cell content in a sample, composition, or population ensures that the CD57− T cells, e.g., cells with a capacity to proliferate, do not make up a minority population in incoming material. Enriching for CD27+ cells may also ensure that CD27− and/or CD57+ cells do not make up a minority population in incoming material. Thus, in some embodiments, insuring a low frequency of CD57+ T cells or a reduced fraction of proliferating cells could reduce incidences relating to prolonged process times, increased cellular differentiation, and/or failure to meet harvest criteria during the engineering processes.

In some aspects, the provided embodiments are based on the observation that during a process for engineering T cell compositions, such as a manufacturing process for generating compositions containing recombinant receptor-expressing T cells for cell therapy, many cells express or upregulate markers that are associated with stimulation or activation of T cells, including CD25 and CD69 following stimulation, such as incubation of cells in the presence of anti-CD3/anti-CD8 antibodies. In some aspects, only a subset of cells are observed to enter the cell cycle, as shown based on expression of Ki67. In some cases, Ki67+ cells primarily include cells expressing CD27 and CD28, whereas Ki67-populations were observed to be enriched for CD57+ cells and exhibited CD27−CD28− phenotypes. In some aspects, CD57+ cells were observed herein to exhibit phenotypes associated with stimulation or activation, and persisted throughout early stage of the manufacturing process. In some aspects, the frequency of CD57+ T cells decreased after approximately 48 hours after stimulation, which typically which coincided with T-cell expansion and increased viability. In some aspects, particular types of cells, such as CD57+ cells (e.g. CD57+ T cells), exhibited low or no expansion during stimulation or cultivation, while continuing to use growth factors and/or activation reagents, resulting in process and product heterogeneity.

In some aspects, it was observed that when CD57+ cells (e.g. CD57+ T cells) were selected and combined with CD57− cells (e.g. CD57+ T cells) at various ratios prior to stimulation, the frequency of CD57+ cells in the cell composition prior to stimulation (e.g., input composition) was associated with longer process duration. In some aspects, it was also observed that cell compositions, such as compositions containing CAR+ T cells, did not expand or proliferate when 95% or more, such as 100% of the T cells in the composition were CD57+ T cells. It is also observed herein that incoming compositions containing lower frequencies of CD57+ T cells yield engineered cell compositions exhibit more consistent CD4+:CD8+ ratios, as well as CD4+:CD8+ ratios closer to 1:1.

In some aspects, while CD27+ T cells can contribute to expanding cells during a manufacturing process for generating engineered T cells, CD57+ cells e.g. CD57+ T cells) in general did not expand and were observed to contribute minimally to the cells in the engineered cell composition (e.g., cell composition for administration). Thus, the presence of CD57+ T cells can impact the manufacturing process, and also was observed to contribute to variability in the process, e.g., during cultivation and/or expansion, and other cell composition attributes. In some aspects, as provided herein, selective depletion of CD57+ T cells prior to, during, or before any of the steps of the methods provided herein, e.g., in the beginning of a manufacturing process, such as prior to stimulation of cells, can improve the consistency, quality and potency of the engineered cell composition. As an alternative approach, selective enrichment of CD27+ cells prior to, during, or before any of the steps of the method provided herein, can improve the consistency, quality and potency of the engineered cell composition.

Thus, in some embodiments, the provided methods can decrease process duration for generating a cell therapy, including a cell therapy derived from a plurality of donors, and thus, in certain aspects, improve consistency of manufacturing schedules. Further, in some aspects, the speed and efficiency of the provided methods for generating engineered cells for cell therapy allow for easier planning and coordination of cell therapy treatments, such as autologous therapy, to a broader population of subjects than what may be possible by some alternative methods. In some aspects, the provided engineered cells and methods of producing such cells can reduce the costs associated with adoptive cell therapy, while also increasing consistency and availability of such procedures.

In some embodiments, the provided engineered cells, compositions and methods can be used regardless of the HLA type or subtype of a subject (e.g., a patient) to whom the cells may be administered, which can, in some aspects, permit "off-the-shelf" delivery to a wider variety of recipients. In some embodiments, the provided compositions and methods can be used to provide adoptive cell therapy using allogeneic cells engineered to treat a disease or disorder. In some cases, using allogeneic cells can provide certain advantages. In some embodiments, cells with known safety and efficacy profiles can be prepared for a wider variety of patients. For example, cells can be derived from a healthy donor and delivered to a subject that may be too sick to provide cells suitable for genetic engineering. In some cases, a subject may have a defect or disease in the cells or cell type typically used for a particular adoptive cell therapy regimen, such that cells from a healthy donor can be used that replace or supplement the diseased cells. In some cases, the ability to engineer or administer allogeneic cells permits the preparation of cells in advance, which can reduce the time needed before being delivered to a patient. In some cases, the engineered allogeneic cells may present lower risks of causing graft-versus-host disease or host-versus-graft disease.

In certain embodiments, the provided methods successfully remove at least a portion of non-proliferative cells at any point (e.g., the initiation) during the process of generating cells useful for a cell therapy, e.g., populations or compositions of engineered T cells. In some aspects, at least a portion of non-proliferative cells may be removed before, during, or after any step in any of the methods provided herein. In some aspects, this is achieved through selecting out CD57+ cells (e.g. CD57+ T cells) prior to the initiation or such processes, or by screening to ensure that only cell compositions or population having no or low CD57+ T cell content are used for such processes, improve the success the processes, e.g., the rate or frequency of successfully generating cell population suitable for use in a cell therapy. In some aspects, this is achieved through enriching for CD27+ cells (e.g. CD27+ T cells) prior to the initiation or such processes, or by screening to ensure that only cell compositions or population having high CD27+ T cell content are used for such processes.

In some embodiments, CD57+ cells are depleted from a donor sample. In some embodiments, the donor sample is from an individual donor. In some embodiments, the the donor sample is a pooled cell population comprising cells from the plurality of different donors. In some aspects, depletion of CD57+ cells is achieved through selecting out CD57+ cells (e.g. CD57+ T cells) prior to another step of such processes, including genetically engineering. In some embodiments, selecting out CD57+ cells (e.g. CD57+ T cells) is performed prior to stimulating T cells. In some embodiments, selecting out CD57+ cells (e.g. CD57+ T cells) is performed after stimulating cells. In some embodiments, selecting out CD57+ cells (e.g. CD57+ T cells) is performed prior to genetically engineering (e.g. knocking out and/or knocking in) cells. In some embodiments, selecting out CD57+ cells (e.g. CD57+ T cells) is performed on a donor sample from an individual donor. In some embodiments, each of the individual donor samples depleted for CD57+ cells from a plurality of different individual donors are then combined to produce a pooled donor cell population. In some embodiments, each of the individual donor samples from a plurality of different individual donors are combined prior to the depleting for CD57+ T cells, such that a pooled donor sample is depleted for CD57+ cells.

In some embodiments, CD27+ cells are enriched from a donor sample. In some aspects, enrichment of CD27+ cells is achieved through selecting for CD27+ cells (e.g. CD27+ T cells) prior to another step of such processes, including genetically engineering. In some embodiments, selecting for CD27+ cells (e.g. CD27+ T cells) is performed prior to stimulating T cells. In some embodiments, selecting for CD27+ cells (e.g. C27+ T cells) is performed after stimulating cells. In some embodiments, selecting for CD27+ cells (e.g. CD27+ T cells) is performed prior to genetically engineering (e.g. knocking out and/or knocking in) cells. In some embodiments, selecting for CD27+ cells (e.g. CD27+ T cells) is performed on a donor sample from an individual donor. In some embodiments, each of the individual donor samples enriched for CD27+ cells from a plurality of different individual donors are then combined to produce a pooled donor cell population. In some embodiments, each of the individual donor samples from a plurality of different individual donors are combined prior to the enriching for CD27+ T cells, such that a pooled donor sample is enriched for CD27+ cells.

In some embodiments, the provided methods decrease the required duration and number of doublings of the cells, e.g., during proliferation, cultivation, or expansion, to harvesting to yield a requisite number of T cells for use as a cell therapy. Thus, without wishing to be bound by theory, some embodiments contemplate that the provided methods increase or verify a sufficient number of incoming donor cells, such as cells from a donor sample, that exhibit improved proliferative capacity.

In some embodiments, the cell therapies generated from populations of enriched CD57− T cells contain T cells with a lesser degree of differentiation than cell therapies generated from alternative processes. In certain embodiments, the reduced cell differentiation of the cell therapies improves the consistency among the cell therapies generated by the provided processes (e.g., as compared to alternative processes, e.g., cell therapies that are generated from populations of cells containing variable amounts of CD57+ T cells). In certain embodiments, the reduced cell differentiation of the cell therapies, including cell therapies derived from a plurality of different donors, improves the product quality profiles of the cell therapies.

Particular aspects contemplate that CD57 is expressed by NK and NKT cells in addition to T cells, all of which may be present in a biological sample, e.g., leukapheresis material. Thus, in some embodiments, negative selection for CD57+ cells (e.g. CD57+ T cells) reduces residual non-T cells and improves T cell purity. Thus, the provided methods increase the purity of populations of T cells that are processed, such as by stimulation, transduction, or expansion, as well as the T cell purity of resulting cell therapies.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. Compositions of Enriched CD57− T Cells Genetically Engineered with a Recombinant Receptor Provided herein are engineered T cell compositions from a plurality of different donors, and methods of producing the same. In some embodiments, provided herein is a method of preparing a T cell composition from a donor pool that is or includes obtaining a plurality of engineering T cell compositions from a plurality of different donors, each engineered T cell composition containing T cells enriched for T cells surface negative for CD57 (CD57−) from a donor sample from an individual donor of the plurality of different donors, wherein the T cells include T cells genetically engineered with a recombinant receptor; and combining the plurality of engineered T cell compositions to produce a donor pooled engineered T cell composition. In some embodiments, provided herein is a method of preparing a T cell composition from a donor pool that is or includes obtaining a plurality of engineering T cell compositions from a plurality of different donors, each engineered T cell composition containing T cells enriched for T cells surface positive for CD27 (CD27+) from a donor sample from an individual donor of the plurality of different donors, wherein the T cells include T cells genetically engineered with a recombinant receptor; and combining the plurality of engineered T cell compositions to produce a donor pooled engineered T cell composition. In some embodiments, the T cells of the genetically engineered composition are engineered with the same recombinant receptor. In some embodiments, each of the T cells expressing a recombinant receptor in the engineered T cell composition express the same recombinant receptor.

In some embodiments, an engineered T cell composition is generated from an individual donor. In some embodiments, an engineered T cell composition generated from an individual donor is combined with one or more other engineered T cell compositions generated from an individual donor, to comprise a pooled engineered T cell composition from a plurality of different donors. In some embodiments, an engineered T cell composition is generated from a plurality of different donors. In some embodiments, donor samples from a plurality of different donors are combined to generated a pooled donor sample, and the pooled donor sample is engineered to generated an engineered T cell composition from a plurality of different donors.

In some embodiments, the plurality of different donors comprises at least about or about 2 different donors, at least about or about 5 different donors, at least about or about 10 different donors, at least about or about 15 different donors, at least about or about 20 different donors, at least about or about 25 different donors, at least about or about 50 different donors, or at least about or about 100 different donors. In some embodiments, the plurality of different donors comprises at least about or about 2 different donors. In some embodiments, the plurality of different donors comprises at least about or about 5 different donors. In some embodiments, the plurality of different donors comprises at least about or about 10 different donors. In some embodiments, the plurality of different donors comprises at least about or about 15 different donors. In some embodiments, the plurality of different donors comprises at least about or about 20 different donors. In some embodiments, the plurality of different donors comprises at least about or about 25 different donors. In some embodiments, the plurality of different donors comprises at least about or about 50 different donors. In some embodiments, the plurality of different donors comprises at least about or about 100 different donors. In some embodiments, the plurality of different donors comprises fewer than about 25 different donors. In some embodiments, the plurality of different donors comprises fewer than about 50 different donors.

In some embodiments, the plurality of different donors comprises two or more donors that are less than 100% human leukocyte antigen (HLA) matched, less than about 90% HLA matched, less than about 80% HLA matched, less than about 70% HLA matched, less than about 60% HLA matched, or less than about 50% HLA matched. In some embodiments, the plurality of different donors comprises two or more donors that are less than 100% human leukocyte antigen (HLA) matched. In some embodiments, the plurality of different donors comprises two or more donors that are less than 90% human leukocyte antigen (HLA) matched. In some embodiments, the plurality of different donors comprises two or more donors that are less than 80% human leukocyte antigen (HLA) matched. In some embodiments, the plurality of different donors comprises two or more donors that are less than 70% human leukocyte antigen (HLA) matched. In some embodiments, the plurality of different donors comprises two or more donors that are less than 60% human leukocyte antigen (HLA) matched. In some embodiments, the plurality of different donors comprises two or more donors that are less than 50% human leukocyte antigen (HLA) matched.

In some embodiments, the plurality of different donors comprises at least one donor that is healthy or is not suspected of having a disease or condition at the time the cells are obtained from the at least one donor. In some embodiments, the plurality of different donors comprises at least one donor that has a disease or condition at the time the cells are obtained from the at least one donor. In some embodiments, each of the donors of the plurality of different donors is healthy or is not suspected of having a disease or condition at the time the cells are obtained from each of the different donors.

In some embodiments, the engineered T cell composition includes T cells from a donor pool, including a population of cells enriched in human T cells that are surface negative for CD57 (CD57−), wherein the population of cells is from a plurality of different donors, and wherein the plurality of different donors comprises at least two donors that are not 100% human leukocyte antigen (HLA) matched. In some embodiments, the engineered T cell composition includes T cells from a donor pool, including a population of cells enriched in human T cells that are surface positive for CD27 (CD27+), wherein the population of cells is from a plurality of different donors, and wherein the plurality of different donors comprises at least two donors that are not 100% human leukocyte antigen (HLA) matched. In some embodiments, the T cells include T cells genetically engineered with a recombinant receptor.

In some embodiments, an engineered T cell composition is produced by (a) selecting T cells enriched for T cells surface negative for CD57 (CD57−) from the sample from the individual donor, thereby generating a CD57 depleted T cell population; and (b) introducing a heterologous nucleic acid encoding the recombinant receptor into the CD57 depleted cell population, thereby generating the engineered T cell composition. In some embodiments, an engineered T cell composition is produced by (a) selecting T cells enriched for T cells surface positive for CD27 (CD27+) from the sample from the individual donor, thereby generating a CD27 enriched T cell population; and (b) introducing a heterologous nucleic acid encoding the recombinant receptor into the CD27 enriched cell population, thereby generating the engineered T cell composition.

In some embodiments, the recombinant receptor is capable of binding to a target antigen that is associated with, specific to and/or expressed on a cell or tissue of a disease or a condition. In some embodiments, the disease or the condition is an infectious disease or disorder, an autoimmune disease, an inflammatory disease or a tumor or a cancer. In some embodiments, the target antigen is a tumor antigen. In some embodiments, the target antigen is selected from among αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrin receptor A2 (EPHa2), estrogen receptor, Fc receptor like 5 (FCRLS; also known as Fc receptor homolog 5 or FCRHS), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha(IL-22Rα), IL-13 receptor alpha 2 (IL-13Rα2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen or an antigen associated with a universal tag and/or biotinylated molecules and/or molecules expressed by HIV, HCV, HBV or other pathogens.

In some embodiments, the recombinant receptor is or comprises a functional non-TCR antigen receptor or a TCR or antigen-binding fragment thereof. In some embodiments, the recombinant receptor is a chimeric antigen receptor (CAR). In some embodiments, the recombinant receptor comprises an extracellular domain comprising an antigen-binding domain, a spacer and/or a hinge region, a transmembrane domain and an intracellular signaling domain comprising a costimulatory signaling region. In some embodiments, the extracellular domain comprises an antigen-binding domain comprising an scFv. In some embodiments, the intracellular signaling domain is or comprises a primary signaling domain, a signaling domain that is capable of inducing a primary activation signal in a T cell, a signaling domain of a T cell receptor (TCR) component and/or a signaling domain comprising an immunoreceptor tyrosine-based activation motif (ITAM). In some embodiments, the intracellular signaling domain is or comprises an intracellular signaling domain of a CD3 chain, optionally a CD3-zeta (CD3ζ) chain or a signaling portion thereof. In some embodiments, the intracellular signaling domain is an intracellular signaling domain of a CD3-zeta (CD3ζ) chain or a signaling portion thereof. In some embodiments, the costimulatory signaling region comprises an intracellular signaling domain of a CD28, a 4-1BB or an ICOS or a signaling portion thereof. In some embodiments, the costimulatory signaling region comprises an intracellular signaling domain of a 4-1BB or a signaling portion thereof.

In certain embodiments, the engineered T cell composition is or includes viable T cells, CD3+ T cells, CD4+ T cells, and/or CD8+ T cells. In particular embodiments, the cells of the engineered T cell composition are or include viable T cells, CD3+ T cells, CD4+ T cells, and/or CD8+ T cells or a combination of any of the foregoing. In various embodiments, the cells of the engineered T cell composition are or include viable CD57− T cells, CD57− CD3+ T cells, CD57− CD4+ T cells, CD57− CD8+ T cells, or a combination of any of the foregoing. In various embodiments, the cells of the engineered T cell composition are or include viable CD27+ T cells, CD27+ CD3+ T cells, CD27+ CD4+ T cells, CD27+ CD8+ T cells, or a combination of any of the foregoing. In some embodiments, the engineered T cell composition includes CD4+ and CD8+ T cells. In some embodiments, the engineered T cell composition comprises a ratio of CD4+ to CD8+ T cells of between at or about 1:5 and at or about 5:1. In some embodiments, the engineered T cell composition comprises a ratio of CD4+ to CD8+ T cells of between at or about 1:3 and at or about 3:1. In some embodiments, the engineered T cell composition comprises a ratio of CD4+ to CD8+ T cells of between at or about 1:2 and at or about 2:1. In some embodiments, the engineered T cell composition comprises a ratio of CD4+ to CD8+ T cells of about 1:1.

In some embodiments, the engineered T cell composition includes greater than or greater than at or about 75% CD3+/CD57− cells. In some embodiments, the engineered T cell composition includes greater than at or about 80% CD3+/CD57− cells. In some embodiments, the engineered T cell composition includes greater than at or about 85% CD3+/CD57− cells. In some embodiments, the engineered T cell includes greater than at or about 90% CD3+/CD57− cells. In some embodiments, the engineered T cell composition includes or greater than at or about 75% CD3+/CD57− cells. In some embodiments, the engineered T cell composition includes greater than or greater than at or about 40% CD3+/CD57−/recombinant receptor+ cells. In some embodiments, the engineered T cell composition includes greater than at or about 45% CD3+/CD57−/recombinant receptor+ cells. In some embodiments, the engineered T cell composition includes greater than at or about 50% CD3+/CD57−/recombinant receptor+ cells. In some embodiments, the engineered T cell composition includes greater than at or about 55% CD3+/CD57−/recombinant receptor+ cells. In some embodiments, the engineered T cell composition includes greater than at or about 55% CD3+/CD57−/recombinant receptor+ cells. In some embodiments, the engineered T cell composition includes greater than at or about 60% CD3+/CD57−/recombinant receptor+ cells. In some embodiments, the engineered T cell composition includes greater than at or about 65% CD3+/CD57−/recombinant receptor+ cells. In some embodiments, the engineered T cell composition includes greater than at or about 70% CD3+/CD57−/recombinant receptor+ cells.

In some embodiments, the frequency of CD57+ T cells in the composition is less than about or about 35%, 30%, 20%, 10%, 5%, 1% or 0.1% of the frequency of CD57+ T cells in a population of cells not enriched in human T cells that are surface negative for CD57 (CD57−). In some embodiments, the frequency of CD57+ T cells in the composition is less than about or about 30% of the frequency of CD57+ T cells in a population of cells not enriched in human T cells that are surface negative for CD57 (CD57−). In some embodiments, the frequency of CD57+ T cells in the composition is less than about or about 20% of the frequency of CD57+ T cells in a population of cells not enriched in human T cells that are surface negative for CD57 (CD57−). In some embodiments, the frequency of CD57+ T cells in the composition is less than about or about 10% of the frequency of CD57+ T cells in a population of cells not enriched in human T cells that are surface negative for CD57 (CD57−). In some embodiments, the frequency of CD57+ T cells in the composition is less than about or about 5% of the frequency of CD57+ T cells in a population of cells not enriched in human T cells that are surface negative for CD57 (CD57−). In some embodiments, the frequency of CD57+ T cells in the composition is less than about or about 1% of the frequency of CD57+ T cells in a population of cells not enriched in human T cells that are surface negative for CD57 (CD57−). In some embodiments, the frequency of CD57+ T cells in the composition is less than about or about 0.1% of the frequency of CD57+ T cells in a population of cells not enriched in human T cells that are surface negative for CD57 (CD57−).

In some embodiments, the composition comprises less than about 20% CD57+ T cells, less than about 15% CD57+ T cells, less than about 10% CD57+ T cells, less than about 5% CD57+ T cells, less than about 1% CD57+ T cells, or less than about 0.1% CD57+ T cells. In some embodiments, the composition comprises less than about 20% CD57+ T cells. In some embodiments, the composition comprises less than about 15% CD57+ T cells. In some embodiments, the composition comprises less than about 10% CD57+ T cells. In some embodiments, the composition comprises less than about 5% CD57+ T cells. In some embodiments, the composition comprises less than about 1% CD57+ T cells. In some embodiments, the composition comprises less than about 0.1% CD57+ T cells. In some embodiments, the composition is free or essentially free of CD57+ T cells.

In some embodiments, the cells of the composition exhibit a lower coefficient of variation (CV) in expression of one or more molecules, compared to that of a population of cells not enriched in human T cells that are surface negative for CD57 (CD57−). In some embodiments, the coefficient of variation (CV) of the cells of the composition is at least 20% lower, at least 40% lower, at least 60% lower, or at least 80% lower than that of a population of cells not enriched in human T cells that are surface negative for CD57 (CD57−). In some embodiments, the coefficient of variation (CV) of the cells of the composition is at least 20% lower than that of a population of cells not enriched in human T cells that are surface negative for CD57 (CD57−). In some embodiments, the coefficient of variation (CV) of the cells of the composition is at least 40% lower than that of a population of cells not enriched in human T cells that are surface negative for CD57 (CD57−). In some embodiments, the coefficient of variation (CV) of the cells of the composition is at least 60% lower than that of a population of cells not enriched in human T cells that are surface negative for CD57 (CD57−). In some embodiments, the coefficient of variation (CV) of the cells of the composition is at least 80% lower than that of a population of cells not enriched in human T cells that are surface negative for CD57 (CD57−). In some embodiments, the coefficient of variation (CV) of the cells of the composition is at least 90% lower than that of a population of cells not enriched in human T cells that are surface negative for CD57 (CD57−). In some embodiments, the one or more molecules comprises a marker of naïve T cells, optionally CD27, Ki67, CD25, CD28, CCR7, and/or CD45RA. In some embodiments, the one or more molecules is CD27, Ki67, CD25, CD28, CCR7, and/or CD45RA. In some embodiments, the one or more molecules is CD27. In some embodiments, the one or more molecules is Ki67. In some embodiments, the cells of the composition exhibit a lower coefficient of variation (CV) in expression of CD27 and/or Ki67, compared to that of a population of cells not enriched in human T cells that are surface negative for CD57 (CD57−). In some embodiments, the cells of the composition exhibit a lower coefficient of variation (CV) in expression of CD27, compared to that of a population of cells not enriched in human T cells that are surface negative for CD57 (CD57−). In some embodiments, the cells of the composition exhibit a lower coefficient of variation (CV) in expression of Ki67, compared to that of a population of cells not enriched in human T cells that are surface negative for CD57 (CD57−). In some embodiments, the cells of the composition exhibit a lower coefficient of variation (CV) in expression of CD27 and Ki67, compared to that of a population of cells not enriched in human T cells that are surface negative for CD57 (CD57−). In some embodiments, the coefficient of variation (CV) of the cells of the composition is at least 20% lower, at least 40% lower, at least 60% lower, or at least 80% lower than that of a population of cells not enriched in human T cells that are surface negative for CD57 (CD57−). In some embodiments, the coefficient of variation (CV) of the cells of the composition is at least 20% lower than that of a population of cells not enriched in human T cells that are surface negative for CD57 (CD57−). In some embodiments, the coefficient of variation (CV) of the cells of the composition is at least 40% lower than that of a population of cells not enriched in human T cells that are surface negative for CD57 (CD57−). In some embodiments, the coefficient of variation (CV) of the cells of the composition is at least 60% lower than that of a population of cells not enriched in human T cells that are surface negative for CD57 (CD57−). In some embodiments, the coefficient of variation (CV) of the cells of the composition is at least 80% lower than that of a population of cells not enriched in human T cells that are surface negative for CD57 (CD57−). In some embodiments, the coefficient of variation (CV) of the cells of the composition is at least 90% lower than that of a population of cells not enriched in human T cells that are surface negative for CD57 (CD57−).

In some embodiments, the engineered T cell composition includes greater than or greater than at or about 75% CD3+/CD27+ cells. In some embodiments, the engineered T cell composition includes greater than at or about 80% CD3+/CD27+ cells. In some embodiments, the engineered T cell composition includes greater than at or about 85% CD3+/CD27+ cells. In some embodiments, the engineered T cell includes greater than at or about 90% CD3+/CD27+ cells. In some embodiments, the engineered T cell composition includes or greater than at or about 75% CD3+/CD27+ cells. In some embodiments, the engineered T cell composition includes greater than or greater than at or about 40% CD3+/CD27+/recombinant receptor+ cells. In some embodiments, the engineered T cell composition includes greater than at or about 45% CD3+/CD27+/recombinant receptor+ cells. In some embodiments, the engineered T cell composition includes greater than at or about 50% CD3+/CD27+/recombinant receptor+ cells. In some embodiments, the engineered T cell composition includes greater than at or about 55% CD3+/CD27+/recombinant receptor+ cells. In some embodiments, the engineered T cell composition includes greater than at or about 55% CD3+/CD27+/recombinant receptor+ cells. In some embodiments, the engineered T cell composition includes greater than at or about 60% CD3+/CD27+/recombinant receptor+ cells. In some embodiments, the engineered T cell composition includes greater than at or about 65% CD3+/CD27+/recombinant receptor+ cells. In some embodiments, the engineered T cell composition includes greater than at or about 70% CD3+/CD27+/recombinant receptor+ cells.

In some embodiments, the frequency of CD27− T cells in the composition is less than about or about 35%, 30%, 20%, 10%, 5%, 1% or 0.1% of the frequency of CD27− T cells in a population of cells not enriched in human T cells that are surface positive for CD27 (CD27+). In some embodiments, the frequency of CD27− T cells in the composition is less than about or about 30% of the frequency of CD27− T cells in a population of cells not enriched in human T cells that are surface positive for CD27 (CD27+). In some embodiments, the frequency of CD27− T cells in the composition is less than about or about 20% of the frequency of CD27− T cells in a population of cells not enriched in human T cells that are surface positive for CD27 (CD27+). In some embodiments, the frequency of CD27− T cells in the composition is less than about or about 10% of the frequency of CD27− T cells in a population of cells not enriched in human T cells that are surface positive for CD27 (CD27+). In some embodiments, the frequency of CD27− T cells in the composition is less than about or about 5% of the frequency of CD27-T cells in a population of cells not enriched in human T cells that are surface positive for CD27 (CD27+). In some embodiments, the frequency of CD27− T cells in the composition is less than about or about 1% of the frequency of CD27− T cells in a population of cells not enriched in human T cells that are surface positive for CD27 (CD27+). In some embodiments, the frequency of CD27− T cells in the composition is less than about or about 0.1% of the frequency of CD27− T cells in a population of cells not enriched in human T cells that are surface positive for CD27 (CD27+).

In some embodiments, the composition comprises less than about 20% CD27− T cells, less than about 15% CD27− T cells, less than about 10% CD27− T cells, less than about 5% CD27− T cells, less than about 1% CD27− T cells, or less than about 0.1% CD27− T cells. In some embodiments, the composition comprises less than about 20% CD27− T cells. In some embodiments, the composition comprises less than about 15% CD27− T cells. In some embodiments, the composition comprises less than about 10% CD27− T cells. In some embodiments, the composition comprises less than about 5% CD27− T cells. In some embodiments, the composition comprises less than about 1% CD27− T cells. In some embodiments, the composition comprises less than about 0.1% CD27− T cells. In some embodiments, the composition is free or essentially free of CD27− T cells.

In some embodiments, the cells of the composition exhibit a lower coefficient of variation (CV) in expression of one or more molecules, compared to that of a population of cells not enriched in human T cells that are surface positive for CD27 (CD27+). In some embodiments, the coefficient of variation (CV) of the cells of the composition is at least 20% lower, at least 40% lower, at least 60% lower, or at least 80% lower than that of a population of cells not enriched in human T cells that are surface positive for CD27 (CD27+). In some embodiments, the coefficient of variation (CV) of the cells of the composition is about 20% lower than that of a population of cells not enriched in human T cells that are surface positive for CD27 (CD27+). In some embodiments, the coefficient of variation (CV) of the cells of the composition is about 40% lower than that of a population of cells not enriched in human T cells that are surface positive for CD27 (CD27+). In some embodiments, the coefficient of variation (CV) of the cells of the composition is about 60% lower than that of a population of cells not enriched in human T cells that are surface positive for CD27 (CD27+). In some embodiments, the coefficient of variation (CV) of the cells of the composition is about 80% lower than that of a population of cells not enriched in human T cells that are surface positive for CD27 (CD27+). In some embodiments, the coefficient of variation (CV) of the cells of the composition is about 90% lower than that of a population of cells not enriched in human T cells that are surface positive for CD27 (CD27+). In some embodiments, the one or more molecules comprises a marker of naïve T cells. In some embodiments, the one or more molecules is Ki67, CD25, CD28, CCR7, and/or CD45RA. In some embodiments, the one or more molecules is CD28. In some embodiments, the one or more molecules is CD45RA. In some embodiments, the one or more molecules is Ki67. In some embodiments, the cells of the composition exhibit a lower coefficient of variation (CV) in expression of Ki67, compared to that of a population of cells not enriched in human T cells that are surface positive for CD27 (CD27+).

In some embodiments, the T cells of the composition comprise T cells knocked out for expression of (i) an endogenous major histocompatibility complex (MHC) or a component thereof, optionally beta-2-microglobulin 032M); and/or (ii) an endogenous T cell receptor (TCR) or a component thereof, optionally T cell receptor alpha constant (TRAC). In some embodiments, the endogenous MHC is comprises MHC class I protein or a component thereof. In some embodiments, the endogenous MHC comprises beta-2-microglobulin 032M). In some embodiments, the endogenous TCR or a component thereof comprises T cell receptor alpha constant (TRAC) and/or T cell receptor beta constant (TRBC). In some embodiments, the endogenous TCR or a component thereof comprises T-cell receptor alpha constant (TRAC). In some embodiments, the T cells of the composition comprise T cells knocked out for expression of (i) beta-2-microglobulin (132M); and/or (ii) T cell receptor alpha constant (TRAC). In some embodiments, the T cells of the composition comprise T cells knocked out for expression of (i) beta-2-microglobulin (132M); and (ii) T cell receptor alpha constant (TRAC). In some embodiments, the heterologous polynucleotide encoding a recombinant receptor is inserted into the genetic locus of the TRAC gene.

In some embodiments, the composition is for treatment of a subject having a disease or condition. In some embodiments, the composition is for use in a treating a subject having a disease or condition. In some embodiments, the composition is for use in manufacture of a medicament for treating a disease or condition. In some embodiments, the disease or condition is a cancer or a tumor.

In some embodiments, the cells of the composition are formulated for administration as one or more unit doses and the cells comprise at least about 100 unit doses of the cells, at least about 200 unit doses of the cells, at least about 300 unit doses of the cells, at least about 400 unit doses of the cells, at least about 500 unit doses of the cells, at least about 600 unit doses, at least about or at least about 1,000 unit doses of the cells. In some embodiments, the unit dose comprises between about 10 and 75 million cells per milliliter. In some embodiments, the unit dose comprises between and between about $5.0\times10^6$ and $2.25\times10^7$, $5.0\times10^6$ and $2.0\times10^7$, $5.0\times10^6$ and $1.5\times10^7$, $5.0\times10^6$ and $1.0\times10^7$, $5.0\times10^6$ and $7.5\times10^6$, $7.5\times10^6$ and $2.25\times10^7$, $7.5\times10^6$ and $2.0\times10^7$, $7.5\times10^6$ and $1.5\times10^7$, $7.5\times10^6$ and $1.0\times10^7$, $1.0\times10^7$ and $2.25\times10^7$, $1.0\times10^7$ and $2.0\times10^7$, $1.0\times10^7$ and $1.5\times10^7$, $1.5\times10^7$ and $2.25\times10^7$, $1.5\times10^7$ and $2.0\times10^7$, or $2.0\times10^7$ and $2.25\times10^7$ cells, optionally between and between about $5.0\times10^6$ and $2.25\times10^7$, $5.0\times10^6$ and $2.0\times10^7$, $5.0\times10^6$ and $1.5\times10^7$, $5.0\times10^6$ and $1.0\times10^7$, $5.0\times10^6$ and $7.5\times10^6$, $7.5\times10^6$ and $2.25\times10^7$, $7.5\times10^6$ and $2.0\times10^7$, $7.5\times10^6$ and $1.5\times10^7$, $7.5\times10^6$ and $1.0\times10^7$, $1.0\times10^7$ and $2.25\times10^7$, $1.0\times10^7$ and $2.0\times10^7$, $1.0\times10^7$ and $1.5\times10^7$, $1.5\times10^7$ and $2.25\times10^7$, $1.5\times10^7$ and $2.0\times10^7$, or $2.0\times10^7$ and $2.25\times10^7$ recombinant receptor-expressing cells. In some embodiments, the composition is comprised in a container. In some embodiments, the unit dose contains about $5.0\times10^6$ recombinant receptor-expressing cells. In some embodiments, the unit dose contains about $1.0\times10^7$ recombinant receptor-expressing cells. In some embodiments, the unit dose contains about $1.5\times10^7$ recombinant receptor-expressing cells. In some embodiments, the unit dose contains about $3.0\times10^7$ recombinant receptor-expressing cells. In some embodiments, the unit dose contains about $4.5\times10^7$ recombinant receptor-expressing cells. In some embodiments, the unit dose contains about $6.0\times10^7$ recombinant receptor-expressing cells. In some embodiments, the unit dose contains about $8.0\times10^7$ recombinant receptor-expressing cells. In some embodiments, the unit dose contains about $1.0\times10^8$ recombinant receptor-expressing cells. In some embodiments, the unit dose contains about $1.5\times10^8$ recombinant receptor-expressing cells. In some embodiments, the unit dose contains about $3.0\times10^8$ recombinant receptor-expressing cells. In some embodiments, the unit dose contains about $4.5\times10^8$ recombinant receptor-expressing cells. In some embodiments, the unit dose contains about $6.0\times10^8$ recombinant receptor-expressing cells. In some embodiments, the unit dose contains about $8.0\times10^8$ recombinant receptor-expressing cells. In some embodiments, the unit dose contains about $1.0\times10^9$ recombinant receptor-expressing cells.

In some embodiments, the container is a bag, optionally a freezing bag. In some embodiments, the composition is comprised in a freezing bag filled with the composition to a volume that is between or between about 15 mL and 150 mL, 20 mL and 100 mL, 20 mL and 80 mL, 20 mL and 60 mL, 20 mL and 40 mL, 40 mL and 100 mL, 40 mL and 80 mL, 40 mL and 60 mL, 60 mL and 100 mL, 60 mL and 80 mL or 80 mL and 100 mL, each inclusive; or at least or at least about 15 mL, at least or at least about 20 mL, at least or at least about 30 mL, at least or at least about 40 mL, at least or at least about 50 mL, at least or at least about 60 mL, at least or at least about 70 mL, at least or at least about 80 mL or at least or at least about 90 mL; and/or no more than 100 mL.

In some embodiments, the cells of the composition are for administration to at least 2 subjects, at least 5 subjects, at least 10 subjects, at least 25 subjects, at least 50 subjects, at least 100 subjects, at least 200 subjects, at least 500 subjects, or at least 1,000 subjects. In some embodiments, the cells of the composition are for administration to at least 2 subjects. In some embodiments, the cells of the composition are for administration to at least 5 subjects. In some embodiments, the cells of the composition are for administration to at least 10 subjects. In some embodiments, the cells of the composition are for administration to at least 25 subjects. In some embodiments, the cells of the composition are for administration to at least 50 subjects. In some embodiments, the cells of the composition are for administration to at least 100 subjects. In some embodiments, the cells of the composition are for administration to at least 200 subjects. In some embodiments, the cells of the composition are for administration to at least 500 subjects. In some embodiments, the cells of the composition are for administration to at least 1,000 subjects.

In some embodiments, the composition comprises a cryprotectant. In some embodiments, the composition comprises a pharmaceutically acceptable excipient.

II. Methods of Producing Compositions of Enriched CD57− T Cells Genetically Engineered with a Recombinant Receptor In some embodiments, the provided methods include isolating, selecting, or enriching cells or populations of cells from a biological sample (e.g. a donor sample) to generate one or more compositions of enriched cells, e.g., CD57− T cells, engineered with a recombinant receptor. In some embodiments, the provided methods include isolating, selecting, or enriching cells or populations of cells from a biological sample (e.g. a donor sample) to generate one or more compositions of enriched cells, e.g., CD27+ T cells, engineered with a recombinant receptor. In some embodiments, the provided methods include isolation of cells or populations thereof from biological samples (e.g. donor samples), such as those obtained from allogeneic sources. In some embodiments, the allogeneic sources are one or more donors, such as one or more donors. In some embodiments, the one or more donors does not have a particular disease or condition or is not in need of a cell therapy or to which cell therapy will be administered.

In some embodiments, provided herein is a method of preparing a T cell composition from a donor pool that is or includes (A) obtaining a plurality of engineered T cell compositions from a plurality of different donors, each engineered T cell composition including T cells enriched for T cells surface negative for CD57 (CD57−) from a donor sample from an individual donor of the plurality of different donors, wherein the T cells include T cells genetically engineered with a recombinant receptor; and (B) combining the plurality of engineered T cell compositions to produce a donor pooled engineered T cell composition. In some embodiments, each of the plurality of T cell compositions is generated by a process that is or includes (a) selecting T cells enriched for T cells surface negative for CD57 (CD57−) from a donor sample from the individual donor, thereby generating a CD57 depleted T cell population; and (b) introducing a heterologous nucleic acid encoding the recombinant receptor into the CD57 depleted cell population, thereby generating the engineered T cell composition. In some embodiments, provided herein is a method of preparing a T cell composition from a donor pool that is or includes (A) obtaining a plurality of engineered T cell compositions from a plurality of different donors, each engineered T cell composition including T cells enriched for T cells surface positive for CD27 (CD27+) from a donor sample from an individual donor of the plurality of different donors, wherein the T cells include T cells genetically engineered with a recombinant receptor; and (B) combining the plurality of engineered T cell compositions to produce a donor pooled engineered T cell composition. In some embodiments, each of the plurality of T cell compositions is generated by a process that is or includes (a) selecting T cells enriched for T cells surface positive for CD27 (CD27+) from a donor sample from the individual donor, thereby generating a CD27 enriched T cell population; and (b) introducing a heterologous nucleic acid encoding the recombinant receptor into the CD27 enriched cell population, thereby generating the engineered T cell composition. In some embodiments, the recombinant receptor expressed by T cells in the engineered T cell composition is the same recombinant receptor. In some aspects, each T cell in the engineered T cell composition expressing a recombinant receptor expresses the same recombinant receptor.

In some aspects, provided herein is a method of preparing a T cell composition from a donor pool that is or includes (a) selecting T cells enriched for T cells surface negative for CD57 (CD57−) from a donor sample from an individual donor, thereby generating a CD57 depleted T cell population; (b) genetically engineering the CD57 depleted T cell population, thereby producing an engineered T cell composition, the genetic engineering being or including (1) knocking out expression of (i) an endogenous major histocompatibility complex (MHC) or a component thereof, optionally beta-2-microglobulin 032M); and/or (ii) an endogenous T cell receptor (TCR) or a component thereof, optionally TRAC, in cells of the CD57 depleted T cell population; and (2) introducing a heterologous nucleic acid encoding the recombinant receptor into the cells of the knocked out T cell composition into the cells of the CD57 depleted T cell population, optionally wherein the heterologous nucleic acid is inserted into a locus of a gene encoding for the endogenous MHC and/or the endogenous TCR; wherein the knocking out in (1) and the introducing in (2) can be carried out concurrently or successively in either order; (c) repeating steps (a) and (b) for a plurality of different donors to produce a plurality of engineered T cell compositions, wherein each engineered T cell composition is generated from cells from an individual donor of the plurality of different donors; and (d) combining a the plurality of engineered T cell compositions from a the plurality of different individual donors.

In some aspects, provided herein is a method of preparing a T cell composition from a donor pool that is or includes (a) selecting T cells enriched for T cells surface positive for CD27 (CD27+) from a donor sample from an individual donor, thereby generating a CD27 enriched T cell population; (b) genetically engineering the CD27 enriched T cell population, thereby producing an engineered T cell composition, the genetic engineering being or including (1) knocking out expression of (i) an endogenous major histocompatibility complex (MHC) or a component thereof, optionally beta-2-microglobulin (β32M); and/or (ii) an endogenous T cell receptor (TCR) or a component thereof, optionally TRAC, in cells of the CD27 enriched T cell population; and (2) introducing a heterologous nucleic acid encoding the recombinant receptor into the cells of the knocked out T cell composition into the cells of the CD27 enriched T cell population, optionally wherein the heterologous nucleic acid is inserted into a locus of a gene encoding for the endogenous MHC and/or the endogenous TCR; wherein the knocking out in (1) and the introducing in (2) can be carried out concurrently or successively in either order; (c) repeating steps (a) and (b) for a plurality of different donors to produce a plurality of engineered T cell compositions, wherein each engineered T cell composition is generated from cells from an individual donor of the plurality of different donors; and (d) combining a the plurality of engineered T cell compositions from a the plurality of different individual donors.

In some aspects, provided herein is a method of preparing a T cell composition from a donor pool that is or includes (a) selecting for one of (i) cells surface positive for a T cell marker and (ii) cells surface negative for CD57 (CD57−) from a donor sample from a plurality of different donors, thereby generating an enriched population of cells; and (b) selecting, from the enriched population of cells, the other of (i) cells surface of a T cell marker and (ii) CD57-cells, thereby generating a CD57 depleted population. In some aspects, the donor sample is a pooled sample having cells from the plurality of different donors, whereby the method produces a pooled CD57 depleted T cell population. In some aspects, provided herein is a method of preparing a T cell composition from a donor pool that is or includes (a) selecting for one of (i) cells surface positive for a T cell marker and (ii) cells surface positive for CD27 (CD27+) from a donor sample from a plurality of different donors, thereby generating an enriched population of cells; and (b) selecting, from the enriched population of cells, the other of (i) cells surface positive for a T cell marker and (ii) CD27+ cells, thereby generating a CD27 enriched population. In some aspects, the donor sample is a pooled sample having cells from the plurality of different donors, whereby the method produces a pooled CD27 enriched T cell population.

In some aspects, provided herein is method of preparing a T cell composition from a donor pool that is or includes selecting for T cells that are surface negative for CD57 (CD57−) from a donor sample, wherein the donor sample is a pooled cell population enriched for human T cells from a plurality of different donors, thereby generating a pooled CD57 depleted T cell population. In some aspects provided herein is a method of preparing a T cell composition from a donor pool that is or includes selecting for T cells from a donor sample, wherein the donor sample is a pooled cell population enriched for human T cells that are surface negative for CD57 (CD57) from a plurality of different donors, thereby generating a pooled CD57 depleted T cell population. In some aspects, provided herein is method of preparing a T cell composition from a donor pool that is or includes selecting for T cells that are surface positive for CD27 (CD27+) from a donor sample, wherein the donor sample is a pooled cell population enriched for human T cells from a plurality of different donors, thereby generating a pooled CD27 enriched T cell population. In some aspects provided herein is a method of preparing a T cell composition from a donor pool that is or includes selecting for T cells from a donor sample, wherein the donor sample is a pooled cell population enriched for human T cells that are surface positive for CD27 from a plurality of different donors, thereby generating a pooled CD27 enriched T cell population.

In some aspects, provided herein is a method of preparing a T cell composition from a donor pool that is or includes (a) selecting for T cells that are surface negative for CD57 (CD57−) from a donor sample, wherein the donor sample is enriched for human T cells from an individual donor, thereby generating a CD57 depleted T cell population; (b) repeating step (a) for a plurality of different individual donors; and (c) combining each of the CD57 depleted T cell populations from each of the individual donors, thereby generating a pooled CD57 depleted T cell population. In some aspects, provided herein is a method of preparing a T cell composition from a donor pool that is or includes (a) selecting for T cells from a donor sample, wherein the sample is enriched for human T cells that are surface negative for CD57 (CD57−) from an individual donor, thereby generating a CD57 depleted T cell population; (b) repeating step (a) for a plurality of different donors; and (c) combining each of the CD57 depleted T cell populations from each of the individual donors, thereby generating a pooled CD57 depleted T cell population.

In some aspects, provided herein is a method of preparing a T cell composition from a donor pool that is or includes (a) selecting for T cells that are surface positive for CD27 (CD27+) from a donor sample, wherein the donor sample is enriched for human T cells from an individual donor, thereby generating a CD27 enriched T cell population; (b) repeating step (a) for a plurality of different individual donors; and (c) combining each of the CD27 enriched T cell populations from each of the individual donors, thereby generating a pooled CD27 enriched T cell population. In some aspects, provided herein is a method of preparing a T cell composition from a donor pool that is or includes (a) selecting for T cells from a donor sample, wherein the sample is enriched for human T cells that are surface positive for CD27 (CD27+) from an individual donor, thereby generating a CD27 enriched T cell population; (b) repeating step (a) for a plurality of different donors; and (c) combining each of the CD27 enriched T cell populations from each of the individual donors, thereby generating a pooled CD27 enriched T cell population.

Also provided herein is a method of preparing a T cell composition from a donor pool that is or comprises (i) selecting for one of (a) cells surface positive for CD3 (CD3+), CD4 (CD4+), and/or CD8 (CD8+) and (b) cells surface negative for CD57 (CD57−) from a donor sample, thereby generating an enriched population of cells; (ii) selecting, from the enriched population of cells, the other of (a) CD3+, CD4+, and/or CD8+ cells and (b) CD57-cells, thereby generating a CD57 depleted T cell population; (iii) stimulating cells of the CD57 depleted T cell population under stimulating conditions; (iv) knocking out expression of (a) an endogenous major histocompatibility complex (MHC) or a component thereof, optionally beta-2-microglobulin 032M); and/or (b) an endogenous T cell receptor (TCR) or a component thereof, optionally T cell receptor alpha constant (TRAC), in the stimulated cells; (v) introducing a heterologous polynucleotide encoding a recombinant receptor into the knocked out cells, optionally into a locus of a gene encoding for TRAC, thereby generating an engineered T cell population; (vi) incubating the engineered cells for up to 96 hours, optionally at a temperature of at or about 37°±2° C.; and (vii) cultivating the cells under conditions to promote proliferation or expansion, wherein the donor sample is a sample derived from an individual donor and any of steps (i) through (vii) are repeated separately for each donor sample from a plurality of different donors prior to combining the plurality of donor samples into a pooled CD57 depleted T cell composition.

Also provided herein is a method of preparing a T cell composition from a donor pool that is or comprises (i) selecting for one of (a) cells surface positive for CD3 (CD3+), CD4 (CD4+), and/or CD8 (CD8+) and (b) cells surface positive for CD27 (CD27+) from a donor sample, thereby generating an enriched population of cells; (ii) selecting, from the enriched population of cells, the other of (a) CD3+, CD4+, and/or CD8+ cells and (b) CD27+ cells, thereby generating a CD27 enriched T cell population; (iii) stimulating cells of the CD27 enriched T cell population under stimulating conditions; (iv) knocking out expression of (a) an endogenous major histocompatibility complex (MHC) or a component thereof, optionally beta-2-microglobulin 032M); and/or (b) an endogenous T cell receptor (TCR) or a component thereof, optionally T cell receptor alpha constant (TRAC), in the stimulated cells; (v) introducing a heterologous polynucleotide encoding a recombinant receptor into the knocked out cells, optionally into a locus of a gene encoding for TRAC, thereby generating an engineered T cell population; (vi) incubating the engineered cells for up to 96 hours, optionally at a temperature of at or about 37°±2° C.; and (vii) cultivating the cells under conditions to promote proliferation or expansion, wherein the donor sample is a sample derived from an individual donor and any of steps (i) through (vii) are repeated separately for each donor sample from a plurality of different donors prior to combining the plurality of donor samples into a pooled CD27 enriched T cell composition.

In some aspects, the CD57 depleted T cell population and/or the pooled CD57 depleted T cell population is genetically engineered. In some aspects, the CD27 enriched T cell population and/or the pooled CD27 enriched T cell population is genetically engineered. In some embodiments, the genetic engineering includes introducing a heterologous polypeptide encoding a recombinant receptor into cells of the population. In some embodiments, the genetic engineering further includes genetic disrupting, such as by targeted disruption of one or more molecules, such as one or more genetic loci. In some embodiments, genetically disrupted cells are said to be "knocked out." The introducing the heterologous polypeptide and the genetic disruption (e.g. knocking out) are performed concurrently. In some embodiments, the introducing the heterologous polypeptide and the genetic disruption (e.g. knocking out) are performed sequentially, in either order. In some embodiments, the heterologous polypeptide is introduced into a disrupted (e.g. knocked out) genetic locus of a T cell.

A. Donors

In some embodiments, the engineered compositions generated from the isolation, selection, or enriching of one or more donor samples can be used regardless of the HLA type or subtype of the donor. In some embodiments, the engineered compositions generated from the isolation, selection, or enriching of one or more donor samples can be used regardless of the HLA type or subtype of a subject to which the engineered compositions may be administered. That the engineered composition can be used regardless of donor and/or subject HLA type or subtype can, in some aspects, permit "off-the-shelf" delivery to a wider variety of recipients. In some embodiments, the provided compositions and methods can be used to provide adoptive cell therapy using allogeneic cells engineered to treat a disease or disorder. In some cases, using allogeneic cells can provide certain advantages. In some embodiments, cells with known safety and efficacy profiles can be prepared for a wider variety of patients. For example, cells can be derived from a healthy donor and delivered to a subject that may be too sick to provide cells suitable for genetic engineering. In some cases, a subject may have a defect or disease in the cells or cell type typically used for a particular adoptive cell therapy regimen, such that cells from a healthy donor can be used that replace or supplement the diseased cells. In some cases, the ability to engineer or administer allogeneic cells permits the preparation of cells in advance, which can reduce the time needed before being delivered to a patient. In some cases, the engineered allogeneic cells may present lower risks of causing graft-versus-host disease or host-versus-graft disease.

In some aspects, the donor sample is a sample is from an individual donor. In some aspects, samples from a plurality of different individual donors are combined into a donor sample. In some aspects, the donor sample is from samples from a plurality of different individual donors. In some aspects, the donor sample is from a plurality of different donors. In some aspects, the individual donor is a human. In some aspects, each of the plurality of different donors is a human. In some aspects, the plurality of different donors are human donors.

In some aspects, the individual donor is not a patient in need of a particular therapeutic intervention, such as the adoptive cell therapy for which cells are being isolated, processed, and/or engineered. In some aspects, each of the individual donors of the plurality of different donors is not a patient in need of a particular therapeutic intervention, such as the adoptive cell therapy for which cells are being isolated, processed, and/or engineered. In some aspects, the plurality of different donors are not patients in need of a particular therapeutic intervention, such as the adoptive cell therapy for which cells are being isolated, processed, and/or engineered.

In some aspects, the individual donor is a patient in need of a particular therapeutic intervention, such as the adoptive cell therapy for which cells are being isolated, processed, and/or engineered. In some aspects, each of the individual donors of the plurality of different donors is a patient in need of a particular therapeutic intervention, such as the adoptive cell therapy for which cells are being isolated, processed, and/or engineered. In some aspects, the plurality of different donors are patients in need of a particular therapeutic intervention, such as the adoptive cell therapy for which cells are being isolated, processed, and/or engineered.

In some aspects, the generated engineered compositions of enriched cells, e.g. CD57− T cells are for use in treating a subject. In some aspects, the generated engineered compositions of enriched cells, e.g. CD27+ T cells are for use in treating a subject. In some embodiments, the subject is not a donor. In some embodiments, the subject is not one of a plurality of different donors. In some embodiments, the T cells of the composition are not derived from the subject. In some embodiments, at least a portion of the T cells of the composition are not derived from the subject. In some embodiments, less than 100% of the T cells of the composition are HLA-identical to the T cells of the subject. In some embodiments, at least a portion of the T cells of the composition are allogeneic to the subject. In some embodiments, all of the T cells of the composition are allogeneic to the subject.

In some aspects, the generated engineered compositions of enriched cells, e.g. CD57− T cells are for use in treating a subject. In some aspects, the generated engineered compositions of enriched cells, e.g. CD27+ T cells are for use in treating a subject. In some embodiments, the subject is a donor. In some embodiments, the subject is one of a plurality of different donors. In some embodiments, at least a portion of the T cells of the composition are not derived from the subject. In some embodiments, less than 100% of the T cells of the composition are HLA-identical to the T cells of the subject. In some embodiments, at least a portion of the T cells of the composition are allogeneic to the subject.

In some embodiments, the sample (e.g. donor sample) comprises primary human T cells from an individual donor. In some embodiments, each of the samples (e.g. donor samples) from a plurality of different individual donors are combined. In some embodiments, the sample (e.g. donor sample) comprises primary human T cells from a plurality of different donors. In some embodiments, the plurality of different donors comprises at least about or about 2 different donors, at least about or about 5 different donors, at least about or about 10 different donors, at least about or about 15 different donors, at least about or about 20 different donors, at least about or about 25 different donors, at least about or about 50 different donors, or at least about or about 100 different donors. In some embodiments, the plurality of different donors comprises about 2 different donors. In some embodiments, the plurality of donors comprises about 5 different donors. In some embodiments, the plurality of different donors comprises about 10 different donors. In some embodiments, the plurality of different donors comprises about 15 different donors. In some embodiments, the plurality of different donors comprises about 20 different donors. In some embodiments, the plurality of different donors comprises about 25 different donors. In some embodiments, the plurality of different donors comprises about 30 different donors. In some embodiments, the plurality of different donors comprises about 40 different donors. In some embodiments, the plurality of different donors comprises about 50 different donors. In some embodiments, the plurality of different donors comprises about 60 different donors. In some embodiments, the plurality of different donors comprises about 80 different donors. In some embodiments, the plurality of different donors comprises about 100 different donors.

In some embodiments, one or more donors is evaluated for human leukocyte antigen (HLA) matching. HLA matching depends on the level of resolution and which HLA loci (e.g. "markers") are assessed. In some cases, between about 6 markers and about 12 markers are assessed to determine HLA match. For example, 10 HLA markers that may be assessed are the HLA-A, —B, —C, -DRB1, and -DQB1 loci. In such cases, two individuals would be 100% HLA matched if they share all loci (e.g. 10/10). For example, 8 HLA markers that may be assessed are the HLA-A, —B, —C, and -DRB1 loci. In such cases, two individuals would be 100% HLA matched if they share all loci (e.g. 8/8). Tiercy, Haematologica. 2016; 101(6):680-7.

In some embodiments, a donor is evaluated for at least 6, at least 7, at least 8, at least 9, at least 10, at least 11, or at least 12 HLA markers. In some embodiments, one or more donors is evaluated for HLA matching to one or more other donors, where a 100% HLA match indicates that the donors being evaluated for matching match for each HLA marker being evaluated (e.g. 6/6, 8/8, 10/10, or 12/12 markers). In some embodiments, the plurality of different donors comprises two or more donors that are less than 100% human leukocyte antigen (HLA) matched, less than about 90% HLA matched, less than about 80% HLA matched, less than about 70% HLA matched, less than about 60% HLA matched, or less than about 50% HLA matched. In some embodiments, the plurality of different donors comprises two or more donors that are less than 100% human leukocyte antigen (HLA) matched. In some embodiments, the plurality of different donors comprises two or more donors that are less than about 90% HLA matched. In some embodiments, the plurality of different donors comprises two or more donors that are less than about 80% HLA matched. In some embodiments, the plurality of different donors comprises two or more donors that are less than about 70% HLA matched. In some embodiments, the plurality of different donors comprises two or more donors that are less than about 60% HLA matched. In some embodiments, the plurality of different donors comprises two or more donors that are less than about 50% HLA matched. In some embodiments, the plurality of different donors comprises at least two donors that are not 100% HLA matched.

In some embodiments, the individual donor is healthy or is not suspected of having a disease or condition at the time the donor sample is obtained from the individual donor. In some embodiments, each of the individual donors of a plurality of different individual donors is healthy or is not suspected of having a disease or condition at the time the donor samples are obtained from the individual donors. In some embodiments, the plurality of different donors comprises least one donor that is healthy or is not suspected of having a disease or condition at the time the donor sample is obtained from the at least one donor. In some embodiments, the plurality of different donors are healthy or are not suspected of having a disease or condition at the time the donor samples are obtained from the plurality of different donors. In some embodiments, the individual donor has a disease or condition at the time the donor sample is obtained from the individual donor. In some embodiments, each of the individual donors has a disease or condition at the time the donor samples are obtained from the individual donors. In some embodiments, the plurality of different donors comprises at least one donor that has a disease or condition at the time the donor sample is obtained from the at least one donor. In some embodiments, the plurality of different donors are healthy or are not suspected of having a disease or condition at the time the donor samples are obtained from the donors.

In some embodiments, an individual is selected as a donor based on the frequency of T cells expressing CD57 and/or CD27 in a sample from the individual. In some embodiments, an individual is selected as a donor based on a low frequency of CD57+ cells among T cells in the sample. In some embodiments, an individual is selected as a donor if the frequency of CD57− cells among T cells in a sample from the individual is less than about 50%, less than about 40%, less than about 30%, less than about 2%, or less than about 10%. In some embodiments, an individual is selected as a donor if the frequency of CD57− cells among T cells in a sample from the individual is between about 0% and about 50%, or between about 0% and about 30%. In some embodiments, an individual is selected as a donor if the frequency of CD57− cells among T cells in a sample from the individual is less than about 50%. In some embodiments, an individual is selected as a donor if the frequency of CD57− cells among T cells in a sample from the individual is less than about 40%. In some embodiments, an individual is selected as a donor if the frequency of CD57− cells among T cells in a sample from the individual is less than about 30%. In some embodiments, an individual is selected as a donor if the frequency of CD57− cells among T cells in a sample from the individual is less than about 20%. In some embodiments, an individual is selected as a donor if the frequency of CD57− cells among T cells in a sample from the individual is less than about 10%.

In some embodiments, an individual is selected as a donor based on a high frequency of CD27+ cells among T cells in the sample. In some embodiments, an individual is selected as a donor if the frequency of CD27+ cells among T cells in a sample from the individual is at least about 50%, at least about 60%, at least about 70%, at least about 80%, or at least about 90%. In some embodiments, an individual is selected as a donor if the frequency of CD27+ cells among T cells in a sample from the individual is between about 50% and about 100%, or between about 70% and about 100%. In some embodiments, an individual is selected as a donor if the frequency of CD27+ cells among T cells in a sample from the individual is at least about 50%. In some embodiments, an individual is selected as a donor if the frequency of CD27+ cells among T cells in a sample from the individual is at least about 60%. In some embodiments, an individual is selected as a donor if the frequency of CD27+ cells among T cells in a sample from the individual is at least about 70%. In some embodiments, an individual is selected as a donor if the frequency of CD27+ cells among T cells in a sample from the individual is at least about 80%. In some embodiments, an individual is selected as a donor if the frequency of CD27+ cells among T cells in a sample from the individual is at least about 90%.

B. Samples and Cell Preparation

In particular embodiments, the provided methods are used in connection with isolating, selecting, or enriching cells from a biological sample to generate one or more populations of enriched cells, e.g., CD57− T cells (a CD57 depleted T cell population and/or a pooled CD57 depleted T cell population). In particular embodiments, the provided methods are used in connection with isolating, selecting, or enriching cells from a biological sample to generate one or more populations of enriched cells, e.g., CD27+ T cells (a CD27 enriched T cell population and/or a pooled CD27 enriched T cell population). In some embodiments, the provided methods include isolation of cells or populations thereof from biological samples (e.g. donor samples), such as a donor sample obtained from or derived from one or more donors, such as one not having a particular disease or condition or not in need of a cell therapy or to which cell therapy will be administered.

In some aspects, the donor sample is a sample is from an individual donor. In some aspects, samples from a plurality of different individual donors are combined into a donor sample. In some aspects, the donor sample is from samples from a plurality of different individual donors. In some aspects, the donor sample is from a plurality of different donors. In some aspects, the individual donor is a human. In some aspects, each of the plurality of different donors is a human. In some aspects, the plurality of different donors are human donors.

In some aspects, the generated one or more populations of enriched cells, e.g. CD57− T cells (a CD57 depleted T cell population and/or a pooled CD57 depleted T cell population) are for use in treating a subject. In some aspects, the generated one or more populations of enriched cells, e.g. CD27+ T cells (a CD27 enriched T cell population and/or a pooled CD27 enriched T cell population) are for use in treating a subject. In some embodiments, the subject is not a donor. In some aspects, the subject is a human, such as a subject who is a patient in need of a particular therapeutic intervention, such as the adoptive cell therapy for which cells are being isolated, processed, and/or engineered. Accordingly, the cells in some embodiments are primary cells, e.g., primary human cells.

In some embodiments, the sample (e.g. donor sample) comprises primary human T cells from an individual donor. In some embodiments, each of the samples (e.g. donor samples) from a plurality of different individual donors are combined. In some embodiments, the sample (e.g. donor sample) comprises primary human T cells from a plurality of different donors.

The samples include tissue, fluid, and other samples taken directly from the donor. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources. In some embodiments, the samples are from allogeneic sources (e.g. donors). In some embodiments, the samples are from autologous sources (e.g. donors). In some embodiments, the sample is or comprises a whole blood sample, a buffy coat sample, a peripheral blood mononuclear cells (PBMC) sample, an unfractionated T cell sample, a lymphocyte sample, a white blood cell sample, an apheresis product, or a leukapheresis product.

In some examples, cells from the circulating blood of a donor are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets.

In some embodiments, the blood cells collected from the donor are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, Ca++/Mg++ free PBS. In certain embodiments, components of a blood cell sample are removed and the cells directly resuspended in culture media.

In some embodiments, the sample containing cells (e.g., a donor sample, such as an apheresis product or a leukapheresis product) is washed in order to remove one or more anti-coagulants, such as heparin, added during apheresis or leukapheresis.

In some embodiments, the sample containing cells (e.g., donor sample, such as a whole blood sample, a buffy coat sample, a peripheral blood mononuclear cells (PBMC) sample, an unfractionated T cell sample, a lymphocyte sample, a white blood cell sample, an apheresis product, or a leukapheresis product) is cryopreserved and/or cryoprotected (e.g., frozen) and then thawed and optionally washed prior to any steps for isolating, selecting, activating, stimulating, disrupting (e.g. knocking out), engineering (e.g. knocking in), transducing, transfecting, incubating, culturing, harvesting, formulating a population of the cells, and/or administering the formulated cell population to a subject.

In some embodiments, a sample (e.g. donor sample) containing autologous Peripheral Blood Mononuclear Cells (PBMCs) from a subject is collected in a method suitable to ensure appropriate quality for manufacturing. In one aspect, the sample containing PBMCs (e.g. donor sample) is derived from fractionated whole blood. In some embodiments, whole blood from a donor is fractionated by leukapheresis using a centrifugal force and making use of the density differences between cellular phenotypes, when autologous mononuclear cells (MNCs) are preferentially enriched while other cellular phenotypes, such as red blood cells, are reduced in the collected cell composition. In some embodiments, autologous plasma is concurrently collected during the MNC collection, which in some aspects can allow for extended leukapheresis product stability. In one aspect, the autologous plasma is added to the leukapheresis product to improve the buffering capacity of the leukapheresis product matrix. In some aspects, a total volume of whole blood processed in order to generate the leukapheresis product is or is about 2 L, 4 L, 6 L, 8 L, 10 L, 12 L, 14 L, 16 L, 18 L, or 20 L, or is any value between any of the foregoing. In some embodiments, the volume of autologous plasma collected is or is about 10 mL, 50 mL, 100 mL, 150 mL, 200 mL, 250 mL, or 300 mL, or more, or is a volume between any of the foregoing. In some embodiments, the leukapheresis product is subjected to a procedure, e.g., washing and formulation for in-process cryopreservation, within about 48 hours of the leukapheresis collection completion. In some embodiments, the leukapheresis product is subjected to one or more wash steps, e.g., within about 2 hours, 6 hours, 12 hours, 18 hours, 24 hours, 36 hours, or 48 hours of the leukapheresis collection completion. In some aspects, the one or more wash step removes the anticoagulant during leukapheresis collection, cellular waste that may have accumulated in the leukapheresis product, residual platelets and/or cellular debris. In some embodiments, one or more buffer exchange is performed during the one or more wash step. In some embodiments, the sample or is or includes an apheresis product. In some embodiments, the sample is or includes a leukapheresis product.

In particular embodiments, an apheresis product or a leukapheresis product is cryopreserved and/or cryoprotected (e.g., frozen) and then thawed before being subjected to a cell enrichment, selection or isolation step (e.g., a T cell selection or isolation step) as described infra. In some embodiments, after a cryopreserved and/or cryoprotected apheresis product or leukapheresis product is subjected to a T cell selection or isolation step, no additional cryopreservation and/or cryoprotection step is performed during or between any of the subsequent steps, such as the steps of activating, stimulating, disrupting (e.g. knocking out) engineering (e.g. knocking in), transducing, transfecting, incubating, culturing, harvesting, formulating a population of the cells, and/or administering the formulated cell population to a subject. For example, T cells selected from a thawed cryopreserved and/or cryoprotected apheresis product or leukapheresis product are not again cryopreserved and/or cryoprotected before being thawed and optionally washed for a downstream process, such as T cell activation/stimulation or transduction.

In particular embodiments, an apheresis product or a leukapheresis product is cryopreserved and/or cryoprotected (e.g., frozen) at a density of, of about, or at least $5\times10^6$ cells/mL, $10\times10^6$ cells/mL, $20\times10^6$ cells/mL, $30\times10^6$ cells/mL, $40\times10^6$ cells/mL, $50\times10^6$ cells/mL, $60\times10^6$ cells/mL, $70\times10^6$ cells/mL, $80\times10^6$ cells/mL, $90\times10^6$ cells/mL, $100\times10^6$ cells/mL, $110\times10^6$ cells/mL, $120\times10^6$ cells/mL, $130\times10^6$ cells/mL, $140\times10^6$ cells/mL, or $150\times10^6$ cells/mL, or any value between any of the foregoing, in a cryopreservation solution or buffer. In some embodiments, the cryopreservation solution or buffer is or contains, for example, a DMSO solution optionally comprising human serum albumin (HSA), or other suitable cell freezing media.

In particular embodiments, the cryopreserved and/or cryoprotected apheresis product or leukapheresis product is banked (e.g., without T cell selection before freezing the sample), which, in some aspects, can allow more flexibility for subsequent manufacturing steps. In some aspects, the cryopreserved and/or cryoprotected apheresis product or leukapheresis product is aliquoted into multiple cryopreservation container such as bags, which can each individually or in combination be used in processing of the product. For example, when the total number of viable cells in the apheresis product or leukapheresis product is less than $15\times10^9$ cells, the cryopreserved and/or cryoprotected apheresis product or leukapheresis product is aliquoted into four cryopreservation container such as bags. In some embodiments, when the total number of viable cells in the apheresis product or leukapheresis product is $15\text{-}30\times10^9$ cells, the cryopreserved and/or cryoprotected apheresis product or leukapheresis product is aliquoted into eight cryopreservation container such as bags.

In one aspect, banking cells before selection increases cell yields for a downstream process, and banking cells earlier may mean they are healthier and may be easier to meet manufacturing success criteria. In another aspect, once thawed, the cryopreserved and/or cryoprotected apheresis product or leukapheresis product can be subject to one or more different selection methods. Advantages of this approach are, among other things, to enhance the availability, efficacy, and/or other aspects of cells of a cell therapy for treatment of a disease or condition of a subject, such as in the donor of the sample and/or another recipient.

In some embodiments, the donor is also the subject and/or the donor has or is suspected of having a disease or condition. In some embodiments, the donor is an individual donor. In some embodiments, the individual donor has or is suspected of having a disease or condition. In some embodiments, the donor is a plurality of different donors. In some embodiments, or at least one donor of the plurality of different donors has or is suspected of having a disease or condition. In some embodiments, the sample (e.g. donor sample, such as an apheresis or leukapheresis sample) is collected and cryopreserved and/or cryoprotected prior to or without prior cell selection (e.g., without prior T cell selection, such as selection by chromatography), at a time after the donor is diagnosed with a disease or condition. In some aspects, the time of cryopreservation also is before the donor has received one or more of the following: any initial treatment for the disease or condition, any targeted treatment or any treatment labeled for treatment for the disease or condition, or any treatment other than radiation and/or chemotherapy. In some embodiments, the sample is collected after a first relapse of a disease following initial treatment for the disease, and before the subject receives subsequent treatment for the disease. The initial and/or subsequent treatments may be a therapy other than a cell therapy. In some embodiments, the collected cells may be used in a cell therapy following initial and/or subsequent treatments. In one aspect, the cryopreserved and/or cryoprotected sample (e.g. donor sample) without prior cell selection may help reduce up-front costs, such as those associated with non-treatment patients in a randomized clinic trial who may crossover and require treatment later.

In some embodiments, the donor is also the subject and/or the donor has or is suspected of having a disease or condition. In some embodiments, the donor is an individual donor. In some embodiments, the individual donor has or is suspected of having a disease or condition. In some embodiments, the donor is a plurality of different donors. In some embodiments, at least one donor of the plurality of different donors has or is suspected of having a disease or condition. In some embodiments, the sample (e.g. the donor sample, such as an apheresis or leukapheresis sample) is collected and cryopreserved and/or cryoprotected prior to or without prior cell selection (e.g., without prior T cell selection, such as selection by chromatography), at a time after a second relapse of a disease following a second line of treatment for the disease, and before the subject receives subsequent treatment for the disease. In some embodiments, patients are identified as being likely to relapse after a second line of treatment, for example, by assessing certain risk factors. In some embodiments, the risk factors are based on disease type and/or genetics, such as double-hit lymphoma, primary refractory cancer, or activated B-cell lymphoma. In some embodiments, the risk factors are based on clinical presentation, such as early relapse after first-line treatment, or other poor prognostic indicators after treatment (e.g., IPI (International Prognostic Index)>2).

In some embodiments, the donor is also the subject and/or the donor has or is suspected of having a disease or condition. In some embodiments, the donor is an individual donor. In some embodiments, the individual donor has or is suspected of having a disease or condition. In some embodiments, the donor is a plurality of different donors. In some embodiments, at least one donor of the plurality of different donors has or is suspected of having a disease or condition. In some embodiments, the sample (e.g. donor sample, such as an apheresis or leukapheresis sample) is collected and cryopreserved and/or cryoprotected prior to or without prior cell selection (e.g., without prior T cell selection, such as selection by chromatography), at a time before the donor is diagnosed with a disease. In some aspects, the donor may be determined to be at risk for developing a disease. In some aspects, the donor may be a healthy subject. In certain cases, the donor may elect to bank or store cells without being deemed at risk for developing a disease or being diagnosed with a disease in the event that cell therapy is required at a later stage in life. In some embodiments, a donor may be deemed at risk for developing a disease based on factors such as genetic mutations, genetic abnormalities, genetic disruptions, family history, protein abnormalities (such as deficiencies with protein production and/or processing), and lifestyle choices that may increase the risk of developing a disease. In some embodiments, the cells are collected as a prophylactic.

In some embodiments, the cryopreserved and/or cryoprotected sample of cells (e.g. donor sample, such as an apheresis or leukapheresis sample), such as a sample of cells that has not been subjected to a prior cell selection (e.g., without prior T cell selection, such as selection by chromatography) is stored, or banked, for a period of time greater than or equal to 12 hours, 24 hours, 36 hours, or 48 hours, or greater than or equal to 0.5 days, one day, 1.5 days, or two days. In some embodiments, the sample is stored or banked for a period of time greater than or equal to 1 week, 2 weeks, 3 weeks, or 4 weeks. In some embodiments, the sample is placed into long-term storage or long-term banking. In some aspects, the sample is stored for a period of time greater than or equal to 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, 40 years, or more.

In some embodiments, an apheresis or leukapheresis sample taken from a donor (e.g. a donor sample) is shipped in a cooled environment to a storage or processing facility, and/or cryogenically stored at the storage facility or processed at the processing facility. In some embodiments, the donor is an individual donor. In some embodiments, the donor is a plurality of different donors. In some embodiments, before shipping, the sample (e.g. donor sample) is processed, for example, by selecting T cells, such as CD3+ T cells, CD4+ T cells, and/or CD8+ T cells. In some embodiments, such processing is performed after shipping and before cryogenically storing the sample (e.g. donor sample). In some embodiments, the processing is performed after thawing the sample (e.g. donor sample) following cryogenically storage.

In some embodiments, the donor is also the subject and/or the donor has or is suspected of having a disease or condition. In some embodiments, the donor is an individual donor. In some embodiments, the individual donor has or is suspected of having a disease or condition. In some embodiments, the donor is a plurality of different donors. In some embodiments, at least one donor of the plurality of different donors has or is suspected of having a disease or condition. By allowing donors to store their cells at a stage when the donors, and thus their cells, have not undergone extensive treatment for a disease and/or prior to contracting of a disease or condition or diagnosis thereof, such cells may have certain advantages for use in cell therapy compared to cells harvested after one or after multiple rounds of treatment. For example, cells harvested before one or more rounds of treatment may be healthier, may exhibit higher levels of certain cellular activities, may grow more rapidly, and/or may be more receptive to genetic manipulation than cells that have undergone several rounds of treatment. Another example of an advantage according to embodiments described herein may include convenience. For example, by collecting, optionally processing, and storing a donor's cells before they are needed for cell therapy, the cells would be readily available if and when a recipient later needs them. This could increase apheresis lab capacity, providing technicians with greater flexibility for scheduling the apheresis collection process.

In some embodiments, the donor sample is frozen e.g., cryopreserved and/or cryoprotected, prior to any steps of selecting, incubating, activating, stimulating, engineering (e.g. knocking out and/or knocking in), transducing, transfecting, cultivating, expanding, harvesting, and/or formulating the cells. Exemplary methods and systems for cryogenic storage and processing of cells from a sample, such as an apheresis sample, can include those described in WO2018170188. In some embodiments, the method and systems involve collecting apheresis before the patient needs cell therapy, and then subjecting the apheresis sample to cryopreservation for later use in a process for engineering the cells, e.g. T cells, with a recombinant receptor (e.g. CAR). In some cases, such processes can include those described herein. In some embodiments, an apheresis sample (e.g. donor sample) is collected from a donor (e.g. an individual donor or a plurality of different donors) and cryopreserved prior to subsequent T cell selection, activation, stimulation, disrupting (e.g. knocking out), engineering (e.g. knocking in), transduction, transfection, incubation, culturing, harvest, formulation of a population of the cells, and/or administration of the formulated cell population to a subject. In such examples, the cryopreserved apheresis sample (e.g. donor sample) is thawed prior to subjecting the sample (e.g. donor sample) to one or more selection steps, such as any as described herein.

In some embodiments, the cryopreserved and/or cryoprotected sample of cells (e.g. donor sample, such as an apheresis or leukapheresis sample), such as a sample of cells that has not been subjected to a prior cell selection (e.g., without prior T cell selection, such as selection by chromatography) is thawed prior to its use for downstream processes for manufacture of a cell population for cell therapy, for example, a T cell population containing CAR+ T cells. In some embodiments, such a cryopreserved and/or cryoprotected sample of cells (e.g. donor sample, such as an apheresis or leukapheresis sample) is used in connection with the process provided herein for engineered a T cell therapy, such as a CAR+ T cell therapy. In particular examples, no further step of cryopreservation is carried out prior to or during the harvest/formulation steps.

In some embodiments, a cryopreserved and/or cryoprotected apheresis product or leukapheresis product (e.g. a donor sample) is thawed. In some embodiments, the thawed cell composition is subjected to dilution (e.g., with a serum-free medium) and/or wash (e.g., with a serum-free medium), which in some cases can remove or reduce unwanted or undesired components. In some cases, the dilution and/or wash removes or reduces the presence of a cryoprotectant, e.g. DMSO, contained in the thawed sample, which otherwise may negatively impact cellular viability, yield, recovery upon extended room temperature exposure. In some embodiments, the dilution and/or wash allows media exchange of a thawed cryopreserved product into a serum-free medium, such as in PCT/US2018/064627, which is incorporated herein by reference.

In some embodiments, the serum-free medium comprises a basal medium (e.g. OpTimizer™ T-Cell Expansion Basal Medium (ThermoFisher), supplemented with one or more supplement. In some embodiments, the one or more supplement is serum-free. In some embodiments, the serum-free medium comprises a basal medium supplemented with one or more additional components for the maintenance, expansion, and/or activation of a cell (e.g., a T cell), such as provided by an additional supplement (e.g. OpTimizer™ T-Cell Expansion Supplement (ThermoFisher)). In some embodiments, the serum-free medium further comprises a serum replacement supplement, for example, an immune cell serum replacement, e.g., ThermoFisher, #A2596101, the CTS™ Immune Cell Serum Replacement, or the immune cell serum replacement described in Smith et al. *Clin Transl Immunology.* 2015 January; 4(1): e31. In some embodiments, the serum-free medium further comprises a free form of an amino acid such as L-glutamine. In some embodiments, the serum-free medium further comprises a dipeptide form of L-glutamine (e.g., L-alanyl-L-glutamine), such as the dipeptide in Glutamax™ (ThermoFisher). In some embodiments, the serum-free medium further comprises one or more recombinant cytokines, such as recombinant human IL-2, recombinant human IL-7, and/or recombinant human IL-15.

C. Selection Of CD57− T Cells and/or Depletion Of CD57+ T Cells

In some embodiments, a CD57− enriched population (the pooled CD57 depleted T cell population and/or the CD57 depleted T cell population) is obtained from a biological sample (e.g. a donor sample). In particular embodiments, the pooled CD57 depleted T cell population and/or the CD57 depleted T cell population is selected, isolated, or enriched from the biological sample (e.g. the donor sample). In some embodiments, a donor sample is a sample from an individual donor. In some embodiments, a donor sample includes cells from a plurality of different donors. In some embodiments, a plurality of samples, each from a different individual donor, are combined to produce a donor sample.

In some embodiments, the donor sample is derived from an individual donor. In some embodiments, a donor sample from an individual donor is enriched for CD57− T cells to produce a CD57 depleted T cell population. In some embodiments, CD57 depleted T cell populations from a plurality of different individual donors are combined to produced a pooled CD57 depleted T cell population. In some embodiments, the donor sample is derived from a plurality of different donors. In some embodiments, a donor sample from a plurality of different donors is enriched for CD57− T cells to produce a pooled CD57− T cell population.

In particular embodiments, CD57+ T cells are removed, separated, or depleted from a biological sample (e.g. a donor sample). In certain embodiments, at least 25%, 30%, 35%, 40%, 45%, 50%, 55%, 60%, 65%, 70%, 75%, 80%, 85%, 90%, 95%, 99%, or 99.9% CD57+ T cells are removed, separated, or depleted from the donor sample.

In particular embodiments, subsets of cells, e.g., subsets of T cells, are selected, isolated, or enriched from the donor sample prior to selecting, isolating, or enriching CD57− T cells from the donor sample. In some embodiments, subsets of cells, e.g., T cells are selected, isolated, or enriched from the population of enriched CD57− T cells.

In some embodiments, the pooled CD57 depleted T cell population and/or the CD57 depleted T cell population contains, contains about, or contains less than 50%, 45%, 40%, 35%, 30%, 25%, 20%, 15%, 10%, 5%, 1%, 0.1%, 0.01%, or 0.001% of the CD57+ T cells of the donor sample, e.g., prior the selection, isolation, or enrichment. In particular embodiments, the pooled CD57 depleted T cell population and/or the CD57 depleted T cell population contains, contains about, or contains less than 20% of the CD57+ T cells of the donor sample. In certain embodiments, the pooled CD57 depleted T cell population and/or the CD57 depleted T cell population contains, contains about, or contains less than 5% of the CD57+ T cells of the donor sample. In some embodiments, the pooled CD57 depleted T cell population and/or the CD57 depleted T cell population contains, contains about, or contains less than 1% of the CD57+ T cells of the donor sample e.g., prior the selection, isolation, or enrichment. In various embodiments, the pooled CD57 depleted T cell population and/or the CD57 depleted T cell population contains, contains about, or contains less than 0.1% of the CD57+ T cells of the donor sample. In particular embodiments, the pooled CD57 depleted T cell population and/or the CD57 depleted T cell population contains, contains about, or contains less than 0.01% of the CD57+ T cells of the donor sample. In some embodiments, the frequency of the CD57+ T cells in the pooled CD57 depleted T cell population and/or the CD57 depleted T cell population is less than at or about 35%, 30%, 20%, 10%, 5%, 1%, or 0.1% of the frequency of CD57+ T cells in the donor sample. In some embodiments, the pooled CD57 depleted T cell population and/or the CD57 depleted T cell population comprises less than at or about 3%, less than at or about 2%, less than at or about 1%, less than at or about 0.1%, or less than at or about 0.01% CD57+ T cells. In some embodiments, the the pooled CD57 depleted T cell population and/or the CD57 depleted T cell population is free or is essentially free of CD57+ T cells.

In some embodiments, the pooled CD57 depleted T cell population and/or the CD57 depleted T cell population exhibit a lower coefficient of variation (CV) in expression of one or more molecules, compared to that of the cells of the donor sample. In some embodiments the one or more molecules is a marker of naïve T cells, optionally CD27, Ki67, CD25, CD28, CCR7, and/or CD45RA. In some embodiments the one or more molecules is CD27. In some embodiments, the cells of the CD57 depleted T cell population and/or the pooled CD57 depleted T cell population exhibit a lower CV in expression of CD27.

In particular embodiments, the cells of the pooled CD57 depleted T cell population and/or the CD57 depleted T cell population are less differentiated than the cells of the donor sample, e.g., prior the selection, isolation, or enrichment. In certain embodiments, the pooled CD57 depleted T cell population and/or the CD57 depleted T cell population contains a greater frequency of naïve-like cells than the donor sample. In certain embodiments, the pooled CD57 depleted T cell population and/or the CD57 depleted T cell population includes, includes about, or includes at least at or about 25%, 30%, 35%, 40%, 45%, 50%, 55%, 60%, 65%, 70%, 75%, 80%, 85%, 90%, 95%, 100%, 125%, 150%, 1-fold, 2-fold, 3-fold, 4-fold, 5-fold, or 10 fold more naïve-like cells than the donor sample e.g., prior the selection, isolation, or enrichment. In some embodiments, naïve-like cells include naïve T cells or central memory T cells. In some embodiments, naïve-like cells can include cells positive or expressing high levels of one or more surface markers, e.g., CD28+, CD62 L+, CCR7+, CD27+, CD127+, CD4+, CD8+, CD45RA+, and/or CD45RO+ T cells. In some aspects, the cells are CD27+. In some aspects, the cells are CD28+. In some aspects, the cells are CCR7+. In particular aspects, CCR7 is expressed by naïve or naïve-like T cells (e.g. CCR7+ CD45RA+ or CCR7+ CD27+) and central memory T cells (CCR7+ CD45RA−). In certain embodiments, naïve-like T cells or the T cells that are surface positive for a marker expressed on naïve-like T cells are CCR7+ CD45RA+, where the cells are CD27+ or CD27−. In certain embodiments, naïve-like T cells or the T cells that are surface positive for a marker expressed on naïve-like T cells are CD27+ CCR7+, where the cells are CD45RA+ or CD45RA−. In certain embodiments, naïve-like T cells or the T cells that are surface positive for a marker expressed on naïve-like T cells are CD62 L-CCR7+. In certain embodiments, naïve-like cells include cells at an early stage of differentiation (e.g., cells that are CCR7+ CD27+).

In certain embodiments, central memory T cells may include cells in various differentiation states and may be characterized by positive or high expression (e.g., surface expression) of certain cell markers and/or negative or low expression (e.g., surface expression) of other cell markers. In some aspects, less differentiated cells, e.g., central memory cells, are longer lived and exhaust less rapidly, thereby increasing persistence and durability. In some aspects, a responder to a cell therapy, such as a CAR-T cell therapy, has increased expression of central memory genes. See, e.g., Fraietta et al. (2018) Nat Med. 24(5):563-571. In some aspects, central memory T cells are characterized by positive or high expression of CD45RO, CD62L, CCR7, CD28, CD3, and/or CD127. In some aspects, central memory T cells are characterized by negative or low expression of CD45RA and/or granzyme B. In certain embodiments, central memory T cells or the T cells that are surface positive for a marker expressed on central memory T cells are CCR7+ CD45RA−.

In particular embodiments, the pooled CD57 depleted T cell population and/or the CD57 depleted T cell population includes, includes about, or includes at least at or about 25%, 30%, 35%, 40%, 45%, 50%, 55%, 60%, 65%, 70%, 75%, 80%, 85%, 90%, 95%, 100%, 125%, 150%, 1-fold, 2-fold, 3-fold, 4-fold, 5-fold, or 10 fold more CD27+ T cells than the biological sample e.g., prior the selection, isolation, or enrichment. In particular embodiments, the pooled CD57 depleted T cell population and/or the CD57 depleted T cell population includes, includes about, or includes at least at or about 25%, 30%, 35%, 40%, 45%, 50%, 55%, 60%, 65%, 70%, 75%, 80%, 85%, 90%, 95%, 100%, 125%, 150%, 1-fold, 2-fold, 3-fold, 4-fold, 5-fold, or 10 fold more CD28+ T cells than the biological sample e.g., prior the selection, isolation, or enrichment. In various embodiments, the pooled CD57 depleted T cell population and/or the CD57 depleted T cell population includes, includes about, or includes at least at or about 25%, 30%, 35%, 40%, 45%, 50%, 55%, 60%, 65%, 70%, 75%, 80%, 85%, 90%, 95%, 100%, 125%, 150%, 1-fold, 2-fold, 3-fold, 4-fold, 5-fold, or 10 fold more CD25+ T cells than the biological sample e.g., prior the selection, isolation, or enrichment. In certain embodiments, the pooled CD57 depleted T cell population and/or the CD57 depleted T cell population includes, includes about, or includes at least at or about 25%, 30%, 35%, 40%, 45%, 50%, 55%, 60%, 65%, 70%, 75%, 80%, 85%, 90%, 95%, 100%, 125%, 150%, 1-fold, 2-fold, 3-fold, 4-fold, 5-fold, or 10 fold more CCR7+ T cells than the biological sample e.g., prior the selection, isolation, or enrichment. In certain embodiments, the pooled CD57 depleted T cell population and/or the CD57 depleted T cell population includes, includes about, or includes at least at or about 25%, 30%, 35%, 40%, 45%, 50%, 55%, 60%, 65%, 70%, 75%, 80%, 85%, 90%, 95%, 100%, 125%, 150%, 1-fold, 2-fold, 3-fold, 4-fold, 5-fold, or 10 fold more CD45RA+ cells than the biological sample e.g., prior the selection, isolation, or enrichment.

In certain embodiments, T cells, e.g., CD3+ T cells, are selected, isolated, or enriched from the donor sample prior to selecting, isolating, or enriching CD57− T cells from the donor sample. In some embodiments, T cells, e.g., CD3+ T cells, are selected, isolated, or enriched from the pooled CD57 depleted T cell population and/or the CD57 depleted T cell population. In particular embodiments, selecting, isolating or enriching T cells, e.g. CD3+ T cells, involves positive selection of the cells from the donor sample.

In some embodiments, CD57+ cells are selected, isolated, or enriched from a donor sample, cell composition, or cell population, thereby producing isolated or selected CD57+ cells and a pooled CD57 depleted T cell population and/or a CD57 depleted T cell population.

In certain embodiments, CD3+ T cells are enriched, selected, or isolated from the pooled CD57 depleted T cell population and/or the CD57 depleted T cell population, thereby generating a population of enriched CD57− CD3+ T cells and a non-selected population of enriched CD57− cells. In certain embodiments, CD3+ T cells are enriched, selected, or isolated from the non-selected population of enriched CD57− cells, thereby generating a population of enriched CD57−CD3+ T cells. In various embodiments, CD3+ T cells are enriched, selected, or isolated from the pooled CD57 depleted T cell population and/or the CD57 depleted T cell population, thereby generating a population of enriched CD57− CD3+ T cells and a non-selected population enriched for CD57− cells, and then CD4+ or CD8+ T cells are enriched, selected, or isolated from the non-selected population of enriched CD57− cells, thereby generating a population of enriched CD57−CD4+ T cells or CD57−CD8+ T cells.

In certain embodiments, subsets of T cells, e.g., CD4+ or CD8+ T cells, are selected, isolated, or enriched from the donor sample prior to selecting, isolating, or enriching CD57− T cells from the donor sample. In some embodiments, subsets of T cells, e.g., CD4+ or CD8+ T cells, are selected, isolated, or enriched from the pooled CD57 depleted T cell population and/or the CD57 depleted T cell population. In particular embodiments, the selecting, isolating or enriching a subset of T cells, e.g. CD4+ or CD8+ T cells, involves positive selection of the cells from the sample.

In some embodiments, CD57+ cells are selected, isolated, or enriched from a sdonor ample, cell composition, or cell population, thereby producing isolated or selected CD57+ cells and a pooled CD57 depleted T cell population and/or a CD57 depleted T cell population. In certain embodiments, CD57+ cells are selected, isolated, or enriched from a biological sample, thereby producing isolated or selected CD57+ cells and a pooled CD57 depleted T cell population and/or a CD57 depleted T cell population.

In particular embodiments, CD4+ T cells are enriched, selected, or isolated from the pooled CD57 depleted T cell population and/or the CD57 depleted T cell population, thereby generating a population of enriched CD57− CD4+ T cells and a non-selected population enriched for CD57− cells. In certain embodiments, CD8+ T cells are enriched, selected, or isolated from the pooled CD57 depleted T cell population and/or the CD57 depleted T cell population, thereby generating a population of enriched CD57− CD8+ T cells and a non-selected population of enriched CD57− cells. In certain embodiments, CD8+ T cells are enriched, selected, or isolated from the non-selected population of enriched CD57-cells, thereby generating a population of enriched CD57−CD8+ T cells. In particular embodiments, CD4+ T cells are enriched, selected, or isolated from the non-selected population of enriched CD57− cells, thereby generating a population of enriched CD57−CD4+ T cells.

In particular embodiments, CD4+ T cells are enriched, selected, or isolated from the pooled CD57 depleted T cell population and/or the CD57 depleted T cell population, thereby generating a population of enriched CD57− CD4+ T cells and a non-selected population enriched for CD57− cells, and then CD8+ T cells are enriched, selected, or isolated from the non-selected population of enriched CD57-cells, thereby generating a population of enriched CD57− CD8+ T cells. In various embodiments, CD4+ T cells are enriched, selected, or isolated from the pooled CD57 depleted T cell population and/or the CD57 depleted T cell population, thereby generating a population of enriched CD57− CD4+ T cells and a non-selected population enriched for CD57− cells, and then CD8+ T cells are enriched, selected, or isolated from the non-selected population of enriched CD57− cells, thereby generating a population of enriched CD57−CD8+ T cells.

In particular embodiments, (1) CD4+ T cells are enriched, selected, or isolated from a donor sample, thereby generating a population of enriched CD4+ T cells and a non-selected population enriched for CD4− cells; (2) CD8+ T cells are enriched, selected, or isolated from the non-selected population of enriched CD4− cells, thereby generating a population of enriched CD8+ T cells; and (3) CD57+ T cells are depleted from the enriched CD4+ and CD8+ T cell populations, generating populations of enriched CD57− CD4+ and CD57−CD8+ T cells. In particular embodiments, (1) CD8+ T cells are enriched, selected, or isolated from a donor sample, thereby generating a population of enriched CD8+ T cells and a non-selected population enriched for CD8− cells; (2) CD4+ T cells are enriched, selected, or isolated from the non-selected population of enriched CD4− cells, thereby generating a population of enriched CD4+ T cells; and (3) CD57+ T cells are depleted from the enriched CD4+ and CD8+ T cell populations, generating populations of enriched CD57−CD4+ and CD57−CD8+ T cells.

In particular embodiments, CD4+ T cells are enriched, selected, or isolated from a donor sample, thereby generating an enriched population of CD4+ T cells, and then CD57+ cells are removed from the enriched population of CD4+ T cells, thereby generating a population of enriched CD57− CD4+ T cells. In particular embodiments, CD8+ T cells are enriched, selected, or isolated from a donor sample, thereby generating an enriched population of CD8+ T cells, and then CD57+ cells are removed from the enriched population of CD8+ T cells, thereby generating a population of enriched CD57−CD8+ T cells.

In some embodiments, the pooled CD57 depleted T cell population and/or the CD57 depleted T cell population is frozen, e.g., cryopreserved and/or cryoprotected, after isolation, selection and/or enrichment. In particular embodiments, a population of enriched CD57− CD4+ T cells is frozen, e.g., cryopreserved and/or cryoprotected, after isolation, selection and/or enrichment. In certain embodiments, a population of enriched CD57− CD8+ T cells is frozen, e.g., cryopreserved and/or cryoprotected, after isolation, selection and/or enrichment. In certain embodiments, a population of enriched CD57− CD3+ T cells is frozen, e.g., cryopreserved and/or cryoprotected, after isolation, selection and/or enrichment. In some embodiments, the pooled CD57 depleted T cell population and/or the CD57 depleted T cell population is frozen e.g., cryopreserved and/or cryoprotected, prior to any steps of incubating, activating, stimulating, engineering (e.g. knocking out and/or knocking in), transducing, transfecting, cultivating, expanding, harvesting, and/or formulating the population of cells. In particular embodiments, a population of enriched CD57− CD4+ T cells is frozen e.g., cryopreserved and/or cryoprotected, prior to any steps of incubating, activating, stimulating, engineering (e.g. knocking out and/or knocking in), transducing, transfecting, cultivating, expanding, harvesting, and/or formulating the population of cells. In some embodiments, a population of enriched CD57− CD8+ T cells is frozen e.g., cryopreserved and/or cryoprotected, prior to any steps of incubating, activating, stimulating, engineering (e.g. knocking out and/or knocking in), transducing, transfecting, cultivating, expanding, harvesting, and/or formulating the population of cells. In some embodiments, a population of enriched CD57−CD3+ T cells is frozen e.g., cryopreserved and/or cryoprotected, prior to any steps of incubating, activating, stimulating, engineering (e.g. knocking out and/or knocking in), transducing, transfecting, cultivating, expanding, harvesting, and/or formulating the population of cells. In particular embodiments, the one or more cryoprotected input compositions is stored, e.g., at or at about −80° C., for between 12 hours and 7 days, between 24 hours and 120 hours, or between 2 days and 5 days. In particular embodiments, the one or more cryoprotected input compositions is stored at or at about −80° C., for an amount of time of less than 10 days, 9 days, 8 days, 7 days, 6 days, or 5 days, 4 days, 3 days, 2 days, or 1 day. In some embodiments, the one or more cryoprotected input compositions is stored at or at about −70° C. or −80° C. for less than 3 days, such as for about 2 days.

In some embodiments, "depleting" or "removing" when referring to one or more particular cell type or cell population, refers to decreasing the number or percentage of the cell type or population, e.g., compared to the total number of cells in or volume of the composition, or relative to other cell types, such as by negative selection based on markers expressed by the population or cell, or by positive selection based on a marker not present on the cell population or cell to be depleted. In general, the terms depleting or removing does not require complete removal of the cell, cell type, or population from the composition.

In some embodiments, "enriching" when referring to one or more particular cell type or cell population, refers to increasing the number or percentage of the cell type or population, e.g., compared to the total number of cells in or volume of the composition, or relative to other cell types, such as by positive selection based on markers expressed by the population or cell, or by negative selection based on a marker not present on the cell population or cell to be depleted. In general, the term enriching does not require complete removal of other cells, cell type, or populations from the composition and does not require that the cells so enriched be present at or even near 100% in the enriched composition.

In some aspects, cell populations or cell compositions obtained from a donor, such as a human donor, for cell therapy, e.g., adoptive cell therapy, can exhibit low growth or slow growth, such that they do not reach (e.g., no growth) the threshold for harvesting cells (e.g., harvest criterion) for generating a therapeutic composition, or do not reach the threshold for harvesting cells (e.g., harvest criterion) for generating a therapeutic composition within a specific period of time (e.g., slow growth). In some aspects, some of such cell populations can contain a high frequency of CD57+ cells, such as a frequency of CD57+ above a threshold value. In other aspects, cell populations or cell compositions obtained from a donor, such as a human donor, for cell therapy, e.g., adoptive cell therapy, can exhibit improved growth compared to the populations exhibiting no growth or slow growth. In some aspects, such cell populations or cell compositions can contain a low frequency of CD57+ cells, such as a frequency of CD57+ cells less than a threshold value. In some aspects, cell populations or cell compositions that exhibit improved growth can exhibit phenotypes or express markers associated with naïve-like or central memory-like phenotypes, such as CD27+, CD28+ and/or CCR7+. In some embodiments, the provided methods are based on observations that there is variability or heterogeneity in CD57+ T cell expression among T cells in a donor sample (e.g. leukapheresis or apheresis sample) from a human, which, in some aspects, can results in variability in the phenotype and function of engineered T cell compositions produced for use in adoptive cell therapy from a plurality of different donors, even using the same manufacturing process. In particular embodiments, the provided methods control for or reduce such variability by selecting, isolating, or enriching CD57− T cells from a donor sample, such as by removing, separating, or depleting CD57+ T cells from the donor sample. Such cells can then be used in processes to engineer or manufacture cells for cell therapy to minimize variability among products, while also improving particular product attributes and features, such as the ability to expand and persist upon administration to a subject.

D. Selection of CD27+ T Cells and/or Depletion of CD27− T Cells

In some embodiments, a CD27+ enriched population (the pooled CD27 enriched T cell population and/or the CD27 enriched T cell population) is obtained from a biological sample (e.g. a donor sample). In particular embodiments, the pooled CD27 enriched T cell population and/or the CD27 enriched T cell population is selected, isolated, or enriched from the biological sample (e.g. the donor sample). In some embodiments, a donor sample is a sample from an individual donor. In some embodiments, a donor sample includes cells from a plurality of different donors. In some embodiments, a plurality of samples, each from a different individual donor, are combined to produce a donor sample.

In some embodiments, the donor sample is derived from an individual donor. In some embodiments, a donor sample from an individual donor is enriched for CD27+ T cells to produce a CD27 enriched T cell population. In some embodiments, CD27 enriched T cell populations from a plurality of different individual donors are combined to produced a pooled CD27 enriched T cell population. In some embodiments, the donor sample is derived from a plurality of different donors. In some embodiments, a donor sample from a plurality of different donors is enriched for CD27+ T cells to produce a pooled CD27+ T cell population.

In particular embodiments, CD27− T cells are removed, separated, or depleted from a biological sample (e.g. a donor sample). In certain embodiments, at least 25%, 30%, 35%, 40%, 45%, 50%, 55%, 60%, 65%, 70%, 75%, 80%, 85%, 90%, 95%, 99%, or 99.9% CD27− T cells are removed, separated, or depleted from the donor sample.

In particular embodiments, subsets of cells, e.g., subsets of T cells, are selected, isolated, or enriched from the donor sample prior to selecting, isolating, or enriching CD27+ T cells from the donor sample. In some embodiments, subsets of cells, e.g., T cells are selected, isolated, or enriched from the population of enriched CD27+ T cells.

In some embodiments, the pooled CD27 enriched T cell population and/or the CD27 enriched T cell population contains, contains about, or contains less than 50%, 45%, 40%, 35%, 30%, 25%, 20%, 15%, 10%, 5%, 1%, 0.1%, 0.01%, or 0.001% of the CD27− T cells of the donor sample, e.g., prior the selection, isolation, or enrichment. In particular embodiments, the pooled CD27 enriched T cell population and/or the CD27 enriched T cell population contains, contains about, or contains less than 20% of the CD27− T cells of the donor sample. In certain embodiments, the pooled CD27 enriched T cell population and/or the CD27 enriched T cell population contains, contains about, or contains less than 5% of the CD27− T cells of the donor sample. In some embodiments, the pooled CD27 enriched T cell population and/or the CD27 enriched T cell population contains, contains about, or contains less than 1% of the CD27-+ T cells of the donor sample e.g., prior the selection, isolation, or enrichment. In various embodiments, the pooled CD27 enriched T cell population and/or the CD27 enriched T cell population contains, contains about, or contains less than 0.1% of the CD27− T cells of the donor sample. In particular embodiments, the pooled CD27 enriched T cell population and/or the CD27 enriched T cell population contains, contains about, or contains less than 0.01% of the CD27− T cells of the donor sample. In some embodiments, the frequency of the CD27− T cells in the pooled CD27 enriched T cell population and/or the CD27 enriched T cell population is less than at or about 35%, 30%, 20%, 10%, 5%, 1%, or 0.1% of the frequency of CD27− T cells in the donor sample. In some embodiments, the pooled CD27 enriched T cell population and/or the CD27 enriched T cell population comprises less than at or about 3%, less than at or about 2%, less than at or about 1%, less than at or about 0.1%, or less than at or about 0.01% CD27− T cells. In some embodiments, the pooled CD27 enriched T cell population and/or the CD27 enriched T cell population is free or is essentially free of CD27− T cells.

In some embodiments, the pooled CD27 enriched T cell population and/or the CD27 enriched T cell population exhibit a lower coefficient of variation (CV) in expression of one or more molecules, compared to that of the cells of the donor sample. In some embodiments the one or more molecules is a marker of naïve T cells, optionally Ki67, CD25, CD28, CCR7, and/or CD45RA. In some embodiments the one or more molecules is Ki67. In some embodiments, the cells of the CD27 enriched T cell population and/or the pooled CD27 enriched T cell population exhibit a lower CV in expression of Ki67.

In particular embodiments, the cells of the pooled CD27 enriched T cell population and/or the CD27 enriched T cell population are less differentiated than the cells of the donor sample, e.g., prior the selection, isolation, or enrichment. In certain embodiments, the pooled CD27 enriched T cell population and/or the CD27 enriched T cell population contains a greater frequency of naïve-like cells than the donor sample. In certain embodiments, the pooled CD27 enriched T cell population and/or the CD27 enriched T cell population includes, includes about, or includes at least at or about 25%, 30%, 35%, 40%, 45%, 50%, 55%, 60%, 65%, 70%, 75%, 80%, 85%, 90%, 95%, 100%, 125%, 150%, 1-fold, 2-fold, 3-fold, 4-fold, 5-fold, or 10 fold more naïve-like cells than the donor sample e.g., prior the selection, isolation, or enrichment. In some embodiments, naïve-like cells include naïve T cells or central memory T cells. In some embodiments, naïve-like cells can include cells positive or expressing high levels of one or more surface markers, e.g., CD28+, CD62 L+, CCR7+, CD27+, CD127+, CD4+, CD8+, CD45RA+, and/or CD45RO+ T cells. In some aspects, the cells are CD28+. In some aspects, the cells are CCR7+. In particular aspects, CCR7 is expressed by naïve or naïve-like T cells (e.g. CCR7+ CD45RA+ or CCR7+ CD27+) and central memory T cells (CCR7+ CD45RA−). In certain embodiments, naïve-like T cells or the T cells that are surface positive for a marker expressed on naïve-like T cells are CCR7+ CD45RA+, where the cells are CD27+ or CD27−. In certain embodiments, naïve-like T cells or the T cells that are surface positive for a marker expressed on naïve-like T cells are CD27+ CCR7+, where the cells are CD45RA+ or CD45RA−. In certain embodiments, naïve-like T cells or the T cells that are surface positive for a marker expressed on naïve-like T cells are CD62 L-CCR7+. In certain embodiments, naïve-like cells include cells at an early stage of differentiation (e.g., cells that are CCR7+ CD27+).

In certain embodiments, central memory T cells may include cells in various differentiation states and may be characterized by positive or high expression (e.g., surface expression) of certain cell markers and/or negative or low expression (e.g., surface expression) of other cell markers. In some aspects, less differentiated cells, e.g., central memory cells, are longer lived and exhaust less rapidly, thereby increasing persistence and durability. In some aspects, a responder to a cell therapy, such as a CAR-T cell therapy, has increased expression of central memory genes. See, e.g., Fraietta et al. (2018) Nat Med. 24(5):563-571. In some aspects, central memory T cells are characterized by positive or high expression of CD45RO, CD62 L, CCR7, CD28, CD3, and/or CD127. In some aspects, central memory T cells are characterized by negative or low expression of CD45RA and/or granzyme B. In certain embodiments, central memory T cells or the T cells that are surface positive for a marker expressed on central memory T cells are CCR7+ CD45RA−.

In particular embodiments, the pooled CD27 enriched T cell population and/or the CD27 enriched T cell population includes, includes about, or includes at least at or about 25%, 30%, 35%, 40%, 45%, 50%, 55%, 60%, 65%, 70%, 75%, 80%, 85%, 90%, 95%, 100%, 125%, 150%, 1-fold, 2-fold, 3-fold, 4-fold, 5-fold, or 10 fold less CD57+ T cells than the biological sample e.g., prior the selection, isolation, or enrichment. In particular embodiments, the pooled CD27 enriched T cell population and/or the CD27 enriched T cell population includes, includes about, or includes at least at or about 25%, 30%, 35%, 40%, 45%, 50%, 55%, 60%, 65%, 70%, 75%, 80%, 85%, 90%, 95%, 100%, 125%, 150%, 1-fold, 2-fold, 3-fold, 4-fold, 5-fold, or 10 fold more CD28+ T cells than the biological sample e.g., prior the selection, isolation, or enrichment. In various embodiments, the pooled CD27 enriched T cell population and/or the CD27 enriched T cell population includes, includes about, or includes at least at or about 25%, 30%, 35%, 40%, 45%, 50%, 55%, 60%, 65%, 70%, 75%, 80%, 85%, 90%, 95%, 100%, 125%, 150%, 1-fold, 2-fold, 3-fold, 4-fold, 5-fold, or 10 fold more CD25+ T cells than the biological sample e.g., prior the selection, isolation, or enrichment. In certain embodiments, the pooled CD27 enriched T cell population and/or the CD27 enriched T cell population includes, includes about, or includes at least at or about 25%, 30%, 35%, 40%, 45%, 50%, 55%, 60%, 65%, 70%, 75%, 80%, 85%, 90%, 95%, 100%, 125%, 150%, 1-fold, 2-fold, 3-fold, 4-fold, 5-fold, or 10 fold more CCR7+ T cells than the biological sample e.g., prior the selection, isolation, or enrichment. In certain embodiments, the pooled CD27 enriched T cell population and/or the CD27 enriched T cell population includes, includes about, or includes at least at or about 25%, 30%, 35%, 40%, 45%, 50%, 55%, 60%, 65%, 70%, 75%, 80%, 85%, 90%, 95%, 100%, 125%, 150%, 1-fold, 2-fold, 3-fold, 4-fold, 5-fold, or 10 fold more CD45RA+ cells than the biological sample e.g., prior the selection, isolation, or enrichment.

In certain embodiments, T cells, e.g., CD3+ T cells, are selected, isolated, or enriched from the donor sample prior to selecting, isolating, or enriching CD27+ T cells from the donor sample. In some embodiments, T cells, e.g., CD3+ T cells, are selected, isolated, or enriched from the pooled CD27 enriched T cell population and/or the CD27 enriched T cell population. In particular embodiments, selecting, isolating or enriching T cells, e.g. CD3+ T cells, involves positive selection of the cells from the donor sample.

In some embodiments, CD27− cells are selected, isolated, or enriched from a donor sample, cell composition, or cell population, thereby producing isolated or selected CD27− cells and a pooled CD27 enriched T cell population and/or a CD27 enriched T cell population.

In certain embodiments, CD3+ T cells are enriched, selected, or isolated from the pooled CD27 enriched T cell population and/or the CD27 enriched T cell population, thereby generating a population of enriched CD27+ CD3+ T cells and a non-selected population of enriched CD27+ cells. In certain embodiments, CD3+ T cells are enriched, selected, or isolated from the non-selected population of enriched CD27+ cells, thereby generating a population of enriched CD27+ CD3+ T cells. In various embodiments, CD3+ T cells are enriched, selected, or isolated from the pooled CD27 enriched T cell population and/or the CD27 enriched T cell population, thereby generating a population of enriched CD27+ CD3+ T cells and a non-selected population enriched for CD27+ cells, and then CD4+ or CD8+ T cells are enriched, selected, or isolated from the non-selected population of enriched CD27+ cells, thereby generating a population of enriched CD27+ CD4+ T cells or CD27+ CD8+ T cells.

In certain embodiments, subsets of T cells, e.g., CD4+ or CD8+ T cells, are selected, isolated, or enriched from the donor sample prior to selecting, isolating, or enriching CD27+ T cells from the donor sample. In some embodiments, subsets of T cells, e.g., CD4+ or CD8+ T cells, are selected, isolated, or enriched from the pooled CD27 enriched T cell population and/or the CD27 enriched T cell population. In particular embodiments, the selecting, isolating or enriching a subset of T cells, e.g. CD4+ or CD8+ T cells, involves positive selection of the cells from the sample.

In some embodiments, CD27− cells are selected, isolated, or enriched from a donor sample, cell composition, or cell population, thereby producing isolated or selected CD27− cells and a pooled CD27 enriched T cell population and/or a CD27 enriched T cell population. In certain embodiments, CD27− cells are selected, isolated, or enriched from a biological sample, thereby producing isolated or selected CD27− cells and a pooled CD27 enriched T cell population and/or a CD27 enriched T cell population.

In particular embodiments, CD4+ T cells are enriched, selected, or isolated from the pooled CD27 enriched T cell population and/or the CD27 enriched T cell population, thereby generating a population of enriched CD27+ CD4+ T cells and a non-selected population enriched for CD27+ cells. In certain embodiments, CD8+ T cells are enriched, selected, or isolated from the pooled CD27 enriched T cell population and/or the CD27 enriched T cell population, thereby generating a population of enriched CD27+ CD8+ T cells and a non-selected population of enriched CD27+ cells. In certain embodiments, CD8+ T cells are enriched, selected, or isolated from the non-selected population of enriched CD27+ cells, thereby generating a population of enriched CD27+ CD8+ T cells. In particular embodiments, CD4+ T cells are enriched, selected, or isolated from the non-selected population of enriched CD27+ cells, thereby generating a population of enriched CD27+ CD4+ T cells.

In particular embodiments, CD4+ T cells are enriched, selected, or isolated from the pooled CD27 enriched T cell population and/or the CD27 enriched T cell population, thereby generating a population of enriched CD27+ CD4+ T cells and a non-selected population enriched for CD27+ cells, and then CD8+ T cells are enriched, selected, or isolated from the non-selected population of enriched CD27+ cells, thereby generating a population of enriched CD27+ CD8+ T cells. In various embodiments, CD4+ T cells are enriched, selected, or isolated from the pooled CD27 enriched T cell population and/or the CD27 enriched T cell population, thereby generating a population of enriched CD27+ CD4+ T cells and a non-selected population enriched for CD27+ cells, and then CD8+ T cells are enriched, selected, or isolated from the non-selected population of enriched CD27+ cells, thereby generating a population of enriched CD27+ CD8+ T cells.

In particular embodiments, (1) CD4+ T cells are enriched, selected, or isolated from a donor sample, thereby generating a population of enriched CD4+ T cells and a non-selected population enriched for CD4− cells; (2) CD8+ T cells are enriched, selected, or isolated from the non-selected population of enriched CD4− cells, thereby generating a population of enriched CD8+ T cells; and (3) CD27+ T cells are enriched, selected, or isolated from the enriched CD4+ and CD8+ T cell populations, generating populations of enriched CD27+ CD4+ and CD57−CD8+ T cells. In particular embodiments, (1) CD8+ T cells are enriched, selected, or isolated from a donor sample, thereby generating a population of enriched CD8+ T cells and a non-selected population enriched for CD8− cells; (2) CD4+ T cells are enriched, selected, or isolated from the non-selected population of enriched CD4− cells, thereby generating a population of enriched CD4+ T cells; and (3) CD27+ cells are enriched, selected, or isolated from the enriched CD4+ and CD8+ T cell populations, generating populations of enriched CD27+ CD4+ and CD57−CD8+ T cells.

In particular embodiments, CD4+ T cells are enriched, selected, or isolated from a donor sample, thereby generating an enriched population of CD4+ T cells, and then CD27+ cells are selected, enriched, or isolated from the enriched population of CD4+ T cells, thereby generating a population of enriched CD27+ CD4+ T cells. In particular embodiments, CD8+ T cells are enriched, selected, or isolated from a donor sample, thereby generating an enriched population of CD8+ T cells, and then CD27+ cells are enriched, selected, or isolated from the enriched population of CD8+ T cells, thereby generating a population of enriched CD27+ CD8+ T cells.

In some embodiments, the pooled CD27 enriched T cell population and/or the CD27 enriched T cell population is frozen, e.g., cryopreserved and/or cryoprotected, after isolation, selection and/or enrichment. In particular embodiments, a population of enriched CD27+ CD4+ T cells is frozen, e.g., cryopreserved and/or cryoprotected, after isolation, selection and/or enrichment. In certain embodiments, a population of enriched CD27+ CD8+ T cells is frozen, e.g., cryopreserved and/or cryoprotected, after isolation, selection and/or enrichment. In certain embodiments, a population of enriched CD27+ CD3+ T cells is frozen, e.g., cryopreserved and/or cryoprotected, after isolation, selection and/or enrichment. In some embodiments, the pooled CD27 enriched T cell population and/or the CD27 enriched T cell population is frozen e.g., cryopreserved and/or cryoprotected, prior to any steps of incubating, activating, stimulating, engineering (e.g. knocking out and/or knocking in), transducing, transfecting, cultivating, expanding, harvesting, and/or formulating the population of cells. In particular embodiments, a population of enriched CD27+ CD4+ T cells is frozen e.g., cryopreserved and/or cryoprotected, prior to any steps of incubating, activating, stimulating, engineering (e.g. knocking out and/or knocking in), transducing, transfecting, cultivating, expanding, harvesting, and/or formulating the population of cells. In some embodiments, a population of enriched CD27+−CD8+ T cells is frozen e.g., cryopreserved and/or cryoprotected, prior to any steps of incubating, activating, stimulating, engineering (e.g. knocking out and/or knocking in), transducing, transfecting, cultivating, expanding, harvesting, and/or formulating the population of cells. In some embodiments, a population of enriched CD27+ CD3+ T cells is frozen e.g., cryopreserved and/or cryoprotected, prior to any steps of incubating, activating, stimulating, engineering (e.g. knocking out and/or knocking in), transducing, transfecting, cultivating, expanding, harvesting, and/or formulating the population of cells. In particular embodiments, the one or more cryoprotected input compositions is stored, e.g., at or at about −80° C., for between 12 hours and 7 days, between 24 hours and 120 hours, or between 2 days and 5 days. In particular embodiments, the one or more cryoprotected input compositions is stored at or at about −80° C., for an amount of time of less than 10 days, 9 days, 8 days, 7 days, 6 days, or 5 days, 4 days, 3 days, 2 days, or 1 day. In some embodiments, the one or more cryoprotected input compositions is stored at or at about −70° C. or −80° C. for less than 3 days, such as for about 2 days.

In some embodiments, "depleting" or "removing" when referring to one or more particular cell type or cell population, refers to decreasing the number or percentage of the cell type or population, e.g., compared to the total number of cells in or volume of the composition, or relative to other cell types, such as by negative selection based on markers expressed by the population or cell, or by positive selection based on a marker not present on the cell population or cell to be depleted. In general, the terms depleting or removing does not require complete removal of the cell, cell type, or population from the composition.

In some embodiments, "enriching" when referring to one or more particular cell type or cell population, refers to increasing the number or percentage of the cell type or population, e.g., compared to the total number of cells in or volume of the composition, or relative to other cell types, such as by positive selection based on markers expressed by the population or cell, or by negative selection based on a marker not present on the cell population or cell to be depleted. In general, the term enriching does not require complete removal of other cells, cell type, or populations from the composition and does not require that the cells so enriched be present at or even near 100% in the enriched composition.

In some aspects, cell populations or cell compositions obtained from a donor, such as a human donor, for cell therapy, e.g., adoptive cell therapy, can exhibit low growth or slow growth, such that they do not reach (e.g., no growth) the threshold for harvesting cells (e.g., harvest criterion) for generating a therapeutic composition, or do not reach the threshold for harvesting cells (e.g., harvest criterion) for generating a therapeutic composition within a specific period of time (e.g., slow growth). In some aspects, some of such cell populations can contain a high frequency of CD27− cells, such as a frequency of CD27− above a threshold value. In other aspects, cell populations or cell compositions obtained from a donor, such as a human donor, for cell therapy, e.g., adoptive cell therapy, can exhibit improved growth compared to the populations exhibiting no growth or slow growth. In some aspects, such cell populations or cell compositions can contain a low frequency of CD27− cells, such as a frequency of CD27− cells less than a threshold value. In some aspects, cell populations or cell compositions that exhibit improved growth can exhibit phenotypes or express markers associated with naïve-like or central memory-like phenotypes, such as CD27+, CD28+ and/or CCR7+. In some embodiments, the provided methods are based on observations that there is variability or heterogeneity in CD57+ T cell expression among T cells in a donor sample (e.g. leukapheresis or apheresis sample) from a human, which, in some aspects, can results in variability in the phenotype and function of engineered T cell compositions produced for use in adoptive cell therapy from a plurality of different donors, even using the same manufacturing process. In particular embodiments, the provided methods control for or reduce such variability by selecting, isolating, or enriching CD27+ T cells from a donor sample, such as by enriching, selecting, or isolated CD27+ T cells from the donor sample. Such cells can then be used in processes to engineer or manufacture cells for cell therapy to minimize variability among products, while also improving particular product attributes and features, such as the ability to expand and persist upon administration to a subject.

1. Cell Selection

In some embodiments, selection, isolation, or enrichment of the pooled CD57 depleted T cell population and/or the CD57 depleted T cell population includes one or more preparation and/or non-affinity based cell separation steps. In some embodiments, selection, isolation, or enrichment of the pooled CD27 enriched T cell population and/or the CD27 enriched T cell population includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components. In some embodiments, the methods include density-based cell separation methods, such as the preparation of white blood cells from peripheral blood by lysing the red blood cells and centrifugation through a Percoll or Ficoll gradient. In certain embodiments, methods, techniques, and reagents for selection, isolation, and enrichment are described, for example, in PCT Application Nos. WO2013124474 and WO2015164675, which are hereby incorporated by reference in their entirety.

In certain embodiments, CD57− cells are isolated, enriched, or selected in a process or procedure that involves one or more selection steps. In some embodiments, the one or more selection steps are or involve negative selection. In certain embodiments, CD57− cells are isolated, enriched, or selected by separation or removal of CD57+ cells. In certain embodiments, a pooled CD57 depleted T cell population and/or a CD57 depleted T cell population results from negative selection of CD57+ cells from the population. In certain embodiments, CD27+ cells are isolated, enriched, or selected in a process or procedure that involves one or more selection steps. In some embodiments, the one or more selection steps are or involve negative selection. In certain embodiments, CD27+ cells are isolated, enriched, or selected by separation or removal of CD27− cells. In certain embodiments, a pooled CD27 enriched T cell population and/or a Cd27 enriched T cell population results from negative selection of CD27− cells from the population.

In certain embodiments, a bivalent antibody is used to link CD57+ cells to a large density cell or bead. In certain embodiments, a bivalent antibody is used to link CD27− cells to a large density cell or bead. This technology has been used most prominently with red blood cells (e.g. RosetteSep™ STEMCELL Technologies), or any other similar or suitable technology to couple target cells, e.g., CD57+ or CD27− T cells, to density gradients for removal.

In some embodiments, at least a portion of the selection step includes incubation of cells with a selection reagent. The incubation with a selection reagent or reagents, e.g., as part of selection methods which may be performed using one or more selection reagents for selection of one or more different cell types based on the expression or presence in or on the cell of one or more specific molecules, such as surface markers, e.g., surface proteins, intracellular markers, or nucleic acid. In certain embodiments, such surface proteins may include CD57, CD4, or CD8. In certain embodiments, such surface proteins may include CD27, CD4, or CD8. In certain embodiments, such surface proteins may include CD57. In certain embodiments, such surface proteins may include CD27. In certain embodiments, such surface proteins may include CD4 and/or CD8. In certain embodiments, such surface proteins may include CD3. In some embodiments, any known method using a selection reagent or reagents for separation based on such markers may be used. In some embodiments, the selection reagent or reagents result in a separation that is affinity- or immunoaffinity-based separation. For example, the selection in some aspects includes incubation with a reagent or reagents for separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner. In some embodiments, the reagent or reagents for separation of cells is or include antibodies or antigen binding fragments thereof that bind to or recognize CD4, CD8, or CD57. In some embodiments, the reagent or reagents for separation of cells is or include antibodies or antigen binding fragments thereof that bind to or recognize CD4, CD8, or CD27. In some embodiments, the reagent or reagents for separation of cells is or include antibodies or antigen binding fragments thereof that bind to or recognize CD57. In some embodiments, the reagent or reagents for separation of cells is or include antibodies or antigen binding fragments thereof that bind to or recognize CD27. In some embodiments, the reagent or reagents for separation of cells is or include antibodies or antigen binding fragments thereof that bind to or recognize CD4 or CD8. In some embodiments, the reagent or reagents for separation of cells is or include antibodies or antigen binding fragments thereof that bind to or recognize CD3.

In some aspects of such processes, a volume of cells is mixed with an amount of a desired affinity-based selection reagent. The immunoaffinity-based selection can be carried out using any system or method that results in a favorable energetic interaction between the cells being separated and the molecule specifically binding to the marker on the cell, e.g., the antibody or other binding partner on the solid surface, e.g., particle. In some embodiments, methods are carried out using particles such as beads, e.g. magnetic beads, that are coated with a selection agent (e.g. antibody) specific to the marker of the cells. The particles (e.g. beads) can be incubated or mixed with cells in a container, such as a tube or bag, while shaking or mixing, with a constant cell density-to-particle (e.g., bead) ratio to aid in promoting energetically favored interactions. In other cases, the methods include selection of cells in which all or a portion of the selection is carried out in the internal cavity of a centrifugal chamber, for example, under centrifugal rotation. In some embodiments, incubation of cells with selection reagents, such as immunoaffinity-based selection reagents, is performed in a centrifugal chamber. In certain embodiments, the isolation or separation is carried out using a system, device, or apparatus described in International Patent Application, Publication Number WO2009/072003, or US 20110003380 A1. In one example, the system is a system as described in International Publication Number WO2016/073602.

In some embodiments, by conducting such selection steps or portions thereof (e.g., incubation with antibody-coated particles, e.g., magnetic beads) in the cavity of a centrifugal chamber, the user is able to control certain parameters, such as volume of various solutions, addition of solution during processing and timing thereof, which can provide advantages compared to other available methods. For example, the ability to decrease the liquid volume in the cavity during the incubation can increase the concentration of the particles (e.g. bead reagent) used in the selection, and thus the chemical potential of the solution, without affecting the total number of cells in the cavity. This in turn can enhance the pairwise interactions between the cells being processed and the particles used for selection. In some embodiments, carrying out the incubation step in the chamber, e.g., when associated with the systems, circuitry, and control as described herein, permits the user to effect agitation of the solution at desired time(s) during the incubation, which also can improve the interaction.

In some embodiments, at least a portion of the selection step is performed in a centrifugal chamber, which includes incubation of cells with a selection reagent. In some aspects of such processes, a volume of cells is mixed with an amount of a desired affinity-based selection reagent that is far less than is normally employed when performing similar selections in a tube or container for selection of the same number of cells and/or volume of cells according to manufacturer's instructions. In some embodiments, an amount of selection reagent or reagents that is/are no more than 5%, no more than 10%, no more than 15%, no more than 20%, no more than 25%, no more than 50%, no more than 60%, no more than 70% or no more than 80% of the amount of the same selection reagent(s) employed for selection of cells in a tube or container-based incubation for the same number of cells and/or the same volume of cells according to manufacturer's instructions is employed.

In some embodiments, for selection, e.g., immunoaffinity-based selection of the cells, the cells are incubated in the cavity of the chamber in a population that also contains the selection buffer with a selection reagent, such as a molecule that specifically binds to a surface marker on a cell that it desired to enrich and/or deplete, but not on other cells in the population, such as an antibody, which optionally is coupled to a scaffold such as a polymer or surface, e.g., bead, e.g., magnetic bead, such as magnetic beads coupled to monoclonal antibodies specific for CD4 and CD8. In some embodiments, for selection, e.g., immunoaffinity-based selection of the cells, the cells are incubated in the cavity of the chamber in a population that also contains the selection buffer with a selection reagent, such as a molecule that specifically binds to a surface marker on a cell that it desired to enrich and/or deplete, but not on other cells in the population, such as an antibody, which optionally is coupled to a scaffold such as a polymer or surface, e.g., bead, e.g., magnetic bead, such as magnetic beads coupled to monoclonal antibodies specific for CD3. In some embodiments, as described, the selection reagent is added to cells in the cavity of the chamber in an amount that is substantially less than (e.g. is no more than 5%, 10%, 20%, 30%, 40%, 50%, 60%, 70% or 80% of the amount) as compared to the amount of the selection reagent that is typically used or would be necessary to achieve about the same or similar efficiency of selection of the same number of cells or the same volume of cells when selection is performed in a tube with shaking or rotation. In some embodiments, the incubation is performed with the addition of a selection buffer to the cells and selection reagent to achieve a target volume with incubation of the reagent of, for example, 10 mL to 200 mL, such as at least or about at least or about or 10 mL, 20 mL, 30 mL, 40 mL, 50 mL, 60 mL, 70 mL, 80 mL, 90 mL, 100 mL, 150 mL or 200 mL. In some embodiments, the selection buffer and selection reagent are pre-mixed before addition to the cells. In some embodiments, the selection buffer and selection reagent are separately added to the cells. In some embodiments, the selection incubation is carried out with periodic gentle mixing condition, which can aid in promoting energetically favored interactions and thereby permit the use of less overall selection reagent while achieving a high selection efficiency.

In some embodiments, the total duration of the incubation with the selection reagent is from or from about 5 minutes to 6 hours, such as 30 minutes to 3 hours, for example, at least or about at least 30 minutes, 60 minutes, 120 minutes or 180 minutes.

In some embodiments, the incubation generally is carried out under mixing conditions, such as in the presence of spinning, generally at relatively low force or speed, such as speed lower than that used to pellet the cells, such as from or from about 600 rpm to 1700 rpm (e.g. at or about or at least 600 rpm, 1000 rpm, or 1500 rpm or 1700 rpm), such as at an RCF at the sample or wall of the chamber or other container of from or from about 80 g to 100 g (e.g. at or about or at least 80 g, 85 g, 90 g, 95 g, or 100 g). In some embodiments, the spin is carried out using repeated intervals of a spin at such low speed followed by a rest period, such as a spin and/or rest for 1, 2, 3, 4, 5, 6, 7, 8, 9, or 10 seconds, such as a spin at approximately 1 or 2 seconds followed by a rest for approximately 5, 6, 7, or 8 seconds.

In some embodiments, such process is carried out within the entirely closed system to which the chamber is integral. In some embodiments, this process (and in some aspects also one or more additional step, such as a previous wash step washing a sample containing the cells, such as an apheresis sample) is carried out in an automated fashion, such that the cells, reagent, and other components are drawn into and pushed out of the chamber at appropriate times and centrifugation effected, so as to complete the wash and binding step in a single closed system using an automated program.

In some embodiments, after the incubation and/or mixing of the cells and selection reagent and/or reagents, the incubated cells are subjected to a separation to select for cells based on the presence or absence of the particular reagent or reagents. In some embodiments, the separation is performed in the same closed system in which the incubation of cells with the selection reagent was performed. In some embodiments, after incubation with the selection reagents, incubated cells, including cells in which the selection reagent has bound are transferred into a system for immunoaffinity-based separation of the cells. In some embodiments, the system for immunoaffinity-based separation is or contains a magnetic separation column.

Such separation steps can be based on positive selection, in which the cells having bound the reagents, e.g. antibody or binding partner, are retained for further use, and/or negative selection, in which the cells having not bound to the reagent, e.g., antibody or binding partner, are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

In some embodiments, the process steps further include negative and/or positive selection of the incubated and cells, such as using a system or apparatus that can perform an affinity-based selection. In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed (marker+) at a relatively higher level (markerhigh) on the positively or negatively selected cells, respectively.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types. In certain embodiments, separation steps are repeated and or performed more than once, where the positively or negatively selected fraction from one step is subjected to the same separation step, such as a repeated positive or negative selection. In some examples, a single separation step is repeated and/or performed more than once, for example to increase the purity of the selected cells and/or to further remove and/or deplete the negatively selected cells from the negatively selected fraction. In certain embodiments, one or more separation steps are performed two times, three times, four times, five times, six times, seven times, eight times, nine times, ten times, or more than ten times. In certain embodiments, the one or more selection steps are performed and/or repeated between one and ten times, between one and five times, or between three and five times.

For example, in some aspects, specific subpopulations of T cells, such as cells positive or expressing high levels of one or more surface markers, e.g., CD3+, CD4+, CD8+, or CD57+ T cells, are isolated by positive or negative selection techniques. In some aspects, specific subpopulations of T cells, such as cells positive or expressing high levels of one or more surface markers, e.g., CD3+, CD4+, CD8+, or CD27− T cells, are isolated by positive or negative selection techniques. In some embodiments, such cells are selected by incubation with one or more antibody or binding partner that specifically binds to such markers. In some embodiments, the antibody or binding partner can be conjugated, such as directly or indirectly, to a solid support or matrix to effect selection, such as a magnetic bead or paramagnetic bead. For example, in some embodiments, CD4+ T cells, CD8+ T cells, or CD57+ T cells may be selected, e.g., positively selected, with CD4 Microbeads, CD8 Microbeads, or CD57 Microbeads (Miltenyl Biotec). For example, in some embodiments, CD4+ T cells, CD8+ T cells, or CD27− T cells may be selected, e.g., positively selected, with CD4 Microbeads, CD8 Microbeads, or CD27 Microbeads (Miltenyl Biotec). For example, in some embodiments, CD3+ T cells may be selected, e.g., positively selected, with CD3 Microbeads (Miltenyl Biotec).

In certain embodiments, CD57− cells are separated from a PBMC sample by negative selection of cells positive for CD57 expression. In certain embodiments, CD27+ cells are separated from a PBMC sample by negative selection of cells negative for CD27 expression. In various embodiments, T cells are separated from a PBMC sample by negative selection of markers expressed on non-T cells, such as B cells, monocytes, or other white blood cells, such as CD14. In some aspects, a CD3+ selection step is used to separate T cells from non-T cells. Such a CD3+ population can be further sorted into sub-populations by positive or negative selection for CD4+ or CD8+, and/or markers expressed or expressed to a relatively higher degree on one or more naïve-like, memory, and/or effector T cell subpopulations. In some aspects, a CD4+ or CD8+ selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naïve-like, memory, and/or effector T cell subpopulations.

In some embodiments, CD8+ cells are further enriched for or depleted of CD57− T cells, such as by positive or negative selection based on surface expression of CD57. In certain embodiments, CD4+ cells are further enriched for or depleted of CD57− T cells, such as by positive or negative selection based on surface expression of CD57. In certain embodiments, CD3+ cells are further enriched for or depleted of CD57− T cells, such as by positive or negative selection based on surface expression of CD57. In some embodiments, CD8+ cells are further enriched for or depleted of CD27+ T cells, such as by positive or negative selection based on surface expression of CD27. In certain embodiments, CD4+ cells are further enriched for or depleted of CD27+ T cells, such as by positive or negative selection based on surface expression of CD27. In certain embodiments, CD3+ cells are further enriched for or depleted of CD27+ T cells, such as by positive or negative selection based on surface expression of CD27.

In some embodiments, CD8+ cells are further enriched for or depleted of naïve, central memory, effector memory, and/or central memory stem cells, such as by positive or negative selection based on surface antigens associated with the respective subpopulation. In some embodiments, enrichment for central memory T (TCM) cells is carried out to increase efficacy, such as to improve long-term survival, expansion, and/or engraftment following administration, which in some aspects is particularly robust in such subpopulations. See Terakura et al., (2012) Blood. 1:72-82; Wang et al. (2012) J Immunother. 35(9):689-701. In some embodiments, combining TCM-enriched CD8+ T cells and CD4+ T cells further enhances efficacy.

In some aspects, the same CD4 expression-based selection step used in preparing the CD8+ cell population or subpopulation, also is used to generate the CD4+ cell population or sub-population, such that both the positive and negative fractions from the CD4-based separation are retained and used in subsequent steps of the methods, optionally following one or more further positive or negative selection steps. In some embodiments, the selection for the CD4+ cell population and the selection for the CD8+ cell population are carried out simultaneously. In some embodiments, the CD4+ cell population and the selection for the CD8+ cell population are carried out sequentially, in either order. In some embodiments, methods for selecting cells can include those as described in published U.S. App. No. US20170037369. In some embodiments, the selected CD4+ cell population and the selected CD8+ cell population may be combined subsequent to the selecting. In some aspects, the selected CD4+ cell population and the selected CD8+ cell population may be combined in a bioreactor bag as described herein.

In various embodiments, a donor sample, e.g., a sample of PBMCs or other white blood cells, is subjected to selection of CD57+ T cells, wherein the negative fractions containing enriched CD57− cells are retained. In some embodiments, the negative fraction enriched with CD57− cells is subjected to selection of CD3+ T cells, where the positive fraction is retained. In certain embodiments, CD8+ T cells are selected from the negative fraction enriched with CD57− cells. In some embodiments, the negative fraction enriched with CD57− cells is subjected to selection of CD8+ T cells, where both the negative and positive fractions are retained. In certain embodiments, CD4+ T cells are selected from the negative fraction. In particular embodiments, from the negative fraction enriched with CD57− cells, are subjected to selection of CD4+ T cells, where both the negative and positive fractions are retained. In certain embodiments, CD8+ T cells are selected from the negative fraction.

In various embodiments, a donor sample, e.g., a sample of PBMCs or other white blood cells, is subjected to selection of CD27− T cells, wherein the negative fractions containing enriched CD27+ cells are retained. In some embodiments, the negative fraction enriched with CD27+ cells is subjected to selection of CD3+ T cells, where the positive fraction is retained. In certain embodiments, CD8+ T cells are selected from the negative fraction enriched with CD27+ cells. In some embodiments, the negative fraction enriched with CD27+ cells is subjected to selection of CD8+ T cells, where both the negative and positive fractions are retained. In certain embodiments, CD4+ T cells are selected from the negative fraction. In particular embodiments, from the negative fraction enriched with CD27+ cells, are subjected to selection of CD4+ T cells, where both the negative and positive fractions are retained. In certain embodiments, CD8+ T cells are selected from the negative fraction.

In some aspects, the incubated sample or population of cells (e.g. the donor sample) to be separated is incubated with a selection reagent containing small, magnetizable or magnetically responsive material, such as magnetically responsive particles or microparticles, such as paramagnetic beads (e.g., such as Dynalbeads or MACS® beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select. In some aspects, the selection agent is or includes a paramagnetic bead and an attached antibody or antigen binding fragment thereof that binds to or recognizes CD3, CD4, CD8, or CD57. In some aspects, the selection agent is or includes a paramagnetic bead and an attached antibody or antigen binding fragment thereof that binds to or recognizes CD3, CD4, CD8, or CD27. In some embodiments, the selection agent is a CD3, CD4, CD8, or CD57 MACS® microbead. In some embodiments, the selection agent is a CD3, CD4, CD8, or CD27 MACS® microbead.

In some embodiments, the magnetic particle or bead comprises a magnetically responsive material bound to a specific binding member, such as an antibody or other binding partner. Many well-known magnetically responsive materials for use in magnetic separation methods are known, e.g., those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 also may be used.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some aspects, separation is achieved in a procedure in which the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In some embodiments, the affinity-based selection is via magnetic-activated cell sorting (MACS) (Miltenyi Biotech, Auburn, CA). Magnetic Activated Cell Sorting (MACS), e.g., CliniMACS systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells. In various embodiments, the selection agent is a CD3, CD4, CD8, or CD57 MACS® microbead. In certain embodiments, the non-target cells are labelled and depleted from the heterogeneous population of cells. In various embodiments, the selection agent is a CD3, CD4, CD8, or CD27 MACS® microbead.

In some embodiments, the suboptimal yield concentration of the affinity reagent is a concentration below a concentration used or required to achieve an optimal or maximal yield of bound cells in a given selection or enrichment involving incubating cells with the reagent and recovering or separating cells having bound to the reagent ("yield," for example, being the number of the cells so-recovered or selected compared to the total number of cells in the incubation that are targeted by the reagent or to which the reagent is specific or that have a marker for which the reagent is specific and capable of binding). The suboptimal yield concentration generally is a concentration or amount of the reagent that in such process or step achieves less than all, e.g., no more than 70% yield of bound cells, e.g., CD57+, CD4+, or CD8+ T cells, upon recovery of the cells having bound to the reagent. The suboptimal yield concentration generally is a concentration or amount of the reagent that in such process or step achieves less than all, e.g., no more than 70% yield of bound cells, e.g., CD27−, CD4+, or CD8+ T cells, upon recovery of the cells having bound to the reagent. In some embodiments, the suboptimal yield concentration generally is a concentration or amount of the reagent that in such process or step achieves less than all, e.g., no more than 70% yield of bound cells, e.g., CD3+ T cells, upon recovery of the cells having bound to the reagent. In some embodiments, no more than at or about 50%, 45%, 40%, 30%, or 25% yield is achieved by the suboptimal concentration of the affinity reagent. The concentration may be expressed in terms of number or mass of particles or surfaces per cell and/or number of mass or molecules of agent (e.g., antibody, such as antibody fragment) per cell.

In some embodiments, e.g., when operating in a suboptimal yield concentration for each or one or more of two or more selection reagents with affinity to CD57+, CD4+, or CD8+ T cells, one or more of such reagents is used at a concentration that is higher than one or more of the other such reagent(s), in order to bias the ratio of the cell type recognized by that reagent as compared to the cell type(s) recognized by the other(s). In some embodiments, e.g., when operating in a suboptimal yield concentration for each or one or more of two or more selection reagents with affinity to CD57+, CD3+, CD4+, or CD8+ T cells, one or more of such reagents is used at a concentration that is higher than one or more of the other such reagent(s), in order to bias the ratio of the cell type recognized by that reagent as compared to the cell type(s) recognized by the other(s). In some embodiments, e.g., when operating in a suboptimal yield concentration for each or one or more of two or more selection reagents with affinity to CD27−, CD4+, or CD8+ T cells, one or more of such reagents is used at a concentration that is higher than one or more of the other such reagent(s), in order to bias the ratio of the cell type recognized by that reagent as compared to the cell type(s) recognized by the other(s). In some embodiments, e.g., when operating in a suboptimal yield concentration for each or one or more of two or more selection reagents with affinity to CD27−, CD3+, CD4+, or CD8+ T cells, one or more of such reagents is used at a concentration that is higher than one or more of the other such reagent(s), in order to bias the ratio of the cell type recognized by that reagent as compared to the cell type(s) recognized by the other(s). For example, the reagent specifically binding to the marker for which it is desired to bias the ratio may be included at a concentration (e.g., agent or mass per cells) that is increased by half, 1-fold, 2-fold, 3-fold, 4-fold, 5-fold, 10-fold, or more, compared to other(s), depending on how much it is desired to increase the ratio. In some embodiments, when operating in the suboptimal range and/or with enough cells to achieve saturation of reagents, the amount of immunoaffinity reagent is proportional to the approximate yield of enriched cells. In certain embodiments, an appropriate amount or concentration of immunoaffinity reagents that depend on the desired ratio of the generated population containing the enriched or selected cells, e.g., CD57−, CD4+, or CD8+ T cells, can be determined as a matter of routine. In certain embodiments, an appropriate amount or concentration of immunoaffinity reagents that depend on the desired ratio of the generated population containing the enriched or selected cells, e.g., CD27+, CD4+, or CD8+ T cells, can be determined as a matter of routine. In certain embodiments, an appropriate amount or concentration of immunoaffinity reagents that depend on the desired ratio of the generated population containing the enriched or selected cells, e.g., CD3+ T cells, can be determined as a matter of routine.

In some embodiments, the separation and/or isolation steps are carried out using magnetic beads in which immunoaffinity reagents are reversibly bound, such as via a peptide ligand interaction with a streptavidin mutein as described in WO 2015/164675. Exemplary of such magnetic beads are Streptamers®. In some embodiments, the separation and/or steps is carried out using magnetic beads, such as those commercially available from Miltenyi Biotec.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, magnetizable particles or antibodies conjugated to cleavable linkers, etc. In some embodiments, the magnetizable particles are biodegradable.

In some embodiments, the isolation and/or selection results in one or more populations of enriched T cells, e.g., CD57− T cells, CD3+ T cells, CD4+ T cells, and/or CD8+ T cells. In some embodiments, the isolation and/or selection results in one or more populations of enriched T cells, e.g., CD27+ T cells, CD3+ T cells, CD4+ T cells, and/or CD8+ T cells. In some embodiments, two or more separate population of enriched T cells are isolated, selected, enriched, or obtained from a single donor sample. In some embodiments, separate populations are isolated, selected, enriched, and/or obtained from separate donor samples collected, taken, and/or obtained from the same individual donor.

In certain embodiments, the isolation and/or selection results in one or more populations of enriched T cells (e.g. the CD57 depleted T cell population and/or the pooled CD57 depleted T cell population) that includes at least 60%, at least 65%, at least 70%, at least 75%, at least 80%, at least 85%, at least 90%, at least 95%, at least 98%, at least 99%, at least 99.5%, at least 99.9%, or at or at about 100% CD57− CD3+ T cells. In particular embodiment, the pooled CD57 depleted T cell population and/or the CD57 depleted T cell population consists essentially of CD57− CD3+ T cells.

In certain embodiments, the isolation and/or enrichment results in a populations of enriched CD57− CD4+ T cells that includes at least 60%, at least 65%, at least 70%, at least 75%, at least 80%, at least 85%, at least 90%, at least 95%, at least 98%, at least 99%, at least 99.5%, at least 99.9%, or at or at about 100% CD57− CD4+ T cells. In certain embodiments, the input composition of CD4+ T cells includes less than 40%, less than 35%, less than 30%, less than 25%, less than 20%, less than 15%, less than 10%, less than 5%, less than 1%, less than 0.1%, or less than 0.01% CD8+ T cells, and/or contains no CD8+ T cells, and/or is free or substantially free of CD8+ T cells. In some embodiments, the population of enriched T cells consists essentially of CD57− CD4+ T cells.

In certain embodiments, the isolation and/or enrichment results in a populations of enriched CD57− CD8+ T cells that includes at least 60%, at least 65%, at least 70%, at least 75%, at least 80%, at least 85%, at least 90%, at least 95%, at least 98%, at least 99%, at least 99.5%, at least 99.9%, or at or at about 100% CD57− CD8+ T cells. In certain embodiments, the population of CD8+ T cells contains less than 40%, less than 35%, less than 30%, less than 25%, less than 20%, less than 15%, less than 10%, less than 5%, less than 1%, less than 0.1%, or less than 0.01% CD4+ T cells, and/or contains no CD4+ T cells, and/or is free of or substantially free of CD4+ T cells. In some embodiments, the pooled CD57 depleted T cell population and/or the CD57 depleted T cell population consists essentially of CD57− CD8+ T cells. In some embodiments, the pooled CD57 depleted T cell population and/or the CD57 depleted T cell population consists essentially of CD57− CD4+ T cells. In some embodiments, the pooled CD57 depleted T cell population and/or the CD57 depleted T cell population consists essentially of CD57− CD3+ T cells.

In certain embodiments, the isolation and/or selection results in one or more populations of enriched T cells (e.g. the CD27 enriched T cell population and/or the pooled CD27 enriched T cell population) that includes at least 60%, at least 65%, at least 70%, at least 75%, at least 80%, at least 85%, at least 90%, at least 95%, at least 98%, at least 99%, at least 99.5%, at least 99.9%, or at or at about 100% CD27+ CD3+ T cells. In particular embodiment, the pooled CD27 enriched T cell population and/or the CD27 enriched T cell population consists essentially of CD27+ CD3+ T cells.

In certain embodiments, the isolation and/or enrichment results in a populations of enriched CD27+ CD4+ T cells that includes at least 60%, at least 65%, at least 70%, at least 75%, at least 80%, at least 85%, at least 90%, at least 95%, at least 98%, at least 99%, at least 99.5%, at least 99.9%, or at or at about 100% CD27+ CD4+ T cells. In certain embodiments, the input composition of CD4+ T cells includes less than 40%, less than 35%, less than 30%, less than 25%, less than 20%, less than 15%, less than 10%, less than 5%, less than 1%, less than 0.1%, or less than 0.01% CD8+ T cells, and/or contains no CD8+ T cells, and/or is free or substantially free of CD8+ T cells. In some embodiments, the population of enriched T cells consists essentially of CD27+ CD4+ T cells.

In certain embodiments, the isolation and/or enrichment results in a populations of enriched CD27+ CD8+ T cells that includes at least 60%, at least 65%, at least 70%, at least 75%, at least 80%, at least 85%, at least 90%, at least 95%, at least 98%, at least 99%, at least 99.5%, at least 99.9%, or at or at about 100% CD27+ CD8+ T cells. In certain embodiments, the population of CD8+ T cells contains less than 40%, less than 35%, less than 30%, less than 25%, less than 20%, less than 15%, less than 10%, less than 5%, less than 1%, less than 0.1%, or less than 0.01% CD4+ T cells, and/or contains no CD4+ T cells, and/or is free of or substantially free of CD4+ T cells. In some embodiments, the pooled CD27 enriched T cell population and/or the CD27 enriched T cell population consists essentially of CD27+ CD8+ T cells. In some embodiments, the pooled CD27 enriched T cell population and/or the CD27 enriched T cell population consists essentially of CD27+ CD4+ T cells. In some embodiments, the pooled CD27 enriched T cell population and/or the CD27 enriched T cell population consists essentially of CD27+ CD3+ T cells.

a. Cell Selection by Chromatography

In aspects of the methods provided herein, cells of a donor sample, e.g., T cells, are selected by chromatographic isolation, such as by column chromatography including affinity chromatography or gel permeation chromatography. In some embodiments, cells, e.g., CD57− T cells, are isolated, selected, or enriched by chromatographic isolation, such as by column chromatography including affinity chromatography or gel permeations chromatography. In some embodiments, the method employs a receptor binding reagent that binds to a receptor molecule (e.g., CD57) that is located on the surface of a target cell, such as the cell to be isolated, selected, or enriched (e.g., CD57+ cells). In some embodiments, cells, e.g., CD27+ T cells, are isolated, selected, or enriched by chromatographic isolation, such as by column chromatography including affinity chromatography or gel permeations chromatography. In some embodiments, the method employs a receptor binding reagent that binds to a receptor molecule (e.g., CD27) that is located on the surface of a target cell, such as the cell to be isolated, selected, or enriched (e.g., CD27+ cells). Such methods may be described as (traceless) cell affinity chromatography technology (CATCH) and may include any of the methods or techniques described in PCT Application Nos. WO2013124474 and WO2015164675, which are hereby incorporated by reference in its entirety. In particular embodiments, CD57+ cells are negatively selected by chromatographic isolation. In particular embodiments, CD27− cells are negatively selected by chromatographic isolation.

In some embodiments, the target cells (e.g., CD57+ cells), have or express a receptor molecule on the cell surface, such that the cells to be isolated, selected, or enriched are defined by the presence of at least one common specific receptor molecule (e.g., CD57). In some embodiments, the target cells (e.g., CD27− cells), have or express a receptor molecule on the cell surface, such that the cells to be isolated, selected, or enriched are defined by the presence of at least one common specific receptor molecule (e.g., CD27). In some embodiments, the donor sample containing the target cell may also contain additional cells that are devoid of the receptor molecule. For example, in some embodiments, T cells are isolated, enriched, and or elected from a donor sample containing multiple cells types, e.g., red blood cells or B cells. In certain embodiments, CD57+ cells are isolated, enriched, and or selected from a donor sample containing multiple cells types, e.g., red blood cells or B cells, thereby providing isolated CD57+ cells and a non-selected population of cells, e.g., a population of enriched CD57− T cells. In certain embodiments, CD27− cells are isolated, enriched, and or selected from a donor sample containing multiple cells types, e.g., red blood cells or B cells, thereby providing isolated CD27− cells and a non-selected population of cells, e.g., a population of enriched CD27+ T cells.

In some embodiments, the receptor binding reagent is comprised in a chromatography column, e.g., bound directly or indirectly to the chromatography matrix (e.g., stationary phase). In some embodiments, the receptor binding reagent is present on the chromatography matrix (e.g., stationary phase) at the time the sample (e.g. donor sample) is added to the column. In some embodiments, the receptor binding reagent is capable of being bound indirectly to the chromatography matrix (e.g., stationary phase) through a reagent, e.g., an affinity reagent as described herein. In some embodiments, the affinity reagent is bound covalently or non-covalently to the stationary phase of the column. In some embodiments, the affinity reagent is reversibly immobilized on the chromatography matrix (e.g., stationary phase). In some cases, the affinity reagent is immobilized on the chromatography matrix (e.g., stationary phase) via covalent bonds. In some aspects, the affinity reagent is reversibly immobilized on the chromatography matrix (e.g., stationary phase) non-covalently.

In some embodiments, the receptor binding reagent may be present, for example bound directly to (e.g., covalently or non-covalently) or indirectly via an affinity reagent, on the chromatography matrix (e.g., stationary phase) at the time the sample is added to the chromatography column (e.g., stationary phase). Thus, upon addition of the sample (e.g. donor sample), target cells can be bound by the receptor binding reagent and immobilized on the chromatography matrix (e.g., stationary phase) of the column. Alternatively, in some embodiments, the receptor binding reagent can be added to the sample (e.g. donor sample). In this way, the receptor binding reagent binds to the target cells (e.g., T cells) in the sample (e.g. donor sample), and the sample can then be added to a chromatography matrix (e.g., stationary phase) comprising the affinity reagent, where the receptor binding reagent, already bound to the target cells, binds to the affinity reagent, thereby immobilizing the target cells on the chromatography matrix (e.g., stationary phase). In some embodiments, the receptor binding reagent binds to the affinity reagent as described herein, for example as described herein, via binding partner C, as described herein, comprised in the receptor binding reagent.

In some aspects, a receptor binding reagent is added to the sample (e.g. donor sample). In certain embodiments, the receptor binding reagent has a binding site B, which specifically binds to the receptor molecule on the surface of the cell, e.g., the target cell. In some aspects, the receptor binding reagent also includes a binding partner C, which can specifically and reversibly bind to a binding site Z of an affinity reagent. For example, in certain aspects, a receptor binding reagent that binds to or recognizes CD57 is added to the sample (e.g. donor sample), which binds to CD57 on the surface of cells positive for CD57 expression at binding site B. In certain aspects, a receptor binding reagent that binds to or recognizes CD27 is added to the sample (e.g. donor sample), which binds to CD27 on the surface of cells positive for CD27 expression at binding site B.

In certain aspects, the affinity reagent may also contain two or more binding sites Z that can be bound by the binding partner C, thereby providing a multimerization of the receptor binding reagent. This affinity reagent used herein can thus also be a multimerization reagent. The affinity reagent may, for example, be streptavidin, a streptavidin mutein, avidin, an avidin mutein or a mixture thereof. In some aspects, different chromatography matrices are coupled to different affinity reagents, and may be layered into a column forming a multicomponent system for separation.

In some embodiments, two or more receptor binding reagents associate with, such as are reversibly or irreversibly bound to, the affinity reagent, such as via the one or plurality of binding sites Z present on the affinity reagent. In some cases, this results in the receptor binding reagents being closely arranged to each other such that an avidity effect can take place if a target cell having (at least two copies of) a cell surface molecule (e.g., selection marker) is brought into contact with the receptor binding reagent that is able to bind the particular molecule (e.g., selection marker).

In some embodiments, two or more different receptor binding reagents that are the same, i.e. have the same selection marker binding specificity, can be reversibly bound to the affinity reagent. In some embodiments, it is possible to use at least two different receptor binding reagents, and in some cases, three or four different receptor binding reagents that bind to different selection markers. In some aspects, each of the at least two receptor binding reagents can bind to a different molecule (e.g., selection marker), such as a first molecule, second molecule and so on. In some cases, the different molecules (e.g., selection markers), such as cell surface molecules, can be present on the same target cell. In other cases, the different molecules (e.g., selection markers), such as cell surface molecules, can be present on different target cells that are present in the same population of cells. In some case, a third, fourth and so on receptor binding reagents can be associated with the same reagent, each containing a further different binding site.

In some embodiments, the two or more different receptor binding reagents contain the same binding partner C. In some embodiments, the two or more different receptor binding reagents contain different binding partners. In some aspects, a first receptor binding reagent can have a binding partner C1 that can specifically bind to a binding site Z1 present on the affinity reagent and a second receptor binding reagent can have a binding partner C2 that can specifically bind to the binding site Z1 or to a binding site Z2 present on the affinity reagent. Thus, in some instances, the plurality of binding sites Z comprised by the affinity reagent includes binding sites Z1 and Z2, which are capable of reversibly binding to binding partners C1 and C2, respectively, comprised by the receptor binding reagent. In some embodiments, C1 and C2 are the same, and/or Z1 and Z2 are the same. In other aspects, one or more of the plurality of binding sites Z can be different. In other instances, one or more of the plurality of binding partners C may be different. It is within a level of a skilled artisan to choose any combination of different binding partners C that are compatible with an affinity reagent containing the binding sites Z, as long as each of the binding partners C are able to interact, such as specifically bind, with one of the binding sites Z.

In certain embodiments the sample, e.g., the donor sample containing the cells and the receptor binding reagent (e.g. antibody), is loaded on or contacted with a chromatography matrix containing an attached or immobilized affinity reagent (e.g. binding reagent). In particular aspects, the affinity reagent has a plurality of binding sites Z that specifically bind to the binding partner C of the receptor binding reagent. In certain aspects, the receptor binding reagent binds to the affinity reagent by the interaction between the binding partner C and the binding site Z. Thus, in some embodiments, the cell, e.g., the target cell, is immobilized via the complex that is formed by the one or more binding sites Z of the affinity reagent and the binding site Z of receptor binding reagent on the chromatography matrix. In further aspects, the cells, e.g., the target cell, may be depleted from the sample (e.g. the donor sample), such as by rinsing, releasing, or washing the remaining sample from the chromatography matrix. In particular aspects, the receptor binding reagent may either be included in the sample that contains the cells or it may applied or contacted to the chromatography matrix for binding to the attached affinity or multimerization reagent, such as before the sample is added to the chromatography matrix.

In some embodiments, the chromatography matrix is used to remove or separate target cells from a sample (e.g. a donor sample), e.g., by negative selection. For example, in certain embodiments, a sample (e.g. a donor sample containing CD57+ cells and CD57− cells is contacted or incubated with a receptor binding reagent that binds to and or recognizes CD57. In certain embodiments, the sample (e.g. the donor sample) and the receptor binding reagents are loaded onto the matrix, where, in some aspects, a complex is formed by the immobilized or attached affinity reagent, the receptor binding reagent, and a CD57+ T cell. In some embodiments, unbound cells are removed or rinsed from the chromatography matrix, thereby removing the bound CD57+ cells and providing a sample, e.g., a population, enriched for CD57− cells (e.g. a CD57 depleted T cell population and/or a pooled CD57 depleted T cell population). For example, in certain embodiments, a sample (e.g. a donor sample containing CD27− cells and CD27+ cells is contacted or incubated with a receptor binding reagent that binds to and or recognizes CD27. In certain embodiments, the sample (e.g. the donor sample) and the receptor binding reagents are loaded onto the matrix, where, in some aspects, a complex is formed by the immobilized or attached affinity reagent, the receptor binding reagent, and a CD27− T cell. In some embodiments, unbound cells are removed or rinsed from the chromatography matrix, thereby removing the bound CD27− cells and providing a sample, e.g., a population, enriched for CD27+ cells (e.g. a CD27 enriched T cell population and/or a pooled CD27 enriched T cell population).

In certain embodiments, the chromatography matrix is used to isolate, select, or enrich target cells from a sample (e.g. a donor sample), e.g., by positive selection. For example, in some embodiments, a sample containing CD4+ or CD8+ T cells and other cells, e.g., non-T cell immune cells, is contacted or incubated with a receptor binding reagent that binds to and or recognizes CD4 or CD8. In certain embodiments, the sample and the receptor binding reagents are loaded onto the matrix, where, in some aspects, a complex is formed by the immobilized or attached affinity reagent, the receptor binding reagent, and CD4+ or CD8+ T cell. In certain embodiments, unbound cells are removed or rinsed from the chromatography matrix. In particular embodiments, the immobilized CD4+ or CD8+ cells may be removed or released by the addition of the competition reagent, such as by disrupting the complex. In some aspects, the separated, released, or eluted CD4+ or CD8+ T cells are thus a sample, composition, or population of cells enriched for CD4+ or CD8+ T cells.

In certain embodiments, the chromatography matrix is used to isolate, select, or enrich target cells from a sample (e.g. a donor sample), e.g., by positive selection. For example, in some embodiments, a sample containing CD3+ T cells and other cells, e.g., non-T cell immune cells, is contacted or incubated with a receptor binding reagent that binds to and or recognizes CD3. In certain embodiments, the sample and the receptor binding reagents are loaded onto the matrix, where, in some aspects, a complex is formed by the immobilized or attached affinity reagent, the receptor binding reagent, and CD3+ T cell. In certain embodiments, unbound cells are removed or rinsed from the chromatography matrix. In particular embodiments, the immobilized CD3+ cells may be removed or released by the addition of the competition reagent, such as by disrupting the complex. In some aspects, the separated, released, or eluted CD3+ T cells are thus a sample, composition, or population of cells enriched for CD3+ T cells.

In some aspects, a competition reagent is loaded onto the chromatography column. In some embodiments, a reversible bond formed between binding partner C and binding site Z can be disrupted by a competition reagent. In particular embodiments, the competition reagent has a binding site that is able to bind to the binding site Z of the affinity reagent. In some embodiments, a competition reagent can be a biotin, a biotin derivative or analog or a streptavidin-binding peptide capable of competing for binding with the binding partner C for the one or more binding sites Z. In certain embodiments, the competition reagent forms a complex with the affinity reagent, and is thereby immobilized on the chromatography matrix. In some embodiments, the binding partner C and the competition reagent are different, and the competition reagent exhibits a higher binding affinity for the one or more binding sites Z compared to the affinity of the binding partner. In particular aspects of any of the methods provided herein, addition of a competition reagent to the stationary phase of the chromatography column to disrupt the binding of the selection agent (e.g., the receptor-binding agent) to the affinity reagent is not required to detach the target cells (e.g., T cells) from the chromatography matrix (e.g., stationary phase).

As a result of this competitive binding, the binding between the receptor binding reagent and the affinity reagent at binding partner C and binding site Z is displaced. In particular embodiments, adding or loading the competition reagent to a chromatography matrix with an attached complex containing the affinity reagent, receptor binding reagent, and the cell, e.g., the target cell, elutes the cell from the chromatography matrix. In some aspects, the receptor binding reagent has a low affinity towards the receptor molecule of the cell at binding site B, such that the receptor binding reagent dissociates from the cell in the presence of the competition reagent. Thus, in some embodiments, the cells, e.g., the target cells, are eluted from the chromatography matrix free or essentially free of bound receptor binding molecules.

In some embodiments, an elution sample from the eluate of the first chromatography column, which includes the cells, e.g., the target cells, the competition reagent, and the receptor binding reagent, is collected. In certain embodiments, the elution sample is loaded onto a second chromatography column, which has a suitable stationary phase that is both an affinity chromatography matrix and, at the same time, can act as gel permeation matrix. In particular embodiments, the affinity chromatography matrix has an affinity reagent immobilized thereon. In some aspects, the receptor binding reagent and the competition reagent bind to a binding site Z on the affinity reagent, and are thereby immobilized on the chromatography matrix. As a result, in certain aspects, the elution sample containing the isolated target cells is depleted of the receptor binding reagent and the competition reagent. Thus, in some aspects, the target cells, being freed of any reactants, are now in a condition for further use, for example, for processing by any of the methods described herein.

In some embodiments, the cells, e.g., the target cells of the sample (e.g. donor sample), may be depleted from the sample, such as by rinsing, releasing, or washing the remaining sample from the chromatography matrix (e.g., stationary phase). In some embodiments, one or more (e.g., 2, 3, 4, 5, 6) wash steps are used to remove unbound cells and debris from the chromatography matrix (e.g., stationary phase). In some embodiments, at least two wash steps are performed. In some embodiments, the sample is allowed to penetrate the matrix for at least or about 5, 10, 15, 16, 20, 25, 30, 35, 40, 45, 50, 55, 60, 70, 80, 90, 100, or 120 minutes before one or more wash steps are performed. In some embodiments, a wash step is performed at, about, or at least 5, 10, 15, 20, 25, 30, 35, 40, 45, 50, 55, 60, 70, 80, 90, 100, or 120 minutes after the sample is added to the chromatography column (e.g., stationary phase). In some embodiments, a wash step is performed at, about, or at least 5, 10, 15, 20, 25, 30, 35, 40, 45, 50, 55, or 60 minutes after the sample is added to the chromatography column (e.g., stationary phase). In some embodiments, one or more wash steps are performed within or within about 120, 100, 90, 80, 70, 60, 55, 50, 45, 40, 35, 30, 25, 20, 15, 10, or 5 minutes following addition of the sample to the chromatography column (e.g., stationary phase). In some embodiments, one or more wash steps are performed within or within about 60, 55, 50, 45, 40, 35, 30, 25, 20, 15, 10, or 5 minutes following addition of the sample to the chromatography column (e.g., stationary phase). In some embodiments, one or more wash steps are performed within or within about 5 to 60 minutes following addition of the sample to the chromatography column (e.g., stationary phase). In some embodiments, one or more wash steps are performed within or within about 5 to 50 minutes following addition of the sample to the chromatography column (e.g., stationary phase). In some embodiments, one or more wash steps are performed within or within about 5 to 40 minutes following addition of the sample to the chromatography column (e.g., stationary phase). In some embodiments, one or more wash steps are performed within or within about 5 to 30 minutes following addition of the sample to the chromatography column (e.g., stationary phase). In some embodiments, one or more wash steps are performed within or within about 5 to 20 minutes following addition of the sample to the chromatography column (e.g., stationary phase). In some embodiments, one or more wash steps are performed within or within about 5 to 10 minutes following addition of the sample to the chromatography column (e.g., stationary phase). In some embodiments, one or more wash steps are performed within or within about 10 to 60 minutes following addition of the sample to the chromatography column (e.g., stationary phase). In some embodiments, one or more wash steps are performed within or within about 20 to 60 minutes following addition of the sample to the chromatography column (e.g., stationary phase). In some embodiments, one or more wash steps are performed within or within about 30 to 60 minutes following addition of the sample to the chromatography column (e.g., stationary phase). In some embodiments, one or more wash steps are performed within or within about 40 to 60 minutes following addition of the sample to the chromatography column (e.g., stationary phase). In some embodiments, one or more wash steps are performed within or within about 50 to 60 minutes following addition of the sample to the chromatography column (e.g., stationary phase).

In some embodiments, multiple rounds of cell selection steps are carried out, where the positively or negatively selected fraction from one step is subjected to another selection step, such as a subsequent positive or negative selection. In certain embodiments, methods, techniques, and reagents for selection, isolation, and enrichment are described, for example, in PCT Application No. WO2015164675, which is hereby incorporated by reference in its entirety.

In some embodiments, a single selection step can be used to isolate target cells (e.g., CD57-T cells) from a sample (e.g. a donor sample). In some embodiments, a single selection step can be used to isolate target cells (e.g., CD27+ T cells) from a sample (e.g. a donor sample). In some embodiments, the single selection step can be performed on a single chromatography column. In some examples, a single selection step can deplete cells expressing multiple markers simultaneously. Likewise, multiple cell types can simultaneously be positively selected. In certain embodiments, selection steps are repeated and or performed more than once, where the positively or negatively selected fraction from one step is subjected to the same selection step, such as a repeated positive or negative selection. In some examples, a single selection step is repeated and/or performed more than once, for example to increase the purity of the selected cells and/or to further remove and/or deplete the negatively selected cells from the negatively selected fraction. In certain embodiments, one or more selection steps are performed two times, three times, four times, five times, six times, seven times, eight times, nine times, ten times, or more than ten times. In certain embodiments, the one or more selection steps are performed and/or repeated between one and ten times, between one and five times, or between three and five times. In some embodiments, two selection steps are performed.

Cell selection may be performed using one or more chromatography columns. In some embodiments, the one or more chromatography columns are included in a closed system. In some embodiments, the closed system is an automated closed system, for example requiring minimal or no user (e.g., human) input. In some embodiments, cell selection is performed sequentially (e.g., a sequential selection technique). In some embodiments, the one or more chromatography columns are arranged sequentially. For example, a first column may be oriented such that the output of the column (e.g., eluent) can be fed, e.g., via connected tubing, to a second chromatography column. In some embodiments, a plurality of chromatography columns may be arranged sequentially. In some embodiments, cell selection may be achieved by carrying out sequential positive and negative selection steps, the subsequent step subjecting the negative and/or positive fraction from the previous step to further selection, where the entire process is carried out in the same tube or tubing set.

In some embodiments, a sample (e.g. a donor sample) containing target cells is subjected to a sequential selection in which a first selection is effected to enrich for one of the CD4+ or CD8+ populations, and the non-selected cells from the first selection are used as the source of cells for a second selection to enrich for the other of the CD4+ or CD8+ populations. In some embodiments, a further selection or selections can be effected to enrich for sub-populations of one or both of the CD4+ or CD8+ population, for example, central memory T ($T_{CM}$) cells, naïve T cells, and/or cells positive for or expressing high levels of one or more surface markers, e.g., CD28+, CD62 L+, CCR7+, CD27+, CD127+, CD4+, CD8+, CD45RA+, and/or CD45RO+. In some embodiments, a sample containing target cells (e.g. a donor sample) is subjected to a sequential selection in which a first selection is effected to enrich for a CD3+ population, and the selected cells are used as the source of cells for a second selection to enrich for CD3+ populations. In some embodiments, a sample containing target cells (e.g. a donor sample) is subjected to a sequential selection in which a first selection is effected to enrich for a CD3+ population on a first stationary phase (e.g., in a first chromatograph column), and the flow through containing unbound cells is used as the source of cells for a second selection to enrich for a CD3+ population on a second stationary phase (e.g., in a second chromatograph column), wherein the first and second stationary phases are arranged sequentially. In some embodiments, a further selection or selections can be effected to enrich for sub-populations of the CD3+ population, for example, central memory T ($T_{CM}$) cells, naïve T cells, and/or cells positive for or expressing high levels of one or more surface markers, e.g., CD28+, CD62 L+, CCR7+, CD27+, CD127+, CD4+, CD8+, CD45RA+, and/or CD45RO+. In some embodiments, a sample containing target cells (e.g. a donor sample) is subjected to a sequential selection in which a first selection is effected to enrich for a CD3+ population, and the selected cells are used as the source of cells for a second selection to enrich for CD4+ populations. In some embodiments, a further selection or selections can be effected to enrich for sub-populations of the CD3+ CD4+ population, for example, central memory T ($T_{CM}$) cells, naïve T cells, and/or cells positive for or expressing high levels of one or more surface markers, e.g., CD28+, CD62 L+, CCR7+, CD27+, CD127+, CD4+, CD8+, CD45RA+, and/or CD45RO+. In some embodiments, a sample containing target cells (e.g. a donor sample) is subjected to a sequential selection in which a first selection is effected to enrich for a CD3+ population, and the selected cells are used as the source of cells for a second selection to enrich for CD8+ populations. In some embodiments, a further selection or selections can be effected to enrich for sub-populations of the CD3+ CD8+ population, for example, central memory T ($T_{CM}$) cells, naïve T cells, and/or cells positive for or expressing high levels of one or more surface markers, e.g., CD28+, CD62 L+, CCR7+, CD27+, CD127+, CD4+, CD8+, CD45RA+, and/or CD45RO+. It is contemplated that in some aspects, specific subpopulations of T cells (e.g., CD3+ cells), such as cells positive or expressing high levels of one or more surface markers, e.g., CD28+, CD62 L+, CCR7+, CD27+, CD127+, CD4+, CD8+, CD45RA+, and/or CD45RO+ T cells, are selected by positive or negative sequential selection techniques.

In some embodiments, a sample containing target cells (e.g. a donor sample) is subjected to a sequential selection in which a first selection is effected to enrich for a CD57− population, and the selected cells are used as the source of cells for a second selection to enrich for CD3+ populations. In some embodiments, a sample containing target cells (e.g. a donor sample) is subjected to a sequential selection in which a first selection is effected to enrich for a CD57− population on a first stationary phase (e.g., in a first chromatograph column), and the flow through containing unbound cells is used as the source of cells for a second selection to enrich for a CD3+ population on a second stationary phase (e.g., in a second chromatograph column), wherein the first and second stationary phases are arranged sequentially. In some embodiments, a further selection or selections can be effected to enrich for sub-populations of the CD57− population, for example, central memory T ($T_{CM}$) cells, naïve T cells, and/or cells positive for or expressing high levels of one or more surface markers, e.g., CD28+, CD62 L+, CCR7+, CD27+, CD127+, CD4+, CD8+, CD45RA+, and/or CD45RO+. In some embodiments, a sample containing target cells is subjected to a sequential selection in which a first selection is effected to enrich for a CD57− population, and the selected cells are used as the source of cells for a second selection to enrich for CD3+ populations. In some embodiments, a further selection or selections can be effected to enrich for sub-populations of the CD57−CD3+ population, for example, central memory T ($T_{CM}$) cells, naïve T cells, and/or cells positive for or expressing high levels of one or more surface markers, e.g., CD28+, CD62 L+, CCR7+, CD27+, CD127+, CD4+, CD8+, CD45RA+, and/or CD45RO+. It is contemplated that in some aspects, specific subpopulations of T cells (e.g., CD57− cells), such as cells positive or expressing high levels of one or more surface markers, e.g., CD28+, CD62 L+, CCR7+, CD27+, CD127+, CD4+, CD8+, CD45RA+, and/or CD45RO+ T cells, are selected by positive or negative sequential selection techniques.

In some embodiments, a sample containing target cells (e.g. a donor sample) is subjected to a sequential selection in which a first selection is effected to enrich for a CD27+ population, and the selected cells are used as the source of cells for a second selection to enrich for CD3+ populations. In some embodiments, a sample containing target cells (e.g. a donor sample) is subjected to a sequential selection in which a first selection is effected to enrich for a CD27+ population on a first stationary phase (e.g., in a first chromatograph column), and the flow through containing unbound cells is used as the source of cells for a second selection to enrich for a CD3+ population on a second stationary phase (e.g., in a second chromatograph column), wherein the first and second stationary phases are arranged sequentially. In some embodiments, a further selection or selections can be effected to enrich for sub-populations of the CD27+ population, for example, central memory T ($T_{CM}$) cells, naïve T cells, and/or cells positive for or expressing high levels of one or more surface markers, e.g., CD28+, CD62 L+, CCR7+, CD127+, CD4+, CD8+, CD45RA+, and/or CD45RO+. In some embodiments, a sample containing target cells is subjected to a sequential selection in which a first selection is effected to enrich for a CD27+ population, and the selected cells are used as the source of cells for a second selection to enrich for CD3+ populations. In some embodiments, a further selection or selections can be effected to enrich for sub-populations of the CD27+ CD3+ population, for example, central memory T ($T_{CM}$) cells, naïve T cells, and/or cells positive for or expressing high levels of one or more surface markers, e.g., CD28+, CD62 L+, CCR7+, CD127+, CD4+, CD8+, CD45RA+, and/or CD45RO+. It is contemplated that in some aspects, specific subpopulations of T cells (e.g., CD27+ cells), such as cells positive or expressing high levels of one or more surface markers, e.g., CD28+, CD62 L+, CCR7+, CD127+, CD4+, CD8+, CD45RA+, and/or CD45RO+ T cells, are selected by positive or negative sequential selection techniques.

In some embodiments, a sample containing target cells (e.g. a donor c sample is subjected to a sequential selection in which a first selection is effected to enrich for a CD3+ population, and the selected cells are used as the source of cells for a second selection to enrich for CD57− populations. In some embodiments, a sample containing target cells (e.g. a donor sample) is subjected to a sequential selection in which a first selection is effected to enrich for a CD3+ population on a first stationary phase (e.g., in a first chromatograph column), and the flow through containing unbound cells is used as the source of cells for a second selection to enrich for a CD57− population on a second stationary phase (e.g., in a second chromatograph column), wherein the first and second stationary phases are arranged sequentially. In some embodiments, a sample containing target cells (e.g. a donor c sample is subjected to a sequential selection in which a first selection is effected to enrich for a CD3+ population, and the selected cells are used as the source of cells for a second selection to enrich for CD27+ populations. In some embodiments, a sample containing target cells (e.g. a donor sample) is subjected to a sequential selection in which a first selection is effected to enrich for a CD3+ population on a first stationary phase (e.g., in a first chromatograph column), and the flow through containing unbound cells is used as the source of cells for a second selection to enrich for a CD27+ population on a second stationary phase (e.g., in a second chromatograph column), wherein the first and second stationary phases are arranged sequentially. In some embodiments, a further selection or selections can be effected to enrich for sub-populations of the CD3+ population, for example, central memory T ($T_{CM}$) cells, naïve T cells, and/or cells positive for or expressing high levels of one or more surface markers, e.g., CD28+, CD62 L+, CCR7+, CD27+, CD127+, CD4+, CD8+, CD45RA+, and/or CD45RO+. In some embodiments, a sample containing target cells is subjected to a sequential selection in which a first selection is effected to enrich for a CD3+ population, and the selected cells are used as the source of cells for a second selection to enrich for CD57− populations. In some embodiments, a further selection or selections can be effected to enrich for sub-populations of the CD3+ CD57− population, for example, central memory T ($T_{CM}$) cells, naïve T cells, and/or cells positive for or expressing high levels of one or more surface markers, e.g., CD28+, CD62 L+, CCR7+, CD27+, CD127+, CD4+, CD8+, CD45RA+, and/or CD45RO+. It is contemplated that in some aspects, specific subpopulations of T cells (e.g., CD57− cells), such as cells positive or expressing high levels of one or more surface markers, e.g., CD28+, CD62 L+, CCR7+, CD27+, CD127+, CD4+, CD8+, CD45RA+, and/or CD45RO+ T cells, are selected by positive or negative sequential selection techniques. In some embodiments, a sample containing target cells is subjected to a sequential selection in which a first selection is effected to enrich for a CD3+ population, and the selected cells are used as the source of cells for a second selection to enrich for CD27+ populations. In some embodiments, a further selection or selections can be effected to enrich for sub-populations of the CD3+ CD27+ population, for example, central memory T ($T_{CM}$) cells, naïve T cells, and/or cells positive for or expressing high levels of one or more surface markers, e.g., CD28+, CD62 L+, CCR7+, CD127+, CD4+, CD8+, CD45RA+, and/or CD45RO+. It is contemplated that in some aspects, specific subpopulations of T cells (e.g., CD27+− cells), such as cells positive or expressing high levels of one or more surface markers, e.g., CD28+, CD62 L+, CCR7+, CD127+, CD4+, CD8+, CD45RA+, and/or CD45RO+ T cells, are selected by positive or negative sequential selection techniques.

In some embodiments, cell selection is performed in parallel (e.g., parallel selection technique). In some embodiments, the one or more chromatography columns are arranged in parallel. For example, two or more columns may be arranged such that a sample (e.g. a donor cell sample) is loaded onto two or more columns at the same time via tubing that allows for the sample to be added to each column, for example, without the need for the sample to traverse through a first column. For example, using a parallel selection technique, cell selection may be achieved by carrying out positive and/or negative selection steps simultaneously, for example in a closed system where the entire process is carried out in the same tube or tubing set. In some embodiments, a sample containing target cells (e.g. a donor sample) is subjected to a parallel selection in which the sample is load onto two or more chromatography columns, where each column effects selection of a cell population.

In some embodiments, the two or more chromatography columns effect selection of CD57−, CD3+, CD4+, or CD8+ populations individually. In some embodiments, the two or more chromatography columns, including affinity chromatography or gel permeation chromatography, independently effect selection of the same cell population. For example, the two or more chromatography columns may effect selection of CD57− cells. In some embodiments, the two or more chromatography columns, including affinity chromatography or gel permeation chromatography, independently effect selection of different cell populations. For example, the two or more chromatography columns independently may effect selection of CD57− cells, CD4+ cells, CD3+ and/or CD8+ cells. In some embodiments, a further selection or selections, for example using sequential selection techniques, can be effected to enrich for sub-populations of one or all cell populations selected via parallel selection. For example, selected cells may be further selected for central memory T ($T_{CM}$) cells, naïve T cells, and/or cells positive for or expressing high levels of one or more surface markers, e.g., CD28+, CD62 L+, CCR7+, CD27+, CD127+, CD4+, CD8+, CD45RA+, and/or CD45RO+. In some embodiments, a sample containing target cells (e.g. a donor sample) is subjected to a parallel selection in which parallel selection is effected to enrich for a CD57− population on the two or more columns. In some embodiments, a further selection or selections can be effected to enrich for sub-populations of the CD57− population, for example, central memory T ($T_{CM}$) cells, naïve T cells, and/or cells positive for or expressing high levels of one or more surface markers, e.g., CD28+, CD62 L+, CCR7+, CD27+, CD127+, CD4+, CD8+, CD45RA+, and/or CD45RO+. In some embodiments, a sample containing target cells (e.g. a donor sample) is subjected to a parallel selection in which a selection is effected to enrich for a CD57− population and a CD3+ population on the two or more columns, independently. In some embodiments, a further selection or selections can be effected to enrich for sub-populations of the CD57− and CD3+ populations, for example, central memory T ($T_{CM}$) cells, naïve T cells, and/or cells positive for or expressing high levels of one or more surface markers, e.g., CD28+, CD62 L+, CCR7+, CD27+, CD127+, CD4+, CD8+, CD45RA+, and/or CD45RO+. In some embodiments, a sample containing target cells (e.g. a donor sample) is subjected to a parallel selection in which a selection is effected to enrich for a CD57− population and a CD4+ population on the two or more columns, independently. In some embodiments, a further selection or selections can be effected to enrich for sub-populations of the CD57− and CD4+ populations, for example, central memory T ($T_{CM}$) cells, naïve T cells, and/or cells positive for or expressing high levels of one or more surface markers, e.g., CD28+, CD62 L+, CCR7+, CD27+, CD127+, CD4+, CD8+, CD45RA+, and/or CD45RO+. In some embodiments, a sample containing target cells (e.g. a donor sample) is subjected to a parallel selection in which parallel selection is effected to enrich for a CD57− population and a CD8+ population. In some embodiments, a further selection or selections can be effected to enrich for sub-populations of the CD57− and CD8+ populations, for example, central memory T ($T_{CM}$) cells, naïve T cells, and/or cells positive for or expressing high levels of one or more surface markers, e.g., CD28+, CD62 L+, CCR7+, CD27+, CD127+, CD4+, CD8+, CD45RA+, and/or CD45RO+. In some embodiments, a sample containing target cells (e.g. a donor sample) is subjected to a parallel selection in which parallel selection is effected to enrich for a CD4+ population and a CD8+ population. In some embodiments, a further selection or selections can be effected to enrich for sub-populations of the CD4+ and CD8+ populations, for example, central memory T ($T_{CM}$) cells, naïve T cells, and/or cells positive for or expressing high levels of one or more surface markers, e.g., CD28+, CD62 L+, CCR7+, CD27+, CD127+, CD4+, CD8+, CD45RA+, and/or CD45RO+. It is contemplated that in some aspects, specific subpopulations of T cells (e.g., CD3+, CD4+, CD8+ T cells), such as cells positive or expressing high levels of one or more surface markers, e.g., CD28+, CD62 L+, CCR7+, CD27+, CD127+, CD4+, CD8+, CD45RA+, and/or CD45RO+ T cells, are selected by positive or negative parallel selection techniques. In some embodiments, sequential and parallel selection techniques can be used in combination.

In some embodiments, the two or more chromatography columns effect selection of CD27+, CD3+, CD4+, or CD8+ populations individually. In some embodiments, the two or more chromatography columns, including affinity chromatography or gel permeation chromatography, independently effect selection of the same cell population. For example, the two or more chromatography columns may effect selection of CD27+ cells. In some embodiments, the two or more chromatography columns, including affinity chromatography or gel permeation chromatography, independently effect selection of different cell populations. For example, the two or more chromatography columns independently may effect selection of CD27+ cells, CD4+ cells, CD3+ and/or CD8+ cells. In some embodiments, a further selection or selections, for example using sequential selection techniques, can be effected to enrich for sub-populations of one or all cell populations selected via parallel selection. For example, selected cells may be further selected for central memory T ($T_{CM}$) cells, naïve T cells, and/or cells positive for or expressing high levels of one or more surface markers, e.g., CD28+, CD62 L+, CCR7+, CD127+, CD4+, CD8+, CD45RA+, and/or CD45RO+. In some embodiments, a sample containing target cells (e.g. a donor sample) is subjected to a parallel selection in which parallel selection is effected to enrich for a CD27+ population on the two or more columns. In some embodiments, a further selection or selections can be effected to enrich for sub-populations of the CD27+ population, for example, central memory T ($T_{CM}$) cells, naïve T cells, and/or cells positive for or expressing high levels of one or more surface markers, e.g., CD28+, CD62 L+, CCR7+, CD127+, CD4+, CD8+, CD45RA+, and/or CD45RO+. In some embodiments, a sample containing target cells (e.g. a donor sample) is subjected to a parallel selection in which a selection is effected to enrich for a CD27+ population and a CD3+ population on the two or more columns, independently. In some embodiments, a further selection or selections can be effected to enrich for sub-populations of the CD27+ and CD3+ populations, for example, central memory T ($T_{CM}$) cells, naïve T cells, and/or cells positive for or expressing high levels of one or more surface markers, e.g., CD28+, CD62 L+, CCR7+, CD127+, CD4+, CD8+, CD45RA+, and/or CD45RO+. In some embodiments, a sample containing target cells (e.g. a donor sample) is subjected to a parallel selection in which a selection is effected to enrich for a CD27+ population and a CD4+ population on the two or more columns, independently. In some embodiments, a further selection or selections can be effected to enrich for sub-populations of the CD27+ and CD4+ populations, for example, central memory T ($T_{CM}$) cells, naïve T cells, and/or cells positive for or expressing high levels of one or more surface markers, e.g., CD28+, CD62 L+, CCR7+, CD127+, CD4+, CD8+, CD45RA+, and/or CD45RO+. In some embodiments, a sample containing target cells (e.g. a donor sample) is subjected to a parallel selection in which parallel selection is effected to enrich for a CD27+ population and a CD8+ population. In some embodiments, a further selection or selections can be effected to enrich for sub-populations of the CD27+ and CD8+ populations, for example, central memory T ($T_cM$) cells, naïve T cells, and/or cells positive for or expressing high levels of one or more surface markers, e.g., CD28+, CD62 L+, CCR7+, CD127+, CD4+, CD8+, CD45RA+, and/or CD45RO+.

In some embodiments, two columns are used for parallel selection. In some embodiments, the two columns select for the same cell type (e.g., same selection marker). In some embodiments, the two columns each select for CD57− T cells. In some embodiments, the two columns each select for CD27+ T cells. In some embodiments, the two columns select for different cell types (e.g., different selection marker). In some embodiments, one of the two columns selects for CD57− T cells and the other of the two columns selects for CD3+ cells. In some embodiments, one of the two columns selects for CD27+ T cells and the other of the two columns selects for CD3+ cells.

In some embodiments, one or more selection steps are carried out at one or more time points or following certain steps of the process for creating an engineered cell composition. In some embodiments, a selection step includes multiple selection steps for, for example, further purifying the engineered cell composition, selection of specific cell subtypes, selection of viable cells, selection of engineered cells, and/or adjusting the ratio, total number, or concentration of cells. In some embodiments, a selection step is performed prior to incubation. In some embodiments, a selection step is performed prior to harvesting and collection.

In some embodiments, the cell composition is from an individual donor. In some embodiments, each of the cell compositions from an individual donor have been combined to produce a pooled cell composition from a plurality of individual donors. In some embodiments, the cell composition is from a plurality of different donors. In some aspects, cells compositions derived from individual donors are each separately subjected to one or more additional selection steps at one or more time points or following certain steps of the process for creating an engineered cell composition, and then combined to create a pooled cell composition.

In some aspects, such methods (e.g., selection steps) are achieved by a single process stream, such as in a closed system, by employing sequential selections in which a plurality of different cell populations from a stimulated and/or engineered cell composition, as provided herein, are enriched and/or isolated. In the stimulated and/or engineered cell composition is derived from an individual donor. In some embodiments, the stimulated and/or engineered cell composition is derived from a plurality of different donors. In some aspects, carrying out the separation or isolation in the same vessel or set of vessels, e.g., tubing set, is achieved by carrying out sequential positive and negative selection steps, the subsequent step subjecting the negative and/or positive fraction from the previous step to further selection, where the entire process is carried out in the same tube or tubing set. In one embodiment, a composition of stimulated and/or engineered cells containing target cells is subjected to a sequential selection in which a first selection is effected to enrich for one of the CD4+ or CD8+ populations, and the non-selected cells from the first selection are used as the source of cells for a second selection to enrich for the other of the CD4+ or CD8+ populations. In some embodiments, a further selection or selections can be effected to enrich for sub-populations of one or both of the CD4+ or CD8+ population, for example, CD57− cells. In some embodiments, a further selection or selections can be effected to enrich for sub-populations of one or both of the CD4+ or CD8+ population, for example, CD27+ cells. In some embodiments, a composition of stimulated and/or engineered cells containing target cells is subjected to a sequential selection for viable cells. In some embodiments, the ratio or total number of cells in the composition of stimulated and/or engineered cells containing target cells is controlled or adjusted.

In some aspects, such methods (e.g., selection steps) are achieved by a single process stream, such as in a closed system, by employing sequential selections in which a plurality of different cell populations from compositions of stimulated and/or engineered cells, as provided herein, are enriched and/or isolated. In some aspects, carrying out the separation or isolation in the same vessel or set of vessels, e.g., tubing set, is achieved by carrying out sequential negative and postive selection steps, the subsequent step subjecting the negative and/or positive fraction from the previous step to further selection, where the entire process is carried out in the same tube or tubing set. In one embodiment, a composition of stimulated and/or engineered cells containing target cells is subjected to a sequential selection in which a first selection is effected to remove CD57+ populations. In some embodiments, a further selection or selections can be effected to enrich for one or both of CD4+ or CD8+ population, for example, CD57−CD4+ or CD57−CD8+ cells. In one embodiment, a composition of stimulated and/or engineered cells containing target cells is subjected to a sequential selection in which a first selection is effected to remove CD27− populations. In some embodiments, a further selection or selections can be effected to enrich for one or both of CD4+ or CD8+ population, for example CD27+ CD4+ or CD27+ CD8+ cells. In some embodiments, a composition of stimulated and/or engineered cells containing target cells is subjected to a sequential selection for viable cells. In some embodiments, the ratio or total number of cells in the output composition of stimulated and/or engineered cells containing target cells is controlled or adjusted.

In one embodiment, a composition of stimulated and/or engineered cells containing target cells is subjected to a sequential selection in which a first selection is effected to enrich for a CD3+ population. In some embodiments, a further selection or selections can be effected to enrich for sub-populations of the CD3+ population, for example, CD57− cells. In some embodiments, the further selection or selections can be effected to enrich for viable cells. In some embodiments, the further selection or selections can be effected to enrich subpopulations of CD57−CD3+ cells, for example CD3+ CD57−CD4+ or CD57−CD3+ CD8+ cells that are viable. In some embodiments, a further selection or selections can be effected to enrich for sub-populations of the CD3+ population, for example, CD27+ cells. In some embodiments, the further selection or selections can be effected to enrich for viable cells. In some embodiments, the further selection or selections can be effected to enrich subpopulations of CD27+ CD3+ cells, for example CD27+ CD3+ CD4+ or CD27+ CD3+ CD8+ cells that are viable. In some embodiments, selecting viable cells includes or consists of removing dead cells from the composition of stimulated and/or engineered cells or subpopulations thereof.

In one embodiment, a composition of stimulated and/or engineered cells containing target cells is subjected to a sequential selection in which a first selection is effected to remove CD57+ cells. In some embodiments, a further selection or selections can be effected to enrich for sub-populations of the CD57− population, for example, CD4+ and/or CD8+ cells. In one embodiment, a composition of stimulated and/or engineered cells containing target cells is subjected to a sequential selection in which a first selection is effected to remove CD27− cells. In some embodiments, a further selection or selections can be effected to enrich for sub-populations of the CD27+ population, for example, CD4+ and/or CD8+ cells. In some embodiments, the further selection or selections can be effected to enrich for viable cells. In some embodiments, selecting viable cells includes or consists of removing dead cells from the output composition of stimulated and/or engineered cells or subpopulations thereof.

In some embodiments, the methods (e.g., selection steps) disclosed in this Section do not need to be carried out using sequential selection techniques. In some embodiments, the methods (e.g., selection steps) disclosed in this Section can be carried out using sequential selection techniques in combination with parallel selection techniques. In some embodiments, the selection step does not employ sequential selection or may employ sequential selection that does not occur in a closed system or in a set of vessels using the same tubing. In some embodiments, the selection step is accomplished in a single step, for example using a single chromatography column. In some embodiments, the selection step is accomplished using a parallel selection technique. For example, the selection step is achieved by carrying out positive and/or negative selection steps simultaneously, for example in a closed system where the entire process is carried out in the same tube or tubing set. In some embodiments, a composition of stimulated and/or engineered cells containing target cells is subjected to a parallel selection in which the composition of stimulated and/or engineered cells is loaded onto two or more chromatography columns, where each column effects selection of a cell population. In some embodiments, the two or more chromatography columns effect selection of CD57−, CD3+, CD4+, or CD8+ populations individually. In some embodiments, the two or more chromatography columns effect selection of the same cell population. For example, the two or more chromatography columns may effect selection of CD57− cells. In some embodiments, the two or more chromatography columns effect selection of CD27+, CD3+, CD4+, or CD8+ populations individually. In some embodiments, the two or more chromatography columns effect selection of the same cell population. For example, the two or more chromatography columns may effect selection of CD27+ cells. In some embodiments, the two or more chromatography columns, including affinity chromatography or gel permeation chromatography, independently effect selection of the same cell population. In some embodiments, the two or more chromatography columns, including affinity chromatography or gel permeation chromatography, independently effect selection of different cell populations. In some embodiments, a further selection or selections can be effected to enrich for subpopulations of one or all cell populations selected via parallel selection. In some embodiments, a composition of stimulated and/or engineered cells containing target cells (e.g., CD57− cells) is subjected to a parallel selection in which parallel selection is effected to enrich for a CD4+ population and a CD8+ population or a CD3+ population. In some embodiments, a composition of stimulated and/or engineered cells containing target cells (e.g., CD27+ cells) is subjected to a parallel selection in which parallel selection is effected to enrich for a CD4+ population and a CD8+ population or a CD3+ population.

In some embodiments, a selection step can be carried out using beads labeled with selection agents as described herein, and the positive and negative fractions from the first selection step can be retained, followed by further positive selection of the positive fraction to enrich for a second selection marker, such as by using beads labeled with a second selection agent or by subjecting the positive fraction to column chromatography as described above. In some embodiments, one or more selection steps are carried out using column chromatography as described herein. In some embodiments, selection steps are accomplished using one or more methods including bead separation and column chromatography. In some embodiments, the selection are accomplished using column chromatography.

In some aspects, isolating the plurality of populations in a single or in the same isolation or separation vessel or set of vessels, such as a single column or set of columns, and/or same tube, or tubing set or using the same separation matrix or media or reagents, such as the same magnetic matrix, affinity-labeled solid support, or antibodies or other binding partners, include features that streamline the isolation, for example, resulting in reduced cost, time, complexity, need for handling of samples, use of resources, reagents, or equipment. In some aspects, such features are advantageous in that they minimize cost, efficiency, time, and/or complexity associated with the methods, and/or avoid potential harm to the cell product, such as harm caused by infection, contamination, and/or changes in temperature. The methods provided herein allow for multiple selection steps to enrich target populations both prior to or following cell selection combined with on-column stimulation.

The methods provided herein further allow for the selection and enrichment of successfully stimulated and/or engineered cell compositions. For example, in some embodiments, the sequential selection, parallel selection, or single selection procedures described above may be used to identify stimulated cells expressing recombinant receptors (e.g., CARs, TCRs). In some embodiments, cells expressing the recombinant receptor (e.g., CAR) can be further enriched for sub-population cells, e.g., CD4+ CAR+ T cells, CD8+ CAR+ T cells, and/or viable cells. In some embodiments, the selection step allows control or adjustment of the ratio, concentration, or total number of cells expressing a recombinant receptor (e.g., CAR, TCR) and/or subpopulations thereof.

In general, binding capacity of a stationary phase (e.g., selection resin) affects how much stationary phase is needed in order to select a certain number of target moieties, e.g., target cells such as T cells. The binding capacity, e.g., the number of target cells that can be immobilized per mL of the stationary phase (e.g., selection resin), can be used to determine or control the number of captured target cells on one or more columns. One or more chromatography column can be used for the on-column cell selection and stimulation disclosed herein. When multiple columns are used, they can be arranged sequentially, in parallel, or in a suitable combination thereof. Thus, the binding capacity of a stationary phase (e.g., selection resin) can be used to standardize the reagent amount in a single-column approach or the reagent amount for each column in a multiple-column approach.

In some embodiments, the binding capacity of the stationary phase used herein is the maximum number of target cells bound to the stationary phase at given solvent and cell concentration conditions, when an excess of target cells are loaded onto the stationary phase. In some embodiments, the binding capacity is or is about 100 million±25 million target cells (e.g., T cells) per mL of stationary phase. In some embodiments, the static binding capacity of the stationary phase (e.g., selection resin) disclosed herein ranges between about 75 million and about 125 million target cells per mL of stationary phase. In one aspect, the binding capacity of the stationary phase used herein for on-column cell selection and stimulation is a static binding capacity. In some embodiments, the static binding capacity is the maximum amount of cells capable of being immobilized on the stationary phase, e.g., at certain solvent and cell concentration conditions. In some embodiments, the static binding capacity of the stationary phase (e.g., selection resin) disclosed herein ranges between about 50 million and about 100 million target cells per mL of stationary phase. In some embodiments, the static binding capacity is or is about 100 million±25 million target cells (e.g., T cells) per mL of stationary phase. In some embodiments, the static binding capacity of the stationary phase (e.g., selection resin) disclosed herein ranges between about 75 million and about 125 million target cells per mL of stationary phase. In some embodiments, the static binding capacity of the stationary phase (e.g., selection resin) is between about 10 million and about 20 million, between about 20 million and about 30 million, between about 30 million and about 40 million, between about 40 million and about 50 million, between about 50 million and about 60 million, between about 60 million and about 70 million, between about 70 million and about 80 million, between about 80 million and about 90 million, between about 90 million and about 100 million, between about 110 million and about 120 million, between about 120 million and about 130 million, between about 130 million and about 140 million, between about 140 million and about 150 million, between about 150 million and about 160 million, between about 160 million and about 170 million, between about 170 million and about 180 million, between about 180 million and about 190 million, or between about 190 million and about 200 million target cells per mL of stationary phase.

In some embodiments, the binding capacity of the stationary phase used herein is the number of target cells that bind to the stationary phase under given flow conditions before a significant breakthrough of unbound target cells occurs. In one aspect, the binding capacity of the stationary phase used herein for on-column cell selection is a dynamic binding capacity, i.e., the binding capacity under operating conditions in a packed chromatography column during sample application. In some embodiments, the dynamic binding capacity is determined by loading a sample containing a known concentration of the target cells and monitoring the flow-through, and the target cells will bind the stationary phase to a certain break point before unbound target cells will flow through the column. In some embodiments, the dynamic binding capacity is or is about 100 million±25 million target cells (e.g., T cells) per mL of stationary phase. In some embodiments, the dynamic binding capacity of the stationary phase (e.g., selection resin) disclosed herein is between or is between about 75 million and about 125 million target cells per mL of stationary phase. In some embodiments, the dynamic binding capacity of the stationary phase (e.g., selection resin) disclosed herein ranges between about 50 million and about 100 million target cells per mL of stationary phase. In some embodiments, the dynamic binding capacity of the stationary phase (e.g., selection resin) is between about 10 million and about 20 million, between about 20 million and about 30 million, between about 30 million and about 40 million, between about 40 million and about 50 million, between about 50 million and about 60 million, between about 60 million and about 70 million, between about 70 million and about 80 million, between about 80 million and about 90 million, between about 90 million and about 100 million, between about 110 million and about 120 million, between about 120 million and about 130 million, between about 130 million and about 140 million, between about 140 million and about 150 million, between about 150 million and about 160 million, between about 160 million and about 170 million, between about 170 million and about 180 million, between about 180 million and about 190 million, or between about 190 million and about 200 million target cells per mL of stationary phase.

In some embodiments, the stationary phase is 20 mL. In some embodiments, the stationary phase has a binding capacity of 2 billion±0.5 billion cells.

Generally, a chromatographic method is a fluid chromatography, typically a liquid chromatography. In some aspects, the chromatography can be carried out in a flow through mode in which a fluid sample containing the cells, e.g., the target cells, is applied, for example, by gravity flow or by a pump on one end of a column containing the chromatography matrix and in which the fluid sample exists the column at the other end of the column. In addition the chromatography can be carried out in an "up and down" mode in which a fluid sample containing the cells to be isolated is applied, for example, by a pipette on one end of a column containing the chromatography matrix packed within a pipette tip and in which the fluid sample enters and exists the chromatography matrix/pipette tip at the other end of the column. Alternatively, the chromatography can also be carried out in a batch mode in which the chromatography material (stationary phase) is incubated with the sample that contains the cells, for example, under shaking, rotating or repeated contacting and removal of the fluid sample, for example, by means of a pipette.

In some aspects, any material may be employed as chromatography matrix in the context of the invention, as long as the material is suitable for the chromatographic isolation of cells. In particular aspects, a suitable chromatography material is at least innocuous or essentially innocuous, e.g., not detrimental to cell viability, when used in a packed chromatography column under desired conditions for cell isolation and/or cell separation. In some aspects, the chromatography matrix remains in a predefined location, typically in a predefined position, whereas the location of the sample to be separated and of components included therein is being altered. Thus, in some aspects, the chromatography matrix is a "stationary phase."

Typically, the respective chromatography matrix has the form of a solid or semi-solid phase, whereas the sample that contains the target cell to be isolated/separated is a fluid phase. The mobile phase used to achieve chromatographic separation is likewise a fluid phase. The chromatography matrix can be a particulate material (of any suitable size and shape) or a monolithic chromatography material, including a paper substrate or membrane (cf. the Example Section). Thus, the chromatography can be both column chromatography as well as planar chromatography. In addition to standard chromatography columns, columns allowing a bidirectional flow or pipette tips can be used for column based/flow through mode based chromatographic separation of cells as described here. Thus, in some cases, pipette tips or columns allowing a bidirectional flow are also comprised by chromatography columns useful in the present methods. In some aspects, a particulate matrix material is used, and the particulate matrix material may, for example, have a mean particle size of about 5 μm to about 200 μm, or from about 5 μm to about 400 μm, or from about 5 μm to about 600 μm. In some aspects, planar chromatography is used, and the matrix material may be any material suitable for planar chromatography, such as conventional cellulose-based or organic polymer based membranes (for example, a paper membrane, a nitrocellulose membrane or a polyvinylidene difluoride (PVDF) membrane) or silica coated glass plates. In one embodiment, the chromatography matrix/stationary phase is a non-magnetic material or non-magnetizable material.

In some aspects, the chromatography matrix/stationary phase is a non-magnetic material or non-magnetisable material. Such material may include derivatized silica or a crosslinked gel. A crosslinked gel (which is typically manufactured in a bead form) may be based on a natural polymer, such as a crosslinked polysaccharide. An example of a polysaccharide matrix includes, but is not limited to, an agarose gel (for example, Superflow™ agarose or a Sepharose® material such as Superflow™ Sepharose® that are commercially available in different bead and pore sizes) or a gel of crosslinked dextran(s). A further illustrative example is a particulate cross-linked agarose matrix, to which dextran is covalently bonded, that is commercially available (in various bead sizes and with various pore sizes) as Sephadex® or Superdex®, both available from GE Healthcare. Another illustrative example of such a chromatography material is Sephacryl® which is also available in different bead and pore sizes from GE Healthcare.

In some embodiments, a crosslinked gel may also be based on a synthetic polymer, such as on a polymer class that does not occur in nature. Suitable examples include but are not limited to agarose gels or a gel of crosslinked dextran(s). A crosslinked gel may also be based on a synthetic polymer, i.e. on a polymer class that does not occur in nature. Usually such a synthetic polymer on which a chromatography stationary phase for cell separation is based is a polymer that has polar monomer units, and which is therefore in itself polar. Thus, in some cases, such a polar polymer is hydrophilic. Hydrophilic molecules, also termed lipophobic, in some aspects contain moieties that can form dipole-dipole interactions with water molecules. In general, hydrophobic molecules, also termed lipophilic, have a tendency to separate from water.

Illustrative examples of suitable synthetic polymers are polyacrylamide(s), a styrene-divinylbenzene gel and a copolymer of an acrylate and a diol or of an acrylamide and a diol. An illustrative example is a polymethacrylate gel, commercially available as a Fractogel®. A further example is a copolymer of ethylene glycol and methacrylate, commercially available as a Toyopearl®. In some embodiments a chromatography stationary phase may also include natural and synthetic polymer components, such as a composite matrix or a composite or a co-polymer of a polysaccharide and agarose, e.g. a polyacrylamide/agarose composite, or of a polysaccharide and N,N'-methylenebisacrylamide. An illustrative example of a copolymer of a dextran and N,N'-methylenebisacryl-amide is the above-mentioned Sephacryl® series of material. A derivatized silica may include silica particles that are coupled to a synthetic or to a natural polymer. Examples of such embodiments include, but are not limited to, polysaccharide grafted silica, polyvinylpyrrolidone grafted silica, polyethylene oxide grafted silica, poly(2-hydroxyethylaspartamide) silica and poly(N-isopropylacrylamide) grafted silica.

A chromatography matrix employed in the present invention is in some embodiments a gel filtration (also known as size exclusion) matrix, for example, when used in a removal cartridge as described herein. A gel filtration can be characterized by the property that it is designed to undergo, at least essentially, no interaction with the cells to be separated. Hence, a gel filtration matrix allows the separation of cells or other biological entities as defined herein largely on the basis of their size. A respective chromatography matrix is typically a particulate porous material as mentioned above. The chromatography matrix may have a certain exclusion limit, which is typically defined in terms of a molecular weight above which molecules are entirely excluded from entering the pores. The respective molecular weight defining the size exclusion limit may be selected to be below the weight corresponding to the weight of a target cell (or biological entity) to be isolated. In such an embodiment the target cell is prevented from entering the pores of the size exclusion chromatography matrix. Likewise, a stationary phase that is an affinity chromatography matrix may have pores that are of a size that is smaller than the size of a chosen target cell. In illustrative embodiments the affinity chromatography matrix and/or the gel filtration matrix has a mean pore size of 0 to about 500 nm.

Other components present in a sample (e.g. a donor sample) such as receptor binding molecules or a competition reagent may have a size that is below the exclusion limit of the pores and this can enter the pores of the size exclusion chromatography matrix. Of such components that are able to partially or fully enter the pore volume, larger molecules, with less access to the pore volume will usually elute first, whereas the smallest molecules elute last. In some embodiments the exclusion limit of the size exclusion chromatography matrix is selected to be below the maximal width of the target cell. Hence, components that have access to the pore volume will usually remain longer in/on the size exclusion chromatography matrix than target cell. Thus, target cells can be collected in the eluate of a chromatography column separately from other matter/components of a sample. Therefore components such as a receptor binding reagent, or where, applicable a competition reagent, elute at a later point of time from a gel filtration matrix than the target cell. This separation effect will be further increased, if the gel permeation matrix comprises an affinity reagent (usually covalently bound thereon) that comprises binding sites, for example binding sites Z that are able to bind reagents such as a receptor binding reagent and/or a competition reagent present in a sample. The receptor binding reagent and/or the competition reagent will be bound by the binding sites Z of the affinity reagent and thereby immobilized on the gel permeation matrix. This method is usually carried out in a removal cartridge as used in the present invention and in some embodiments a method, a combination and a kit according to the invention include and/or employ such a gel filtration matrix. In a respective method cells are accordingly separated on the basis of size.

A chromatography matrix employed in the present invention may also include magnetically attractable matter such as one or more magnetically attractable particles or a ferrofluid. A respective magnetically attractable particle may comprise a multimerization reagent or an affinity reagent with binding site that is capable of binding a target cell. Magnetically attractable particles may contain diamagnetic, ferromagnetic, paramagnetic or superparamagnetic material. Superparamagnetic material responds to a magnetic field with an induced magnetic field without a resulting permanent magnetization. Magnetic particles based on iron oxide are for example commercially available as Dynabeads® from Dynal Biotech, as magnetic MicroBeads from Miltenyi Biotec, as magnetic porous glass beads from CPG Inc., as well as from various other sources, such as Roche Applied Science, BIOCLON, BioSource International Inc., micromod, AMBION, Merck, Bangs Laboratories, Polysciences, or Novagen Inc., to name only a few. Magnetic nanoparticles based on superparamagnetic Co and FeCo, as well as ferromagnetic Co nanocrystals have been described, for example by Bitten, A. et al. (J. Biotech. (2004), 112, 47-63). However, in some embodiments a chromatography matrix employed in the present invention is void of any magnetically attractable matter.

Receptor Binding Reagent

As described above, in certain aspects, the methods provided herein employ a receptor binding reagent. In some embodiments, the reagent, as described in this Section, is a receptor binding reagent. In some embodiments, the receptor binding reagent binds to a molecule on the surface of a cell, such as a cell surface molecule. In some instances, the cell surface molecule is a selection marker. In some embodiments, the receptor binding reagent is capable of specifically binding to a selection marker expressed by one or more of the cells in a sample. In some embodiments, reference to specific binding to a molecule, such as a cell surface molecule or cell surface receptor, throughout the disclosure does not necessarily mean that the agent binds only to such molecule. For example, a reagent that specifically binds to a molecule may bind to other molecules, generally with much lower affinity as determined by, e.g., immunoassays, BIAcore®, KinExA 3000 instrument (Sapidyne Instruments, Boise, ID), or other assays. In some cases, the ability of a reagent, under specific binding conditions, to bind to a target molecule such that its affinity or avidity is at least 5 times as great, such as at least 10, 20, 30, 40, 50, 100, 250 or 500 times as great, or even at least 1000 times as great as the average affinity or avidity of the same agent to a collection of random peptides or polypeptides of sufficient statistical size.

In some embodiments, the cells, e.g., target cells (e.g., T cells), have or express a molecule on the cell surface, e.g., a selection marker, such that the cells to be selected are defined by the presence of at least one common specific molecule (e.g., selection marker). In some embodiments, the sample (e.g. the donor sample) containing the target cell may also contain additional cells that are devoid of the molecule (e.g., selection marker). For example, in some embodiments, T cells may be selected from a sample (e.g. a donor sample) containing multiple cells types, e.g., red blood cells or B cells. Selection marker and receptor molecule may be used interchangeably herein to refer to a cell surface molecule.

In some embodiments, the receptor molecule that is located on the cell surface, e.g., the target cell surface may be any molecule as long as it remains covalently or non-covalently bonded to the cell surface during a chromatographic separation process in a method according to the invention. The receptor molecule is a molecule against which a receptor binding reagent may be directed. In some embodiments the receptor is a peptide or a protein, such as a membrane receptor protein. In some embodiments the receptor is a lipid, a polysaccharide or a nucleic acid. A receptor that is a protein may be a peripheral membrane protein or an integral membrane protein. It may in some embodiments have one or more domains that span the membrane. In certain embodiments, the receptor molecule is a surface protein of an immune cell, e.g., CD4, CD8, or CD57. In certain embodiments, the receptor molecule is a surface protein of an immune cell, e.g., CD4, CD8, or CD27. In some cases, for T cells the receptor molecule is CD3. In some cases, for T cells the receptor molecule is CD4 or CD8. In some embodiments the receptor molecule may be an antigen defining a desired cell population or subpopulation, for instance a population or subpopulation of blood cells, e.g. lymphocytes (e.g. T cells, CD57− T cells, CD4+ T cells, or CD8+ T cells). In some embodiments the receptor molecule may be an antigen defining a desired cell population or subpopulation, for instance a population or subpopulation of blood cells, e.g. lymphocytes (e.g. T cells, CD27+ T cells, CD4+ T cells, or CD8+ T cells).

In some aspects, the cell surface molecule, e.g., selection marker, may be an antigen defining a desired cell population or subpopulation, for instance a population or subpopulation of blood cells, e.g. lymphocytes (e.g. T cells, T-helper cells, for example, CD57− T cells, CD3+ T cells, CD8+ Tcells, CD4+ T-helper cells, B cells or natural killer cells), monocytes, or stem cells, e.g. CD34− positive peripheral stem cells or Nanog or Oct-4 expressing stem cells. In some aspects, the cell surface molecule, e.g., selection marker, may be an antigen defining a desired cell population or subpopulation, for instance a population or subpopulation of blood cells, e.g. lymphocytes (e.g. T cells, T-helper cells, for example, CD27+ T cells, CD3+ T cells, CD8+ Tcells, CD4+ T-helper cells, B cells or natural killer cells), monocytes, or stem cells, e.g. CD34-positive peripheral stem cells or Nanog or Oct-4 expressing stem cells. In some embodiments, the selection marker can be a marker expressed on the surface of T cells or a subset of T cells, such as CD57, CD25, CD28, CD62 L, CCR7, CD27, CD127, CD3, CD4, CD8, CD45RA, and/or CD45RO. Examples of T-cells include cells such as CMV-specific CD8+ T-lymphocytes, cytotoxic T-cells, memory T-cells and regulatory T-cells (Treg). An illustrative example of Treg includes CD4 CD25 CD45RA Treg cells and an illustrative example of memory T-cells includes CD62 L CD8+ specific central memory T-cells.

In some embodiments, the receptor binding reagent has or contains a binding site B. In certain embodiments, the binding site B is monovalent. In some aspects, a monovalent binding site B is or contains a monovalent antibody fragment or a proteinaceous binding molecule with immunoglobulin-like functions, an aptamer or an MHC molecule. Examples of monovalent antibody fragments include, but are not limited to a Fab fragment, an Fv fragment, and a single-chain Fv fragment (scFv), including a divalent single-chain Fv fragment. Examples of (recombinant) antibody fragments are Fab fragments, Fv fragments, single-chain Fv fragments (scFv), a divalent antibody fragment such as an (Fab)2'-fragment, diabodies, triabodies (Iliades, P., et al., FEBS Lett (1997) 409, 437-441), decabodies (Stone, E., et al., Journal of Immunological Methods (2007) 318, 88-94) and other domain antibodies (Holt, L. J., et al., Trends Biotechnol. (2003), 21, 11, 484-490). In some embodiments one or more binding sites of the receptor molecule binding reagent may be a bivalent proteinaceous artificial binding molecule such as a dimeric lipocalin mutein that is also known as "duocalin". In some embodiments the receptor binding reagent may have a single second binding site, i.e., it may be monovalent. Examples of monovalent receptor binding reagents include, but are not limited to, a monovalent antibody fragment, a proteinaceous binding molecule with antibody-like binding properties or an MHC molecule.

Yet further examples of suitable proteinaceous binding molecules are an EGF-like domain, a Kringle-domain, a fibronectin type I domain, a fibronectin type II domain, a fibronectin type III domain, a PAN domain, a Gla domain, a SRCR domain, a Kunitz/Bovine pancreatic trypsin Inhibitor domain, tendamistat, a Kazal-type serine protease inhibitor domain, a Trefoil (P-type) domain, a von Willebrand factor type C domain, an Anaphylatoxin-like domain, a CUB domain, a thyroglobulin type I repeat, LDL-receptor class A domain, a Sushi domain, a Link domain, a Thrombospondin type I domain, an immunoglobulin domain or a an immunoglobulin-like domain (for example, domain antibodies or camel heavy chain antibodies), a C-type lectin domain, a MAM domain, a von Willebrand factor type A domain, a Somatomedin B domain, a WAP-type four disulfide core domain, a F5/8 type C domain, a Hemopexin domain, an SH2 domain, an SH3 domain, a Laminin-type EGF-like domain, a C2 domain, "Kappabodies" (cf. Ill. et al., Protein Eng (1997) 10, 949-57, a so called "minibody" (Martin et al., EMBO J (1994) 13, 5303-5309), a diabody (cf. Holliger et al., PNAS USA (1993)90, 6444-6448), a so called "Janusis" (cf. Traunecker et al., EMBO J (1991) 10, 3655-3659, or Traunecker et al., Int J Cancer (1992) Suppl 7, 51-52), a nanobody, a microbody, an affilin, an affibody, a knottin, ubiquitin, a zinc-finger protein, an autofluorescent protein or a leucine-rich repeat protein. An example of a nucleic acid molecule with antibody-like functions is an aptamer. An aptamer folds into a defined three-dimensional motif and shows high affinity for a given target structure.

In particular aspects, the receptor binding protein contains a binding partner C. In some aspects, the binding partner C included in the receptor binding reagent may for instance be hydrocarbon-based (including polymeric) and include nitrogen-, phosphorus-, sulphur-, carben-, halogen- or pseudohalogen groups. It may be an alcohol, an organic acid, an inorganic acid, an amine, a phosphine, a thiol, a disulfide, an alkane, an amino acid, a peptide, an oligopeptide, a polypeptide, a protein, a nucleic acid, a lipid, a saccharide, an oligosaccharide, or a polysaccharide. As further examples, it may also be a cation, an anion, a polycation, a polyanion, a polycation, an electrolyte, a polyelectrolyte, a carbon nanotube or carbon nanofoam. Generally, such a binding partner has a higher affinity to the binding site of the multimerization reagent than to other matter. Examples of a respective binding partner include, but are not limited to, a crown ether, an immunoglobulin, a fragment thereof and a proteinaceous binding molecule with antibody-like functions.

In some embodiments the binding partner C that is included in the receptor binding reagent includes biotin and the affinity reagent includes a streptavidin analog or an avidin analog that reversibly binds to biotin. In some embodiments the binding partner C that is included in the receptor binding reagent includes a biotin analog that reversibly binds to streptavidin or avidin, and the affinity reagent includes streptavidin, avidin, a streptavidin analog or an avidin analog that reversibly binds to the respective biotin analog. In some embodiments the binding partner C that is included in the receptor binding reagent includes a streptavidin or avidin binding peptide and the affinity reagent includes streptavidin, avidin, a streptavidin analog or an avidin analog that reversibly binds to the respective streptavidin or avidin binding peptide.

In some embodiments the binding partner that is included in the receptor binding reagent may include a streptavidin-binding peptide In some embodiments, the peptide sequence contains a sequence with the general formula His-Pro-Xaa, where Xaa is glutamine, asparagine, or methionine, such as contained in the sequence set forth in SEQ ID NO: 78. In some embodiments, the peptide sequence has the general formula set forth in SEQ ID NO: 69, such as set forth in SEQ ID NO: 79. In one example, the peptide sequence is Trp-Arg-His-Pro-Gln-Phe-Gly-Gly (also called Strep-Tag®, set forth in SEQ ID NO: 75). In one example, the peptide sequence is Ala-Trp-Arg-His-Pro-Gln-Phe-Gly-Gly (also called Strep-Tag®, set forth in SEQ ID NO: 90). In one example, the peptide sequence is Trp-Ser-His-Pro-Gln-Phe-Glu-Lys (also called Strep Tag® II, set forth in SEQ ID NO: 69), which is described in U.S. Pat. No. 6,103,493, for example, and is commercially available under the trademark Strep-Tactin®. The streptavidin binding peptides might, for example, be single peptides such as the "Strep-Tag®" described in U.S. Pat. No. 5,506,121, for example, or streptavidin binding peptides having a sequential arrangement of two or more individual binding modules as described in International Patent Publication WO 02/077018 or U.S. Pat. No. 7,981,632.

In some embodiment the binding partner C of the receptor binding reagent includes a moiety known to the skilled artisan as an affinity tag. In such an embodiment the affinity reagent includes a corresponding binding partner, for example, an antibody or an antibody fragment, known to bind to the affinity tag. As a few illustrative examples of known affinity tags, the binding partner that is included in the receptor binding reagent may include dinitrophenol or digoxigenin, oligohistidine, polyhistidine, an immunoglobulin domain, maltose-binding protein, glutathione-S-transferase (GST), chitin binding protein (CBP) or thioredoxin, calmodulin binding peptide (CBP), FLAG'-peptide, the HA-tag, the VSV-G-tag, the HSV-tag, the T7 epitope, maltose binding protein (MBP), the HSV epitope of the sequence of herpes simplex virus glycoprotein D, the "myc" epitope of the transcription factor c-myc of the sequence, the V5-tag, or glutathione-S-transferase (GST). In such an embodiment the complex formed between the one or more binding sites of the affinity reagent, in this case an antibody or antibody fragment, and the antigen can be disrupted competitively by adding the free antigen, i.e. the free peptide (epitope tag) or the free protein (such as MBP or CBP). The affinity tag might also be an oligonucleotide tag. Such an oligonucleotide tag may, for instance, be used to hybridize to an oligonucleotide with a complementary sequence, linked to or included in the affinity reagent.

In line with International Patent Application Publication No. WO 2013/011011 (the entire content of which is incorporated herein by reference for all purpose), the strength of the binding between the receptor binding reagent and a receptor molecule on a target cell may not be not essential for the reversibility of the binding of the target cell to the affinity reagent via the receptor binding reagent. Rather, irrespective of the strength of the binding, meaning whether the equilibrium dissociation constant ($K_D$) for the binding between the receptor binding reagent via the binding site B and the receptor molecule is of low affinity, for example, in the range of a $K_D$ of about $10^{-3}$ to about $10^{-7}$M, or of high affinity, for example, in the range of a $K_D$ of about $10^{-7}$ to about $1\times10^{-10}$ M, a target cell can be reversibly stained as long as the dissociation of the binding of the receptor binding reagent via the binding site B and the receptor molecule occurs sufficiently fast. In this regard the dissociation rate constant ($k_{off}$) for the binding between the receptor binding reagent via the binding site B and the receptor molecule may have a value of about $3\times10^{-5}$ $sec^{-1}$ or greater (this dissociation rate constant is the constant characterizing the dissociation reaction of the complex formed between the binding site B of the receptor binding reagent and the receptor molecule on the surface of the target cell). The association rate constant ($k_{on}$) for the association reaction between the binding site B of the receptor binding reagent and the receptor molecule on the surface of the target cell may have any value. In order to ensure a sufficiently reversible binding between receptor molecule and receptor binding reagent it is advantageous to select the $k_{off}$ value of the binding equilibrium to have a value of about 3×10-5 $sec^{-1}$ or greater, of about $5\times10^{-5}$ $sec^{-1}$ or greater, such as or as about $1\times10^{-4}$ $sec^{-1}$ or greater, $5\times10^{7}$ $sec^{-1}$ or greater, $1\times10^{-3}$ $sec^{-1}$ or greater, $5\times10^{-3}$ $sec^{-1}$ or greater, a $1\times10^{-2}$ $sec^{-1}$ or greater, $1\times10^{-1}$ $sec^{-1}$ or greater or $5\times10^{-1}$ $sec^{-1}$ or greater. It is noted here that the values of the kinetic and thermodynamic constants as used herein, refer to conditions of atmospheric pressure, i.e. 1.013 bar, and room temperature, i.e. 25° C.

In some embodiments the receptor binding reagent has a single (monovalent) binding site B capable of specifically binding to the receptor molecule. In some embodiments the receptor binding reagent has at least two (i.e., a plurality of binding sites B including three, four or also five identical binding sites B), capable of binding to the receptor molecule. In any of these embodiment the binding of the receptor molecule via (each of) the binding site(s) B may have a koff value of about 3×10-5 sec-1 or greater. Thus, the receptor binding reagent can be monovalent (for example a monovalent antibody fragment or a monovalent artificial binding molecule (proteinaceous or other) such as a mutein based on a polypeptide of the lipocalin family (also known as "Anticalin®), or a bivalent molecule such as an antibody or a fragment in which both binding sites are retained such as an F(ab')2 fragment. In some embodiments the receptor molecule may be a multivalent molecule such as a pentameric IgE molecule, provided the $k_{off}$ rate is 3×10-5 sec-1 or greater. In some embodiments, the Fab is an anti-CD57 Fab. In particular embodiments, the Fab is an anti-CD4 Fab. In some embodiments, the Fab is an anti-CD8 Fab.

In some embodiments of the invention, it is on a molecular level not the $k_{off}$ rate (of 3×10-5 sec-1 or greater) of the binding of the receptor binding reagent via the at least binding site B and the receptor molecule on the target cell that provides for the (traceless) isolation of biological material via reversible cell affinity chromatography technology described here. Rather, and as described, for example, in U.S. Pat. No. 7,776,562 or International Patent application WO02/054065, a low affinity binding between the receptor molecule and the binding site B of the binding receptor binding reagent together with an avidity effect mediated via the immobilized affinity reagent allows for a reversibly and traceless isolation of a target cell. In these embodiments a complex between the two or more binding sites Z of the affinity reagent and the binding partner C of at least two receptor binding reagents can form, allowing a reversible immobilization and subsequent elution of the target cells from the affinity chromatography matrix (via addition of the competing agent that will disrupt the binding (complex) formed between the binding partner C and the binding sites Z which in turn leads to the dissociation of the receptor binding reagent from the target cell. As mentioned above, such a low binding affinity may be characterized by a dissociation constant ($K_D$) in the range from about $1.0\times10^{-3}$M to about $1.0\times10^{-7}$ M for the binding of the receptor binding reagent via the binding site B and the receptor molecule on the target cell surface.

In some embodiments, the selection marker may be CD57 and the receptor-binding agent specifically binds CD57. In some aspects, the receptor-binding agent that specifically binds CD57 may be selected from the group consisting of an anti-CD57-antibody, a divalent antibody fragment of an anti-CD57 antibody, a monovalent antibody fragment of an anti-CD57-antibody, and a proteinaceous CD57 binding molecule with antibody-like binding properties. In some embodiments, the selection agent comprises an anti-CD57 Fab fragment.

In some embodiments, the selection marker may be CD27 and the receptor-binding agent specifically binds CD27. In some aspects, the receptor-binding agent that specifically binds CD27 may be selected from the group consisting of an anti-CD27-antibody, a divalent antibody fragment of an anti-CD27 antibody, a monovalent antibody fragment of an anti-CD27-antibody, and a proteinaceous CD27 binding molecule with antibody-like binding properties. In some embodiments, the selection agent comprises an anti-CD27 Fab fragment.

In some embodiments, the selection marker may be CD4 and the receptor-binding agent specifically binds CD4. In some aspects, the receptor-binding agent that specifically binds CD4 may be selected from the group consisting of an anti-CD4-antibody, a divalent antibody fragment of an anti-CD4 antibody, a monovalent antibody fragment of an anti-CD4-antibody, and a proteinaceous CD4 binding molecule with antibody-like binding properties. In some embodiments, an anti-CD4-antibody, such as a divalent antibody fragment or a monovalent antibody fragment (e.g. CD4 Fab fragment) can be derived from antibody 13B8.2 or a functionally active mutant of 13B8.2 that retains specific binding for CD4. For example, exemplary mutants of antibody 13B8.2 or m13B8.2 are described in U.S. Pat. Nos. 7,482,000, U.S. Patent Appl. No. US2014/0295458 or International Patent Application No. WO2013/124474; and Bes, C, et al. J Biol Chem 278, 14265-14273 (2003). The mutant Fab fragment termed "m13B8.2" carries the variable domain of the CD4 binding murine antibody 13B8.2 and a constant domain containing constant human CH1 domain of type gamma for the heavy chain and the constant human light chain domain of type kappa, as described in U.S. Pat. No. 7,482,000. In some embodiments, the anti-CD4 antibody, e.g. a mutant of antibody 13B8.2, contains the amino acid replacement H91A in the variable light chain, the amino acid replacement Y92A in the variable light chain, the amino acid replacement H35A in the variable heavy chain and/or the amino acid replacement R53A in the variable heavy chain, each by Kabat numbering. In some aspects, compared to variable domains of the 13B8.2 Fab fragment in m13B8.2 the His residue at position 91 of the light chain (position 93 in SEQ ID NO: 96) is mutated to Ala and the Arg residue at position 53 of the heavy chain (position 55 in SEQ ID NO: 95) is mutated to Ala. In some embodiments, the reagent that is reversibly bound to anti-CD4 or a fragment thereof is commercially available or derived from a reagent that is commercially available (e.g. catalog No. 6-8000-206 or 6-8000-205 or 6-8002-100; IBA GmbH, Gottingen, Germany). In some embodiments, the receptor-binding agent comprises an anti-CD4 Fab fragment. In some embodiments, the anti-CD4 Fab fragment comprises a variable heavy chain having the sequence set forth by SEQ ID NO:95 and a variable light chain having the sequence set forth by SEQ ID NO:96. In some embodiments, the anti-CD4 Fab fragment comprises the CDRs of the variable heavy chain having the sequence set forth by SEQ ID NO:95 and the CDRs of the variable light chain having the sequence set forth by SEQ ID NO:96.

In some embodiments, the selection marker may be CD8 and the receptor-binding agent specifically binds CD8. In some aspects, the receptor-binding agent that specifically binds CD8 may be selected from the group consisting of an anti-CD8-antibody, a divalent antibody fragment of an anti-CD8 antibody, a monovalent antibody fragment of an anti-CD8-antibody, and a proteinaceous CD8 binding molecule with antibody-like binding properties. In some embodiments, an anti-CD8-antibody, such as a divalent antibody fragment or a monovalent antibody fragment (e.g. CD8 Fab fragment) can be derived from antibody OKT8 (e.g. ATCC CRL-8014) or a functionally active mutant thereof that retains specific binding for CD8. In some embodiments, the reagent that is reversibly bound to anti-CD8 or a fragment thereof is commercially available or derived from a reagent that is commercially available (e.g. catalog No. 6-8003 or 6-8000-201; IBA GmbH, Gottingen, Germany). In some embodiments, the receptor-binding agent comprises an anti-CD8 Fab fragment. In some embodiments, the anti-CD8 Fab fragment comprises a variable heavy chain having the sequence set forth by SEQ ID NO:97 and a variable light chain having the sequence set forth by SEQ ID NO:98. In some embodiments, the anti-CD8 Fab fragment comprises the CDRs of the variable heavy chain having the sequence set forth by SEQ ID NO:97 and the CDRs of the variable light chain having the sequence set forth by SEQ ID NO:98.

In some embodiments, the selection marker may be CD3 and the receptor-binding agent specifically binds CD3. In some aspects, the receptor-binding agent that specifically binds CD3 may be selected from the group consisting of an anti-CD3-antibody, a divalent antibody fragment of an anti-CD3 antibody, a monovalent antibody fragment of an anti-CD3-antibody, and a proteinaceous CD3 binding molecule with antibody-like binding properties. In some embodiments, an anti-CD3-antibody, such as a divalent antibody fragment or a monovalent antibody fragment (e.g. CD3 Fab fragment) can be derived from antibody OKT3 (e.g. ATCC CRL-8001; see e.g., Stemberger et al. PLoS One. 2012; 7(4): e35798) or a functionally active mutant thereof that retains specific binding for CD3. In some embodiments, the reagent that is reversibly bound to anti-CD3 or a fragment thereof is commercially available or derived from a reagent that is commercially available (e.g. catalog No. 6-8000-201, 6-8001-100; IBA GmbH, Gottingen, Germany). In some embodiments, the receptor-binding agent comprises an anti-CD3 Fab fragment. In some embodiments, the anti-CD3 Fab fragment comprises a variable heavy chain having the sequence set forth by SEQ ID NO:93 and a variable light chain having the sequence set forth by SEQ ID NO:94. In some embodiments, the anti-CD3 Fab fragment comprises the CDRs of the variable heavy chain having the sequence set forth by SEQ ID NO: 93 and the CDRs of the variable light chain having the sequence set forth by SEQ ID NO:94.

In any of the above examples, the divalent antibody fragment may be an (Fab)2'-fragment, or a divalent single-chain Fv fragment while the monovalent antibody fragment may be selected from the group consisting of a Fab fragment, an Fv fragment, and a single-chain Fv fragment (scFv). In any of the above examples, the proteinaceous binding molecule with antibody-like binding properties may be an aptamer, a mutein based on a polypeptide of the lipocalin family, a glubody, a protein based on the ankyrin scaffold, a protein based on the crystalline scaffold, an adnectin, and an avimer.

In certain embodiments, the isolation and/or selection by chromatographic isolation results in one or more populations of enriched T cells (e.g. a CD57 depleted T cell population and/or a pooled CD57 depleted T cell population) that includes at least 60%, at least 65%, at least 70%, at least 75%, at least 80%, at least 85%, at least 90%, at least 95%, at least 98%, at least 99%, at least 99.5%, at least 99.9%, or at or at about 100% CD57− CD3+ T cells. In particular embodiment, the CD57 depleted T cell population and/or the pooled CD57 depleted T cell population consists essentially of CD57− CD3+ T cells.

In certain embodiments, the isolation and/or selection by chromatographic isolation results in one or more populations of enriched T cells (e.g. a CD27 enriched T cell population and/or a pooled CD27 enriched T cell population) that includes at least 60%, at least 65%, at least 70%, at least 75%, at least 80%, at least 85%, at least 90%, at least 95%, at least 98%, at least 99%, at least 99.5%, at least 99.9%, or at or at about 100% CD27+ CD3+ T cells. In particular embodiment, the Cd27 enriched T cell population and/or the pooled CD27 enriched T cell population consists essentially of CD27+ CD3+ T cells.

In certain embodiments, the isolation and/or enrichment by chromatographic isolation results in a populations of enriched CD57−CD4+ T cells that includes at least 60%, at least 65%, at least 70%, at least 75%, at least 80%, at least 85%, at least 90%, at least 95%, at least 98%, at least 99%, at least 99.5%, at least 99.9%, or at or at about 100% CD57− CD4+ T cells. In certain embodiments, the input composition of CD4+ T cells includes less than 40%, less than 35%, less than 30%, less than 25%, less than 20%, less than 15%, less than 10%, less than 5%, less than 1%, less than 0.1%, or less than 0.01% CD8+ T cells, and/or contains no CD8+ T cells, and/or is free or substantially free of CD8+ T cells. In some embodiments, the CD57 depleted T cell population and/or the pooled CD57 depleted T cell population consists essentially of CD57− CD4+ T cells.

In certain embodiments, the isolation and/or enrichment by chromatographic isolation results in a populations of enriched CD27+ CD4+ T cells that includes at least 60%, at least 65%, at least 70%, at least 75%, at least 80%, at least 85%, at least 90%, at least 95%, at least 98%, at least 99%, at least 99.5%, at least 99.9%, or at or at about 100% CD27+ CD4+ T cells. In certain embodiments, the input composition of CD4+ T cells includes less than 40%, less than 35%, less than 30%, less than 25%, less than 20%, less than 15%, less than 10%, less than 5%, less than 1%, less than 0.1%, or less than 0.01% CD8+ T cells, and/or contains no CD8+ T cells, and/or is free or substantially free of CD8+ T cells. In some embodiments, the CD27 enriched T cell population and/or the pooled CD27 enriched T cell population consists essentially of CD27+ CD4+ T cells.

In certain embodiments, the isolation and/or enrichment by chromatographic isolation results in a populations of enriched CD57− CD8+ T cells that includes at least 60%, at least 65%, at least 70%, at least 75%, at least 80%, at least 85%, at least 90%, at least 95%, at least 98%, at least 99%, at least 99.5%, at least 99.9%, or at or at about 100% CD57− CD8+ T cells. In certain embodiments, the population of CD8+ T cells contains less than 40%, less than 35%, less than 30%, less than 25%, less than 20%, less than 15%, less than 10%, less than 5%, less than 1%, less than 0.1%, or less than 0.01% CD4+ T cells, and/or contains no CD4+ T cells, and/or is free of or substantially free of CD4+ T cells. In some embodiments, the CD57 depleted T cell population and/or the pooled CD57 depleted T cell population consists essentially of CD57− CD8+ T cells.

In certain embodiments, the isolation and/or enrichment by chromatographic isolation results in a populations of enriched CD27+ CD8+ T cells that includes at least 60%, at least 65%, at least 70%, at least 75%, at least 80%, at least 85%, at least 90%, at least 95%, at least 98%, at least 99%, at least 99.5%, at least 99.9%, or at or at about 100% CD27+ CD8+ T cells. In certain embodiments, the population of CD8+ T cells contains less than 40%, less than 35%, less than 30%, less than 25%, less than 20%, less than 15%, less than 10%, less than 5%, less than 1%, less than 0.1%, or less than 0.01% CD4+ T cells, and/or contains no CD4+ T cells, and/or is free of or substantially free of CD4+ T cells. In some embodiments, the CD27 enriched T cell population and/or the pooled CD27 enriched T cell population consists essentially of CD27+ CD8+ T cells.

2. Selected Compositions

In certain embodiments, the provided CD57 depleted T cell population and/or the pooled CD57 depleted T cell population are used in connection with methods for stimulating, activating, engineering (e.g. knocking in and/or knocking out), transducing, cultivating, or expanding T cells, to produce an engineered T cell composition. In some embodiments, the CD57 depleted T cell population and/or the pooled CD57 depleted T cell population result from isolation, selection, or enrichment, e.g., of a biological sample (e.g. a donor sample), such as a donor cell population containing one or more immune cells.

In some embodiments, the CD57 depleted T cell population is from an individual donor. In some embodiments, the CD57 depleted T cell population from an individual donor is combined with a CD57 depleted T cell population from at least one other individual donor to produce a pooled CD57 depleted T cell population. In some embodiments, each of the CD57 depleted T cell populations from a plurality of individual donors are combined to produce a pooled CD57 depleted T cell population. In some embodiments, the pooled CD57 depleted T cell population is from a plurality of different donors.

In some embodiments, the CD57 depleted T cell population and/or the pooled CD57 depleted T cell population contains less than or less than about 10%, 5%, 1%, or 0.1% CD57+ T cells. In particular embodiments, the CD57 depleted T cell population and/or the pooled CD57 depleted T cell population contains less than or less than about 25%, 20%, 15%, 10%, or 5% of the frequency of CD57+ T cells that were present the donor sample. In certain embodiments, at least 85%, 90%, 95%, or 99% of the CD4+ T cells of the population are CD57−CD4+ T cells. In particular embodiments, at least 85%, 90%, 95%, or 99% of the CD8+ T cells of the population are CD57−CD8+ T cells. In particular embodiments, at least 85%, 90%, 95%, or 99% of the CD3+ T cells of the population are CD57−CD3+ T cells.

In certain embodiments, the CD57 depleted T cell population and/or the pooled CD57 depleted T cell population is or includes viable T cells, CD3+ T cells, CD4+ T cells, and/or CD8+ T cells. In particular embodiments, the cells of the CD57 depleted T cell population and/or the pooled CD57 depleted T cell population are or include viable T cells, CD3+ T cells, CD4+ T cells, and/or CD8+ T cells or a combination of any of the foregoing. In various embodiments, the cells of the CD57 depleted T cell population and/or the pooled CD57 depleted T cell population are or include viable CD57− T cells, CD57− CD3+ T cells, CD57− CD4+ T cells, CD57− CD8+ T cells, or a combination of any of the foregoing. In some embodiments, the CD57 depleted T cell population and/or the pooled CD57 depleted T cell population includes CD4+ and CD8+ T cells. In some embodiments, the CD57 depleted T cell population and/or the pooled CD57 depleted T cell population comprises a ratio of CD4+ to CD8+ T cells of between at or about 1:5 and at or about 5:1. In some embodiments, the CD57 depleted T cell population and/or the pooled CD57 depleted T cell population comprises a ratio of CD4+ to CD8+ T cells of between at or about 1:3 and at or about 3:1. In some embodiments, the CD57 depleted T cell population and/or the pooled CD57 depleted T cell population comprises a ratio of CD4+ to CD8+ T cells of between at or about 1:2 and at or about 2:1.

In certain embodiments, enriching T cells includes selecting or removing CD57+ cells from a biological sample, and then separately selecting for CD4+ T cells and CD8+ T cells from the population negatively selected for CD57, such as to generated a population of enriched CD57−CD4+ T cells and a population of enriched CD57−CD8+ T cells. In some embodiments, these populations remain separate, such as are subsequently separately cryoprotected and stored and/or are separately engineered to express a recombinant receptor. In particular embodiments, the separate populations are combined, such as at a ratio of 1:1 CD57−CD4+ T cells to CD57−CD8+ T cells.

In some embodiments, the CD57 depleted T cell population and/or the pooled CD57 depleted T cell population includes greater than or greater than at or about 75% CD3+/CD57− cells. In some embodiments, the CD57 depleted T cell population and/or the pooled CD57 depleted T cell population includes greater than at or about 80% CD3+/CD57− cells. In some embodiments, the CD57 depleted T cell population and/or the pooled CD57 depleted T cell population includes greater than at or about 85% CD3+/CD57− cells. In some embodiments, the CD57 depleted T cell population and/or the pooled CD57 depleted T cell population includes greater than at or about 90% CD3+/CD57− cells. In some embodiments, the CD57 depleted T cell population and/or the pooled CD57 depleted T cell population includes or greater than at or about 75% CD3+/CD57− cells.

Particular embodiments contemplate that the amount of CD57 expression, e.g., amount of CD57+ T cells, in a sample, population, or composition containing cells may be measured by any suitable known means. In some embodiments, CD57 expression is measured in a sample, population, or composition to measure, assess, or determine the amount, frequency, or percentage of CD57+ cells, e.g., CD57+ T cells in the sample, population, or composition. In certain embodiments, CD57 expression is measured in a sample, population, or composition to measure, assess, or determine the amount, frequency, or percentage of CD57+ cells, e.g., CD57+ T cells in the sample, population, or composition.

In some embodiments, cell compositions having a higher percentage of CD57+ cells can result in a lower percentage of cells capable of proliferative expansion. In some cases, an engineered cell composition with a high percentage of CD57+ cells is associated with a reduced proliferative capacity and may result in prolonged process times, higher doublings to achieve threshold cell numbers, increased cellular differentiation and/or failure to meet a harvest criterion in a manufacturing process for producing an engineered T cell composition for cell therapy.

Also provided in some aspects are methods for identifying a population of cells capable of expansion, the method including measuring the frequency of CD57+ cells in the population, wherein the population of cells is identified as capable of expansion if frequency of CD57+ cells are below a threshold frequency. In some of any such embodiments, the threshold frequency is a percentage that is less than at or about 35%, 30%, 20%, 10%, 5%, 1%, or 0.1%. In some of any such embodiments, a population that is capable of expansion expands at least at or about 2-fold, 4-fold, 8-fold, or 16-fold within 4, 5, 6, 7 or 8 days of cultivation under conditions that promote proliferation or expansion.

Also provided in some aspects are methods for determining the capacity of expansion of a population of T cells, the method including measuring a value of a trait associated with CD57 expression in a population of T cells, wherein the if a population of T cells is determined as capable of expansion if the value of the trait is less than at or about a threshold value of the trait.

In some embodiments, the threshold the threshold value: i) is at, at about, or within 25%, within 20%, within 15%, within 10%, or within 5% below a mean or median measurement of the trait associated with CD57 expression, and/or is below one standard deviation less than at or about the mean or median measurement, in a plurality of reference T cell populations; ii) is below a lowest measurement of the trait associated with CD57 expression, optionally within 50%, within 25%, within 20%, within 15%, within 10%, or within 5% below the lowest measurement, in a population from among a plurality of reference T cell populations; iii) is below a mean or median measurement of the trait associated with CD57 expression calculated from among more than 65%, 75%, 80%, 85% of samples from a plurality of reference T cell compositions; wherein the plurality of reference T cell populations are a plurality of populations that did not expand when cultivated under conditions that promote proliferation or expansion of T cells, optionally wherein the cells did not expand by at least at or about 2-fold, 4-fold, 8-fold, or 16-fold within 4, 5, 6, 7 or 8 days of cultivation.

In some embodiments, the trait is a level or amount of CD57 polypeptide expressed in the total T cells, CD4+ T cells, or CD8+ T cells. In some embodiments, the trait is a frequency, percentage, or amount of CD57+ T cells, CD57+ CD4+ T cells, or CD57+ CD8+ T cells present in the cell population. In some embodiments, the trait is a level or amount of CD57 polypeptide expressed in the CD3+ T cells. In some embodiments, the trait is a frequency, percentage, or amount of CD57+ CD3+ T cells T cells present in the cell population. In some embodiments, the trait is a level or amount of CD57 mRNA present in the T cells in the cell population. In some embodiments, the trait is a level or amount of chromatin accessibility of the gene encoding CD57 (B3GAT1).

In certain embodiments, the provided CD27 enriched T cell population and/or the pooled CD27 enriched T cell population are used in connection with methods for stimulating, activating, engineering (e.g. knocking in and/or knocking out), transducing, cultivating, or expanding T cells, to produce an engineered T cell composition. In some embodiments, the CD27 enriched T cell population and/or the pooled CD27 enriched T cell population result from isolation, selection, or enrichment, e.g., of a biological sample (e.g. a donor sample), such as a donor cell population containing one or more immune cells.

In some embodiments, the CD27 enriched T cell population is from an individual donor. In some embodiments, the CD27 enriched T cell population from an individual donor is combined with a CD27 enriched T cell population from at least one other individual donor to produce a pooled CD27 enriched T cell population. In some embodiments, each of the CD27 enriched T cell populations from a plurality of individual donors are combined to produce a pooled CD27 enriched T cell population. In some embodiments, the pooled CD27 enriched T cell population is from a plurality of different donors.

In some embodiments, the CD27 enriched T cell population and/or the pooled CD27 enriched T cell population contains less than or less than about 10%, 5%, 1%, or 0.1% CD27− T cells. In particular embodiments, the CD27 enriched T cell population and/or the pooled CD27 enriched T cell population contains less than or less than about 25%, 20%, 15%, 10%, or 5% of the frequency of CD27-T cells that were present the donor sample. In certain embodiments, at least 85%, 90%, 95%, or 99% of the CD4+ T cells of the population are CD27+ CD4+ T cells. In particular embodiments, at least 85%, 90%, 95%, or 99% of the CD8+ T cells of the population are CD27+ CD8+ T cells. In particular embodiments, at least 85%, 90%, 95%, or 99% of the CD3+ T cells of the population are CD27+ CD3+ T cells.

In certain embodiments, the CD27 enriched T cell population and/or the pooled CD27 enriched T cell population is or includes viable T cells, CD3+ T cells, CD4+ T cells, and/or CD8+ T cells. In particular embodiments, the cells of the CD27 enriched T cell population and/or the pooled CD27 enriched T cell population are or include viable T cells, CD3+ T cells, CD4+ T cells, and/or CD8+ T cells or a combination of any of the foregoing. In various embodiments, the cells of the CD27 enriched T cell population and/or the pooled CD27 enriched T cell population are or include viable CD27+ T cells, CD27+ CD3+ T cells, CD27+ CD4+ T cells, CD27+ CD8+ T cells, or a combination of any of the foregoing. In some embodiments, the CD27 enriched T cell population and/or the pooled CD27 enriched T cell population includes CD4+ and CD8+ T cells. In some embodiments, the CD27 enriched T cell population and/or the pooled CD27 enriched T cell population comprises a ratio of CD4+ to CD8+ T cells of between at or about 1:5 and at or about 5:1. In some embodiments, the CD27 enriched T cell population and/or the pooled CD27 enriched T cell population comprises a ratio of CD4+ to CD8+ T cells of between at or about 1:3 and at or about 3:1. In some embodiments, the CD27 enriched T cell population and/or the pooled CD27 enriched T cell population comprises a ratio of CD4+ to CD8+ T cells of between at or about 1:2 and at or about 2:1.

In certain embodiments, enriching T cells includes selecting or removing CD27− cells from a biological sample, and then separately selecting for CD4+ T cells and CD8+ T cells from the population negatively selected for CD27, such as to generated a population of enriched CD27+ CD4+ T cells and a population of enriched CD27+ CD8+ T cells. In some embodiments, these populations remain separate, such as are subsequently separately cryoprotected and stored and/or are separately engineered to express a recombinant receptor. In particular embodiments, the separate populations are combined, such as at a ratio of 1:1 CD27+ CD4+ T cells to CD27+ CD8+ T cells.

In some embodiments, the CD27 enriched T cell population and/or the pooled CD27 enriched T cell population includes greater than or greater than at or about 75% CD3+/CD27+ cells. In some embodiments, the CD27 enriched T cell population and/or the pooled CD27 enriched T cell population includes greater than at or about 80% CD3+/CD27+ cells. In some embodiments, the CD27 enriched T cell population and/or the pooled CD27 enriched T cell population includes greater than at or about 85% CD3+/CD27+ cells. In some embodiments, the CD27 enriched T cell population and/or the pooled CD27 enriched T cell population includes greater than at or about 90% CD3+/CD27+ cells. In some embodiments, the CD27 enriched T cell population and/or the pooled CD27 enriched T cell population includes or greater than at or about 75% CD3+/CD27+ cells.

Particular embodiments contemplate that the amount of CD27 expression, e.g., amount of CD27+ T cells, in a sample, population, or composition containing cells may be measured by any suitable known means. In some embodiments, CD27 expression is measured in a sample, population, or composition to measure, assess, or determine the amount, frequency, or percentage of CD27− cells, e.g., CD27− T cells in the sample, population, or composition. In certain embodiments, CD27 expression is measured in a sample, population, or composition to measure, assess, or determine the amount, frequency, or percentage of CD27− cells, e.g., CD27− T cells in the sample, population, or composition.

In some embodiments, cell compositions having a higher percentage of CD27− cells can result in a lower percentage of cells capable of proliferative expansion. In some cases, an engineered cell composition with a high percentage of CD27− cells is associated with a reduced proliferative capacity and may result in prolonged process times, higher doublings to achieve threshold cell numbers, increased cellular differentiation and/or failure to meet a harvest criterion in a manufacturing process for producing an engineered T cell composition for cell therapy.

Also provided in some aspects are methods for identifying a population of cells capable of expansion, the method including measuring the frequency of CD27− cells in the population, wherein the population of cells is identified as capable of expansion if frequency of CD27− cells are below a threshold frequency. In some of any such embodiments, the threshold frequency is a percentage that is less than at or about 35%, 30%, 20%, 10%, 5%, 1%, or 0.1%. In some of any such embodiments, a population that is capable of expansion expands at least at or about 2-fold, 4-fold, 8-fold, or 16-fold within 4, 5, 6, 7 or 8 days of cultivation under conditions that promote proliferation or expansion.

Also provided in some aspects are methods for determining the capacity of expansion of a population of T cells, the method including measuring a value of a trait associated with CD27 expression in a population of T cells, wherein the if a population of T cells is determined as capable of expansion if the value of the trait is less than at or about a threshold value of the trait.

In some embodiments, the threshold the threshold value: i) is at, at about, or within 25%, within 20%, within 15%, within 10%, or within 5% below a mean or median measurement of the trait associated with CD27 expression, and/or is below one standard deviation less than at or about the mean or median measurement, in a plurality of reference T cell populations; ii) is below a lowest measurement of the trait associated with CD27 expression, optionally within 50%, within 25%, within 20%, within 15%, within 10%, or within 5% below the lowest measurement, in a population from among a plurality of reference T cell populations; iii) is below a mean or median measurement of the trait associated with CD27 expression calculated from among more than 65%, 75%, 80%, 85% of samples from a plurality of reference T cell compositions; wherein the plurality of reference T cell populations are a plurality of populations that did not expand when cultivated under conditions that promote proliferation or expansion of T cells, optionally wherein the cells did not expand by at least at or about 2-fold, 4-fold, 8-fold, or 16-fold within 4, 5, 6, 7 or 8 days of cultivation.

In some embodiments, the trait is a level or amount of CD27 polypeptide expressed in the total T cells, CD4+ T cells, or CD8+ T cells. In some embodiments, the trait is a frequency, percentage, or amount of CD27− T cells, CD27-CD4+ T cells, or CD27-CD8+ T cells present in the cell population. In some embodiments, the trait is a level or amount of CD27 polypeptide expressed in the CD3+ T cells. In some embodiments, the trait is a frequency, percentage, or amount of CD27-CD3+ T cells T cells present in the cell population. In some embodiments, the trait is a level or amount of CD27 mRNA present in the T cells in the cell population. In some embodiments, the trait is a level or amount of chromatin accessibility of the gene encoding CD27 (CD27).

In some embodiments, wherein the method further includes measuring a second value of second a trait associated with the expression of one or more second gene products in a population of T cells, wherein the population is capable of expanding if the value of the trait is less than at or about the threshold value of the trait and if the second value of the second trait is greater than at or about a second threshold of the second trait.

In some embodiments, the second gene product a marker associated with a naïve-like T cell. In some embodiments, the one or more second gene product is selected from CD27, CD28, CCR7, or CD45RA. In some embodiments, the one or more second gene product is CD27 and CD28.

In certain embodiments, negative expression, e.g., negative expression of CD57 or CD57−, is an expression equal to or less than the level of background expression, e.g., as detected using a standard technique, such as a technique involving antibody-staining. In certain embodiments, negative expression, e.g., negative expression of CD27 or CD27+, is an expression equal to or less than the level of background expression, e.g., as detected using a standard technique, such as a technique involving antibody-staining. In certain embodiments, negative expression is equal to or less than the level of background expression as detected by suitable techniques for assessing protein or gene expression, such as but not limited to immunohistochemistry, immunofluorescence, or flow cytometry based techniques. In some embodiments, positive expression, e.g., of a particular protein, is or includes surface expression of the protein in an amount, level, or concentration above background. In particular embodiments, negative expression, e.g., of a particular protein, is or includes surface expression of the protein in an amount, level, or concentration at or below background.

In certain embodiments, the methods provided herein include one or more steps of assessing, measuring, determining, and/or quantifying the expression of one or more proteins or genes (e.g., CD57) in a sample, population, or composition, such as to quantify cells in the sample, composition, or population with positive or negative expression for the protein or gene (e.g., CD57). In certain embodiments, the methods provided herein include one or more steps of assessing, measuring, determining, and/or quantifying the expression of one or more proteins or genes (e.g., CD27) in a sample, population, or composition, such as to quantify cells in the sample, composition, or population with positive or negative expression for the protein or gene (e.g., CD27). Such steps may include assessing, measuring, determining, and/or quantifying any suitable trait associated with expression, such as measuring levels of protein, surface protein, mRNA, or gene accessibility, e.g., epigenetic gene accessibility.

In some embodiments, the expression of a protein (e.g., CD57) is or includes assessing, measuring, determining, and/or quantifying a level, amount, or concentration of the protein, or a protein encoded by the gene, expressed on the surface of cells. In some embodiments, the expression of a protein (e.g., CD27) is or includes assessing, measuring, determining, and/or quantifying a level, amount, or concentration of the protein, or a protein encoded by the gene, expressed on the surface of cells. In particular embodiments, the expression of a protein (e.g., CD57) is assessed by assessing, measuring, determining, and/or quantifying the surface expression of the protein, e.g., the level, amount, or concentration of the protein on the surface of the cells. In particular embodiments, the expression of a protein (e.g., CD27) is assessed by assessing, measuring, determining, and/or quantifying the surface expression of the protein, e.g., the level, amount, or concentration of the protein on the surface of the cells. In particular embodiments, the amount, frequency, or percentage of cells positive for surface expression of the protein, e.g., cells with surfaces having a greater amount, concentration, or density of proteins on the surface that is greater than the background signal of the technique used to measure the surface protein. In particular embodiments, the surface expression of a protein (e.g., CD57) is measured by immunohistochemistry, immunofluorescence, or flow cytometry based techniques. In particular embodiments, the surface expression of a protein (e.g., CD27) is measured by immunohistochemistry, immunofluorescence, or flow cytometry based techniques. In some embodiments, the amount, frequency, or percentage of cells positive for surface expression of a protein is determined by a suitable known technique such as an immunohistochemistry, immunofluorescence, or flow cytometry based technique.

In particular embodiments, the amount, frequency, or percentage of cells that are negative or positive for protein expression, e.g., surface expression, in the sample, composition, or population is determined by flow cytometry. In some embodiments, the protein is CD3, CD4, CD8, CD25, CD27, CD28, CD57, CCR7, or CD45RA. In particular embodiments, the protein is CD57. In particular embodiments, the protein is CD27.

In particular embodiments, the expression of a protein (e.g., CD57) in a sample, population, or composition is or includes any suitable method for assessing, measuring, determining, and/or quantifying the level, amount, or concentration of protein. In particular embodiments, the expression of a protein (e.g., CD27) in a sample, population, or composition is or includes any suitable method for assessing, measuring, determining, and/or quantifying the level, amount, or concentration of protein. Such methods include, but are not limited to, detection with immunoassays, nucleic acid-based or protein-based aptamer techniques, HPLC (high precision liquid chromatography), peptide sequencing (such as Edman degradation sequencing or mass spectrometry (such as MS/MS), optionally coupled to HPLC), and microarray adaptations of any of the foregoing (including nucleic acid, antibody or protein-protein (i.e., non-antibody) arrays). In some embodiments, the immunoassay is or includes methods or assays that detect proteins based on an immunological reaction, e.g., by detecting the binding of an antibody or antigen binding antibody fragment to a gene product. Immunoassays include, but are not limited to, quantitative immunocytochemistry or immunohistochemistry, ELISA (including direct, indirect, sandwich, competitive, multiple and portable ELISAs (see, e.g., U.S. Pat. No. 7,510,687), western blotting (including one, two or higher dimensional blotting or other chromatographic means, optionally including peptide sequencing), enzyme immunoassay (EIA), RIA (radioimmunoassay), and SPR (surface plasmon resonance).

In certain embodiments, the expression of a protein or its corresponding gene is measured, assessed, or quantified by measuring an mRNA (or cDNA product derived from the mRNA) that encodes the protein (e.g., CD57). In certain embodiments, the expression of a protein or its corresponding gene is measured, assessed, or quantified by measuring an mRNA (or cDNA product derived from the mRNA) that encodes the protein (e.g., CD27). In particular embodiments, the amount or level of the mRNA (or corresponding cDNA) is assessed, measured, determined, and/or quantified by any suitable means (PCR), including reverse transcriptase (rt) PCR, droplet digital PCR, real-time and quantitative PCR methods (including, e.g., TAQMAN®, molecular beacon, LIGHTUP™, SCORPION™ SIMPLEPROBES®; see, e.g., U.S. Pat. Nos. 5,538,848; 5,925,517; 6,174,670; 6,329,144; 6,326,145 and 6,635,427); northern blotting; Southern blotting, e.g., of reverse transcription products and derivatives; array based methods, including blotted arrays, microarrays, or in situ-synthesized arrays; and sequencing, e.g., sequencing by synthesis, pyrosequencing, dideoxy sequencing, or sequencing by ligation, or any other known assay methods such as discussed in Shendure et al., Nat. Rev. Genet. 5:335-44 (2004) or Nowrousian, Euk. Cell 9(9): 1300-1310 (2010), including such specific platforms as HELICOS®, ROCHE® 454, ILLUMINA®/SOLEXA®, ABI SOLiD®, and POLONATOR® sequencing. In some embodiments, the expression of mRNA is determined by a next generation sequencing method such as RNA sequencing (RNA-Seq). RNA sequencing methods have been adapted for the most common DNA sequencing platforms (HiSeq systems (Illumina), 454 Genome Sequencer FLX System (Roche), Applied Biosystems SOLiD (Life Technologies), IonTorrent (Life Technologies)). These platforms require initial reverse transcription of RNA into cDNA. Conversely, the single molecule sequencer HeliScope (Helicos BioSciences) is able to use RNA as a template for sequencing.

In some embodiments, the expression of a protein or its corresponding gene is or includes an epigenetic analysis of the protein. In some embodiments, a population of cells is assessed for the accessibility of a gene, e.g., the accessibility of B3GAT1 which encodes CD57. In some embodiments, the expression of a protein or its corresponding gene is or includes an epigenetic analysis of the protein. In some embodiments, a population of cells is assessed for the accessibility of a gene, e.g., the accessibility of the CD27 gene encoding CD27. The epigenetic analysis may be performed by any suitable known means, including but not limited to Assay for Transposase-Accessible Chromatin using sequencing (ATAC-seq) to examine chromatin accessibility.

In some embodiments, the population of enriched CD57− cells (e.g. the pooled CD57 depleted T cell population, the CD57 depleted T cell population, and/or the engineered T cell composition) contains, contains about, or contains less than at or about 25%, 20%, 15%, 12%, 10%, 9%, 8%, 7%, 6%, 5%, 4%, 3%, 2%, 1%, 0.5%, 0.1%, 0.01%, or 0.001%, CD57+ T cells. In certain embodiments, the population of enriched CD57− cells is essentially free of CD57+ cells. In particular embodiments, the population of enriched CD57− cells contains less than at or about 20% CD57+ cells. In certain embodiments, the population of enriched CD57− cells contains less than at or about 10% CD57+ cells. In some embodiments, the population of enriched CD57− cells contains less than at or about 5% CD57+ cells. In various embodiments, the population of enriched CD57− cells contains less than at or about 1%, 0.1%, or 0.01% CD57+ cells.

In certain embodiments, the CD57 depleted T cell population and/or the pooled CD57 depleted T cell population contains, contains about, or contains at least at or about 60%, 65%, 70%, 75%, 80%, 85%, 90%, 95%, 97%, 98%, 99%, 99.5%, 99.9%, 99.99%, or 100% or about 100% CD57− T cells. In certain embodiments, the CD57 depleted T cell population and/or the pooled CD57 depleted T cell population contains at least at or about 80% CD57− T cells. In certain embodiments, the CD57 depleted T cell population and/or the pooled CD57 depleted T cell population contains at least at or about 95% CD57− T cells. In various embodiments, the CD57 depleted T cell population and/or the pooled CD57 depleted T cell population contains at least at or about 99%, 99.9%, or 99.99% CD57− T cells. In particular embodiments, all or essentially all of the cells of the CD57 depleted T cell population and/or the pooled CD57 depleted T cell population are CD57− T cells. In some embodiments, the CD57 depleted T cell population and/or the pooled CD57 depleted T cell population contains, contains about, or contains at least at or about 60%, 65%, 70%, 75%, 80%, 85%, 90%, 95%, 97%, 98%, 99%, 99.5%, 99.9%, 99.99%, or 100% or about 100% CD57−CD3+ T cells. In certain embodiments, the CD57 depleted T cell population and/or the pooled CD57 depleted T cell population contains at least at or about 70% CD57− CD3+ T cells. In certain embodiments, the CD57 depleted T cell population and/or the pooled CD57 depleted T cell population contains at least at or about 80% CD57− CD3+ T cells. In certain embodiments, the CD57 depleted T cell population and/or the pooled CD57 depleted T cell population contains at least at or about 95% CD57− CD3+ T cells. In various embodiments, the CD57 depleted T cell population and/or the pooled CD57 depleted T cell population contains at least at or about 99%, 99.9%, or 99.99% CD57− CD3+ T cells. In particular embodiments, all or essentially all of the cells of the CD57 depleted T cell population and/or the pooled CD57 depleted T cell population are CD57− CD3+ T cells.

In some embodiments, the population of enriched CD27+ cells (e.g. the pooled CD27 enriched T cell population, the CD27 enriched T cell population, and/or the engineered T cell composition) contains, contains about, or contains less than at or about 25%, 20%, 15%, 12%, 10%, 9%, 8%, 7%, 6%, 5%, 4%, 3%, 2%, 1%, 0.5%, 0.1%, 0.01%, or 0.001%, CD27− T cells. In certain embodiments, the population of enriched CD27+ cells is essentially free of CD27− cells. In particular embodiments, the population of enriched CD27+ cells contains less than at or about 20% CD27− cells. In certain embodiments, the population of enriched CD27+ cells contains less than at or about 10% CD27-cells. In some embodiments, the population of enriched CD27+ cells contains less than at or about 5% CD27− cells. In various embodiments, the population of enriched CD27+ cells contains less than at or about 1%, 0.1%, or 0.01% CD27− cells.

In certain embodiments, the CD27 enriched T cell population and/or the pooled CD27 enriched T cell population contains, contains about, or contains at least at or about 60%, 65%, 70%, 75%, 80%, 85%, 90%, 95%, 97%, 98%, 99%, 99.5%, 99.9%, 99.99%, or 100% or about 100% CD27+ T cells. In certain embodiments, the CD27 enriched T cell population and/or the pooled CD27 enriched T cell population contains at least at or about 80% CD27+ T cells. In certain embodiments, the CD27 enriched T cell population and/or the pooled CD27 enriched T cell population contains at least at or about 95% CD27+ T cells. In various embodiments, the CD27 enriched T cell population and/or the pooled CD27 enriched T cell population contains at least at or about 99%, 99.9%, or 99.99% CD27+ T cells. In particular embodiments, all or essentially all of the cells of the CD27 enriched T cell population and/or the pooled CD27 enriched T cell population are CD27+ cells. In some embodiments, the CD27 enriched T cell population and/or the pooled CD27 enriched T cell population contains, contains about, or contains at least at or about 60%, 65%, 70%, 75%, 80%, 85%, 90%, 95%, 97%, 98%, 99%, 99.5%, 99.9%, 99.99%, or 100% or about 100% CD27+ CD3+ T cells. In certain embodiments, the CD27 enriched T cell population and/or the pooled CD27 enriched T cell population contains at least at or about 70% CD27+ CD3+ T cells. In certain embodiments, the CD27 enriched T cell population and/or the pooled CD27 enriched T cell population contains at least at or about 80% CD27+ CD3+ T cells. In certain embodiments, the CD27 enriched T cell population and/or the pooled CD27 enriched T cell population contains at least at or about 95% CD27+ CD3+ T cells. In various embodiments, the CD27 enriched T cell population and/or the pooled CD27 enriched T cell population contains at least at or about 99%, 99.9%, or 99.99% CD27+ CD3+ T cells. In particular embodiments, all or essentially all of the cells of the CD27 enriched T cell population and/or the pooled CD27 enriched T cell population are CD27+ CD3+ T cells.

In particular embodiments, the cells of the population of enriched CD57− T cells (e.g. the pooled CD57 depleted T cell population, the CD57 depleted T cell population, and/or the engineered T cell composition) are or include viable cells. In particular embodiments, the cells of the population of enriched CD27+ T cells (e.g. the pooled CD27 enriched T cell population, the CD27 enriched T cell population, and/or the engineered T cell composition) are or include viable cells. In some embodiments, cell viability is assessed with an assay that may include, but is not limited to, dye uptake assays (e.g., calcein AM assays), XTT cell viability assays, and dye exclusion assays (e.g., trypan blue, Eosin, or propidium dye exclusion assays). In particular embodiments, a viable cell has negative expression of one or more apoptotic markers, e.g., Annexin V or active Caspase 3. In some embodiments, the viable cell is negative for the expression of one or more apoptosis marker that may include, but are not limited to, a caspase or an active caspase, e.g., caspase 2, caspase 3, caspase 6, caspase 7, caspase 8, caspase 9, or caspase 10, Bcl-2 family members, e.g., Bax, Bad, and Bid, Annexin V, or TUNEL staining. In particular embodiments, the viable cells are active caspase 3 negative. In certain embodiments, the viable cells are Annexin V negative. In certain embodiments, at least at or about 60%, at least at or about 65%, at least at or about 70%, at least at or about 75%, at least at or about 80%, at least at or about 85%, at least at or about 90%, at least at or about 95%, at least at or about 97%, at least at or about 99%, at least at or about 99.5%, at least at or about 99.9%, or 100% or about 100% of the cells of the CD57 depleted T cell population and/or the pooled CD57 depleted T cell population are viable cells. In some embodiments, the viable cells are or include viable CD3+, viable CD4+, viable CD8+, viable CD57−, viable CD57−CD3+, viable CD57−CD4+, or viable CD57−CD8+ T cells, or a combination of any of the foregoing. In certain embodiments, at least at or about 60%, at least at or about 65%, at least at or about 70%, at least at or about 75%, at least at or about 80%, at least at or about 85%, at least at or about 90%, at least at or about 95%, at least at or about 97%, at least at or about 99%, at least at or about 99.5%, at least at or about 99.9%, or 100% or about 100% of the cells of the CD27 enriched T cell population and/or the pooled CD27 enriched T cell population are viable cells. In some embodiments, the viable cells are or include viable CD3+, viable CD4+, viable CD8+, viable CD27+−, viable CD27+ CD3+, viable CD27+ CD4+, or viable CD27+ CD8+ T cells, or a combination of any of the foregoing. In some embodiments, the viable cells are active caspase 3 negative. In particular embodiments, the viable cells are Annexin V negative.

In certain embodiments, the CD57 depleted T cell population and/or the pooled CD57 depleted T cell population contains, contains about, or contains at least at or about 60%, 65%, 70%, 75%, 80%, 85%, 90%, 95%, 97%, 98%, 99%, 99.5%, 99.9%, 99.99%, or 100% or about 100% CD57− CD4+ T cells. In certain embodiments, the CD57 depleted T cell population and/or the pooled CD57 depleted T cell population contains at least at or about 80% CD57− CD4+ T cells. In certain embodiments, the CD57 depleted T cell population and/or the pooled CD57 depleted T cell population contains at least at or about 90% CD57− T cells. In various embodiments, the CD57 depleted T cell population and/or the pooled CD57 depleted T cell population contains at least at or about 95% CD57− CD4+ T cells. In particular embodiments, all or essentially all of the cells of the CD57 depleted T cell population and/or the pooled CD57 depleted T cell population are CD57− CD4+ T cells. In some embodiments, the CD57 depleted T cell population and/or the pooled CD57 depleted T cell population contains, contains about, or contains at least at or about 60%, 65%, 70%, 75%, 80%, 85%, 90%, 95%, 97%, 98%, 99%, 99.5%, 99.9%, 99.99%, or 100% or about 100% CD57−CD8+ T cells. In certain embodiments, the CD57 depleted T cell population and/or the pooled CD57 depleted T cell population contains at least at or about 80% CD57− CD8+ T cells. In certain embodiments, the CD57 depleted T cell population and/or the pooled CD57 depleted T cell population contains at least at or about 90% CD57− CD8+ T cells. In various embodiments, the CD57 depleted T cell population and/or the pooled CD57 depleted T cell population contains at least at or about 95%, CD57− CD8+ T cells. In particular embodiments, all or essentially all of the cells of the CD57 depleted T cell population and/or the pooled CD57 depleted T cell population are CD57− CD8+ T cells. In some embodiments, the CD57 depleted T cell population and/or the pooled CD57 depleted T cell population contains, contains about, or contains at least at or about 60%, 65%, 70%, 75%, 80%, 85%, 90%, 95%, 97%, 98%, 99%, 99.5%, 99.9%, 99.99%, or 100% or about 100% CD57−CD3+ T cells. In certain embodiments, the CD57 depleted T cell population and/or the pooled CD57 depleted T cell population contains at least at or about 80% CD57− CD3+ T cells. In certain embodiments, the CD57 depleted T cell population and/or the pooled CD57 depleted T cell population contains at least at or about 90% CD57− CD3+ T cells. In various embodiments, the CD57 depleted T cell population and/or the pooled CD57 depleted T cell population contains at least at or about 95%, CD57− CD3+ T cells. In particular embodiments, all or essentially all of the cells of the CD57 depleted T cell population and/or the pooled CD57 depleted T cell population are CD57− CD3+ T cells.

In certain embodiments, the CD27 enriched T cell population and/or the pooled CD27 enriched T cell population contains, contains about, or contains at least at or about 60%, 65%, 70%, 75%, 80%, 85%, 90%, 95%, 97%, 98%, 99%, 99.5%, 99.9%, 99.99%, or 100% or about 100% CD27+ CD4+ T cells. In certain embodiments, the CD27 enriched T cell population and/or the pooled CD27 enriched T cell population contains at least at or about 80% CD27+ CD4+ T cells. In certain embodiments, the CD27 enriched T cell population and/or the pooled CD27 enriched T cell population contains at least at or about 90% CD27+ cells. In various embodiments, the CD27 enriched T cell population and/or the pooled CD27 enriched T cell population contains at least at or about 95% CD27+ CD4+ T cells. In particular embodiments, all or essentially all of the cells of the CD27 enriched T cell population and/or the pooled CD27 enriched T cell population are CD27+ CD4+ T cells. In some embodiments, the CD27 enriched T cell population and/or the pooled CD27 enriched T cell population contains, contains about, or contains at least at or about 60%, 65%, 70%, 75%, 80%, 85%, 90%, 95%, 97%, 98%, 99%, 99.5%, 99.9%, 99.99%, or 100% or about 100% CD27+ CD8+ T cells. In certain embodiments, the CD27 enriched T cell population and/or the pooled CD27 enriched T cell population contains at least at or about 80% CD27+ CD8+ T cells. In certain embodiments, the CD27 enriched T cell population and/or the pooled CD27 enriched T cell population contains at least at or about 90% CD27+ CD8+ T cells. In various embodiments, the CD27 enriched T cell population and/or the pooled CD27 enriched T cell population contains at least at or about 95%, CD27+ CD8+ T cells. In particular embodiments, all or essentially all of the cells of the CD27 enriched T cell population and/or the pooled CD27 enriched T cell population are CD27+ CD8+ T cells. In some embodiments, the CD27 enriched T cell population and/or the pooled CD27 enriched T cell population contains, contains about, or contains at least at or about 60%, 65%, 70%, 75%, 80%, 85%, 90%, 95%, 97%, 98%, 99%, 99.5%, 99.9%, 99.99%, or 100% or about 100% CD27+ CD3+ T cells. In certain embodiments, the CD27 enriched T cell population and/or the pooled CD27 enriched T cell population contains at least at or about 80% CD27+ CD3+ T cells. In certain embodiments, the CD27 enriched T cell population and/or the pooled CD27 enriched T cell population contains at least at or about 90% CD27+ CD3+ T cells. In various embodiments, the CD27 enriched T cell population and/or the pooled CD27 enriched T cell population contains at least at or about 95%, CD27+ CD3+ T cells. In particular embodiments, all or essentially all of the cells of the CD27 enriched T cell population and/or the pooled CD27 enriched T cell population are CD27+ CD3+ T cells.

In particular embodiments, a frequency of the cells of the population of enriched CD57− cells are naïve-like cells. In some embodiments, a naïve-like T cell is a T cell that is positive for the expression of one or more markers that indicate that the cell is naïve and/or is a naïve-like cell. In certain embodiments, a naïve-like T cell is a cell that is positive for the expression of a marker that is associated with a naïve or naïve-like state in T cells. In particular embodiments, a naïve-like T cell is a T cell that is negative for the expression of one or more markers that indicates that the cell is not naïve and/or is a not a naïve-like cell. In certain embodiments, a non-naïve or non-naïve-like state in a T cells includes, for example but not limited to, effector T ($T_{EFF}$) cells, memory T cells, central memory T cells ($T_{CM}$), effector memory T ($T_{EM}$) cells, and combinations thereof.

In some embodiments, a naïve-like T cell is positive for the expression of at least one or more markers that indicate that the cell is naïve and/or is a naïve-like cell, and/or is associated with a naïve or naïve-like state in T cells. In some embodiments, the markers are expressed on the cell surface. In certain embodiments, the naïve-like T cell is negative for the expression of at least one or more markers that indicate that the cell is non-naïve and/or is a non-naïve-like cell, and/or is associated with a non-naïve or non-naïve-like state in T cells.

Markers that indicate that the T cell is naïve and/or is a naïve-like T cell, and/or are associated with a naïve or naïve-like state in T cells include, but are not limited to, CD27, CD28, CD45RA, CD62 L, and/or CCR7. In some embodiments, the naïve-like T cell, e.g., the naïve-like CD4+ and/or CD8+ T cell, is positive for expression of CD27, CD28, CD45RA, and/or CCR7. In certain embodiments, the naïve-like T cell is positive for the surface expression of one or more of CD27, CD28, CD45RA, and/or CCR7. In some embodiments, the naïve-like T cell, e.g., the naïve-like CD4+ and/or CD8+ T cell, is negative for expression of CD62 L. In some embodiments, the naïve-like T cell, e.g., the naïve-like CD3+ T cell, is negative for expression of CD62 L. In some embodiments, the naïve-like T cell, e.g., the naïve-like CD3+, CD4+, and/or CD8+ T cell, is negative for expression of CD62 L.

Markers that indicate that the cell is a non-naïve and/or is a non-naïve-like T cell, and/or are associated with a non-naïve or non-naïve-like state in T cells include, but are not limited to, CD25, CD45RO, CD56, KLRG1, and/or CD95. In some embodiments, the naïve-like T cell, e.g., a naïve-like CD4+ and/or CD8+ T cell, is negative for expression of CD25, CD45RO, CD56, and/or KLRG1. In particular embodiments, the naïve-like T cell, e.g., a naïve-like CD4+ and/or CD8+ T cell, has low expression of a marker associated with non-naïve or non-naïve-like cells. In some embodiments, the naïve-like T cell, e.g., a naïve-like CD3+ T cell, is negative for expression of CD25, CD45RO, CD56, and/or KLRG1. In particular embodiments, the naïve-like T cell, e.g., a naïve-like CD3+ T cell, has low expression of a marker associated with non-naïve or non-naïve-like cells. In particular embodiments, the naïve-like T cell has low expression of CD95. In certain embodiments, the naïve-like T cell is negative for the surface expression of one or more of CD25, CD45RO, CD56, and/or KLRG1.

In some embodiments, low expression of a marker associated with non-naïve or non-naïve-like cells is or includes at least 10%, at least 20%, at least 30%, at least 40%, at least 50%, at least 60%, at least 70%, at least 80%, at least 90%, at least 95%, or at least 99% less expression than the expression of the marker in a cell that is a non-naïve-like cells, and/or a cell that is positive for one or more markers that indicate that the cell is a non-naïve and/or is a non-naïve-like T cell, and/or are associated with a non-naïve or non-naïve-like state in T cells. In certain embodiments, low expression of a marker associated with non-naïve or non-naïve-like cells is or includes at least 10%, at least 20%, at least 30%, at least 40%, at least 50%, at least 60%, at least 70%, at least 80%, at least 90%, at least 95%, or at least 99% less expression than the expression of the marker in an effector T ($T_{EFF}$) cell, a memory T cell, a central memory T cell ($T_{CM}$), and/or an effector memory T ($T_{EM}$) cell.

In some embodiments, markers that indicate that the cell is a non-naïve and/or is a non-naïve-like T cell, and/or are associated with a non-naïve or non-naïve-like state in T cells include one or more cytokines. For example, in certain embodiments, a non-naïve or non-naïve-like T cell is negative for the expression and/or the production of one or more of IL-2, IFN-γ, IL-4, and IL-10. In some embodiments, the one or more cytokines are secreted. In particular embodiments, the one or more cytokines are expressed internally by the non-naïve-like T cells, for example, during or after treatment with an agent that prevents, inhibits, or reduces secretion.

In certain embodiments, a naïve-like T cell, e.g., a naïve-like CD57− T cell, is positive for the expression, e.g., surface expression, of CD45RA and CCR7. In certain embodiments, a naïve-like T cell, e.g., a naïve-like CD27+ T cell, is positive for the expression, e.g., surface expression, of CD45RA and CCR7. In particular embodiments, a naïve-like CD4+ T cell is positive for the expression, e.g., surface expression, of CD45RA and CCR7. In some embodiments, a naïve-like CD8+ T cell is positive for the expression, e.g., surface expression, of CD45RA and CCR7. In some embodiments, a naïve-like CD3+ T cell is positive for the expression, e.g., surface expression, of CD45RA and CCR7. In particular embodiments, a naïve-like T cell is positive for the expression, e.g., surface expression, of CD45RA, CD27, and CCR7 and is negative for the expression, e.g., surface expression of CD45RO. In particular embodiments, a naïve-like CD4+ T cell is positive for the expression, e.g., surface expression, of CD45RA, CD27, and CCR7 and is negative for the expression, e.g., surface expression of CD45RO. In some embodiments, a naïve-like CD8+ T cell is positive for the expression, e.g., surface expression, of CD45RA, CD27, and CCR7 and is negative for the expression, e.g., surface expression of CD45RO. In some embodiments, a naïve-like CD3+ T cell is positive for the expression, e.g., surface expression, of CD45RA, CD27, and CCR7 and is negative for the expression, e.g., surface expression of CD45RO.

In certain embodiments, the population of enriched CD57− T cells (e.g. the pooled CD57 depleted T cell population and/or the CD57 depleted T cell population) contains, contains about, or contains at least at or about 10%, 15%, 20%, 25%, 30%, 35%, 40%, 45%, or 50% T cells that are positive for CD25 expression. In various embodiments, the CD57 depleted T cell population and/or the pooled CD57 depleted T cell population contains, contains about, or contains at least at or about 10%, 15%, 20%, 25%, 30%, 35%, 40%, 45%, or 50% CD57− CD25+ T cells. In various embodiments, the CD57 depleted T cell population and/or the pooled CD57 depleted T cell population contains between or between about 10% and 60%, 20% and 50%, or 25% and 40% CD25+ T cells, each inclusive. In some embodiments, the CD57 depleted T cell population and/or the pooled CD57 depleted T cell population contains between or between about 10% and 60%, 20% and 50%, or 25% and 40% CD57− CD25+ T cells, each inclusive.

In certain embodiments, the population of enriched CD27+ T cells (e.g. the pooled CD27 enriched T cell population and/or the CD27 enriched T cell population) contains, contains about, or contains at least at or about 10%, 15%, 20%, 25%, 30%, 35%, 40%, 45%, or 50% T cells that are positive for CD25 expression. In various embodiments, the CD27 enriched T cell population and/or the pooled CD27 enriched T cell population contains, contains about, or contains at least at or about 10%, 15%, 20%, 25%, 30%, 35%, 40%, 45%, or 50% CD27+ CD25+ T cells. In various embodiments, the CD27 enriched T cell population and/or the pooled CD27 enriched T cell population contains between or between about 10% and 60%, 20% and 50%, or 25% and 40% CD25+ T cells, each inclusive. In some embodiments, the CD27 enriched T cell population and/or the pooled CD27 enriched T cell population contains between or between about 10% and 60%, 20% and 50%, or 25% and 40% CD27+ CD25+ T cells, each inclusive.

In certain embodiments, the CD57 depleted T cell population and/or the pooled CD57 depleted T cell population contains, contains about, or contains at least at or about 10%, 15%, 20%, 25%, 30%, 35%, 40%, 45%, or 50% T cells that are positive for CD27 expression. In various embodiments, the CD57 depleted T cell population and/or the pooled CD57 depleted T cell population contains, contains about, or contains at least at or about 10%, 15%, 20%, 25%, 30%, 35%, 40%, 45%, or 50% CD57− CD27+ T cells. In various embodiments, the CD57 depleted T cell population and/or the pooled CD57 depleted T cell population contains between or between about 10% and 60%, 20% and 50%, or 25% and 40% CD27+ T cells, each inclusive. In some embodiments, the CD57 depleted T cell population and/or the pooled CD57 depleted T cell population contains between or between about 10% and 60%, 20% and 50%, or 25% and 40% CD57− CD27+ T cells, each inclusive. In certain embodiments, the CD57 depleted T cell population and/or the pooled CD57 depleted T cell population contains at least at or about 25% CD27+ T cells.

In certain embodiments, the CD27 enriched T cell population and/or the pooled CD27 enriched T cell population contains, contains about, or contains at least at or about 10%, 15%, 20%, 25%, 30%, 35%, 40%, 45%, or 50% T cells that are negative for CD57 expression. In various embodiments, the CD27 enriched T cell population and/or the pooled CD27 enriched T cell population contains, contains about, or contains at least at or about 10%, 15%, 20%, 25%, 30%, 35%, 40%, 45%, or 50% CD57−CD27+ T cells. In various embodiments, the CD27 enriched T cell population and/or the pooled CD27 enriched T cell population contains between or between about 10% and 60%, 20% and 50%, or 25% and 40% CD57− T cells, each inclusive. In some embodiments, the CD27 enriched T cell population and/or the pooled CD27 enriched T cell population contains between or between about 10% and 60%, 20% and 50%, or 25% and 40% CD57−CD27+ T cells, each inclusive. In certain embodiments, the CD27 enriched T cell population and/or the pooled CD27 enriched T cell population contains at least at or about 25% CD57− T cells.

In particular embodiments, the CD57 depleted T cell population and/or the pooled CD57 depleted T cell population contains, contains about, or contains at least at or about 10%, 15%, 20%, 25%, 30%, 35%, 40%, 45%, or 50% T cells that are positive for CD28 expression. In various embodiments, the CD57 depleted T cell population and/or the pooled CD57 depleted T cell population contains, contains about, or contains at least at or about 5%, 10%, 15%, 20%, 25%, 30%, 35%, 40%, 45%, or 50% CD57− CD28+ T cells. In certain embodiments, the CD57 depleted T cell population and/or the pooled CD57 depleted T cell population contains between or between about at or about 5% and at or about 50%, at or about 5% and at or about 35%, or at or about 10% and at or about 25% CD28+ T cells, each inclusive. In some embodiments, the CD57 depleted T cell population and/or the pooled CD57 depleted T cell population contains between or between at or about 5% and at or about 50%, at or about 5% and at or about 35%, or at or about 10% and at or about 25% CD57− CD28+ T cells, each inclusive. In certain embodiments the CD57 depleted T cell population and/or the pooled CD57 depleted T cell population contains at least at or about 25% CD28+ T cells.

In particular embodiments, the CD27 enriched T cell population and/or the pooled CD27 enriched T cell population contains, contains about, or contains at least at or about 10%, 15%, 20%, 25%, 30%, 35%, 40%, 45%, or 50% T cells that are positive for CD28 expression. In various embodiments, the CD27 enriched T cell population and/or the pooled CD27 enriched T cell population contains, contains about, or contains at least at or about 5%, 10%, 15%, 20%, 25%, 30%, 35%, 40%, 45%, or 50% CD27+ CD28+ T cells. In certain embodiments, the CD27 enriched T cell population and/or the pooled CD27 enriched T cell population contains between or between about at or about 5% and at or about 50%, at or about 5% and at or about 35%, or at or about 10% and at or about 25% CD28+ T cells, each inclusive. In some embodiments, the CD27 enriched T cell population and/or the pooled CD27 enriched T cell population contains between or between at or about 5% and at or about 50%, at or about 5% and at or about 35%, or at or about 10% and at or about 25% CD27+ CD28+ T cells, each inclusive. In certain embodiments the CD27 enriched T cell population and/or the pooled CD27 enriched T cell population contains at least at or about 25% CD28+ T cells.

In some embodiments, the CD57 depleted T cell population and/or the pooled CD57 depleted T cell population contains, contains about, or contains at least at or about 10%, 15%, 20%, 25%, 30%, 35%, 40%, 45%, or 50% T cells that are positive for CCR7 expression. In certain embodiments, the CD57 depleted T cell population and/or the pooled CD57 depleted T cell population contains, contains about, or contains at least at or about 5%, 10%, 15%, 20%, 25%, 30%, 35%, 40%, 45%, or 50% CD57− CCR7+ T cells. In some embodiments, the CD57 depleted T cell population and/or the pooled CD57 depleted T cell population contains between or between about at or about 5% and at or about 50%, at or about 5% and at or about 35%, or at or about 10% and at or about 25% CCR7+ T cells, each inclusive. In particular embodiments, the CD57 depleted T cell population and/or the pooled CD57 depleted T cell population contains between or between about at or about 5% and at or about 50%, at or about 5% and at or about 35%, or at or about 10% and at or about 25% CD57− CCR7+ T cells, each inclusive. In some embodiments, the CD57 depleted T cell population and/or the pooled CD57 depleted T cell population contains at least at or about 25% CCR7+ T cells.

In some embodiments, the CD27 enriched T cell population and/or the pooled CD27 enriched T cell population contains, contains about, or contains at least at or about 10%, 15%, 20%, 25%, 30%, 35%, 40%, 45%, or 50% T cells that are positive for CCR7 expression. In certain embodiments, the CD27 enriched T cell population and/or the pooled CD27 enriched T cell population contains, contains about, or contains at least at or about 5%, 10%, 15%, 20%, 25%, 30%, 35%, 40%, 45%, or 50% CD27+ CCR7+ T cells. In some embodiments, the CD27 enriched T cell population and/or the pooled CD27 enriched T cell population contains between or between about at or about 5% and at or about 50%, at or about 5% and at or about 35%, or at or about 10% and at or about 25% CCR7+ T cells, each inclusive. In particular embodiments, the CD27 enriched T cell population and/or the pooled CD27 enriched T cell population contains between or between about at or about 5% and at or about 50%, at or about 5% and at or about 35%, or at or about 10% and at or about 25% CD27+ CCR7+ T cells, each inclusive. In some embodiments, the CD27 enriched T cell population and/or the pooled CD27 enriched T cell population contains at least at or about 25% CCR7+ T cells.

In some embodiments, the CD57 depleted T cell population and/or the pooled CD57 depleted T cell population contains, contains about, or contains at least at or about 10%, 15%, 20%, 25%, 30%, 35%, 40%, 45%, or 50% T cells that are positive for CD45RA expression. In certain embodiments, the CD57 depleted T cell population and/or the pooled CD57 depleted T cell population contains, contains about, or contains at least at or about 5%, 10%, 15%, 20%, 25%, 30%, 35%, 40%, 45%, or 50% CD57− CD45RA+ T cells. In come embodiments, the CD57 depleted T cell population and/or the pooled CD57 depleted T cell population contains between or between about at or about 5% and at or about 50%, at or about 5% and at or about 35%, or at or about 10% and at or about 25% CD45RA+ T cells, each inclusive. In particular embodiments, the CD57 depleted T cell population and/or the pooled CD57 depleted T cell population contains between or between about at or about 5% and at or about 50%, at or about 5% and at or about 35%, or at or about 10% and at or about 25% CD57− CD45RA+ T cells, each inclusive. In some embodiments, the CD57 depleted T cell population and/or the pooled CD57 depleted T cell population contains at least at or about 25% CD45RA+ T cells.

In some embodiments, the CD27 enriched T cell population and/or the pooled CD27 enriched T cell population contains, contains about, or contains at least at or about 10%, 15%, 20%, 25%, 30%, 35%, 40%, 45%, or 50% T cells that are positive for CD45RA expression. In certain embodiments, the CD27 enriched T cell population and/or the pooled CD27 enriched T cell population contains, contains about, or contains at least at or about 5%, 10%, 15%, 20%, 25%, 30%, 35%, 40%, 45%, or 50% CD27+ CD45RA+ T cells. In come embodiments, the CD27 enriched T cell population and/or the pooled CD27 enriched T cell population contains between or between about at or about 5% and at or about 50%, at or about 5% and at or about 35%, or at or about 10% and at or about 25% CD45RA+ T cells, each inclusive. In particular embodiments, the CD27 enriched T cell population and/or the pooled CD27 enriched T cell population contains between or between about at or about 5% and at or about 50%, at or about 5% and at or about 35%, or at or about 10% and at or about 25% CD27+ CD45RA+ T cells, each inclusive. In some embodiments, the CD27 enriched T cell population and/or the pooled CD27 enriched T cell population contains at least at or about 25% CD45RA+ T cells.

In some embodiments, the frequency of the naïve-like cells in the depleted population (e.g. the pooled CD57 depleted T cell population and/or the CD57 depleted T cell population) is at least at or about 10%, 20%, 30%, 40%, or 50% greater than at or about the frequency of naïve-like cells in the biological sample. In some embodiments, the frequency of one or more of CD25+ T cells, CD27+ T cells, CD28+ T cells, CCR7+ T cells, or CD45RA+ T cells in the CD57 depleted T cell population and/or the pooled CD57 depleted T cell population is at least at or about 10%, 20%, 30%, 40%, or 50% greater than at or about the frequency of the respective cells in the biological sample. In some embodiments, the CD57 depleted T cell population and/or the pooled CD57 depleted T cell population comprises at least at or about 15%, 20%, 25%, 30%, 35%, or 40% CD27+ T cells. In some embodiments, the CD57 depleted T cell population and/or the pooled CD57 depleted T cell population comprises at least at or about 10%, 15%, 20%, 25%, 25%, 30%, 35%, or 40% CD28+ T cells. In some embodiments, the CD57 depleted T cell population and/or the pooled CD57 depleted T cell population comprises at least at or about 10%, 15%, 20%, 25%, 30%, 35%, 40%, 50%, 60%, 70% or 80% CD27+ CD28+ T cells. In some embodiments, the CD57 depleted T cell population and/or the pooled CD57 depleted T cell population comprises at least at or about 70% or 80% CD27+ CD28+ T cells. In some embodiments, the CD57 depleted T cell population and/or the pooled CD57 depleted T cell population comprises at least at or about 10%, 15%, 20%, or 25% CCR7+ T cells.

In some embodiments, the frequency of the naïve-like cells in the depleted population (e.g. the pooled CD27 enriched T cell population and/or the CD27 enriched T cell population) is at least at or about 10%, 20%, 30%, 40%, or 50% greater than at or about the frequency of naïve-like cells in the biological sample. In some embodiments, the frequency of one or more of CD25+ T cells, CD27+ T cells, CD28+ T cells, CCR7+ T cells, or CD45RA+ T cells in the CD27 enriched T cell population and/or the pooled CD27 enriched T cell population is at least at or about 10%, 20%, 30%, 40%, or 50% greater than at or about the frequency of the respective cells in the biological sample. In some embodiments, the CD27 enriched T cell population and/or the pooled CD27 enriched T cell population comprises at least at or about 15%, 20%, 25%, 30%, 35%, or 40% CD27+ T cells. In some embodiments, the CD27 enriched T cell population and/or the pooled CD27 enriched T cell population comprises at least at or about 10%, 15%, 20%, 25%, 25%, 30%, 35%, or 40% CD28+ T cells. In some embodiments, the CD27 enriched T cell population and/or the pooled CD27 enriched T cell population comprises at least at or about 10%, 15%, 20%, 25%, 30%, 35%, 40%, 50%, 60%, 70% or 80% CD27+ CD28+ T cells. In some embodiments, the CD27 enriched T cell population and/or the pooled CD27 enriched T cell population comprises at least at or about 70% or 80% CD27+ CD28+ T cells. In some embodiments, the CD27 enriched T cell population and/or the pooled CD27 enriched T cell population comprises at least at or about 10%, 15%, 20%, or 25% CCR7+ T cells.

In certain embodiments, the selected cell compositions (e.g. the CD57 depleted T cell population and/or the pooled CD57 depleted T cell population) includes a population of cells for use in genetic engineering, e.g., cells that will be genetically engineered or that will undergo a process to produce genetically engineered cells. In certain embodiments, the cells will be treated with, contacted with, or incubated with a nucleic acid that encodes a recombinant receptor. In certain embodiments, the input composition contains T cells, viable T cells, CD57− T cells, CD3+ T cells, CD4+ T cells, CD8+ T cells, and/or subpopulations thereof.

In certain embodiments, the selected cell compositions (e.g. the CD27 enriched T cell population and/or the pooled CD27 enriched T cell population) includes a population of cells for use in genetic engineering, e.g., cells that will be genetically engineered or that will undergo a process to produce genetically engineered cells. In certain embodiments, the cells will be treated with, contacted with, or incubated with a nucleic acid that encodes a recombinant receptor. In certain embodiments, the input composition contains T cells, viable T cells, CD27+ T cells, CD3+ T cells, CD4+ T cells, CD8+ T cells, and/or subpopulations thereof.

In some embodiments, cell viability is assessed with an assay that may include, but is not limited to, dye uptake assays (e.g., calcein AM assays), XTT cell viability assays, and dye exclusion assays (e.g., trypan blue, Eosin, or propidium dye exclusion assays). In particular embodiments, a viable cell has negative expression of one or more apoptotic markers, e.g., Annexin V or active Caspase 3. In some embodiments, the viable cell is negative for the expression of one or more apoptosis marker that may include, but are not limited to, a caspase or an active caspase, e.g., caspase 2, caspase 3, caspase 6, caspase 7, caspase 8, caspase 9, or caspase 10, Bcl-2 family members, e.g., Bax, Bad, and Bid, Annexin V, or TUNEL staining. In particular embodiments, the viable cells are active caspase 3 negative. In certain embodiments, the viable cells are Annexin V negative.

In some embodiments, the input composition comprises a population of enriched CD57-T cells, e.g., viable CD57− T cells (e.g. the CD57 depleted T cell population and/or the pooled CD57 depleted T cell population). In some embodiments, at least 60%, at least 65%, at least 70%, at least 75%, at least 80%, at least 85%, at least 90%, at least 95%, at least 98%, at least 99%, at least 99.5%, at least 99.9%, or at or at about 100% of the cells of the input population (e.g. the CD57 depleted T cell population and/or the pooled CD57 depleted T cell population) are CD57− T cells, e.g., viable CD57− T cells. In some embodiments, at least 60%, at least 65%, at least 70%, at least 75%, at least 80%, at least 85%, at least 90%, at least 95%, at least 98%, at least 99%, at least 99.5%, at least 99.9%, or at or at about 100% of the cells of the CD57 depleted T cell population are CD57− T cells, e.g., viable CD57− T cells. In some embodiments, at least 60%, at least 65%, at least 70%, at least 75%, at least 80%, at least 85%, at least 90%, at least 95%, at least 98%, at least 99%, at least 99.5%, at least 99.9%, or at or at about 100% of the cells of the pooled CD57 depleted T cell population are CD57− T cells, e.g., viable CD57− T cells. In some embodiments, the input population (e.g. the CD57 depleted T cell population and/or the pooled CD57 depleted T cell population) consists essentially of CD57− T cells, e.g., viable CD57− T cells. In some embodiments, the CD57 depleted T cell population consists essentially of CD57− T cells, e.g., viable CD57− T cells. In some embodiments, the pooled CD57 depleted T cell population consists essentially of CD57− T cells, e.g., viable CD57− T cells.

In certain embodiments, the input population (e.g. the CD57 depleted T cell population and/or the pooled CD57 depleted T cell population) is a population of cells enriched for enriched CD3+ T cells. In particular embodiments, the input population (e.g. the CD57 depleted T cell population and/or the pooled CD57 depleted T cell population) is or includes at least 60%, at least 65%, at least 70%, at least 75%, at least 80%, at least 85%, at least 90%, at least 95%, at least 98%, at least 99%, at least 99.5%, at least 99.9%, or at or at about 100% cells that are CD3+ T cells. In particular embodiments, the input population (e.g. the CD57 depleted T cell population and/or the pooled CD57 depleted T cell population) is or includes at least 60%, at least 65%, at least 70%, at least 75%, at least 80%, at least 85%, at least 90%, at least 95%, at least 98%, at least 99%, at least 99.5%, at least 99.9%, or at or at about 100% cells that are CD3+ T cells. In some embodiments, the input population (e.g. the CD57 depleted T cell population and/or the pooled CD57 depleted T cell population) consists essentially of CD3+ T cells. In particular embodiments, the input population (e.g. the CD57 depleted T cell population and/or the pooled CD57 depleted T cell population) is or includes at least 60%, at least 65%, at least 70%, at least 75%, at least 80%, at least 85%, at least 90%, at least 95%, at least 98%, at least 99%, at least 99.5%, at least 99.9%, or at or at about 100% cells CD3+ T cells that are CD57−, e.g. viable CD57− T cells.

In certain embodiments, the input population (e.g. the CD57 depleted T cell population and/or the pooled CD57 depleted T cell population) is a population of cells enriched for enriched CD4+ T cells and CD8+ T cells, e.g., CD4+ T cells and CD8+ T cells. In particular embodiments, the input population (e.g. the CD57 depleted T cell population and/or the pooled CD57 depleted T cell population) is or includes at least 60%, at least 65%, at least 70%, at least 75%, at least 80%, at least 85%, at least 90%, at least 95%, at least 98%, at least 99%, at least 99.5%, at least 99.9%, or at or at about 100% cells that are CD3+ T cells (CD4+ and CD8+ T cells). In particular embodiments, the input population (e.g. the CD57 depleted T cell population and/or the pooled CD57 depleted T cell population) is or includes at least 60%, at least 65%, at least 70%, at least 75%, at least 80%, at least 85%, at least 90%, at least 95%, at least 98%, at least 99%, at least 99.5%, at least 99.9%, or at or at about 100% cells that are CD4+ and CD8+ T cells. In some embodiments, the input population (e.g. the CD57 depleted T cell population and/or the pooled CD57 depleted T cell population) consists essentially of CD4+ and CD8+ T cells. In particular embodiments, the input population (e.g. the CD57 depleted T cell population and/or the pooled CD57 depleted T cell population) is or includes at least 60%, at least 65%, at least 70%, at least 75%, at least 80%, at least 85%, at least 90%, at least 95%, at least 98%, at least 99%, at least 99.5%, at least 99.9%, or at or at about 100% cells CD3+ T cells (CD4+ and CD8+ T cells) that are CD57−, e.g. viable CD57− T cells.

In certain embodiments, the input population (e.g. the CD57 depleted T cell population and/or the pooled CD57 depleted T cell population) is a population of enriched CD4+ T cells. In particular embodiments, at least 60%, at least 65%, at least 70%, at least 75%, at least 80%, at least 85%, at least 90%, at least 95%, at least 98%, at least 99%, at least 99.5%, at least 99.9%, or at or at about 100% of the cells of the input population (e.g. the CD57 depleted T cell population and/or the pooled CD57 depleted T cell population) are CD4+ T cells. In some embodiments, the input population consists essentially of CD4+ T cells. In particular embodiments, the input population (e.g. the CD57 depleted T cell population and/or the pooled CD57 depleted T cell population) is or includes at least 60%, at least 65%, at least 70%, at least 75%, at least 80%, at least 85%, at least 90%, at least 95%, at least 98%, at least 99%, at least 99.5%, at least 99.9%, or at or at about 100% cells CD4+ T cells that are CD57−, e.g. viable CD57− T cells.

In certain embodiments, the input population (e.g. the CD57 depleted T cell population and/or the pooled CD57 depleted T cell population) is a population of enriched CD8+ T cells. In particular embodiments, at least 60%, at least 65%, at least 70%, at least 75%, at least 80%, at least 85%, at least 90%, at least 95%, at least 98%, at least 99%, at least 99.5%, at least 99.9%, or at or at about 100% of the cells of the input population (e.g. the CD57 depleted T cell population and/or the pooled CD57 depleted T cell population) are CD8+ T cells. In some embodiments, the input population (e.g. the CD57 depleted T cell population and/or the pooled CD57 depleted T cell population) consists essentially of CD8+ T cells. In particular embodiments, the input population (e.g. the CD57 depleted T cell population and/or the pooled CD57 depleted T cell population) is or includes at least 60%, at least 65%, at least 70%, at least 75%, at least 80%, at least 85%, at least 90%, at least 95%, at least 98%, at least 99%, at least 99.5%, at least 99.9%, or at or at about 100% cells CD8+ T cells that are CD57−, e.g. viable CD57− T cells.

In some embodiments, cells from a population of enriched CD57−CD4+ T cells and cells from a population of enriched CD57−CD8+ T cells are mixed, combined, and/or pooled to generate an input population (e.g. the CD57 depleted T cell population and/or the pooled CD57 depleted T cell population) containing CD57−CD4+ T cells and CD57−CD8+ T cells. In certain embodiments, the populations of enriched CD57−CD4+ T cells and CD57−CD8+ T cells are pooled, mixed, and/or combined prior to stimulating cells, e.g., culturing the cells under stimulating conditions. In particular embodiments, the populations of enriched CD57−CD4+ and CD57−CD8+ T cells are pooled, mixed, and/or combined subsequent to freezing, e.g., cryopreserving, and thawing the populations of enriched CD57−CD4+ and CD57−CD8+ T cells.

In certain embodiments, the input population (e.g. the CD57 depleted T cell population and/or the pooled CD57 depleted T cell population) is produced, generated, or made by mixing, pooling, and/or combining cells from a population of enriched CD57−CD4+ cells with cells from a population of enriched CD57−CD8+ cells. In certain embodiments, the population of enriched CD57−CD4+ T cells contains at least 60%, 65%, 70%, 75%, 80%, 85%, 90%, 95%, 98%, 99%, or 99.9% CD57−CD4+ T cells. In particular embodiments, the population of enriched CD57−CD4+ T cells contains 100% CD57−CD4+ T cells or contains about 100% CD57−CD4+ T cells. In certain embodiments, the population of enriched T cells includes or contains less than 20%, less than 10%, less than 5%, less than 1%, less than 0.1%, or less than 0.01% CD57−CD8+ T cells, and/or contains no CD57−CD8+ T cells, and/or is free or substantially free of CD57−CD8+ T cells. In some embodiments, the populations of cells consist essentially of CD57−CD4+ T cells. In certain embodiments, the population of enriched CD57−CD8+ T cells contains at least 75%, 80%, 85%, 90%, 95%, 98%, 99%, or 99.9% CD57−CD8+ T cells, or contains or contains about 100% CD57−CD8+ T cells. In certain embodiments, the population of enriched CD57−CD8+ T cells includes or contains less than 20%, less than 10%, less than 5%, less than 1%, less than 0.1%, or less than 0.01% CD57−CD4+ T cells, and/or contains no CD57−CD4+ T cells, and/or is free or substantially free of CD57−CD4+ T cells. In some embodiments, the populations of cells consist essentially of CD57−CD8+ T cells.

In some embodiments, the input composition comprises a population of enriched CD27+ T cells, e.g., viable CD27+ T cells (e.g. the CD27 enriched T cell population and/or the pooled CD27 enriched T cell population). In some embodiments, at least 60%, at least 65%, at least 70%, at least 75%, at least 80%, at least 85%, at least 90%, at least 95%, at least 98%, at least 99%, at least 99.5%, at least 99.9%, or at or at about 100% of the cells of the input population (e.g. the CD27 enriched T cell population and/or the pooled CD27 enriched T cell population) are CD27+ T cells, e.g., viable CD27+ T cells. In some embodiments, at least 60%, at least 65%, at least 70%, at least 75%, at least 80%, at least 85%, at least 90%, at least 95%, at least 98%, at least 99%, at least 99.5%, at least 99.9%, or at or at about 100% of the cells of the CD27 enriched T cell population are CD27+ T cells, e.g., viable CD27+ T cells. In some embodiments, at least 60%, at least 65%, at least 70%, at least 75%, at least 80%, at least 85%, at least 90%, at least 95%, at least 98%, at least 99%, at least 99.5%, at least 99.9%, or at or at about 100% of the cells of the pooled CD27 enriched T cell population are CD27+ T cells, e.g., viable CD27+ T cells. In some embodiments, the input population (e.g. the CD27 enriched T cell population and/or the pooled CD27 enriched T cell population) consists essentially of CD27+ T cells, e.g., viable CD27+ T cells. In some embodiments, the CD27 enriched T cell population consists essentially of CD27+ T cells, e.g., viable CD27+ T cells. In some embodiments, the pooled CD27 enriched T cell population consists essentially of CD27+ T cells, e.g., viable CD27+ T cells.

In certain embodiments, the input population (e.g. the CD27 enriched T cell population and/or the pooled CD27 enriched T cell population) is a population of cells enriched for enriched CD3+ T cells. In particular embodiments, the input population (e.g. the CD27 enriched T cell population and/or the pooled CD27 enriched T cell population) is or includes at least 60%, at least 65%, at least 70%, at least 75%, at least 80%, at least 85%, at least 90%, at least 95%, at least 98%, at least 99%, at least 99.5%, at least 99.9%, or at or at about 100% cells that are CD3+ T cells. In particular embodiments, the input population (e.g. the CD27 enriched T cell population and/or the pooled CD27 enriched T cell population) is or includes at least 60%, at least 65%, at least 70%, at least 75%, at least 80%, at least 85%, at least 90%, at least 95%, at least 98%, at least 99%, at least 99.5%, at least 99.9%, or at or at about 100% cells that are CD3+ T cells. In some embodiments, the input population (e.g. the CD27 enriched T cell population and/or the pooled CD27 enriched T cell population) consists essentially of CD3+ T cells. In particular embodiments, the input population (e.g. the CD27 enriched T cell population and/or the pooled CD27 enriched T cell population) is or includes at least 60%, at least 65%, at least 70%, at least 75%, at least 80%, at least 85%, at least 90%, at least 95%, at least 98%, at least 99%, at least 99.5%, at least 99.9%, or at or at about 100% cells CD3+ T cells that are CD27+, e.g. viable CD27+ T cells.

In certain embodiments, the input population (e.g. the CD27 enriched T cell population and/or the pooled CD27 enriched T cell population) is a population of cells enriched for enriched CD4+ T cells and CD8+ T cells, e.g., CD4+ T cells and CD8+ T cells. In particular embodiments, the input population (e.g. the CD27 enriched T cell population and/or the pooled CD27 enriched T cell population) is or includes at least 60%, at least 65%, at least 70%, at least 75%, at least 80%, at least 85%, at least 90%, at least 95%, at least 98%, at least 99%, at least 99.5%, at least 99.9%, or at or at about 100% cells that are CD3+ T cells (CD4+ and CD8+ T cells). In particular embodiments, the input population (e.g. the CD27 enriched T cell population and/or the pooled CD27 enriched T cell population) is or includes at least 60%, at least 65%, at least 70%, at least 75%, at least 80%, at least 85%, at least 90%, at least 95%, at least 98%, at least 99%, at least 99.5%, at least 99.9%, or at or at about 100% cells that are CD4+ and CD8+ T cells. In some embodiments, the input population (e.g. the CD27 enriched T cell population and/or the pooled CD27 enriched T cell population) consists essentially of CD4+ and CD8+ T cells. In particular embodiments, the input population (e.g. the CD27 enriched T cell population and/or the pooled CD27 enriched T cell population) is or includes at least 60%, at least 65%, at least 70%, at least 75%, at least 80%, at least 85%, at least 90%, at least 95%, at least 98%, at least 99%, at least 99.5%, at least 99.9%, or at or at about 100% cells CD3+ T cells (CD4+ and CD8+ T cells) that are CD27+, e.g. viable CD27+ T cells.

In certain embodiments, the input population (e.g. the CD27 enriched T cell population and/or the pooled CD27 enriched T cell population) is a population of enriched CD4+ T cells. In particular embodiments, at least 60%, at least 65%, at least 70%, at least 75%, at least 80%, at least 85%, at least 90%, at least 95%, at least 98%, at least 99%, at least 99.5%, at least 99.9%, or at or at about 100% of the cells of the input population (e.g. the CD27 enriched T cell population and/or the pooled CD27 enriched T cell population) are CD4+ T cells. In some embodiments, the input population consists essentially of CD4+ T cells. In particular embodiments, the input population (e.g. the CD27 enriched T cell population and/or the pooled CD27 enriched T cell population) is or includes at least 60%, at least 65%, at least 70%, at least 75%, at least 80%, at least 85%, at least 90%, at least 95%, at least 98%, at least 99%, at least 99.5%, at least 99.9%, or at or at about 100% cells CD4+ T cells that are CD27+, e.g. viable CD27+ T cells.

In certain embodiments, the input population (e.g. the CD27 enriched T cell population and/or the pooled CD27 enriched T cell population) is a population of enriched CD8+ T cells. In particular embodiments, at least 60%, at least 65%, at least 70%, at least 75%, at least 80%, at least 85%, at least 90%, at least 95%, at least 98%, at least 99%, at least 99.5%, at least 99.9%, or at or at about 100% of the cells of the input population (e.g. the CD27 enriched T cell population and/or the pooled CD27 enriched T cell population) are CD8+ T cells. In some embodiments, the input population (e.g. the CD27 enriched T cell population and/or the pooled CD27 enriched T cell population) consists essentially of CD8+ T cells. In particular embodiments, the input population (e.g. the CD27 enriched T cell population and/or the pooled CD27 enriched T cell population) is or includes at least 60%, at least 65%, at least 70%, at least 75%, at least 80%, at least 85%, at least 90%, at least 95%, at least 98%, at least 99%, at least 99.5%, at least 99.9%, or at or at about 100% cells CD8+ T cells that are CD27+, e.g. viable CD27+ T cells.

In some embodiments, cells from a population of enriched CD27+ CD4+ T cells and cells from a population of enriched CD27+ CD8+ T cells are mixed, combined, and/or pooled to generate an input population (e.g. the CD27 enriched T cell population and/or the pooled CD27 enriched T cell population) containing CD27+ CD4+ T cells and CD27+ CD8+ T cells. In certain embodiments, the populations of enriched CD27+ CD4+ T cells and CD27+ CD8+ T cells are pooled, mixed, and/or combined prior to stimulating cells, e.g., culturing the cells under stimulating conditions. In particular embodiments, the populations of enriched CD27+ CD4+ and CD27+ CD8+ T cells are pooled, mixed, and/or combined subsequent to freezing, e.g., cryopreserving, and thawing the populations of enriched CD27+ CD4+ and CD27+ CD8+ T cells.

In certain embodiments, the input population (e.g. the CD27 enriched T cell population and/or the pooled CD27 enriched T cell population) is produced, generated, or made by mixing, pooling, and/or combining cells from a population of enriched CD27+ CD4+ cells with cells from a population of enriched CD27+ CD8+ cells. In certain embodiments, the population of enriched CD27+ CD4+ T cells contains at least 60%, 65%, 70%, 75%, 80%, 85%, 90%, 95%, 98%, 99%, or 99.9% CD27+ CD4+ T cells. In particular embodiments, the population of enriched CD27+ CD4+ T cells contains 100% CD27+ CD4+ T cells or contains about 100% CD27+ CD4+ T cells. In certain embodiments, the population of enriched T cells includes or contains less than 20%, less than 10%, less than 5%, less than 1%, less than 0.1%, or less than 0.01% CD27+ CD8+ T cells, and/or contains no CD27+ CD8+ T cells, and/or is free or substantially free of CD27+ CD8+ T cells. In some embodiments, the populations of cells consist essentially of CD27+ CD4+ T cells. In certain embodiments, the population of enriched CD27+ CD8+ T cells contains at least 75%, 80%, 85%, 90%, 95%, 98%, 99%, or 99.9% CD27+ CD8+ T cells, or contains or contains about 100% CD27+ CD8+ T cells. In certain embodiments, the population of enriched CD27+ CD8+ T cells includes or contains less than 20%, less than 10%, less than 5%, less than 1%, less than 0.1%, or less than 0.01% CD27+ CD4+ T cells, and/or contains no CD27+ CD4+ T cells, and/or is free or substantially free of CD27+ CD4+ T cells. In some embodiments, the populations of cells consist essentially of CD27+ CD8+ T cells.

In certain embodiments, CD4+ T cells and CD8+ T cells are pooled, mixed, and/or combined at a ratio of between 1:10 and 10:1, between 1:5 and 5:1, between 4:1 and 1:4, between 1:3 and 3:1, between 2:1 and 1:2, between 1.5:1 and 1:1.5, between 1.25:1 and 1:1.25, between 1.2:1 and 1:1.2, between 1.1:1 and 1:1.1, or about 1:1 or 1:1 CD4+ T cells to CD8+ T cells. In particular embodiments, viable CD4+ T cells and viable CD8+ T cells are pooled, mixed, and/or combined at a ratio of between 1:10 and 10:1, between 1:5 and 5:1, between 4:1 and 1:4, between 1:3 and 3:1, between 2:1 and 1:2, between 1.5:1 and 1:1.5, between 1.25:1 and 1:1.25, between 1.2:1 and 1:1.2, between 1.1:1 and 1:1.1, or about 1:1 or 1:1 CD4+ T cells to CD8+ T cells.

In particular embodiments, the input composition (e.g. the CD57 depleted T cell population and/or the pooled CD57 depleted T cell population) has an amount of, of about, or of at least $50\times10^6$, $100\times10^6$, $150\times10^6$, $200\times10^6$, $250\times10^6$, $300\times10^6$, $350\times10^6$, $400\times10^6$, $450\times10^6$, $500\times10^6$, $550\times10^6$, $600\times10^6$, $700\times10^6$, $800\times10^6$, $900\times10^6$, $1,000\times10^6$, $1,100\times10^6$, or $1,200\times10^6$ T cells, such as viable T cells, viable CD3+ T cells, or viable mixed CD4+ and CD8+ T cells. In particular embodiments, the input composition (e.g. the CD57 depleted T cell population and/or the pooled CD57 depleted T cell population) has an amount of, of about, or of at least $50\times10^6$, $100\times10^6$, $150\times10^6$, $200\times10^6$, $250\times10^6$, $300\times10^6$, $350\times10^6$, $400\times10^6$, $450\times10^6$, $500\times10^6$, $550\times10^6$, $600\times10^6$ CD4+ T cells, e.g., viable CD4+ T cells. In certain embodiments, the input composition (e.g. the CD57 depleted T cell population and/or the pooled CD57 depleted T cell population) has an amount of, of about, or of at least $50\times10^6$, $100\times10^6$, $150\times10^6$, $200\times10^6$, $250\times10^6$, $300\times10^6$, $350\times10^6$, $400\times10^6$, $450\times10^6$, $500\times10^6$, $550\times10^6$, $600\times10^6$ CD8+ T cells, e.g., viable CD8+ T cells. In particular embodiments, the input composition (e.g. the CD27 enriched T cell population and/or the pooled CD27 enriched T cell population) has an amount of, of about, or of at least $50\times10^6$, $100\times10^6$, $150\times10^6$, $200\times10^6$, $250\times10^6$, $300\times10^6$, $350\times10^6$, $400\times10^6$, $450\times10^6$, $500\times10^6$, $550\times10^6$, $600\times10^6$, $700\times10^6$, $800\times10^6$, $900\times10^6$, $1,000\times10^6$, $1,100\times10^6$, or $1,200\times10^6$ T cells, such as viable T cells, viable CD3+ T cells, or viable mixed CD4+ and CD8+ T cells. In particular embodiments, the input composition (e.g. the CD27 enriched T cell population and/or the pooled CD27 enriched T cell population) has an amount of, of about, or of at least $50\times10^6$, $100\times10^6$, $150\times10^6$, $200\times10^6$, $250\times10^6$, $300\times10^6$, $350\times10^6$, $400\times10^6$, $450\times10^6$, $500\times10^6$, $550\times10^6$, $600\times10^6$ CD4+ T cells, e.g., viable CD4+ T cells. In certain embodiments, the input composition (e.g. the CD27 enriched T cell population and/or the pooled CD27 enriched T cell population) has an amount of, of about, or of at least $50\times10^6$, $100\times10^6$, $150\times10^6$, $200\times10^6$, $250\times10^6$, $300\times10^6$, $350\times10^6$, $400\times10^6$, $450\times10^6$, $500\times10^6$, $550\times10^6$, $600\times10^6$ CD8+ T cells, e.g., viable CD8+ T cells. In some embodiments, the amount of cells is an amount of viable CD4+ and CD8+ T cells pooled, mixed and/or combined together in the same composition. In such embodiments, the CD4+ and CD8+ T cell are present at a ratio of between 1:3 and 3:1, between 2:1 and 1:2, between 1.5:1 and 1:1.5, between 1.25:1 and 1:1.25, between 1.2:1 and 1:1.2, between 1.1:1 and 1:1.1, or about 1:1 or 1:1 CD4+ T cells to CD8+ T cells. In some embodiments, the amount of cells is an amount of viable CD4+ and CD8+ T cells pooled, mixed and/or combined together at a ratio of about 1:1 or 1:1 CD4+ T cells to CD8+ T cells.

In particular embodiments, the input composition (e.g. the CD57 depleted T cell population and/or the pooled CD57 depleted T cell population) has an amount of between or between about $300\times10^6$ and $600\times10^6$ T cells, e.g., viable CD3+ cells, or mixed viable CD4+ and viable CD8+ cells (e.g., mixed at or at about a 1:1 ratio). In particular embodiments, the input composition (e.g. the CD27 enriched T cell population and/or the pooled CD27 enriched T cell population) has an amount of between or between about $300\times10^6$ and $600\times10^6$ T cells, e.g., viable CD3+ cells, or mixed viable CD4+ and viable CD8+ cells (e.g., mixed at or at about a 1:1 ratio). In some embodiments, the input population has an amount of or of about $300\times10^6$, e.g., viable CD3+ cells, or mixed viable CD4+ and viable CD8+ cells (e.g., mixed at or at about a 1:1 ratio). In some embodiments, the input population has an amount of or of about $400\times10^6$, e.g., viable CD3+ cells or mixed viable CD4+ and viable CD8+ cells (e.g., mixed at or at about a 1:1 ratio). In some embodiments, the input population has an amount of or of about $500\times10^6$, e.g., viable CD3+ cells or mixed viable CD4+ and viable CD8+ cells (e.g., mixed at or at about a 1:1 ratio). In some embodiments, the input population has an amount of or of about $600\times10^6$, e.g., viable CD3+ cells or mixed viable CD4+ and viable CD8+ cells (e.g., mixed at or at about a 1:1 ratio). In some embodiments, the input population has an amount of or of about $700\times10^6$, e.g., viable CD3+ cells or mixed viable CD4+ and viable CD8+ cells (e.g., mixed at or at about a 1:1 ratio). In some embodiments, the input population has an amount of or of about $800\times10^6$, e.g., viable CD3+ cells or mixed viable CD4+ and viable CD8+ cells (e.g., mixed at or at about a 1:1 ratio). In some embodiments, the input population has an amount of or of about $900\times10^6$, e.g., viable CD3+ cells or mixed viable CD4+ and viable CD8+ cells (e.g., mixed at or at about a 1:1 ratio). In some embodiments, the input population has an amount of or of about $100\times10^7$, e.g., viable CD3+ cells or mixed viable CD4+ and viable CD8+ cells (e.g., mixed at or at about a 1:1 ratio). In some embodiments, the input population has an amount of or of about $110\times10^7$, e.g., viable CD3+ cells or mixed viable CD4+ and viable CD8+ cells (e.g., mixed at or at about a 1:1 ratio). In some embodiments, the input population has an amount of or of about $120\times10^7$, e.g., viable CD3+ cells or mixed viable CD4+ and viable CD8+ cells (e.g., mixed at or at about a 1:1 ratio).

In certain embodiments, CD4+ T cells and CD8+ T cells are pooled, mixed, and/or combined such that the input composition (e.g. the CD57 depleted T cell population and/or the pooled CD57 depleted T cell population) has up to or up to about a target number (2n) of T cells, such as viable T cells, viable CD3+ T cells, or viable mixed CD4+ and CD8+ T cells. In certain embodiments, CD4+ T cells and CD8+ T cells are pooled, mixed, and/or combined such that the input composition (e.g. the CD27 enriched T cell population and/or the pooled CD27 enriched T cell population) has up to or up to about a target number (2n) of T cells, such as viable T cells, viable CD3+ T cells, or viable mixed CD4+ and CD8+ T cells. In certain embodiments where a composition comprising enriched CD4+ T cells contains at least n of CD4+ T cells and a composition comprising enriched CD8+ T cells (e.g., derived from the same donor, e.g., from the same aphresis or leukaphresis sample from the donor, as the CD4+ T cell composition) contains at least n of CD8+ T cells, n of CD4+ T cells from the CD4+ T cell composition and n of CD8+ T cells from the CD8+ T cell composition are pooled, mixed, and/or combined (i.e. at 1:1 CD4+ to CD8+ ratio) to generate an input composition containing the target number (2n) of T cells. In certain embodiments where a composition comprising enriched CD4+ T cells contains no more than (e.g., fewer than) n of CD4+ T cells and a composition comprising enriched CD8+ T cells (e.g., derived from the same donor, e.g., from the same aphresis or leukaphresis sample from the donor, as the CD4+ T cell composition) contains no more than (e.g., fewer than) n of CD8+ T cells, all of the cells of the CD4+ T cell composition and all of the cells of the CD8+ T cell composition are pooled, mixed, and/or combined to generate the input composition. In these embodiments, the input composition may contain fewer than the target number (2n) of T cells. In certain embodiments where a composition comprising enriched CD4+ T cells contains fewer than n of CD4+ T cells and a composition comprising enriched CD8+ T cells (e.g., derived from the same donor, e.g., from the same aphresis or leukaphresis sample from the donor, as the CD4+ T cell composition) contains more than n of CD8+ T cells, or vice versa, cells of the CD4+ or CD8+ T cell composition are used to supplement the alternative cell type such that the input composition contains up to the target number (2n) of T cells. In any of the preceding embodiments, the target number 2n can be $300\times10^6$, $350\times10^6$, $400\times10^6$, $450\times10^6$, $500\times10^6$, $550\times10^6$, $600\times10^6$, $700\times10^6$, $800\times10^6$, $900\times10^6$, $1,000\times10^6$, $1,100\times10^6$, or $1,200\times10^6$.

In certain embodiments, $450\times10^6$ CD4+ T cells from a composition comprising enriched CD4+ T cells and $450\times10^6$ CD8+ T cells from a composition comprising enriched CD8+ T cells (e.g., derived from the same donor, e.g., from the same aphresis or leukaphresis sample from the donor, as the CD4+ T cell composition) are pooled, mixed, and/or combined to generate an input composition (e.g. the CD57 depleted T cell population and/or the pooled CD57 depleted T cell population) containing $900\times10^6$ CD4+ and CD8+ T cells. In certain embodiments, $450\times10^6$ CD4+ T cells from a composition comprising enriched CD4+ T cells and $450\times10^6$ CD8+ T cells from a composition comprising enriched CD8+ T cells (e.g., derived from the same donor, e.g., from the same aphresis or leukaphresis sample from the donor, as the CD4+ T cell composition) are pooled, mixed, and/or combined to generate an input composition (e.g. the CD27 enriched T cell population and/or the pooled CD27 enriched T cell population) containing $900\times10^6$ CD4+ and CD8+ T cells. In certain embodiments, when a composition comprising enriched CD4+ T cells contains fewer than $450\times10^6$ CD4+ T cells and a composition comprising enriched CD8+ T cells (e.g., derived from the same donor, e.g., from the same aphresis or leukaphresis sample from the donor, as the CD4+ T cell composition) contains fewer than $450\times10^6$ CD8+ T cells, all of the cells of the CD4+ T cell composition and all of the cells of the CD8+ T cell composition are pooled, mixed, and/or combined to generate the input composition. In certain embodiments, when either of the compositions contains fewer than $450\times10^6$ CD4+ or CD8+ cells while the other composition contains more than $450\times10^6$ CD8+ cells or CD4+ cells, then up to $900\times10^6$ CD4+ T cells and CD8+ T cells are combined to generate an input composition. The total number of CD4+ and CD8+ T cells in the input composition may be lower than $900\times10^6$. In other words, cells of the composition comprising enriched CD4+ T cells may be used to supplement the composition comprising enriched CD8+ T cells, or vice versa, in order to generate an input composition comprising up to the target number (2n) of T cells, e.g., up to $900\times10^6$ T cells to be subjected to stimulation.

Although in the above embodiments, the cell selection, isolation, separation, enrichment, and/or purification processes are discussed in the context of preparing an selected composition (e.g. a pooled CD57 depleted T cell population and/or a CD57 depleted T cell population), it should be understood that the cell selection, isolation, separation, enrichment, and/or purification processes disclosed herein can be used during, prior to, or between any of the subsequent steps (e.g., activation, stimulation, engineering, transduction, transfection, incubation, culturing, harvest, formulation, and/or administering a formulated cell population to a subject), in any suitable combination and/or order. For example, a T cell selection, isolation, separation, enrichment, and/or purification step can be performed between T cell activation/stimulation and T cell transduction. In another example, a T cell selection, isolation, separation, enrichment, and/or purification step can be performed after T cell transduction, but prior to harvesting, prior to collecting, and/or prior to formulating the cells. In a particular example, a T cell selection, isolation, separation, enrichment, and/or purification step can be performed immediately prior to harvesting the cells as a refining or clarification step. In some embodiments, a T cell selection step by chromatography is performed between T cell activation/stimulation and T cell transduction. In some embodiments, a T cell selection step by chromatography is performed after T cell transduction, but prior to harvesting, prior to collecting, and/or prior to formulating the cells. In some embodiments, a T cell selection step by chromatography is performed immediately prior to harvesting the cells. Further, it should be understood that the cell selection, isolation, separation, enrichment, and/or purification processes disclosed herein can be used during, prior to, or between any steps of combining CD57 depleted T cell populations from a plurality of different individual donors to created a pooled CD57 depleted T cell population. It should also be understood that the cell selection, isolation, separation, enrichment, and/or purification processes disclosed herein can be used during, prior to, or between any steps of combining CD27 enriched T cell populations from a plurality of different individual donors to created a pooled CD27 enriched T cell population.

In some embodiments, the selected composition (e.g. the CD57 depleted T cell population and/or the pooled CD57 depleted T cell population) is subjected to one or more dilution and/or wash step, e.g., with a serum-free medium, prior to stimulating the cells, e.g., culturing the cells under stimulating conditions. In some embodiments, the selected composition (e.g. the CD27 enriched T cell population and/or the pooled CD27 enriched T cell population) is subjected to one or more dilution and/or wash step, e.g., with a serum-free medium, prior to stimulating the cells, e.g., culturing the cells under stimulating conditions. In some embodiments, the dilution and/or wash step allows media exchange into a serum-free medium, such as one described in PCT/US2018/064627, which is incorporated herein by reference.

In some embodiments, the serum-free medium comprises a basal medium (e.g. OpTmizer™ T-Cell Expansion Basal Medium (ThermoFisher)), supplemented with one or more supplement. In some embodiments, the one or more supplement is serum-free. In some embodiments, the serum-free medium comprises a basal medium supplemented with one or more additional components for the maintenance, expansion, and/or activation of a cell (e.g., a T cell), such as provided by an additional supplement (e.g. OpTmizer™ T-Cell Expansion Supplement (ThermoFisher)). In some embodiments, the serum-free medium further comprises a serum replacement supplement, for example, an immune cell serum replacement, e.g., ThermoFisher, #A2596101, the CTS™ Immune Cell Serum Replacement, or the immune cell serum replacement described in Smith et al. Clin Transl Immunology. 2015 January; 4(1): e31. In some embodiments, the serum-free medium further comprises a free form of an amino acid such as L-glutamine. In some embodiments, the serum-free medium further comprises a dipeptide form of L-glutamine (e.g., L-alanyl-L-glutamine), such as the dipeptide in Glutamax™ (ThermoFisher). In some embodiments, the serum-free medium further comprises one or more recombinant cytokines, such as recombinant human IL-2, recombinant human IL-7, and/or recombinant human IL-15.

In some embodiments, the selected composition (e.g. the CD57 depleted T cell population and/or the pooled CD57 depleted T cell population) is generated by mixing, combining, and/or pooling a population enriched in CD57−CD8+ T cells generated from a starting sample, e.g. a donor sample, such as PBMCs or a leukaphresis sample, with a population enriched in CD57−CD4+ T cells generated from the starting sample, e.g. the donor sample. In some embodiments, the population enriched in CD57−CD4+ T cells is generated from the CD8-negative fraction generated during the process of generating the population enriched in CD8+ T cells from the starting sample (e.g. the donor sample). In particular embodiments, the selected composition (e.g. the CD57 depleted T cell population and/or the pooled CD57 depleted T cell population) has a ratio of or of about 1:1 CD4+ T cells to CD8+ T cells, and is subjected to one or more wash step, e.g., with a serum-free medium described in PCT/US2018/064627, prior to stimulating the cells, e.g., culturing the cells under stimulating conditions. In some embodiments, the one or more wash step allows media exchange from a PBS/EDTA buffer containing albumin into the serum-free medium, which is also used in cell stimulation.

In some embodiments, the selected composition (e.g. the CD27 enriched T cell population and/or the pooled CD27 enriched T cell population) is generated by mixing, combining, and/or pooling a population enriched in CD27+ CD8+ T cells generated from a starting sample, e.g. a donor sample, such as PBMCs or a leukaphresis sample, with a population enriched in CD27+ CD4+ T cells generated from the starting sample, e.g. the donor sample. In some embodiments, the population enriched in CD27+ CD4+ T cells is generated from the CD8-negative fraction generated during the process of generating the population enriched in CD8+ T cells from the starting sample (e.g. the donor sample). In particular embodiments, the selected composition (e.g. the CD27 enriched T cell population and/or the pooled CD27 enriched T cell population) has a ratio of or of about 1:1 CD4+ T cells to CD8+ T cells, and is subjected to one or more wash step, e.g., with a serum-free medium described in PCT/US2018/064627, prior to stimulating the cells, e.g., culturing the cells under stimulating conditions. In some embodiments, the one or more wash step allows media exchange from a PBS/EDTA buffer containing albumin into the serum-free medium, which is also used in cell stimulation.

E. Genetic Engineering of Populations of Enriched CD57− Cells

Provided herein are engineered T cell compositions from a plurality of different donors, and methods of producing the same. In some embodiments, provided herein is a method of preparing a T cell composition from a donor pool that is or includes obtaining a plurality of engineering T cell compositions from a plurality of different donors, each engineered T cell composition containing T cells enriched for T cells surface negative for CD57 (CD57−) from a donor sample from an individual donor of the plurality of different donors, wherein the T cells include T cells genetically engineered with a recombinant receptor; and combining the plurality of engineered T cell compositions to produce a donor pooled engineered T cell composition. In some embodiments, provided herein is a method of preparing a T cell composition from a donor pool that is or includes obtaining a plurality of engineering T cell compositions from a plurality of different donors, each engineered T cell composition containing T cells enriched for T cells surface positive for CD27 (CD27+) from a donor sample from an individual donor of the plurality of different donors, wherein the T cells include T cells genetically engineered with a recombinant receptor; and combining the plurality of engineered T cell compositions to produce a donor pooled engineered T cell composition. In some embodiments, the T cells of the genetically engineered composition are engineered with the same recombinant receptor. In some embodiments, each of the T cells expressing a recombinant receptor in the engineered T cell composition express the same recombinant receptor.

In some embodiments, an engineered T cell composition is generated from an individual donor. In some embodiments, an engineered T cell composition generated from an individual donor is combined with one or more other engineered T cell compositions generated from an individual donor, to comprise a pooled engineered T cell composition from a plurality of different donors. In some embodiments, an engineered T cell composition is generated from a plurality of different donors. In some embodiments, donor samples from a plurality of different donors are combined to generate a pooled donor sample, and the pooled donor sample is engineered to generate an engineered T cell composition from a plurality of different donors.

Among provided methods are methods for genetically engineering (e.g. knocking in and/or knocking out) one or more populations of T cells, e.g. a CD57 depleted T cell population and/or a pooled CD57 depleted T cell population. Also among provided methods are methods for genetically engineering (e.g. knocking in and/or knocking out) one or more populations of T cells, e.g. a CD27 enriched T cell population and/or a pooled CD27 enriched T cell population. The genetic engineering processes disclosed herein can be used during, prior to, after, or between any steps of combining cell populations from a plurality of different individual donors to create a pooled T cell composition. In some aspects, the genetic engineering is performed prior to any steps of combining cell compositions from a plurality of individual donors. For example, the genetic engineering may be performed on a cell population (e.g. a CD57 depleted T cell population) from an individual donor, and the engineered cell composition from the individual donor may be combined thereafter with an engineered cell composition from one or more other individual donors, to produce a pooled engineered composition. In some aspects, the genetic engineering is performed subsequent to combining cell compositions from a plurality of individual donors. For example, the genetic engineering may be performed on a cell population from a plurality of different donors (e.g. a pooled CD57 depleted T cell population), to produce a pooled engineered composition.

In some embodiments, provided herein are methods of genetically engineering a cell population. In some embodiments, the cell population that is genetically engineered is a CD57 depleted T cell population or a pooled CD57 depleted T cell population. In some embodiments, the cell population that is genetically engineered is a CD27 enriched T cell population or a pooled CD27 enriched T cell population. In some embodiments, the genetic engineering includes introducing a heterologous polynucleotide encoding a recombinant receptor in a population of cells. In some aspects, the genetic engineering is or includes disrupting (e.g. knocking out) one or more molecules (e.g. a genetic locus or a portion thereof) in a population of cells. In some embodiments, the genetic engineering includes introducing a heterologous polynucleotide encoding a recombinant receptor in a population of cells and disrupting (e.g. knocking out) one or more molecules (e.g. a genetic locus or a portion thereof). In some embodiments, geneting engineering is or includes introducing the heterologous polynucleotide by targeted insertion (e.g. knocking in) into a knocked out genetic locus or a portion thereof. In some aspects, the introducing of the heterologous polynucleotide is performed concurrently with the disrupting (e.g. knocking out). In some aspects, the introducing of the heterologous polynucleotide and the disrupted are performed sequentially, in either order. In some aspects, the heterologous polynucleotide encodes a recombinant receptor that is a chimeric antigen receptor (CAR). In some embodiments, the CAR is knocked into a disrupted molecule (e.g. a genetic locus or portion thereof). In some aspects, the chimeric antigen receptor (CAR) is knocked into the TRAC locus or a portion thereof.

In some embodiments, the introducing is performed by any method for generic engineering provided herein, e.g., in Section II.D. In some aspects, the provided methods can include incubating transduced T cells under conditions to permit integration of the viral vector into the genome of the cells.

In some embodiments, the populations of T cells, e.g. the CD57 depleted T cell population and/or the pooled CD57 depleted T cell population, are stimulated or activated, such as by stimulating the cells of the population under conditions to activate the T cells of population, such as any stimulating condition described herein, e.g., in Section III.E. In some embodiments, the CD57 depleted T cell population and/or the pooled CD57 depleted T cell population is stimulated or activated prior to the genetic engineering.

In some embodiments, the populations of T cells, e.g. the CD27 enriched T cell population and/or the pooled CD27 enriched T cell population, are stimulated or activated, such as by stimulating the cells of the population under conditions to activate the T cells of population, such as any stimulating condition described herein, e.g., in Section III.E. In some embodiments, the CD27 enriched T cell population and/or the pooled CD27 enriched T cell population is stimulated or activated prior to the genetic engineering.

The provided methods can include methods in which the engineered cells are not further cultivated for the purpose of expanding the population of cells. For example, in some aspects, the cells that are harvested have not undergone any incubation or cultivation where the amount of total viable cells is increased at the end of the incubation or cultivation as compared to the number of total viable cells at the beginning of the incubation or cultivation. In some embodiments, the cells that are harvested have not undergone any incubation or cultivation step explicitly for the purpose of increasing (e.g., expanding) the total number of viable cells at the end of the incubation or cultivation process compared to the beginning of said incubation or cultivation process. In some embodiments, the cells are incubated or cultivated under conditions that may result in expansion, but the incubating or cultivating conditions are not carried out for purposes of expanding the cell population. In some embodiments, the cells that are harvested may have undergone expansion despite having been manufactured in a process that does not include an expansion step. In some embodiments, a manufacturing process that does not include an expansion step is referred to as a non-expanded or minimally expanded process. A "non-expanded" process may also be referred to as a "minimally expanded" process. In some embodiments, a non-expanded or minimally expanded process may result in cells having undergone expansion despite the process not including a step for expansion. In some embodiments, the cells that are harvested may have undergone an incubation or cultivating step that includes a media composition designed to reduce, suppress, minimize, or eliminate expansion of a cell population as a whole. In some embodiments, the collected, harvested, or formulated cells have not previously undergone an incubation or cultivation that was performed in a bioreactor, or under conditions where the cells were rocked, rotated, shaken, or perfused for all or a portion of the incubation or cultivation.

In certain embodiments, the engineered T cell compositions are cultivated, e.g., cultivated under conditions that promote or allow for T cell division, growth, or expansion, such as for a fixed amount of time or until a threshold limit for expansion is achieved. In some aspects the cultivation is performed by any method described herein, such as in Section II.F.

In particular embodiments, provided herein are methods for generating a genetically engineered T cell composition from one or more initial populations of CD57− T cells (e.g. the CD57 depleted T cell population and/or the pooled CD57 depleted T cell population). In particular embodiments, provided herein are methods for generating a genetically engineered T cell composition from one or more initial populations of CD27+ T cells (e.g. the CD27 enriched T cell population and/or the pooled CD27 enriched T cell population). In some embodiments, the initial population is derived from an individual donor. In some embodiments, the initial population from an individual donor is combined with an initial population from at least one other individual donor to produce a pooled initial population from a plurality of different donors. In some embodiments, the initial population is derived from a plurality of different donors. In some embodiments, the CD57 depleted T cell population and/or the pooled CD57 depleted T cell population is stimulated under conditions that activate the T cells of the population, thereby generating a stimulated population. In some embodiments, the CD27 enriched T cell population and/or the pooled CD27 enriched T cell population is stimulated under conditions that activate the T cells of the population, thereby generating a stimulated population. In some embodiments, the stimulated population is derived from an individual donor. In some embodiments, a stimulated population from an individual donor is combined with a stimulated composition from one or more other individual donors to produce a stimulated composition from a plurality of donors. In some embodiments, the stimulated population is derived from a plurality of different donors. In certain embodiments, the stimulating, e.g., culturing the cells under stimulating conditions, is performed for a set or fixed amount of time, such as an amount of time under 2 days or for an amount of time between 18 hours and 30 hours. In some aspects, the stimulating with the stimulatory reagent is carried out for at or about 20 hours±4 hours.

In certain embodiments, a heterologous polynucleotide is introduced to cells of the stimulated population, thereby generating a transformed population. In particular embodiments, the cells are incubated either during or after genetically engineering the cells, for example, for an amount of time sufficient to allow for integration of a heterologous or recombinant polynucleotide encoding a recombinant protein or to allow for the expression of the recombinant protein. In certain embodiments, the cells are incubated for a set or fixed amount of time, such as an amount of time greater than 18 hours or less than 4 days, e.g., 72 hours±6 hours. In any of the provided embodiments, the introducing can be carried out on cells after they have been stimulated with the stimulatory reagent. In some embodiments, the engineering step is started or initiated within a set amount of time from when the stimulating is started or initiated, such as within 30 hours from when the stimulatory reagent is added, cultured, or contacted to the cells. In particular embodiments, the engineering step is started or initiated between 18 hours and 30 hours, such as 20 hours±4 hours, after the stimulatory reagent is added, cultured, or contacted to the cells.

In certain embodiments, the transformed population is then expanded, such as for a set amount of time or until a threshold expansion is achieved, thereby resulting in an expanded population. In some embodiments, the transformed population is derived from an individual donor. In some embodiments, a transformed population from an individual donor is combined with a transformed population from one or more other individual donors to produce a transformed population from a plurality of donors. In some embodiments, the transformed population is derived from a plurality of different donors. In particular embodiments, the transformed population or the expanded population is harvested or collected, and optionally formulated, such as for administration to a subject or for cryopreservation. In some embodiments, the population is or contains CD57− CD4+ T cells and CD57−CD8+ T cells. In some embodiments, the population is or contains CD57− CD3+ T cells. In some embodiments, the population is or contains CD27+ CD4+ T cells and CD27+ CD8+ T cells. In some embodiments, the population is or contains CD27+ CD3+ T cells.

In particular embodiments, the populations of enriched T cells (e.g. the CD57 depleted T cell population and/or the pooled CD57 depleted T cell population) may be collected, formulated for cryoprotection, frozen (e.g., cryoprotected), and/or stored below 0° C., below −20° C., or at or below −70 C or −80° C. prior to, during, or after any stage or step of the process for generating engineered compositions of enriched T cells expressing recombinant receptors. In some embodiments, the populations of enriched T cells are the CD27 enriched T cell population and/or the pooled CD27 enriched T cell population. In some embodiments, the cells may be stored for an amount of time under 1, 2, 3, 4, 5, 6, 7, 8, 9, or 10 days, or an amount of time under 1, 2, 3, 4, 5, 6, 7, 8 weeks, or for an amount of time at least 1, 2, 3, 4, 5, 6, 7, or 8 weeks, or for more than 8 weeks. After storage, the populations of enriched T cells may be thawed and the processing may be resumed from the same point in the process. In some embodiments, initial populations of enriched T cells (e.g. the CD57 depleted T cell population and/or the pooled CD57 depleted T cell population) are cryoprotected and stored prior to further processing, e.g., incubation under stimulating conditions. In some embodiments, the initial population of enriched T cells is the CD27 enriched T cell population and/or the pooled CD27 enriched T cell population. In particular embodiments, cultivated and/or formulated compositions of engineered T cells are cryoprotected and stored prior to being administered to as subject, e.g., as an autologous cell therapy.

In certain embodiments, the methods provided herein are used in connection with a process whereby engineered cells are generated by a process that includes steps for stimulating the cells and then introducing (e.g. knocking in) a polynucleotide encoding a recombinant receptor, e.g., a CAR, into the cells, such as at a knocked out genetic locus or portion thereof. In some embodiments, the genetic engineering further includes disrupting (e.g. knocking out) one or more genetic loci or a portion thereof. In particular embodiments, the stimulating is performed for between 18 and 30 hours, such as for about 24 hours, and the introduction of the polynucleotide is subsequently performed. In certain embodiments, the cells are harvested or collected, such as to be formulated for cryopreservation or administrated to a subject, within 3 days after the introduction of the polynucleotide is initiated. In some embodiments, the harvested or collected cells are derived from an individual donor. In some embodiments, the harvested or collected cells from an individual donor are combined with the harvested or collected cells from one or more other individual donors to produce harvested or collected cells from a plurality of different donors. In some embodiments, the harvested or collected cells are derived from a plurality of different donors. In various embodiments, the cells are harvested or collected, such as to be formulated for cryopreservation or administered to a subject, within 4 days after the incubation under stimulatory conditions is initiated. In some embodiments, the formulated population is derived from an individual donor. In some embodiments, a formulated population from an individual donor is combined with a formulated population from one or more other individual donors to produce a formulated population from a plurality of different donors. In some embodiments, the formulated population is derived from a plurality of different donors.

In certain embodiments, provided herein are methods for generating a genetically engineered T cell composition from two initial CD57 depleted T cell populations and/or pooled CD57 depleted T cell populations. In some embodiments, the two populations of enriched CD57− T cells are separately incubated under stimulating conditions, thereby generating two separate stimulated populations. In certain embodiments, provided herein are methods for generating a genetically engineered T cell composition from two initial CD27 enriched T cell populations and/or pooled CD27 enriched T cell populations. In some embodiments, the two populations of enriched CD27+ T cells are separately incubated under stimulating conditions, thereby generating two separate stimulated populations. In certain embodiments, a heterologous polynucleotide is introduced to cells of the two separate stimulated populations, thereby generating two separate transformed populations. In certain embodiments, the two separate transformed populations are then expanded, such as for a set amount of time or until a threshold expansion is achieved, thereby resulting in two separate expanded populations. In particular embodiments, the two separate transformed populations or the two separate expanded populations are harvested or collected, and optionally formulated, such as for administration to a subject or for cryopreservation. In particular embodiments, the two separate populations originate or are derived from the same biological sample or different biological samples from the same individual donor. In particular embodiments, the two separate populations originate or are derived from different biological samples from different donors. In some embodiments, the two separate populations are or contain a population of enriched CD57− CD4+ T cells and a separate population of CD57− CD8+ T cells. In some embodiments, the two separate populations are or contain a population of enriched CD57− CD4+ T cells and a separate population of CD27+ CD8+ T cells.

Also provided are methods for identifying a population of cells capable of expanding or proliferating, such as during an incubation or cultivation under conditions that promote T cell proliferation or expansion, such as any such conditions described herein, e.g., Section II.F. In some embodiments, such methods are or include measuring the frequency of CD57+ cells in the population, wherein if the frequency of CD57+ cells are below a threshold frequency, the population is capable of expanding. In some embodiments, such methods are or include measuring the frequency of CD27− cells in the population, wherein if the frequency of CD27− cells are below a threshold frequency, the population is capable of expanding. In some embodiments, the threshold frequency is less than 30%, 25%, 20%, 15%, 10%, 5%, or 1%. In some embodiments, the threshold is or is about 20%. In some embodiments, a population that is capable of expanding expands at least 2-fold, 3-fold, 4-fold, or 5-fold within 10, 11, 12, 13, or 14 days during a cultivation under conditions that promote proliferation or expansion. In certain embodiments, a population that is capable of expanding expands at least 4-fold within 11 days during a cultivation, e.g., a cultivation provided herein such as in Section II.F.

In some embodiments, the method is or includes measuring a value of a trait associated with CD57 expression of a population of T cells, wherein the population of T cells is capable of expansion cell therapy if the value of the trait is less than a threshold value of the trait. In some embodiments, the trait is a level or amount of a polypeptide encoded by the CD57 present in the total T cells, CD4+ T cells, or CD8+ T cells of the dose. In certain embodiments, the trait is a level or amount of a polypeptide encoded by the CD57 present on the surface of the total T cells, CD4+ T cells, or CD8+ T cells of the dose, in particular embodiments, the trait is a frequency, percentage, or amount of T cells, CD4+ T cells, or CD8+ T cells present positive for expression of the CD57. In some embodiments, the trait is a level or amount of mRNA of the second gene present in the T cells. In particular embodiments a level or amount of accessibility of the CD57.

In certain embodiments, the threshold value is at, at about, or within 25%, within 20%, within 15%, within 10%, or within 5% below a mean or median measurement of the trait associated with CD57 expression, and/or is below one standard deviation less than the mean or median measurement, in a plurality of reference T cell populations. In certain embodiments, the threshold value is below a lowest measurement of the trait associated with CD57 expression, optionally within 50%, within 25%, within 20%, within 15%, within 10%, or within 5% below the lowest measurement, in a population from among a plurality of reference T cell populations. In some embodiments, the threshold is below a mean or median measurement of the trait associated with CD57 expression calculated from among more than 65%, 75%, 80%, 85% of samples from a plurality of reference T cell compositions.

In some embodiments, the method is or includes measuring a value of a trait associated with CD27 expression of a population of T cells, wherein the population of T cells is capable of expansion cell therapy if the value of the trait is greater than a threshold value of the trait. In some embodiments, the trait is a level or amount of a polypeptide encoded by the CD27 present in the total T cells, CD4+ T cells, or CD8+ T cells of the dose. In certain embodiments, the trait is a level or amount of a polypeptide encoded by the CD27 present on the surface of the total T cells, CD4+ T cells, or CD8+ T cells of the dose, in particular embodiments, the trait is a frequency, percentage, or amount of T cells, CD4+ T cells, or CD8+ T cells present positive for expression of the CD27. In some embodiments, the trait is a level or amount of mRNA of the second gene present in the T cells. In particular embodiments a level or amount of accessibility of the CD27.

In certain embodiments, the threshold value is at, at about, or within 25%, within 20%, within 15%, within 10%, or within 5% above a mean or median measurement of the trait associated with CD27 expression, and/or is above one standard deviation more than the mean or median measurement, in a plurality of reference T cell populations. In certain embodiments, the threshold value is above a lowest measurement of the trait associated with CD27 expression, optionally within 50%, within 25%, within 20%, within 15%, within 10%, or within 5% above the highest measurement, in a population from among a plurality of reference T cell populations. In some embodiments, the threshold is above a mean or median measurement of the trait associated with CD27 expression calculated from among more than 65%, 75%, 80%, 85% of samples from a plurality of reference T cell compositions.

In particular embodiments, the plurality of reference T cell populations are a plurality of populations that did not expand when cultivated under conditions that promote proliferation or expansion of T cells, optionally wherein the cells did not expand by at least 3-fold, 4-fold, or 5 fold, within 10, 11, 12, 13, or 14 days of cultivation, e.g., a cultivation as described herein, such as in Section III.C. In some embodiments, the reference T cell populations did not expand by at least 4-fold within 11 days of cultivation.

In some embodiments, the harvesting is performed at or after the time in which the engineered T cell composition or the expanded population of T cells include a threshold number of T cells, viable T cells, engineered T cells or viable engineered T cells, or a threshold concentration of T cells, viable T cells, engineered T cells or viable engineered T cells. In some embodiments, the threshold number or concentration of T cells, viable T cells, engineered T cells or viable engineered T cells is reached within at or about 4, 5, 6 or 7 days after the initiation of stimulation.

In some embodiments, among a plurality of compositions of engineered T cells or populations of expanded T cells, the threshold number or concentration of T cells, viable T cells, engineered T cells or viable engineered T cells is reached within at or about 5 or 6 days after the initiation of stimulation in at least at or about or at least at or about 70%, 80%, 90% or 95% of the plurality. In some embodiments, the threshold number or concentration of T cells, viable T cells, engineered T cells or viable engineered T cells is reached within at or about 2, 3, 4 or 5 population doublings after the initiation of stimulation.

In some embodiments, the method also includes measuring a value of a trait associated with the expression of a second gene, such that the composition, such as the engineered composition, is capable of expanding if the value of the trait associated with CD57 expression is less than the threshold value and if a trait associated with expression of the second gene is greater than a second threshold. In some embodiments, the second gene is a marker of a naïve-like cells, such as but not limited to CD25, CD27, CD28, CCR7, or CD45RA. In some embodiments, the second gene encodes CD27.

In some embodiments, the method also includes measuring a value of a trait associated with the expression of a second gene, such that the composition, such as the engineered composition, is capable of expanding if the value of the trait associated with CD27 expression is greater than the threshold value and if a trait associated with expression of the second gene is greater than a second threshold. In some embodiments, the second gene is a marker of a naïve-like cells, such as but not limited to CD25, CD28, CCR7, or CD45RA.

1. Genetic Engineering of a Recombinant Receptor

Provided herein are methods of preparing engineered T cell compositions enriched for CD57− T cells. Also provided herein are engineered T cell compositions enriched for CD57− T cells produced by the methods. In some embodiments, the engineered T cell compositions are produced by genetically engineering a CD57− enriched population, (e.g. a CD57 depleted T cell population and/or a pooled CD57 depleted T cell population). In some embodiments, a CD57 depleted T cell population from an individual donor is genetically engineered to produce an engineered T cell composition. In some embodiments, a CD57 depleted T cell population from an individual donor is genetically engineered and then combined with a genetically engineered T cell composition of one or more other individual donors to produce a donor pooled engineered T cell composition from a plurality of donors. In some embodiments, a pooled CD57 depleted T cell population from a plurality of donors is genetically engineered to produce a donor pooled engineered T cell composition from a plurality of donors.

In some embodiments, the genetic engineering comprises introducing a heterologous nucleic acid encoding the recombinant receptor into the CD57 depleted cell population, thereby generating the engineered T cell composition. In some embodiments, the genetic engineering comprises introducing a heterologous nucleic acid encoding the recombinant receptor into the pooled CD57 depleted cell population, thereby generating the donor pooled engineered T cell composition.

Also provided herein are methods of preparing engineered T cell compositions enriched for CD27+ T cells. Also provided herein are engineered T cell compositions enriched for CD27+ T cells produced by the methods. In some embodiments, the engineered T cell compositions are produced by genetically engineering a CD27+ enriched population, (e.g. a CD27 enriched T cell population and/or a pooled CD27 enriched T cell population). In some embodiments, a CD27 enriched T cell population from an individual donor is genetically engineered to produce an engineered T cell composition. In some embodiments, a CD27 enriched T cell population from an individual donor is genetically engineered and then combined with a genetically engineered T cell composition of one or more other individual donors to produce a donor pooled engineered T cell composition from a plurality of donors. In some embodiments, a pooled CD27 enriched T cell population from a plurality of donors is genetically engineered to produce a donor pooled engineered T cell composition from a plurality of donors.

In some embodiments, the genetic engineering comprises introducing a heterologous nucleic acid encoding the recombinant receptor into the CD27 enriched cell population, thereby generating the engineered T cell composition. In some embodiments, the genetic engineering comprises introducing a heterologous nucleic acid encoding the recombinant receptor into the pooled CD27 enriched cell population, thereby generating the donor pooled engineered T cell composition.

Introduction of the polynucleotides, e.g., heterologous or recombinant polynucleotides, encoding the recombinant receptor into a cell may be carried out using any of a number of known vectors. Such vectors include viral, including adeno-associated, lentiviral and gammaretroviral systems. Exemplary methods include those for transfer of heterologous polynucleotides encoding the receptors, including via viral, e.g., adeno-associated, retroviral or lentiviral, transduction. In some embodiments, a population of stimulated cells is genetically engineered, such as to introduce a heterologous or recombinant polynucleotide encoding a recombinant receptor, thereby generating a population of transformed cells (also referred to herein as a transformed population of cells).

In particular embodiments, the cells are genetically engineered, transformed, or transduced after the cells have been stimulated, activated, and/or incubated under stimulating conditions, such as by any of the methods provided herein, e.g., in Section III.E. In some embodiments, the CD57 depleted T cell population and/or the pooled CD57 depleted T cell population is stimulated under conditions to activate the T cells of the population prior to the genetic engineering. In some embodiments, the CD57 depleted T cell population is stimulated under conditions to activate the T cells of the population prior to the genetic engineering. In some embodiments, the pooled CD57 depleted T cell population is stimulated under conditions to activate the T cells of the population prior to the genetic engineering. In particular embodiments, the one or more stimulated populations have been previously enriched for CD57− T cells. In some embodiments, the CD27 enriched T cell population and/or the pooled CD27 enriched T cell population is stimulated under conditions to activate the T cells of the population prior to the genetic engineering. In some embodiments, the CD27 enriched T cell population is stimulated under conditions to activate the T cells of the population prior to the genetic engineering. In some embodiments, the pooled CD27 enriched T cell population is stimulated under conditions to activate the T cells of the population prior to the genetic engineering. In particular embodiments, the one or more stimulated populations have been previously enriched for CD27+ T cells. In particular embodiments, the one or more stimulated populations have been previously enriched for one or more of CD3+, CD4+, and/or CD8+ T cells.

In certain embodiments, methods for genetic engineering are carried out by contacting or introducing one or more cells of a population (e.g. the CD57 depleted T cell population and/or the pooled CD57 depleted T cell population) with a polynucleotide encoding a recombinant protein, e.g. a recombinant receptor. In certain embodiments, the population is the CD27 enriched T cell population and/or the pooled CD27 enriched T cell population. In certain embodiments, the nucleic acid molecule or polynucleotide is heterologous to the cells. In particular embodiments, the heterologous polynucleotide is not native to the cells. In certain embodiments, the heterologous polynucleotide is not native to any vector, e.g., viral vector, from which it is delivered. In certain embodiments, the heterologous heterologous polynucleotide encodes a protein, e.g., a recombinant protein, that is not natively expressed by the cell. In particular embodiments, the heterologous nucleic polynucleotide is or contains a nucleic acid sequence that is not found in the cell prior to the introduction.

In some embodiments, the cells, e.g., stimulated cells, are engineered, e.g., transduced or in the presence of a transduction adjuvant. Exemplary transduction adjuvants include, but are not limited to, polycations, fibronectin or fibronectin-derived fragments or variants, and RetroNectin. In certain embodiments, the cells are engineered in the presence of polycations, fibronectin or fibronectin-derived fragments or variants, and/or RetroNectin. In particular embodiments, the cells are engineered in the presence of a polycation that is polybrene, DEAE-dextran, protamine sulfate, poly-L-lysine, or a cationic liposome. In particular embodiments, the cells are engineered in the presence of protamine sulfate.

In some embodiments, the genetic engineering, e.g., transduction, is carried out in serum free media. In some embodiments, the serum free media is a defined or well-defined cell culture media. In certain embodiments, the serum free media is a controlled culture media that has been processed, e.g., filtered to remove inhibitors and/or growth factors. In some embodiments, the serum free media contains proteins. In certain embodiments, the serum-free media may contain serum albumin, hydrolysates, growth factors, hormones, carrier proteins, and/or attachment factors.

In particular embodiments, the cells are engineered in the presence of one or more cytokines. In certain embodiments, the one or more cytokines are recombinant cytokines. In particular embodiments, the one or more cytokines are human recombinant cytokines. In certain embodiments, the one or more cytokines bind to and/or are capable of binding to receptors that are expressed by and/or are endogenous to T cells. In particular embodiments, the one or more cytokines is or includes a member of the 4-alpha-helix bundle family of cytokines. In some embodiments, members of the 4-alpha-helix bundle family of cytokines include, but are not limited to, interleukin-2 (IL-2), interleukin-4 (IL-4), interleukin-7 (IL-7), interleukin-9 (IL-9), interleukin 12 (IL-12), interleukin 15 (IL-15), granulocyte colony-stimulating factor (G-CSF), and granulocyte-macrophage colony-stimulating factor (GM-CSF). In some embodiments, the one or more cytokines is or includes IL-15. In particular embodiments, the one or more cytokines is or includes IL-7. In particular embodiments, the one or more cytokines is or includes recombinant IL-2.

In some embodiments, the cells are genetically engineered, transformed, or transduced in the presence of the same or similar media as was present during the stimulation. In some embodiments, the cells are genetically engineered, transformed, or transduced in the presence of the same or similar media as was present during the genetic disrupting. In certain embodiments, the cells are genetically disrupted, engineered, transformed, or transduced, in media having the same cytokines at the same concentrations as the media present during stimulation.

In some embodiments, the cells are genetically engineered, transformed, or transduced in the presence of the same or similar media as was present during the stimulation. In some embodiments, the cells are genetically engineered, transformed, or transduced in media having the same cytokines as the media present during stimulation. In certain embodiments, the cells are genetically engineered, transformed, or transduced, in media having the same cytokines at the same concentrations as the media present during stimulation.

a. Targeted Integration (e.g. Knocking In)

In some of the embodiments provided herein, a heterologous polynucleotide is introduced into the cells of CD57− enriched population (e.g. a CD57 depleted T cell population and/or a pooled CD57 depleted T cell population). In some of the embodiments provided herein, a heterologous polynucleotide is introduced into the cells of CD27+ enriched population (e.g. a CD27 enriched T cell population and/or a pooled CD27 enriched T cell population). In some embodiments, the heterologous polynucleotide encodes a rebominant receptor. In some embodiments the heterologous polynucleotide is introduced by targeted insertion (e.g. knocking in). In some embodiments, the heterologous polynucleotide is inserted (e.g. knocked in) into a genetic locus or a portion thereof, such as a disrupted (e.g. knocked out) genetic locus.

Homology-directed repair (HDR) can be utilized for genetic engineering, e.g. knocking in, of cells. In some embodiments, the cells are a CD57 depleted T cell population and/or a pooled CD57 depleted T cell population. In some embodiments, the cells are a CD27 enriched T cell population and/or a pooled CD27 enriched T cell population. In some embodiments, genetic engineering (e.g. knocking in) comprises targeted integration of a specific portion of the template polynucleotide containing a transgene, e.g., nucleic acid sequence encoding a recombinant receptor, at a particular location in the genome, e.g., the TRAC and/or β2M locus. In some embodiments, the presence of a genetic disruption (e.g., a DNA break) and a template polynucleotide containing one or more homology arms (e.g., containing nucleic acid sequences homologous sequences surrounding the genetic disruption) can induce or direct HDR, with homologous sequences acting as a template for DNA repair. Based on homology between the endogenous gene sequence surrounding the genetic disruption and the 5' and/or 3' homology arms included in the template polynucleotide, cellular DNA repair machinery can use the template polynucleotide to repair the DNA break and resynthesize genetic information at the site of the genetic disruption, thereby effectively inserting or integrating the transgene sequences in the template polynucleotide at or near the site of the genetic disruption. In some embodiments, the genetic disruption, e.g., at the TRAC and/or β2M locus, can be generated by any of the methods for generating a targeted genetic disruption described herein.

Also provided are polynucleotides, e.g., template polynucleotides described herein. In some embodiments, the provided polynucleotides can be employed in the methods described herein, e.g., involving HDR, to target transgene sequences encoding a portion of a recombinant receptor, e.g., recombinant TCR, at the endogenous TRAC and/or β2M locus. In some embodiments, the provided polynucleotides can be employed in the methods described herein, e.g., involving HDR, to target transgene sequences encoding a portion of a recombinant receptor, e.g., recombinant TCR, at the endogenous TRAC locus.

In some embodiments, the template polynucleotide is or comprises a polynucleotide containing a transgene (exogenous or heterologous nucleic acids sequences) encoding a recombinant receptor or a portion thereof (e.g., one or more chain(s), region(s) or domain(s) of the recombinant receptor), and homology sequences (e.g., homology arms) that are homologous to sequences at or near the endogenous genomic site, e.g., at the endogenous TRAC and/or β2M locus. In some aspects, the template polynucleotide is introduced as a linear DNA fragment or comprised in a vector. In some aspects, the step for inducing genetic disruption and the step for targeted integration (e.g., by introduction of the template polynucleotide) are performed simultaneously or sequentially.

(i) Homology-Directed Repair (HDR)

In some embodiments, homology-directed repair (HDR) can be utilized for targeted integration or insertion of one or more nucleic acid sequences, e.g., transgene sequences, at one or more target site(s) in the genome, e.g., the TRAC and/or β2M locus. In some embodiments, homology-directed repair (HDR) can be utilized for targeted integration or insertion of one or more nucleic acid sequences, e.g., transgene sequences, at one or more target site(s) in the genome, e.g., the TRAC locus. In some embodiments, the nuclease-induced HDR can be used to alter a target sequence, integrate a transgene at a particular target location, and/or to edit or repair a mutation in a particular target gene.

Alteration of nucleic acid sequences at the target site can occur by HDR with an exogenously provided template polynucleotide (also referred to as donor polynucleotide or template sequence). For example, the template polynucleotide provides for alteration of the target sequence, such as insertion of the transgene contained within the template polynucleotide. In some embodiments, a plasmid or a vector can be used as a template for homologous recombination. In some embodiments, a linear DNA fragment can be used as a template for homologous recombination. In some embodiments, a single stranded template polynucleotide can be used as a template for alteration of the target sequence by alternate methods of homology directed repair (e.g., single strand annealing) between the target sequence and the template polynucleotide. Template polynucleotide-effected alteration of a target sequence depends on cleavage by a nuclease, e.g., a targeted nuclease such as CRISPR/Cas9. Cleavage by the nuclease can comprise a double strand break or two single strand breaks.

In some embodiments, "recombination" refers to a process of exchange of genetic information between two polynucleotides. In some embodiments, "homologous recombination (HR)" refers to the specialized form of such exchange that takes place, for example, during repair of double-strand breaks in cells via homology-directed repair mechanisms. This process requires nucleotide sequence homology, uses a template polynucleotide to template repair of a target DNA (i.e., the one that experienced the double-strand break, e.g., target site in the endogenous gene), and is variously known as "non-crossover gene conversion" or "short tract gene conversion," because it leads to the transfer of genetic information from the template polynucleotide to the target. In some embodiments, such transfer can involve mismatch correction of heteroduplex DNA that forms between the broken target and the template polynucleotide, and/or "synthesis-dependent strand annealing," in which the template polynucleotide is used to resynthesize genetic information that will become part of the target, and/or related processes. Such specialized HR often results in an alteration of the sequence of the target molecule such that part or all of the sequence of the template polynucleotide is incorporated into the target polynucleotide.

In some embodiments, a template polynucleotide, e.g., polynucleotide containing transgene, is integrated into the genome of a cell via homology-independent mechanisms. The methods comprise creating a double-stranded break (DSB) in the genome of a cell and cleaving the template polynucleotide molecule using a nuclease, such that the template polynucleotide is integrated at the site of the DSB. In some embodiments, the template polynucleotide is integrated via non-homology dependent methods (e.g., NHEJ). Upon in vivo cleavage the template polynucleotides can be integrated in a targeted manner into the genome of a cell at the location of a DSB. The template polynucleotide can include one or more of the same target sites for one or more of the nucleases used to create the DSB. Thus, the template polynucleotide may be cleaved by one or more of the same nucleases used to cleave the endogenous gene into which integration is desired. In some embodiments, the template polynucleotide includes different nuclease target sites from the nucleases used to induce the DSB. As described herein, the genetic disruption of the target site or target position can be created by any mechanisms, such as ZFNs, TALENs, CRISPR/Cas9 system, or TtAgo nucleases.

In some embodiments, DNA repair mechanisms can be induced by a nuclease after (1) a single double-strand break, (2) two single strand breaks, (3) two double stranded breaks with a break occurring on each side of the target site, (4) one double stranded break and two single strand breaks with the double strand break and two single strand breaks occurring on each side of the target site (5) four single stranded breaks with a pair of single stranded breaks occurring on each side of the target site, or (6) one single stranded break. In some embodiments, a single-stranded template polynucleotide is used and the target site can be altered by alternative HDR.

Template polynucleotide-effected alteration of a target site depends on cleavage by a nuclease molecule. Cleavage by the nuclease can comprise a nick, a double strand break, or two single strand breaks, e.g., one on each strand of the DNA at the target site. After introduction of the breaks on the target site, resection occurs at the break ends resulting in single stranded overhanging DNA regions.

In canonical HDR, a double-stranded template polynucleotide is introduced, comprising homologous sequence to the target site that will either be directly incorporated into the target site or used as a template to insert the transgene or correct the sequence of the target site. After resection at the break, repair can progress by different pathways, e.g., by the double Holliday junction model (or double strand break repair, DSBR, pathway) or the synthesis-dependent strand annealing (SDSA) pathway.

In the double Holliday junction model, strand invasion by the two single stranded overhangs of the target site to the homologous sequences in the template polynucleotide occurs, resulting in the formation of an intermediate with two Holliday junctions. The junctions migrate as new DNA is synthesized from the ends of the invading strand to fill the gap resulting from the resection. The end of the newly synthesized DNA is ligated to the resected end, and the junctions are resolved, resulting in the insertion at the target site, e.g., insertion of the transgene in template polynucleotide. Crossover with the template polynucleotide may occur upon resolution of the junctions.

In the SDSA pathway, only one single stranded overhang invades the template polynucleotide and new DNA is synthesized from the end of the invading strand to fill the gap resulting from resection. The newly synthesized DNA then anneals to the remaining single stranded overhang, new DNA is synthesized to fill in the gap, and the strands are ligated to produce the modified DNA duplex.

In alternative HDR, a single strand template polynucleotide, e.g., template polynucleotide, is introduced. A nick, single strand break, or double strand break at the target site, for altering a desired target site, is mediated by a nuclease molecule, and resection at the break occurs to reveal single stranded overhangs. Incorporation of the sequence of the template polynucleotide to correct or alter the target site of the DNA typically occurs by the SDSA pathway, as described herein.

In some embodiments, other DNA repair pathways such as single strand annealing (SSA), single-stranded break repair (SSBR), mismatch repair (MMR), base excision repair (BER), nucleotide excision repair (NER), intrastrand cross-link (ICL), translesion synthesis (TLS), error-free postreplication repair (PRR) can be employed by the cell to repair a double-stranded or single-stranded break created by the nucleases.

(ii) Placement of the Genetic Disruption (e.g., DNA Strand Breaks)

Targeted integration results in the transgene being integrated into a specific gene or locus in the genome. The transgene may be integrated anywhere at or near one of the at least one target site(s) or site in the genome. In some embodiments, the transgene is integrated at or near one of the at least one target site(s), for example, within 300, 250, 200, 150, 100, 50, 10, 5, 4, 3, 2, 1 or fewer base pairs upstream or downstream of the site of cleavage, such as within 100, 50, 10, 5, 4, 3, 2, 1 base pairs of either side of the target site, such as within 50, 10, 5, 4, 3, 2, 1 base pairs of either side of the target site. In some embodiments, the integrated sequence comprising the transgene does not include any vector sequences (e.g., viral vector sequences). In some embodiments, the integrated sequence includes a portion of the vector sequences (e.g., viral vector sequences).

The double strand break or single strand break in one of the strands should be sufficiently close to the site for targeted integration such that an alteration is produced in the desired region, e.g., insertion of transgene or correction of a mutation occurs. In some embodiments, the distance is not more than 10, 25, 50, 100, 200, 300, 350, 400 or 500 nucleotides. In some embodiments, it is believed that the break should be sufficiently close to the site for targeted integration such that the break is within the region that is subject to exonuclease-mediated removal during end resection. In some embodiments, the targeting domain is configured such that a cleavage event, e.g., a double strand or single strand break, is positioned within 1, 2, 3, 4, 5, 10, 15, 20, 25, 30, 35, 40, 45, 50, 60, 70, 80, 90, 100, 150, 200, 300, 350, 400 or 500 nucleotides of the region desired to be altered, e.g., site for targeted insertion. The break, e.g., a double strand or single strand break, can be positioned upstream or downstream of the region desired to be altered, e.g., site for targeted insertion. In some embodiments, a break is positioned within the region desired to be altered, e.g., within a region defined by at least two mutant nucleotides. In some embodiments, a break is positioned immediately adjacent to the region desired to be altered, e.g., immediately upstream or downstream of site for targeted integration.

In some embodiments, a single strand break is accompanied by an additional single strand break, positioned by a second gRNA molecule. For example, the targeting domains are configured such that a cleavage event, e.g., the two single strand breaks, are positioned within 1, 2, 3, 4, 5, 10, 15, 20, 25, 30, 35, 40, 45, 50, 60, 70, 80, 90, 100, 150, 200, 300, 350, 400 or 500 nucleotides of a site for targeted integration. In some embodiments, the first and second gRNA molecules are configured such, that when guiding a Cas9 nickase, a single strand break will be accompanied by an additional single strand break, positioned by a second gRNA, sufficiently close to one another to result in alteration of the desired region. In some embodiments, the first and second gRNA molecules are configured such that a single strand break positioned by said second gRNA is within 10, 20, 30, 40, or 50 nucleotides of the break positioned by said first gRNA molecule, e.g., when the Cas9 is a nickase. In some embodiments, the two gRNA molecules are configured to position cuts at the same position, or within a few nucleotides of one another, on different strands, e.g., essentially mimicking a double strand break.

In some embodiments, in which a gRNA (unimolecular (or chimeric) or modular gRNA) and Cas9 nuclease induce a double strand break for the purpose of inducing HDR-mediated insertion of transgene or correction, the cleavage site is between 0-200 bp (e.g., 0-175, 0 to 150, 0 to 125, 0 to 100, 0 to 75, 0 to 50, 0 to 25, 25 to 200, 25 to 175, 25 to 150, 25 to 125, 25 to 100, 25 to 75, 25 to 50, 50 to 200, 50 to 175, 50 to 150, 50 to 125, 50 to 100, 50 to 75, 75 to 200, 75 to 175, 75 to 150, 75 to 125, 75 to 100 bp) away from the site for targeted integration. In some embodiments, the cleavage site is between 0-100 bp (e.g., 0 to 75, 0 to 50, 0 to 25, 25 to 100, 25 to 75, 25 to 50, 50 to 100, 50 to 75 or 75 to 100 bp) away from the site for targeted integration.

In some embodiments, one can promote HDR by using nickases to generate a break with overhangs. In some embodiments, the single stranded nature of the overhangs can enhance the cell's likelihood of repairing the break by HDR as opposed to, e.g., NHEJ.

Specifically, in some embodiments, HDR is promoted by selecting a first gRNA that targets a first nickase to a first target site, and a second gRNA that targets a second nickase to a second target site which is on the opposite DNA strand from the first target site and offset from the first nick. In some embodiments, the targeting domain of a gRNA molecule is configured to position a cleavage event sufficiently far from a preselected nucleotide, e.g., the nucleotide of a coding region, such that the nucleotide is not altered. In some embodiments, the targeting domain of a gRNA molecule is configured to position an intronic cleavage event sufficiently far from an intron/exon border, or naturally occurring splice signal, to avoid alteration of the exonic sequence or unwanted splicing events. In some embodiments, the targeting domain of a gRNA molecule is configured to position in an early exon, to allow deletion or knock-out of the endogenous gene, and/or allow in-frame integration of the transgene at or near one of the at least one target site(s).

In some embodiments, a double strand break can be accompanied by an additional double strand break, positioned by a second gRNA molecule. In some embodiments, a double strand break can be accompanied by two additional single strand breaks, positioned by a second gRNA molecule and a third gRNA molecule.

In some embodiments, two gRNAs, e.g., independently, unimolecular (or chimeric) or modular gRNA, are configured to position a double-strand break on both sides of a site for targeted integration.

(iii) Template Polynucleotides

A template polynucleotide having homology with sequences at or near one or more target site(s) in the endogenous DNA can be used to alter the structure of a target DNA, e.g., targeted insertion of the transgene. In some embodiments, the template polynucleotide contains homology sequences (e.g., homology arms) flanking the transgene, e.g., nucleic acid sequences encoding a recombinant receptor, for targeted insertion. In some embodiments, the homology sequences target the transgene at one or more of the TRAC and/or β2M loci. In some embodiments, the template polynucleotide includes additional sequences (coding or non-coding sequences) between the homology arms, such as a regulatory sequences, such as promoters and/or enhancers, splice donor and/or acceptor sites, internal ribosome entry site (IRES), sequences encoding ribosome skipping elements (e.g., 2A peptides), markers and/or SA sites, and/or one or more additional transgenes.

The sequence of interest in the template polynucleotide may comprise one or more sequences encoding a functional polypeptide (e.g., a cDNA), with or without a promoter.

In some embodiments, the transgene contained in the template polynucleotide comprises a sequence encoding a cell surface receptor (e.g., a recombinant receptor) or a chain thereof, an antibody, an antigen, an enzyme, a growth factor, a nuclear receptor, a hormone, a lymphokine, a cytokine, a reporter, functional fragments or functional variants of any of the herein and combinations of the herein. The transgene may encode a one or more proteins useful in cancer therapies, for example one or more chimeric antigen receptors (CARs) and/or a recombinant T cell receptor (TCR). In some embodiments, the transgene can encode any of the recombinant receptors described in Section W herein or any chains, regions and/or domains thereof. In some embodiments, the transgene encodes a recombinant T cell receptor (TCR) or any chains, regions and/or domains thereof.

(iv) Delivery of Template Polynucletides

In some embodiments, the polynucleotide, e.g., a polynucleotide such as a template polynucleotide encoding the chimeric receptor, are introduced into the cells in nucleotide form, e.g., as a polynucleotide or a vector. In particular embodiments, the polynucleotide contains a transgene that encodes the chimeric receptor or a portion thereof.

In some embodiments, the template polynucleotide is introduced into the cell for engineering, in addition to the agent(s) capable of inducing a targeted genetic disruption, e.g., nuclease and/or gRNAs. In some embodiments, the template polynucleotide(s) may be delivered prior to, simultaneously or after the agent(s) capable of inducing a targeted genetic disruption is introduced into a cell. In some embodiments, the template polynucleotide(s) are delivered simultaneously with the agents. In some embodiments, the template polynucleotides are delivered prior to the agents, for example, seconds to hours to days before the agents, including, but not limited to, 1 to 60 minutes (or any time therebetween) before the agents, 1 to 24 hours (or any time therebetween) before the agents or more than 24 hours before the agents. In some embodiments, the template polynucleotides are delivered after the agents, seconds to hours to days after the agents, including immediately after delivery of the agent, e.g., between or between about between 30 seconds to 4 hours, such as about 30 seconds, 1 minute, 2 minutes, 3 minutes, 4 minutes, 5 minutes, 6 minutes, 6 minutes, 8 minutes, 9 minutes, 10 minutes, 15 minutes, 20 minutes, 30 minutes, 40 minutes, 50 minutes, 60 minutes, 90 minutes, 2 hours, 3 hours or 4 hours after delivery of the agents and/or preferably within 4 hours of delivery of the agents. In some embodiments, the template polynucleotide is delivered more than 4 hours after delivery of the agents. In some embodiments, the template polynucleotides are delivered after the agents, for example, including, but not limited to, within 1 second to 60 minutes (or any time therebetween) after the agents, 1 to 4 hours (or any time therebetween) after the agents or more than 4 hours after the agents.

In some embodiments, the template polynucleotides may be delivered using the same delivery systems as the agent(s) capable of inducing a targeted genetic disruption, e.g., nuclease and/or gRNAs. In some embodiments, the template polynucleotides may be delivered using different same delivery systems as the agent(s) capable of inducing a targeted genetic disruption, e.g., nuclease and/or gRNAs. In some embodiments, the template polynucleotide is delivered simultaneously with the agent(s). In other embodiments, the template polynucleotide is delivered at a different time, before or after delivery of the agent(s). Any of the delivery method described herein for delivery of nucleic acids in the agent(s) capable of inducing a targeted genetic disruption, e.g., nuclease and/or gRNAs, can be used to deliver the template polynucleotide.

In some embodiments, the one or more agent(s) and the template polynucleotide are delivered in the same format or method. For example, in some embodiments, the one or more agent(s) and the template polynucleotide are both comprised in a vector, e.g., viral vector. In some embodiments, the template polynucleotide is encoded on the same vector backbone, e.g. AAV genome, plasmid DNA, as the Cas9 and gRNA. In some aspects, the one or more agent(s) and the template polynucleotide are in different formats, e.g., ribonucleic acid-protein complex (RNP) for the Cas9-gRNA agent and a linear DNA for the template polynucleotide, but they are delivered using the same method. In some aspects, the one or more agent(s) and the template polynucleotide are in different formats, e.g., ribonucleic acid-protein complex (RNP) for the Cas9-gRNA agent and the template polynucleotide is in contained in an AAV vector, and the RNP is delivered using a physical delivery method (e.g., electroporation) and the template polynucleotide is delivered via transduction of AAV viral preparations. In some aspects, the template polynucleotide is delivered immediately after, e.g., within about 1, 2, 3, 4, 5, 10, 20, 30, 40, 50 or 60 minutes after, the delivery of the one or more agent(s).

In some embodiments, the template polynucleotide is a linear or circular nucleic acid molecule, such as a linear or circular DNA or linear RNA, and can be delivered using any of the methods described in herein for delivering nucleic acid molecules into the cell.

In particular embodiments, the polynucleotide, e.g., the template polynucleotide, are introduced into the cells in nucleotide form, e.g., as or within a non-viral vector. In some embodiments, the non-viral vector is or includes a polynucleotide, e.g., a DNA or RNA polynucleotide, that is suitable for transduction and/or transfection by any suitable and/or known non-viral method for gene delivery, such as but not limited to microinjection, electroporation, transient cell compression or squeezing (e.g., as described in Lee, et al. (2012) *Nano Lett* 12: 6322-27), lipid-mediated transfection, peptide-mediated delivery, e.g., cell-penetrating peptides, or a combination thereof. In some embodiments, the non-viral polynucleotide is delivered into the cell by a non-viral method described herein, such as a non-viral method.

In some embodiments, the template polynucleotide sequence can be comprised in a vector molecule containing sequences that are not homologous to the region of interest in the genomic DNA. In some embodiments, the virus is a DNA virus (e.g., dsDNA or ssDNA virus). In some embodiments, the virus is an RNA virus (e.g., ssRNA or dsRNA virus). Exemplary viral vectors/viruses include, e.g., retroviruses, lentiviruses, adenovirus, adeno-associated virus (AAV), vaccinia viruses, poxviruses, and herpes simplex viruses, or any of the viruses described elsewhere herein.

In some embodiments, the template polynucleotide can be transferred into cells using recombinant infectious virus particles, such as, e.g., vectors derived from simian virus 40 (SV40), adenoviruses, adeno-associated virus (AAV). In some embodiments, the template polynucleotide are transferred into T cells using recombinant lentiviral vectors or retroviral vectors, such as gamma-retroviral vectors (see, e.g., Koste et al. (2014) Gene Therapy 2014 Apr. 3. doi: 10.1038/gt. 2014.25; Carlens et al. (2000) Exp Hematol 28(10): 1137-46; Alonso-Camino et al. (2013) Mol Ther Nucl Acids 2, e93; Park et al., Trends Biotechnol. 2011 Nov. 29(11): 550-557) or HW-1 derived lentiviral vectors.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), or spleen focus forming virus (SFFV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109).

In some embodiments, the template polynucleotides and nucleases may be on the same vector, for example an AAV vector (e.g., AAV6). In some embodiments, the template polynucleotides are delivered using an AAV vector and the agent(s) capable of inducing a targeted genetic disruption, e.g., nuclease and/or gRNAs are delivered as a different form, e.g., as mRNAs encoding the nucleases and/or gRNAs. In some embodiments, the template polynucleotides and nucleases are delivered using the same type of method, e.g., a viral vector, but on separate vectors. In some embodiments, the template polynucleotides are delivered in a different delivery system as the agents capable of inducing a genetic disruption, e.g., nucleases and/or gRNAs. In some embodiments, the template polynucleotide is excised from a vector backbone in vivo, e.g., it is flanked by gRNA recognition sequences. In some embodiments, the template polynucleotide is on a separate polynucleotide molecule as the Cas9 and gRNA. In some embodiments, the Cas9 and the gRNA are introduced in the form of a ribonucleoprotein (RNP) complex, and the template polynucleotide is introduced as a polynucleotide molecule, e.g., in a vector or a linear nucleic acid molecule, e.g., linear DNA. Types or nucleic acids and vectors for delivery include any of those described herein.

b. Transduction

In some embodiments, genetically engineering the cells is or includes introducing the polynucleotide, e.g., the heterologous polynucleotide, into the cells by transduction. In some embodiments, the cells are from an individual donor. In some embodiments, the cells are from a plurality of different donors. In some embodiments, the cells are transduced with a viral vector. In some embodiments, the virus is an adeno-associated viral vector or a retroviral vector, such as a gammaretroviral vector or a lentiviral vector. Methods of lentiviral transduction are known. Exemplary methods are described in, e.g., Wang et al. (2012) J. Immunother. 35(9): 689-701; Cooper et al. (2003) Blood. 101:1637-1644; Verhoeyen et al. (2009) Methods Mol Biol. 506: 97-114; and Cavalieri et al. (2003) Blood. 102(2): 497-505.

In some embodiments, the transduction is carried out by contacting one or more cells of a population (e.g. a CD57 depleted T cell population and/or a pooled CD57 depleted T cell population) with a nucleic acid molecule encoding the recombinant protein, e.g. recombinant receptor. In some embodiments, the transduction is carried out by contacting one or more cells of a population (e.g. a CD27 enriched T cell population and/or a pooled CD27 enriched T cell population) with a nucleic acid molecule encoding the recombinant protein, e.g. recombinant receptor. In some embodiments, the contacting can be effected with centrifugation, such as spinoculation (e.g. centrifugal inoculation). Such methods include any of those as described in International Publication Number WO2016/073602. Exemplary centrifugal chambers include those produced and sold by Biosafe SA, including those for use with the Sepax® and Sepax® 2 system, including an A-200/F and A-200 centrifugal chambers and various kits for use with such systems. Exemplary chambers, systems, and processing instrumentation and cabinets are described, for example, in U.S. Pat. Nos. 6,123,655, 6,733,433 and Published U.S. Patent Application, Publication No.: US 2008/0171951, and published international patent application, publication no. WO 00/38762, the contents of each of which are incorporated herein by reference in their entirety. Exemplary kits for use with such systems include, but are not limited to, single-use kits sold by BioSafe SA under product names CS-430.1, CS-490.1, CS-600.1 or CS-900.2.

In some embodiments, the provided methods are used in connection with transducing a viral vector containing a polynucleotide encoding a recombinant receptor into, into about, or into less than $300\times10^6$ cells, e.g., viable T cells of a stimulated cell population. In certain embodiments, at or about $100\times10^6$ cells, e.g., viable T cells of a stimulated cell population are transduced.

In some embodiments, the transduction is performed in serum free media. In some embodiments, the transduction is performed in the presence of IL-2, IL-7, and IL-15. In particular embodiments, the cells, e.g., the cells of the stimulated cell population contain at least 80%, at least 85%, at least 90%, or at least 95% cells that are CD4+ T cells or CD8+ T cells. In some embodiments, the transduction is performed for between 24 and 48 hours, between 36 and 12 hours, between 18 and 30 hours, or for or for about 24 hours. In certain embodiments, the transduction step is initiated within two days, within 36 hours, or within 30 hours of the start or initiation of the incubation, e.g., the incubation under stimulating conditions.

In some embodiments, the system is included with and/or placed into association with other instrumentation, including instrumentation to operate, automate, control and/or monitor aspects of the transduction step and one or more various other processing steps performed in the system, e.g. one or more processing steps that can be carried out with or in connection with the centrifugal chamber system as described herein or in International Publication Number WO2016/073602. This instrumentation in some embodiments is contained within a cabinet. In some embodiments, the instrumentation includes a cabinet, which includes a housing containing control circuitry, a centrifuge, a cover, motors, pumps, sensors, displays, and a user interface. An exemplary device is described in U.S. Pat. Nos. 6,123,655, 6,733,433 and US 2008/0171951.

In some embodiments, the system comprises a series of containers, e.g., bags, tubing, stopcocks, clamps, connectors, and a centrifuge chamber. In some embodiments, the containers, such as bags, include one or more containers, such as bags, containing the cells to be transduced and the viral vector particles, in the same container or separate containers, such as the same bag or separate bags. In some embodiments, the system further includes one or more containers, such as bags, containing medium, such as diluent and/or wash solution, which is pulled into the chamber and/or other components to dilute, resuspend, and/or wash components and/or populations during the methods. The containers can be connected at one or more positions in the system, such as at a position corresponding to an input line, diluent line, wash line, waste line and/or output line.

In some embodiments, the chamber is associated with a centrifuge, which is capable of effecting rotation of the chamber, such as around its axis of rotation. Rotation may occur before, during, and/or after the incubation in connection with transduction of the cells and/or in one or more of the other processing steps. Thus, in some embodiments, one or more of the various processing steps is carried out under rotation, e.g., at a particular force. The chamber is typically capable of vertical or generally vertical rotation, such that the chamber sits vertically during centrifugation and the side wall and axis are vertical or generally vertical, with the end wall(s) horizontal or generally horizontal.

In some embodiments, the population containing cells and population containing viral vector particles, and optionally air, can be combined or mixed prior to providing the populations to the cavity. In some embodiments, the population containing cells and population containing viral vector particles, and optionally air, are provided separately and combined and mixed in the cavity. In some embodiments, a population containing cells, a population containing viral vector particles, and optionally air, can be provided to the internal cavity in any order. In any of such some embodiments, a population containing cells and viral vector particles is the input composition once combined or mixed together, whether such is combined or mixed inside or outside the centrifugal chamber and/or whether cells and viral vector particles are provided to the centrifugal chamber together or separately, such as simultaneously or sequentially.

In some embodiments, intake of the volume of gas, such as air, occurs prior to the incubating the cells and viral vector particles, such as rotation, in the transduction method. In some embodiments, intake of the volume of gas, such as air, occurs during the incubation of the cells and viral vector particles, such as rotation, in the transduction method.

In some embodiments, the liquid volume of the cells or viral vector particles that make up the transduction population, and optionally the volume of air, can be a predetermined volume. The volume can be a volume that is programmed into and/or controlled by circuitry associated with the system.

In some embodiments, intake of the transduction population, and optionally gas, such as air, is controlled manually, semi-automatically and/or automatically until a desired or predetermined volume has been taken into the internal cavity of the chamber. In some embodiments, a sensor associated with the system can detect liquid and/or gas flowing to and from the centrifuge chamber, such as via its color, flow rate and/or density, and can communicate with associated circuitry to stop or continue the intake as necessary until intake of such desired or predetermined volume has been achieved. In some aspects, a sensor that is programmed or able only to detect liquid in the system, but not gas (e.g. air), can be made able to permit passage of gas, such as air, into the system without stopping intake. In some such embodiments, a non-clear piece of tubing can be placed in the line near the sensor while intake of gas, such as air, is desired. In some embodiments, intake of gas, such as air, can be controlled manually.

In aspects of the provided methods, the internal cavity of the centrifuge chamber is subjected to high speed rotation. In some embodiments, rotation is effected prior to, simultaneously, subsequently or intermittently with intake of the liquid input composition, and optionally air. In some embodiments, rotation is effected subsequent to intake of the liquid input composition, and optionally air. In some embodiments, rotation is by centrifugation of the centrifugal chamber at a relative centrifugal force at the inner surface of side wall of the internal cavity and/or at a surface layer of the cells of at or about or at least at or about 200 g, 300 g, 400 g, 500 g, 600 g, 700 g, 800 g, 1000 g, 1100 g, 1500, 1600 g, 1800 g, 2000 g, 2200 g, 2500 g, 3000 g, 3200 g, 3500 g or 4000 g. In some embodiments, rotation is by centrifugation at a force that is greater than or about 1100 g, such as by greater than or about 1200 g, greater than or about 1400 g, greater than or about 1600 g, greater than or about 1800 g, greater than or about 2000 g, greater than or about 2400 g, greater than or about 2800 g, greater than or about 3000 g or greater than or about 3200 g. In particular embodiments, the rotation by centrifugation is at a force between 600 g and 800 g. In particular embodiments, the rotation by centrifugation is at a force of or of about 693 g. In some embodiments, rotation is by centrifugation at a force that is or is about 1600 g.

In some embodiments, the gas, such as air, in the cavity of the chamber is expelled from the chamber. In some embodiments, the gas, such as air, is expelled to a container that is operably linked as part of the closed system with the centrifugal chamber. In some embodiments, the container is a free or empty container. In some embodiments, the air, such as gas, in the cavity of the chamber is expelled through a filter that is operably connected to the internal cavity of the chamber via a sterile tubing line. In some embodiments, the air is expelled using manual, semi-automatic or automatic processes. In some embodiments, air is expelled from the chamber prior to, simultaneously, intermittently or subsequently with expressing the output population containing incubated cells and viral vector particles, such as cells in which transduction has been initiated or cells have been transduced with a viral vector, from the cavity of the chamber.

In some embodiments, the transduction and/or other incubation is performed as or as part of a continuous or semi-continuous process. In some embodiments, a continuous process involves the continuous intake of the cells and viral vector particles, e.g., the transduction composition (either as a single pre-existing composition or by continuously pulling into the same vessel, e.g., cavity, and thereby mixing, its parts), and/or the continuous expression or expulsion of liquid, and optionally expelling of gas (e.g. air), from the vessel, during at least a portion of the incubation, e.g., while centrifuging. In some embodiments, the continuous intake and continuous expression are carried out at least in part simultaneously. In some embodiments, the continuous intake occurs during part of the incubation, e.g., during part of the centrifugation, and the continuous expression occurs during a separate part of the incubation. The two may alternate. Thus, the continuous intake and expression, while carrying out the incubation, can allow for a greater overall volume of sample to be processed, e.g., transduced.

In some embodiments, the incubation is part of a continuous process, the method including, during at least a portion of the incubation, effecting continuous intake of said transduction composition into the cavity during rotation of the chamber and during a portion of the incubation, effecting continuous expression of liquid and, optionally expelling of gas (e.g. air), from the cavity through the at least one opening during rotation of the chamber.

In some embodiments, the semi-continuous incubation is carried out by alternating between effecting intake of the composition into the cavity, incubation, expression of liquid from the cavity and, optionally expelling of gas (e.g. air) from the cavity, such as to an output container, and then intake of a subsequent (e.g., second, third, etc.) composition containing more cells and other reagents for processing, e.g., viral vector particles, and repeating the process. For example, in some embodiments, the incubation is part of a semi-continuous process, the method including, prior to the incubation, effecting intake of the transduction composition into the cavity through said at least one opening, and subsequent to the incubation, effecting expression of fluid from the cavity; effecting intake of another transduction composition comprising cells and the viral vector particles into said internal cavity; and incubating the another transduction composition in said internal cavity under conditions whereby said cells in said another transduction composition are transduced with said vector. The process may be continued in an iterative fashion for a number of additional rounds. In this respect, the semi-continuous or continuous methods may permit production of even greater volume and/or number of cells.

In some embodiments, a portion of the transduction incubation is performed in the centrifugal chamber, which is performed under conditions that include rotation or centrifugation.

In particular embodiments, transduction of the cells with the viral vector is or includes spinoculation, e.g., centrifugation of a mixture containing the cells and the viral particles. In some embodiments, the composition containing cells and viral particles can be rotated, generally at relatively low force or speed, such as speed lower than that used to pellet the cells, such as from or from about 600 rpm to 1700 rpm (e.g. at or about or at least 600 rpm, 1000 rpm, or 1500 rpm or 1700 rpm). In some embodiments, the rotation is carried at a force, e.g., a relative centrifugal force, of from or from about 100 g to 4000 g (e.g. at or about or at least at or about 100 g, 200 g, 300 g, 400 g, 500 g, 600 g, 700 g, 800 g, 900 g, 1000 g, 1500 g, 2000 g, 2500 g, 3000 g or 3500 g), as measured for example at an internal or external wall of the chamber or cavity.

In some embodiments, the cells are spinoculated with the viral vector at a force, e.g., a relative centrifugal force, of between or between about 100 g and 4000 g, 200 g and 1,000 g, 500 g and 1200 g, 1000 g and 2000 g, 600 g and 800 g, 1200 g and 1800 g, or 1500 g and 1800 g. In certain embodiments, the cells are spinoculated with the viral vector particle for, for at least, or for about 100 g, 200 g, 300 g, 400 g, 500 g, 600 g, 700 g, 800 g, 900 g, 1000 g, 1200 g, 1500 g, 1600 g, 2000 g, 2500 g, 3000 g, 3200 g, or 3500 g. In some embodiments, the cells are transduced with the viral vector at a force of or of about 692 g. In particular embodiments, the cells are transduced with the viral vector at a force of or of about 1600 g. In some embodiments, the force is the force at the internal surface of the side wall of the internal cavity and/or at a surface layer of the cells.

In certain embodiments, the cells are spinoculated, e.g., the cell composition containing cells and viral vector is rotated, for greater than or about 5 minutes, such as greater than or about 10 minutes, greater than or about 15 minutes, greater than or about 20 minutes, greater than or about 30 minutes, greater than or about 45 minutes, greater than or about 60 minutes, greater than or about 90 minutes or greater than or about 120 minutes; or between or between about 5 minutes and 120 minutes, 30 minutes and 90 minutes, 15 minutes and 60 minutes, 15 minutes and 45 minutes, 30 minutes and 60 minutes or 45 minutes and 60 minutes, each inclusive. In some embodiments, the cells are spinoculated with the viral vector for or for about 30 minutes. In certain embodiments, the cells are spinoculated with the viral vector for or for about 60 minutes.

In some embodiments, the method of transduction includes a spinoculation, e.g., a rotation or centrifugation of the transduction composition, and optionally air, in the centrifugal chamber for greater than or about 5 minutes, such as greater than or about 10 minutes, greater than or about 15 minutes, greater than or about 20 minutes, greater than or about 30 minutes, greater than or about 45 minutes, greater than or about 60 minutes, greater than or about 90 minutes or greater than or about 120 minutes. In some embodiments, the transduction composition, and optionally air, is rotated or centrifuged in the centrifugal chamber for greater than 5 minutes, but for no more than 60 minutes, no more than 45 minutes, no more than 30 minutes or no more than 15 minutes. In particular embodiments, the transduction includes rotation or centrifugation for or for about 60 minutes.

In some embodiments, the method of transduction includes rotation or centrifugation of the transduction composition, and optionally air, in the centrifugal chamber for between or between about 10 minutes and 60 minutes, 15 minutes and 60 minutes, 15 minutes and 45 minutes, 30 minutes and 60 minutes or 45 minutes and 60 minutes, each inclusive, and at a force at the internal surface of the side wall of the internal cavity and/or at a surface layer of the cells of, of about, or at 1000 g, 1100 g, 1200 g, 1400 g, 1500 g, 1600 g, 1800 g, 2000 g, 2200 g, 2400 g, 2800 g, 3200 g or 3600 g. In particular embodiments, the method of transduction includes rotation or centrifugation of the transduction composition, e.g., the cells and the viral vector particles, at or at about 1600 g for or for about 60 minutes.

c. Viral Vector Particles

In some embodiments, recombinant nucleic acids are transferred or introduced into cells (e.g. cells of a CD57 depleted T cell population and/or cells of a pooled CD57 depleted T cell population) using recombinant infectious virus particles, such as, e.g., vectors derived from simian virus 40 (SV40), adenoviruses, adeno-associated virus (AAV). In some embodiments, recombinant nucleic acids are transferred or introduced into cells (e.g. cells of a CD27 enriched T cell population and/or cells of a pooled CD27 enriched T cell population) using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt. 2014.25; Carlens et al. (2000) Exp Hematol 28(10): 1137-46; Alonso-Camino et al. (2013) Mol Ther Nucl Acids 2, e93; Park et al., Trends Biotechnol. 2011 Nov. 29(11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), or spleen focus forming virus (SFFV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

The viral vector genome is typically constructed in a plasmid form that can be transfected into a packaging or producer cell line. In any of such examples, the nucleic acid encoding a recombinant protein, such as a recombinant receptor, is inserted or located in a region of the viral vector, such as generally in a non-essential region of the viral genome. In some embodiments, the nucleic acid is inserted into the viral genome in the place of certain viral sequences to produce a virus that is replication defective.

Any of a variety of known methods can be used to produce retroviral particles whose genome contains an RNA copy of the viral vector genome. In some embodiments, at least two components are involved in making a virus-based gene delivery system: first, packaging plasmids, encompassing the structural proteins as well as the enzymes necessary to generate a viral vector particle, and second, the viral vector itself, i.e., the genetic material to be transferred. Biosafety safeguards can be introduced in the design of one or both of these components.

In some embodiments, the packaging plasmid can contain all retroviral, such as HW-1, proteins other than envelope proteins (Naldini et al., 1998). In other embodiments, viral vectors can lack additional viral genes, such as those that are associated with virulence, e.g. vpr, vif, vpu and nef, and/or Tat, a primary transactivator of HW. In some embodiments, lentiviral vectors, such as HIV-based lentiviral vectors, comprise only three genes of the parental virus: gag, pol and rev, which reduces or eliminates the possibility of reconstitution of a wild-type virus through recombination.

In some embodiments, the viral vector genome is introduced into a packaging cell line that contains all the components necessary to package viral genomic RNA, transcribed from the viral vector genome, into viral particles. Alternatively, the viral vector genome may comprise one or more genes encoding viral components in addition to the one or more sequences, e.g., recombinant nucleic acids, of interest. In some aspects, in order to prevent replication of the genome in the target cell, however, endogenous viral genes required for replication are removed and provided separately in the packaging cell line.

In some embodiments, a packaging cell line is transfected with one or more plasmid vectors containing the components necessary to generate the particles. In some embodiments, a packaging cell line is transfected with a plasmid containing the viral vector genome, including the LTRs, the cis-acting packaging sequence and the sequence of interest, i.e. a nucleic acid encoding an antigen receptor, such as a CAR; and one or more helper plasmids encoding the virus enzymatic and/or structural components, such as Gag, pol and/or rev. In some embodiments, multiple vectors are utilized to separate the various genetic components that generate the retroviral vector particles. In some such embodiments, providing separate vectors to the packaging cell reduces the chance of recombination events that might otherwise generate replication competent viruses. In some embodiments, a single plasmid vector having all of the retroviral components can be used.

A packaging cell is used to form a virus particle that is capable of infecting a target cell. Such a cell includes a 293 cell, which can package adenovirus. A viral vector used in gene therapy is usually generated by a producer cell line that packages a nucleic acid vector into a viral particle. The vector typically contains the minimal viral sequences required for packaging and subsequent integration into a host or target cell (if applicable), with other viral sequences being replaced by an expression cassette encoding the protein to be expressed, e.g., Cas9. For example, an AAV vector used in gene therapy typically only possesses inverted terminal repeat (ITR) sequences from the AAV genome which are required for packaging and gene expression in the host or target cell. The missing viral functions are supplied in trans by the packaging cell line. Henceforth, the viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In some embodiments, the retroviral vector particle, such as lentiviral vector particle, is pseudotyped to increase the transduction efficiency of host cells. For example, a retroviral vector particle, such as a lentiviral vector particle, in some embodiments is pseudotyped with a VSV-G glycoprotein, which provides a broad cell host range extending the cell types that can be transduced. In some embodiments, a packaging cell line is transfected with a plasmid or polynucleotide encoding a non-native envelope glycoprotein, such as to include xenotropic, polytropic or amphotropic envelopes, such as Sindbis virus envelope, GALV or VSV-G.

In some embodiments, the packaging cell line provides the components, including viral regulatory and structural proteins, that are required in trans for the packaging of the viral genomic RNA into lentiviral vector particles. In some embodiments, the packaging cell line may be any cell line that is capable of expressing lentiviral proteins and producing functional lentiviral vector particles. In some aspects, suitable packaging cell lines include 293 (ATCC CCL X), 293T, HeLA (ATCC CCL 2), D17 (ATCC CCL 183), MDCK (ATCC CCL 34), BHK (ATCC CCL-10) and Cf2Th (ATCC CRL 1430) cells.

In some embodiments, the packaging cell line stably expresses the viral protein(s). For example, in some aspects, a packaging cell line containing the gag, pol, rev and/or other structural genes but without the LTR and packaging components can be constructed. In some embodiments, a packaging cell line can be transiently transfected with nucleic acid molecules encoding one or more viral proteins along with the viral vector genome containing a nucleic acid molecule encoding a heterologous protein, and/or a nucleic acid encoding an envelope glycoprotein.

In some embodiments, the viral vectors and the packaging and/or helper plasmids are introduced via transfection or infection into the packaging cell line. The packaging cell line produces viral vector particles that contain the viral vector genome. Methods for transfection or infection are well known. Non-limiting examples include calcium phosphate, DEAE-dextran and lipofection methods, electroporation and microinjection.

When a recombinant plasmid and the retroviral LTR and packaging sequences are introduced into a special cell line (e.g., by calcium phosphate precipitation for example), the packaging sequences may permit the RNA transcript of the recombinant plasmid to be packaged into viral particles, which then may be secreted into the culture media. The media containing the recombinant retroviruses in some embodiments is then collected, optionally concentrated, and used for gene transfer. For example, in some aspects, after cotransfection of the packaging plasmids and the transfer vector to the packaging cell line, the viral vector particles are recovered from the culture media and titered by standard methods used by those of skill in the art.

In some embodiments, a retroviral vector, such as a lentiviral vector, can be produced in a packaging cell line, such as an exemplary HEK 293T cell line, by introduction of plasmids to allow generation of lentiviral particles. In some embodiments, a packaging cell is transfected and/or contains a polynucleotide encoding gag and pol, and a polynucleotide encoding a recombinant receptor, such as an antigen receptor, for example, a CAR. In some embodiments, the packaging cell line is optionally and/or additionally transfected with and/or contains a polynucleotide encoding a rev protein. In some embodiments, the packaging cell line is optionally and/or additionally transfected with and/or contains a polynucleotide encoding a non-native envelope glycoprotein, such as VSV-G. In some such embodiments, approximately two days after transfection of cells, e.g. HEK 293T cells, the cell supernatant contains recombinant lentiviral vectors, which can be recovered and titered.

Recovered and/or produced retroviral vector particles can be used to transduce target cells using the methods as described. Once in the target cells, the viral RNA is reverse-transcribed, imported into the nucleus and stably integrated into the host genome. One or two days after the integration of the viral RNA, the expression of the recombinant protein, e.g. antigen receptor, such as CAR, can be detected.

d. Incubation with Viral Vector

In particular embodiments, transforming or transducing the cells (e.g. the CD57− enriched T cells) is or includes one or more steps of incubating the cells, e.g., in the presence of the viral vector. In particular embodiments, transforming or transducing the cells (e.g. the CD27+ enriched T cells) is or includes one or more steps of incubating the cells, e.g., in the presence of the viral vector. In some embodiments, cells, e.g., cells of the transformed cell population, are incubated subsequent to genetically engineering, transforming, transducing, or transfecting the cells.

In certain embodiments, the incubation is performed under static conditions, such as conditions that do not involve centrifugation, shaking, rotating, rocking, or perfusion, e.g., continuous or semi-continuous perfusion of the media. In some embodiments, either prior to or shortly after, e.g., within 5, 15, or 30 minutes, the initiation of the incubation, the cells are transferred (e.g., transferred under sterile conditions) to a container such as a bag or vial, and placed in an incubator.

In some embodiments, the incubation is performed in serum free media. In some embodiments, the serum free media is a defined and/or well-defined cell culture media. In certain embodiments, the serum free media is a controlled culture media that has been processed, e.g., filtered to remove inhibitors and/or growth factors. In some embodiments, the serum free media contains proteins. In certain embodiments, the serum-free media may contain serum albumin, hydrolysates, growth factors, hormones, carrier proteins, and/or attachment factors.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, at least a portion of the incubation is carried out in the internal cavity of a centrifugal chamber, for example, under centrifugal rotation, such as described in International Publication Number WO2016/073602.

In some embodiments, the cells, and optionally the heterologous or recombinant polypeptide, e.g., the viral vectors, are transferred into a container for the incubation. In some embodiments, the container is a vial. In particular embodiments, the container is a bag. In some embodiments, the cells, and optionally the heterologous or recombinant polypeptide, are transferred into the container under closed or sterile conditions. In some embodiments, the container, e.g., the vial or bag, is then placed into an incubator for all or a portion of the incubation. In particular embodiments, incubator is set at, at about, or at least 16° C., 24° C., or 35° C. In some embodiments, the incubator is set at 37° C., at about at 37° C., or at 37° C.±2° C., ±1° C., ±0.5° C., or ±0.1° C.

In particular embodiments, the cells are incubated in the presence of one or more cytokines. In certain embodiments, the one or more cytokines are recombinant cytokines. In particular embodiments, the one or more cytokines are human recombinant cytokines. In certain embodiments, the one or more cytokines bind to and/or are capable of binding to receptors that are expressed by and/or are endogenous to T cells. In particular embodiments, the one or more cytokines is or includes a member of the 4-alpha-helix bundle family of cytokines. In some embodiments, members of the 4-alpha-helix bundle family of cytokines include, but are not limited to, interleukin-2 (IL-2), interleukin-4 (IL-4), interleukin-7 (IL-7), interleukin-9 (IL-9), interleukin 12 (IL-12), interleukin 15 (IL-15), granulocyte colony-stimulating factor (G-CSF), and granulocyte-macrophage colony-stimulating factor (GM-CSF). In some embodiments, the one or more cytokines is or includes IL-15. In particular embodiments, the one or more cytokines is or includes IL-7. In particular embodiments, the one or more cytokines is or includes recombinant IL-2.

In some embodiments, the cells are incubated in the absence of recombinant cytokines.

In some embodiments, all or a portion of the incubation is performed in basal media. In some embodiments, the basal media is a balanced salt solution (e.g., PBS, DPBS, HBSS, EBSS). In some embodiments, the basal media is selected from Dulbecco's Modified Eagle's Medium (DMEM), Minimal Essential Medium (MEM), Basal Medium Eagle (BME), F-10, F-12, RPMI 1640, Glasgow's Minimal Essential Medium (GMEM), alpha Minimal Essential Medium (alpha MEM), Iscove's Modified Dulbecco's Medium, and M199. In some embodiments, the base media is a complex medium (e.g., RPMI-1640, IMDM). In some embodiments, the base medium is OpTmizer™ CTS™ T-Cell Expansion Basal Medium (ThermoFisher).

In some embodiments, the basal medium contains a mixture of inorganic salts, sugars, amino acids, and, optionally, vitamins, organic acids and/or buffers or other well known cell culture nutrients. In addition to nutrients, the medium also helps maintain pH and osmolality. In some aspects, the reagents of the basal media support cell growth, proliferation and/or expansion. A wide variety of commercially available basal media are well known to those skilled in the art, and include Dulbeccos' Modified Eagles Medium (DMEM), Roswell Park Memorial Institute Medium (RPMI), Iscove modified Dulbeccos' medium and Hams medium. In some embodiments, the basal medium is Iscove's Modified Dulbecco's Medium, RPMI-1640, or α-MEM.

In certain embodiments, the basal media is supplemented with additional additives. In some embodiments, the basal media is not supplemented with any additional additives. Additives to cell culture media may include, but is not limited to nutrients, sugars, e.g., glucose, amino acids, vitamins, or additives such as ATP and NADH.

In some embodiments, cells are incubated with the heterologous polynucleotide, e.g., the viral vector. In certain embodiments, the cells are incubated the cells with the polynucleotide, e.g., viral vector, for, for about, or for at least 18 hours, 24 hours, 30 hours, 36 hours, 40 hours, 48 hours, 54 hours, 60 hours, 72 hours, 84 hours, 96 hours, or more than 96 hours. In certain embodiments, the total duration of the incubation is, is about, or is at least 12 hours, 18 hours, 24 hours, 30 hours, 36 hours, 42 hours, 48 hours, 54 hours, 60 hours, 72 hours, 84 hours, 96 hours, 108 hours, or 120 hours. In particular embodiments, the incubation is completed at, at about, or within 120 hours, 108 hours, 96 hours, 84 hours, 72 hours, 60 hours, 54 hours, 48 hours, 42 hours, 36 hours, 30 hours, 24 hours, 18 hours, or 12 hours. In some embodiments, the total duration of the incubation is between or between about 12 hour and 120 hours, 18 hour and 96 hours, 24 hours and 72 hours, or 24 hours and 48 hours, inclusive. In some embodiments, the total duration of the incubation is between or about between 1 hour and 48 hours, 4 hours and 36 hours, 8 hours and 30 hours or 12 hours and 24 hours, inclusive.

2. Genetic Disruption (Knock Out)

In particular embodiments, the cells (e.g. the CD57 depleted T cell population and/or the pooled CD57 depleted T cell population) are genetically disrupted. In particular embodiments, the cells (e.g. the CD27 enriched T cell population and/or the pooled CD27 enriched T cell population) are genetically disrupted. In some embodiments, the genetic disrupting is or comprises disrupting expression of one or more molecules of interest, such as by making a gene encoding the molecule inoperative or causing a permanent change in the nucleic acid (e.g. DNA) leading to the loss of function of the gene encoding the molecule. In some embodiment, disrupting the expression of one or more molecules of interests is referred to as "knocking out" the one or more molecules or a gene encoding for the one or more molecules.

In some embodiments, a CD57 depleted T cell population is knocked out for one or more molecules of interest. In some embodiments, a pooled CD57 depleted T cell population is knocked out for one or more molecules of interest. In some embodiments, a CD27 enriched T cell population is knocked out for one or more molecules of interest. In some embodiments, a pooled CD27 enriched T cell population is knocked out for one or more molecules of interest. In particular embodiments, the molecule of interest is an immune gene that is involved in inducing or stimulating an immune response. In some embodiments, the immune gene is a major histocompatibility complex (MHC), one or more genes encoding for a T-cell receptor (TCR), or a component thereof or beta 2-microglobulin (beta 2m).

Among provided methods are methods for genetically engineering (e.g. disrupting or "knocking out") one or more populations of T cells, e.g. a CD57 depleted T cell population and/or a pooled CD57 depleted T cell population. Also among provided methods are methods for genetically engineering (e.g. disrupting or "knocking out") one or more populations of T cells, e.g. a CD27 enriched T cell population and/or a pooled CD27 enriched T cell population. The genetic engineering processes disclosed herein can be used during, prior to, after, or between any steps of combining cell populations from a plurality of different individual donors to create a pooled T cell composition. In some aspects, the genetic engineering (e.g. knocking out) is performed prior to any steps of combining cell compositions from a plurality of individual donors. For example, the genetic engineering (e.g. knocking out) may be performed on a cell population (e.g. a CD57 depleted T cell population) from an individual donor, and the cell composition from the individual donor may be combined thereafter with an engineered cell composition from one or more other individual donors, to produce a pooled engineered composition. In some embodiments, the cell population is a CD27 enriched T cell population. In some aspects, the genetic engineering (e.g. knocking out) is performed subsequent to combining cell compositions from a plurality of individual donors. For example, the genetic engineering (e.g. knocking out) may be performed on a cell population from a plurality of different donors (e.g. a pooled CD57 depleted T cell population), to produce a pooled engineered composition. In some embodiments, the cell population from a plurality of different donors is a pooled CD27 enriched T cell population.

In some embodiments, the disrupting (e.g. knocking out) is performed concurrently with the introducing of a heterologous polynucleotide into a cell population. In some embodiments, the disrupting (e.g. knocking out) and the introducing of a heterologous polynucleotide into a cell population are carried out sequentially, in either order.

In some embodiments, genetic disruption comprises one or more targeted genetic disruptions (e.g. knock out) induced at one or more genes encoding for a major histocompatibility complex (MHC) and/or one or more genes encoding for a T-cell receptor (TCR) or a component thereof. In some embodiments, genetic disruption comprises one or more targeted genetic disruptions (e.g. knock out) induced at one or more genes encoding for a T-cell receptor (TCR) or a component thereof. In some embodiments, the targeted genetic disruption is induced at one or more of the genes encoding TCRα constant domain (also known as TCRα constant region; encoded by TRAC in humans) and/or the TCRβ constant domain (also known as TCRβ constant region; encoded by TRBC in humans). In some embodiments, targeted genetic disruption is induced at the TRAC locus. In some embodiments, targeted genetic disruption is induced at the TRBC locus.

In some embodiments, genetic disruption comprises one or more targeted genetic disruptions (e.g. knock out) induced at one or more genes encoding for a major histocompatibility complex (MHC) or a component thereof. In some embodiments, genetic disruption comprises one or more targeted genetic disruptions (e.g. knock out) induced at one or more genes encoding for a MHC class I molecule or a component thereof. In some embodiments, the MHC class I molecule is beta-2-microglobulin (β2M). In some embodiments, genetic disruption comprises one or more targeted genetic disruptions induced at the endogenous beta-2-microglobulin (β2M) gene. In some embodiments, targeted genetic disruption is induced at the 132M locus.

In some embodiments, genetic disruption comprises one or more targeted genetic disruptions induced at the endogenous TRCalpha constain gene (TRAC) and at the endogenous beta-2-microglobulin (β2M) gene. In some embodiments, targeted genetic disruption is induced at the TRAC locus and the β2M locus.

In some embodiments, targeted genetic disruption results in a DNA break or a nick. In some embodiments, at the site of the DNA break, action of cellular DNA repair mechanisms can result in knock-out, insertion, missense or frameshift mutation, such as a biallelic frameshift mutation, deletion of all or part of the gene. In some embodiments, the genetic disruption can be targeted to one or more exon of a gene or portion thereof, such as within the first or second exon. In some embodiments, a DNA binding protein or DNA-binding nucleic acid, which specifically binds to or hybridizes to the sequences at a region near one of the at least one target site(s), is used for targeted disruption. In some aspects, in the absence of exogenous template polynucleotides for HDR the disruption, the targeted genetic disruption results in a deletion, mutation and or insertion within an exon of the gene. In some embodiments, template polynucleotides, e.g., template polynucleotides that include nucleic acid sequences encoding a recombinant receptor and homology sequences, can be introduced for targeted integration of the recombinant receptor-encoding sequences at or near the site of the genetic disruption by HDR (see Section I.B. herein).

In some embodiments, the genetic disruption is carried by introducing one or more agent(s) capable of inducing a genetic disruption. In some embodiments, such agents comprise a DNA binding protein or DNA-binding nucleic acid that specifically binds to or hybridizes to the gene. In some embodiments, the agent comprises various components, such as a fusion protein comprising a DNA-targeting protein and a nuclease or an RNA-guided nuclease. In some embodiments, the agents can target one or more target locations, e.g., at a TRAC gene and/or a β2M gene.

In some embodiments, the genetic disruption occurs at a target site (also referred to and/or known as "target position," "target DNA sequence," or "target location"). In some embodiments, target site is or includes a site on a target DNA (e.g., genomic DNA) that is modified by the one or more agent(s) capable of inducing a genetic disruption, e.g., a Cas9 molecule complexed with a gRNA that specifies the target site. For example, in some embodiments, the target site may include locations in the DNA, e.g., at an endogenous TRAC and/or β2M locus, where cleavage or DNA breaks occur. In some aspects, integration of nucleic acid sequences by HDR can occur at or near the target site or target sequence. In some embodiments, a target site can be a site between two nucleotides, e.g., adjacent nucleotides, on the DNA into which one or more nucleotides is added. The target site may comprise one or more nucleotides that are altered by a template polynucleotide. In some embodiments, the target site is within a target sequence (e.g., the sequence to which the gRNA binds). In some embodiments, a target site is upstream or downstream of a target sequence.

In some embodiments, the cell includes an agent that reduces expression and/or surface expression of the endogenous TRAC gene. In some embodiments, an inhibitory nucleic acid, such as siRNA or shRNA, is used to repress TRAC expression. In some embodiments, the cell includes an agent that reduces expression and/or surface expression of the endogenous β2M gene. In some embodiments, an inhibitory nucleic acid, such as siRNA or shRNA, is used to repress β2M expression. Methods of using inhibitory agents, including inhibitory nucleic acids, including using RNA interference technology, such as siRNA or shRNA, to repress cell expression of a β2M molecule and/or a TRAC molecule are well within the level of a skilled artisan. Commercially available reagents, such as siRNA or shRNA reagents, are readily available.

In some embodiments, the cells are genetically disrupted after the cells have been stimulated, activated, and/or stimulated under conditions to activate the T cells in the population, such as by any of the methods provided herein, e.g., in Section III.E. In particular embodiments, the one or more stimulated populations have been previously enriched for CD57− T cells. In particular embodiments, the one or more stimulated populations have been previously enriched for CD27+ T cells. In particular embodiments, the one or more stimulated populations have been previously enriched for one of more of CD3+, CD4+, and/or CD8+ T cells. In some embodiments, the stimulated cells, optionally enriched for one or more of CD3+, CD4+, and/or CD8+ T cells, are derived from an individual donor. In some embodiments, the stimulated cells, optionally enriched for one or more of CD3+, CD4+, and/or CD8+ T cells, are derived from an individual donor and combined with stimulated cells from one or more other individual donors to produce stimulated cells from a plurality of different donors. In some embodiments, the stimulated cells, optionally enriched for one or more of CD3+, CD4+, and/or CD8+ T cells, are derived from a plurality of donors.

a. Target Sites at the Endogenous β2M and TRAC Genes

In some embodiments, the cells (e.g., cells of the CD57 depleted T cell population and/or the pooled CD57 depleted T cell population) includes reduced expression and/or surface expression of an endogenous MHC protein and/or an endogenous beta-2-microglobulin (β2M) protein in the cell. In some embodiments, the cells (e.g., cells of the CD27 enriched T cell population and/or the pooled CD27 enriched T cell population) includes reduced expression and/or surface expression of an endogenous MHC protein and/or an endogenous beta-2-microglobulin (β2M) protein in the cell. In some embodiments, targeting β2M can provide or further provide a broad reduction or elimination of MHC class I expression in the engineered cells, since β2M is a component of MHC class I, which, in some cases, can be necessary for the stable expression of an MHC class I molecule on the cell surface.

In some embodiments, the cell can comprise or additionally comprise a disruption of the gene that encodes, or an agent that reduces expression of, β2M. In some embodiments, gene editing methods are used to repress or disrupt β2M. Methods using CRISPR systems for knockout of a/32M gene are known in the art. Commercially available kits, gRNA vectors and donor vectors, for knockout of a β2M gene, via CRISPR also are readily available. For example, commercially available reagents for knockout of a β2M gene are available, for example, from GeneCopoeia (see e.g. catalog number HTN215171).

In some embodiments, the genetic disruption is targeted at the endogenous gene loci that encode TCRα. In some embodiments, the genetic disruption is targeted at the gene encoding TCRα constant domain (TRAC in humans).

In some embodiments, a "T cell receptor" or "TCR," including the endogenous TCRs, is a molecule that contains a variable α and β chains (also known as TCRα and TCRβ, respectively) or a variable γ and δ chains (also known as TCRγ and TCRδ, respectively), or antigen-binding portions thereof, and which is capable of specifically binding to a peptide bound to an MHC molecule. In some embodiments, the TCR is in the αβ form. Typically, TCRs that exist in αβ and γδ forms are generally structurally similar, but T cells expressing them may have distinct anatomical locations or functions. Typically, one T cell expresses one type of TCR. A TCR can be found on the surface of a cell or in soluble form. Generally, a TCR is found on the surface of T cells (or T lymphocytes) where it is generally responsible for recognizing antigens bound to major histocompatibility complex (MHC) molecules.

In some embodiments, a TCR can contain a variable domain and a constant domain (also known as a constant region), a transmembrane domain and/or a short cytoplasmic tail (see, e.g., Janeway et al., *Immunobiology: The Immune System in Health and Disease,* 3' Ed., Current Biology Publications, p. 4:33, 1997). In some embodiments, a TCR chain contains one or more constant domain. For example, the extracellular portion of a given TCR chain (e.g., TCRα chain or TCRβ chain) can contain two immunoglobulin-like domains, such as a variable domain (e.g., Vα or Vβ; typically amino acids 1 to 116 based on Kabat numbering Kabat et al., "Sequences of Proteins of Immunological Interest, U.S. Dept. Health and Human Services, Public Health Service National Institutes of Health, 1991, $5^{th}$ ed.) and a constant domain (e.g., a chain constant domain or TCR Cα, typically positions 117 to 259 of the chain based on Kabat numbering or β chain constant domain or TCR Cβ, typically positions 117 to 295 of the chain based on Kabat) adjacent to the cell membrane. For example, in some cases, the extracellular portion of the TCR formed by the two chains contains two membrane-proximal constant domains, and two membrane-distal variable domains.

In some embodiments, the endogenous TCR Ca is encoded by the TRAC gene (IMGT nomenclature). In certain embodiments, a genetic disruption is targeted at, near, or within a TRAC locus. In particular embodiments, the genetic disruption is targeted at, near, or within an open reading frame of the TRAC locus. In certain embodiments, the genetic disruption is targeted at, near, or within an open reading frame that encodes a TCRα constant domain.

In some aspects, the transgene (e.g., exogenous nucleic acid sequences) within the template polynucleotide can be used to guide the location of target sites and/or homology arms. In some aspects, the target site of genetic disruption can be used as a guide to design template polynucleotides and/or homology arms used for HDR. In some embodiments, the genetic disruption can be targeted near a desired site of targeted integration of transgene sequences (e.g., encoding a recombinant TCR or a portion thereof). In some aspects, the target site is within an exon of the open reading frame of the TRAC and/or β2M locus. In some aspects, the target site is within an exon of the open reading frame of the TRAC locus. In some aspects, the target site is within an exon of the open reading frame of the β2M locus. In some aspects, the target site is within an intron of the open reading frame of the TRAC and/or β2M locus. In some aspects, the target site is within an intron of the open reading frame of the TRAC locus. In some aspects, the target site is within an intron of the open reading frame of the β2M locus.

In some embodiments, the genetic disruption, e.g., DNA break, is targeted at or in close proximity to the beginning of the coding region (e.g., the early coding region, e.g., within 500 bp from the start codon or the remaining coding sequence, e.g., downstream of the first 500 bp from the start codon). In some embodiments, the genetic disruption, e.g., DNA break, is targeted at early coding region of a gene of interest, e.g., TRAC and/or β2M, including sequence immediately following a transcription start site, within a first exon of the coding sequence, or within 500 bp of the transcription start site (e.g., less than 500, 450, 400, 350, 300, 250, 200, 150, 100 or 50 bp), or within 500 bp of the start codon (e.g., less than 500, 450, 400, 350, 300, 250, 200, 150, 100 or 50 bp).

In some embodiments, the target site is within an exon of the endogenous TRAC locus. In certain embodiments, the target site is within an intron of the endogenous TRAC locus. In some aspects, the target site is within a regulatory or control element, e.g., a promoter, 5' untranslated region (UTR) or 3' UTR, of the TRAC locus. In certain embodiments, the target site is within an open reading frame of an endogenous TRAC locus. In particular embodiments, the target site is within an exon within the open reading frame of the TRAC locus.

In some embodiments, the target site is within an exon of the endogenous β2M locus. In certain embodiments, the target site is within an intron of the endogenous β2M locus. In some aspects, the target site is within a regulatory or control element, e.g., a promoter, 5' untranslated region (UTR) or 3' UTR, of the β2M locus. In certain embodiments, the target site is within an open reading frame of an endogenous β2M locus. In particular embodiments, the target site is within an exon within the open reading frame of the β2M locus.

In particular embodiments, the genetic disruption, e.g., DNA break, is targeted at or within an open reading frame of a gene or locus of interest, e.g., TRAC and/or β2M. In some embodiments, the genetic disruption is targeted at or within an intron within the open reading frame of a gene or locus of interest. In some embodiments, the genetic disruption is targeted within an exon within the open reading frame of the gene or locus of interest.

In particular embodiments, a genetic disruption, e.g., DNA break, is targeted at or within an intron. In certain embodiments, a genetic disruption, e.g., DNA break, is targeted at or within an exon. In some embodiments, a genetic disruption, e.g., DNA break, is targeted at or within an exon of a gene of interest, e.g., TRAC and/or β2M.

In some embodiments, a genetic disruption, e.g., DNA break, is targeted within an exon of the TRAC gene, open reading frame, or locus. In certain embodiments, the genetic disruption is within the first exon, second exon, third exon, or fourth exon of the TRAC gene, open reading frame, or locus. In particular embodiments, the genetic disruption is within the first exon of the TRAC gene, open reading frame, or locus. In some embodiments, the genetic disruption is within 500 base pairs (bp) downstream from the 5' end of the first exon in the TRAC gene, open reading frame, or locus. In particular embodiments, the genetic disruption is between the most 5' nucleotide of exon 1 and upstream of the most 3' nucleotide of exon 1. In certain embodiments, the genetic disruption is within 400 bp, 350 bp, 300 bp, 250 bp, 200 bp, 150 bp, 100 bp, or 50 bp downstream from the 5' end of the first exon in the TRAC gene, open reading frame, or locus. In particular embodiments, the genetic disruption is between 1 bp and 400 bp, between 50 and 300 bp, between 100 bp and 200 bp, or between 100 bp and 150 bp downstream from the 5' end of the first exon in the TRAC, open reading frame, or locus, each inclusive. In certain embodiments, the genetic disruption is between 100 bp and 150 bp downstream from the 5' end of the first exon in the TRAC gene, open reading frame, or locus, inclusive.

In some embodiments, a genetic disruption, e.g., DNA break, is targeted within an exon of the β2M gene, open reading frame, or locus. In certain embodiments, the genetic disruption is within the first exon, second exon, third exon, or fourth exon of the β2M gene, open reading frame, or locus. In particular embodiments, the genetic disruption is within the first exon of the β2M gene, open reading frame, or locus. In some embodiments, the genetic disruption is within 500 base pairs (bp) downstream from the 5' end of the first exon in the β2M gene, open reading frame, or locus. In particular embodiments, the genetic disruption is between the most 5' nucleotide of exon 1 and upstream of the most 3' nucleotide of exon 1. In certain embodiments, the genetic disruption is within 400 bp, 350 bp, 300 bp, 250 bp, 200 bp, 150 bp, 100 bp, or 50 bp downstream from the 5' end of the first exon in the β2M gene, open reading frame, or locus. In particular embodiments, the genetic disruption is between 1 bp and 400 bp, between 50 and 300 bp, between 100 bp and 200 bp, or between 100 bp and 150 bp downstream from the 5' end of the first exon in the β2M, open reading frame, or locus, each inclusive. In certain embodiments, the genetic disruption is between 100 bp and 150 bp downstream from the 5' end of the first exon in the β2M gene, open reading frame, or locus, inclusive.

b. Methods of Genetic Disruption

In some aspects, a methods of repressing or disrupting a genes is carried out by effecting a disruption in the gene, such as a knock-out, insertion, missense or frameshift mutation, such as a biallelic frameshift mutation, deletion of all or part of the gene, e.g., one or more exon or portion thereof, and/or knock-in. In some aspects, the disruption of the molecule or gene is carried out by gene editing, such as using a DNA binding protein or DNA-binding nucleic acid, which specifically binds to or hybridizes to the gene at a region targeted for disruption. In some aspects, the disruption results in a deletion, mutation and or insertion within the gene, such as within an exon of the gene. In some aspects, the disruption an the introducing of a heterologous polynucleotide are performed concurrently. In some aspects, the disruption an the introducing of a heterologous polynucleotide are performed sequentially, in either order.

Methods for generating a genetic disruption, including those described herein, can involve the use of one or more agent(s) capable of inducing a genetic disruption, such as engineered systems to induce a genetic disruption, a cleavage and/or a double strand break (DSB) or a nick in a target site or target position in the endogenous DNA such that repair of the break by an error born process such as non-homologous end joining (NHEJ) or repair using a repair template HDR can result in the knock out of a gene and/or the insertion of a sequence of interest (e.g., exogenous nucleic acid sequences or transgene encoding a portion of a chimeric receptor) at or near the target site or position. Also provided are one or more agent(s) capable of inducing a genetic disruption, for use in the methods provided herein. In some aspects, the one or more agent(s) can be used in combination with the template nucleotides provided herein, for homology directed repair (HDR) mediated targeted integration of the transgene sequences.

In some embodiments, the one or more agent(s) capable of inducing a genetic disruption comprises a DNA binding protein or DNA-binding nucleic acid that specifically binds to or hybridizes to a particular site or position in the genome, e.g., a target site or target position. In some aspects, the targeted genetic disruption, e.g., DNA break or cleavage, of the endogenous genes encoding TCR is achieved using a protein or a nucleic acid is coupled to or complexed with a gene editing nuclease, such as in a chimeric or fusion protein. In some aspects, the targeted genetic disruption, e.g., DNA break or cleavage, of the endogenous genes encoding major histocompatibility complex (MHC) is achieved using a protein or a nucleic acid is coupled to or complexed with a gene editing nuclease, such as in a chimeric or fusion protein. In some embodiments, the one or more agent(s) capable of inducing a genetic disruption comprises an RNA-guided nuclease, or a fusion protein comprising a DNA-targeting protein and a nuclease.

In some embodiments, the agent comprises various components, such as an RNA-guided nuclease, or a fusion protein comprising a DNA-targeting protein and a nuclease. In some embodiments, the targeted genetic disruption is carried out using a DNA-targeting molecule that includes a DNA-binding protein such as one or more zinc finger protein (ZFP) or transcription activator-like effectors (TALEs), fused to a nuclease, such as an endonuclease. In some embodiments, the targeted genetic disruption is carried out using RNA-guided nucleases such as a clustered regularly interspaced short palindromic nucleic acid (CRISPR)-associated nuclease (Cas) system (including Cas and/or Cfp1). In some embodiments, the targeted genetic disruption is carried using agents capable of inducing a genetic disruption, such as sequence-specific or targeted nucleases, including DNA-binding targeted nucleases and gene editing nucleases such as zinc finger nucleases (ZFN) and transcription activator-like effector nucleases (TALENs), and RNA-guided nucleases such as a CRISPR-associated nuclease (Cas) system, specifically designed to be targeted to the at least one target site(s), sequence of a gene or a portion thereof. Exemplary ZFNs, TALEs, and TALENs are described in, e.g., Lloyd et al., Frontiers in Immunology, 4(221): 1-7 (2013).

Zinc finger proteins (ZFPs), transcription activator-like effectors (TALEs), and CRISPR system binding domains can be "engineered" to bind to a predetermined nucleotide sequence, for example via engineering (altering one or more amino acids) of the recognition helix region of a naturally occurring ZFP or TALE protein. Engineered DNA binding proteins (ZFPs or TALEs) are proteins that are non-naturally occurring. Rational criteria for design include application of substitution rules and computerized algorithms for processing information in a database storing information of existing ZFP and/or TALE designs and binding data. See, e.g., U.S. Pat. Nos. 6,140,081; 6,453,242; and 6,534,261; see also WO 98/53058; WO 98/53059; WO 98/53060; WO 02/016536 and WO 03/016496 and U.S. Publication No. 20110301073.

In some embodiments, the one or more agent(s) specifically targets the at least one target site(s), e.g., at or near a gene of interest, e.g., TRAC and/or β2M. In some embodiments, the agent comprises a ZFN, TALEN or a CRISPR/Cas9 combination that specifically binds to, recognizes, or hybridizes to the target site(s). In some embodiments, the CRISPR/Cas9 system includes an engineered crRNA/tracr RNA ("single guide RNA") to guide specific cleavage. In some embodiments, the agent comprises nucleases based on the Argonaute system (e.g., from *T. thermophilus*, known as 'TtAgo', (Swarts et al. (2014) Nature 507(7491): 258-261). Targeted cleavage using any of the nuclease systems described herein can be exploited to insert the sequences of a transgene, e.g., nucleic acid sequences encoding a recombinant receptor, into a specific target location, e.g., at endogenous TCR genes, using either HDR or NHEJ-mediated processes.

In some embodiments, a "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP. Among the ZFPs are artificial ZFP domains targeting specific DNA sequences, typically 9-18 nucleotides long, generated by assembly of individual fingers. ZFPs include those in which a single finger domain is approximately 30 amino acids in length and contains an alpha helix containing two invariant histidine residues coordinated through zinc with two cysteines of a single beta turn, and having two, three, four, five, or six fingers. Generally, sequence-specificity of a ZFP may be altered by making amino acid substitutions at the four helix positions (−1, 2, 3, and 6) on a zinc finger recognition helix. Thus, for example, the ZFP or ZFP-containing molecule is non-naturally occurring, e.g., is engineered to bind to a target site of choice.

In some cases, the DNA-targeting molecule is or comprises a zinc-finger DNA binding domain fused to a DNA cleavage domain to form a zinc-finger nuclease (ZFN). For example, fusion proteins comprise the cleavage domain (or cleavage half-domain) from at least one Type IIS restriction enzyme and one or more zinc finger binding domains, which may or may not be engineered. In some cases, the cleavage domain is from the Type IIS restriction endonuclease FokI, which generally catalyzes double-stranded cleavage of DNA, at 9 nucleotides from its recognition site on one strand and 13 nucleotides from its recognition site on the other. See, e.g., U.S. Pat. Nos. 5,356,802; 5,436,150 and 5,487,994; Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269: 978-982. Some gene-specific engineered zinc fingers are available commercially. For example, a platform called CompoZr, for zinc-finger construction is available that provides specifically targeted zinc fingers for thousands of targets. See, e.g., Gaj et al., *Trends in Biotechnology*, 2013, 31(7), 397-405. In some cases, commercially available zinc fingers are used or are custom designed.

In some embodiments, the one or more target site(s), e.g., within TRAC and/or β2M genes can be targeted for genetic disruption by engineered ZFNs.

Transcription Activator like Effector (TALE) are proteins from the bacterial species *Xanthomonas* comprise a plurality of repeated sequences, each repeat comprising di-residues in position 12 and 13 (RVD) that are specific to each nucleotide base of the nucleic acid targeted sequence. Binding domains with similar modular base-per-base nucleic acid binding properties (MBBBD) can also be derived from different bacterial species. The new modular proteins have the advantage of displaying more sequence variability than TAL repeats. In some embodiments, RVDs associated with recognition of the different nucleotides are HD for recognizing C, NG for recognizing T, NI for recognizing A, NN for recognizing G or A, NS for recognizing A, C, G or T, HG for recognizing T, IG for recognizing T, NK for recognizing G, HA for recognizing C, ND for recognizing C, HI for recognizing C, HN for recognizing G, NA for recognizing G, SN for recognizing G or A and YG for recognizing T, TL for recognizing A, VT for recognizing A or G and SW for recognizing A. In some embodiments, critical amino acids 12 and 13 can be mutated towards other amino acid residues in order to modulate their specificity towards nucleotides A, T, C and G and in particular to enhance this specificity.

In some embodiments, a "TALE DNA binding domain" or "TALE" is a polypeptide comprising one or more TALE repeat domains/units. The repeat domains, each comprising a repeat variable diresidue (RVD), are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. TALE proteins may be designed to bind to a target site using canonical or non-canonical RVDs within the repeat units. See, e.g., U.S. Pat. Nos. 8,586,526 and 9,458,205.

In some embodiments, a "TALE-nuclease" (TALEN) is a fusion protein comprising a nucleic acid binding domain typically derived from a Transcription Activator Like Effector (TALE) and a nuclease catalytic domain that cleaves a nucleic acid target sequence. The catalytic domain comprises a nuclease domain or a domain having endonuclease activity, like for instance I-TevI, ColE7, NucA and Fok-I. In a particular embodiment, the TALE domain can be fused to a meganuclease like for instance I-CreI and I-OnuI or functional variant thereof. In some embodiments, the TALEN is a monomeric TALEN. A monomeric TALEN is a TALEN that does not require dimerization for specific recognition and cleavage, such as the fusions of engineered TAL repeats with the catalytic domain of I-TeeI described in WO2012138927. TALENs have been described and used for gene targeting and gene modifications (see, e.g., Boch et al. (2009) Science 326(5959): 1509-12.; Moscou and Bogdanove (2009) Science 326(5959): 1501; Christian et al. (2010) Genetics 186(2): 757-61; Li et al. (2011) Nucleic Acids Res 39(1): 359-72).

In some embodiments, the TRAC gene can be targeted for genetic disruption by engineered TALENs. In some embodiments, the β2M gene can be targeted for genetic disruption by engineered TALENs. In some embodiments, the TRAC gene and the β2M gene can be targeted for genetic disruption by engineered TALENs.

In some embodiments, a "TtAgo" is a prokaryotic Argonaute protein thought to be involved in gene silencing. TtAgo is derived from the bacteria *Thermus thermophilus*. See, e.g. Swarts et al, (2014) Nature 507(7491): 258-261, Sheng et al., (2013) Proc. Natl. Acad. Sci. U.S.A. 111, 652). A "TtAgo system" is all the components required including e.g. guide DNAs for cleavage by a TtAgo enzyme.

In some embodiments, an engineered zinc finger protein, TALE protein or CRISPR/Cas system is not found in nature and whose production results primarily from an empirical process such as phage display, interaction trap or hybrid selection. See e.g., U.S. Pat. Nos. 5,789,538; 5,925,523; 6,007,988; 6,013,453; 6,200,759; WO 95/19431; WO 96/06166; WO 98/53057; WO 98/54311; WO 00/27878; WO 01/60970; WO 01/88197 and WO 02/099084.

Zinc finger and TALE DNA-binding domains can be engineered to bind to a predetermined nucleotide sequence, for example via engineering (altering one or more amino acids) of the recognition helix region of a naturally occurring zinc finger protein or by engineering of the amino acids involved in DNA binding (the repeat variable diresidue or RVD region). Therefore, engineered zinc finger proteins or TALE proteins are proteins that are non-naturally occurring. Non-limiting examples of methods for engineering zinc finger proteins and TALEs are design and selection. A designed protein is a protein not occurring in nature whose design/composition results principally from rational criteria. Rational criteria for design include application of substitution rules and computerized algorithms for processing information in a database storing information of existing ZFP or TALE designs (canonical and non-canonical RVDs) and binding data. See, for example, U.S. Pat. Nos. 9,458,205; 8,586,526; 6,140,081; 6,453,242; and 6,534,261; see also WO 98/53058; WO 98/53059; WO 98/53060; WO 02/016536 and WO 03/016496.

Various methods and compositions for targeted cleavage of genomic DNA have been described. Such targeted cleavage events can be used, for example, to induce targeted mutagenesis, induce targeted deletions of cellular DNA sequences, and facilitate targeted recombination at a predetermined chromosomal locus. See, e.g., U.S. Pat. Nos. 9,255,250; 9,200,266; 9,045,763; 9,005,973; 9,150,847; 8,956,828; 8,945,868; 8,703,489; 8,586,526; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publications 20030232410; 20050208489; 20050026157; 20050064474; 20060063231; 20080159996; 201000218264; 20120017290; 20110265198; 20130137104; 20130122591; 20130177983; 20130196373; 20140120622; 20150056705; 20150335708; 20160030477 and 20160024474, the disclosures of which are incorporated by reference in their entireties.

Also provided are one or more agents capable of introducing a genetic disruption. Also provided are polynucleotides (e.g., nucleic acid molecules) encoding one or more components of the one or more agent(s) capable of inducing a genetic disruption.

In some embodiments, gene repression is achieved using an inhibitory nucleic acid molecule that is an RNA interfering agent, which can be used to selectively suppress or repress expression of the gene. For example, gene repression can be carried out by RNA interference (RNAi), short interfering RNA (siRNA), short hairpin (shRNA), antisense, and/or ribozymes. In some embodiments, RNA interfering agents also can include other RNA species that can be processed intracellularly to produce shRNAs including, but not limited to, RNA species identical to a naturally occurring miRNA precursor or a designed precursor of an miRNA-like RNA.

In some embodiments, an RNA interfering agent is at least a partly double-stranded RNA having a structure characteristic of molecules that are known in the art to mediate inhibition of gene expression through an RNAi mechanism or an RNA strand comprising at least partially complementary portions that hybridize to one another to form such a structure. When an RNA contains complementary regions that hybridize with each other, the RNA will be said to self-hybridize. In some embodiments, an inhibitory nucleic acid, such as an RNA interfering agent, includes a portion that is substantially complementary to a target gene. In some embodiments, an RNA interfering agent targeted to a transcript can also be considered targeted to the gene that encodes and directs synthesis of the transcript. In some embodiments, a target region can be a region of a target transcript that hybridizes with an antisense strand of an RNA interfering agent. In some embodiments, a target transcript can be any RNA that is a target for inhibition by RNA interference.

In some embodiments, an RNA interfering agent is considered to be "targeted" to a transcript and to the gene that encodes the transcript if (1) the RNAi agent comprises a portion, e.g., a strand, that is at least approximately 80%, approximately 85%, approximately 90%, approximately 91%, approximately 92%, approximately 93%, approximately 94%, approximately 95%, approximately 96%, approximately 97%, approximately 98%, approximately 99%, or approximately 100% complementary to the transcript over a region about 15-29 nucleotides in length, e.g., a region at least approximately 15, approximately 17, approximately 18, or approximately 19 nucleotides in length; and/or (2) the Tm of a duplex formed by a stretch of 15 nucleotides of one strand of the RNAi agent and a 15 nucleotide portion of the transcript, under conditions (excluding temperature) typically found within the cytoplasm or nucleus of mammalian cells is no more than approximately 15° C. lower or no more than approximately 10° C. lower, than the Tm of a duplex that would be formed by the same 15 nucleotides of the RNA interfering agent and its exact complement; and/or (3) the stability of the transcript is reduced in the presence of the RNA interfering agent as compared with its absence.

In some embodiments, an RNA interfering agent optionally includes one or more nucleotide analogs or modifications. One of ordinary skill in the art will recognize that RNAi agents can include ribonucleotides, deoxyribonucleotide, nucleotide analogs, modified nucleotides or backbones, etc. In some embodiments, RNA interfering agents may be modified following transcription. In some embodiments, RNA interfering agents can contain one or more strands that hybridize or self-hybridize to form a structure that includes a duplex portion between about 15-29 nucleotides in length, optionally having one or more mismatched or unpaired nucleotides within the duplex.

In some embodiments, the term "short, interfering RNA" (siRNA) refers to a nucleic acid that includes a double-stranded portion between about 15-29 nucleotides in length and optionally further includes a single-stranded overhang {e.g., 1-6 nucleotides in length) on either or both strands. In some embodiments, the double-stranded portion can be between 17-21 nucleotides in length, e.g., 19 nucleotides in length. In some embodiments, the overhangs are present on the 3' end of each strand, can be about or approximately 2 to 4 nucleotides long, and can be composed of DNA or nucleotide analogs. An siRNA may be formed from two RNA strands that hybridize together, or may alternatively be generated from a longer double-stranded RNA or from a single RNA strand that includes a self-hybridizing portion, such as a short hairpin RNA. One of ordinary skill in the art will appreciate that one or more mismatches or unpaired nucleotides can be present in the duplex formed by the two siRNA strands. In some embodiments, one strand of an siRNA (the "antisense" or "guide" strand) includes a portion that hybridizes with a target nucleic acid, e.g., an mRNA transcript. In some embodiments, the antisense strand is perfectly complementary to the target over about 15-29 nucleotides, sometimes between 17-21 nucleotides, e.g., 19 nucleotides, meaning that the siRNA hybridizes to the target transcript without a single mismatch over this length. However, one of ordinary skill in the art will appreciate that one or more mismatches or unpaired nucleotides may be present in a duplex formed between the siRNA strand and the target transcript.

In some embodiments, a short hairpin RNA (shRNA) is a nucleic acid molecule comprising at least two complementary portions hybridized or capable of hybridizing to form a duplex structure sufficiently long to mediate RNAi (typically between 15-29 nucleotides in length), and at least one single-stranded portion, typically between approximately 1 and 10 nucleotides in length that forms a loop connecting the ends of the two sequences that form the duplex. In some embodiments, the structure may further comprise an overhang. In some embodiments, the duplex formed by hybridization of self-complementary portions of the shRNA may have similar properties to those of siRNAs and, in some cases, shRNAs can be processed into siRNAs by the conserved cellular RNAi machinery. Thus shRNAs can be precursors of siRNAs and can be similarly capable of inhibiting expression of a target transcript. In some embodiments, an shRNA includes a portion that hybridizes with a target nucleic acid, e.g., an mRNA transcript, and can be perfectly complementary to the target over about 15-29 nucleotides, sometimes between 17-21 nucleotides, e.g., 19 nucleotides. However, one of ordinary skill in the art will appreciate that one or more mismatches or unpaired nucleotides may be present in a duplex formed between the shRNA strand and the target transcript.

c. Delivery of Agents for Genetic Disruption

In some embodiments, the targeted genetic disruption, e.g., DNA break, of the endogenous genes encoding TRAC and/or β2M in humans is carried out by delivering or introducing one or more agent(s) capable of inducing a genetic disruption, e.g., Cas9 and/or gRNA components, to a cell (e.g. a cell of the CD57 depleted T cell population and/or the pooled CD57 depleted T cell population), using any of a number of known delivery method or vehicle for introduction or transfer to cells, for example, using lentiviral delivery vectors, or any of the known methods or vehicles for delivering Cas9 molecules and gRNAs. In some embodiments, the targeted genetic disruption, e.g., DNA break, of the endogenous genes encoding TRAC and/or β2M in humans is carried out by delivering or introducing one or more agent(s) capable of inducing a genetic disruption, e.g., Cas9 and/or gRNA components, to a cell (e.g. a cell of the CD27 enriched T cell population and/or the pooled CD27 enriched T cell population), using any of a number of known delivery method or vehicle for introduction or transfer to cells, for example, using lentiviral delivery vectors, or any of the known methods or vehicles for delivering Cas9 molecules and gRNAs. Exemplary methods are described in, e.g., Wang et al. (2012)1 *Immunother.* 35(9): 689-701; Cooper et al. (2003) *Blood.* 101:1637-1644; Verhoeyen et al. (2009) *Methods Mol Biol.* 506: 97-114; and Cavalieri et al. (2003) *Blood.* 102(2): 497-505. In some embodiments, nucleic acid sequences encoding one or more components of one or more agent(s) capable of inducing a genetic disruption, e.g., DNA break, is introduced into the cells, e.g., by any methods for introducing nucleic acids into a cell described herein or known. In some embodiments, a vector encoding components of one or more agent(s) capable of inducing a genetic disruption such as a CRISPR guide RNA and/or a Cas9 enzyme can be delivered into the cell.

In some embodiments, the one or more agent(s) capable of inducing a genetic disruption, e.g., one or more agent(s) that is a Cas9/gRNA, is introduced into the cell as a ribonucleoprotein (RNP) complex. RNP complexes include a sequence of ribonucleotides, such as an RNA or a gRNA molecule, and a protein, such as a Cas9 protein or variant thereof. For example, the Cas9 protein is delivered as RNP complex that comprises a Cas9 protein and a gRNA molecule targeting the target sequence, e.g., using electroporation or other physical delivery method. In some embodiments, the RNP is delivered into the cell via electroporation or other physical means, e.g., particle gun, Calcium Phosphate transfection, cell compression or squeezing. In some embodiments, the RNP can cross the plasma membrane of a cell without the need for additional delivery agents (e.g., small molecule agents, lipids, etc.). In some embodiments, delivery of the one or more agent(s) capable of inducing genetic disruption, e.g., CRISPR/Cas9, as an RNP offers an advantage that the targeted disruption occurs transiently, e.g., in cells to which the RNP is introduced, without propagation of the agent to cell progenies. For example, delivery by RNP minimizes the agent from being inherited to its progenies, thereby reducing the chance of off-target genetic disruption in the progenies. In such cases, the genetic disruption and the integration of transgene can be inherited by the progeny cells, but without the agent itself, which may further introduce off-target genetic disruptions, being passed on to the progeny cells.

Agent(s) and components capable of inducing a genetic disruption, e.g., a Cas9 molecule and gRNA molecule, can be introduced into target cells in a variety of forms using a variety of delivery methods and formulations, described in, e.g., WO 2015/161276; US 2015/0056705, US 2016/0272999, US 2017/0211075; or US 2017/0016027. The delivery methods and formulations can be used to deliver template polynucleotides and/or other agents to the cell in prior or subsequent steps of the methods described herein.

In some embodiments, DNA encoding Cas9 molecules and/or gRNA molecules, or RNP complexes comprising a Cas9 molecule and/or gRNA molecules, can be delivered into cells by known methods or as described herein. For example, Cas9-encoding and/or gRNA-encoding DNA can be delivered, e.g., by vectors (e.g., viral or non-viral vectors), non-vector based methods (e.g., using naked DNA or DNA complexes), or a combination thereof. In some embodiments, the polynucleotide containing the agent(s) and/or components thereof is delivered by a vector (e.g., viral vector/virus or plasmid). The vector may be any described herein.

In some aspects, a CRISPR enzyme (e.g. Cas9 nuclease) in combination with (and optionally complexed with) a guide sequence is delivered to the cell. For example, one or more elements of a CRISPR system is derived from a type I, type II, or type III CRISPR system. For example, one or more elements of a CRISPR system are derived from a particular organism comprising an endogenous CRISPR system, such as *Streptococcus pyogenes, Staphylococcus aureus* or *Neisseria meningitides*.

In some embodiments, a Cas9 nuclease (e.g., that encoded by mRNA from *Staphylococcus aureus* or from *Streptococcus pyogenes*, e.g. pCW-Cas9, Addgene #50661, Wang et al. (2014) *Science,* 3:343-80-4; or nuclease or nickase lentiviral vectors available from Applied Biological Materials (ABM; Canada) as Cat. No. K002, K003, K005 or K006) and a guide RNA specific to the target gene (e.g. TRAC and/or β2M in humans) are introduced into cells. In some embodiments, gRNA sequences that is or comprises a targeting domain sequence targeting the target site in a particular gene, such as the TRAC and/or β2M genes, designed or identified. A genome-wide gRNA database for CRISPR genome editing is publicly available, which contains exemplary single guide RNA (sgRNA) sequences targeting constitutive exons of genes in the human genome or mouse genome (see e.g., genescript.com/gRNA-database.html; see also, Sanjana et al. (2014) Nat. Methods, 11:783-4). In some aspects, the gRNA sequence is or comprises a sequence with minimal off-target binding to a non-target site or position.

In some embodiments, the polynucleotide containing the agent(s) and/or components thereof or RNP complex is delivered by a non-vector based method (e.g., using naked DNA or DNA complexes). For example, the DNA or RNA or proteins or combination thereof, e.g., ribonucleoprotein (RNP) complexes, can be delivered, e.g., by organically modified silica or silicate (Ormosil), electroporation, transient cell compression or squeezing (e.g., as described in Lee, et al. (2012) *Nano Lett* 12: 6322-27, Kollmannsperger et al (2016) Nat Comm 7, 10372 doi:10.1038/ncomms10372).), gene gun, sonoporation, magnetofection, lipid-mediated transfection, dendrimers, inorganic nanoparticles, calcium phosphates, or a combination thereof.

In some embodiments, delivery via electroporation comprises mixing the cells with the Cas9- and/or gRNA-encoding DNA or RNP complex in a cartridge, chamber or cuvette and applying one or more electrical impulses of defined duration and amplitude. In some embodiments, delivery via electroporation is performed using a system in which cells are mixed with the Cas9- and/or gRNA-encoding DNA in a vessel connected to a device (e.g., a pump) which feeds the mixture into a cartridge, chamber or cuvette wherein one or more electrical impulses of defined duration and amplitude are applied, after which the cells are delivered to a second vessel.

In some embodiments, the delivery vehicle is a non-viral vector. In some embodiments, the non-viral vector is an inorganic nanoparticle. Exemplary inorganic nanoparticles include, e.g., magnetic nanoparticles (e.g., $Fe_3MnO_2$) and silica. The outer surface of the nanoparticle can be conjugated with a positively charged polymer (e.g., polyethylenimine, polylysine, polyserine) which allows for attachment (e.g., conjugation or entrapment) of payload. In some embodiments, the non-viral vector is an organic nanoparticle. Exemplary organic nanoparticles include, e.g., SNALP liposomes that contain cationic lipids together with neutral helper lipids which are coated with polyethylene glycol (PEG), and protamine-nucleic acid complexes coated with lipid. Exemplary lipids and/or polymers are known and can be used in the provided embodiments.

In some embodiments, the vehicle has targeting modifications to increase target cell update of nanoparticles and liposomes, e.g., cell specific antigens, monoclonal antibodies, single chain antibodies, aptamers, polymers, sugars, and cell penetrating peptides (e.g., described in US 2016/0272999). In some embodiments, the vehicle uses fusogenic and endosome-destabilizing peptides/polymers. In some embodiments, the vehicle undergoes acid-triggered conformational changes (e.g., to accelerate endosomal escape of the cargo). In some embodiments, a stimulus-cleavable polymer is used, e.g., for release in a cellular compartment. For example, disulfide-based cationic polymers that are cleaved in the reducing cellular environment can be used.

In some embodiments, the delivery vehicle is a biological non-viral delivery vehicle. In some embodiments, the vehicle is an attenuated bacterium (e.g., naturally or artificially engineered to be invasive but attenuated to prevent pathogenesis and expressing the transgene (e.g., *Listeria monocytogenes*, certain *Salmonella* strains, *Bifidobacterium longum*, and modified *Escherichia coli*), bacteria having nutritional and tissue-specific tropism to target specific cells, bacteria having modified surface proteins to alter target cell specificity). In some embodiments, the vehicle is a genetically modified bacteriophage (e.g., engineered phages having large packaging capacity, less immunogenicity, containing mammalian plasmid maintenance sequences and having incorporated targeting ligands). In some embodiments, the vehicle is a mammalian virus-like particle. For example, modified viral particles can be generated (e.g., by purification of the "empty" particles followed by ex vivo assembly of the virus with the desired cargo). The vehicle can also be engineered to incorporate targeting ligands to alter target tissue-specificity. In some embodiments, the vehicle is a biological liposome. For example, the biological liposome is a phospholipid-based particle derived from human cells, e.g., erythrocyte ghosts, which are red blood cells broken down into spherical structures derived from the subject (e.g., tissue targeting can be achieved by attachment of various tissue or cell-specific ligands), or secretory exosomes-subject-derived membrane-bound nanovescicles (30-100 nm) of endocytic origin (e.g., can be produced from various cell types and can therefore be taken up by cells without the need for targeting ligands).

In some embodiments, RNA encoding Cas9 molecules and/or gRNA molecules, can be delivered into cells, e.g., target cells described herein, by known methods or as described herein. For example, Cas9-encoding and/or gRNA-encoding RNA can be delivered, e.g., by microinjection, electroporation, transient cell compression or squeezing (e.g., as described in Lee, et al. (2012) *Nano Lett* 12: 6322-27), lipid-mediated transfection, peptide-mediated delivery, or a combination thereof.

In some embodiments, delivery via electroporation comprises mixing the cells with the RNA encoding Cas9 molecules and/or gRNA molecules in a cartridge, chamber or cuvette and applying one or more electrical impulses of defined duration and amplitude. In some embodiments, delivery via electroporation is performed using a system in which cells are mixed with the RNA encoding Cas9 molecules and/or gRNA molecules in a vessel connected to a device (e.g., a pump) which feeds the mixture into a cartridge, chamber or cuvette wherein one or more electrical impulses of defined duration and amplitude are applied, after which the cells are delivered to a second vessel.

In some embodiments, Cas9 molecules can be delivered into cells by known methods or as described herein. For example, Cas9 protein molecules can be delivered, e.g., by microinjection, electroporation, transient cell compression or squeezing (e.g., as described in Lee, et al. (2012) *Nano Lett* 12: 6322-27), lipid-mediated transfection, peptide-mediated delivery, or a combination thereof. Delivery can be accompanied by DNA encoding a gRNA or by a gRNA.

In some embodiments, delivery via electroporation comprises mixing the cells with the Cas9 molecules with or without gRNA molecules in a cartridge, chamber or cuvette and applying one or more electrical impulses of defined duration and amplitude. In some embodiments, delivery via electroporation is performed using a system in which cells are mixed with the Cas9 molecules with or without gRNA molecules in a vessel connected to a device (e.g., a pump) which feeds the mixture into a cartridge, chamber or cuvette wherein one or more electrical impulses of defined duration and amplitude are applied, after which the cells are delivered to a second vessel.

In some embodiments, the polynucleotide containing the agent(s) and/or components thereof is delivered by a combination of a vector and a non-vector based method. For example, a virosome comprises a liposome combined with an inactivated virus (e.g., HW or influenza virus), which can result in more efficient gene transfer than either a viral or a liposomal method alone.

In some embodiments, more than one agent(s) or components thereof are delivered to the cell. For example, in some embodiments, agent(s) capable of inducing a genetic disruption of two or more locations in the genome, e.g., the TRAC and/or β2M loci, are delivered to the cell. In some embodiments, agent(s) and components thereof are delivered using one method. For example, in some embodiments, agent(s) for inducing a genetic disruption of the TRAC and/or β2M loci are delivered as polynucleotides encoding the components for genetic disruption. In some embodiments, one polynucleotide can encode agents that target the TRAC and/or β2M loci. In some embodiments, two or more different polynucleotides can encode the agents that target TRAC and/or β2M loci. In some embodiments, the agents capable of inducing a genetic disruption can be delivered as ribonucleoprotein (RNP) complexes, and two or more different RNP complexes can be delivered together as a mixture, or separately.

In some embodiments, one or more nucleic acid molecules other than the one or more agent(s) capable of inducing a genetic disruption and/or component thereof, e.g., the Cas9 molecule component and/or the gRNA molecule component, such as a template polynucleotide for HDR-directed integration (e.g., described in Section I.B. herein), are delivered. In some embodiments, the nucleic acid molecule, e.g., template polynucleotide, is delivered at the same time as one or more of the components of the Cas system. In some embodiments, the nucleic acid molecule is delivered before or after (e.g., less than about 1 minute, 5 minutes, 10 minutes, 15 minutes, 30 minutes, 1 hour, 2 hours, 3 hours, 6 hours, 9 hours, 12 hours, 1 day, 2 days, 3 days, 1 week, 2 weeks, or 4 weeks) one or more of the components of the Cas system are delivered. In some embodiments, the nucleic acid molecule, e.g., template polynucleotide, is delivered by a different means from one or more of the components of the Cas system, e.g., the Cas9 molecule component and/or the gRNA molecule component. The nucleic acid molecule, e.g., template polynucleotide, can be delivered by any of the delivery methods described herein. For example, the nucleic acid molecule, e.g., template polynucleotide, can be delivered by a viral vector, e.g., a retrovirus or a lentivirus, and the Cas9 molecule component and/or the gRNA molecule component can be delivered by electroporation. In some embodiments, the nucleic acid molecule, e.g., template polynucleotide, includes one or more transgenes, e.g., transgenes that encode a recombinant TCR, a recombinant CAR and/or other gene products.

d. Depletion of CD3+ T Cells

In some embodiments, a CD57 depleted and/or CD27 enriched T cell population (e.g. a T cell population or a pooled T cell population) is knocked out for one or more genes encoding a T-cell receptor (TCR) or a component thereof. In some embodiments the one or more genes is T cell receptor alpha constant (TRAC). In some embodiments, TRAC knockout disrupts formation of the TCR complex, and thereby CD3 cell surface expression, such that a cell knocked out for TRAC does not exhibit cell surface expression of CD3. In some embodiments, a CD57 depleted and/or CD27 enriched T cell population knocked out for TRAC is subject to depletion of CD3+ cells by any of the methods described herein. In some embodiments, depletion of CD3+ cells removes non-edited cells of the CD57 depleted and/or CD27 enriched T cell population that still express CD3. It is observed herein that CD3+ cells may be depleted from a T cell population by CD3 negative selection to produce a T cell population with >99% purity for CD3− T cells. Such methods may reduce the likelihood that the resulting T cell population, when administered to an allogeneic subject, will not cause TCR-mediated graft-versus-host disease (GvHD).

In some embodiments, a CD3 depleted population (a CD3 depleted T cell population and/or a pooled CD3 depleted T cell population) is obtained by depleting CD3+ cells from a CD57 depleted and/or CD27 enriched T cell population that has been knocked out for one or more genes encoding a TCR or a component thereof. For example, in some embodiments, a CD57 depleted T cell population (e.g. a CD57 depleted T cell population or a pooled CD57 depleted T cell population) knocked out for one or more genes encoding a TCR or a component thereof (e.g. TRAC) is depleted of CD3+ cells. In some embodiments, a CD27 enriched T cell population (e.g. a CD27 enriched T cell population or a pooled CD27 enriched T cell population) knocked out for one or more genes encoding a TCR or a component thereof (e.g. TRAC) is depleted of CD3+ cells.

In some embodiments, a donor sample from an individual donor is enriched for CD57− T cells and knocked out for one or more genes encoding a TCR or a component thereof (e.g. TRAC), to produce a knocked out CD57 depleted T cell population, which is subsequently depleted of CD3+ cells (a CD3 depleted T cell population). In some embodiments, CD57 depleted T cell populations knocked out for one or more genes encoding a TCR or a component thereof (e.g. TRAC) from a plurality of different individual donors are combined to produced a pooled knocked out CD57 depleted T cell population, which is subsequently depleted of CD3+ cells (a pooled CD3 depleted T cell population). In some embodiments, the donor sample is derived from a plurality of different donors. In some embodiments, a donor sample from a plurality of different donors is enriched for CD57− T cells and knocked out for one or more genes encoding a TCR or a component thereof (e.g. TRAC) to produce a pooled knocked out CD57− T cell population.

In particular embodiments, CD3+ T cells are removed, separated, or depleted from a knocked out CD57 depleted T cell population. In certain embodiments, at least 25%, 30%, 35%, 40%, 45%, 50%, 55%, 60%, 65%, 70%, 75%, 80%, 85%, 90%, 95%, 99%, or 99.9% CD3+ T cells are removed, separated, or depleted from the knocked out CD57 depleted T cell population.

In some embodiments, the CD3 depleted T cell population and/or the pooled CD3 depleted T cell population contains, contains about, or contains less than 50%, 45%, 40%, 35%, 30%, 25%, 20%, 15%, 10%, 5%, 1%, 0.1%, 0.01%, or 0.001% of the CD3+ T cells of the CD57 depleted T cell population and/or the pooled CD57 depleted T cell population, e.g., prior the selection, isolation, or enrichment. In particular embodiments, the pooled CD3 depleted T cell population and/or the CD3 depleted T cell population contains, contains about, or contains less than 20% of the CD3+ T cells of the pooled CD57 depleted T cell population and/or the CD57 depleted T cell population. In particular embodiments, the pooled CD3 depleted T cell population and/or the CD3 depleted T cell population contains, contains about, or contains less than 5% of the CD3+ T cells of the pooled CD57 depleted T cell population and/or the CD57 depleted T cell population. In particular embodiments, the pooled CD3 depleted T cell population and/or the CD3 depleted T cell population contains, contains about, or contains less than 1% of the CD3+ T cells of the pooled CD57 depleted T cell population and/or the CD57 depleted T cell population in particular embodiments, the pooled CD3 depleted T cell population and/or the CD3 depleted T cell population contains, contains about, or contains less than 0.1% of the CD3+ T cells of the pooled CD57 depleted T cell population and/or the CD57 depleted T cell population. In particular embodiments, the pooled CD3 depleted T cell population and/or the CD3 depleted T cell population contains, contains about, or contains less than 0.01% of the CD3+ T cells of the pooled CD57 depleted T cell population and/or the CD57 depleted T cell population. In some embodiments, the frequency of the CD3+ T cells in the pooled CD3 depleted T cell population and/or the CD3 depleted T cell population is less than at or about 35%, 30%, 20%, 10%, 5%, 1%, or 0.1% of the frequency of CD3+ T cells in the pooled CD57 depleted T cell population and/or the CD57 depleted T cell population. In some embodiments, the pooled CD3 depleted T cell population and/or the CD57 depleted T cell population comprises less than at or about 3%, less than at or about 2%, less than at or about 1%, less than at or about 0.1%, or less than at or about 0.01% CD3+ T cells. In some embodiments, the pooled CD3 depleted T cell population and/or the CD3 depleted T cell population is free or is essentially free of CD3+ T cells.

In some embodiments, a donor sample from an individual donor is enriched for CD27+ T cells and knocked out for one or more genes encoding a TCR or a component thereof (e.g. TRAC), to produce a knocked out CD27 enriched T cell population, which is subsequently depleted of CD3+ cells (a CD3 depleted T cell population). In some embodiments, CD27 enriched T cell populations knocked out for one or more genes encoding a TCR or a component thereof (e.g. TRAC) from a plurality of different individual donors are combined to produced a pooled knocked out CD27 enriched T cell population, which is subsequently depleted of CD3+ cells (a pooled CD3 depleted T cell population). In some embodiments, the donor sample is derived from a plurality of different donors. In some embodiments, a donor sample from a plurality of different donors is enriched for CD27+ T cells and knocked out for one or more genes encoding a TCR or a component thereof (e.g. TRAC) to produce a pooled knocked out CD27+ T cell population.

In particular embodiments, CD3+ T cells are removed, separated, or depleted from a knocked out CD27 enriched T cell population. In certain embodiments, at least 25%, 30%, 35%, 40%, 45%, 50%, 55%, 60%, 65%, 70%, 75%, 80%, 85%, 90%, 95%, 99%, or 99.9% CD3+ T cells are removed, separated, or depleted from the knocked out CD27 enriched T cell population.

In some embodiments, the CD3 depleted T cell population and/or the pooled CD3 depleted T cell population contains, contains about, or contains less than 50%, 45%, 40%, 35%, 30%, 25%, 20%, 15%, 10%, 5%, 1%, 0.1%, 0.01%, or 0.001% of the CD3+ T cells of the CD27 enriched T cell population and/or the pooled CD27 enriched T cell population, e.g., prior the selection, isolation, or enrichment. In particular embodiments, the pooled CD3 depleted T cell population and/or the CD3 depleted T cell population contains, contains about, or contains less than 20% of the CD3+ T cells of the pooled CD27 enriched T cell population and/or the CD27 enriched T cell population. In particular embodiments, the pooled CD3 depleted T cell population and/or the CD3 depleted T cell population contains, contains about, or contains less than 5% of the CD3+ T cells of the pooled CD27 enriched T cell population and/or the CD27 enriched T cell population. In particular embodiments, the pooled CD3 depleted T cell population and/or the CD3 depleted T cell population contains, contains about, or contains less than 1% of the CD3+ T cells of the pooled CD27 enriched T cell population and/or the CD27 enriched T cell population in particular embodiments, the pooled CD3 depleted T cell population and/or the CD3 depleted T cell population contains, contains about, or contains less than 0.1% of the CD3+ T cells of the pooled CD27 enriched T cell population and/or the CD27 enriched T cell population. In particular embodiments, the pooled CD3 depleted T cell population and/or the CD3 depleted T cell population contains, contains about, or contains less than 0.01% of the CD3+ T cells of the pooled CD27 enriched T cell population and/or the CD27 enriched T cell population. In some embodiments, the frequency of the CD3+ T cells in the pooled CD3 depleted T cell population and/or the CD3 depleted T cell population is less than at or about 35%, 30%, 20%, 10%, 5%, 1%, or 0.1% of the frequency of CD3+ T cells in the pooled CD27 enriched T cell population and/or the CD27 enriched T cell population. In some embodiments, the pooled CD3 depleted T cell population and/or the CD27 enriched T cell population comprises less than at or about 3%, less than at or about 2%, less than at or about 1%, less than at or about 0.1%, or less than at or about 0.01% CD3+ T cells. In some embodiments, the pooled CD3 depleted T cell population and/or the CD3 depleted T cell population is free or is essentially free of CD3+ T cells.

In some embodiments, the pooled CD3 depleted T cell population and/or the CD3 depleted T cell population is frozen, e.g., cryopreserved and/or cryoprotected, after isolation, selection and/or enrichment. In particular embodiments, a population of enriched CD3− CD4+ T cells is frozen, e.g., cryopreserved and/or cryoprotected, after isolation, selection and/or enrichment. In certain embodiments, a population of enriched CD3− CD8+ T cells is frozen, e.g., cryopreserved and/or cryoprotected, after isolation, selection and/or enrichment. In some embodiments, the pooled CD3 depleted T cell population and/or the CD3 depleted T cell population is frozen e.g., cryopreserved and/or cryoprotected, prior to any steps of expanding, harvesting, and/or formulating the population of cells. In particular embodiments, a population of enriched CD3-CD4+ T cells is frozen e.g., cryopreserved and/or cryoprotected, prior to any steps of cultivating, expanding, harvesting, and/or formulating the population of cells. In some embodiments, a population of enriched CD3-CD8+ T cells is frozen e.g., cryopreserved and/or cryoprotected, prior to any steps of cultivating, expanding, harvesting, and/or formulating the population of cells.

In particular embodiments, the one or more cryoprotected input compositions is stored, e.g., at or at about −80° C., for between 12 hours and 7 days, between 24 hours and 120 hours, or between 2 days and 5 days. In particular embodiments, the one or more cryoprotected input compositions is stored at or at about −80° C., for an amount of time of less than 10 days, 9 days, 8 days, 7 days, 6 days, or 5 days, 4 days, 3 days, 2 days, or 1 day. In some embodiments, the one or more cryoprotected input compositions is stored at or at about −70° C. or −80° C. for less than 3 days, such as for about 2 days.

In some embodiments, "depleting" or "removing" when referring to one or more particular cell type or cell population, refers to decreasing the number or percentage of the cell type or population, e.g., compared to the total number of cells in or volume of the composition, or relative to other cell types, such as by negative selection based on markers expressed by the population or cell, or by positive selection based on a marker not present on the cell population or cell to be depleted. In general, the terms depleting or removing does not require complete removal of the cell, cell type, or population from the composition. In some embodiments, CD3+ cells are depleted by any of the methods described in Section II.D.

3. Exemplary Features of the Genetically Engineered Cells

In particular embodiments, the provided methods produce compositions of genetically engineered T cells enriched for CD57− T cells. In some embodiments, the provided methods produce compositions of genetically engineered T cells enriched for CD27+ T cells. In some embodiments, the engineered T cell composition is from an individual donor. In some embodiments, the engineered T cell composition from an individual donor is combined with an engineered T cell composition from one or more other individual donors to produce a pooled engineered T cell composition from a plurality of different donors. In some embodiments, the engineered T cell composition is a pooled engineered T cell composition from a plurality of different donors.

In some embodiments, the provided cells and methods include those in which expression of β2M is eliminated or reduced, which, in some cases, can result in reduced surface expression of MHC class I. In some embodiments, expression of a regulatory molecule or gene that regulates expression of β2M is targeted for reduction, disruption, deletion or elimination in the cell. In some cases, the β2M gene is directly targeted using an agent that represses, disrupts, deletes or eliminates expression of the β2M gene. In some embodiments, the provided cells and methods include cells having no more than 50%, 40%, 30%, 20%, 10%, 5% or less of the expression of the endogenous β2M as compared to a reference or corresponding cell in which the β2M has not been repressed or disrupted. In some embodiments, a plurality of cells are reduced or disrupted for the β2M. In some aspects, provided is a composition in which at least or at least about 20%, 25%, 30%, 35%, 40%, 45%, 50%, 55%, 60%, 65%, 70%, 75%, 80%, 85%, 90% or 95% of cells in the composition contain the genetic disruption of or a reduction in expression of the β2M or of a regulatory molecule or gene regulating expression of the 132M. In some embodiments, a gene regulating expression of β2M or the β2M gene is disrupted. In some embodiments, the cell or a plurality of cells in a composition (e.g. greater than or about 50%, 55%, 60%, 65%, 70%, 75%, 80%, 85%, 90%, 95%, or more) contain the genetic disruption, do not express the endogenous β2M gene or a regulatory molecule regulating expression of β2M, do not contain a contiguous β2M gene or the gene of a regulatory molecule regulating expression of β2M and/or do not express β2M or the regulatory molecule regulating expression of β2M. In some embodiments, the cell or a plurality of cells in a composition (e.g. at least or greater than about 50%, 60%, 65%, 70%. 75%, 80%, 85%, 90% or 95% of cells in a composition of cells) are knocked out or disrupted in both alleles of the β2M gene or the gene of a regulatory molecule regulating expression of β2M, i.e. comprise a biallelic deletion, in such percentage of cells.

In some embodiments, the provided cells and methods include those in which expression of TRAC is eliminated or reduced, which, in some cases, can result in reduced surface expression of a TCR In some embodiments, expression of a regulatory molecule or gene that regulates expression of TRAC is targeted for reduction, disruption, deletion or elimination in the cell. In some cases, the TRAC gene is directly targeted using an agent that represses, disrupts, deletes or eliminates expression of the TRAC gene. In some embodiments, the provided cells and methods include cells having no more than 50%, 40%, 30%, 20%, 10%, 5% or less of the expression of the endogenous TRAC as compared to a reference or corresponding cell in which the TRAC has not been repressed or disrupted. In some embodiments, a plurality of cells are reduced or disrupted for the TRAC. In some aspects, provided is a composition in which at least or at least about 20%, 25%, 30%, 35%, 40%, 45%, 50%, 55%, 60%, 65%, 70%, 75%, 80%, 85%, 90% or 95% of cells in the composition contain the genetic disruption of or a reduction in expression of the TRAC or of a regulatory molecule or gene regulating expression of the TRAC. In some embodiments, a gene regulating expression of TRAC or the TRAC gene is disrupted. In some embodiments, the cell or a plurality of cells in a composition (e.g. greater than or about 50%, 55%, 60%, 65%, 70%, 75%, 80%, 85%, 90%, 95%, or more) contain the genetic disruption, do not express the endogenous TRAC gene or a regulatory molecule regulating expression of TRAC, do not contain a contiguous TRAC gene or the gene of a regulatory molecule regulating expression of TRAC and/or do not express TRAC or the regulatory molecule regulating expression of TRAC. In some embodiments, the cell or a plurality of cells in a composition (e.g. at least or greater than about 50%, 60%, 65%, 70%. 75%, 80%, 85%, 90% or 95% of cells in a composition of cells) are knocked out or disrupted in both alleles of the TRAC gene or the gene of a regulatory molecule regulating expression of TRAC, i.e. comprise a biallelic deletion, in such percentage of cells.

In some embodiments, the provided cells and methods include those in which cell surface expression of CD3 is eliminated or reduced, which, in some cases, can result in reduced surface expression of a TCR. In some embodiments, the provided cells and methods include cell populations having about 50%, 40%, 30%, 20%, 10%, 5% fewer cells exhibiting cell surface expression of CD3 as compared to a reference or corresponding cell population in which CD3+ cells are not depleted. In some embodiments, a plurality of cells are reduced or eliminated for CD3 cell surface expression. In some aspects, provided is a composition in which at least or at least about 20%, 25%, 30%, 35%, 40%, 45%, 50%, 55%, 60%, 65%, 70%, 75%, 80%, 85%, 90% or 95% of cells in the composition do not express CD3.

Any of a variety of known methods for validating or confirming knockdown or knockout of a target gene can be employed. Exemplary of such methods include, but are not limited to, northern blotting, PCR, including RT-PCR or qRT-PCR, proliferation assays, reporter assays or protein detection methods (e.g. flow cytometry for surface staining of encoded protein).

In some embodiments, the level or degree of expression can be determined via standard procedures. It is within the level of a skilled artisan to empirically determine or confirm the extent to which the regulatory molecule or gene has been repressed or disrupted, as well as the extent to which expression of the MHC and/or TCR molecule (or all alleles or haplotypes of the MHC molecule) has been affected or reduced. In some embodiments, immunoaffinity reagents can be used to select or identify the cells. In some embodiments, the particular MHC and/or TRC expression is confirmed by flow cytometry. In some cases, broadly reactive or monomorphic antibodies can be used that generally recognize more than one MHC allele, such as a particular MHC class or classes. In some aspects, one or more allele specific antibody can be used. It is within the level of a skilled artisan to choose the particular antibody depending on the particular endogenous MHC expressed by the cell and/or the specificity of MHC detection that is desired. Various anti-MHC antibodies, including anti-HLA antibodies, are well known in the art and available from commercial and private sources. Various anti-TCR antibodies are well known in the art and available from commercial and private sources.

F. Stimulation

Provided herein are methods for stimulating CD57− enriched T cell populations, such as a CD57 depleted T cell population or a pooled CD57 deleted T cell population. In some embodiments, a CD57 depleted T cell population from an individual donor is stimulated to produce a stimulated T cell pouation. In some embodiments, a stimulated CD57 depleted T cell population from an individual donor is combined with a stimulated CD57 depleted T cell population from one or more other individual donors to produce a stimulated T cell population from a plurality of different donors. In some embodiments, a pooled CD57 depleted T cell population from a plurality of different donors is stimulated to produce a stimulated T cell pouation from the plurality of different donors.

Also provided herein are methods for stimulating CD27+ enriched T cell populations, such as a CD27 enriched T cell population or a pooled CD27 enriched T cell population. In some embodiments, a CD27 enriched T cell population from an individual donor is stimulated to produce a stimulated T cell pouation. In some embodiments, a stimulated CD27 enriched T cell population from an individual donor is combined with a stimulated CD27 enriched T cell population from one or more other individual donors to produce a stimulated T cell population from a plurality of different donors. In some embodiments, a pooled CD27 enriched T cell population from a plurality of different donors is stimulated to produce a stimulated T cell pouation from the plurality of different donors.

In some embodiments, the provided methods are used in connection with stimulating cells of the CD57 depleted T cell population and/or the pooled CD57 depleted T cell population, under conditions to activate the T cells of the composition. In some embodiments, the provided methods are used in connection with stimulating cells of the CD27 enriched T cell population and/or the pooled CD27 enriched T cell population, under conditions to activate the T cells of the composition. In some embodiments, the stimulating conditions include conditions that activate or stimulate, and/or are capable of activing or stimulating a signal in the cell, e.g., a CD4+ or a CD8+ T cell, such as a signal generated from a TCR and/or a coreceptor. In some embodiments, the stimulating conditions include one or more steps of culturing, cultivating, incubating, activating, propagating the cells with and/or in the presence of a stimulatory reagent, e.g., a reagent that activates or stimulates, and/or is capable of activing or stimulating a signal in the cell. In some embodiments, the stimulatory reagent stimulates and/or activates a TCR and/or a coreceptor. In particular embodiments, the stimulatory reagent is a reagent described in Section II.E.1.

In certain embodiments, the CD57 depleted T cell population and/or the pooled CD57 depleted T cell population are incubated under stimulating conditions prior to genetically engineering (e.g. knocking in and/or knocking out) the cells, e.g., transfecting and/or transducing the cell such as by a technique provided in Sections II.D. In particular embodiments, one or more populations of enriched CD57− T cells (e.g. the CD57 depleted T cell population and/or the pooled CD57 depleted T cell population) are incubated under stimulating conditions after the one or more compositions have been isolated, selected, enriched, or obtained from a biological sample (e.g. a donor samples). In particular embodiments, the one or more populations of enriched CD57− T cells (e.g. the CD57 depleted T cell population and/or the pooled CD57 depleted T cell population) have been previously cryoperserved and stored, and are thawed prior to the incubation. In some embodiments, the thawed population is derived from an individual donor. In some embodiments, a thawed population from an individual donor is combined with a thawed population from one or more other individual donors to produce a thawed population from a plurality of donors. In some embodiments, the thawed population is derived from a plurality of different donors.

In certain embodiments, the one or more populations of enriched CD57− T cells (e.g. the CD57 depleted T cell population and/or the pooled CD57 depleted T cell population) are or include two separate populations of enriched CD57− T cells. In particular embodiments, the two separate compositions of enriched T cells, e.g., two separate compositions of enriched T cells selected, isolated, and/or enriched from the same biological sample (e.g. donor sample), are separately incubated under stimulating conditions. In certain embodiments, the two separate compositions include a composition of enriched CD57− CD4+ T cells. In particular embodiments, the two separate compositions include a composition of enriched CD57− CD8+ T cells. In particular embodiments, the two separate compositions include a composition of enriched CD57− CD3+ T cells. In some embodiments, two separate compositions of enriched CD57− CD4+ T cells and enriched CD57− CD8+ T cells are separately incubated under stimulating conditions. In some embodiments, a single composition of enriched T cells is incubated under stimulating conditions. In certain embodiments, the single composition is a composition of enriched CD57− CD4+ T cells. In certain embodiments, the single composition is a composition of enriched CD57− CD8+ T cells. In certain embodiments, the single composition is a composition of enriched CD57− CD3+ T cells. In some embodiments, the single composition is a composition of enriched CD57−CD4+ and CD57− CD8+ T cells that have been combined from separate compositions prior to the incubation.

In some embodiments, the provided methods are or include stimulating populations of enriched CD57− T cells (e.g. a CD57 depleted T cell population and/or a pooled CD57 depleted T cell population). In certain embodiments, the provided methods include one or more steps for stimulating populations of enriched CD57–CD4+ T cells. In particular embodiments, the provided methods include one or more steps for stimulating populations of enriched CD57–CD8+ T cells. In certain embodiments, the populations of enriched CD57– CD4+ T cells and populations of enriched CD57– CD8+ T cells are stimulated such as by incubating the cells under stimulating conditions, e.g., any stimulating conditions described herein such as in Section II.E. In particular embodiments, the stimulating conditions are or include the presence of a stimulatory reagent. In certain embodiments, separate populations of enriched CD57– CD4+ T cells and enriched CD57– CD8+ T cells are separately stimulated. In particular embodiments, separate populations of enriched CD57– CD4+ T cells and enriched CD57– CD8+ T cells are combined or mixed prior to being stimulated, such that a combined composition of enriched CD57–CD4+ T cells and CD57– CD8+ T cells is stimulated.

In certain embodiments, a method or process for stimulating T cells includes selecting or removing CD57+ cells from a donor sample, and then separately selecting for CD4+ T cells and CD8+ T cells from the population negatively selected for CD57, such as to generated a population of enriched CD57–CD4+ T cells and a population of enriched CD57–CD8+ T cells. In certain embodiments, the separate populations of enriched CD57–CD4+ T cells and enriched CD57–CD8+ T cells are separately incubated under stimulating conditions. In particular embodiments, the separate populations of enriched CD57–CD4+ T cells and enriched CD57–CD8+ T cells are combined, such as a separately incubated under stimulating conditions. In some embodiments, the stimulating includes the presence of a stimulatory reagent. In certain embodiments, the stimulatory reagent is or includes an anti-CD3 and anti-CD28 antibody conjugated paramagnetic bead. In particular embodiments, the stimulatory reagent is or includes a streptavidin mutein oligomeric particle with reversibly bound anti-CD3 and anti-CD28 Fabs.

In some embodiments, the population of enriched CD57– CD4+ T cells that is incubated under stimulating conditions includes at least at or about 60%, at least at or about 65%, at least at or about 70%, at least at or about 75%, at least at or about 80%, at least at or about 85%, at least at or about 90%, at least at or about 95%, at least at or about 98%, at least at or about 99%, at least at or about 99.5%, at least at or about 99.9%, or at or at about 100% CD57– CD4+ T cells. In certain embodiments, the composition of enriched CD57– CD4+ T cells that is incubated under stimulating conditions includes less than at or about 40%, less than at or about 35%, less than at or about 30%, less than at or about 25%, less than at or about 20%, less than at or about 15%, less than at or about 10%, less than at or about 5%, less than at or about 1%, less than at or about 0.1%, or less than at or about 0.01% T cells that are positive for CD57 expression or negative for CD4 expression.

In certain embodiments, the population of enriched CD57– CD8+ T cells that is incubated under stimulating conditions includes at least at or about 60%, at least at or about 65%, at least at or about 70%, at least at or about 75%, at least at or about 80%, at least at or about 85%, at least at or about 90%, at least at or about 95%, at least at or about 98%, at least at or about 99%, at least at or about 99.5%, at least at or about 99.9%, or at or at about 100% CD57– CD8+ T cells. In certain embodiments, the composition of enriched CD57– CD4+ T cells that is incubated under stimulating conditions includes less than at or about 40%, less than at or about 35%, less than at or about 30%, less than at or about 25%, less than at or about 20%, less than at or about 15%, less than at or about 10%, less than at or about 5%, less than at or about 1%, less than at or about 0.1%, or less than at or about 0.01% T cells that are positive for CD57 expression or negative for CD8 expression. In certain embodiments, the composition of enriched CD57– CD8+ T cells that is incubated under stimulating conditions includes less than at or about 40%, less than at or about 35%, less than at or about 30%, less than at or about 25%, less than at or about 20%, less than at or about 15%, less than at or about 10%, less than at or about 5%, less than at or about 1%, less than at or about 0.1%, or less than at or about 0.01% T cells that are positive for CD57 expression or negative for CD8 expression.

In certain embodiments, the population of enriched CD57– CD3+ T cells that is incubated under stimulating conditions includes at least at or about 60%, at least at or about 65%, at least at or about 70%, at least at or about 75%, at least at or about 80%, at least at or about 85%, at least at or about 90%, at least at or about 95%, at least at or about 98%, at least at or about 99%, at least at or about 99.5%, at least at or about 99.9%, or at or at about 100% CD57– CD3+ T cells. In certain embodiments, the composition of enriched CD57– CD3+ T cells that is incubated under stimulating conditions includes less than at or about 40%, less than at or about 35%, less than at or about 30%, less than at or about 25%, less than at or about 20%, less than at or about 15%, less than at or about 10%, less than at or about 5%, less than at or about 1%, less than at or about 0.1%, or less than at or about 0.01% T cells that are positive for CD57 expression or negative for CD3 expression.

In certain embodiments, separate compositions of enriched CD57–CD4+ and CD57–CD8+ T cells are combined into a single composition and are incubated under stimulating conditions. In certain embodiments, separate stimulated compositions of enriched CD57–CD4+ and enriched CD57– CD8+ T cells are combined into a single composition after the incubation has been performed and/or completed.

In certain embodiments, the CD27 enriched T cell population and/or the pooled CD27 enriched T cell population are incubated under stimulating conditions prior to genetically engineering (e.g. knocking in and/or knocking out) the cells, e.g., transfecting and/or transducing the cell such as by a technique provided in Sections II.D. In particular embodiments, one or more populations of enriched CD27+ T cells (e.g. the CD27 enriched T cell population and/or the pooled CD27 enriched T cell population) are incubated under stimulating conditions after the one or more compositions have been isolated, selected, enriched, or obtained from a biological sample (e.g. a donor samples). In particular embodiments, the one or more populations of enriched CD27+ T cells (e.g. the CD27 enriched T cell population and/or the pooled CD27 enriched T cell population) have been previously cryoperserved and stored, and are thawed prior to the incubation. In some embodiments, the thawed population is derived from an individual donor. In some embodiments, a thawed population from an individual donor is combined with a thawed population from one or more other individual donors to produce a thawed population from a plurality of donors. In some embodiments, the thawed population is derived from a plurality of different donors.

In certain embodiments, the one or more populations of enriched CD27+ T cells (e.g. the CD27 enriched T cell population and/or the pooled CD27 enriched T cell population) are or include two separate populations of enriched CD27+ T cells. In particular embodiments, the two separate compositions of enriched T cells, e.g., two separate compositions of enriched T cells selected, isolated, and/or enriched from the same biological sample (e.g. donor sample), are separately incubated under stimulating conditions. In certain embodiments, the two separate compositions include a composition of enriched CD27+ CD4+ T cells. In particular embodiments, the two separate compositions include a composition of enriched CD27+ CD8+ T cells. In particular embodiments, the two separate compositions include a composition of enriched CD27+ CD3+ T cells. In some embodiments, two separate compositions of enriched CD27+ CD4+ T cells and enriched CD27+ CD8+ T cells are separately incubated under stimulating conditions. In some embodiments, a single composition of enriched T cells is incubated under stimulating conditions. In certain embodiments, the single composition is a composition of enriched CD27+ CD4+ T cells. In certain embodiments, the single composition is a composition of enriched CD27+ CD8+ T cells. In certain embodiments, the single composition is a composition of enriched CD27+ CD3+ T cells. In some embodiments, the single composition is a composition of enriched CD27+ CD4+ and CD27+ CD8+ T cells that have been combined from separate compositions prior to the incubation.

In some embodiments, the provided methods are or include stimulating populations of enriched CD27+ T cells (e.g. a CD27 enriched T cell population and/or a pooled CD27 enriched T cell population). In certain embodiments, the provided methods include one or more steps for stimulating populations of enriched CD27+ CD4+ T cells. In particular embodiments, the provided methods include one or more steps for stimulating populations of enriched CD27+ CD8+ T cells. In certain embodiments, the populations of enriched CD27+ CD4+ T cells and populations of enriched CD27+ CD8+ T cells are stimulated such as by incubating the cells under stimulating conditions, e.g., any stimulating conditions described herein such as in Section II.E. In particular embodiments, the stimulating conditions are or include the presence of a stimulatory reagent. In certain embodiments, separate populations of enriched CD27+ CD4+ T cells and enriched CD27+ CD8+ T cells are separately stimulated. In particular embodiments, separate populations of enriched CD27+ CD4+ T cells and enriched CD27+ CD8+ T cells are combined or mixed prior to being stimulated, such that a combined composition of enriched CD27+CD4+ T cells and CD27+ CD8+ T cells is stimulated.

In certain embodiments, a method or process for stimulating T cells includes selecting or removing CD27− cells from a donor sample, and then separately selecting for CD4+ T cells and CD8+ T cells from the population negatively selected for CD27, such as to generated a population of enriched CD27+ CD4+ T cells and a population of enriched CD27+ CD8+ T cells. In certain embodiments, the separate populations of enriched CD27+ CD4+ T cells and enriched CD27+ CD8+ T cells are separately incubated under stimulating conditions. In particular embodiments, the separate populations of enriched CD27+ CD4+ T cells and enriched CD27+ CD8+ T cells are combined, such as a separately incubated under stimulating conditions. In some embodiments, the stimulating includes the presence of a stimulatory reagent. In certain embodiments, the stimulatory reagent is or includes an anti-CD3 and anti-CD28 antibody conjugated paramagnetic bead. In particular embodiments, the stimulatory reagent is or includes a streptavidin mutein oligomeric particle with reversibly bound anti-CD3 and anti-CD28 Fabs.

In some embodiments, the population of enriched CD27+ CD4+ T cells that is incubated under stimulating conditions includes at least at or about 60%, at least at or about 65%, at least at or about 70%, at least at or about 75%, at least at or about 80%, at least at or about 85%, at least at or about 90%, at least at or about 95%, at least at or about 98%, at least at or about 99%, at least at or about 99.5%, at least at or about 99.9%, or at or at about 100% CD27+ CD4+ T cells. In certain embodiments, the composition of enriched CD27+ CD4+ T cells that is incubated under stimulating conditions includes less than at or about 40%, less than at or about 35%, less than at or about 30%, less than at or about 25%, less than at or about 20%, less than at or about 15%, less than at or about 10%, less than at or about 5%, less than at or about 1%, less than at or about 0.1%, or less than at or about 0.01% T cells that are negative for CD27 expression or negative for CD4 expression.

In certain embodiments, the population of enriched CD27+ CD8+ T cells that is incubated under stimulating conditions includes at least at or about 60%, at least at or about 65%, at least at or about 70%, at least at or about 75%, at least at or about 80%, at least at or about 85%, at least at or about 90%, at least at or about 95%, at least at or about 98%, at least at or about 99%, at least at or about 99.5%, at least at or about 99.9%, or at or at about 100% CD27+ CD8+ T cells. In certain embodiments, the composition of enriched CD27+ CD4+ T cells that is incubated under stimulating conditions includes less than at or about 40%, less than at or about 35%, less than at or about 30%, less than at or about 25%, less than at or about 20%, less than at or about 15%, less than at or about 10%, less than at or about 5%, less than at or about 1%, less than at or about 0.1%, or less than at or about 0.01% T cells that are negative for CD27 expression or negative for CD8 expression. In certain embodiments, the composition of enriched CD27+ CD8+ T cells that is incubated under stimulating conditions includes less than at or about 40%, less than at or about 35%, less than at or about 30%, less than at or about 25%, less than at or about 20%, less than at or about 15%, less than at or about 10%, less than at or about 5%, less than at or about 1%, less than at or about 0.1%, or less than at or about 0.01% T cells that are negative for CD27 expression or negative for CD8 expression.

In certain embodiments, the population of enriched CD27+ CD3+ T cells that is incubated under stimulating conditions includes at least at or about 60%, at least at or about 65%, at least at or about 70%, at least at or about 75%, at least at or about 80%, at least at or about 85%, at least at or about 90%, at least at or about 95%, at least at or about 98%, at least at or about 99%, at least at or about 99.5%, at least at or about 99.9%, or at or at about 100% CD27+ CD3+ T cells. In certain embodiments, the composition of enriched CD27+ CD3+ T cells that is incubated under stimulating conditions includes less than at or about 40%, less than at or about 35%, less than at or about 30%, less than at or about 25%, less than at or about 20%, less than at or about 15%, less than at or about 10%, less than at or about 5%, less than at or about 1%, less than at or about 0.1%, or less than at or about 0.01% T cells that are negative for CD27 expression or negative for CD3 expression.

In certain embodiments, separate compositions of enriched CD27+ CD4+ and CD27+ CD8+ T cells are combined into a single composition and are incubated under stimulating conditions. In certain embodiments, separate stimulated compositions of enriched CD27+ CD4+ and enriched CD27+ CD8+ T cells are combined into a single composition after the incubation has been performed and/or completed.

In some embodiments, the incubation under stimulating conditions can include culture, cultivation, stimulation, activation, propagation, including by incubation in the presence of stimulating conditions, for example, conditions designed to induce proliferation, expansion, activation, and/or survival of cells in the population, to mimic antigen exposure, and/or to prime the cells for genetic engineering, such as for the introduction of a recombinant antigen receptor. In particular embodiments, the stimulating conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some aspects, the stimulation and/or incubation under stimulating conditions is carried out in accordance with techniques such as those described in U.S. Pat. No. 6,040,177 to Riddell et al., Klebanoff et al. (2012) *J Immunother.* 35(9): 651-660, Terakura et al. (2012) Blood. 1:72-82, and/or Wang et al. (2012) *J Immunother.* 35(9):689-701.

In some embodiments, the CD57− T cells (e.g. the CD57 depleted T cell population and/or the pooled CD57 depleted T cell population) are expanded by adding to the culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some embodiments, the CD27+ T cells (e.g. the CD27 enriched T cell population and/or the pooled CD27 enriched T cell population) are expanded by adding to the culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25° C., generally at least about 30 degrees, and generally at or about 37° C. In some embodiments, a temperature shift is effected during culture, such as from 37° C. to 35° C. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In particular embodiments, the stimulating conditions include incubating, culturing, and/or cultivating the cells with a stimulatory reagent. In particular embodiments, the stimulatory reagent is a reagent described in Section III.A.1. In certain embodiments, the stimulatory reagent contains or includes a bead. In particular embodiments, the stimulatory reagent contains or includes an oligomeric reagent, e.g., an oligomeric streptavidin mutein reagent. In certain embodiments, the start and or initiation of the incubation, culturing, and/or cultivating cells under stimulating conditions occurs when the cells are come into contact with and/or are incubated with the stimulatory reagent. In particular embodiments, the cells are incubated prior to, during, and/or subsequent to genetically engineering the cells, e.g., introducing a recombinant polynucleotide into the cell such as by transduction or transfection. In some embodiments, the composition of enriched T cells are incubated at a ratio of stimulatory reagent and/or beads to cells at or at about 3:1, 2.5:1, 2:1, 1.5:1, 1.25:1, 1.2:1, 1.1:1, 1:1, 0.9:1, 0.8:1, 0.75:1, 0.67:1, 0.5:1, 0.3:1, or 0.2:1. In particular embodiments, the ratio of stimulatory reagent and/or beads to cells is between 2.5:1 and 0.2:1, between 2:1 and 0.5:1, between 1.5:1 and 0.75:1, between 1.25:1 and 0.8:1, between 1.1:1 and 0.9:1. In particular embodiments, the ratio of stimulatory reagent to cells is about 1:1 or is 1:1.

In some embodiments, the cells are stimulated in the presence of, of about, or of at least 0.01 μg, 0.02 μg, 0.03 μg, 0.04 μg, 0.05 μg, 0.1 μg, 0.2 μg, 0.3 μg, 0.4 μg, 0.5 μg, 0.75 μg, 1 μg, 2 μg, 3 μg, 4 μg, 5 μg, 6 μg, 7 μg, 8 μg, 9 μg, or 10 μg of the stimulatory reagent per $10^6$ cells. In some embodiments, the cells are stimulated in the presence of or of about 4 μg of the stimulatory reagent per $10^6$ cells. In particular embodiments, the cells are stimulated in the presence of or of about 0.8 μg of the stimulatory reagent per $10^6$ cells.

In certain embodiments, the cells, e.g., cells of the input population, are stimulated or subjected to stimulation e.g., cultured under stimulating conditions such as in the presence of a stimulatory reagent, at a density of, of about, or at least $0.01\times10^6$ cells/mL, $0.1\times10^6$ cells/mL, $0.5\times10^6$ cells/mL, $1.0\times10^6$ cells/mL, $1.5\times10^6$ cells/mL, $2.0\times10^6$ cells/mL, $2.5\times10^6$ cells/mL, $3.0\times10^6$ cells/mL, $4.0\times10^6$ cells/mL, $5.0\times10^6$ cells/mL, $10\times10^6$ cells/mL, or $50\times10^6$ cells/mL. In certain embodiments, the cells, e.g., cells of the input population, are stimulated or subjected to stimulation e.g., cultured under stimulating conditions such as in the presence of a stimulatory reagent, at a density of, of about, or at least $3.0\times10^6$ cells/mL. In certain embodiments, the cells of the input are viable cells.

In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor. Exemplary stimulatory reagents are described below.

In some embodiments, at least a portion of the incubation in the presence of one or more stimulating conditions or a stimulatory agents is carried out in the internal cavity of a centrifugal chamber, for example, under centrifugal rotation, such as described in International Publication Number WO2016/073602. In some embodiments, at least a portion of the incubation performed in a centrifugal chamber includes mixing with a reagent or reagents to induce stimulation and/or activation. In some embodiments, cells, such as selected cells, are mixed with a stimulating condition or stimulatory agent in the centrifugal chamber. In some aspects of such processes, a volume of cells is mixed with an amount of one or more stimulating conditions or agents that is far less than is normally employed when performing similar stimulations in a cell culture plate or other system.

In some embodiments, the stimulating agent is added to cells in the cavity of the chamber in an amount that is substantially less than (e.g. is no more than 5%, 10%, 20%, 30%, 40%, 50%, 60%, 70% or 80% of the amount) as compared to the amount of the stimulating agent that is typically used or would be necessary to achieve about the same or similar efficiency of selection of the same number of cells or the same volume of cells when selection is performed without mixing in a centrifugal chamber, e.g. in a tube or bag with periodic shaking or rotation. In some embodiments, the incubation is performed with the addition of an incubation buffer to the cells and stimulating agent to achieve a target volume with incubation of the reagent of, for example, 10 mL to 200 mL, such as at least or about at least or about or 10 mL, 20 mL, 30 mL, 40 mL, 50 mL, 60 mL, 70 mL, 80 mL, 90 mL, 100 mL, 150 mL or 200 mL. In some embodiments, the incubation buffer and stimulating agent are pre-mixed before addition to the cells. In some embodiments, the incubation buffer and stimulating agent are separately added to the cells. In some embodiments, the stimulating incubation is carried out with periodic gentle mixing condition, which can aid in promoting energetically favored interactions and thereby permit the use of less overall stimulating agent while achieving stimulating and activation of cells.

In some embodiments, the incubation generally is carried out under mixing conditions, such as in the presence of spinning, generally at relatively low force or speed, such as speed lower than that used to pellet the cells, such as from or from about 600 rpm to 1700 rpm (e.g. at or about or at least 600 rpm, 1000 rpm, or 1500 rpm or 1700 rpm), such as at an RCF at the sample or wall of the chamber or other container of from or from about 80 g to 100 g (e.g. at or about or at least 80 g, 85 g, 90 g, 95 g, or 100 g). In some embodiments, the spin is carried out using repeated intervals of a spin at such low speed followed by a rest period, such as a spin and/or rest for 1, 2, 3, 4, 5, 6, 7, 8, 9, or 10 seconds, such as a spin at approximately 1 or 2 seconds followed by a rest for approximately 5, 6, 7, or 8 seconds.

In some embodiments, the total duration of the incubation, e.g. with the stimulating agent, is between or between about 1 hour and 96 hours, 1 hour and 72 hours, 1 hour and 48 hours, 4 hours and 36 hours, 8 hours and 30 hours or 12 hours and 24 hours, such as at least or about at least 6 hours, 12 hours, 18 hours, 24 hours, 36 hours or 72 hours. In some embodiments, the further incubation is for a time between or about between 1 hour and 48 hours, 4 hours and 36 hours, 8 hours and 30 hours or 12 hours and 24 hours, inclusive.

In some embodiments, the stimulation, e.g. culturing the cells under stimulating conditions, is performed for, for about, or for less than, 48 hours, 42 hours, 36 hours, 30 hours, 24 hours, 22 hours, 20 hours, 18 hours, 16 hours, or 12 hours. In some embodiments, the stimulation, e.g. culturing the cells under stimulating conditions, is performed for 20±4 hours or between or between about 16 hours and 24 hours. In particular embodiments, the stimulation, e.g. culturing the cells under stimulating conditions, is performed for between or between about 36 hours and 12 hours, 30 hours and 18 hours, or for or for about 24 hours, or 22 hours. In some embodiments, the stimulation, e.g. culturing the cells under stimulating conditions, is performed for, for about, or for less than, 2 days or one day.

In particular embodiments, an amount of, of about, or of at least $50\times10^6$, $100\times10^6$, $150\times10^6$, $200\times10^6$, $250\times10^6$, $300\times10^6$, $350\times10^6$, $400\times10^6$, $450\times10^6$, $500\times10^6$, $550\times10^6$, $600\times10^6$, $700\times10^6$, $800\times10^6$, $900\times10^6$, or $1,000\times10^6$ cells of the selected population (e.g. the CD57 depleted T cell population and/or the pooled CD57 depleted T cell population) are stimulated or subjected to stimulation, e.g., cultured under stimulating conditions. In particular embodiments, the amount of the selected population (e.g. the CD57 depleted T cell population and/or the pooled CD57 depleted T cell population) that is stimulated, e.g., cultured under stimulating conditions, is at or about $50\times10^6$ cells, at or about $100\times10^6$ cells, at or about $150\times10^6$ cells, at or about $200\times10^6$ cells, at or about $250\times10^6$ cells, at or about $300\times10^6$ cells, at or about $350\times10^6$ cells, at or about $400\times10^6$ cells, at or about $450\times10^6$ cells, at or about $500\times10^6$ cells, at or about $550\times10^6$ cells, at or about $600\times10^6$ cells, at or about $700\times10^6$ cells, at or about $800\times10^6$ cells, at or about $900\times10^6$ cells, or at or about $1,000\times10^6$ cells, or any value between any of the foregoing. In particular embodiments, an amount of or of about $900\times10^6$ cells of the selected population (e.g. the CD57 depleted T cell population and/or the pooled CD57 depleted T cell population) is stimulated, e.g., cultured under stimulating conditions. In some embodiments, the selected population is the CD27 depleted T cell population and/or the pooled CD27 depleted T cell population. In some embodiments, the selected population is the CD27 enriched T cell population and/or the pooled CD27 enriched T cell population.

In particular embodiments, the selected composition (e.g. the CD57 depleted T cell population and/or the pooled CD57 depleted T cell population) comprises viable CD4+ T cells and viable CD8+ T cells, at a ratio of between 1:10 and 10:1, between 1:5 and 5:1, between 4:1 and 1:4, between 1:3 and 3:1, between 2:1 and 1:2, between 1.5:1 and 1:1.5, between 1.25:1 and 1:1.25, between 1.2:1 and 1:1.2, between 1.1:1 and 1:1.1, or about 1:1, or 1:1 viable CD4+ T cells to viable CD8+ T cells. In particular embodiments, the selected composition (e.g. the CD57 depleted T cell population and/or the pooled CD57 depleted T cell population) comprises viable CD4+ T cells and viable CD8+ T cells, at a ratio of about 1:1 or 1:1 viable CD4+ T cells to viable CD8+ T cells. In particular embodiments, an amount of or of about $450\times10^6$ CD4+ cells of the selected population (e.g. the CD57 depleted T cell population and/or the pooled CD57 depleted T cell population) are stimulated, e.g., cultured under stimulating conditions. In particular embodiments, an amount of or of about $450\times10^6$ CD8+ cells of the selected population (e.g. the CD57 depleted T cell population and/or the pooled CD57 depleted T cell population) are stimulated, e.g., cultured under stimulating conditions. In particular embodiments, an amount of or of about $450\times10^6$ CD4+ T cells and an amount of or of about $450\times10^6$ CD8+ T cells of the selected population (e.g. the CD57 depleted T cell population and/or the pooled CD57 depleted T cell population) are stimulated, e.g., cultured under stimulating conditions. In some embodiments, the selected population is the CD27 depleted T cell population and/or the pooled CD27 depleted T cell population. In some embodiments, the selected population is the CD27 enriched T cell population and/or the pooled CD27 enriched T cell population.

In particular embodiments, the stimulating conditions include incubating, culturing, and/or cultivating a composition of enriched T cells with and/or in the presence of one or more cytokines. In particular embodiments, the one or more cytokines are recombinant cytokines. In some embodiments, the one or more cytokines are human recombinant cytokines. In certain embodiments, the one or more cytokines bind to and/or are capable of binding to receptors that are expressed by and/or are endogenous to T cells. In particular embodiments, the one or more cytokines is or includes a member of the 4-alpha-helix bundle family of cytokines. In some embodiments, members of the 4-alpha-helix bundle family of cytokines include, but are not limited to, interleukin-2 (IL-2), interleukin-4 (IL-4), interleukin-7 (IL-7), interleukin-9 (IL-9), interleukin 12 (IL-12), interleukin 15 (IL-15), granulocyte colony-stimulating factor (G-CSF), and granulocyte-macrophage colony-stimulating factor (GM-CSF). In some embodiments, the one or more cytokines is or includes IL-15. In particular embodiments, the one or more cytokines is or includes IL-7. In particular embodiments, the one or more cytokines is or includes IL-2.

In certain embodiments, the amount or concentration of the one or more cytokines are measured and/or quantified with International Units (IU). International units may be used to quantify vitamins, hormones, cytokines, vaccines, blood products, and similar biologically active substances. In some embodiments, IU are or include units of measure of the potency of biological preparations by comparison to an international reference standard of a specific weight and strength e.g., WHO 1st International Standard for Human IL-2, 86/504. International Units are the only recognized and standardized method to report biological activity units that are published and are derived from an international collaborative research effort. In particular embodiments, the IU for population, sample, or source of a cytokine may be obtained through product comparison testing with an analogous WHO standard product. For example, in some embodiments, the IU/mg of a population, sample, or source of human recombinant IL-2, IL-7, or IL-15 is compared to the WHO standard IL-2 product (NIBSC code: 86/500), the WHO standard IL-17 product (NIBSC code: 90/530) and the WHO standard IL-15 product (NIBSC code: 95/554), respectively.

In some embodiments, the biological activity in IU/mg is equivalent to (ED50 in ng/ml)-1×106. In particular embodiments, the ED50 of recombinant human IL-2 or IL-15 is equivalent to the concentration required for the half-maximal stimulation of cell proliferation (XTT cleavage) with CTLL-2 cells. In certain embodiments, the ED50 of recombinant human IL-7 is equivalent to the concentration required for the half-maximal stimulation for proliferation of PHA-activated human peripheral blood lymphocytes. Details relating to assays and calculations of IU for IL-2 are discussed in Wadhwa et al., Journal of Immunological Methods (2013), 379 (1-2): 1-7; and Gearing and Thorpe, Journal of Immunological Methods (1988), 114 (1-2): 3-9; details relating to assays and calculations of IU for IL-15 are discussed in Soman et al. Journal of Immunological Methods (2009) 348 (1-2): 83-94.

In some embodiments, the cells, e.g., the selected cells, such as the CD57 depleted T cell population and/or the pooled CD57 depleted T cell population, are stimulated or subjected to stimulation in the presence of a cytokine, e.g., a recombinant human cytokine, at a concentration of between 1 IU/mL and 1,000 IU/mL, between 10 IU/mL and 50 IU/mL, between 50 IU/mL and 100 IU/mL, between 100 IU/mL and 200 IU/mL, between 100 IU/mL and 500 IU/mL, between 250 IU/mL and 500 IU/mL, or between 500 IU/mL and 1,000 IU/mL. In some embodiments, the cells are the CD27 depleted T cell population and/or the pooled CD27 depleted T cell population. In some embodiments, the selected cells are the CD27 enriched T cell population and/or the pooled CD27 enriched T cell population.

In some embodiments, the cells, e.g., the selected cells, are stimulated or subjected to stimulation in the presence of recombinant IL-2, e.g., human recombinant IL-2, at a concentration between 1 IU/mL and 500 IU/mL, between 10 IU/mL and 250 IU/mL, between 50 IU/mL and 200 IU/mL, between 50 IU/mL and 150 IU/mL, between 75 IU/mL and 125 IU/mL, between 100 IU/mL and 200 IU/mL, or between 10 IU/mL and 100 IU/mL. In particular embodiments, cells, e.g., cells of the input population, are stimulated or subjected to stimulation in the presence of recombinant IL-2 at a concentration at or at about 50 IU/mL, 60 IU/mL, 70 IU/mL, 80 IU/mL, 90 IU/mL, 100 IU/mL, 110 IU/mL, 120 IU/mL, 130 IU/mL, 140 IU/mL, 150 IU/mL, 160 IU/mL, 170 IU/mL, 180 IU/mL, 190 IU/mL, or 100 IU/mL. In some embodiments, the cells, e.g., the selected cells, are stimulated or subjected to stimulation in the presence of or of about 100 IU/mL of recombinant IL-2, e.g., human recombinant IL-2.

In some embodiments, the cells, e.g., the selected cells, are stimulated or subjected to stimulation in the presence of recombinant IL-7, e.g., human recombinant IL-7, at a concentration between 100 IU/mL and 2,000 IU/mL, between 500 IU/mL and 1,000 IU/mL, between 100 IU/mL and 500 IU/mL, between 500 IU/mL and 750 IU/mL, between 750 IU/mL and 1,000 IU/mL, or between 550 IU/mL and 650 IU/mL. In particular embodiments, the cells, e.g., the selected cells, are stimulated or subjected to stimulation in the presence of IL-7 at a concentration at or at about 50 IU/mL, 100 IU/mL, 150 IU/mL, 200 IU/mL, 250 IU/mL, 300 IU/mL, 350 IU/mL, 400 IU/mL, 450 IU/mL, 500 IU/mL, 550 IU/mL, 600 IU/mL, 650 IU/mL, 700 IU/mL, 750 IU/mL, 800 IU/mL, 750 IU/mL, 750 IU/mL, 750 IU/mL, or 1,000 IU/mL. In particular embodiments, the cells, e.g., the selected cells, are stimulated or subjected to stimulation in the presence of or of about 600 IU/mL of recombinant IL-7, e.g., human recombinant IL-7.

In some embodiments, the cells, e.g., the selected cells, are stimulated or subjected to stimulation in the presence of recombinant IL-15, e.g., human recombinant IL-15, at a concentration between 1 IU/mL and 500 IU/mL, between 10 IU/mL and 250 IU/mL, between 50 IU/mL and 200 IU/mL, between 50 IU/mL and 150 IU/mL, between 75 IU/mL and 125 IU/mL, between 100 IU/mL and 200 IU/mL, or between 10 IU/mL and 100 IU/mL. In particular embodiments, cells, e.g., a cell of the selected population, are stimulated or subjected to stimulation in the presence of recombinant IL-15 at a concentration at or at about 50 IU/mL, 60 IU/mL, 70 IU/mL, 80 IU/mL, 90 IU/mL, 100 IU/mL, 110 IU/mL, 120 IU/mL, 130 IU/mL, 140 IU/mL, 150 IU/mL, 160 IU/mL, 170 IU/mL, 180 IU/mL, 190 IU/mL, or 200 IU/mL. In some embodiments, the cells, e.g., the selected cells, are stimulated or subjected to stimulation in the presence of or of about 100 IU/mL of recombinant IL-15, e.g., human recombinant IL-15.

In particular embodiments, the cells, e.g., cells from the selected population, are stimulated or subjected to stimulation under stimulating conditions in the presence of IL-2, IL-7, and/or IL-15. In some embodiments, the IL-2, IL-7, and/or IL-15 are recombinant. In certain embodiments, the IL-2, IL-7, and/or IL-15 are human. In particular embodiments, the one or more cytokines are or include human recombinant IL-2, IL-7, and/or IL-15. In certain embodiments, the cells are stimulated or subjected to stimulation under stimulating conditions in the presence of recombinant IL-2, IL-7, and IL-15. In certain embodiments, the cells are stimulated or subjected to stimulation under stimulating conditions in the presence of recombinant IL-2 of or of about 100 IU/mL, recombinant IL-7 of or of about 600 IU/mL, and recombinant IL-15 of or of about 100 IU/mL.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some aspects, stimulation is carried out in accordance with techniques such as those described in U.S. Pat. No. 6,040,177 to Riddell et al., Klebanoff et al. (2012) J Immunother. 35(9): 651-660, Terakura et al. (2012) Blood. 1:72-82, and/or Wang et al. (2012) J Immunother. 35(9):689-701.

In some embodiments, the stimulation is performed in serum free media. In some embodiments, the serum free media is a defined and/or well-defined cell culture media. In certain embodiments, the serum free media is a controlled culture media that has been processed, e.g., filtered to remove inhibitors and/or growth factors. In some embodiments, the serum free media contains proteins. In certain embodiments, the serum-free media may contain serum albumin, hydrolysates, growth factors, hormones, carrier proteins, and/or attachment factors.

In some embodiments, the stimulation is performed in serum free media described herein or in PCT/US2018/064627. In some embodiments, the serum-free medium comprises a basal medium (e.g. OpTmizer™ T-Cell Expansion Basal Medium (ThermoFisher)), supplemented with one or more supplement. In some embodiments, the one or more supplement is serum-free. In some embodiments, the serum-free medium comprises a basal medium supplemented with one or more additional components for the maintenance, expansion, and/or activation of a cell (e.g., a T cell), such as provided by an additional supplement (e.g. OpTmizer™ T-Cell Expansion Supplement (ThermoFisher)). In some embodiments, the serum-free medium further comprises a serum replacement supplement, for example, an immune cell serum replacement, e.g., ThermoFisher, #A2596101, the CTS™ Immune Cell Serum Replacement, or the immune cell serum replacement described in Smith et al. *Clin Transl Immunology.* 2015 January; 4(1): e31. In some embodiments, the serum-free medium further comprises a free form of an amino acid such as L-glutamine. In some embodiments, the serum-free medium further comprises a dipeptide form of L-glutamine (e.g., L-alanyl-L-glutamine), such as the dipeptide in Glutamax™ (ThermoFisher). In some embodiments, the serum-free medium further comprises one or more recombinant cytokines, such as recombinant human IL-2, recombinant human IL-7, and/or recombinant human IL-15. In some embodiments, at least a portion of the stimulation in the presence of one or more stimulating conditions or a stimulatory reagent is carried out in the internal cavity of a centrifugal chamber, for example, under centrifugal rotation, such as described in International Publication Number WO2016/073602 which is incorporated by reference. In some embodiments, at least a portion of the stimulation performed in a centrifugal chamber includes mixing with a reagent or reagents to induce stimulation and/or activation. In some embodiments, cells, such as selected cells, are mixed with a stimulating condition or stimulatory agent in the centrifugal chamber. In some aspects of such processes, a volume of cells is mixed with an amount of one or more stimulating conditions or agents that is far less than is normally employed when performing similar stimulations in a cell culture plate or other system.

In some embodiments, the stimulation generally is carried out under mixing conditions, such as in the presence of spinning, generally at relatively low force or speed, such as speed lower than that used to pellet the cells, such as from or from about 600 rpm to 1700 rpm (e.g. at or about or at least 600 rpm, 1000 rpm, or 1500 rpm or 1700 rpm), such as at an RCF at the sample or wall of the chamber or other container of from or from about 80 g to 100 g (e.g. at or about or at least 80 g, 85 g, 90 g, 95 g, or 100 g). In some embodiments, the spin is carried out using repeated intervals of a spin at such low speed followed by a rest period, such as a spin and/or rest for 1, 2, 3, 4, 5, 6, 7, 8, 9, or 10 seconds, such as a spin at approximately 1 or 2 seconds followed by a rest for approximately 5, 6, 7, or 8 seconds.

In certain embodiments, the stimulation is performed under static conditions, such as conditions that do not involve centrifugation, shaking, rotating, rocking, or perfusion, e.g., continuous or semi-continuous perfusion of the media. In some embodiments, either prior to or shortly after, e.g., within 5, 15, or 30 minutes, the initiation, the cells are transferred (e.g., transferred under sterile conditions) to a container such as a bag or vial, and placed in an incubator. In particular embodiments, incubator is set at, at about, or at least 16° C., 24° C., or 35° C. In some embodiments, the incubator is set at 37° C., at about at 37° C., or at 37° C.±2° C., ±1° C., ±0.5° C., or ±0.1° C. In particular embodiments, the stimulation under static condition is performed in a cell culture bag placed in an incubator. In some embodiments, the culture bag is composed of a single-web polyolefin gas permeable film which enables monocytes, if present, to adhere to the bag surface.

In particular aspects, the methods employ reversible systems in which at least one reagent (e.g., an affinity reagent or a stimulatory reagent) capable of binding to a molecule on the surface of a cell (cell surface molecule), is reversibly associated with a reagent (e.g., affinity reagent or stimulatory reagent). In some cases, the reagent contains a plurality of binding sites capable of reversibly binding to the reagent (e.g., an affinity reagent or stimulatory reagent). In some cases, the reagent (e.g., affinity reagent or stimulatory reagent) is a multimerization reagent. In some embodiments, the at least one reagent (e.g., an affinity reagent or stimulatory reagent) contains at least one binding site B that can specifically bind an epitope or region of the molecule and also contains a binding partner C that specifically binds to at least one binding site Z of the reagent (e.g., affinity reagent or stimulatory reagent). In some cases, the binding interaction between the binding partner C and the at least one binding site Z is a non-covalent interaction. In some embodiments, the binding interaction, such as non-covalent interaction, between the binding partner C and the at least one binding site Z is reversible.

In some embodiments, the reversible association can be mediated in the presence of a substance, such as a competition reagent, that is or contains a binding site that also is able to bind to the at least one binding site Z. Generally, the substance (e.g. competition reagent) can act as a competitor due to a higher binding affinity for the binding site Z present in the reagent and/or due to being present at higher concentrations than the binding partner C, thereby detaching and/or dissociating the binding partner C from the reagent. In some embodiments, the affinity of the substance (e.g. competition reagent) for the at least one binding site Z is greater than the affinity of the binding partner C of the agent (e.g., an affinity reagent or stimulatory reagent) for the at least one binding site Z. Thus, in some cases, the bond between the binding site Z of the reagent and the binding partner C of the reagent (e.g., an affinity reagent or stimulatory reagent) can be disrupted by addition of the substance (e.g. competition reagent), thereby rendering the association of the reagent (e.g., an affinity reagent or stimulatory reagent) and reagent (e.g., affinity reagent or stimulatory reagent) reversible.

Reagents that can be used in such reversible systems are described and known in the art, see e.g., U.S. Pat. Nos. 5,168,049; 5,506,121; 6,103,493; 7,776,562; 7,981,632; 8,298,782; 8,735,540; 9,023,604; and International published PCT Appl. Nos. WO2013/124474 and WO2014/076277. Non-limiting examples of reagents and binding partners capable of forming a reversible interaction, as well as substances (e.g. competition agents) capable of reversing such binding, are described below.

In some embodiments, the stimulation results in activation and/or proliferation of the cells, for example, prior to transduction.

1. Stimulatory Reagents

In particular embodiments, the stimulating conditions include incubating, culturing, and/or cultivating the cells with a stimulatory reagent. In certain embodiments, the stimulatory reagent contains or includes a bead. In certain embodiments, the initiation of the stimulation occurs when the cells are incubated or contacted with the stimulatory reagent. In particular embodiments, the stimulatory reagent contains or includes an oligomeric reagent, e.g., a streptavidin mutein oligomer. In particular embodiments, the stimulatory reagent activates and/or is capable of activating one or more intracellular signaling domains of one or more components of a TCR complex and/or one or more intracellular signaling domains of one or more costimulatory molecules.

In some embodiments, the stimulating conditions or stimulatory reagents include one or more agent, e.g., ligand, which is capable of activating an intracellular signaling domain of a TCR complex. In some embodiments, an agent as contemplated herein can include, but is not limited to, RNA, DNA, proteins (e.g., enzymes), antigens, polyclonal antibodies, monoclonal antibodies, antibody fragments, carbohydrates, lipids lectins, or any other biomolecule with an affinity for a desired target. In some embodiments, the desired target is a T cell receptor and/or a component of a T cell receptor. In certain embodiments, the desired target is CD3. In certain embodiment, the desired target is a T cell costimulatory molecule, e.g., CD28, CD137 (4-1-BB), OX40, or ICOS. The one or more agents may be attached directly or indirectly to the bead by a variety of known methods. The attachment may be covalent, noncovalent, electrostatic, or hydrophobic and may be accomplished by a variety of attachment means, including for example, a chemical means, a mechanical means, or an enzymatic means. In some embodiments, the agent is an antibody or antigen binding fragment thereof, such as a Fab. In some embodiments, a biomolecule (e.g., a biotinylated anti-CD3 antibody) may be attached indirectly to the bead via another biomolecule (e.g., anti-biotin antibody) that is directly attached to the bead.

In some embodiments, the stimulatory reagent contains one or more agents (e.g. antibody) that is attached to a bead (e.g., a paramagnetic bead) and specifically binds to one or more of the following macromolecules on a cell (e.g., a T cell): CD2, CD3, CD4, CD5, CD8, CD25, CD27, CD28, CD29, CD31, CD44, CD45RA, CD45RO, CD54 (ICAM-1), CD127, MHCI, MHCII, CTLA-4, ICOS, PD-1, OX40, CD27 L (CD70), 4-1BB (CD137), 4-1BBL, CD30L, LIGHT, IL-2R, IL-12R, IL-1R, IL-15R; IFN-gammaR, TNF-alphaR, IL-4R, IL-10R, CD18/CD11a (LFA-1), CD62 L (L-selectin), CD29/CD49d (VLA-4), Notch ligand (e.g. Delta-like 1/4, Jagged 1/2, etc.), CCR1, CCR2, CCR3, CCR4, CCR5, CCR7, and CXCR3 or fragment thereof including the corresponding ligands to these macromolecules or fragments thereof. In some embodiments, an agent (e.g. antibody) attached to the bead specifically binds to one or more of the following macromolecules on a cell (e.g. a T cell): CD28, CD62 L, CCR7, CD27, CD127, CD3, CD4, CD8, CD45RA, and/or CD45RO.

In some embodiments, one or more of the agents attached to the bead is an antibody. The antibody can include a polyclonal antibody, monoclonal antibody (including full length antibodies which have an immunoglobulin Fc region), antibody compositions with polyepitopic specificity, multispecific antibodies (e.g., bispecific antibodies, diabodies, and single-chain molecules, as well as antibody fragments (e.g., Fab, F(ab')2, and Fv). In some embodiments, the stimulatory reagent is an antibody fragment (including antigen-binding fragment), e.g., a Fab, Fab'-SH, Fv, scFv, or (Fab')2 fragment. It will be appreciated that constant regions of any isotype can be used for the antibodies contemplated herein, including IgG, IgM, IgA, IgD, and IgE constant regions, and that such constant regions can be obtained from any human or animal species (e.g., murine species).

In some embodiments, the agent is an antibody that binds to and/or recognizes one or more components of a T cell receptor. In particular embodiments, the agent is an anti-CD3 antibody. In certain embodiments, the agent is an antibody that binds to and/or recognizes a coreceptor. In some embodiments, the stimulatory reagent comprises an anti-CD28 antibody. In some embodiments, the stimulatory reagent comprises an anti-CD28 antibody and an anti-CD3 antibody. In some embodiments, the stimulatory reagent comprises one or more stimulatory agents. In some embodiments, the stimulatory reagent comprises a primary and a secondary stimulatory agent. In some embodiments, the first stimulatory agent is an anti-CD3 antibody or antigen-binding fragment thereof, for example as described herein, and the second stimulatory agent is an anti-CD28 antibody or antigen-binding fragment thereof, for example as described herein. In some embodiments, the first stimulatory agent is an anti-CD3 Fab, for example as described herein, and the second stimulatory agent is an anti-CD28 Fab, for example as described herein.

In some embodiments, the cells, e.g., cells of the input composition, are stimulated in the presence of a ratio of stimulatory reagent to cells at or at about 3:1, 2.5:1, 2:1, 1.5:1, 1.25:1, 1.2:1, 1.1:1, 1:1, 0.9:1, 0.8:1, 0.75:1, 0.67:1, 0.5:1, 0.3:1, or 0.2:1. In particular embodiments, the ratio of stimulatory reagent to cells is between 2.5:1 and 0.2:1, between 2:1 and 0.5:1, between 1.5:1 and 0.75:1, between 1.25:1 and 0.8:1, between 1.1:1 and 0.9:1. In particular embodiments, the ratio of stimulatory reagent to cells is about 1:1 or is 1:1. In particular embodiments, the ratio of stimulatory reagent to cells is about 0.3:1 or is 0.3:1. In particular embodiments, the ratio of stimulatory reagent to cells is about 0.2:1 or is 0.2:1.

In some embodiments, the cells are stimulated in the presence of, of about, or of at least 0.01 μg, 0.02 μg, 0.03 μg, 0.04 μg, 0.05 μs, 0.1 μs, 0.2 μs, 0.3 μs, 0.4 μg, 0.5 μg, 0.75 μg, 1 μg, 2 μg, 3 μg, 4 μg, 5 μg, 6 μg, 7 μg, 8 μg, 9 μg, or 10 μg of the stimulatory reagent per $10^6$ cells. In some embodiments, the cells are stimulated in the presence of or of about 4 μg per $10^6$ cells. In particular embodiments, the cells are stimulated or subjected to stimulation in the presence of or of about 3 μg per $10^6$ cells. In particular embodiments, the cells are stimulated or subjected to stimulation in the presence of or of about 2.5 μg per $10^6$ cells. In particular embodiments, the cells are stimulated or subjected to stimulation in the presence of or of about 2 μg per $10^6$ cells. In particular embodiments, the cells are stimulated or subjected to stimulation in the presence of or of about 1.8 μg per $10^6$ cells. In particular embodiments, the cells are stimulated or subjected to stimulation in the presence of or of about 1.6 μg per $10^6$ cells. In particular embodiments, the cells are stimulated or subjected to stimulation in the presence of or of about 1.4 μg per $10^6$ cells. In particular embodiments, the cells are stimulated or subjected to stimulation in the presence of or of about 1.2 μg per $10^6$ cells. In particular embodiments, the cells are stimulated or subjected to stimulation in the presence of or of about 1 μg per $10^6$ cells. In particular embodiments, the cells are stimulated in the presence of or of about 0.8 μg per $10^6$ cells. In various embodiments, the cells are stimulated in the presence of or of about 0.8 μg per $10^6$ cells.

In some embodiments, the stimulatory reagent binds to a molecule on the surface of a cell, which binding between the stimulatory reagent and the molecule is capable of inducing, delivering, or modulating a stimulatory signal in the cells. In some instances, the cell surface molecule (e.g. receptor) is a signaling molecule. In some such cases, the stimulatory reagent is capable of specifically binding to a signaling molecule expressed by one or more target cells (e.g., T cells). In some instances, the stimulatory reagent is any agent that is capable of inducing or delivering a stimulatory signal in a cell (e.g., a T cell) upon binding to a cell surface molecule, such as a receptor. In some embodiments, the stimulatory signal can be immunostimulatory, in which case the stimulatory agent is capable of inducing, delivering, or modulating a signal that is involved in or that does stimulate an immune response by the cell (e.g. T cell), e.g., increase immune cell proliferation or expansion, immune cell activation, immune cell differentiation, cytokine secretion, cytotoxic activity or one or more other functional activities of an immune cell. In some embodiments, the stimulatory signal can be inhibitory, in which case the stimulatory reagent is capable of inducing, delivering, or modulating a stimulatory signal in the cell (e.g. T cell) that is involved in or that does inhibit an immune response, e.g. inhibits or decreases immune cell proliferation or expansion, immune cell activation, immune cell differentiation, cytokine secretion, cytotoxic activity or one or more other functional activities of an immune cell.

In some embodiments, the stimulatory reagent comprises a primary stimulatory agent. In some embodiments, the primary stimulatory agent binds to a receptor molecule on the surface of the selected cells of the sample. Thus, in some cases, the primary stimulatory agent delivers, induces, or modulates a stimulatory signal. In some aspects, the delivering, inducing, or modulating of a stimulatory signal by the primary stimulatory agent effects the stimulation of the cells. Thus, in some cases, the primary stimulatory agent delivers a stimulatory signal or provides a primary activation signal to the cells, thereby stimulating and/or activating the cells. In some embodiments, the primary stimulatory agent further induces downregulation of a selection marker. As used herein, downregulation may encompass a reduction in expression, e.g., cell surface expression, of a selection marker compared to an earlier time point.

In some embodiments, the target cells (e.g., T cells) comprise TCR/CD3 complexes and costimulatory molecules, such as CD28. In this case, the primary stimulatory agent binds to a TCR/CD3 complex, thereby delivering a stimulatory signal (e.g., a primary signal, e.g., primary activation signal) in the T cells, and the secondary stimulatory agent binds to a costimulatory CD28 molecule. In particular aspects, the primary stimulatory agent and/or the secondary stimulatory agent further induce downregulation of a selection marker (e.g., a selection marker used to immobilize the target cells (e.g., T cells)).

In some embodiments, the primary stimulatory agent delivers a TCR/CD3 complex-associated stimulatory signal (e.g., primary signal) in the cells, e.g., T cells. In some embodiments, the primary stimulatory agent specifically binds to a molecule containing an immunoreceptor tyrosine-based activation motif or ITAM. In some aspects, the primary stimulatory agent specifically binds CD3. In some cases, a primary stimulatory agent that specifically binds CD3 may be selected from the group consisting of an anti-CD3-antibody, a divalent antibody fragment of an anti-CD3 antibody, a monovalent antibody fragment of an anti-CD3-antibody, and a proteinaceous CD3 binding molecule with antibody-like binding properties. The divalent antibody fragment may be a F(ab')2-fragment, or a divalent single-chain Fv fragment while the monovalent antibody fragment may be selected from the group consisting of a Fab fragment, an Fv fragment, and a single-chain Fv fragment (scFv). In some cases, a proteinaceous CD3 binding molecule with antibody-like binding properties may be an aptamer, a mutein based on a polypeptide of the lipocalin family, a glubody, a protein based on the ankyrin scaffold, a protein based on the crystalline scaffold, an adnectin, or an avimer.

In some embodiments, an anti-CD3 Fab fragment can be derived from the CD3 binding monoclonal antibody produced by the hybridoma cell line OKT3 (ATCC® CRL-8001™; see also U.S. Pat. No. 4,361,549). The variable domain of the heavy chain and the variable domain of the light chain of the anti-CD3 antibody OKT3 are described in Arakawa et al J. Biochem. 120, 657-662 (1996) and comprise the amino acid sequences set forth in SEQ ID NOs: 93 and 94, respectively. In some embodiments, the anti-CD3 Fab comprises the CDRs of the variable heavy and light chains set forth in SEQ ID NOs: 93 and 94, respectively.

In some embodiments, the stimulatory agent comprises a secondary stimulatory agent. In some embodiments, the secondary stimulatory agent binds to a molecule on the surface of the cells, such as a cell surface molecule, e.g., receptor molecule. In some embodiments, the secondary stimulatory agent is capable of enhancing, dampening, or modifying a stimulatory signal delivered through the molecule bound by the first stimulatory agent. In some embodiments, the secondary stimulatory agent delivers, induces, or modulates a stimulatory signal, e.g., a second or an additional stimulatory signal. In some aspects, the secondary stimulatory agent enhances or potentiates a stimulatory signal induced by the primary stimulatory agent. In some embodiments, the secondary stimulatory agent binds to an accessory molecule and/or can stimulate or induce an accessory or secondary stimulatory signal in the cell. In some aspects, the secondary stimulatory agent binds to a costimulatory molecule and/or provides a costimulatory signal.

In some embodiments, the stimulatory agent, which can comprise the secondary stimulatory agent, binds, e.g. specifically binds, to a second molecule that can be a costimulatory molecule, an accessory molecule, a cytokine receptor, a chemokine receptor, an immune checkpoint molecule, or a member of the TNF family or the TNF receptor family.

In some embodiments, the molecule on the cell, e.g., T cell, may be CD28 and the secondary stimulatory agent) specifically binds CD28. In some aspects, the secondary stimulatory agent that specifically binds CD28 may be selected from the group consisting of an anti-CD28-antibody, a divalent antibody fragment of an anti-CD28 antibody, a monovalent antibody fragment of an anti-CD28-antibody, and a proteinaceous CD28 binding molecule with antibody-like binding properties. The divalent antibody fragment may be an F(ab')2-fragment, or a divalent single-chain Fv fragment while the monovalent antibody fragment may be selected from the group consisting of a Fab fragment, an Fv fragment, and a single-chain Fv fragment (scFv). A proteinaceous CD28 binding molecule with antibody-like binding properties may be an aptamer, a mutein based on a polypeptide of the lipocalin family, a glubody, a protein based on the ankyrin scaffold, a protein based on the crystalline scaffold, an adnectin, and an avimer.

In some embodiments, an anti-CD28 Fab fragment can be derived from antibody CD28.3 (deposited as a synthetic single chain Fv construct under GenBank Accession No. AF451974.1; see also Vanhove et al, BLOOD, 15 Jul. 2003, Vol. 102, No. 2, pages 564-570) the variable heavy and light chains of which comprise SEQ ID NO: 91 and 92, respectively. In some embodiments, the anti-CD28 Fab comprises the CDRs of the variable heavy and light chains set forth in SEQ ID NOs:91 and 92, respectively.

In some embodiments, the molecule on the cell, e.g., T cell, is CD90 and the secondary stimulatory agent specifically binds CD90. In some aspects, the secondary stimulatory agent that specifically binds CD90 may be selected from the group consisting of an anti-CD90-antibody, a divalent antibody fragment of an anti-CD90 antibody, a monovalent antibody fragment of an anti-CD90-antibody, and a proteinaceous CD90 binding molecule with antibody-like binding properties. The antibody or antigen-binding fragment can be derived from any known in the art. See e.g. anti-CD90 antibody G7 (Biolegend, cat. no. 105201).

In some embodiments, the molecule on the cell, e.g., T cell, is CD95 and the secondary stimulatory agent specifically binds CD95. In some aspects, the secondary stimulatory agent that specifically binds CD95 may be selected from the group consisting of an anti-CD95-antibody, a divalent antibody fragment of an anti-CD95 antibody, a monovalent antibody fragment of an anti-CD95-antibody, and a proteinaceous CD95 binding molecule with antibody-like binding properties. The antibody or antigen-binding fragment can be derived from any known in the art. For example, in some aspects, the anti-CD90 antibody can be monoclonal mouse anti-human CD95 CH11 (Upstate Biotechnology, Lake Placid, NY) or can be anti-CD95 mAb 7C11 or anti-APO-1, such as described in Paulsen et al. *Cell Death & Differentiation* 18.4 (2011): 619-631.

In some embodiments, the molecule on the cell, e.g., T cell or B cell, may be CD137 and the secondary stimulatory agent specifically binds CD137. In some aspects, the secondary stimulatory agent that specifically binds CD137 may be selected from the group consisting of an anti-CD137-antibody, a divalent antibody fragment of an anti-CD137 antibody, a monovalent antibody fragment of an anti-CD137-antibody, and a proteinaceous CD137 binding molecule with antibody-like binding properties. The antibody or antigen-binding fragment can be derived from any known in the art. For example, the anti-CD137 antibody can be LOB12, IgG2a or LOB12.3, IgG1 as described in Taraban et al. Eur J Immunol. 2002 December; 32(12):3617-27. See also e.g. U.S. Pat. Nos. 6,569,997, 6,303,121, Mittler et al. Immunol Res. 2004; 29(1-3):197-208.

In some embodiments, the molecule on the cell, e.g. B cell, may be CD40 and the secondary stimulatory agent specifically binds CD40. In some aspects, the secondary stimulatory agent that specifically binds CD40 may be selected from the group consisting of an anti-CD40-antibody, a divalent antibody fragment of an anti-CD40 antibody, a monovalent antibody fragment of an anti-CD40-antibody, and a proteinaceous CD40 binding molecule with antibody-like binding properties.

In some embodiments, the molecule on the cell, e.g., T cell, may be CD40 L (CD154) and the secondary stimulatory agent specifically binds CD40 L. In some aspects, the secondary stimulatory agent that specifically binds CD40 L may be selected from the group consisting of an anti-CD40 L-antibody, a divalent antibody fragment of an anti-CD40 L antibody, a monovalent antibody fragment of an anti-CD40 L-antibody, and a proteinaceous CD40 L binding molecule with antibody-like binding properties. The antibody or antigen-binding fragment can be derived from any known in the art. For example, the anti-CD40 L antibody can in some aspects be Hu5C8, as described in Blair et al. JEM vol. 191 no. 4 651-660. See also e.g. WO1999061065, US20010026932, U.S. Pat. No. 7,547,438, WO2001056603.

In some embodiments, the molecule on the cell, e.g., T cell, may be inducible T cell Costimulator (ICOS) and the secondary stimulatory agent specifically binds ICOS. In some aspects, the secondary stimulatory agent that specifically binds ICOS may be selected from the group consisting of an anti-ICOS-antibody, a divalent antibody fragment of an anti-ICOS antibody, a monovalent antibody fragment of an anti-ICOS-antibody, and a proteinaceous ICOS binding molecule with antibody-like binding properties. The antibody or antigen-binding fragment can be derived from any known in the art. See e.g. US20080279851 and Deng et al. Hybrid Hybridomics. 2004 June; 23(3):176-82.

In some embodiments, the molecule on the cell, e.g., T cell, may be Linker for Activation of T cells (LAT) and the secondary stimulatory agent) specifically binds LAT. In some aspects, the secondary stimulatory agent that specifically binds LAT may be selected from the group consisting of an anti-LAT-antibody, a divalent antibody fragment of an anti-LAT antibody, a monovalent antibody fragment of an anti-LAT-antibody, and a proteinaceous LAT binding molecule with antibody-like binding properties. The antibody or antigen-binding fragment can be derived from any known in the art.

In some embodiments, the molecule on the cell, e.g., T cell, may be CD27 and the secondary stimulatory agent specifically binds CD27. In some aspects, the secondary stimulatory agent that specifically binds CD27 may be selected from the group consisting of an anti-CD27-antibody, a divalent antibody fragment of an anti-CD27 antibody, a monovalent antibody fragment of an anti-CD27-antibody, and a proteinaceous CD27 binding molecule with antibody-like binding properties. The antibody or antigen-binding fragment can be derived from any known in the art. See e.g. WO2008051424.

In some embodiments, the molecule on the cell, e.g., T cell, may be OX40 and the secondary stimulatory agent specifically binds OX40. In some aspects, the secondary stimulatory agen) that specifically binds OX40 may be selected from the group consisting of an anti-OX40-antibody, a divalent antibody fragment of an anti-OX40 antibody, a monovalent antibody fragment of an anti-OX40-antibody, and a proteinaceous OX40 binding molecule with antibody-like binding properties. The antibody or antigen-binding fragment can be derived from any known in the art. See e.g. WO2013038191, Melero et al. Clin Cancer Res. 2013 Mar. 1; 19(5):1044-53.

In some embodiments, the molecule on the cell, e.g., T cell, may be HVEM and the secondary stimulatory agent specifically binds HVEM. In some aspects, the secondary stimulatory agent that specifically binds HVEM may be selected from the group consisting of an anti-HVEM-antibody, a divalent antibody fragment of an anti-HVEM antibody, a monovalent antibody fragment of an anti-HVEMantibody, and a proteinaceous HVEM binding molecule with antibody-like binding properties. The antibody or antigen-binding fragment can be derived from any known in the art. See e.g. WO2006054961, WO2007001459, Park et al. *Cancer Immunol Immunother.* 2012 February; 61(2):203-14.

In any of the above examples, the divalent antibody fragment may be a (Fab)2'-fragment, or a divalent single-chain Fv fragment while the monovalent antibody fragment may be selected from the group consisting of a Fab fragment, an Fv fragment, and a single-chain Fv fragment (scFv). In any of the above examples, the proteinaceous binding molecule with antibody-like binding properties may be an aptamer, a mutein based on a polypeptide of the lipocalin family, a glubody, a protein based on the ankyrin scaffold, a protein based on the crystalline scaffold, an adnectin, and an avimer.

In some aspects, the stimulatory agent specifically targets a molecule expressed on the surface of the target cells in which the molecule is a TCR, a chimeric antigen receptor, or a molecule comprising an immunoreceptor tyrosine-based activation motif or ITAM. For example, the molecule expressed on the surface of the target cell is selected from a T cell or B cell antigen receptor complex, a CD3 chain, a CD3 zeta, an antigen-binding portion of a T cell receptor or a B cell receptor, or a chimeric antigen receptor. In some cases, the stimulatory agent targets peptide:MHC class I complexes.

In some embodiments, the stimulatory agent binds to a His-tagged extracellular domain of a molecule expressed on the surface of the target cells. In some cases, the stimulatory agent contains the peptide sequence Trp-Ser-His-Pro-Gln-Phe-Glu-Lys (also called Strep-Tag® II, set forth in SEQ ID NO: 69) conjugated with a nickel charged trisNTA (also called His-STREPPER or His/Strep-Tag®II Adapter). In some embodiments, the molecule expressed on the surface of the target cells that is His-tagged is CD19.

In some embodiments, the stimulatory agent specifically binds to the antibody portion of the recombinant receptor, e.g., CAR. In some cases, the antibody portion of the recombinant receptor includes at least a portion of an immunoglobulin constant region, such as a hinge region, e.g., an IgG4 hinge region, and/or a CH1/CL and/or Fc region. In some embodiments, the constant region or portion is of a human IgG, such as IgG4 or IgG1. In some cases, the reagent is loaded with αIgG that recognizes the IgG4 spacer.

In some embodiments, the desired target is a T cell receptor and/or a component of a T cell receptor. In certain embodiments, the desired target is CD3. In certain embodiment, the desired target is a T cell costimulatory molecule, e.g., CD28, CD137 (4-1-BB), OX40, or ICOS.

In some embodiments, for example when the stimulatory agent is not bound to a stimulatory reagent or a receptor-binding agent reagent, the stimulatory agent is an antibody, a divalent antibody fragment, a $F(ab)_2$, or a divalent single-chain Fv fragment. In some embodiments, when the stimulatory agent is not bound to the reagent, the stimulatory agent does not include a binding partner C.

a. Bead Reagents

In certain embodiments, the stimulatory reagent contains a particle, e.g., a bead, that is conjugated or linked to one or more agents, e.g., biomolecules, that are capable of activating and/or expanding cells, e.g., T cells. In some embodiments, the one or more agents are bound to a bead. In some embodiments, the bead is biocompatible, i.e., composed of a material that is suitable for biological use. In some embodiments, the beads are non-toxic to cultured cells, e.g., cultured T cells. In some embodiments, the beads may be any particles which are capable of attaching agents in a manner that permits an interaction between the agent and a cell.

In some embodiments, the stimulatory reagent contains a bead and one or more agents that directly interact with a macromolecule on the surface of a cell. In certain embodiments, the bead (e.g., a paramagnetic bead) interacts with a cell via one or more agents (e.g., an antibody) specific for one or more macromolecules on the cell (e.g., one or more cell surface proteins). In certain embodiments, the bead (e.g., a paramagnetic bead) is labeled with a first agent described herein, such as a primary antibody (e.g., an anti-biotin antibody) or other biomolecule, and then a second agent, such as a secondary antibody (e.g., a biotinylated anti-CD3 antibody) or other second biomolecule (e.g., streptavidin), is added, whereby the secondary antibody or other second biomolecule specifically binds to such primary antibodies or other biomolecule on the particle.

In some embodiments, the bead has a diameter of greater than about 0.001 μm, greater than about 0.01 μm, greater than about 0.1 μm, greater than about 1.0 μm, greater than about 10 μm, greater than about 50 μm, greater than about 100 μm or greater than about 1000 μm and no more than about 1500 μm. In some embodiments, the bead has a diameter of about 1.0 μm to about 500 μm, about 1.0 μm to about 150 μm, about 1.0 μm to about 30 μm, about 1.0 μm to about 10 μm, about 1.0 μm to about 5.0 μm, about 2.0 μm to about 5.0 μm, or about 3.0 μm to about 5.0 μm. In some embodiments, the bead has a diameter of about 3 μm to about 5 μm. In some embodiments, the bead has a diameter of at least or at least about or about 0.001 μm, 0.01 μm, 0.1 μm, 0.5 μm, 1.0 μm, 1.5 μm, 2.0 μm, 2.5 μm, 3.0 μm, 3.5 μm, 4.0 μm, 4.5 μm, 5.0 μm, 5.5 μm, 6.0 μm, 6.5 μm, 7.0 μm, 7.5 μm, 8.0 μm, 8.5 μm, 9.0 μm, 9.5 μm, 10 μm, 12 μm, 14 μm, 16 μm, 18 μm or 20 μm. In certain embodiments, the bead has a diameter of or about 4.5 μm. In certain embodiments, the bead has a diameter of or about 2.8 μm.

In some embodiments, the beads have a density of greater than 0.001 $g/cm^3$, greater than 0.01 $g/cm^3$, greater than 0.05 $g/cm^3$, greater than 0.1 $g/cm^3$, greater than 0.5 $g/cm^3$, greater than 0.6 $g/cm^3$, greater than 0.7 $g/cm^3$, greater than 0.8 $g/cm^3$, greater than 0.9 $g/cm^3$, greater than 1 $g/cm^3$, greater than 1.1 $g/cm^3$, greater than 1.2 $g/cm^3$, greater than 1.3 $g/cm^3$, greater than 1.4 $g/cm^3$, greater than 1.5 $g/cm^3$, greater than 2 $g/cm^3$, greater than 3 $g/cm^3$, greater than 4 $g/cm^3$, or greater than 5 $g/cm^3$. In some embodiments, the beads have a density of between about 0.001 $g/cm^3$ and about 100 $g/cm^3$, about 0.01 $g/cm^3$ and about 50 $g/cm^3$, about 0.1 $g/cm^3$ and about 10 $g/cm^3$, about 0.1 $g/cm^3$ and about 0.5 $g/cm^3$, about 0.5 $g/cm^3$ and about 1 $g/cm^3$, about 0.5 $g/cm^3$ and about 1.5 $g/cm^3$, about 1 $g/cm^3$ and about 1.5 $g/cm^3$, about 1 $g/cm^3$ and about 2 $g/cm^3$, or about 1 $g/cm^3$ and about 5 $g/cm^3$. In some embodiments, the beads have a density of about 0.5 $g/cm^3$, about 0.5 $g/cm^3$, about 0.6 $g/cm^3$, about 0.7 $g/cm^3$, about 0.8 $g/cm^3$, about 0.9 $g/cm^3$, about 1.0 $g/cm^3$, about 1.1 $g/cm^3$, about 1.2 $g/cm^3$, about 1.3 $g/cm^3$, about 1.4 $g/cm^3$, about 1.5 $g/cm^3$, about 1.6 $g/cm^3$, about 1.7 $g/cm^3$, about 1.8 $g/cm^3$, about 1.9 $g/cm^3$, or about 2.0 $g/cm^3$. In certain embodiments, the beads have a density of about 1.6 $g/cm^3$. In particular embodiments, the beads or particles have a density of about 1.5 $g/cm^3$. In certain embodiments, the particles have a density of about 1.3 $g/cm^3$ In certain embodiments, a plurality of the beads has a uniform density. In certain embodiments, a uniform density comprises a density standard deviation of less than 10%, less than 5%, or less than 1% of the mean bead density.

In some embodiments, the bead contains at least one material at or near the bead surface that can be coupled, linked, or conjugated to an agent. In some embodiments, the bead is surface functionalized, i.e. comprises functional groups that are capable of forming a covalent bond with a binding molecule, e.g., a polynucleotide or a polypeptide. In particular embodiments, the bead comprises surface-exposed carboxyl, amino, hydroxyl, tosyl, epoxy, and/or chloromethyl groups. In particular embodiments, the beads comprise surface exposed agarose and/or sepharose. In certain embodiments, the bead surface comprises attached stimulatory reagents that can bind or attach binding molecules. In particular embodiments, the biomolecules are polypeptides. In some embodiments, the beads comprise surface exposed protein A, protein G, or biotin.

In some embodiments, the bead reacts in a magnetic field. In some embodiments, the bead is a magnetic bead. In some embodiments, the magnetic bead is paramagnetic. In particular embodiments, the magnetic bead is superparamagnetic. In certain embodiments, the beads do not display any magnetic properties unless they are exposed to a magnetic field.

In particular embodiments, the bead comprises a magnetic core, a paramagnetic core, or a superparamagnetic core. In some embodiments, the magnetic core contains a metal. In some embodiments, the metal can be, but is not limited to, iron, nickel, copper, cobalt, gadolinium, manganese, tantalum, zinc, zirconium or any combinations thereof. In certain embodiments, the magnetic core comprises metal oxides (e.g., iron oxides), ferrites (e.g., manganese ferrites, cobalt ferrites, nickel ferrites, etc.), hematite and metal alloys (e.g., CoTaZn). In some embodiments, the magnetic core comprises one or more of a ferrite, a metal, a metal alloy, an iron oxide, or chromium dioxide. In some embodiments, the magnetic core comprises elemental iron or a compound thereof. In some embodiments, the magnetic core comprises one or more of magnetite (Fe3O4), maghemite (γFe2O3), or greigite (Fe3S4). In some embodiments, the inner core comprises an iron oxide (e.g., $Fe_3O_4$).

In certain embodiments, the bead contains a magnetic, paramagnetic, and/or superparamagnetic core that is covered by a surface functionalized coat or coating. In some embodiments, the coat can contain a material that can include, but is not limited to, a polymer, a polysaccharide, a silica, a fatty acid, a protein, a carbon, agarose, sepharose, or a combination thereof. In some embodiments, the polymer can be a polyethylene glycol, poly (lactic-co-glycolic acid), polyglutaraldehyde, polyurethane, polystyrene, or a polyvinyl alcohol. In certain embodiments, the outer coat or coating comprises polystyrene. In particular embodiments, the outer coating is surface functionalized.

In some embodiments, the stimulatory reagent comprises a bead that contains a metal oxide core (e.g., an iron oxide core) and a coat, wherein the metal oxide core comprises at least one polysaccharide (e.g., dextran), and wherein the coat comprises at least one polysaccharide (e.g., amino dextran), at least one polymer (e.g., polyurethane) and silica. In some embodiments the metal oxide core is a colloidal iron oxide core. In certain embodiments, the one or more agents include an antibody or antigen-binding fragment thereof. In particular embodiments, the one or more agents include an anti-CD3 antibody and an anti-CD28 antibody. In some embodiments, the stimulatory reagent comprises an anti-CD3 antibody, anti-CD28 antibody, and an anti-biotin antibody. In some embodiments, the stimulatory reagent comprises an anti-biotin antibody. In some embodiments, the bead has a diameter of about 3 μm to about 10 μm. In some embodiments, the bead has a diameter of about 3 μm to about 5 μm. In certain embodiments, the bead has a diameter of about 3.5 μm.

In some embodiments, the stimulatory reagent comprises one or more agents that are attached to a bead comprising a metal oxide core (e.g., an iron oxide inner core) and a coat (e.g., a protective coat), wherein the coat comprises polystyrene. In certain embodiments, the beads are monodisperse, paramagnetic (e.g., superparamagnetic) beads comprising a paramagnetic (e.g., superparamagnetic) iron core, e.g., a core comprising magnetite ($Fe_3O_4$) and/or maghemite ($\gamma Fe_2O_3$) c and a polystyrene coat or coating. In some embodiments, the bead is non-porous. In some embodiments, the beads contain a functionalized surface to which the one or more agents are attached. In certain embodiments, the one or more agents are covalently bound to the beads at the surface. In some embodiments, the one or more agents include an antibody or antigen-binding fragment thereof. In some embodiments, the one or more agents include an anti-CD3 antibody and an anti-CD28 antibody. In some embodiments, the one or more agents include an anti-CD3 antibody and/or an anti-CD28 antibody, and an antibody or antigen fragment thereof capable of binding to a labeled antibody (e.g., biotinylated antibody), such as a labeled anti-CD3 or anti-CD28 antibody. In certain embodiments, the beads have a density of about 1.5 g/$cm^3$ and a surface area of about 1 $m^2$/g to about 4 $m^2$/g. In particular embodiments; the beads are monodisperse superparamagnetic beads that have a diameter of about 4.5 μm and a density of about 1.5 &m'. In some embodiments, the beads the beads are monodisperse superparamagnetic beads that have a mean diameter of about 2.8 μm and a density of about 1.3 g/$cm^3$.

In some embodiments, the population of enriched T cells is incubated with stimulatory reagent a ratio of beads to cells at or at about 3:1, 2.5:1, 2:1, 1.5:1, 1.25:1, 1.2:1, 1.1:1, 1:1, 0.9:1, 0.8:1, 0.75:1, 0.67:1, 0.5:1, 0.3:1, or 0.2:1. In particular embodiments, the ratio of beads to cells is between 2.5:1 and 0.2:1, between 2:1 and 0.5:1, between 1.5:1 and 0.75:1, between 1.25:1 and 0.8:1, between 1.1:1 and 0.9:1. In particular embodiments, the ratio of beads to cells is about 1:1 or is 1:1.

b. Oligomeric Streptavidin Mutein Reagent

In particular embodiments, the stimulatory reagent contains an oligomeric reagent, e.g., a streptavidin mutein reagent, that is conjugated, linked, or attached to one or more agent, e.g., ligand, which is capable of activating an intracellular signaling domain of a TCR complex. In some embodiments, the one or more agents have an attached binding domain or binding partner (e.g., a binding partner C) that is capable of binding to oligomeric reagent at a particular binding sites (e.g., binding site Z). In some embodiments, a plurality of the agent is reversibly bound to the oligomeric reagent. In various embodiments, the oligomeric reagent has a plurality of the particular binding sites which, in certain embodiments, are reversibly bound to a plurality of agents at the binding domain (e.g., binding partner C). In some embodiments, the amount of bound agents are reduced or decreased in the presence of a competition reagent, e.g., a reagent that is also capable of binding to the particular binding sites (e.g., binding site Z).

In some embodiments, the oligomeric stimulatory reagent is or includes a reversible system in which at least one agent (e.g., an agent that is capable of producing a signal in a cell such as a T cell) is associated, e.g., reversibly associated, with the oligomeric reagent. Non-limiting examples of oligomeric stimulatory reagents may be found, for example, in International published PCT Appl. No. WO 2018/197949, the contents of which are incorporated herein by reference in their entirety. In some embodiments, the reagent contains a plurality of binding sites capable of binding, e.g., reversibly binding, to the agent. In some cases, the reagent is an oligomeric particle reagent having at least one attached agent capable of producing a signal in a cell such as a T cell. In some embodiments, the agent contains at least one binding site, e.g., a binding site B, that can specifically bind an epitope or region of the molecule and also contains a binding partner, also referred to herein as a binding partner C, that specifically binds to at least one binding site of the reagent, e.g., binding site Z of the reagent. In some embodiments, the binding interaction between the binding partner C and the at least one binding site Z is a non-covalent interaction. In some cases, the binding interaction between the binding partner C and the at least one binding site Z is a covalent interaction. In some embodiments, the binding interaction, such as non-covalent interaction, between the binding partner C and the at least one binding site Z is reversible.

Substances that may be used as oligomeric reagents in such reversible systems are known, see e.g., U.S. Pat. Nos. 5,168,049; 5,506,121; 6,103,493; 7,776,562; 7,981,632; 8,298,782; 8,735,540; 9,023,604; and International published PCT Appl. Nos. WO2013/124474 and WO2014/076277. Non-limiting examples of reagents and binding partners capable of forming a reversible interaction, as well as substances (e.g. competition reagents) capable of reversing such binding, are described below.

In some embodiments, the oligomeric reagent is an oligomer of streptavidin, streptavidin mutein or analog, avidin, an avidin mutein or analog (such as neutravidin) or a mixture thereof, in which such oligomeric reagent contains one or more binding sites for reversible association with the binding domain of the agent (e.g., a binding partner C). In some embodiments, the binding domain of the agent can be a biotin, a biotin derivative or analog, or a streptavidin-binding peptide or other molecule that is able to specifically bind to streptavidin, a streptavidin mutein or analog, avidin or an avidin mutein or analog.

In certain embodiments, one or more agents (e.g., agents that are capable of producing a signal in a cell such as a T cell) associate with, such as are reversibly bound to, the oligomeric reagent, such as via the plurality of the particular binding sites (e.g., binding sites Z) present on the oligomeric reagent. In some cases, this results in the agents being closely arranged to each other such that an avidity effect can take place if a target cell having (at least two copies of) a cell surface molecule that is bound by or recognized by the agent is brought into contact with the agent.

In some embodiments, the oligomeric reagent is a streptavidin oligomer, a streptavidin mutein oligomer, a streptavidin analog oligomer, an avidin oligomer, an oligomer composed of avidin mutein or avidin analog (such as neutravidin) or a mixture thereof. In particular embodiments, the oligomeric reagents contain particular binding sites that are capable of binding to a binding domain (e.g., the binding partner C) of an agent. In some embodiments, the binding domain can be a biotin, a biotin derivative or analog, or a streptavidin-binding peptide or other molecule that is able to specifically bind to streptavidin, a streptavidin mutein or analog, avidin or an avidin mutein or analog. The methods provided herein further contemplate that the oligomeric reagent may comprise a molecule capable of binding to an oligohistidine affinity tag, a glutathione-S-transferase, calmodulin or an analog thereof, calmodulin binding peptide (CBP), a FLAG-peptide, an HA-tag, maltose binding protein (MBP), an HSV epitope, a myc epitope, and/or a biotinylated carrier protein.

In some embodiments, the streptavidin can be wild-type streptavidin, streptavidin muteins or analogs, such as streptavidin-like polypeptides. Likewise, avidin, in some aspects, includes wild-type avidin or muteins or analogs of avidin such as neutravidin, a deglycosylated avidin with modified arginines that typically exhibits a more neutral pi and is available as an alternative to native avidin. Generally, deglycosylated, neutral forms of avidin include those commercially available forms such as “Extravidin”, available through Sigma Aldrich, or “NeutrAvidin” available from Thermo Scientific or Invitrogen, for example.

In some embodiments, the reagent is a streptavidin or a streptavidin mutein or analog. In some embodiments, wild-type streptavidin (wt-streptavidin) has the amino acid sequence disclosed by Argarana et al, Nucleic Acids Res. 14 (1986) 1871-1882 (SEQ ID NO: 66). In general, streptavidin naturally occurs as a tetramer of four identical subunits, i.e. it is a homo-tetramer, where each subunit contains a single binding site for biotin, a biotin derivative or analog or a biotin mimic. An exemplary sequence of a streptavidin subunit is the sequence of amino acids set forth in SEQ ID NO: 66, but such a sequence also can include a sequence present in homologs thereof from other *Streptomyces* species. In particular, each subunit of streptavidin may exhibit a strong binding affinity for biotin with an equilibrium dissociation constant ($K_D$) on the order of about $10^{-14}$ M. In some cases, streptavidin can exist as a monovalent tetramer in which only one of the four binding sites is functional (Howarth et al. (2006) Nat. Methods, 3:267-73; Zhang et al. (2015) Biochem. Biophys. Res. Commun., 463:1059-63)), a divalent tetramer in which two of the four binding sites are functional (Fairhead et al. (2013) J. Mol. Biol., 426:199-214), or can be present in monomeric or dimeric form (Wu et al. (2005) J. Biol. Chem., 280:23225-31; Lim et al. (2010) Biochemistry, 50:8682-91).

In some embodiments, streptavidin may be in any form, such as wild-type or unmodified streptavidin, such as a streptavidin from a *Streptomyces* species or a functionally active fragment thereof that includes at least one functional subunit containing a binding site for biotin, a biotin derivative or analog or a biotin mimic, such as generally contains at least one functional subunit of a wild-type streptavidin from *Streptomyces avidinii* set forth in SEQ ID NO: 66 or a functionally active fragment thereof. For example, in some embodiments, streptavidin can include a fragment of wild-type streptavidin, which is shortened at the N- and/or C-terminus. Such minimal streptavidins include any that begin N-terminally in the region of amino acid positions 10 to 16 of SEQ ID NO: 66 and terminate C-terminally in the region of amino acid positions 133 to 142 of SEQ ID NO: 66. In some embodiments, a functionally active fragment of streptavidin contains the sequence of amino acids set forth in SEQ ID NO: 67. In some embodiments, streptavidin, such as set forth in SEQ ID NO: 67, can further contain an N-terminal methionine at a position corresponding to Ala13 with numbering set forth in SEQ ID NO: 66. Reference to the position of residues in streptavidin or streptavidin muteins is with reference to numbering of residues in SEQ ID NO: 66.

Examples of streptavidins or streptavidin muteins are mentioned, for example, in WO 86/02077, DE 19641876 A1, U.S. Pat. No. 6,022,951, WO 98/40396 or WO 96/24606. Examples of streptavidin muteins are known, see e.g., U.S. Pat. Nos. 5,168,049; 5,506,121; 6,022,951; 6,156, 493; 6,165,750; 6,103,493; or 6,368,813; or International published PCT App. No. WO2014/076277.

In some embodiments, a streptavidin mutein can contain amino acids that are not part of an unmodified or wild-type streptavidin or can include only a part of a wild-type or unmodified streptavidin. In some embodiments, a streptavidin mutein contains at least one subunit that can have one more amino acid substitutions (replacements) compared to a subunit of an unmodified or wild-type streptavidin, such as compared to the wild-type streptavidin subunit set forth in SEQ ID NO: 66 or a functionally active fragment thereof, e.g. set forth in SEQ ID NO: 67.

In some embodiments, the equilibrium dissociation constant ($K_D$), of streptavidin or a streptavidin mutein for a binding domain is less than $1\times10^{7}$ M, $5\times10^{7}$ M, $1\times10^{-5}$ M, $5\times10^{-5}$M, $1\times10^{-6}$ M, $5\times10^{-6}$ M or $1\times10^{7}$ M, but generally greater than $1\times10^{-13}$ M, $1\times10^{-12}$ M or $1\times10^{-11}$ M. For example, peptide sequences (Strep-tags), such as disclosed in U.S. Pat. No. 5,506,121, can act as biotin mimics and demonstrate a binding affinity for streptavidin, e.g., with a $K_D$ of approximately between $10^{-4}$ and $10^{-5}$ M. In some cases, the binding affinity can be further improved by making a mutation within the streptavidin molecule, see e.g. U.S. Pat. No. 6,103,493 or International published PCT App. No. WO2014/076277. In some embodiments, binding affinity can be determined by known methods, such as any described herein.

In some embodiments, the reagent, such as a streptavidin or streptavidin mutein, exhibits binding affinity for a peptide ligand binding partner, which peptide ligand binding partner can be the binding partner C present in the agent (e.g., receptor-binding agent or selection agent). In some embodiments, the peptide sequence contains a sequence with the general formula His-Pro-Xaa, where Xaa is glutamine, asparagine, or methionine, such as contained in the sequence set forth in SEQ ID NO: 83. In some embodiments, the peptide sequence has the general formula set forth in SEQ ID NO: 83, such as set forth in SEQ ID NO: 74. In one example, the peptide sequence is Trp-Arg-His-Pro-Gln-Phe-Gly-Gly (also called Strep Tag®, set forth in SEQ ID NO: 75). In one example, the peptide sequence is Trp-Ser-His-Pro-Gln-Phe-Glu-Lys (also called Strep Tag® II, set forth in SEQ ID NO: 69). In some embodiments, the peptide ligand contains a sequential arrangement of at least two streptavidin-binding modules, wherein the distance between the two modules is at least 0 and not greater than 50 amino acids, wherein one binding module has 3 to 8 amino acids and contains at least the sequence His-Pro-Xaa, where Xaa is glutamine, asparagine, or methionine, and wherein the other binding module has the same or different streptavidin peptide ligand, such as set forth in SEQ ID NO: 84 (see e.g. International Published PCT Appl. No. WO02/077018; U.S. Pat. No. 7,981,632). In some embodiments, the peptide ligand contains a sequence having the formula set forth in any of SEQ ID NO: 76 or 77. In some embodiments, the peptide ligand has the sequence of amino acids set forth in any of SEQ ID NOS: 70-73 or 78-79. In most cases, all these streptavidin binding peptides bind to the same binding site, namely the biotin binding site of streptavidin. If one or more of such streptavidin binding peptides is used as binding partners C, e.g. C1 and C2, the multimerization reagent and/or oligomeric particle reagents bound to the one or more agents via the binding partner C is typically composed of one or more streptavidin muteins.

In some embodiments, the streptavidin mutein is a mutant as described in U.S. Pat. No. 6,103,493. In some embodiments, the streptavidin mutein contains at least one mutation within the region of amino acid positions 44 to 53, based on the amino acid sequence of wild-type streptavidin, such as set forth in SEQ ID NO: 66. In some embodiments, the streptavidin mutein contains a mutation at one or more residues 44, 45, 46, and/or 47. In some embodiments, the streptavidin mutein contains a replacement of Glu at position 44 of wild-type streptavidin with a hydrophobic aliphatic amino acid, e.g. Val, Ala, Ile or Leu, any amino acid at position 45, an aliphatic amino acid, such as a hydrophobic aliphatic amino acid at position 46 and/or a replacement of Val at position 47 with a basic amino acid, e.g. Arg or Lys, such as generally Arg. In some embodiments, Ala is at position 46 and/or Arg is at position 47 and/or Val or Ile is at position 44. In some embodiments, the streptavidin mutant contains residues Va144-Thr45-Ala46-Arg47 based on the amino acid sequence of wild-type streptavidin, such as set forth in exemplary streptavidin muteins containing the sequence of amino acids set forth in SEQ ID NO: 80 or SEQ ID NO: 81 or 82 (also known as streptavidin mutant 1, SAM1) or SEQ ID NO: 86 or 87. In some embodiments, the streptavidin mutein contains residues Ile44-Gly45-Ala46-Arg47 based on the amino acid sequence of wild-type streptavidin, such as set forth in exemplary streptavidin muteins containing the sequence of amino acids set forth in SEQ ID NO: 85, 68, or 73 (also known as SAM2). In some cases, such streptavidin mutein are described, for example, in U.S. Pat. No. 6,103,493, and are commercially available under the trademark Strep-Tactin®. In some embodiments, the mutein streptavidin contains the sequence of amino acids set forth in SEQ ID NO: 86 or SEQ ID NO: 87. In particular embodiments, the molecule is a tetramer of streptavidin or a streptavidin mutein comprising a sequence set forth in any of SEQ ID NOS: 67, 81, 68, 86, 88, 82 or 73, which, as a tetramer, is a molecule that contains 20 primary amines, including 1 N-terminal amine and 4 lysines per monomer.

In some embodiments, streptavidin mutein exhibits a binding affinity characterized by an equilibrium dissociation constant ($K_D$) that is or is less than $3.7\times10^{-5}$ M for the peptide ligand (Trp-Arg-His-Pro-Gln-Phe-Gly-Gly; also called Strep-Tag®, set forth in SEQ ID NO: 75) and/or that is or is less than $7.1\times10^{-5}$ M for the peptide ligand (Trp-Ser-His-Pro-Gln-Phe-Glu-Lys; also called Strep-Tag® II, set forth in SEQ ID NO: 69) and/or that is or is less than $7.0\times10^{-5}$ M, $5.0\times10^{-5}$ M, $1.0\times10^{-5}$ M, $5.0\times10^{-6}$ M, $1.0\times10^{7}$ M, $5.0\times10^{7}$ M, or $1.0\times10^{7}$ M, but generally greater than $1\times10^{-13}$ M, $1\times10^{-12}$ M or $1\times10^{-11}$ M for any of the peptide ligands set forth in any of SEQ ID NOS: 69, 76-78, 70-72, 74, 75, 83, 84.

In some embodiments, the resulting streptavidin mutein exhibits a binding affinity characterized by an equilibrium association constant ($K_A$) that is or is greater than $2.7\times10^{4}$ $M^{-1}$ for the peptide ligand (Trp-Arg-His-Pro-Gln-Phe-Gly-Gly; also called Strep-Tag®, set forth in SEQ ID NO: 75) and/or that is or is greater than $1.4\times10^{4}$ $M^{-1}$ for the peptide ligand (Trp-Ser-His-Pro-Gln-Phe-Glu-Lys; also called Strep-Tag® II, set forth in SEQ ID NO: 69) and/or that is or is greater than $1.43\times10^{4}$ $M^{-1}$, $1.67\times10^{4}$ $M^{-1}$, $2\times10^{4}$ $M^{-1}$, $3.33\times10^{4}$ $M^{-1}$, $5\times10^{4}$ $M^{-1}$, $1\times10^{5}$ $M^{-1}$, $1.11\times10^{5}$ $M^{-1}$, $1.25\times10^{5}M^{-1}$, $1.43\times10^{5}$ $M^{-1}$, $1.67\times10^{5}$ $M^{-1}$, $2\times10^{5}$ $M^{-1}$, $3.33\times10^{5}M^{-1}$, $5\times10^{5}$ $M^{-1}$, $1\times10^{6}$ $M^{-1}$, $1.11\times10^{6}M^{-1}$, $1.25\times10^{6}$ $M^{-1}$, $1.43\times10^{6}$ $M^{-1}$, $1.67\times10^{6}M^{-1}$, $2\times10^{6}M^{-1}$, $3.33\times10^{6}M^{-}$ $_{1}$, $5\times10^{6}$ $M^{-1}$, $1\times10^{7}$ $M^{-1}$, but generally less than $1\times10^{13}$ $M^{-1}$, $1\times10^{12}$ $M^{-1}$ or $1\times10^{11}$ $M^{-1}$ for any of the peptide ligands set forth in any of SEQ ID NOS: 69, 76-78, 70-72, 74, 75, 83, 84.

In particular embodiments, provided herein is an oligomeric particle reagent that is composed of and/or contains a plurality of streptavidin or streptavidin mutein tetramers. In certain embodiments, the oligomeric particle reagent provided herein contains a plurality of binding sites that reversibly bind or are capable of reversibly binding to one or more agents, e.g., a stimulatory agent and/or a selection agent. In some embodiments, the oligomeric particle has a radius, e.g., an average radius, of between 70 nm and 125 nm, inclusive; a molecular weight of between $1\times10^7$ g/mol and $1\times10^9$ g/mol, inclusive; and/or between 1,000 and 5,000 streptavidin or streptavidin mutein tetramers, inclusive. In some embodiments, the oligomeric particle reagent is bound, e.g., reversibly bound, to one or more agents such as an agent that binds to a molecule, e.g. receptor, on the surface of a cell. In certain embodiments, the one or more agents are agents described herein, e.g., in Section II.C.3. In some embodiments, the agent is an anti-CD3 and/or an anti-CD28 antibody or antigen binding fragment thereof, such as an antibody or antigen fragment thereof that contains a binding partner, e.g., a streptavidin binding peptide, e.g. Strep-Tag® II. In particular embodiments, the one or more agents is an anti-CD3 and/or an anti CD28 Fab containing a binding partner, e.g., a streptavidin binding peptide, e.g. Strep-Tag® II.

In some embodiments, provided herein is an oligomeric particle reagent that is composed of and/or contains a plurality of streptavidin or streptavidin mutein tetramers. In certain embodiments, the oligomeric particle reagent provided herein contains a plurality of binding sites that reversibly bind or are capable of reversibly binding to one or more agents, e.g., a stimulatory agent and/or a selection agent. In some embodiments, the oligomeric particle has a radius, e.g., an average radius, of between 80 nm and 120 nm, inclusive; a molecular weight, e.g., an average molecular weight of between $7.5\times10^6$ g/mol and $2\times10^8$ g/mol, inclusive; and/or an amount, e.g., an average amount, of between 500 and 10,000 streptavidin or streptavidin mutein tetramers, inclusive. In some embodiments, the oligomeric particle reagent is bound, e.g., reversibly bound, to one or more agents, such as an agent that binds to a molecule, e.g. receptor, on the surface of a cell. In certain embodiments, the one or more agents are agents described herein, e.g., in Section II.C.3. In some embodiments, the agent is an anti-CD3 and/or an anti-CD28 Fab, such as a Fab that contains a binding partner, e.g., a streptavidin binding peptide, e.g. Strep-Tag® II. In particular embodiments, the one or more agents is an anti-CD3 and/or an anti CD28 Fab containing a binding partner, e.g., a streptavidin binding peptide, e.g. Strep-Tag® II.

In some embodiments, the cells are stimulated in the presence of, of about, or of at least 0.01 μg, 0.02 μg, 0.03 μg, 0.04 μg, 0.05 μs, 0.1 μs, 0.2 μs, 0.3 μs, 0.4 μs, 0.5 μs, 0.75 μs, 1 μg, 2 μg, 3 μg, 4 jag, 5 μg, 6 μg, 7 μg, 8 μg, 9 μg, or 10 μg of the oligomeric stimulatory reagent per $10^6$ cells. In some embodiments, the cells are stimulated in the presence of or of about 4 μg per $10^6$ cells. In some embodiments, the cells are stimulated or subjected to stimulation in the presence of or of about 3 μg per $10^6$ cells. In some embodiments, the cells are stimulated or subjected to stimulation in the presence of or of about 2.75 μg per $10^6$ cells. In some embodiments, the cells are stimulated or subjected to stimulation in the presence of or of about 2.5 μg per $10^6$ cells. In some embodiments, the cells are stimulated or subjected to stimulation in the presence of or of about 2.25 μg per $10^6$ cells. In some embodiments, the cells are stimulated or subjected to stimulation in the presence of or of about 2 μg per $10^6$ cells. In particular embodiments, the cells are stimulated or subjected to stimulation in the presence of or of about 1.8 μg per $10^6$ cells. In particular embodiments, the cells are stimulated or subjected to stimulation in the presence of or of about 1.6 μg per $10^6$ cells. In particular embodiments, the cells are stimulated or subjected to stimulation in the presence of or of about 1.4 μg per $10^6$ cells. In particular embodiments, the cells are stimulated or subjected to stimulation in the presence of or of about 1.2 μg per $10^6$ cells. In particular embodiments, the cells are stimulated or subjected to stimulation in the presence of or of about 1 μs per $10^6$ cells. In particular embodiments, the cells are stimulated in the presence of or of about 0.8 μg per $10^6$ cells. In certain aspects, 4 μg of the oligomeric stimulatory reagent is or includes 3 μg of oligomeric particles and 1 μg of attached agents, e.g., 0.5 μg of anti-CD3 Fabs and 0.5 μs of anti-CD28 Fabs. In some embodiments, the cells are stimulated or subjected to stimulation in the presence of or of about $10\times10^8$, $9\times10^8$, $8\times10^8$, $7\times10^8$, $6\times10^8$, $5\times10^8$, $4\times10^8$, $3\times10^8$, $2\times10^8$, $1\times10^8$ oligomeric reagents. In some embodiments, the cells are stimulated or subjected to stimulation in the presence of or of about $7\times10^8$, $6\times10^8$, $5\times10^8$, $4\times10^8$, $3\times10^8$ oligomeric reagents. In some embodiments, the cells are stimulated or subjected to stimulation in the presence of or of about $7\times10^8$ to $3\times10^8$ oligomeric reagents. In some embodiments, the cells are stimulated or subjected to stimulation in the presence of or of about $6\times10^8$ to $4\times10^8$ oligomeric reagents. In some embodiments, the cells are stimulated or subjected to stimulation in the presence of or of about $6\times10^8$ to $5\times10^8$ oligomeric reagents. In some embodiments, the cells are stimulated or subjected to stimulation in the presence of or of about $5\times10^8$ oligomeric reagents.

In some embodiments, the cells, e.g., selected cells of a sample, are stimulated or subjected to stimulation in the presence of a ratio of oligomeric reagent to cells at or at about 3:1, 2.5:1, 2:1, 1.5:1, 1.25:1, 1.2:1, 1.1:1, 1:1, 0.9:1, 0.8:1, 0.75:1, 0.67:1, 0.5:1, 0.3:1, or 0.2:1. In particular embodiments, the ratio of oligomeric reagent to cells is between 2.5:1 and 0.2:1, between 2:1 and 0.5:1, between 1.5:1 and 0.75:1, between 1.25:1 and 0.8:1, between 1.1:1 and 0.9:1. In particular embodiments, the ratio of oligomeric reagent to cells is about 1:1 or is 1:1. In particular embodiments, the ratio of oligomeric reagent to cells is about 0.3:1 or is 0.3:1. In particular embodiments, the ratio of oligomeric reagent to cells is about 0.2:1 or is 0.2:1.

In certain aspects, within the oligomeric reagent, the mass ratio between the oligomeric particles and the attached agents is about 3:1. In certain aspects, within the oligomeric reagent, the mass ratio among the oligomeric particles, the attached anti-CD3 Fabs, and the attached anti-CD28 Fabs is about 3:0.5:0.5. In certain aspects, 4 μg of the oligomeric reagent is or includes 3 μg of oligomeric particles and 1 μg of attached agents, e.g., 0.5 μg of anti-CD3 Fabs and 0.5 μg of anti-CD28 Fabs. In other examples, 1.2 μg of the oligomeric reagent per $10^6$ cells is or includes 0.9 μg of oligomeric particles and 0.3 μg of attached agents, e.g., 0.15 μg of anti-CD3 Fabs and 0.15 μg of anti-CD28 Fabs, per $10^6$ cells. In some embodiments, the oligomeric reagent is added to a serum-free medium and the stimulation is performed in the serum free medium, e.g., as described in PCT/US2018/064627.

In some embodiments, the serum-free medium comprises a basal medium (e.g. OpTimizer™ T-Cell Expansion Basal Medium (ThermoFisher), supplemented with one or more supplement. In some embodiments, the one or more supplement is serum-free. In some embodiments, the serum-free medium comprises a basal medium supplemented with one or more additional components for the maintenance, expansion, and/or activation of a cell (e.g., a T cell), such as provided by an additional supplement (e.g. OpTimizer™ T-Cell Expansion Supplement (ThermoFisher)). In some embodiments, the serum-free medium further comprises a serum replacement supplement, for example, an immune cell serum replacement, e.g., ThermoFisher, #A2596101, the CTS™ Immune Cell Serum Replacement, or the immune cell serum replacement described in Smith et al. *Clin Transl Immunology.* 2015 January; 4(1): e31. In some embodiments, the serum-free medium further comprises a free form of an amino acid such as L-glutamine. In some embodiments, the serum-free medium further comprises a dipeptide form of L-glutamine (e.g., L-alanyl-L-glutamine), such as the dipeptide in Glutamax™ (ThermoFisher). In some embodiments, the serum-free medium further comprises one or more recombinant cytokines, such as recombinant human IL-2, recombinant human IL-7, and/or recombinant human IL-15.

2. Removal of Stimulatory Reagents

In some embodiments, the stimulatory reagent is removed or separated from the cells or cell populations prior to collecting, harvesting, or formulating the cells. In some embodiments, the stimulatory reagents are removed or separated from the cells or cell populations after or during the incubation, e.g., an incubation described herein such as in Section I.D. In certain embodiments, the cells or cell population undergoes a process, procedure, step, or technique to remove the stimulatory reagent after the incubation but prior to steps for collecting, harvesting, or formulating the cells. In particular embodiments, the cells or cell population undergoes a process, procedure, step, or technique to remove the stimulatory reagent after the incubation. In some aspects, when stimulatory reagent is separated or removed from the cells during the incubation, the cells are returned to the same incubation conditions as prior to the separation or removal for the remaining duration of the incubation.

In certain embodiments, the stimulatory reagent is removed and/or separated from the cells. Without wishing to be bound by theory, particular embodiments contemplate that the binding and/or association between a stimulatory reagent and cells may, in some circumstances, be reduced over time during the incubation. In certain embodiments, one or more agents may be added to reduce the binding and/or association between the stimulatory reagent and the cells. In particular embodiments, a change in cell culture conditions, e.g., the addition of an agent, may reduce the binding and/or association between the stimulatory reagent and the cells. Thus, in some embodiments, the stimulatory reagent may be removed from an incubation, cell culture system, and/or a solution separately from the cells, e.g., without removing the cells from the incubation, cell culture system, and/or a solution as well.

In certain embodiments, the stimulatory reagent is separated and/or removed from the cells after an amount of time. In particular embodiments, the amount of time is an amount of time from the initiation of the stimulation. In particular embodiments the start of the incubation is considered at or at about the time the cells are contacted with the stimulatory reagent and/or a media or solution containing the stimulatory reagent. In particular embodiments, the stimulatory reagent is removed or separated from the cells within or within about 120 hours, 108 hours, 96 hours, 84 hours, 72 hours, 60 hours, 48 hours, 36 hours, 24 hours, or 12 hours, inclusive, of the initiation of the stimulation. In particular embodiments, the stimulatory reagent is removed or separated from the cells at or at about 48 hours after the stimulation is initiated. In certain embodiments, the stimulatory reagent is removed or separated from the cells at or at about 72 hours after the stimulation is initiated. In some embodiments, the stimulatory reagent is removed or separated from the cells at or at about 96 hours after the stimulation is initiated.

a. Removal of Bead Reagents

In certain embodiments, the bead stimulatory reagent, e.g., an anti-CD3/anti-CD28 antibody conjugated paramagnetic bead, is separated or removed from the cells or the cell population. Methods for removing stimulatory reagents (e.g. stimulatory reagents that are or contain particles such as bead particles or magnetizable particles) from cells are known. In some embodiments, the use of competing antibodies, such as non-labeled antibodies, can be used, which, for example, bind to a primary antibody of the stimulatory reagent and alter its affinity for its antigen on the cell, thereby permitting for gentle detachment. In some cases, after detachment, the competing antibodies may remain associated with the particle (e.g. bead particle) while the unreacted antibody is or may be washed away and the cell is free of isolating, selecting, enriching and/or activating antibody. Exemplary of such a reagent is DETACaBEAD (Friedl et al. 1995; Entschladen et al. 1997). In some embodiments, particles (e.g. bead particles) can be removed in the presence of a cleavable linker (e.g. DNA linker), whereby the particle-bound antibodies are conjugated to the linker (e.g. CELLection, Dynal). In some cases, the linker region provides a cleavable site to remove the particles (e.g. bead particles) from the cells after isolation, for example, by the addition of DNase or other releasing buffer. In some embodiments, other enzymatic methods can also be employed for release of a particle (e.g. bead particle) from cells. In some embodiments, the particles (e.g. bead particles or magnetizable particles) are biodegradable.

In some embodiments, the stimulatory reagent is magnetic, paramagnetic, and/or superparamagnetic, and/or contains a bead that is magnetic, paramagnetic, or superparamagnetic, and the stimulatory reagent may be removed from the cells by exposing the cells to a magnetic field. Examples of suitable equipment containing magnets for generating the magnetic field include DynaMag CTS (Thermo Fisher), Magnetic Separator (Takara) and EasySep Magnet (Stem Cell Technologies).

In particular embodiments, the stimulatory reagent is removed or separated from the cells prior to the completion of the provided methods, e.g., prior to harvesting, collecting, and/or formulating engineered cells produced by the methods provided herein. In some embodiments, the stimulatory reagent is removed and/or separated from the cells after engineering, e.g., transducing or transfecting, the cells.

In some embodiments, the stimulatory bead reagent, e.g., the stimulatory magnetic bead reagent, is removed or separated from the cells or cell populations prior to collecting, harvesting, or formulating the cells. In some embodiments, the stimulatory bead reagent, e.g., the stimulatory magnetic bead reagent, are removed or separated from the cells or cell populations by exposure to a magnetic field during or after the incubation, e.g., an incubation described herein such as in Section I-D. In certain embodiments, the cells or cell population are exposed to the magnetic field to remove the stimulatory bead reagent, e.g., the stimulatory magnetic bead reagent, after the incubation but prior to steps for collecting, harvesting, or formulating the cells. In particular embodiments, the cells or cell population undergoes is exposed to the magnetic field to remove the stimulatory bead reagent, e.g., the stimulatory magnetic bead reagent, after the incubation. In some aspects, when the stimulatory bead reagent is separated or removed from the cells or cell population during the incubation, the cells or cell population are returned to the same incubation conditions as prior to the exposure to the magnetic field for the remaining duration of the incubation.

In particular embodiments, the stimulatory bead reagent, e.g., the stimulatory magnetic bead reagent, is removed or separated from the cells, e.g., by exposure to a magnetic field, within or within about 120 hours, 108 hours, 96 hours, 84 hours, 72 hours, 60 hours, 48 hours, 36 hours, 24 hours, or 12 hours, inclusive, of the incubation. In certain embodiments, the stimulatory bead reagent, e.g., the stimulatory magnetic bead reagent, is removed or separated from the cells, e.g., by exposure to a magnetic field, after or after about 72 hours of incubation. In some embodiments, the stimulatory bead reagent, e.g., the stimulatory magnetic bead reagent, is removed or separated from the cells, e.g., by exposure to a magnetic field, after or after about 96 hours of incubation.

b. Removal of Oligomeric Reagents

In some embodiments, the population of incubated T cells was produced or generated in accord with any of the methods provided herein in which a substance, such as a competition agent, was added to T cells to disrupt, such as to lessen and/or terminate, the signaling of the stimulatory agent or agents. In some embodiments, the population of the incubated T cells contains the presence of a substance, such as a competition agent, e.g. biotin or a biotin analog, e.g. D-Biotin. In some embodiments, the substance, such as a competition agent, e.g. biotin or a biotin analog, e.g. D-Biotin, is present in an amount that is at least 1.5-fold greater, at least 2-fold, at least 3-fold, at least 4-fold, at least 5-fold, at least 10-fold, at least 100-fold, at least 1000-fold or more greater than the amount of the substance in a reference population or preparation of cultured T cells in which the substance was not added exogenously during the incubation. In some embodiments, the amount of the substance, such as a competition agent, e.g. biotin or a biotin analog, e.g. D-Biotin, in the population of cultured T cells is from or from about 10 μM to 100 μM, 100 μM to 1 mM, 100 μM to 500 μM or 10 μM to 100 μM. In some embodiments, 10 μM or about 10 μM of biotin or a biotin analog, e.g., D-biotin, is added to the cells or the cell population to separate or remove the oligomeric stimulatory reagent from the cells or cell population.

In certain embodiments, the one or more agents (e.g., agents that stimulate or activate a TCR and/or a coreceptor) associate with, such as are reversibly bound to, the oligomeric reagent, such as via the plurality of the particular binding sites (e.g., binding sites Z) present on the oligomeric reagent. In some cases, this results in the agents being closely arranged to each other such that an avidity effect can take place if a target cell having (at least two copies of) a cell surface molecule that is bound by or recognized by the agent is brought into contact with the agent. In some aspects, the receptor binding reagent has a low affinity towards the receptor molecule of the cell at binding site B, such that the receptor binding reagent dissociates from the cell in the presence of the competition reagent. Thus, in some embodiments, the agents are removed from the cells in the presence of the competition reagent.

In some embodiments, the oligomeric stimulatory reagent is a streptavidin mutein oligomer with reversibly attached anti-CD3 and anti-CD28 Fabs. In some embodiments, the Fabs are attached contain streptavidin binding domains, e.g., that allow for the reversible attachment to the streptavidin mutein oligomer. In some cases, anti-CD3 and anti-CD28 Fabs are closely arranged to each other such that an avidity effect can take place if a T cell expressing CD3 and/or CD28 is brought into contact with the oligomeric stimulatory reagent with the reversibly attached Fabs. In some aspects, the Fabs have a low affinity towards CD3 and CD28, such that the Fabs dissociate from the cell in the presence of the competition reagent, e.g., biotin or a biotin variant or analogue. Thus, in some embodiments, the Fabs are removed or dissociated from the cells in the presence of the competition reagent, e.g., D-biotin.

In some embodiments, the stimulatory oligomeric reagent, e.g., the stimulatory oligomeric streptavidin mutein reagent, is removed or separated from the cells or cell populations prior to collecting, harvesting, or formulating the cells. In some embodiments, stimulatory oligomeric reagent, e.g., the stimulatory oligomeric streptavidin mutein reagent, is removed or separated from the cells or cell populations by contact or exposure to a competition reagent, e.g., biotin or a biotin analog such as D-biotin, after or during the incubation, e.g., an incubation described herein such as in Section I.D. In certain embodiments, the cells or cell population are contacted or exposed to a competition reagent, e.g., biotin or a biotin analog such as D-biotin, to remove stimulatory oligomeric reagent, e.g., the stimulatory oligomeric streptavidin mutein reagent, after the incubation but prior to steps for collecting, harvesting, or formulating the cells. In particular embodiments, the cells or cell population are contacted or exposed to a competition reagent, e.g., biotin or a biotin analog such as D-biotin, to remove the stimulatory oligomeric reagent, e.g., the stimulatory oligomeric streptavidin mutein reagent, after the incubation. In some aspects, when stimulatory oligomeric reagent, e.g., the stimulatory oligomeric streptavidin mutein reagent, is separated or removed from the cells during the incubation, e.g., by contact or exposure to a competition reagent, e.g., biotin or a biotin analog such as D-biotin, the cells are returned to the same incubation conditions as prior to the separation or removal for the remaining duration of the incubation.

In some embodiments, the cells are contacted with, with about, or with at least 0.01 μM, 0.05 μM, 0.1 μM, 0.5 μM, 1 μM, 2 μM, 3 μM, 4 μM, 5 μM, 10 μM, 100 μM, 500 μM, 0.01 μM, 1 mM, or 10 mM of the competition reagent to remove or separate the oligomeric stimulatory reagent from the cells. In various embodiments, the cells are contacted with, with about, or with at least 0.01 μM, 0.05 μM, 0.1 μM, 0.5 μM, 1 μM, 2 μM, 3 μM, 4 μM, 5 μM, 10 μM, 100 μM, 500 μM, 0.01 μM, 1 mM, or 10 mM of biotin or a biotin analog such as D-biotin, to remove or separate the stimulatory streptavidin mutein oligomers with reversibly attached anti-CD3 and anti-CD28 Fabs from the cells.

In particular embodiments, the stimulatory oligomeric reagent, e.g., the stimulatory oligomeric streptavidin mutein reagent, is removed or separated from the cells within or within about 120 hours, 108 hours, 96 hours, 84 hours, 72 hours, 60 hours, 48 hours, 36 hours, 24 hours, or 12 hours, inclusive, of incubation, e.g., in the presence of the stimulatory oligomeric streptavidin mutein reagent. In particular embodiments, the stimulatory reagent is removed or separated from the cells after or after about 48 hours of incubation e.g., in the presence of the stimulatory oligomeric reagent. In certain embodiments, the stimulatory oligomeric reagent, e.g., the stimulatory oligomeric streptavidin mutein reagent, is removed or separated from the cells after or after about 72 hours of incubation. In some embodiments, the stimulatory oligomeric reagent, e.g., the stimulatory oligomeric streptavidin mutein reagent is removed or separated from the cells at or at about 96 hours of incubation.

G. Cultivation

In particular embodiments, processes for generating compositions of engineered T cells provided herein are performed in connection with an optional cultivation step or a step where cells undergo expansion or proliferation in vitro, such as subsequent to an introduction of a heterologous polynucleotide into the cell. In some embodiments, an engineered T cell composition from an individual donor is cultivated. In some embodiments, the cultivated engineered T cell composition from an individual donor is combined with a cultivated engineered T cell composition from one or more other individual donors to produce a cultivated, pooled engineered T cell composition from a plurality of different donors. In some embodiments, a pooled engineered T cell composition from an a plurality of different donors is cultivated.

In some embodiments, the provided methods include one or more steps for cultivating cells, e.g., cultivating cells under conditions that promote proliferation or expansion. In some embodiments, cells are cultivated under conditions that promote proliferation or expansion subsequent to a step of genetically engineering, e.g., introducing a recombinant polypeptide to the cells by transduction or transfection and/or knocking out one or more molecules of interest. In particular embodiments, the cells are cultivated after the cells have been incubated under stimulating conditions and transduced or transfected with a recombinant polynucleotide, e.g., a polynucleotide encoding a recombinant receptor. In particular embodiments, the cells are cultivated after the cells have been incubated under stimulating conditions, disrupted for expression of one or more molecules or intereste, and transduced or transfected with a recombinant polynucleotide, e.g., a polynucleotide encoding a recombinant receptor. Thus, in some aspects, cells of a transformed population of enriched T cells are cultivated. In particular embodiments, the one or more transformed populations have been previously depleted of or separated from CD57+ T cells. In particular embodiments, the one or more transformed populations have been previously depleted of or separated from CD27− T cells. In some aspects, the one or more transformed populations are derived from an individual donor. In some aspects, a transformed population from an individual donor is combined with a transformed population of one or more other individual donors to produce a transformed population from a plurality of different donors. In some aspects, the one or more transformed populations are derived from a plurality of different donors.

In some embodiments, processes for generating compositions of engineered T cells provided herein do not require a cultivation step or a step where cells undergo expansion or proliferation in vitro subsequent to an introduction of a heterologous polynucleotide into the cells. In some embodiments, the process or method for generating or manufacturing engineered cell compositions do not include a step for cultivation, e.g., to expand the number of engineered cells in the therapeutic composition.

In certain embodiments, the one or more populations of engineered T cells are or include two separate populations of enriched T cells. In some embodiments, the two separate populations are derived from an individual donor. In some embodiments, the two separate populations are, or are each, derived from a plurality of different donors. In particular embodiments, two separate populations of enriched T cells, e.g., two separate populations of enriched T cells selected, isolated, and/or enriched from the same biological sample, are separately cultivated under stimulating conditions.

In certain embodiments, the two separate populations include a population of enriched CD4+ T cells, e.g., enriched CD57− CD4+ T cells. In particular embodiments, the two separate populations include a population of enriched CD8+ T cells, e.g., enriched CD57− CD8+ T cells. In some embodiments, two separate populations of enriched CD4+ T cells and enriched CD8+ T cells, e.g., two separate populations of enriched CD57− CD4+ T cells and enriched CD57− CD8+ T cells, are separately cultivated, e.g., under conditions that promote proliferation and/or expansion. In some embodiments, a single population of enriched T cells is cultivated, e.g., a single population including or containing CD57− CD4+ T cells and CD57− CD8+ T cells. In certain embodiments, the single population is a population of enriched CD4+ T cells. In some embodiments, the single population is a population of enriched CD4+ and CD8+ T cells that have been combined from separate populations prior to the cultivation.

In some embodiments, the population of enriched CD4+ T cells (e.g., CD57− CD4+ T cells) that is cultivated, e.g., under conditions that promote proliferation and/or expansion, includes at least at or about 60%, at least at or about 65%, at least at or about 70%, at least at or about 75%, at least at or about 80%, at least at or about 85%, at least at or about 90%, at least at or about 95%, at least at or about 98%, at least at or about 99%, at least at or about 99.5%, at least at or about 99.9%, or at or at about 100% CD4+ T cells (e.g., CD57− CD4+ T cells). In some embodiments, the population includes at least at or about 30%, at least at or about 40%, at least at or about 50%, at least at or about 60%, at least at or about 70%, at least at or about 80%, at least at or about 90%, at least at or about 95%, at least at or about 98%, at least at or about 99%, at least at or about 99.5%, at least at or about 99.9%, or at or at about 100% CD4+ T (e.g., CD57− CD4+ T cells) cells that express the recombinant receptor and/or have been transduced or transfected with the recombinant polynucleotide. In certain embodiments, the population of enriched CD4+ T cells (e.g., CD57− CD4+ T cells) that is cultivated includes less than at or about 40%, less than at or about 35%, less than at or about 30%, less than at or about 25%, less than at or about 20%, less than at or about 15%, less than at or about 10%, less than at or about 5%, less than at or about 1%, less than at or about 0.1%, or less than at or about 0.01% CD8+ T cells, and/or contains no CD8+ T cells, and/or is free or substantially free of CD8+ T cells.

In some embodiments, the population of enriched CD8+ T cells that is cultivated, e.g., under conditions that promote proliferation and/or expansion, includes at least at or about 60%, at least at or about 65%, at least at or about 70%, at least at or about 75%, at least at or about 80%, at least at or about 85%, at least at or about 90%, at least at or about 95%, at least at or about 98%, at least at or about 99%, at least at or about 99.5%, at least at or about 99.9%, or at or at about 100% CD8+ T cells (e.g., CD57−CD8+ T cells). In particular embodiments, the population includes at least at or about 30%, at least at or about 40%, at least at or about 50%, at least at or about 60%, at least at or about 70%, at least at or about 80%, at least at or about 90%, at least at or about 95%, at least at or about 98%, at least at or about 99%, at least at or about 99.5%, at least at or about 99.9%, or at or at about 100% CD8+ T cells (e.g., CD57−CD8+ T cells) that express the recombinant receptor and/or have been transduced or transfected with the recombinant polynucleotide. In certain embodiments, the population of enriched CD8+ T cells that is incubated under stimulating conditions includes less than at or about 40%, less than at or about 35%, less than at or about 30%, less than at or about 25%, less than at or about 20%, less than at or about 15%, less than at or about 10%, less than at or about 5%, less than at or about 1%, less than at or about 0.1%, or less than at or about 0.01% CD4+ T cells, and/or contains no CD4+ T cells, and/or is free or substantially free of CD4+ T cells.

In certain embodiments, the two separate populations include a population of enriched CD4+ T cells, e.g., enriched CD27+ CD4+ T cells. In particular embodiments, the two separate populations include a population of enriched CD8+ T cells, e.g., enriched CD27+ CD8+ T cells. In some embodiments, two separate populations of enriched CD4+ T cells and enriched CD8+ T cells, e.g., two separate populations of enriched CD27+ CD4+ T cells and enriched CD27+ CD8+ T cells, are separately cultivated, e.g., under conditions that promote proliferation and/or expansion. In some embodiments, a single population of enriched T cells is cultivated, e.g., a single population including or containing CD27+ CD4+ T cells and CD27+ CD8+ T cells. In certain embodiments, the single population is a population of enriched CD4+ T cells. In some embodiments, the single population is a population of enriched CD4+ and CD8+ T cells that have been combined from separate populations prior to the cultivation.

In some embodiments, the population of enriched CD4+ T cells (e.g., CD27+ CD4+ T cells) that is cultivated, e.g., under conditions that promote proliferation and/or expansion, includes at least at or about 60%, at least at or about 65%, at least at or about 70%, at least at or about 75%, at least at or about 80%, at least at or about 85%, at least at or about 90%, at least at or about 95%, at least at or about 98%, at least at or about 99%, at least at or about 99.5%, at least at or about 99.9%, or at or at about 100% CD4+ T cells (e.g., CD27+ CD4+ T cells). In some embodiments, the population includes at least at or about 30%, at least at or about 40%, at least at or about 50%, at least at or about 60%, at least at or about 70%, at least at or about 80%, at least at or about 90%, at least at or about 95%, at least at or about 98%, at least at or about 99%, at least at or about 99.5%, at least at or about 99.9%, or at or at about 100% CD4+ T (e.g., CD27+ CD4+ T cells) cells that express the recombinant receptor and/or have been transduced or transfected with the recombinant polynucleotide. In certain embodiments, the population of enriched CD4+ T cells (e.g., CD27+ CD4+ T cells) that is cultivated includes less than at or about 40%, less than at or about 35%, less than at or about 30%, less than at or about 25%, less than at or about 20%, less than at or about 15%, less than at or about 10%, less than at or about 5%, less than at or about 1%, less than at or about 0.1%, or less than at or about 0.01% CD8+ T cells, and/or contains no CD8+ T cells, and/or is free or substantially free of CD8+ T cells.

In some embodiments, the population of enriched CD8+ T cells that is cultivated, e.g., under conditions that promote proliferation and/or expansion, includes at least at or about 60%, at least at or about 65%, at least at or about 70%, at least at or about 75%, at least at or about 80%, at least at or about 85%, at least at or about 90%, at least at or about 95%, at least at or about 98%, at least at or about 99%, at least at or about 99.5%, at least at or about 99.9%, or at or at about 100% CD8+ T cells (e.g., CD27+CD8+ T cells). In particular embodiments, the population includes at least at or about 30%, at least at or about 40%, at least at or about 50%, at least at or about 60%, at least at or about 70%, at least at or about 80%, at least at or about 90%, at least at or about 95%, at least at or about 98%, at least at or about 99%, at least at or about 99.5%, at least at or about 99.9%, or at or at about 100% CD8+ T cells (e.g., CD27+CD8+ T cells) that express the recombinant receptor and/or have been transduced or transfected with the recombinant polynucleotide. In certain embodiments, the population of enriched CD8+ T cells that is incubated under stimulating conditions includes less than at or about 40%, less than at or about 35%, less than at or about 30%, less than at or about 25%, less than at or about 20%, less than at or about 15%, less than at or about 10%, less than at or about 5%, less than at or about 1%, less than at or about 0.1%, or less than at or about 0.01% CD4+ T cells, and/or contains no CD4+ T cells, and/or is free or substantially free of CD4+ T cells.

In some embodiments, the cultivation is performed under conditions that generally include a temperature suitable for the growth of primary immune cells, such as human T lymphocytes, for example, at least at or about 25 degrees Celsius, generally at least at or about 30 degrees, and generally at or about 37 degrees Celsius. In some embodiments, the population of enriched T cells is incubated at a temperature of 25 to 38° C., such as 30 to 37° C., for example at or about 37° C.±2° C. In some embodiments, the incubation is carried out for a time period until the culture, e.g. cultivation or expansion, results in a desired or threshold density, number or dose of cells. In some embodiments, the cultivation is greater than or greater than about or is for about or 24 hours, 48 hours, 72 hours, 96 hours, 5 days, 6 days, 7 days, 8 days, 9 days or more.

In some embodiments, the cells are cultivated to achieve a threshold expansion that is a an amount, concentration, or density of cells that is least 50%, at least at or about 60%, at least at or about 70%, at least at or about 80%, at least at or about 90%, at least at or about 95%, at least at or about 100%, at least at or about 150%, at least at or about 1-fold, at least at or about 2-fold, at least at or about 3-fold, at least at or about 4-fold, at least at or about 5-fold, at least at or about 10-fold, at least at or about 20-fold, at least at or about 50-fold greater as compared to the amount, concentration, or density of cells at the beginning of the cultivation.

As described in the Examples, the number of population doublings inversely correlated with the probability of progression free survival in patients treated with the therapeutic T cell composition (e.g., outpout composition). Thus, in some embodiments, the number of population doublings is no greater than 1, 2, 3, 4, 5, 6, 8, 9, or 10 population doublings. In some embodiments, the number of population doublings is no greater than 1, 2, 3, 4, 5, or 6 population doublings. In some embodiments, reduced numbers of population doublings (e.g., less than or equal to 6) are achieved by expanding T cell compositions (e.g., engineered CD4+, CD+ 8 T cells) that include at least or at least about 55%, 60%, 65%, 70%, 75%, 80%, 85%, 90%, 91%, 92%, 93%, 94%, 95%, 96%, 97%, 98%, or 99% naïve-like and/or central memory T cells. In some embodiments, reduced numbers of population doublings (e.g., less than or equal to 6) are achieved by expanding T cell compositions (e.g., engineered CD4+, CD+ 8 T cells) that include no more than 45%, 40%, 35%, 30%, 25%, 20%, 15%, 10%, 9%, 8%, 7%, 6%, 5%, 4%, 3%, 2%, or 1% CD57+ T cells. In some embodiments, reduced numbers of population doublings (e.g., less than or equal to 6) are achieved by using a seed density of greater than 0.05×10ˆ6 cells/mL, 0.1×10ˆ6 cells/mL, 0.15×10ˆ6 cells/mL, 0.2×10ˆ6 cells/mL, 0.25×10ˆ6 cells/mL, 0.3×10ˆ6 cells/mL, 0.35×10ˆ6 cells/mL, 0.4×10ˆ6 cells/mL, 0.45×10ˆ6 cells/mL, or more.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In particular embodiments, a composition of engineered T cells enriched for CD57− T cells is cultivated in the presence of one or more cytokines. In certain embodiments, the one or more cytokines are recombinant cytokines. In particular embodiments, the one or more cytokines are human recombinant cytokines. In certain embodiments, the one or more cytokines bind to and/or are capable of binding to receptors that are expressed by and/or are endogenous to T cells. In particular embodiments, the one or more cytokines is or includes a member of the 4-alpha-helix bundle family of cytokines. In some embodiments, members of the 4-alpha-helix bundle family of cytokines include, but are not limited to, interleukin-2 (IL-2), interleukin-4 (IL-4), interleukin-7 (IL-7), interleukin-9 (IL-9), interleukin 12 (IL-12), interleukin 15 (IL-15), granulocyte colony-stimulating factor (G-CSF), and granulocyte-macrophage colony-stimulating factor (GM-CSF). In some embodiments, the one or more cytokines is or includes IL-15. In particular embodiments, the one or more cytokines is or includes IL-7. In particular embodiments, the one or more cytokines is or includes recombinant IL-2.

In some aspects, incubation is carried out in accordance with techniques such as those described in U.S. Pat. No. 6,040,177 to Riddell et al., Klebanoff et al. (2012) J Immunother. 35(9): 651-660, Terakura et al. (2012) Blood. 1:72-82, and/or Wang et al. (2012) J Immunother. 35(9):689-701.

In some embodiments, at least a portion of the cultivation is carried out in the internal cavity of a centrifugal chamber, for example, under centrifugal rotation, such as described in International Publication Number WO2016/073602. In some embodiments, at least a portion of the incubation performed in a centrifugal chamber includes mixing with a reagent or reagents to induce stimulation and/or activation. In some embodiments, cells, such as selected cells, are mixed with a stimulating condition or stimulatory agent in the centrifugal chamber. In some aspects of such processes, a volume of cells is mixed with an amount of one or more stimulating conditions or agents that is far less than is normally employed when performing similar stimulations in a cell culture plate or other system.

In some embodiments, the cultivation is performed with the addition of an cultivation buffer to the cells and stimulating agent to achieve a target volume of, for example, 10 mL to 2,000 mL, such as at least or about at least or about or 10 mL, 20 mL, 30 mL, 40 mL, 50 mL, 60 mL, 70 mL, 80 mL, 90 mL, 100 mL, 150 mL, 200 mL, 300 mL, 400 mL, 500 mL, 600 mL, 700 mL, 800 mL, 900 mL, 1,000 mL, 1,200 mL, 1,400 mL, 1,600 mL, 1,800 mL, 2,000 mL, 2,200 mL or 2,400 mL. In some embodiments, the incubation buffer and stimulating agent are pre-mixed before addition to the cells. In some embodiments, the stimulating incubation is carried out with periodic gentle mixing condition, which can aid in promoting energetically favored interactions and thereby permit the use of less overall stimulating agent while achieving stimulating and activation of cells.

In some embodiments, the incubation generally is carried out under mixing conditions, such as in the presence of spinning, generally at relatively low force or speed, such as speed lower than that used to pellet the cells, such as from or from about 600 rpm to 1700 rpm (e.g. at or about or at least 600 rpm, 1000 rpm, or 1500 rpm or 1700 rpm), such as at an RCF at the sample or wall of the chamber or other container of from or from about 80 g to 100 g (e.g. at or about or at least 80 g, 85 g, 90 g, 95 g, or 100 g). In some embodiments, the spin is carried out using repeated intervals of a spin at such low speed followed by a rest period, such as a spin and/or rest for 1, 2, 3, 4, 5, 6, 7, 8, 9, or 10 seconds, such as a spin at approximately 1 or 2 seconds followed by a rest for approximately 5, 6, 7, or 8 seconds.

In particular embodiments, the cultivation is performed in a closed system. In certain embodiments, the cultivation is performed in a closed system under sterile conditions. In particular embodiments, the cultivation is performed in the same closed system as one or more steps of the provided systems. In some embodiments the population of enriched T cells is removed from a closed system and placed in and/or connected to a bioreactor for the cultivation. Examples of suitable bioreactors for the cultivation include, but are not limited to, GE Xuri W25, GE Xuri W5, Sartorius BioSTAT RM 20|50, Finesse SmartRocker Bioreactor Systems, and Pall XRS Bioreactor Systems. In some embodiments, the bioreactor is used to perfuse and/or mix the cells during at least a portion of the cultivation step.

In some embodiments, the mixing is or includes rocking and/or motioning. In some cases, the bioreactor can be subject to motioning or rocking, which, in some aspects, can increase oxygen transfer. Motioning the bioreactor may include, but is not limited to rotating along a horizontal axis, rotating along a vertical axis, a rocking motion along a tilted or inclined horizontal axis of the bioreactor or any combination thereof. In some embodiments, at least a portion of the incubation is carried out with rocking. The rocking speed and rocking angle may be adjusted to achieve a desired agitation. In some embodiments the rock angle is 20°, 19°, 18°, 17°, 16°, 15°, 14°, 13°, 12°, 11°, 10°, 9°, 8°, 7°, 6°, 5°, 4°, 3°, 2° or 1°. In certain embodiments, the rock angle is between 6-16°. In other embodiments, the rock angle is between 7-16°. In other embodiments, the rock angle is between 8-12°. In some embodiments, the rock rate is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 rpm. In some embodiments, the rock rate is between 4 and 12 rpm, such as between 4 and 6 rpm, inclusive.

In some embodiments, the bioreactor maintains the temperature at or near 37° C. and CO2 levels at or near 5% with a steady air flow at, at about, or at least 0.01 L/min, 0.05 L/min, 0.1 L/min, 0.2 L/min, 0.3 L/min, 0.4 L/min, 0.5 L/min, 1.0 L/min, 1.5 L/min, or 2.0 L/min or greater than 2.0 L/min. In certain embodiments, at least a portion of the cultivation is performed with perfusion, such as with a rate of 290 ml/day, 580 ml/day, and/or 1160 ml/day, e.g., depending on the timing in relation to the start of the cultivation and/or density of the cultivated cells. In some embodiments, at least a portion of the cell culture expansion is performed with a rocking motion, such as at an angle of between 5° and 10°, such as 6°, at a constant rocking speed, such as a speed of between 5 and 15 RPM, such as 6 RMP or 10 RPM.

In some embodiments, the at least a portion of the cultivation step is performed under constant perfusion, e.g., a perfusion at a slow steady rate. In some embodiments, the perfusion is or include an outflow of liquid e.g., used media, and an inflow of fresh media. In certain embodiments, the perfusion replaces used media with fresh media. In some embodiments, at least a portion of the cultivation is performed under perfusion at a steady rate of or of about or of at least 100 ml/day, 200 ml/day, 250 ml/day, 275 ml/day, 290 ml/day, 300 ml/day, 350 ml/day, 400 ml/day, 450 ml/day, 500 ml/day, 550 ml/day, 575 ml/day, 580 ml/day, 600 ml/day, 650 ml/day, 700 ml/day, 750 ml/day, 800 ml/day, 850 ml/day, 900 ml/day, 950 ml/day, 1000 ml/day, 1100 ml/day, 1160 ml/day, 1200 ml/day, 1400 ml/day, 1500 ml day, 1600 ml/day, 1800 ml/day, 2000 ml/day, 2200 ml/day, or 2400 ml/day.

In certain embodiments, the engineered T cell composition generated from the provided methods for use in a cell therapy is active and expands, and/or is capable of activation and expansion, in vivo, when administered to a subject. In particular embodiments, the cells display features and/or characteristics that indicate or are associated with in vivo efficacy, activity, and/or expansion. For example, in some embodiments, such features or characters may include the expression of a protein, such as a surface protein, that is associated with activation, proliferation, and/or expansion after administration to a subject in vivo.

In certain embodiments, the engineered T cell compositions that are generated or produced by the provided methods, e.g., for use in a cell therapy, have greater expression of CD25 than the cells that are generated or produced by the alternative and/or exemplary process (e.g., a process of stimulating, engineering and/or cultivating populations of T cells containing higher frequencies of CD57+ T cells). In some embodiments, the cells of the engineered T cell compositions generated or produced by the provided methods have a greater expression of CD25 than T cells that are generated or produced by an alternative and/or exemplary process. In some embodiments, at least 20%, at least 30%, at least 40%, at least 50%, at least 60%, at least 70%, at least 75%, at least 80%, at least 85%, at least 90%, at least 100%, of the T cells of a population generated by the provided process are positive for CD25 staining, e.g., express a detectable amount of CD25. In particular embodiments, the engineered T cell compositions contains a greater frequency of cells that are positive for CD25 than a composition of cells produced or generated by the alternative and/or exemplary process. In some embodiments, the cells of the composition express at least 20%, at least 30%, at least 40%, at least 50%, at least 60%, at least 70%, at least 75%, at least 80%, at least 85%, at least 90%, at least 100%, at least 150%, at least 1-fold, at least 2-fold, at least 3-fold, at least 4-fold, or at least 5-fold, more CD25, e.g., as compared to cells produced or generated by the alternative and/or exemplary process.

In certain embodiments, the compositions of engineered T cells that are generated or produced by the provided methods, e.g., for use in a cell therapy, have greater expression of CD27 than the cells that are generated or produced by the alternative and/or exemplary process (e.g., a process of stimulating, engineering and/or cultivating populations of T cells containing higher frequencies CD57+ T cells). In particular embodiments, the T cells of an engineered composition that is generated or produced by the provided methods have a greater expression of CD27 than T cells that are generated or produced by an alternative and/or exemplary process. In certain embodiments, at least 20%, at least 30%, at least 40%, at least 50%, at least 60%, at least 70%, at least 75%, at least 80%, at least 85%, at least 90%, at least 100%, of the T cells of a composition generated by the provided process are positive for CD27 staining, e.g., express a detectable amount of CD27. In particular embodiments, the composition contains a greater frequency of cells that are positive for CD27 than a composition of cells produced or generated by the alternative and/or exemplary process. In some embodiments, the cells of the composition express at least 20%, at least 30%, at least 40%, at least 50%, at least 60%, at least 70%, at least 75%, at least 80%, at least 85%, at least 90%, at least 100%, at least 150%, at least 1-fold, at least 2-fold, at least 3-fold, at least 4-fold, or at least 5-fold, more CD27, e.g., as compared to cells produced or generated by the alternative and/or exemplary process. In certain embodiments, the engineered T cell compositions generated or produced by the provided methods, e.g., for use in a cell therapy, have a lower coefficient of variation (CV) of CD27 expression than the cells that are generated or produced by the alternative and/or exemplary process (e.g., a process of stimulating, engineering and/or cultivating populations of T cells containing higher frequencies CD57+ T cells). In certain embodiments, the engineered T cell compositions have a lower coefficient of variation (CV) of CD27 expression than the cells that are generated or produced by an alternative and/or exemplary process (e.g., a process of stimulating, engineering and/or cultivating populations of T cells containing higher frequencies CD57+ T cells).

In certain embodiments, the compositions of engineered T cells that are generated or produced by the provided methods, e.g., for use in a cell therapy, have lower expression of CD57 than the cells that are generated or produced by the alternative and/or exemplary process (e.g., a process of stimulating, engineering and/or cultivating populations of T cells containing higher frequencies CD27-T cells). In particular embodiments, the T cells of an engineered composition that is generated or produced by the provided methods have a greater expression of CD57 than T cells that are generated or produced by an alternative and/or exemplary process. In certain embodiments, at least 20%, at least 30%, at least 40%, at least 50%, at least 60%, at least 70%, at least 75%, at least 80%, at least 85%, at least 90%, at least 100%, of the T cells of a composition generated by the provided process are negative for CD57 staining, e.g., do not express a detectable amount of CD57. In particular embodiments, the composition contains a greater frequency of cells that are negative for CD57 than a composition of cells produced or generated by the alternative and/or exemplary process. In some embodiments, the cells of the composition express at least 20%, at least 30%, at least 40%, at least 50%, at least 60%, at least 70%, at least 75%, at least 80%, at least 85%, at least 90%, at least 100%, at least 150%, at least 1-fold, at least 2-fold, at least 3-fold, at least 4-fold, or at least 5-fold, fewer CD57, e.g., as compared to cells produced or generated by the alternative and/or exemplary process. In certain embodiments, the engineered T cell compositions generated or produced by the provided methods, e.g., for use in a cell therapy, have a lower coefficient of variation (CV) of CD57 expression than the cells that are generated or produced by the alternative and/or exemplary process (e.g., a process of stimulating, engineering and/or cultivating populations of T cells containing higher frequencies CD27-T cells). In certain embodiments, the engineered T cell compositions have a lower coefficient of variation (CV) of CD57 expression than the cells that are generated or produced by an alternative and/or exemplary process (e.g., a process of stimulating, engineering and/or cultivating populations of T cells containing higher frequencies CD27− T cells).

In some embodiments, the engineered T cells that are generated or produced by the provided methods, e.g., for use in a cell therapy, have greater expression of Ki67 than the cells that are generated or produced by the alternative and/or exemplary process (e.g., a process of stimulating, engineering and/or cultivating populations of T cells containing higher frequencies CD57+ T cells). In certain embodiments, the engineered T cell compositions have greater expression of Ki67 than the cells that are generated or produced by the alternative and/or exemplary process (e.g., a process of stimulating, engineering and/or cultivating populations of T cells containing higher frequencies CD57+ T cells). In some embodiments, the engineered T cells that are generated or produced by the provided methods, e.g., for use in a cell therapy, have greater expression of Ki67 than the cells that are generated or produced by the alternative and/or exemplary process (e.g., a process of stimulating, engineering and/or cultivating populations of T cells containing higher frequencies CD27− T cells). In certain embodiments, the engineered T cell compositions have greater expression of Ki67 than the cells that are generated or produced by the alternative and/or exemplary process (e.g., a process of stimulating, engineering and/or cultivating populations of T cells containing higher frequencies CD27− T cells). In particular embodiments, the T cells of a composition that is generated or produced by the provided methods have a greater expression of Ki67 than T cells that are generated or produced by an alternative and/or exemplary process. In certain embodiments, at least 20%, at least 30%, at least 40%, at least 50%, at least 60%, at least 70%, at least 75%, at least 80%, at least 85%, at least 90%, at least 100%, of the T cells of a composition generated by the provided process are positive for Ki67 staining, e.g., express a detectable amount of Ki67. In particular embodiments, the composition contains a greater frequency of cells that are positive for Ki67 than a composition of cells produced or generated by the alternative and/or exemplary process. In some embodiments, the cells of the composition express at least 20%, at least 30%, at least 40%, at least 50%, at least 60%, at least 70%, at least 75%, at least 80%, at least 85%, at least 90%, at least 100%, at least 150%, at least 1-fold, at least 2-fold, at least 3-fold, at least 4-fold, or at least 5-fold, more Ki67, e.g., as compared to cells produced or generated by the alternative and/or exemplary process. In certain embodiments, the engineered compositions generated or produced by the provided methods, e.g., for use in a cell therapy, have a lower coefficient of variation (CV) of Ki67 expression than the cells that are generated or produced by the alternative and/or exemplary process (e.g., a process of stimulating, engineering and/or cultivating populations of T cells containing higher frequencies CD57+ T cells). In certain embodiments, the engineered compositions generated or produced by the provided methods, e.g., for use in a cell therapy, have a lower coefficient of variation (CV) of Ki67 expression than the cells that are generated or produced by the alternative and/or exemplary process (e.g., a process of stimulating, engineering and/or cultivating populations of T cells containing higher frequencies CD27− T cells).

In some embodiments, the engineered T cell compositions that are generated or produced by the provided methods, e.g., for use in a cell therapy, have a lower coefficient of variation (CV) of expression of a recombinant receptor (e.g. a chimeric antigen receptor; CAR) than the cells that are generated or produced by the alternative and/or exemplary process (e.g., a process of stimulating, engineering and/or cultivating populations of T cells containing higher frequencies CD57+ T cells). In some embodiments, the engineered T cell compositions have a lower coefficient of variation (CV) of expression of a recombinant receptor (e.g. a chimeric antigen receptor; CAR) than the cells that are generated or produced by an alternative and/or exemplary process (e.g., a process of stimulating, engineering and/or cultivating populations of T cells containing higher frequencies CD57+ T cells). In some embodiments, the engineered T cell compositions that are generated or produced by the provided methods, e.g., for use in a cell therapy, have a lower coefficient of variation (CV) of expression of a recombinant receptor (e.g. a chimeric antigen receptor; CAR) than the cells that are generated or produced by the alternative and/or exemplary process (e.g., a process of stimulating, engineering and/or cultivating populations of T cells containing higher frequencies CD27− T cells). In some embodiments, the engineered T cell compositions have a lower coefficient of variation (CV) of expression of a recombinant receptor (e.g. a chimeric antigen receptor; CAR) than the cells that are generated or produced by an alternative and/or exemplary process (e.g., a process of stimulating, engineering and/or cultivating populations of T cells containing higher frequencies CD27− T cells). In some embodiments, the compositions of engineered T cells that are generated or produced by the provided methods, e.g., for use in a cell therapy, have a lower coefficient of variation (CV) of expression of the recombinant receptor that was introduced into the cells by genetic engineering (e.g. knocking in) than the cells that are generated or produced by the alternative and/or exemplary process (e.g., a process of stimulating, engineering and/or cultivating populations of T cells containing higher frequencies CD57+ T cells). In some embodiments, the compositions of engineered T cells that are generated or produced by the provided methods, e.g., for use in a cell therapy, have a lower coefficient of variation (CV) of expression of the recombinant receptor that was introduced into the cells by genetic engineering (e.g. knocking in) than the cells that are generated or produced by the alternative and/or exemplary process (e.g., a process of stimulating, engineering and/or cultivating populations of T cells containing higher frequencies CD27-T cells).

In particular embodiments, the compositions of engineered T cells that are generated or produced by the provided methods, e.g., for use in a cell therapy, have greater expression of CD28 than the cells that are generated or produced by the alternative and/or exemplary process (e.g., a process of stimulating, engineering and/or cultivating populations of T cells containing higher frequencies of CD57+ T cells). In particular embodiments, the compositions of engineered T cells that are generated or produced by the provided methods, e.g., for use in a cell therapy, have greater expression of CD28 than the cells that are generated or produced by the alternative and/or exemplary process (e.g., a process of stimulating, engineering and/or cultivating populations of T cells containing higher frequencies of CD27-T cells). In some embodiments, the T cells of a composition that is generated or produced by the provided methods have a greater expression of CD28 than T cells that are generated or produced by an alternative and/or exemplary process. In certain embodiments, at least 20%, at least 30%, at least 40%, at least 50%, at least 60%, at least 70%, at least 75%, at least 80%, at least 85%, at least 90%, at least 100%, of the T cells of a composition generated by the provided process are positive for CD28 staining, e.g., express a detectable amount of CD28. In particular embodiments, the composition contains a greater frequency of cells that are positive for CD28 than a composition of cells produced or generated by the alternative and/or exemplary process. In some embodiments, the cells of the composition express at least 20%, at least 30%, at least 40%, at least 50%, at least 60%, at least 70%, at least 75%, at least 80%, at least 85%, at least 90%, at least 100%, at least 150%, at least 1-fold, at least 2-fold, at least 3-fold, at least 4-fold, or at least 5-fold, more CD28, e.g., as compared to cells produced or generated by the alternative and/or exemplary process.

In certain embodiments, the provided methods are used in connection with successfully generating or producing compositions of engineered T cells that are suitable for use in cell therapy. In some embodiments, a composition is successfully generated if the cells of the composition achieve a target cell count, density, and/or expansion during cultivation H. Harvesting, Collecting, and Formulating Cells In some embodiments, one or more process steps (e.g. carried out in the centrifugal chamber and/or closed system) for manufacturing, generating or producing a cell therapy and/or engineered cells may include formulation of cells, such as formulation of genetically engineered cells resulting from the provided processing steps prior to or after the culturing, e.g. cultivation and expansion, and/or one or more other processing steps as described. In some embodiments, the provided methods associated with formulation of cells include processing transduced cells, such as cells transduced and/or expanded using the processing steps described above, in a closed system. In some embodiments, the transduced cells are from an individual donor. In some embodiments, transduced cells from an individual donor are combined with transduced cells of one or more other individual donors to produce transduced cells from a plurality of different donors. In some embodiments, the transduced cells are from a plurality of different donors. In some embodiments, the expanded cells are from an individual donor. In some embodiments, the expanded cells from an individual donor are combined with expanded cells from one or more other individual donors to produce expanded cells from a plurality of different donors. In some embodiments, the expanded cells are derived from a plurality of different donors.

In some embodiments, the stimulatory reagent is removed and/or separated from the cells prior to the formulating. In particular embodiments, the stimulatory reagent is removed and/or separated from the cells after the cultivation. In certain embodiments, the stimulatory agent is removed and/or separated from the cells subsequent to the cultivation and prior to formulating the cultivated cells, e.g., under conditions that promote proliferation and/or expansion. In certain embodiments, the stimulatory reagent is a stimulatory reagent that is described in herein, e.g., in Section III.A.1. In particular embodiments, the stimulatory reagent is removed and/or separated from the cells as described herein, e.g., in Section III.A.2.

In some embodiments, the cells are formulated between 0 days and 10 days, between 0 and 5 days, between 2 days and 7 days, between 0.5 days, and 4 days, or between 1 day and 3 days after the cells after the threshold cell count, density, and/or expansion has been achieved during the cultivation. In certain embodiments, the cells are formulated at or at or about or within 12 hours, 18 hours, 24 hours, 1 day, 2 days, or 3 days after the threshold cell count, density, and/or expansion has been achieved during the cultivation. In some embodiments, the cells are formulated within or within about 1 day after the threshold cell count, density, and/or expansion has been achieved during the cultivation.

In certain embodiments, the amount of time from the initiation of the stimulation to collecting, harvesting, or formulating the cells is, is about, or is less than 36 hours, 42 hours, 48 hours, 54 hours, 60 hours, 72 hours, 84 hours, 96 hours, 108 hours, or 120 hours. In certain embodiments, the amount of time from the initiation of the stimulation to collecting, harvesting, or formulating the cells is, is about, or is less than 1.5 days, 2 days, 3 days, 4 days, or 5 days. In some embodiments, the amount of time from the initiation of the stimulation to collecting, harvesting, or formulating the cells for generating engineered cells, from the initiation of the stimulation to collecting, harvesting, or formulating the cells is between or between about 36 hours and 120 hours, 48 hours and 96 hours, or 48 hours and 72 hours, inclusive, or between or between about 1.5 days and 5 days, 2 days and 4 days, or 2 day and 3 days, inclusive. In particular embodiments, the amount of time from the initiation of incubation to harvesting, collecting, or formulating the cells is, is about, or is less than 48 hours, 72 hours, or 96 hours. In particular embodiments, the amount of time from the initiation of incubation to harvesting, collecting, or formulating the cells is, is about, or is less than 2 days, 3 days, or 4 days. In particular embodiments, the amount of time from the initiation of incubation to harvesting, collecting, or formulating the cells is 48 hours±6 hours, 72 hours±6 hours, or 96 hours±6 hours. In particular embodiments, the amount of time from the initiation of incubation to harvesting, collecting, or formulating the cells is or is about 96 hours or four days.

In certain embodiments, the cells are harvested or collected at least when the integrated vector is detected in the genome. In some embodiments, the cells are harvested or collected prior to stable integrated vector copy number (iVCN) per diploid genome. In particular embodiments, the cells are harvested or collected after the integrated vector is detected in the genome but prior to when a stable iVCN per diploid genome is achieved. In some embodiments, the harvested or collected cells are from an individual donor. In some embodiments, the harvested or collected cells from an individual donor are combined with harvested or collected cells from one or more other individual donors to produce harvested or collected cells from a plurality of different donors. In some embodiments, the harvested or collected cells are from a plurality of different donors.

In some embodiments, the cells are harvested or collected before the iVCN of reaches, reaches about, or reaches at least 5.0, 4.0, 3.0, 2.5, 2.0, 1.75, 1.5, 1.25, 1.2, 1.1, 1.0, 0.9, 0.8, 0.75, 0.7, 0.6, 0.5, 0.4, 0.3, or 0.25 copies per diploid genome. In particular embodiments, the cells are harvested or collected before the iVCN reaches or about 1.0 copy per diploid genome. In some embodiments, the cells are collected or harvested before the iVCN reaches or about 0.5 copies per diploid genome.

In certain embodiments, the cells are harvested prior to, prior to about, or prior to at least one, two, three, four, five, six, eight, ten, twenty, or more cell doublings of the cell population, e.g., doublings that occur during the incubating.

In particular embodiments, the cells are harvested or collected at a time before the total number cells, e.g., total number of incubated cells or cells undergoing the incubation, is greater than or than about one, two, three, four, five, six, eight, ten, twenty, or more than twenty times the number of cells of the input population, e.g., the total number of cells that were contacted with the stimulatory reagent. In some embodiments, the cells are harvested or collected at a time before the total number of incubated cells is greater than or than about one, two, three, four, five, six, eight, ten, twenty, or more than twenty times the total number of cells that were transformed, transduced, or spinoculated, e.g., the total number of cells that were contacted with a viral vector. In certain embodiments, the cells are T cells, viable T cells, CD3+ T cells, CD4+ T cells, CD8+ T cells, CAR expressing T cells, or a combination of any of the foregoing. In particular embodiments, the cells are harvested or collected at a time before the total number of cells is greater than the total number of cells of the input population. In various embodiments, the cells are harvested or collected at a time before the total number of viable CD3+ T cells is greater than the total number of viable CD3+ cells of the input population. In particular embodiments, the cells are harvested or collected at a time before the total number of cells is greater than the total number of cells of the transformed, transduced, or spinoculated cells. In various embodiments, the cells are harvested or collected at a time before the total number of viable CD3+ T cells is greater than the total number of viable CD3+ cells of the transformed, transduced, or spinoculated cells. In various embodiments, the cells are harvested or collected at a time before the total number of viable CD4+ cells and CD8+ cells is greater than the total number of viable CD4+ cells and CD8+ cells of the input population. In particular embodiments, the cells are harvested or collected at a time before the total number of cells is greater than the total number of cells of the transformed, transduced, or spinoculated cells. In various embodiments, the cells are harvested or collected at a time before the total number of viable CD4+ cells and CD8+ cells is greater than the total number of viable CD4+ cells and CD8+ cells of the transformed, transduced, or spinoculated cells.

In some embodiments, the provided methods for manufacturing, generating or producing a cell therapy and/or engineered cells may include formulation of cells, such as formulation of genetically engineered cells resulting from the provided processing steps prior to or after the incubating, engineering, and cultivating, and/or one or more other processing steps as described. In some embodiments, the provided methods associated with formulation of cells include processing transduced cells, such as cells transduced and/or expanded using the processing steps described above, in a closed system. In some embodiments, the dose of cells comprising cells engineered with a recombinant antigen receptor, e.g. CAR or TCR, is provided as a composition or formulation, such as a pharmaceutical composition or formulation. Such compositions can be used in accord with the provided methods, such as in the prevention or treatment of diseases, conditions, and disorders, or in detection, diagnostic, and prognostic methods.

In some cases, the cells are processed in one or more steps (e.g. carried out in the centrifugal chamber and/or closed system) for manufacturing, generating or producing a cell therapy and/or engineered cells may include formulation of cells, such as formulation of genetically engineered cells resulting from the provided processing steps prior to or after the culturing, e.g. cultivation and expansion, and/or one or more other processing steps as described. In some cases, the cells can be formulated in an amount for dosage administration, such as for a single unit dosage administration or multiple dosage administration. In some embodiments, the provided methods associated with formulation of cells include processing transduced cells, such as cells transduced and/or expanded using the processing steps described above, in a closed system.

In certain embodiments, one or more compositions of enriched T cells are formulated. In particular embodiments, one or more compositions of enriched T cells are formulated after the one or more compositions have been engineered and/or cultivated. In particular embodiments, the one or more compositions are input compositions. In some embodiments, the one or more input compositions have been previously cryopreserved and stored, and are thawed prior to the incubation.

In certain embodiments, the formulated cells are output cells. In some embodiments, the formulated cells are derived from an individual donor. In some embodiments, the formulated cells from an individual donor are combined with formulated cells from one or more other individual donors to produce formulated cells from a plurality of different donors. In some embodiments, the formulated cells are derived from a plurality of different donors. In some embodiments, a formulated composition of enriched T cells is an output composition of enriched T cells. In particular embodiments, the formulated CD4+ T cells and formulated CD8+ T cells are the output CD4+ and CD8+ T cells. In particular embodiments, a formulated cell composition, e.g., a formulated composition of enriched CD4+ and CD8+ cells, is an output cell composition, e.g., an output composition of enriched CD4+ and CD8+ cells.

In some embodiments, cells can be formulated into a container, such as a bag or vial. In some embodiments, the cells are formulated between 0 days and 10 days, between 0 and 5 days, between 2 days and 7 days, between 0.5 days, and 4 days, or between 1 day and 3 days after the cells after the threshold cell count, density, and/or expansion has been achieved during the cultivation. In certain embodiments, the cells are formulated at or at or about or within 12 hours, 18 hours, 24 hours, 1 day, 2 days, or 3 days after the threshold cell count, density, and/or expansion has been achieved during the cultivation. In some embodiments, the cells are formulated within or within about 1 day after the threshold cell count, density, and/or expansion has been achieved during the cultivation.

In certain embodiments, the cells are cultivated for a minimum duration or amount of time, for example, so that cells are harvested in a less activated state than if they were formulated at an earlier time point during the cultivation, regardless of when the threshold is achieved. In some embodiments, the cells are cultivated between 0 day and 3 days, e.g., between 0 and 3 days, between 1 and 2 days, at or at about 1 day, at or at about 2 days, or at or at about 3 days, after the threshold cell count, density, and/or expansion has been achieved during the cultivation. In certain embodiments, the cells active the threshold cell count, density, and/or expansion and remain cultivated for a minimum time or duration prior to the formulation. In some embodiments, cells that have achieved the threshold are not formulated until they have been cultivated for a minimum duration and/or amount of time, such as a minimum time or duration of between 1 day and 14 days, 2 days and 7 days, or 3 days and 6 days, or a minimum time or duration of the cultivation of or of about 2 days, 3 days, 4 days, 5 days, 6 days, 7 days, or more than 7 days. In some embodiments, the minimum time or duration of the cultivation is between 3 days and 6 days.

In some embodiments, the cells are formulated in a pharmaceutically acceptable buffer, which may, in some aspects, include a pharmaceutically acceptable carrier or excipient. In some embodiments, the processing includes exchange of a medium into a medium or formulation buffer that is pharmaceutically acceptable or desired for administration to a subject. In some embodiments, the processing steps can involve washing the transduced and/or expanded cells to replace the cells in a pharmaceutically acceptable buffer that can include one or more optional pharmaceutically acceptable carriers or excipients. Exemplary of such pharmaceutical forms, including pharmaceutically acceptable carriers or excipients, can be any described below in conjunction with forms acceptable for administering the cells and compositions to a subject. The pharmaceutical composition in some embodiments contains the cells in amounts effective to treat or prevent the disease or condition, such as a therapeutically effective or prophylactically effective amount.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being treated with the cells, preferably those with activities complementary to the cells, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine.

Compositions in some embodiments are provided as sterile liquid preparations, e.g., isotonic aqueous solutions, suspensions, emulsions, dispersions, or viscous compositions, which may in some aspects be buffered to a selected pH. Liquid compositions can comprise carriers, which can be a solvent or dispersing medium containing, for example, water, saline, phosphate buffered saline, polyol (for example, glycerol, propylene glycol, liquid polyethylene glycol) and suitable mixtures thereof. Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

In some embodiments, the formulation buffer contains a cryopreservative. In some embodiments, the cell are formulated with a cyropreservative solution that contains 1.0% to 30% DMSO solution, such as a 5% to 20% DMSO solution or a 5% to 10% DMSO solution. In some embodiments, the cryopreservation solution is or contains, for example, PBS containing 20% DMSO and 8% human serum albumin (HSA), or other suitable cell freezing media. In some embodiments, the cryopreservative solution is or contains, for example, at least or about 7.5% DMSO. In some embodiments, the processing steps can involve washing the transduced and/or expanded cells to replace the cells in a cryopreservative solution. In some embodiments, the cells are frozen, e.g., cryopreserved or cryoprotected, in media and/or solution with a final concentration of or of about 12.5%, 12.0%, 11.5%, 11.0%, 10.5%, 10.0%, 9.5%, 9.0%, 8.5%, 8.0%, 7.5%, 7.0%, 6.5%, 6.0%, 5.5%, or 5.0% DMSO, or between 1% and 15%, between 6% and 12%, between 5% and 10%, or between 6% and 8% DMSO. In particular embodiments, the cells are frozen, e.g., cryopreserved or cryoprotected, in media and/or solution with a final concentration of or of about 5.0%, 4.5%, 4.0%, 3.5%, 3.0%, 2.5%, 2.0%, 1.5%, 1.25%, 1.0%, 0.75%, 0.5%, or 0.25% HSA, or between 0.1% and −5%, between 0.25% and 4%, between 0.5% and 2%, or between 1% and 2% HSA.

In particular embodiments, the composition of enriched T cells, e.g., T cells that have been stimulated, engineered, and/or cultivated, are formulated, cryopreserved, and then stored for an amount of time. In certain embodiments, the formulated, cryopreserved cells are stored until the cells are released for infusion. In particular embodiments, the formulated cryopreserved cells are stored for between 1 day and 6 months, between 1 month and 3 months, between 1 day and 14 days, between 1 day and 7 days, between 3 days and 6 days, between 6 months and 12 months, or longer than 12 months. In some embodiments, the cells are cryopreserved and stored for, for about, or for less than 1 days, 2 days, 3 days, 4 days, 5 days, 6 days, or 7 days. In certain embodiments, the cells are thawed and administered to a subject after the storage. In certain embodiments, the cells are stored for or for about 5 days.

In some embodiments, the formulation is carried out using one or more processing step including washing, diluting or concentrating the cells, such as the cultured or expanded cells. In some embodiments, the processing can include dilution or concentration of the cells to a desired concentration or number, such as unit dose form compositions including the number of cells for administration in a given dose or fraction thereof. In some embodiments, the processing steps can include a volume-reduction to thereby increase the concentration of cells as desired. In some embodiments, the processing steps can include a volume-addition to thereby decrease the concentration of cells as desired. In some embodiments, the processing includes adding a volume of a formulation buffer to transduced and/or expanded cells. In some embodiments, the volume of formulation buffer is from or from about 10 mL to 1000 mL, such as at least or about at least or about or 50 mL, 100 mL, 200 mL, 300 mL, 400 mL, 500 mL, 600 mL, 700 mL, 800 mL, 900 mL or 1000 mL.

In some embodiments, such processing steps for formulating a cell composition is carried out in a closed system. Exemplary of such processing steps can be performed using a centrifugal chamber in conjunction with one or more systems or kits associated with a cell processing system, such as a centrifugal chamber produced and sold by Biosafe SA, including those for use with the Sepax® or Sepax 2® cell processing systems. An exemplary system and process is described in International Publication Number WO2016/073602. In some embodiments, the method includes effecting expression from the internal cavity of the centrifugal chamber a formulated composition, which is the resulting composition of cells formulated in a formulation buffer, such as pharmaceutically acceptable buffer, in any of the above embodiments as described. In some embodiments, the expression of the formulated composition is to a container, such as a bag that is operably linked as part of a closed system with the centrifugal chamber. In some embodiments, the container, such as bag, is connected to a system at an output line or output position.

In some embodiments, the closed system, such as associated with a centrifugal chamber or cell processing system, includes a multi-port output kit containing a multi-way tubing manifold associated at each end of a tubing line with a port to which one or a plurality of containers can be connected for expression of the formulated composition. In some aspects, a desired number or plurality of output containers, e.g., bags, can be sterilely connected to one or more, generally two or more, such as at least 3, 4, 5, 6, 7, 8 or more of the ports of the multi-port output. For example, in some embodiments, one or more containers, e.g., bags can be attached to the ports, or to fewer than all of the ports. Thus, in some embodiments, the system can effect expression of the output composition into a plurality of output bags.

In some aspects, cells can be expressed to the one or more of the plurality of output bags in an amount for dosage administration, such as for a single unit dosage administration or multiple dosage administration. For example, in some embodiments, the output bags may each contain the number of cells for administration in a given dose or fraction thereof. Thus, each bag, in some aspects, may contain a single unit dose for administration or may contain a fraction of a desired dose such that more than one of the plurality of output bags, such as two of the output bags, or 3 of the output bags, together constitute a dose for administration.

Thus, the containers, e.g., output bags, generally contain the cells to be administered, e.g., one or more unit doses thereof. The unit dose may be an amount or number of the cells to be administered to the subject or twice the number (or more) of the cells to be administered. It may be the lowest dose or lowest possible dose of the cells that would be administered to the subject.

In some embodiments, each of the containers, e.g., bags, individually comprises a unit dose of the cells. Thus in some embodiments, each of the containers comprises the same or approximately or substantially the same number of cells. In some embodiments, each unit dose contains at least or about at least $1\times10^6$, $2\times10^6$, $5\times10^6$, $1\times10^7$, $5\times10^7$, or $1\times10^8$ engineered cells, total cells, T cells, or PBMCs. In some embodiments, the volume of the formulated cell composition in each bag is 10 mL to 100 mL, such as at least or about at least 20 mL, 30 mL, 40 mL, 50 mL, 60 mL, 70 mL, 80 mL, 90 mL or 100 mL.

In some embodiments, such cells produced by the method, or a composition comprising such cells, are administered to a subject for treating a disease or condition.

In particular embodiments, the provided methods have at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% probability or likelihood of successfully generating or producing an engineered T cell composition enriched for CD57− T cells suitable for a cell therapy. In certain embodiments, the probability or likelihood is between 85% and 100%, between 90% and 95%, or between 92% and 94%. In certain embodiments, the provided methods successfully generate or produce an engineered T cell composition enriched for CD57− T cells suitable for a cell therapy from at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% of the donor samples or populations of enriched CD57− T cells.

In particular embodiments, the provided methods have at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% probability or likelihood of successfully generating or producing an engineered T cell composition enriched for CD27+ T cells suitable for a cell therapy. In certain embodiments, the probability or likelihood is between 85% and 100%, between 90% and 95%, or between 92% and 94%. In certain embodiments, the provided methods successfully generate or produce an engineered T cell composition enriched for CD27+ T cells suitable for a cell therapy from at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% of the donor samples or populations of enriched CD27+ T cells.

In certain embodiments, the total duration of the provided process for generating engineered cells, from the initiation of the stimulation to collecting, harvesting, or formulating the cells is, is about, or is less than 36 hours, 42 hours, 48 hours, 54 hours, 60 hours, 72 hours, 84 hours, 96 hours, 108 hours, or 120 hours. In certain embodiments, the total duration of the provided process for generating engineered cells, from the initiation of the stimulation to collecting, harvesting, or formulating the cells is, is about, or is less than 1.5 days, 2 days, 3 days, 4 days, or 5 days. In some embodiments, the total duration of the provided process for generating engineered cells, from the initiation of the stimulation to collecting, harvesting, or formulating the cells is between or between about 36 hours and 120 hours, 48 hours and 96 hours, or 48 hours and 72 hours, inclusive, or between or between about 1.5 days and 5 days, 2 days and 4 days, or 2 days and 3 days, inclusive. In particular embodiments, the amount of time to complete the provided process as measured from the initiation of incubation to harvesting, collecting, or formulating the cells is, is about, or is less than 48 hours, 72 hours, or 96 hours, or is, is about, or is less than 2 days, 3 days, or 4 days. In particular embodiments, the amount of time to complete the provided process as measured from the initiation of incubation to harvesting, collecting, or formulating the cells is 48 hours±6 hours, 72 hours±6 hours, or 96 hours±6 hours.

In some embodiments, the incubation, is completed between or between about 24 hour and 120 hours, 36 hour and 108 hours, 48 hours and 96 hours, or 48 hours and 72 hours, inclusive, after the initiation of the stimulation. In some embodiments, the incubation is completed at, about, or within 120 hours, 108 hours, 96 hours, 72 hours, 48 hours, or 36 hours from the initiation of the stimulation. In particular embodiments, the incubation are completed after 24 hours±6 hours, 48 hours±6 hours, or 72 hours±6 hours. In some embodiments, the incubation is completed between or between about one day and 5 days, 1.5 days and 4.5 days, 2 days and 4 days, or 2 day and 3 days, inclusive, after the initiation of the stimulation. In some embodiments, the incubation is completed at, about, or within 5 days, 4 days, 3 days, 2 days, or 1.5 days from the initiation of the stimulation.

In some embodiments, the entire process is performed with a single population of enriched T cells, e.g., CD4+ and CD8+ T cells or CD3+ cells. In certain embodiments, the process is performed with two or more selected populations of enriched T cells (e.g., CD4 and CD8 cells) that are combined prior to and/or during the process to generate or produce a single output population of enriched T cells. In some embodiments, the enriched T cells are or include engineered T cells, e.g., T cells transduced to express a recombinant receptor.

In some embodiments, a composition of engineered T cells, is generated by (i) incubating an input population of or containing T cells under stimulating conditions for between or between about 18 and 30 hours, inclusive, (ii) introducing a heterologous or recombinant polynucleotide encoding a recombinant receptor into T cells of the stimulated population, (iii) incubating the cells, and then (iv) collecting or harvesting the incubated cells.

In some embodiments, the cells are collected or harvested within between 36 and 108 hours or between 1.5 days and 4.5 days after the incubation under stimulatory conditions is initiated. In particular embodiments, the cells are collected or harvested within 48 hours or two days after the transformed (e.g., genetically engineered, transduced, or transfected) T cells achieve a stable integrated vector copy number (iVCN) per genome that does not increase or decrease by more than 20% within a span of 24-48 hours or one to two days. In some embodiments, the integration is considered stable when the measured iVCN of a cell population is within or within about 20%, 15%, 10%, or 5% of the total vector copy number (VCN) measured in the population. Particular embodiments contemplate that to achieve a stable integration, the cells must be incubated for, for about, or for at least 48 hours, 60 hours, or 72 hours, or one day, 2 days, or 3 days, after the viral vector is contacted or introduced to the cells. In some embodiments, the stable integration occurs within or with about 72 hours of the incubation. In some embodiments, the cells are collected or harvested at a time when the total number of transformed T cells is at or less than the total number of cells of the input population. In various embodiments, the cells are collected or harvested at a time before the cells of the input population have doubled more than three, two, or one time(s).

In certain embodiments, a composition of engineered T cells is generated by (i) incubating an input population comprising T cells under stimulating conditions for between 18 and 30 hours, inclusive, in the presence of a stimulatory reagent, e.g., a stimulatory reagent described herein, (ii) transducing the stimulated T cells with a viral vector encoding a recombinant receptor, such as by spinoculating the stimulated T cells in the presence of the viral vector, (iii) incubating the transduced T cells under static conditions for between or between 18 hours and 96 hours, inclusive, and (iv) harvesting T cells of the transformed population within between or between about 36 and 108 hours after the incubation under stimulatory conditions is initiated.

In some embodiments, the process associated with the provided methods is compared to an alternative process. For example, in some embodiments, the provided methods herein are compared an alternative process that contains a step for expanding the cells. In particular embodiments, the alternative process may differ in one or more specific aspects, but otherwise contains similar or the same features, aspects, steps, stages, reagents, and/or conditions of the process associated with the provided methods. In some embodiments, the alternative process is similar as the process associated with the provided methods, e.g., lacks or does not include expansion, but differs in a manner that includes, but is not limited to, one or more of; different reagents and/or media formulations; presence of serum during the incubation, transduction, transfection, and/or cultivation; different cellular makeup of the input population, e.g., ratio of CD4+ to CD8+ T cells; different stimulating conditions and/or a different stimulatory reagent; different ratio of stimulatory reagent to cells; different vector and/or method of transduction; different timing or order for incubating, transducing, and/or transfecting the cells; absence or difference of one or more recombinant cytokines present during the incubation or transduction (e.g., different cytokines or different concentrations), or different timing for harvesting or collecting the cells.

In some embodiments, the duration or amount of time required to complete the provided process, as measured from the isolation, enrichment, and/or selection input cells (e.g., CD4+ or CD8+ T cells) from a donor sample to the time at which a the engineered cells are collected, formulated, and/or cryoprotected is, is about, or is less than 48 hours, 72 hours, 96 hours, 120 hours, 2 days, 3 days, 4 days, 5 days, 7 days, or 10 days. In some embodiments, isolated, selected, or enriched cells are not cryoprotected prior to the stimulation, and the duration or amount of time required to complete the provided process, as measured from the isolation, enrichment, and/or selection input cells (to the time at which a the output cells are collected, formulated, and/or cryoprotected is, is about, or is less than 48 hours, 72 hours, 96 hours, or 120 hours, or 2 days, 3 days, 4 days, or 5 days.

In certain embodiments, the provided processes are performed on a population of cells, e.g., CD4+ and CD8+ T cells or CD3+ cells, that were isolated, enriched, or selected from a biological sample (e.g. a donor sample). In some aspects, the provided methods can produce or generate a composition of engineered T cells from when a donor sample is collected from an individual donor or a plurality of different donors within a shortened amount of time as compared to other methods or processes. In some embodiments, the provided methods can produce or generate engineered T cells, including any or all times where donor samples, or enriched, isolated, or selected cells are cryopreserved and stored prior to steps for stimulation or transduction, within or within about 10 days, 9 days, 8 days, 7 days, 6 days, 5 days, 4 days, 3 days, 2 days, or within or within about 120 hours, 96 hours, 72 hours, or 48 hours, from when a donor sample is collected from an individual donor or a plurality of different donors to when the engineered T cells are collected, harvested, or formulated (e.g., for cryopreservation or administration). In particular embodiments, the provided methods can produce or generate engineered T cells, including any or all times where donor samples, or enriched, isolated, or selected cells are cryopreserved and stored prior to steps for stimulation or transduction, within between or between about 6 days and 8 days, inclusive, from when the donor sample is collected from an individual donor or a plurality of different donors to when the engineered T cells are collected, harvested, or formulated.

III. Heterologous Polynucleotides Encoding Recombinant Proteins

In some embodiments, the provided methods are or include introducing a heterologous polynucleotide into cells of a population enriched for CD57− cells (e.g. a CD57 depleted T cell population and/or a pooled CD57 depleted T cell population). In some embodiments, a heterologous polynucleotide is introduced into cells of a CD57 depleted T cell population from an individual donor. In some embodiments, a heterologous polynucleotide is introduced into cells of a pooled CD57 depleted T cell population from a plurality of different donors.

In some embodiments, the provided methods are or include introducing a heterologous polynucleotide into cells of a population enriched for CD27+ cells (e.g. a CD27 enriched T cell population and/or a pooled CD27 enriched T cell population). In some embodiments, a heterologous polynucleotide is introduced into cells of a CD27 enriched T cell population from an individual donor. In some embodiments, a heterologous polynucleotide is introduced into cells of a pooled CD27 enriched T cell population from a plurality of different donors.

In some embodiments, the provided methods are or include introducing a heterologous polynucleotide into a population of cells in which the expression or one or more target molecules has been disrupted (e.g. knocked out). In some embodiments, the heterologous polynucleotide encodes a recombinant protein. Such recombinant proteins may include recombinant receptors, such as any described in Section III.A. Introduction of the polynucleotides, e.g., heterologous or recombinant polynucleotides, encoding the recombinant protein into the cell may be carried out using any of a number of known vectors. Such vectors include viral, including adeno-associated and lentiviral and gammaretroviral systems. Exemplary methods include those for transfer of heterologous polynucleotides encoding the receptors, including via viral, e.g., adeno-associated, retroviral or lentiviral, transduction. In some embodiments, a population of stimulated cells is genetically engineered (e.g. knocked in), such as to introduce a heterologous or recombinant polynucleotide encoding a recombinant receptor, thereby generating a population of transformed cells (also referred to herein as a transformed population of cells). In some embodiments, a population of stimulated cells is genetically engineered (e.g. knocked in), such as to introduce a heterologous or recombinant polynucleotide encoding a recombinant receptor into a genetically disrupted (e.g. knocked out) genetic locus or portion thereof, thereby generating a population of transformed cells (also referred to herein as a transformed population of cells).

In certain embodiments, a polynucleotide encoding the recombinant protein, e.g. a recombinant receptor, is introduced to the cells. In certain embodiments, the polynucleotide or nucleic acid molecule is heterologous to the cells. In particular embodiments, the heterologous polynucleotide is not native to the cells. In certain embodiments, the heterologous nucleic acid molecule or heterologous polynucleotide encodes a protein, e.g., a recombinant protein that is not natively expressed by the cell. In particular embodiments, the heterologous nucleic acid molecule or polynucleotide is or contains a nucleic acid sequence that is not found in the cell prior to the contact or introduction.

In particular embodiments, the heterologous polynucleotide encodes a recombinant protein. In certain embodiments, the recombinant protein is a recombinant receptor. In some embodiments, the recombinant protein is a recombinant antigen receptor, such as a recombinant TCR or a chimeric antigen receptor (CAR).

A. Recombinant Receptors

In some embodiments, provided are engineered cells, such as CD57− T cells (e.g. an engineered T cell composition enriched for CD57− T cells), that express or are engineered to express one or more recombinant receptor(s). In some embodiments, an engineered T cell composition enriched for CD57− T cells is from an individual donor. In some embodiments, an engineered T cell composition enriched for CD57− T cells from an individual donor is combined with an engineered T cell composition enriched for CD57− T cells from one or more other individual donors to produce a pooled engineered T cell composition from a plurality of different donors. In some embodiments, an engineered T cell composition enriched for CD57− T cells is from a plurality of different donors.

In some embodiments, provided are engineered cells, such as CD27+ T cells (e.g. an engineered T cell composition enriched for CD27+ T cells), that express or are engineered to express one or more recombinant receptor(s). In some embodiments, an engineered T cell composition enriched for CD27+ T cells is from an individual donor. In some embodiments, an engineered T cell composition enriched for CD27+ T cells from an individual donor is combined with an engineered T cell composition enriched for CD27+ T cells from one or more other individual donors to produce a pooled engineered T cell composition from a plurality of different donors. In some embodiments, an engineered T cell composition enriched for CD27+ T cells is from a plurality of different donors.

Among the receptors are antigen receptors and receptors containing one or more components thereof. The recombinant receptors may include chimeric receptors, such as those containing ligand-binding domains or binding fragments thereof and intracellular signaling domains or regions, functional non-TCR antigen receptors, chimeric antigen receptors (CARs), T cell receptors (TCRs), such as recombinant or transgenic TCRs, chimeric autoantibody receptor (CAAR) and components of any of the foregoing. The recombinant receptor, such as a CAR, generally includes the extracellular antigen (or ligand) binding domain linked to one or more intracellular signaling components, in some aspects via linkers and/or transmembrane domain(s). In some embodiments, the engineered cells express two or more receptors that contain different components, domains or regions. In some aspects, two or more receptors allows spatial or temporal regulation or control of specificity, activity, antigen (or ligand) binding, function and/or expression of the recombinant receptors.

1. Chimeric Antigen Receptors (CARs)

In some embodiments of the provided methods and uses, chimeric receptors, such as a chimeric antigen receptors, contain one or more domains that combine a ligand-binding domain (e.g. antibody or antibody fragment) that provides specificity for a desired antigen (e.g., tumor antigen) with intracellular signaling domains. In some embodiments, the intracellular signaling domain is a stimulating or an activating intracellular domain portion, such as a T cell stimulating or activating domain, providing a primary activation signal or a primary signal. In some embodiments, the intracellular signaling domain contains or additionally contains a costimulatory signaling domain to facilitate effector functions. In some embodiments, chimeric receptors when genetically engineered into immune cells can modulate T cell activity, and, in some cases, can modulate T cell differentiation or homeostasis, thereby resulting in genetically engineered cells with improved longevity, survival and/or persistence in vivo, such as for use in adoptive cell therapy methods.

Exemplary antigen receptors, including CARS, and methods for engineering and introducing such receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) PLoS ONE 8(4): e61338; Turtle et al., Curr. Opin. Immunol., 2012 October; 24(5): 633-39; Wu et al., Cancer, 2012 Mar. 18(2): 160-75. In some aspects, the antigen receptors include a CAR as described in U.S. Pat. No. 7,446,190, and those described in International Patent Application Publication No.: WO/2014055668 A1. Examples of the CARs include CARS as disclosed in any of the aforementioned publications, such as WO2014031687, U.S. Pat. Nos. 8,339,645, 7,446,179, US 2013/0149337, U.S. Pat. Nos. 7,446,190, 8,389,282, Kochenderfer et al., 2013, Nature Reviews Clinical Oncology, 10, 267-276 (2013); Wang et al. (2012) J. Immunother. 35(9): 689-701; and Brentjens et al., Sci Transl Med. 2013 5(177). See also WO2014031687, U.S. Pat. Nos. 8,339,645, 7,446,179, US 2013/0149337, U.S. Pat. Nos. 7,446,190, and 8,389,282.

The chimeric receptors, such as CARS, generally include an extracellular antigen binding domain, such as a portion of an antibody molecule, generally a variable heavy ($V_H$) chain region and/or variable light ($V_L$) chain region of the antibody, e.g., an scFv antibody fragment.

In some embodiments, the antigen targeted by the receptor is a polypeptide. In some embodiments, it is a carbohydrate or other molecule. In some embodiments, the antigen is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

In some embodiments, the antigen targeted by the receptor is or includes αvβ6 integrin (avb6 integrin), B cell maturation antigen (BCMA), B7-H3, B7-H6, carbonic anhydrase 9 (CA9, also known as CAIX or G250), a cancer testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrin receptor A2 (EPHa2), estrogen receptor, Fc receptor like 5 (FCRLS; also known as Fc receptor homolog 5 or FCRHS), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha(IL-22Rα), IL-13 receptor alpha 2 (IL-13Rα2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen is or includes CD20, CD19, CD22, ROR1, CD45, CD21, CD5, CD33, Igkappa, Iglambda, CD79a, CD79b or CD30.

In some embodiments, the antigen is or includes a pathogen-specific or pathogen-expressed antigen. In some embodiments, the antigen is a viral antigen (such as a viral antigen from HIV, HCV, HBV, etc.), bacterial antigens, and/or parasitic antigens.

In some embodiments, the antigen or antigen binding domain is CD19. In some embodiments, the scFv contains a VH and a VL derived from an antibody or an antibody fragment specific to CD19. In some embodiments, the antibody or antibody fragment that binds CD19 is a mouse derived antibody such as FMC63 and SJ25C1. In some embodiments, the antibody or antibody fragment is a human antibody, e.g., as described in U.S. Patent Publication No. US 2016/0152723.

In some embodiments, the scFv is derived from FMC63. FMC63 generally refers to a mouse monoclonal IgG1 antibody raised against Nalm-1 and -16 cells expressing CD19 of human origin (Ling, N. R., et al. (1987). *Leucocyte typing III.* 302). In some embodiments, the FMC63 antibody comprises CDRH1 and H2 set forth in SEQ ID NOS: 38 and 39, respectively, and CDRH3 set forth in SEQ ID NO: 40 or 54 and CDRL1 set forth in SEQ ID NO: 35 and CDR L2 set forth in SEQ ID NO: 36 or 55 and CDR L3 set forth in SEQ ID NO: 37 or 56. In some embodiments, the FMC63 antibody comprises the heavy chain variable region ($V_H$) comprising the amino acid sequence of SEQ ID NO: 41 and the light chain variable region ($V_L$) comprising the amino acid sequence of SEQ ID NO: 42.

In some embodiments, the scFv comprises a variable light chain containing the CDRL1 sequence of SEQ ID NO:35, a CDRL2 sequence of SEQ ID NO:36, and a CDRL3 sequence of SEQ ID NO:37 and/or a variable heavy chain containing a CDRH1 sequence of SEQ ID NO:38, a CDRH2 sequence of SEQ ID NO:39, and a CDRH3 sequence of SEQ ID NO:40. In some embodiments, the scFv comprises a variable heavy chain region set forth in SEQ ID NO:41 and a variable light chain region set forth in SEQ ID NO:42. In some embodiments, the variable heavy and variable light chains are connected by a linker. In some embodiments, the linker is set forth in SEQ ID NO:58. In some embodiments, the scFv comprises, in order, a $V_H$, a linker, and a $V_L$. In some embodiments, the scFv comprises, in order, a $V_L$, a linker, and a $V_H$. In some embodiments, the scFv is encoded by a sequence of nucleotides set forth in SEQ ID NO:43 or a sequence that exhibits at least 85%, 86%, 87%, 88%, 89%, 90%, 91%, 92%, 93%, 94%, 95%, 96%, 97%, 98%, or 99% sequence identity to SEQ ID NO:43. In some embodiments, the scFv comprises the sequence of amino acids set forth in SEQ ID NO:43 or a sequence that exhibits at least 85%, 86%, 87%, 88%, 89%, 90%, 91%, 92%, 93%, 94%, 95%, 96%, 97%, 98%, or 99% sequence identity to SEQ ID NO:43.

In some embodiments the scFv is derived from SJ25C1. SJ25C1 is a mouse monoclonal IgG1 antibody raised against Nalm-1 and -16 cells expressing CD19 of human origin (Ling, N. R., et al. (1987). *Leucocyte typing III.* 302). In some embodiments, the SJ25C1 antibody comprises CDRH1, H2 and H3 set forth in SEQ ID NOS: 47-49, respectively, and CDRL1, L2 and L3 sequences set forth in SEQ ID NOS: 44-46, respectively. In some embodiments, the SJ25C1 antibody comprises the heavy chain variable region ($V_H$) comprising the amino acid sequence of SEQ ID NO: 50 and the light chain variable region ($V_L$) comprising the amino acid sequence of SEQ ID NO: 51.

In some embodiments, the scFv comprises a variable light chain containing the CDRL1 sequence of SEQ ID NO:44, a CDRL2 sequence of SEQ ID NO: 45, and a CDRL3 sequence of SEQ ID NO:46 and/or a variable heavy chain containing a CDRH1 sequence of SEQ ID NO:47, a CDRH2 sequence of SEQ ID NO:48, and a CDRH3 sequence of SEQ ID NO:49. In some embodiments, the scFv comprises a variable heavy chain region set forth in SEQ ID NO:50 and a variable light chain region set forth in SEQ ID NO:51. In some embodiments, the variable heavy and variable light chain are connected by a linker. In some embodiments, the linker is set forth in SEQ ID NO:52. In some embodiments, the scFv comprises, in order, a $V_H$, a linker, and a $V_L$. In some embodiments, the scFv comprises, in order, a $V_L$, a linker, and a $V_H$. In some embodiments, the scFv comprises the sequence of amino acids set forth in SEQ ID NO:53 or a sequence that exhibits at least 85%, 86%, 87%, 88%, 89%, 90%, 91%, 92%, 93%, 94%, 95%, 96%, 97%, 98%, or 99% sequence identity to SEQ ID NO:53.

In some embodiments, the chimeric antigen receptor includes an extracellular portion containing an antibody or antibody fragment. In some aspects, the chimeric antigen receptor includes an extracellular portion containing the antibody or fragment and an intracellular signaling domain. In some embodiments, the antibody or fragment includes an scFv.

In some embodiments, the antibody portion of the recombinant receptor, e.g., CAR, further includes at least a portion of an immunoglobulin constant region, such as a hinge region, e.g., an IgG4 hinge region, and/or a $C_H1/C_L$ and/or Fc region. In some embodiments, the constant region or portion is of a human IgG, such as IgG4 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. Exemplary spacers include, but are not limited to, those described in Hudecek et al. (2013) *Clin. Cancer Res.,* 19:3153, international patent application publication number WO2014031687, U.S. Pat. No. 8,822,647 or published app. No. US2014/0271635.

In some embodiments, the constant region or portion is of a human IgG, such as IgG4 or IgG1. In some embodiments, the spacer has the sequence ESKYGPPCPPCP (set forth in SEQ ID NO: 1), and is encoded by the sequence set forth in SEQ ID NO: 2. In some embodiments, the spacer has the sequence set forth in SEQ ID NO: 3. In some embodiments, the spacer has the sequence set forth in SEQ ID NO: 4. In some embodiments, the constant region or portion is of IgD. In some embodiments, the spacer has the sequence set forth in SEQ ID NO: 5. In some embodiments, the spacer has a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS: 1, 3, 4 or 5. In some embodiments, the spacer has the sequence set forth in SEQ ID NOS: 27-34. In some embodiments, the spacer has a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS: 27-34.

In some embodiments, the antigen receptor comprises an intracellular domain linked directly or indirectly to the extracellular domain. In some embodiments, the chimeric antigen receptor includes a transmembrane domain linking the extracellular domain and the intracellular signaling domain. In some embodiments, the intracellular signaling domain comprises an ITAM. For example, in some aspects, the antigen recognition domain (e.g. extracellular domain) generally is linked to one or more intracellular signaling components, such as signaling components that mimic activation through an antigen receptor complex, such as a TCR complex, in the case of a CAR, and/or signal via another cell surface receptor. In some embodiments, the chimeric receptor comprises a transmembrane domain linked or fused between the extracellular domain (e.g. scFv) and intracellular signaling domain. Thus, in some embodiments, the antigen-binding component (e.g., antibody) is linked to one or more transmembrane and intracellular signaling domains.

In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s). In some aspects, the transmembrane domain contains a transmembrane portion of CD28.

In some embodiments, the extracellular domain and transmembrane domain can be linked directly or indirectly. In some embodiments, the extracellular domain and transmembrane are linked by a spacer, such as any described herein. In some embodiments, the receptor contains extracellular portion of the molecule from which the transmembrane domain is derived, such as a CD28 extracellular portion.

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

The receptor, e.g., the CAR, generally includes at least one intracellular signaling component or components. In some aspects, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from CD3 zeta chain, FcR gamma, CD3 gamma, CD3 delta and CD3 epsilon. In some embodiments, cytoplasmic signaling molecule(s) in the CAR contain(s) a cytoplasmic signaling domain, portion thereof, or sequence derived from CD3 zeta.

In some embodiments, the receptor includes an intracellular component of a TCR complex, such as a TCR CD3 chain that mediates T-cell activation and cytotoxicity, e.g., CD3 zeta chain. Thus, in some aspects, the antigen-binding portion is linked to one or more cell signaling modules. In some embodiments, cell signaling modules include CD3 transmembrane domain, CD3 intracellular signaling domains, and/or other CDtransmembrane domains. In some embodiments, the receptor, e.g., CAR, further includes a portion of one or more additional molecules such as Fc receptor γ, CD8, CD4, CD25, or CD16. For example, in some aspects, the CAR or other chimeric receptor includes a chimeric molecule between CD3-zeta (CD3-ξ) or Fc receptor γ and CD8, CD4, CD25 or CD16.

In some embodiments, upon ligation of the CAR or other chimeric receptor, the cytoplasmic domain or intracellular signaling domain of the receptor activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptors to initiate signal transduction following antigen receptor engagement.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

In some embodiments, the chimeric antigen receptor contains an intracellular domain of a T cell costimulatory molecule. In some embodiments, the CAR includes a signaling domain and/or transmembrane portion of a costimulatory receptor, such as CD28, 4-1BB, OX40, DAP10, and ICOS. In some aspects, the same CAR includes both the activating and costimulatory components. In some embodiments, the chimeric antigen receptor contains an intracellular domain derived from a T cell costimulatory molecule or a functional variant thereof, such as between the transmembrane domain and intracellular signaling domain. In some aspects, the T cell costimulatory molecule is CD28 or 41BB.

In some embodiments, the activating domain is included within one CAR, whereas the costimulatory component is provided by another CAR recognizing another antigen. In some embodiments, the CARs include activating or stimulatory CARs, costimulatory CARs, both expressed on the same cell (see WO2014/055668). In some aspects, the cells include one or more stimulatory or activating CAR and/or a costimulatory CAR. In some embodiments, the cells further include inhibitory CARs (iCARs, see Fedorov et al., Sci. Transl. Medicine, 5(215) (December, 2013), such as a CAR recognizing an antigen other than the one associated with and/or specific for the disease or condition whereby an activating signal delivered through the disease-targeting CAR is diminished or inhibited by binding of the inhibitory CAR to its ligand, e.g., to reduce off-target effects.

In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and CD137 (4-1BB, TNFRSF9) co-stimulatory domains, linked to a CD3 zeta intracellular domain.

In some embodiments, the CAR encompasses one or more, e.g., two or more, costimulatory domains and an activation domain, e.g., primary activation domain, in the cytoplasmic portion. Exemplary CARS include intracellular components of CD3-zeta, CD28, and 4-1BB.

In some embodiments, the antigen receptor further includes a marker and/or cells expressing the CAR or other antigen receptor further includes a surrogate marker, such as a cell surface marker, which may be used to confirm transduction or engineering of the cell to express the receptor. In some aspects, the marker includes all or part (e.g., truncated form) of CD34, a NGFR, or epidermal growth factor receptor, such as truncated version of such a cell surface receptor (e.g., tEGFR). In some embodiments, the nucleic acid encoding the marker is operably linked to a polynucleotide encoding for a linker sequence, such as a cleavable linker sequence, e.g., T2A. For example, a marker, and optionally a linker sequence, can be any as disclosed in published patent application No. WO2014031687. For example, the marker can be a truncated EGFR (tEGFR) that is, optionally, linked to a linker sequence, such as a T2A cleavable linker sequence.

An exemplary polypeptide for a truncated EGFR (e.g. tEGFR) comprises the sequence of amino acids set forth in SEQ ID NO: 7 or 16 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7 or 16. An exemplary T2A linker sequence comprises the sequence of amino acids set forth in SEQ ID NO: 6 or 17 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 6 or 17.

In some embodiments, the marker is a molecule, e.g., cell surface protein, not naturally found on T cells or not naturally found on the surface of T cells, or a portion thereof. In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

In some cases, CARS are referred to as first, second, and/or third generation CARS. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR is one that includes multiple costimulatory domains of different costimulatory receptors.

For example, in some embodiments, the CAR contains an antibody, e.g., an antibody fragment, a transmembrane domain that is or contains a transmembrane portion of CD28 or a functional variant thereof, and an intracellular signaling domain containing a signaling portion of CD28 or functional variant thereof and a signaling portion of CD3 zeta or functional variant thereof. In some embodiments, the CAR contains an antibody, e.g., antibody fragment, a transmembrane domain that is or contains a transmembrane portion of CD28 or a functional variant thereof, and an intracellular signaling domain containing a signaling portion of a 4-1BB or functional variant thereof and a signaling portion of CD3 zeta or functional variant thereof. In some such embodiments, the receptor further includes a spacer containing a portion of an Ig molecule, such as a human Ig molecule, such as an Ig hinge, e.g. an IgG4 hinge, such as a hinge-only spacer.

In some embodiments, the transmembrane domain of the recombinant receptor, e.g., the CAR, is or includes a transmembrane domain of human CD28 (e.g. Accession No. P01747.1) or variant thereof, such as a transmembrane domain that comprises the sequence of amino acids set forth in SEQ ID NO: 8 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 8; in some embodiments, the transmembrane-domain containing portion of the recombinant receptor comprises the sequence of amino acids set forth in SEQ ID NO: 9 or a sequence of amino acids having at least at or about 85%, 86%, 87%, 88%, 89%, 90%, 91%, 92%, 93%, 94%, 95%, 96%, 97%, 98%, 99% or more sequence identity thereto.

In some embodiments, the intracellular signaling component(s) of the recombinant receptor, e.g. the CAR, contains an intracellular costimulatory signaling domain of human CD28 or a functional variant or portion thereof, such as a domain with an LL to GG substitution at positions 186-187 of a native CD28 protein. For example, the intracellular signaling domain can comprise the sequence of amino acids set forth in SEQ ID NO: 10 or 11 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 10 or 11. In some embodiments, the intracellular domain comprises an intracellular costimulatory signaling domain of 4-1BB (e.g. (Accession No. Q07011.1) or functional variant or portion thereof, such as the sequence of amino acids set forth in SEQ ID NO: 12 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 12.

In some embodiments, the intracellular signaling domain of the recombinant receptor, e.g. the CAR, comprises a human CD3 zeta stimulatory signaling domain or functional variant thereof, such as an 112 AA cytoplasmic domain of isoform 3 of human CD3 (Accession No.: P20963.2) or a CD3 zeta signaling domain as described in U.S. Pat. No. 7,446,190 or U.S. Pat. No. 8,911,993. For example, in some embodiments, the intracellular signaling domain comprises the sequence of amino acids as set forth in SEQ ID NO: 13, 14 or 15 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 13, 14 or 15.

In some aspects, the spacer contains only a hinge region of an IgG, such as only a hinge of IgG4 or IgG1, such as the hinge only spacer set forth in SEQ ID NO: 1. In other embodiments, the spacer is or contains an Ig hinge, e.g., an IgG4-derived hinge, optionally linked to a $C_H2$ and/or $C_H3$ domains. In some embodiments, the spacer is an Ig hinge, e.g., an IgG4 hinge, linked to $C_H2$ and $C_H3$ domains, such as set forth in SEQ ID NO: 4. In some embodiments, the spacer is an Ig hinge, e.g., an IgG4 hinge, linked to a $C_H3$ domain only, such as set forth in SEQ ID NO: 3. In some embodiments, the spacer is or comprises a glycine-serine rich sequence or other flexible linker such as known flexible linkers.

For example, in some embodiments, the CAR includes an antibody such as an antibody fragment, including scFvs, a spacer, such as a spacer containing a portion of an immunoglobulin molecule, such as a hinge region and/or one or more constant regions of a heavy chain molecule, such as an Ig-hinge containing spacer, a transmembrane domain containing all or a portion of a CD28-derived transmembrane domain, a CD28-derived intracellular signaling domain, and a CD3 zeta signaling domain. In some embodiments, the CAR includes an antibody or fragment, such as scFv, a spacer such as any of the Ig-hinge containing spacers, a CD28-derived transmembrane domain, a 4-1BB-derived intracellular signaling domain, and a CD3 zeta-derived signaling domain.

In some embodiments, nucleic acid molecules encoding such CAR constructs further includes a sequence encoding a T2A ribosomal skip element and/or a tEGFR sequence, e.g., downstream of the sequence encoding the CAR. In some embodiments, the sequence encodes a T2A ribosomal skip element set forth in SEQ ID NO: 6 or 17, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 6 or 17. In some embodiments, T cells expressing an antigen receptor (e.g. CAR) can also be generated to express a truncated EGFR (EGFRt) as a non-immunogenic selection epitope (e.g. by introduction of a construct encoding the CAR and EGFRt separated by a T2A ribosome switch to express two proteins from the same construct), which then can be used as a marker to detect such cells (see e.g. U.S. Pat. No. 8,802,374). In some embodiments, the sequence encodes an tEGFR sequence set forth in SEQ ID NO: 7 or 16, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7 or 16. In some cases, the peptide, such as T2A, can cause the ribosome to skip (ribosome skipping) synthesis of a peptide bond at the C-terminus of a 2A element, leading to separation between the end of the 2A sequence and the next peptide downstream (see, for example, de Felipe. Genetic Vaccines and Ther. 2:13 (2004) and deFelipe et al. *Traffic* 5:616-626 (2004)). Many 2A elements are known. Examples of 2A sequences that can be used in the methods and nucleic acids disclosed herein, without limitation, 2A sequences from the foot-and-mouth disease virus (F2A, e.g., SEQ ID NO: 21), equine rhinitis A virus (E2A, e.g., SEQ ID NO: 20), Thosea asigna virus (T2A, e.g., SEQ ID NO: 6 or 17), and porcine teschovirus-1 (P2A, e.g., SEQ ID NO: 18 or 19) as described in U.S. Patent Publication No. 20070116690.

The recombinant receptors, such as CARS, expressed by the cells administered to the subject generally recognize or specifically bind to a molecule that is expressed in, associated with, and/or specific for the disease or condition or cells thereof being treated. Upon specific binding to the molecule, e.g., antigen, the receptor generally delivers an immunostimulatory signal, such as an ITAM-transduced signal, into the cell, thereby promoting an immune response targeted to the disease or condition. For example, in some embodiments, the cells express a CAR that specifically binds to an antigen expressed by a cell or tissue of the disease or condition or associated with the disease or condition.

2. T Cell Receptors (TCRs)

In some embodiments, engineered cells, such as CD57− T cells (e.g. an engineered T cell composition enriched for CD57− T cells), used in connection with the provided methods, uses, articles of manufacture or compositions are cells that express a T cell receptor (TCR) or antigen-binding portion thereof that recognizes a peptide epitope or T cell epitope of a target polypeptide, such as an antigen of a tumor, viral or autoimmune protein.

In some embodiments, engineered cells, such as CD527+ T cells (e.g. an engineered T cell composition enriched for CD27+ T cells), used in connection with the provided methods, uses, articles of manufacture or compositions are cells that express a T cell receptor (TCR) or antigen-binding portion thereof that recognizes a peptide epitope or T cell epitope of a target polypeptide, such as an antigen of a tumor, viral or autoimmune protein.

In some embodiments, a "T cell receptor" or "TCR" is a molecule that contains a variable α and β chains (also known as TCRα and TCRβ, respectively) or a variable γ and δ chains (also known as TCRα and TCRβ, respectively), or antigen-binding portions thereof, and which is capable of specifically binding to a peptide bound to an MHC molecule. In some embodiments, the TCR is in the αβ form. Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules.

Unless otherwise stated, the term "TCR" should be understood to encompass full TCRs as well as antigen-binding portions or antigen-binding fragments thereof. In some embodiments, the TCR is an intact or full-length TCR, including TCRs in the αβ form or γδ form. In some embodiments, the TCR is an antigen-binding portion that is less than a full-length TCR but that binds to a specific peptide bound in an MHC molecule, such as binds to an MHC-peptide complex. In some cases, an antigen-binding portion or fragment of a TCR can contain only a portion of the structural domains of a full-length or intact TCR, but yet is able to bind the peptide epitope, such as MHC-peptide complex, to which the full TCR binds. In some cases, an antigen-binding portion contains the variable domains of a TCR, such as variable α chain and variable β chain of a TCR, sufficient to form a binding site for binding to a specific MHC-peptide complex. Generally, the variable chains of a TCR contain complementarity determining regions involved in recognition of the peptide, MHC and/or MHC-peptide complex.

In some embodiments, the variable domains of the TCR contain hypervariable loops, or complementarity determining regions (CDRs), which generally are the primary contributors to antigen recognition and binding capabilities and specificity. In some embodiments, a CDR of a TCR or combination thereof forms all or substantially all of the antigen-binding site of a given TCR molecule. The various CDRs within a variable region of a TCR chain generally are separated by framework regions (FRs), which generally display less variability among TCR molecules as compared to the CDRs (see, e.g., Jores et al., Proc. Nat'l Acad. Sci. U.S.A. 87:9138, 1990; Chothia et al., EMBO J. 7:3745, 1988; see also Lefranc et al., Dev. Comp. Immunol. 27:55, 2003). In some embodiments, CDR3 is the main CDR responsible for antigen binding or specificity, or is the most important among the three CDRs on a given TCR variable region for antigen recognition, and/or for interaction with the processed peptide portion of the peptide-MHC complex. In some contexts, the CDR1 of the alpha chain can interact with the N-terminal part of certain antigenic peptides. In some contexts, CDR1 of the beta chain can interact with the C-terminal part of the peptide. In some contexts, CDR2 contributes most strongly to or is the primary CDR responsible for the interaction with or recognition of the MHC portion of the MHC-peptide complex. In some embodiments, the variable region of the β-chain can contain a further hypervariable region (CDR4 or HVR4), which generally is involved in superantigen binding and not antigen recognition (Kotb (1995) Clinical Microbiology Reviews, 8:411-426).

In some embodiments, a TCR also can contain a constant domain, a transmembrane domain and/or a short cytoplasmic tail (see, e.g., Janeway et al., Immunobiology: The Immune System in Health and Disease, 3rd Ed., Current Biology Publications, p. 4:33, 1997). In some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction.

In some embodiments, a TCR chain contains one or more constant domain. For example, the extracellular portion of a given TCR chain (e.g., α-chain or β-chain) can contain two immunoglobulin-like domains, such as a variable domain (e.g., Vα or Vβ; typically amino acids 1 to 116 based on Kabat numbering Kabat et al., "Sequences of Proteins of Immunological Interest, U.S. Dept. Health and Human Services, Public Health Service National Institutes of Health, 1991, 5th ed.) and a constant domain (e.g., α-chain constant domain or Cα, typically positions 117 to 259 of the chain based on Kabat numbering or β chain constant domain or $C_\beta$, typically positions 117 to 295 of the chain based on Kabat) adjacent to the cell membrane. For example, in some cases, the extracellular portion of the TCR formed by the two chains contains two membrane-proximal constant domains, and two membrane-distal variable domains, which variable domains each contain CDRs. The constant domain of the TCR may contain short connecting sequences in which a cysteine residue forms a disulfide bond, thereby linking the two chains of the TCR. In some embodiments, a TCR may have an additional cysteine residue in each of the α and β chains, such that the TCR contains two disulfide bonds in the constant domains.

In some embodiments, the TCR chains contain a transmembrane domain. In some embodiments, the transmembrane domain is positively charged. In some cases, the TCR chain contains a cytoplasmic tail. In some cases, the structure allows the TCR to associate with other molecules like CD3 and subunits thereof. For example, a TCR containing constant domains with a transmembrane region may anchor the protein in the cell membrane and associate with invariant subunits of the CD3 signaling apparatus or complex. The intracellular tails of CD3 signaling subunits (e.g. CD3γ, CD3δ, CD3ε and CD3 chains) contain one or more immunoreceptor tyrosine-based activation motif or ITAM that are involved in the signaling capacity of the TCR complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds.

In some embodiments, the TCR can be generated from a known TCR sequence(s), such as sequences of Vα,β chains, for which a substantially full-length coding sequence is readily available. Methods for obtaining full-length TCR sequences, including V chain sequences, from cell sources are well known. In some embodiments, nucleic acids encoding the TCR can be obtained from a variety of sources, such as by polymerase chain reaction (PCR) amplification of TCR-encoding nucleic acids within or isolated from a given cell or cells, or synthesis of publicly available TCR DNA sequences.

In some embodiments, the TCR is obtained from a biological source, such as from cells such as from a T cell (e.g. cytotoxic T cell), T-cell hybridomas or other publicly available source. In some embodiments, the T-cells can be obtained from in vivo isolated cells. In some embodiments, the TCR is a thymically selected TCR. In some embodiments, the TCR is a neoepitope-restricted TCR. In some embodiments, the T− cells can be a cultured T-cell hybridoma or clone. In some embodiments, the TCR or antigen-binding portion thereof or antigen-binding fragment thereof can be synthetically generated from knowledge of the sequence of the TCR.

In some embodiments, the TCR is generated from a TCR identified or selected from screening a library of candidate TCRs against a target polypeptide antigen, or target T cell epitope thereof. TCR libraries can be generated by amplification of the repertoire of Vα and Vβ from T cells isolated from a subject, including cells present in PBMCs, spleen or other lymphoid organ. In some cases, T cells can be amplified from tumor-infiltrating lymphocytes (TILs). In some embodiments, TCR libraries can be generated from CD4+ or CD8+ cells. In some embodiments, the TCRs can be amplified from a T cell source of a normal of healthy subject, i.e. normal TCR libraries. In some embodiments, the TCRs can be amplified from a T cell source of a diseased subject, i.e. diseased TCR libraries. In some embodiments, degenerate primers are used to amplify the gene repertoire of Vα and Vβ, such as by RT-PCR in samples, such as T cells, obtained from humans. In some embodiments, scTv libraries can be assembled from naïve Vα and Vβ libraries in which the amplified products are cloned or assembled to be separated by a linker. Depending on the source of the subject and cells, the libraries can be HLA allele-specific. Alternatively, in some embodiments, TCR libraries can be generated by mutagenesis or diversification of a parent or scaffold TCR molecule. In some aspects, the TCRs are subjected to directed evolution, such as by mutagenesis, e.g., of the α or β chain. In some aspects, particular residues within CDRs of the TCR are altered. In some embodiments, selected TCRs can be modified by affinity maturation. In some embodiments, antigen-specific T cells may be selected, such as by screening to assess CTL activity against the peptide. In some aspects, TCRs, e.g. present on the antigen-specific T cells, may be selected, such as by binding activity, e.g., particular affinity or avidity for the antigen.

In some embodiments, the TCR or antigen-binding portion thereof is one that has been modified or engineered. In some embodiments, directed evolution methods are used to generate TCRs with altered properties, such as with higher affinity for a specific MHC-peptide complex. In some embodiments, directed evolution is achieved by display methods including, but not limited to, yeast display (Holler et al. (2003) Nat Immunol, 4, 55-62; Holler et al. (2000) Proc Natl Acad Sci USA, 97, 5387-92), phage display (Li et al. (2005) Nat Biotechnol, 23, 349-54), or T cell display (Chervin et al. (2008) J Immunol Methods, 339, 175-84). In some embodiments, display approaches involve engineering, or modifying, a known, parent or reference TCR. For example, in some cases, a wild-type TCR can be used as a template for producing mutagenized TCRs in which in one or more residues of the CDRs are mutated, and mutants with an desired altered property, such as higher affinity for a desired target antigen, are selected.

In some embodiments, peptides of a target polypeptide for use in producing or generating a TCR of interest are known or can be readily identified. In some embodiments, peptides suitable for use in generating TCRs or antigen-binding portions can be determined based on the presence of an HLA-restricted motif in a target polypeptide of interest, such as a target polypeptide described below. In some embodiments, peptides are identified using available computer prediction models. In some embodiments, for predicting MHC class I binding sites, such models include, but are not limited to, ProPred1 (Singh and Raghava (2001) Bioinformatics 17(12):1236-1237, and SYFPEITHI (see Schuler et al. (2007) Immunoinformatics Methods in Molecular Biology, 409(1): 75-93 2007). In some embodiments, the MHC-restricted epitope is HLA-A0201, which is expressed in approximately 39-46% of all Caucasians and therefore, represents a suitable choice of MHC antigen for use preparing a TCR or other MHC-peptide binding molecule.

HLA-A0201-binding motifs and the cleavage sites for proteasomes and immune-proteasomes using computer prediction models are known. For predicting MHC class I binding sites, such models include, but are not limited to, ProPred1 (described in more detail in Singh and Raghava, ProPred: prediction of HLA-DR binding sites. BIOINFORMATICS 17(12):1236-1237 2001), and SYFPEITHI (see Schuler et al. SYFPEITHI, Database for Searching and T-Cell Epitope Prediction. in Immunoinformatics Methods in Molecular Biology, vol 409(1): 75-93 2007)

In some embodiments, the TCR or antigen binding portion thereof may be a recombinantly produced natural protein or mutated form thereof in which one or more property, such as binding characteristic, has been altered. In some embodiments, a TCR may be derived from one of various animal species, such as human, mouse, rat, or other mammal. A TCR may be cell-bound or in soluble form. In some embodiments, for purposes of the provided methods, the TCR is in cell-bound form expressed on the surface of a cell.

In some embodiments, the TCR is a full-length TCR. In some embodiments, the TCR is an antigen-binding portion. In some embodiments, the TCR is a dimeric TCR (dTCR). In some embodiments, the TCR is a single-chain TCR (sc-TCR). In some embodiments, a dTCR or scTCR have the structures as described in WO 03/020763, WO 04/033685, WO2011/044186.

In some embodiments, the TCR contains a sequence corresponding to the transmembrane sequence. In some embodiments, the TCR does contain a sequence corresponding to cytoplasmic sequences. In some embodiments, the TCR is capable of forming a TCR complex with CD3. In some embodiments, any of the TCRs, including a dTCR or scTCR, can be linked to signaling domains that yield an active TCR on the surface of a T cell. In some embodiments, the TCR is expressed on the surface of cells.

In some embodiments a dTCR contains a first polypeptide wherein a sequence corresponding to a TCR α chain variable region sequence is fused to the N terminus of a sequence corresponding to a TCR α chain constant region extracellular sequence, and a second polypeptide wherein a sequence corresponding to a TCR β chain variable region sequence is fused to the N terminus a sequence corresponding to a TCR β chain constant region extracellular sequence, the first and second polypeptides being linked by a disulfide bond. In some embodiments, the bond can correspond to the native interchain disulfide bond present in native dimeric αβ TCRs. In some embodiments, the interchain disulfide bonds are not present in a native TCR. For example, in some embodiments, one or more cysteines can be incorporated into the constant region extracellular sequences of dTCR polypeptide pair. In some cases, both a native and a non-native disulfide bond may be desirable. In some embodiments, the TCR contains a transmembrane sequence to anchor to the membrane.

In some embodiments, a dTCR contains a TCR α chain containing a variable α domain, a constant α domain and a first dimerization motif attached to the C-terminus of the constant α domain, and a TCR β chain comprising a variable β domain, a constant β domain and a first dimerization motif attached to the C-terminus of the constant β domain, wherein the first and second dimerization motifs easily interact to form a covalent bond between an amino acid in the first dimerization motif and an amino acid in the second dimerization motif linking the TCR α chain and TCR β chain together.

In some embodiments, the TCR is a scTCR. Typically, a scTCR can be generated using methods known, See e.g., Soo Hoo, W. F. et al. PNAS (USA) 89, 4759 (1992); Wülfing, C. and Plüickthun, A., J. Mol. Biol. 242, 655 (1994); Kurucz, I. et al. PNAS (USA) 90 3830 (1993); International published PCT Nos. WO 96/13593, WO 96/18105, WO99/60120, WO99/18129, WO 03/020763, WO2011/044186; and Schlueter, C. J. et al. J. Mol. Biol. 256, 859 (1996). In some embodiments, a scTCR contains an introduced non-native disulfide interchain bond to facilitate the association of the TCR chains (see e.g. International published PCT No. WO 03/020763). In some embodiments, a scTCR is a non-disulfide linked truncated TCR in which heterologous leucine zippers fused to the C-termini thereof facilitate chain association (see e.g. International published PCT No. WO99/60120). In some embodiments, a scTCR contain a TCRα variable domain covalently linked to a TCRβ variable domain via a peptide linker (see e.g., International published PCT No. WO99/18129).

In some embodiments, a scTCR contains a first segment constituted by an amino acid sequence corresponding to a TCR α chain variable region, a second segment constituted by an amino acid sequence corresponding to a TCR β chain variable region sequence fused to the N terminus of an amino acid sequence corresponding to a TCR β chain constant domain extracellular sequence, and a linker sequence linking the C terminus of the first segment to the N terminus of the second segment.

In some embodiments, a scTCR contains a first segment constituted by an a chain variable region sequence fused to the N terminus of an α chain extracellular constant domain sequence, and a second segment constituted by a β chain variable region sequence fused to the N terminus of a sequence β chain extracellular constant and transmembrane sequence, and, optionally, a linker sequence linking the C terminus of the first segment to the N terminus of the second segment.

In some embodiments, a scTCR contains a first segment constituted by a TCR β chain variable region sequence fused to the N terminus of a β chain extracellular constant domain sequence, and a second segment constituted by an α chain variable region sequence fused to the N terminus of a sequence α chain extracellular constant and transmembrane sequence, and, optionally, a linker sequence linking the C terminus of the first segment to the N terminus of the second segment.

In some embodiments, the linker of a scTCRs that links the first and second TCR segments can be any linker capable of forming a single polypeptide strand, while retaining TCR binding specificity. In some embodiments, the linker sequence may, for example, have the formula —P-AA-P— wherein P is proline and AA represents an amino acid sequence wherein the amino acids are glycine and serine. In some embodiments, the first and second segments are paired so that the variable region sequences thereof are orientated for such binding. Hence, in some cases, the linker has a sufficient length to span the distance between the C terminus of the first segment and the N terminus of the second segment, or vice versa, but is not too long to block or reduces bonding of the scTCR to the target ligand. In some embodiments, the linker can contain from or from about 10 to 45 amino acids, such as 10 to 30 amino acids or 26 to 41 amino acids residues, for example 29, 30, 31 or 32 amino acids. In some embodiments, the linker has the formula -PGGG-$(SGGGG)_5$-P- wherein P is proline, G is glycine and S is serine (SEQ ID NO:22). In some embodiments, the linker has the sequence GSADDAKKDAAKKDGKS (SEQ ID NO:23)

In some embodiments, the scTCR contains a covalent disulfide bond linking a residue of the immunoglobulin region of the constant domain of the α chain to a residue of the immunoglobulin region of the constant domain of the 13 chain. In some embodiments, the interchain disulfide bond in a native TCR is not present. For example, in some embodiments, one or more cysteines can be incorporated into the constant region extracellular sequences of the first and second segments of the scTCR polypeptide. In some cases, both a native and a non-native disulfide bond may be desirable.

In some embodiments of a dTCR or scTCR containing introduced interchain disulfide bonds, the native disulfide bonds are not present. In some embodiments, the one or more of the native cysteines forming a native interchain disulfide bonds are substituted to another residue, such as to a serine or alanine. In some embodiments, an introduced disulfide bond can be formed by mutating non-cysteine residues on the first and second segments to cysteine. Exemplary non-native disulfide bonds of a TCR are described in published International PCT No. WO2006/000830.

In some embodiments, the TCR or antigen-binding fragment thereof exhibits an affinity with an equilibrium binding constant for a target antigen of between or between about 10-5 and 10-12 M and all individual values and ranges therein. In some embodiments, the target antigen is an MHC-peptide complex or ligand.

In some embodiments, nucleic acid or nucleic acids encoding a TCR, such as a and 13 chains, can be amplified by PCR, cloning or other suitable means and cloned into a suitable expression vector or vectors. The expression vector can be any suitable recombinant expression vector, and can be used to transform or transfect any suitable host. Suitable vectors include those designed for propagation and expansion or for expression or both, such as plasmids and viruses.

In some embodiments, the vector can a vector of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), or the pEX series (Clontech, Palo Alto, Calif.). In some cases, bacteriophage vectors, such as λG10, λGT11, (Stratagene), λTMBL4, and λNM1149, also can be used. In some embodiments, plant expression vectors can be used and include pBI01, pBI101.2, pBI101.3, pBI121 and pBIN19 (Clontech). In some embodiments, animal expression vectors include pEUK-Cl, pMAM and pMAMneo (Clontech). In some embodiments, a viral vector is used, such as a retroviral vector.

In some embodiments, the recombinant expression vectors can be prepared using standard recombinant DNA techniques. In some embodiments, vectors can contain regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based. In some embodiments, the vector can contain a nonnative promoter operably linked to the nucleotide sequence encoding the TCR or antigen-binding portion (or other MHC-peptide binding molecule). In some embodiments, the promoter can be a non-viral promoter or a viral promoter, such as a cytomegalovirus (CMV) promoter, an SV40 promoter, an RSV promoter, and a promoter found in the long-terminal repeat of the murine stem cell virus. Other known promoters also are contemplated.

In some embodiments, to generate a vector encoding a TCR, the α and β chains are PCR amplified from total cDNA isolated from a T cell clone expressing the TCR of interest and cloned into an expression vector. In some embodiments, the α and β chains are cloned into the same vector. In some embodiments, the α and β chains are cloned into different vectors. In some embodiments, the generated α and β chains are incorporated into a retroviral, e.g. lentiviral, vector.

In some embodiments, the provided methods involve administering to a subject having a disease or condition cells expressing a recombinant antigen receptor. In some embodiments, the cells expressing a recombinant antigen receptor are from a plurality of different donors. In some embodiments, the cells are allogeneic to the subject. Various methods for the introduction of genetically engineered components, e.g., recombinant receptors, e.g., CARs or TCRs, are well known and may be used with the provided methods and compositions. Exemplary methods include those for transfer of nucleic acids encoding the receptors, including via viral, e.g., retroviral or lentiviral, transduction, transposons, and electroporation.

Among the cells expressing the receptors and administered by the provided methods are engineered cells. The genetic engineering generally involves introduction of a nucleic acid encoding the recombinant or engineered component into a composition containing the cells, such as by retroviral transduction, transfection, or transformation.

3. Chimeric Auto-Antibody Receptors (CAARs)

In some embodiments, among the recombinant receptor expressed by the engineered cells used in connection with the provided methods, uses, articles of manufacture and compositions is a chimeric autoantibody receptor (CAAR). In some embodiments, the CAAR is specific for an autoantibody. In some embodiments, a cell expressing the CAAR, such as a T cell engineered to express a CAAR, can be used to specifically bind to and kill autoantibody-expressing cells, but not normal antibody expressing cells. In some embodiments, CAAR-expressing cells can be used to treat an autoimmune disease associated with expression of self-antigens, such as autoimmune diseases. In some embodiments, CAAR-expressing cells can target B cells that ultimately produce the autoantibodies and display the autoantibodies on their cell surfaces, mark these B cells as disease-specific targets for therapeutic intervention. In some embodiments, CAAR-expressing cells can be used to efficiently targeting and killing the pathogenic B cells in autoimmune diseases by targeting the disease-causing B cells using an antigen-specific chimeric autoantibody receptor. In some embodiments, the recombinant receptor is a CAAR, such as any described in U.S. Patent Application Pub. No. US 2017/0051035.

In some embodiments, the CAAR comprises an autoantibody binding domain, a transmembrane domain, and an intracellular signaling region. In some embodiments, the intracellular signaling region comprises an intracellular signaling domain. In some embodiments, the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM). In some embodiments, the intracellular signaling region comprises a secondary or costimulatory signaling region (secondary intracellular signaling regions).

In some embodiments, the autoantibody binding domain comprises an autoantigen or a fragment thereof. The choice of autoantigen can depend upon the type of autoantibody being targeted. For example, the autoantigen may be chosen because it recognizes an autoantibody on a target cell, such as a B cell, associated with a particular disease state, e.g. an autoimmune disease, such as an autoantibody-mediated autoimmune disease. In some embodiments, the autoimmune disease includes pemphigus vulgaris (PV). Exemplary autoantigens include desmoglein 1 (Dsg1) and Dsg3.

4. Multi-Targeting

In some embodiments, the cells used in connection with the provided methods, uses, articles of manufacture and compositions include cells employing multi-targeting strategies, such as expression of two or more genetically engineered receptors on the cell, each recognizing the same of a different antigen and typically each including a different intracellular signaling component. Such multi-targeting strategies are described, for example, in International Patent Application, Publication No.: WO 2014055668 A1 (describing combinations of activating and costimulatory CARs, e.g., targeting two different antigens present individually on off-target, e.g., normal cells, but present together only on cells of the disease or condition to be treated) and Fedorov et al., *Sci. Transl. Medicine,* 5(215) (2013) (describing cells expressing an activating and an inhibitory CAR, such as those in which the activating CAR binds to one antigen expressed on both normal or non-diseased cells and cells of the disease or condition to be treated, and the inhibitory CAR binds to another antigen expressed only on the normal cells or cells which it is not desired to treat).

For example, in some embodiments, the cells include a receptor expressing a first genetically engineered antigen receptor (e.g., CAR or TCR) which is capable of inducing an activating or stimulatory signal to the cell, generally upon specific binding to the antigen recognized by the first receptor, e.g., the first antigen. In some embodiments, the cell further includes a second genetically engineered antigen receptor (e.g., CAR or TCR), e.g., a chimeric costimulatory receptor, which is capable of inducing a costimulatory signal to the immune cell, generally upon specific binding to a second antigen recognized by the second receptor. In some embodiments, the first antigen and second antigen are the same. In some embodiments, the first antigen and second antigen are different.

In some embodiments, the first and/or second genetically engineered antigen receptor (e.g. CAR or TCR) is capable of inducing an activating signal to the cell. In some embodiments, the receptor includes an intracellular signaling component containing ITAM or ITAM-like motifs. In some embodiments, the activation induced by the first receptor involves a signal transduction or change in protein expression in the cell resulting in initiation of an immune response, such as ITAM phosphorylation and/or initiation of ITAM-mediated signal transduction cascade, formation of an immunological synapse and/or clustering of molecules near the bound receptor (e.g. CD4 or CD8, etc.), activation of one or more transcription factors, such as NF-κB and/or AP-1, and/or induction of gene expression of factors such as cytokines, proliferation, and/or survival.

In some embodiments, the first and/or second receptor includes intracellular signaling domains or regions of costimulatory receptors such as CD28, CD137 (4-1BB), OX40, and/or ICOS. In some embodiments, the first and second receptor include an intracellular signaling domain of a costimulatory receptor that are different. In one embodiment, the first receptor contains a CD28 costimulatory signaling region and the second receptor contain a 4-1BB co-stimulatory signaling region or vice versa.

In some embodiments, the first and/or second receptor includes both an intracellular signaling domain containing ITAM or ITAM-like motifs and an intracellular signaling domain of a costimulatory receptor.

In some embodiments, the first receptor contains an intracellular signaling domain containing ITAM or ITAM-like motifs and the second receptor contains an intracellular signaling domain of a costimulatory receptor. The costimulatory signal in combination with the activating signal induced in the same cell is one that results in an immune response, such as a robust and sustained immune response, such as increased gene expression, secretion of cytokines and other factors, and T cell mediated effector functions such as cell killing.

In some embodiments, neither ligation of the first receptor alone nor ligation of the second receptor alone induces a robust immune response. In some aspects, if only one receptor is ligated, the cell becomes tolerized or unresponsive to antigen, or inhibited, and/or is not induced to proliferate or secrete factors or carry out effector functions. In some such embodiments, however, when the plurality of receptors are ligated, such as upon encounter of a cell expressing the first and second antigens, a desired response is achieved, such as full immune activation or stimulation, e.g., as indicated by secretion of one or more cytokine, proliferation, persistence, and/or carrying out an immune effector function such as cytotoxic killing of a target cell.

In some embodiments, the two receptors induce, respectively, an activating and an inhibitory signal to the cell, such that binding by one of the receptor to its antigen activates the cell or induces a response, but binding by the second inhibitory receptor to its antigen induces a signal that suppresses or dampens that response. Examples are combinations of activating CARS and inhibitory CARs or iCARs. Such a strategy may be used, for example, in which the activating CAR binds an antigen expressed in a disease or condition but which is also expressed on normal cells, and the inhibitory receptor binds to a separate antigen which is expressed on the normal cells but not cells of the disease or condition.

In some embodiments, the multi-targeting strategy is employed in a case where an antigen associated with a particular disease or condition is expressed on a non-diseased cell and/or is expressed on the engineered cell itself, either transiently (e.g., upon stimulation in association with genetic engineering) or permanently. In such cases, by requiring ligation of two separate and individually specific antigen receptors, specificity, selectivity, and/or efficacy may be improved.

In some embodiments, the plurality of antigens, e.g., the first and second antigens, are expressed on the cell, tissue, or disease or condition being targeted, such as on the cancer cell. In some aspects, the cell, tissue, disease or condition is multiple myeloma or a multiple myeloma cell. In some embodiments, one or more of the plurality of antigens generally also is expressed on a cell which it is not desired to target with the cell therapy, such as a normal or non-diseased cell or tissue, and/or the engineered cells themselves. In such embodiments, by requiring ligation of multiple receptors to achieve a response of the cell, specificity and/or efficacy is achieved.

B. Nucleic Acids, Vectors and Methods for Genetic Engineering

In some embodiments, the cells, e.g., cells of a population of enriched CD57− T cells (e.g. a CD57 depleted T cell population and/or a pooled CD57 depleted T cell population), are genetically engineered to express a recombinant receptor. In some embodiments, the cells, e.g., cells of a population of enriched CD27+ T cells (e.g. a CD27 enriched T cell population and/or a pooled CD27 enriched T cell population), are genetically engineered to express a recombinant receptor. In some embodiments, the engineering is carried out by introducing one or more polynucleotide(s) that encode the recombinant receptor or portions or components thereof. Also provided are polynucleotides encoding a recombinant receptor, and vectors or constructs containing such nucleic acids and/or polynucleotides.

In some embodiments, the polynucleotide encoding the recombinant receptor contains at least one promoter that is operatively linked to control expression of the recombinant receptor. In some examples, the polynucleotide contains two, three, or more promoters operatively linked to control expression of the recombinant receptor. In some embodiments, polynucleotide can contain regulatory sequences, such as transcription and translation initiation and termination codons, which are specific to the type of host (e.g., bacterium, fungus, plant, or animal) into which the polynucleotide is to be introduced, as appropriate and taking into consideration whether the polynucleotide is DNA- or RNA-based. In some embodiments, the polynucleotide can contain regulatory/control elements, such as a promoter, an enhancer, an intron, a polyadenylation signal, a Kozak consensus sequence, internal ribosome entry sites (IRES), a 2A sequence, and splice acceptor or donor. In some embodiments, the polynucleotide can contain a nonnative promoter operably linked to the nucleotide sequence encoding the recombinant receptor and/or one or more additional polypeptide(s). In some embodiments, the promoter is selected from among an RNA pol I, pol II or pol III promoter. In some embodiments, the promoter is recognized by RNA polymerase II (e.g., a CMV, SV40 early region or adenovirus major late promoter). In another embodiment, the promoter is recognized by RNA polymerase III (e.g., a U6 or H1 promoter). In some embodiments, the promoter can be a non-viral promoter or a viral promoter, such as a cytomegalovirus (CMV) promoter, an SV40 promoter, an RSV promoter, and a promoter found in the long-terminal repeat of the murine stem cell virus. Other known promoters also are contemplated.

In some embodiments, the promoter is or comprises a constitutive promoter. Exemplary constitutive promoters include, e.g., simian virus 40 early promoter (SV40), cytomegalovirus immediate-early promoter (CMV), human Ubiquitin C promoter (UBC), human elongation factor 1α promoter (EF1α), mouse phosphoglycerate kinase 1 promoter (PGK), and chicken β-Actin promoter coupled with CMV early enhancer (CAGG). In some embodiments, the constitutive promoter is a synthetic or modified promoter. In some embodiments, the promoter is or comprises an MND promoter, a synthetic promoter that contains the U3 region of a modified MoMuLV LTR with myeloproliferative sarcoma virus enhancer (see Challita et al. (1995) *J. Virol.* 69(2):748-755). In some embodiments, the promoter is a tissue-specific promoter. In another embodiment, the promoter is a viral promoter. In another embodiment, the promoter is a non-viral promoter. In some embodiments, exemplary promoters can include, but are not limited to, human elongation factor 1 alpha (EF1α) promoter or a modified form thereof or the MND promoter.

In another embodiment, the promoter is a regulated promoter (e.g., inducible promoter). In some embodiments, the promoter is an inducible promoter or a repressible promoter. In some embodiments, the promoter comprises a Lac operator sequence, a tetracycline operator sequence, a galactose operator sequence or a doxycycline operator sequence, or is an analog thereof or is capable of being bound by or recognized by a Lac repressor or a tetracycline repressor, or an analog thereof. In some embodiments, the polynucleotide does not include a regulatory element, e.g. promoter.

In some cases, the nucleic acid sequence encoding the recombinant receptor contains a signal sequence that encodes a signal peptide. In some aspects, the signal sequence may encode a signal peptide derived from a native polypeptide. In other aspects, the signal sequence may encode a heterologous or non-native signal peptide, such as the exemplary signal peptide of the GMCSFR alpha chain set forth in SEQ ID NO:25 and encoded by the nucleotide sequence set forth in SEQ ID NO:24. In some cases, the nucleic acid sequence encoding the recombinant receptor, e.g., chimeric antigen receptor (CAR) contains a signal sequence that encodes a signal peptide. Non-limiting exemplary signal peptides include, for example, the GMCSFR alpha chain signal peptide set forth in SEQ ID NO: 25 and encoded by the nucleotide sequence set forth in SEQ ID NO:24, or the CD8 alpha signal peptide set forth in SEQ ID NO:26.

In some embodiments, the polynucleotide contains a nucleic acid sequence encoding one or more additional polypeptides, e.g., one or more marker(s) and/or one or more effector molecules. In some embodiments, the one or more marker(s) includes a transduction marker, a surrogate marker and/or a selection marker. Among additional nucleic acid sequences introduced, e.g., encoding for one or more additional polypeptide(s), include nucleic acid sequences that can improve the efficacy of therapy, such as by promoting viability and/or function of transferred cells; ucleic acid sequences to provide a genetic marker for selection and/or evaluation of the cells, such as to assess in vivo survival or localization; ucleic acid sequences to improve safety, for example, by making the cell susceptible to negative selection in vivo as described by Lupton S. D. et al., *Mol. and Cell Biol.,* 11:6 (1991); and Riddell et al., *Human Gene Therapy* 3:319-338 (1992); see also WO 1992008796 and WO 1994028143 describing the use of bifunctional selectable fusion genes derived from fusing a dominant positive selectable marker with a negative selectable marker, and U.S. Pat. No. 6,040,177.

In some embodiments, the marker is a transduction marker or a surrogate marker. A transduction marker or a surrogate marker can be used to detect cells that have been introduced with the polynucleotide, e.g., a polynucleotide encoding a recombinant receptor. In some embodiments, the transduction marker can indicate or confirm modification of a cell. In some embodiments, the surrogate marker is a protein that is made to be co-expressed on the cell surface with the recombinant receptor, e.g. CAR. In particular embodiments, such a surrogate marker is a surface protein that has been modified to have little or no activity. In certain embodiments, the surrogate marker is encoded on the same polynucleotide that encodes the recombinant receptor. In some embodiments, the nucleic acid sequence encoding the recombinant receptor is operably linked to a nucleic acid sequence encoding a marker, optionally separated by an internal ribosome entry site (IRES), or a nucleic acid encoding a self-cleaving peptide or a peptide that causes ribosome skipping, such as a 2A sequence. Extrinsic marker genes may in some cases be utilized in connection with engineered cell to permit detection or selection of cells and, in some cases, also to promote cell elimination and/or cell suicide.

Exemplary surrogate markers can include truncated forms of cell surface polypeptides, such as truncated forms that are non-functional and to not transduce or are not capable of transducing a signal or a signal ordinarily transduced by the full-length form of the cell surface polypeptide, and/or do not or are not capable of internalizing. Exemplary truncated cell surface polypeptides including truncated forms of growth factors or other receptors such as a truncated human epidermal growth factor receptor 2 (tHER2), a truncated epidermal growth factor receptor (tEGFR, exemplary tEGFR sequence set forth in SEQ ID NO: 7 or 16) or a prostate-specific membrane antigen (PSMA) or modified form thereof, such as a truncated PSMA (tPSMA). In some aspects, tEGFR may contain an epitope recognized by the antibody cetuximab (Erbitux®) or other therapeutic anti-EGFR antibody or binding molecule, which can be used to identify or select cells that have been engineered with the tEGFR construct and an encoded exogenous protein, and/or to eliminate or separate cells expressing the encoded exogenous protein. See U.S. Pat. No. 8,802,374 and Liu et al., Nature Biotech. 2016 April; 34(4): 430-434). In some aspects, the marker, e.g. surrogate marker, includes all or part (e.g., truncated form) of CD34, a NGFR, a CD19 or a truncated CD19, e.g., a truncated non-human CD19. An exemplary polypeptide for a truncated EGFR (e.g. tEGFR) comprises the sequence of amino acids set forth in SEQ ID NO: 7 or 16 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7 or 16.

In some embodiments, the marker is or comprises a detectable protein, such as a fluorescent protein, such as green fluorescent protein (GFP), enhanced green fluorescent protein (EGFP), such as super-fold GFP (sfGFP), red fluorescent protein (RFP), such as tdTomato, mCherry, mStrawberry, AsRed2, DsRed or DsRed2, cyan fluorescent protein (CFP), blue green fluorescent protein (BFP), enhanced blue fluorescent protein (EBFP), and yellow fluorescent protein (YFP), and variants thereof, including species variants, monomeric variants, codon-optimized, stabilized and/or enhanced variants of the fluorescent proteins. In some embodiments, the marker is or comprises an enzyme, such as a luciferase, the lacZ gene from *E. coli*, alkaline phosphatase, secreted embryonic alkaline phosphatase (SEAP), chloramphenicol acetyl transferase (CAT). Exemplary light-emitting reporter genes include luciferase (luc), β-galactosidase, chloramphenicol acetyltransferase (CAT), β-glucuronidase (GUS) or variants thereof. In some aspects, expression of the enzyme can be detected by addition of a substrate that can be detected upon the expression and functional activity of the enzyme.

In some embodiments, the marker is a selection marker. In some embodiments, the selection marker is or comprises a polypeptide that confers resistance to exogenous agents or drugs. In some embodiments, the selection marker is an antibiotic resistance gene. In some embodiments, the selection marker is an antibiotic resistance gene confers antibiotic resistance to a mammalian cell. In some embodiments, the selection marker is or comprises a Puromycin resistance gene, a Hygromycin resistance gene, a Blasticidin resistance gene, a Neomycin resistance gene, a Geneticin resistance gene or a Zeocin resistance gene or a modified form thereof.

Any of the recombinant receptors and/or the additional polypeptide(s) described herein can be encoded by one or more polynucleotides containing one or more nucleic acid sequences encoding recombinant receptors, in any combinations, orientation or arrangements. For example, one, two, three or more polynucleotides can encode one, two, three or more different polypeptides, e.g., recombinant receptors or portions or components thereof, and/or one or more additional polypeptide(s), e.g., a marker and/or an effector molecule. In some embodiments, one polynucleotide contains a nucleic acid sequence encoding a recombinant receptor, e.g., CAR, or portion or components thereof, and a nucleic acid sequence encoding one or more additional polypeptide(s). In some embodiments, one vector or construct contains a nucleic acid sequence encoding a recombinant receptor, e.g., CAR, or portion or components thereof, and a separate vector or construct contains a nucleic acid sequence encoding one or more additional polypeptide(s). In some embodiments, the nucleic acid sequence encoding the recombinant receptor and the nucleic acid sequence encoding the one or more additional polypeptide(s) are operably linked to two different promoters. In some embodiments, the nucleic acid encoding the recombinant receptor is present upstream of the nucleic acid encoding the one or more additional polypeptide(s). In some embodiments, the nucleic acid encoding the recombinant receptor is present downstream of the nucleic acid encoding one or more additional polypeptide(s).

In certain cases, one polynucleotide contains nucleic acid sequences encode two or more different polypeptide chains, e.g., a recombinant receptor and one or more additional polypeptide(s), e.g., a marker and/or an effector molecule. In some embodiments, the nucleic acid sequences encoding two or more different polypeptide chains, e.g., a recombinant receptor and one or more additional polypeptide(s), are present in two separate polynucleotides. For example, two separate polynucleotides are provided, and each can be individually transferred or introduced into the cell for expression in the cell. In some embodiments, the nucleic acid sequences encoding the marker and the nucleic acid sequences encoding the recombinant receptor are present or inserted at different locations within the genome of the cell. In some embodiments, the nucleic acid sequences encoding the marker and the nucleic acid sequences encoding the recombinant receptor are operably linked to two different promoters.

In some embodiments, such as those where the polynucleotide contains a first and second nucleic acid sequence, the coding sequences encoding each of the different polypeptide chains can be operatively linked to a promoter, which can be the same or different. In some embodiments, the nucleic acid molecule can contain a promoter that drives the expression of two or more different polypeptide chains. In some embodiments, such nucleic acid molecules can be multicistronic (bicistronic or tricistronic, see e.g., U.S. Pat. No. 6,060,273). In some embodiments, the nucleic acid sequences encoding the recombinant receptor and the nucleic acid sequences encoding the one or more additional polypeptide(s) are operably linked to the same promoter and are optionally separated by an internal ribosome entry site (IRES), or a nucleic acid encoding a self-cleaving peptide or a peptide that causes ribosome skipping, such as a 2A element. For example, an exemplary marker, and optionally a ribosome skipping sequence, can be any as disclosed in PCT Pub. No. WO2014031687.

In some embodiments, transcription units can be engineered as a bicistronic unit containing an IRES, which allows coexpression of gene products (e.g. encoding the recombinant receptor and the additional polypeptide) by a message from a single promoter. Alternatively, in some cases, a single promoter may direct expression of an RNA that contains, in a single open reading frame (ORF), two or three genes (e.g. encoding the marker and encoding the recombinant receptor) separated from one another by sequences encoding a self-cleavage peptide (e.g., 2A sequences) or a protease recognition site (e.g., furin). The ORF thus encodes a single polypeptide, which, either during (in the case of 2A) or after translation, is processed into the individual proteins. In some cases, the peptide, such as a T2A, can cause the ribosome to skip (ribosome skipping) synthesis of a peptide bond at the C-terminus of a 2A element, leading to separation between the end of the 2A sequence and the next peptide downstream (see, e.g., de Felipe, Genetic Vaccines and Ther. 2:13 (2004) and de Felipe et al. Traffic 5:616-626 (2004)). Various 2A elements are known. Examples of 2A sequences that can be used in the methods and system disclosed herein, without limitation, 2A sequences from the foot-and-mouth disease virus (F2A, e.g., SEQ ID NO: 21), equine rhinitis A virus (E2A, e.g., SEQ ID NO: 20), Thosea asigna virus (T2A, e.g., SEQ ID NO: 6 or 17), and porcine teschovirus-1 (P2A, e.g., SEQ ID NO: 18 or 19) as described in U.S. Patent Pub. No. 20070116690.

In some embodiments, the polynucleotide encoding the recombinant receptor and/or additional polypeptide is contained in a vector or can be cloned into one or more vector(s). In some embodiments, the one or more vector(s) can be used to transform or transfect a host cell, e.g., a cell for engineering. Exemplary vectors include vectors designed for introduction, propagation and expansion or for expression or both, such as plasmids and viral vectors. In some aspects, the vector is an expression vector, e.g., a recombinant expression vector. In some embodiments, the recombinant expression vectors can be prepared using standard recombinant DNA techniques.

In some embodiments, the vector can be a vector of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), or the pEX series (Clontech, Palo Alto, Calif.). In some cases, bacteriophage vectors, such as λG10, λGT11, (Stratagene), λTMBL4, and λNM1149, also can be used. In some embodiments, plant expression vectors can be used and include pBI01, pBI101.2, pBI101.3, pBI121 and pBIN19 (Clontech). In some embodiments, animal expression vectors include pEUK-Cl, pMAM and pMAMneo (Clontech).

In some embodiments, the vector is a viral vector, such as a retroviral vector. In some embodiments, the polynucleotide encoding the recombinant receptor and/or additional polypeptide(s) are introduced into the cell via retroviral or lentiviral vectors, or via transposons (see, e.g., Baum et al. (2006) Molecular Therapy: The Journal of the American Society of Gene Therapy. 13:1050-1063; Frecha et al. (2010) Molecular Therapy 18:1748-1757; and Hackett et al. (2010) Molecular Therapy 18:674-683).

In some embodiments, one or more polynucleotide(s) are introduced into cells using recombinant infectious virus particles, such as, e.g., vectors derived from simian virus 40 (SV40), adenoviruses, adeno-associated virus (AAV). In particular embodiments, the vector is an AAV vector. In certain embodiments, the AAV vector is selected from among AAV1, AAV2, AAV3, AAV4, AAV5, AAV6, AAV7 or AAV8 vector. In some embodiments, the AAV vector is an AAV2 or AAV6 vector. In some embodiments, the polynucleotide containing the agent(s) and/or template polynucleotide is delivered by a recombinant AAV. In some embodiments, the heterologous polynucleotide, e.g. encoding a recombinant receptor, is delivered by a recombinant AAV. In some embodiments, (i) the polynucleotide containing the agent(s) and/or template polynucleotide and (ii) the heterologous polynucleotide, e.g. encoding a recombinant receptor, are delivered by a recombinant AAV. In some embodiments, (i) the polynucleotide containing the agent(s) and/or template polynucleotide and (ii) the heterologous polynucleotide, e.g. encoding a recombinant receptor, are delivered by the same recombinant AAV. In some embodiments, the AAV can incorporate its genome into that of a host cell, e.g., a target cell as described herein.

In some embodiments, one or more polynucleotide(s) are introduced into T cells using recombinant lentiviral vectors or retroviral vectors, such as gamma-retroviral vectors (see, e.g., Koste et al. (2014) Gene Therapy 2014 Apr. 3. doi: 10.1038/gt. 2014.25; Carlens et al. (2000) Exp Hematol 28(10): 1137-46; Alonso-Camino et al. (2013) Mol Ther Nucl Acids 2, e93; Park et al., Trends Biotechnol. 2011 Nov. 29(11): 550-557.

In some embodiments, the vector is a retroviral vector. In some aspects, a retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109. Methods of lentiviral transduction are known. Exemplary methods are described in, e.g., Wang et al. (2012) J. Immunother.

35(9): 689-701; Cooper et al. (2003) Blood. 101:1637-1644; Verhoeyen et al. (2009) Methods Mol Biol. 506: 97-114; and Cavalieri et al. (2003) Blood. 102(2): 497-505. In some embodiments, the polynucleotide encoding the recombinant receptor and/or one or more additional polypeptide(s), is introduced into a population containing cultured cells, such as by retroviral transduction, transfection, or transformation.

In some embodiments, one or more polynucleotide(s) are introduced into a T cell using electroporation (see, e.g., Chicaybam et al, (2013) PLoS ONE 8(3): e60298 and Van Tedeloo et al. (2000) Gene Therapy 7(16): 1431-1437). In some embodiments, recombinant nucleic acids are transferred into T cells via transposition (see, e.g., Manuri et al. (2010) Hum Gene Ther 21(4): 427-437; Sharma et al. (2013) Molec Ther Nucl Acids 2, e74; and Huang et al. (2009) Methods Mol Biol 506: 115-126). Other methods of introducing and expressing genetic material, e.g., polynucleotides and/or vectors, into immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987) and other approaches described in, e.g., International Pat. App. Pub. No. WO 2014055668, and U.S. Pat. No. 7,446,190.

In some embodiments, the one or more polynucleotide(s) or vector(s) encoding a recombinant receptor and/or additional polypeptide(s) may be introduced into cells, e.g., T cells, either during or after expansion. This introduction of the polynucleotide(s) or vector(s) can be carried out with any suitable retroviral vector, for example. Resulting genetically engineered cells can then be liberated from the initial stimulus (e.g., anti-CD3/anti-CD28 stimulus) and subsequently be stimulated with a second type of stimulus (e.g., via a de novo introduced recombinant receptor). This second type of stimulus may include an antigenic stimulus in form of a peptide/MHC molecule, the cognate (cross-linking) ligand of the genetically introduced receptor (e.g. natural antigen and/or ligand of a CAR) or any ligand (such as an antibody) that directly binds within the framework of the new receptor (e.g. by recognizing constant regions within the receptor). See, for example, Cheadle et al, "Chimeric antigen receptors for T-cell based therapy" Methods Mol Biol. 2012; 907:645-66 or Barrett et al., Chimeric Antigen Receptor Therapy for Cancer Annual Review of Medicine Vol. 65: 333-347 (2014).

In some cases, a vector may be used that does not require that the cells, e.g., T cells, are activated. In some such instances, the cells may be selected and/or transduced prior to activation. Thus, the cells may be engineered prior to, or subsequent to culturing of the cells, and in some cases at the same time as or during at least a portion of the culturing.

C. Cells and Preparation of Cells for Genetic Engineering

In some embodiments, provided are engineered cells, e.g., genetically engineered or modified cells, and methods of engineering cells. In some embodiments, one or more genetic loci of a cell is genetically disrupted (e.g. knocked out). In some embodiments, the genetic locus and/or a portion thereof of TRAC and the genetic locus or a portion thereof of β2M are knocked out in a cell. In some embodiments, a cell is knocked out for TRAC and β2M. In some embodiments, one or more polynucleotides, e.g., encoding a recombinant receptor and/or additional polypeptide(s), such as any described herein, are introduced (e.g. knocked in) into a cell for engineering. In some aspects, the polynucleotides and/or portions thereof are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acid sequences are not naturally occurring, such as a nucleic acid sequences not found in nature or is modified from a nucleic acid sequence found in nature, including one comprising chimeric combinations of nucleic acids encoding various domains from multiple different cell types.

In some embodiments, the disrupting and the introducing of a heterologous polynucleotide are performed concurrently. In some embodiments, the disrupting and the introducing of a heterologous polynucleotide are performed sequentially, in either order. In some embodiments, the heterologous nucleotide is knocked into a genetic locus or portion thereof that has been disrupted in a cell. In some embodiments, the heterologous polynucleotide is knocked into the TRAC locus, which has been knocked out.

The cells generally are eukaryotic cells, such as mammalian cells, and typically are human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from an individual donor or a plurality of donors and/or isolated from an individual donor or a plurality of different donors and frozen. In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. In some embodiments, the cells are allogeneic with reference to the subject to be treated. Among the methods include off-the-shelf methods. In some aspects, such as for off-the-shelf technologies, the cells are pluripotent and/or multipotent, such as stem cells, such as iPSCs. In some embodiments, the methods include isolating cells from an individual donor or a plurality of different donors, preparing, processing, culturing, and/or engineering them, and re-introducing them into a subject, before or after cryopreservation. In some embodiments, the subject is a donor. In some embodiments, the subject is not a donor.

Among the sub-types and subpopulations of T cells and/or of CD4+ and/or of CD8+ T cells are naïve T ($T_N$) cells, effector T cells ($T_{EFF}$), memory T cells and sub types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

In some embodiments, the cells do not express one or more molecules, the gene(s) encoding for which having been genetically disrupted (e.g. knocked out). In some embodiments, the cells include one or more nucleic acids introduced via genetic engineering (e.g. knocking in), and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

In some embodiments, preparation of the engineered cells includes one or more culture and/or preparation steps. The cells for introduction of the nucleic acid encoding the transgenic receptor such as the CAR, may be isolated from a sample, such as a biological sample, e.g., one obtained from or derived from an individual donor or a plurality of different donors. In some embodiments, the donor from which the cells are isolated is one having the disease or condition or in need of a cell therapy or to which cell therapy will be administered. In some embodiments, at least one of a plurality of different donors from which the cells are isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples (e.g. a donor sample) resulting from one or more processing steps, such as separation, centrifugation, genetic engineering (e.g. transduction with viral vector), washing, and/or incubation. The biological sample (e.g. donor sample) can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom. In some aspects, the donor sample is a sample derived from an individual donor. In some aspects, a donor sample from an individual donor is combined with a donor sample or one or more other individual donors to produce a donor sample from a plurality of different donors. In some aspects, the donor sample is derived from a plurality of different donors.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples (e.g. donor samples) include, in the context of cell therapy, e.g., adoptive cell therapy, samples from autologous and allogeneic sources. Donor samples include, in the context of cell therapy, e.g., adoptive cell therapy, samples from allogeneic sources.

In some embodiments, the cells are derived from cell lines, e.g., T cell lines. The cells in some embodiments are obtained from a xenogeneic source, for example, from mouse, rat, non-human primate, and pig.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets.

In some embodiments, the blood cells collected from the individual donor or the plurality of different donors are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., $CD28^+$, CD62 $L^+$, $CCR7^+$, $CD27^+$, $CD127^+$, $CD4^+$, $CD8^+$, $CD45RA^+$, and/or $CD45RO^+$ T cells, are isolated by positive or negative selection techniques.

For example, $CD3^+$, $CD28^+$ T cells can be positively selected using anti-CD3/anti-CD28 conjugated magnetic beads (e.g., DYNABEADS® M-450 CD3/CD28 T Cell Expander).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed ($marker^+$) at a relatively higher level ($marker^{high}$) on the positively or negatively selected cells, respectively.

In some embodiments, T cells are separated from a PBMC sample (e.g. from an individual donor or from a plurality of different donors) by negative selection of markers expressed on non-T cells, such as B cells, monocytes, or other white blood cells, such as CD14. In some aspects, a $CD4^+$ or $CD8^+$ selection step is used to separate $CD4^+$ helper and $CD8^+$ cytotoxic T cells. Such $CD4^+$ and $CD8^+$ populations can be further sorted into sub-populations by positive or negative selection for markers expressed or expressed to a relatively higher degree on one or more naïve, memory, and/or effector T cell subpopulations.

In some embodiments, $CD8^+$ cells are further enriched for or depleted of naïve, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations. See Terakura et al. (2012) Blood. 1:72-82; Wang et al. (2012) *J Immunother* 35(9):689-701. In some embodiments, combining $T_{CM}$-enriched $CD8^+$ T cells and $CD4^+$ T cells further enhances efficacy.

In embodiments, memory T cells are present in both CD62 $L^+$ and CD62 $L^-$ subsets of $CD8^+$ peripheral blood lymphocytes. PBMC can be enriched for or depleted of CD62 $L^-CD8^+$ and/or CD62 $L^+CD8^+$ fractions, such as using anti-CD8 and anti-CD62 L antibodies.

In some embodiments, the enrichment for central memory T ($T_{CM}$) cells is based on positive or high surface expression of CD45RO, CD62 L, CCR7, CD28, CD3, and/or CD127; in some aspects, it is based on negative selection for cells expressing or highly expressing CD45RA and/or granzyme B. In some embodiments, the enrichment for central memory T ($T_{CM}$) cells is based on positive or high surface expression of CD45RO, CD62 L, CCR7, CD28, CD3, CD27, and/or CD127. In some embodiments, the enrichment for central memory T ($T_{CM}$) cells is based on positive or high surface expression of CD62 L, CCR7, CD28, and/or CD27. In some embodiments, the enrichment for central memory T ($T_{CM}$) cells is based on positive or high surface expression of CCR7, CD28, and/or CD27. In some embodiments, the enrichment for central memory T ($T_{CM}$) cells is based on positive or high surface expression of CD28 and CD27. In some aspects, isolation of a $CD8^+$ population enriched for $T_{CM}$ cells is carried out by depletion of cells expressing CD4, CD14, CD45RA, and positive selection or enrichment for cells expressing CD62 L. In some aspects, isolation of a $CD8^+$ population enriched for $T_{CM}$ cells is carried out by depletion of cells expressing CD4, CD14, CD45RA, and positive selection or enrichment for cells expressing CD27 and CD28. In one aspect, enrichment for central memory T ($T_{CM}$) cells is carried out starting with a negative fraction of cells selected based on CD4 expression, which is subjected to a negative selection based on expression of CD14 and CD45RA, and a positive selection based on CD62 L. Such selections in some aspects are carried out simultaneously and in other aspects are carried out sequentially, in either order. In some aspects, the same CD4 expression-based selection step used in preparing the $CD8^+$ cell population or subpopulation, also is used to generate the $CD4^+$ cell population or sub-population, such that both the positive and negative fractions from the CD4-based separation are retained and used in subsequent steps of the methods, optionally following one or more further positive or negative selection steps.

In a particular example, a sample of PBMCs or other white blood cell sample (e.g. a donor sample, such as from an individual donor or from a plurality of different donors) is subjected to selection of $CD4^+$ cells, where both the negative and positive fractions are retained. The negative fraction then is subjected to negative selection based on expression of CD14 and CD45RA or CD19, and positive selection based on a marker characteristic of central memory T cells, such as CD62 L or CCR7, where the positive and negative selections are carried out in either order.

$CD4^+$ T helper cells are sorted into naïve, central memory, and effector cells by identifying cell populations that have cell surface antigens. $CD4^+$ lymphocytes can be obtained by standard methods. In some embodiments, naïve $CD4^+$ T lymphocytes are $CD45RO^-$, $CD45RA^+$, CD62 $L^+$, $CD4^+$ T cells. In some embodiments, central memory $CD4^+$ cells are CD62 $L^+$ and $CD45RO^+$. In some embodiments, effector CD4+ cells are CD62 $L^-$ and $CD45RO^-$.

In one example, to enrich for $CD4^+$ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher © Humana Press Inc., Totowa, NJ).

In some aspects, the sample or population of cells (e.g. a donor sample, such as from an individual donor or a plurality of different donors) to be separated is incubated with small, magnetizable or magnetically responsive material, such as magnetically responsive particles or microparticles, such as paramagnetic beads (e.g., such as Dynabeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, and magnetizable particles or antibodies conjugated to cleavable linkers. In some embodiments, the magnetizable particles are biodegradable.

In some embodiments, the affinity-based selection is via magnetic-activated cell sorting (MACS) (Miltenyi Biotec, Auburn, CA). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Pat. App. Pub. No. WO2009/072003 or US 20110003380.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotec), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood is automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) *J Immunother* 35(9): 651-660, Terakura et al. (2012) Blood. 1:72-82, and Wang et al. (2012) *J Immunother* 35(9):689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) *Lab Chip* 10, 1567-1573; and Godin et al. (2008) J Biophoton. 1(5):355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are generally then frozen to −80° C. at a rate of 1° per minute and stored in the vapor phase of a liquid nitrogen storage tank.

In some embodiments, the cells are incubated and/or cultured prior to or in connection with genetic engineering. The incubation steps can include culture, cultivation, stimulation, activation, and/or propagation. The incubation and/or engineering may be carried out in a culture vessel, such as a unit, chamber, well, column, tube, tubing set, valve, vial, culture dish, bag, or other container for culture or cultivating cells. In some embodiments, the populations or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR, e.g. anti-CD3. In some embodiments, the stimulating conditions include one or more agent, e.g. ligand, which is capable of stimulating a costimulatory receptor, e.g., anti-CD28. In some embodiments, such agents and/or ligands may be, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2, IL-15 and/or IL-7. In some aspects, the IL-2 concentration is at least about 10 units/mL.

In some aspects, incubation is carried out in accordance with techniques such as those described in U.S. Pat. No. 6,040,177, Klebanoff et al. (2012) J Immunother. 35(9): 651-660, Terakura et al. (2012) Blood. 1:72-82, and/or Wang et al. (2012) J Immunother. 35(9):689-701.

In some embodiments, the T cells are expanded by adding to a culture-initiating population feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In some embodiments, antigen-specific T cells, such as antigen-specific CD4+ and/or CD8+ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

IV. Pharmaceutical Compositions and Formulations

In some embodiments, provided herein are therapeutic compositions (e.g., therapeutic T cell compositions) generated by any of the manufacturing processes disclosed herein, e.g., an output composition containing engineered (recombinant receptor-expressing) T cells enriched for CD57− T cells. In some embodiments, provided herein are therapeutic compositions (e.g., therapeutic T cell compositions) generated by any of the manufacturing processes disclosed herein, e.g., an output composition containing engineered (recombinant receptor-expressing) T cells enriched for CD27+ T cells. In some embodiments, a therapeutic composition is from an individual donor. In some embodiments, a therapeutic composition from an individual donor is combined with a therapeutic composition from one or more other individual donors to generate a therapeutic composition from a plurality of different donors. In some embodiments, the therapeutic composition is from a plurality of different donors.

In some embodiments, provided herein are therapeutic compositions (e.g., therapeutic T cell compositions) having any one or more of the features disclosed herein. In some embodiments, the dose of cells comprising cells engineered with a recombinant antigen receptor, e.g. CAR or TCR, is provided as a composition or formulation, such as a pharmaceutical composition or formulation. Such compositions can be used in accord with the provided methods, and/or with the provided articles of manufacture or compositions, such as in the prevention or treatment of diseases, conditions, and disorders, or in detection, diagnostic, and prognostic methods.

In some embodiments, the therapeutic T cell composition contains CD4+ T cells expressing a recombinant receptor and CD8+ T cells expressing a recombinant receptor, wherein at least 80% or of the total receptor+/CD8+ cells in the composition are CD57− and at least 80% of the total receptor+/CD4+ cells in the composition are CD57−. In some embodiments, the therapeutic T cell composition contains CD4+ T cells expressing a recombinant receptor and CD8+ T cells expressing a recombinant receptor, wherein at least 80% or of the total receptor+/CD8+ cells in the composition are CD27+ and at least 80% of the total receptor+/CD4+ cells in the composition are CD27+. In some embodiments, the therapeutic T cell composition is one in which at least or at least about 80%, at least or at least about 85%, at least or at least about 90%, at least or at least about 95%, at least or at least about 96%, at least or at least about 97%, at least or at least about 98%, at least or at least about 99%, about 100%, or 100% of the cells in the composition are CD4+ T cells and CD8+ T cells.

In some embodiments, the therapeutic T cell composition includes CD3+ T cells expressing a recombinant receptor, wherein at least 80% or of the total receptor+/CD3+ cells in the composition are CD57−. In some embodiments, the therapeutic T cell composition includes CD3+ T cells expressing a recombinant receptor, wherein at least 80% or of the total receptor+/CD3+ cells in the composition are CD27+. In some embodiments, the therapeutic T cell composition is one in which at least or at least about 80%, at least or at least about 85%, at least or at least about 90%, at least or at least about 95%, at least or at least about 96%, at least or at least about 97%, at least or at least about 98%, at least or at least about 99%, about 100%, or 100% of the cells in the composition are CD3+ T cells.

In some embodiments, the therapeutic T cell composition contains a defined ratio or of CD4 and CD8 T cells. In some embodiments, the ratio of receptor+/CD4+ T cells to receptor+/CD8+ T cells in the composition is between about 1:3 and about 3:1, such as is at or about 1:1.

In some embodiments, the recombinant receptor is any as described in Section III.A. In some embodiments, the recombinant receptor is capable of binding to a target protein that is associated with, specific to, and/or expressed on a cell or tissue of a disease, disorder or condition. In some embodiments, the recombinant receptor is a chimeric antigen receptor (CAR).

In some embodiment, the number of viable T cells in a provided therapeutic composition is between at or about $10\times10^6$ cells and at or about $200\times10^6$ cells. In some embodiments, number of viable T cells in a provided therapeutic composition is between at or about $10\times10^6$ cells and at or about $100\times10^6$ cells. In some embodiments, number of viable T cells in a provided therapeutic composition is between at or about $10\times10^6$ cells and at or about $70\times10^6$ cells. In some embodiments, number of viable T cells in a provided therapeutic composition is between at or about $10\times10^6$ cells and at or about $50\times10^6$ cells. In some embodiments, the number of viable T cells in a provided therapeutic composition is between at or about $50\times10^6$ cells and at or about $200\times10^6$ cells. In some embodiments, the number of viable T cells in a provided therapeutic composition is between at or about $50\times10^6$ cells and at or about $100\times10^6$ cells. In some embodiments, the number of viable T cells in a provided therapeutic composition is between at or about $50\times10^6$ cells and at or about $70\times10^6$ cells. In some embodiments, the number of viable T cells in a provided therapeutic composition is between at or about $70\times10^6$ cells and at or about $200\times10^6$ cells. In some embodiments, the number of viable T cells in a provided therapeutic composition is between at or about $70\times10^6$ cells and at or about $100\times10^6$ cells. In some embodiments, the number of viable T cells in a provided therapeutic composition is between at or about $100\times10^6$ cells and at or about $200\times10^6$ cells. In some aspects, the volume of the composition is between 1.0 mL and 10 mL. In some embodiments, the volume is at or about 2 mL, at or about 3 mL, at or about 4 mL, at or about 5 mL, at or about 6 mL, at or about 7 mL, at or about 8 mL, at or about 9 mL, or at or about 10 mL, or any value between any of the foregoing.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell or agent and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulation or composition may also contain more than one active ingredient useful for the particular indication, disease, or condition being prevented or treated with the cells or agents, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In some embodiments, the agents or cells are administered in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

The pharmaceutical composition in some embodiments contains agents or cells in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

The agents or cells can be administered by any suitable means, for example, by bolus infusion, by injection, e.g., intravenous or subcutaneous injections, intraocular injection, periocular injection, subretinal injection, intravitreal injection, trans-septal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration. In some embodiments, a given dose is administered by a single bolus administration of the cells or agent. In some embodiments, it is administered by multiple bolus administrations of the cells or agent, for example, over a period of no more than 3 days, or by continuous infusion administration of the cells or agent.

For the prevention or treatment of disease, the appropriate dosage may depend on the type of disease to be treated, the type of agent or agents, the type of cells or recombinant receptors, the severity and course of the disease, whether the agent or cells are administered for preventive or therapeutic purposes, previous therapy, the subject's clinical history and response to the agent or the cells, and the discretion of the attending physician. The compositions are in some embodiments suitably administered to the subject at one time or over a series of treatments.

The cells or agents may be administered using standard administration techniques, formulations, and/or devices. Provided are formulations and devices, such as syringes and vials, for storage and administration of the compositions. With respect to cells, administration can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell or an agent that treats or ameliorates symptoms of neurotoxicity), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the agent or cell populations are administered parenterally. The term "parenteral," as used herein, includes intravenous, intramuscular, subcutaneous, rectal, vaginal, and intraperitoneal administration. In some embodiments, the agent or cell populations are administered to a subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the agent or cells in a solvent, such as in admixture with a suitable carrier, diluent, or excipient such as sterile water, physiological saline, glucose, dextrose, or the like.

The formulations to be used for in vivo administration are generally sterile. Sterility may be readily accomplished, e.g., by filtration through sterile filtration membranes.

V. Methods of Treatment

Provided herein are methods of treatment, e.g., including administering any of the engineered cells or compositions containing engineered cells described herein. In some aspects, also provided are methods of administering any of the engineered cells or compositions containing engineered cells described herein to a subject, such as a subject that has a disease or disorder. In some aspects, also provided are uses of any of the engineered cells or compositions containing engineered cells described herein for treatment of a disease or disorder. In some aspects, also provided are uses of any of the engineered cells or compositions containing engineered cells described herein for the manufacture of a medicament for the treatment of a disease or disorder. In some aspects, also provided are any of the engineered cells or compositions containing engineered cells described herein, for use in treatment of a disease or disorder, or for administration to a subject having a disease or disorder.

Methods for administration of cells for adoptive cell therapy are known and may be used in connection with the provided methods and compositions. For example, adoptive T cell therapy methods are described, e.g., in US Pat. App. Pub. No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338.

In some embodiments, the subject, e.g., a subject having or suspected of having a disease or disorder, is administered a cell therapy having a low or reduced amount of CD57+ T cells. In particular embodiments, the amount or frequency of CD57+ cells in the cell therapy is measured prior to administration. In certain embodiments the cell therapy has less than or less than about 50%, 40%, 30%, 25%, 20%, 15%, 10%, 5%, or 1% CD57+ T cells. In certain embodiments, the amount or frequency of CD57+ cells in the cell therapy is measured, and the cell therapy is administered to the subject if the cell therapy has less than or less than about 50%, 40%, 30%, 25%, 20%, 15%, 10%, 5%, or 1% CD57+ T cells. In some embodiments, the cell therapy has less than or less than about 25% CD57+ T cells. In particular embodiments, the cell therapy has less than or less than about 10% CD57+ T cells. In certain embodiments, the cell therapy has less than or less than about a threshold amount of CD57+ T cells.

In particular embodiments, the subject, e.g., a subject having or suspected of having a disease or disorder, is administered a cell therapy having a low or reduced amount of T cells positive for CD57 expression or a low or reduced amount of a trait associated CD57 expression. In some embodiments, the trait associated with CD57 expression is measured in cells of a cell therapy prior to administering the cell therapy to a subject. In particular, embodiments, the trait associated with CD57 expression is measured in the cells therapy, and the cell therapy is administered to the subject if the cell therapy has less than a threshold value of the trait associated with CD57 expression.

In some embodiments, the subject, e.g., a subject having or suspected of having a disease or disorder, is administered a cell therapy having a low or reduced amount of CD27− T cells. In particular embodiments, the amount or frequency of CD27− cells in the cell therapy is measured prior to administration. In certain embodiments the cell therapy has less than or less than about 50%, 40%, 30%, 25%, 20%, 15%, 10%, 5%, or 1% CD27− T cells. In certain embodiments, the amount or frequency of CD27− cells in the cell therapy is measured, and the cell therapy is administered to the subject if the cell therapy has less than or less than about 50%, 40%, 30%, 25%, 20%, 15%, 10%, 5%, or 1% CD27− T cells. In some embodiments, the cell therapy has less than or less than about 25% CD27− T cells. In particular embodiments, the cell therapy has less than or less than about 10% CD27− T cells. In certain embodiments, the cell therapy has less than or less than about a threshold amount of CD27− T cells.

In particular embodiments, the subject, e.g., a subject having or suspected of having a disease or disorder, is administered a cell therapy having a low or reduced amount of T cells negative for CD27 expression or a high or increased amount of a trait associated CD27 expression. In some embodiments, the trait associated with CD27 expression is measured in cells of a cell therapy prior to administering the cell therapy to a subject. In particular, embodiments, the trait associated with CD27 expression is measured in the cells therapy, and the cell therapy is administered to the subject if the cell therapy has more than a threshold value of the trait associated with CD27 expression.

In particular embodiments, the threshold value is a predetermined value. In some embodiments, the threshold value is experimentally derived. In some embodiments, the threshold value is an average, median, or mean value of the trait measured in a plurality of cell therapies. In some embodiments, the threshold value is experimentally derived from measurements of a plurality cell therapies, e.g., reference cell therapies. In some embodiments, the reference cell therapies are reference compositions of T cells, e.g., T cell compositions including T cells expressing a recombinant receptor. In particular embodiments, the reference compositions of T cells, e.g., T cells expressing a recombinant receptor, are measured prior to administration to subjects.

In particular embodiments, the reference cell therapies or reference T cell compositions are compositions of the cell therapy comprising T cells, e.g., including T cells expressing a recombinant receptor, from among a group of subjects that went on to receive the cell therapy for treating the same a disease, disorder, or condition. In some embodiments, reference cell therapy or reference T cell compositions are T cell compositions that were administered to subjects that went on to develop a partial response or progressive disease.

In some embodiments, the trait associated with the CD57 expression is a level or amount of CD57 polypeptide present in the total T cells, total CD4+ T cells, or total CD8+ T cells. In particular embodiments, the trait is a level or amount of CD57 polypeptide present in the total T cells, CD4+ T cells, or CD8+ T cells of the dose. In some embodiments, the trait is a level or amount of CD57 polypeptide present on the surface of the total T cells, CD4+ T cells, or CD8+ T cells. In various embodiments, the trait is a frequency, percentage, or amount of CD57+ T cells, CD57+ CD4+ T cells, or CD57+ CD8+ T cells. In certain embodiments, the trait is a level or amount of CD57 mRNA present in the T cells of the dose. In some embodiments, the trait is a level or amount of accessibility of the gene encoding CD57 (B3GAT1).

In some embodiments, the trait associated with the CD57 expression is a level or amount of CD57 polypeptide present in the total CD3+ T cells. In particular embodiments, the trait is a level or amount of CD57 polypeptide present in the total CD3+ T cells of the dose. In some embodiments, the trait is a level or amount of CD57 polypeptide present on the surface of the total CD3+ T cells. In various embodiments, the trait is a frequency, percentage, or amount of CD57+ CD3+ T cells. In certain embodiments, the trait is a level or amount of CD57 mRNA present in the T cells of the dose. In some embodiments, the trait is a level or amount of accessibility of the gene encoding CD57 (B3GAT1).

In particular embodiments, the threshold value is, is about, or is within 75%, 60%, 50%, 40%, 30%, 25%, 20%, 15%, 10%, 5%, 1%, or within less than 1% below an average, mean, or median measurement of the trait associated with CD57 expression in a plurality of reference cell therapies or reference T cell compositions. The amount is below one, one half, one third, one forth, one fifth, one sixth, one eighth, or one tenth of a standard deviation less than the average, mean, or median measurement of the trait. In particular embodiments, the threshold value is below a lowest measurement of the trait associated with CD57 expression in a composition from among a plurality of reference T cell compositions or reference cell therapies. In some embodiments, the threshold is within or within about 50%, 40%, 35%, 30%, 25%, 20%, 15%, 10%, 5%, 1%, or within less than 1% below the lowest measurement of the trait measured among the plurality of reference cell therapies or reference T cell compositions. In certain embodiments, threshold value is below an average, median, or mean measurement of the trait associated with CD57 expression calculated from among a frequency in the reference T cell compositions or reference cell therapies. In some embodiments, the threshold value is the average, median, or mean measurement of, of about, or of at least 25%, 33%, 50%, 60%, 65%, 70%, 75%, 80%, 85%, 90%, or 95% of the measurements taken from a plurality of reference T cell compositions.

In some embodiments, the trait associated with the CD27 expression is a level or amount of CD27 polypeptide present in the total T cells, total CD4+ T cells, or total CD8+ T cells. In particular embodiments, the trait is a level or amount of CD27 polypeptide present in the total T cells, CD4+ T cells, or CD8+ T cells of the dose. In some embodiments, the trait is a level or amount of CD27 polypeptide present on the surface of the total T cells, CD4+ T cells, or CD8+ T cells. In various embodiments, the trait is a frequency, percentage, or amount of CD27− T cells, CD27-CD4+ T cells, or CD27-CD8+ T cells. In certain embodiments, the trait is a level or amount of CD27 mRNA present in the T cells of the dose. In some embodiments, the trait is a level or amount of accessibility of the gene encoding CD27.

In some embodiments, the trait associated with the CD27 expression is a level or amount of CD27 polypeptide present in the total CD3+ T cells. In particular embodiments, the trait is a level or amount of CD27 polypeptide present in the total CD3+ T cells of the dose. In some embodiments, the trait is a level or amount of CD27 polypeptide present on the surface of the total CD3+ T cells. In various embodiments, the trait is a frequency, percentage, or amount of CD27-CD3+ T cells. In certain embodiments, the trait is a level or amount of CD27 mRNA present in the T cells of the dose. In some embodiments, the trait is a level or amount of accessibility of the gene encoding CD27.

In particular embodiments, the threshold value is, is about, or is within 75%, 60%, 50%, 40%, 30%, 25%, 20%, 15%, 10%, 5%, 1%, or within less than 1% above an average, mean, or median measurement of the trait associated with CD27 expression in a plurality of reference cell therapies or reference T cell compositions. The amount is above one, one half, one third, one forth, one fifth, one sixth, one eighth, or one tenth of a standard deviation higher than the average, mean, or median measurement of the trait. In particular embodiments, the threshold value is above a highest measurement of the trait associated with CD27 expression in a composition from among a plurality of reference T cell compositions or reference cell therapies. In some embodiments, the threshold is within or within about 50%, 40%, 35%, 30%, 25%, 20%, 15%, 10%, 5%, 1%, or within more than 1% above the highest measurement of the trait measured among the plurality of reference cell therapies or reference T cell compositions. In certain embodiments, threshold value is above an average, median, or mean measurement of the trait associated with CD27 expression calculated from among a frequency in the reference T cell compositions or reference cell therapies. In some embodiments, the threshold value is the average, median, or mean measurement of, of about, or of at least 25%, 33%, 50%, 60%, 65%, 70%, 75%, 80%, 85%, 90%, or 95% of the measurements taken from a plurality of reference T cell compositions.

In particular embodiments, the trait associated with CD57 expression is measured in the cell therapy prior to administering the cell therapy to a subject. In some embodiments, the measurement is used to assess the risk, probability or likelihood that the subject will not experience a complete response. In certain embodiments, the measurement is used to assess the risk, probability or likelihood that the subject will experience a partial response or a progressive disease outcome following administration of a cell therapy. In particular embodiments, the subject is determined to have an increased risk, likelihood, or probability of failing to experiencing a complete response following the administration of the cell therapy if the value of the trait is greater than a threshold value of the trait. In some embodiments, the subject is determined to have an increased risk, likelihood, or probability of experiencing a partial response or a progressive disease following the administration of the cell therapy if the value of the trait is greater than a threshold value of the trait. In some embodiments, the threshold value is any threshold value of the trait associated with CD57 described herein.

In particular embodiments, the trait associated with CD27 expression is measured in the cell therapy prior to administering the cell therapy to a subject. In some embodiments, the measurement is used to assess the risk, probability or likelihood that the subject will not experience a complete response. In certain embodiments, the measurement is used to assess the risk, probability or likelihood that the subject will experience a partial response or a progressive disease outcome following administration of a cell therapy. In particular embodiments, the subject is determined to have an increased risk, likelihood, or probability of failing to experiencing a complete response following the administration of the cell therapy if the value of the trait is less than a threshold value of the trait. In some embodiments, the subject is determined to have an increased risk, likelihood, or probability of experiencing a partial response or a progressive disease following the administration of the cell therapy if the value of the trait is less than a threshold value of the trait. In some embodiments, the threshold value is any threshold value of the trait associated with CD27 described herein.

In some embodiments, subjects considered to have an increased risk of failing to achieve a complete response following administration of a cell therapy go on to achieve a complete response with a frequency of less than or less than about 50%, 40%, 30%, 25%, 20%, 15% 10%, or less than 10% following administration of a dose of the cell therapy. In some embodiments, the subjects considered to have an increased risk of failing to achieve a complete response go on to achieve a complete response with a frequencies of less than 20% following administration of a dose of the cell therapy. In various embodiments, the subjects considered to have an increased risk of failing to achieve a complete response go on to achieve a complete response with a frequencies of or of about 0% following administration of a dose of the cell therapy.

In certain embodiments, subjects considered to have an increased risk of achieving a partial response or a progressive disease outcome following administration of a cell therapy go on to achieve a complete response with a frequency of less than or less than about 50%, 40%, 30%, 25%, 20%, 15% 10%, or less than 10% following administration of a dose of the cell therapy. In various embodiments, the subjects considered to have an increased risk of achieving a partial response or a progressive disease outcome go on to achieve a complete response with a frequencies of less than 20% following administration of a dose of the cell therapy. In various embodiments, the subjects considered to have an increased risk of achieving a partial response or a progressive disease outcome response go on to achieve a complete response with a frequencies of or of about 0% following administration of a dose of the cell therapy.

In particular embodiments, subjects considered to have an increased risk of failing to achieve a complete response receive an increased dose of the cell therapy, for example to improve the likelihood or probability that the subjects will go on to achieve a complete response. In some embodiments, subjects considered to have an increased risk of achieving a partial response or a progressive disease outcome receive an increased dose of the cell therapy, for example to improve the likelihood or probability that the subject will go on to achieve a complete response.

The disease or condition that is treated can be any in which expression of an antigen is associated with and/or involved in the etiology of a disease condition or disorder, e.g. causes, exacerbates or otherwise is involved in such disease, condition, or disorder. Exemplary diseases and conditions can include diseases or conditions associated with malignancy or transformation of cells (e.g. cancer), autoimmune or inflammatory disease, or an infectious disease, e.g. caused by a bacterial, viral or other pathogen. Exemplary antigens, which include antigens associated with various diseases and conditions that can be treated, are described above. In particular embodiments, the chimeric antigen receptor or transgenic TCR specifically binds to an antigen associated with the disease or condition.

Among the diseases, conditions, and disorders are tumors, including solid tumors, hematologic malignancies, and melanomas, and including localized and metastatic tumors, infectious diseases, such as infection with a virus or other pathogen, e.g., HIV, HCV, HBV, CMV, HPV, and parasitic disease, and autoimmune and inflammatory diseases. In some embodiments, the disease, disorder or condition is a tumor, cancer, malignancy, neoplasm, or other proliferative disease or disorder. Such diseases include but are not limited to leukemia, lymphoma, e.g., acute myeloid (or myelogenous) leukemia (AML), chronic myeloid (or myelogenous) leukemia (CML), acute lymphocytic (or lymphoblastic) leukemia (ALL), chronic lymphocytic leukemia (CLL), hairy cell leukemia (HCL), small lymphocytic lymphoma (SLL), Mantle cell lymphoma (MCL), Marginal zone lymphoma, Burkitt lymphoma, Hodgkin lymphoma (HL), non-Hodgkin lymphoma (NHL), Anaplastic large cell lymphoma (ALCL), follicular lymphoma, refractory follicular lymphoma, diffuse large B-cell lymphoma (DLBCL) and multiple myeloma (MM). In some embodiments, disease or condition is a B cell malignancy selected from among acute lymphoblastic leukemia (ALL), adult ALL, chronic lymphoblastic leukemia (CLL), non-Hodgkin lymphoma (NHL), and Diffuse Large B-Cell Lymphoma (DLBCL). In some embodiments, the disease or condition is NHL and the NHL is selected from the group consisting of aggressive NHL, diffuse large B cell lymphoma (DLBCL), NOS (de novo and transformed from indolent), primary mediastinal large B cell lymphoma (PMBCL), T cell/histocyte-rich large B cell lymphoma (TCHRBCL), Burkitt's lymphoma, mantle cell lymphoma (MCL), and/or follicular lymphoma (FL), optionally, follicular lymphoma Grade 3B (FL3B).

In some embodiments, the disease or condition is an infectious disease or condition, such as, but not limited to, viral, retroviral, bacterial, and protozoal infections, immunodeficiency, Cytomegalovirus (CMV), Epstein-Barr virus (EBV), adenovirus, BK polyomavirus. In some embodiments, the disease or condition is an autoimmune or inflammatory disease or condition, such as arthritis, e.g., rheumatoid arthritis (RA), Type I diabetes, systemic lupus erythematosus (SLE), inflammatory bowel disease, psoriasis, scleroderma, autoimmune thyroid disease, Grave's disease, Crohn's disease, multiple sclerosis, asthma, and/or a disease or condition associated with transplant.

In some embodiments, the antigen associated with the disease or disorder is or includes αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen $_{1B}$ (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD133, CD138, CD171, epidermal growth factor protein (EGFR), truncated epidermal growth factor protein (tEGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRLS; also known as Fc receptor homolog 5 or FCRHS), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPCRSD), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha (IL-22Rα), IL-13 receptor alpha 2 (IL-13Rα2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT) vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HW, HCV, HBV or other pathogens. Antigens targeted by the receptors in some embodiments include antigens associated with a B cell malignancy, such as any of a number of known B cell marker. In some embodiments, the antigen is or includes CD20, CD19, CD22, ROR1, CD45, CD21, CD5, CD33, Igkappa, Iglambda, CD79a, CD79b or CD30. In some embodiments, the antigen is or includes a pathogen-specific or pathogen-expressed antigen, such as a viral antigen (e.g., a viral antigen from HW, HCV, HBV), bacterial antigens, and/or parasitic antigens.

In some embodiments, the antibody or an antigen-binding fragment (e.g. scFv or $V_H$ domain) specifically recognizes an antigen, such as CD19. In some embodiments, the antibody or antigen-binding fragment is derived from, or is a variant of, antibodies or antigen-binding fragment that specifically binds to CD19. In some embodiments, the cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from at least one donor other than a subject who is to receive or who ultimately receives the cell therapy, e.g., an individual donor or a plurality of donors. In such embodiments, the cells then are administered to a subject, of the same species. In some embodiments, the individual donor or plurality of donors and the subject are genetically identical. In some embodiments, the individual donor or plurality of donors and the subject are genetically similar. In some embodiments, the subject expresses the same HLA class or supertype as the individual donor or plurality of donors.

In some embodiments, the cell therapy, e.g., adoptive T cell therapy, is carried out by allogeneic transfer, in which the cells are isolated and/or otherwise prepared from at least one donor other than a subject who is to receive or who ultimately receives the cell therapy, e.g., an individual donor or a plurality of different donors. In such embodiments, the cells then are administered to a subject of the same species as the individual donor or the plurality of dofferemt donors. In some embodiments, the cells administered to the subject are not derived from the subject. In some embodiments, at least a portion of the cells administered to the subject are not derived from the subject. In some embodiments, at least two of the plurality of different donors are not genetically identical to each other. In some embodiments, at least two of the plurality of different donors are not genetically similar to each other. In some embodiments, at least two of the plurality of different donors do not express the same HLA class or supertype as each other. In some embodiments, at least one of the plurality of different donors are not genetically identical to the subject. In some embodiments, at least one of the plurality of different donors are not genetically similar to the subject. In some embodiments, at least one of the plurality of different donors do not express the same HLA class or supertype as the subject. In some embodiments, the individual donor is not genetically identical to the subject. In some embodiments, the individual donor is not genetically similar to the subject. In some embodiments, the individual donor does not express the same HLA class or supertype as the subject.

The cells can be administered by any suitable means, for example, by bolus infusion, by injection, e.g., intravenous or subcutaneous injections, intraocular injection, periocular injection, subretinal injection, intravitreal injection, transseptal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration. In some embodiments, a given dose is administered by a single bolus administration of the cells. In some embodiments, it is administered by multiple bolus administrations of the cells, for example, over a period of no more than 3 days, or by continuous infusion administration of the cells. In some embodiments, administration of the cell dose or any additional therapies, e.g., the lymphodepleting therapy, intervention therapy and/or combination therapy, is carried out via outpatient delivery.

For the prevention or treatment of disease, the appropriate dosage may depend on the type of disease to be treated, the type of cells or recombinant receptors, the severity and course of the disease, whether the cells are administered for preventive or therapeutic purposes, previous therapy, the subject's clinical history and response to the cells, and the discretion of the attending physician. The compositions and cells are in some embodiments suitably administered to the subject at one time or over a series of treatments.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents include a cytokine, such as IL-2, for example, to enhance persistence. In some embodiments, the methods comprise administration of a chemotherapeutic agent.

In some embodiments, the methods comprise administration of a chemotherapeutic agent, e.g., a conditioning chemotherapeutic agent, for example, to reduce tumor burden prior to the administration.

Preconditioning subjects with immunodepleting (e.g., lymphodepleting) therapies in some aspects can improve the effects of adoptive cell therapy (ACT).

Thus, in some embodiments, the methods include administering a preconditioning agent, such as a lymphodepleting or chemotherapeutic agent, such as cyclophosphamide, fludarabine, or combinations thereof, to a subject prior to the initiation of the cell therapy. For example, the subject may be administered a preconditioning agent at least 2 days prior, such as at least 3, 4, 5, 6, or 7 days prior, to the initiation of the cell therapy. In some embodiments, the subject is administered a preconditioning agent no more than 7 days prior, such as no more than 6, 5, 4, 3, or 2 days prior, to the initiation of the cell therapy.

In some embodiments, the subject is preconditioned with cyclophosphamide at a dose between or between about 20 mg/kg and 100 mg/kg, such as between or between about 40 mg/kg and 80 mg/kg. In some aspects, the subject is preconditioned with or with about 60 mg/kg of cyclophosphamide. In some embodiments, the cyclophosphamide can be administered in a single dose or can be administered in a plurality of doses, such as given daily, every other day or every three days. In some embodiments, the cyclophosphamide is administered once daily for one or two days. In some embodiments, where the lymphodepleting agent comprises cyclophosphamide, the subject is administered cyclophosphamide at a dose between or between about 100 $mg/m^2$ and 500 $mg/m^2$, such as between or between about 200 $mg/m^2$ and 400 $mg/m^2$, or 250 $mg/m^2$ and 350 $mg/m^2$, inclusive. In some instances, the subject is administered about 300 $mg/m^2$ of cyclophosphamide. In some embodiments, the cyclophosphamide can be administered in a single dose or can be administered in a plurality of doses, such as given daily, every other day or every three days. In some embodiments, cyclophosphamide is administered daily, such as for 1-5 days, for example, for 3 to 5 days. In some instances, the subject is administered about 300 $mg/m^2$ of cyclophosphamide, daily for 3 days, prior to initiation of the cell therapy.

In some embodiments, where the lymphodepleting agent comprises fludarabine, the subject is administered fludarabine at a dose between or between about 1 $mg/m^2$ and 100 $mg/m^2$, such as between or between about 10 $mg/m^2$ and 75 $mg/m^2$, 15 $mg/m^2$ and 50 $mg/m^2$, 20 $mg/m^2$ and 40 $mg/m^2$, or 24 $mg/m^2$ and 35 $mg/m^2$, inclusive. In some instances, the subject is administered about 30 $mg/m^2$ of fludarabine. In some embodiments, the fludarabine can be administered in a single dose or can be administered in a plurality of doses, such as given daily, every other day or every three days. In some embodiments, fludarabine is administered daily, such as for 1-5 days, for example, for 3 to 5 days. In some instances, the subject is administered about 30 $mg/m^2$ of fludarabine, daily for 3 days, prior to initiation of the cell therapy.

In some embodiments, the lymphodepleting agent comprises a combination of agents, such as a combination of cyclophosphamide and fludarabine. Thus, the combination of agents may include cyclophosphamide at any dose or administration schedule, such as those described above, and fludarabine at any dose or administration schedule, such as those described above. For example, in some aspects, the subject is administered 60 mg/kg (~2 $g/m^2$) of cyclophosphamide and 3 to 5 doses of 25 $mg/m^2$ fludarabine prior to the first or subsequent dose.

Following administration of the cells, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable known methods, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells is measured by assaying expression and/or secretion of one or more cytokines, such as CD107a, IFNγ, IL-2, and TNF. In some aspects the biological activity is measured by assessing clinical outcome, such as reduction in tumor burden or load.

In certain embodiments, the engineered cells are further modified in any number of ways, such that their therapeutic or prophylactic efficacy is increased. For example, the engineered CAR or TCR expressed by the population can be conjugated either directly or indirectly through a linker to a targeting moiety. The practice of conjugating compounds, e.g., the CAR or TCR, to targeting moieties is known. See, for instance, Wadwa et al., J. Drug Targeting 3: 1 1 1 (1995), and U.S. Pat. No. 5,087,616.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agent includes a cytokine, such as IL-2, for example, to enhance persistence.

A. Dosing

In some embodiments, a dose of cells is administered to subjects in accord with the provided methods, and/or with the provided articles of manufacture or compositions. In some embodiments, the size or timing of the doses is determined as a function of the particular disease or condition in the subject. In some cases, the size or timing of the doses for a particular disease in view of the provided description may be empirically determined.

In some embodiments, the dose of cells comprising cells engineered with a recombinant antigen receptor, e.g. CAR or TCR, is provided as a composition or formulation, such as a pharmaceutical composition or formulation. Such compositions can be used in accord with the provided methods, and/or with the provided articles of manufacture or compositions, such as in the prevention or treatment of diseases, conditions, and disorders, or in detection, diagnostic, and prognostic methods.

In some embodiments, the dose of cells comprises between at or about $2\times10^5$ of the cells/kg and at or about $2\times10^6$ of the cells/kg, such as between at or about $4\times10^5$ of the cells/kg and at or about $1\times10^6$ of the cells/kg or between at or about $6\times10^5$ of the cells/kg and at or about $8\times10^5$ of the cells/kg. In some embodiments, the dose of cells comprises no more than $2\times10^5$ of the cells (e.g. antigen-expressing, such as CAR-expressing cells) per kilogram body weight of the subject (cells/kg), such as no more than at or about $3\times10^5$ cells/kg, no more than at or about $4\times10^5$ cells/kg, no more than at or about $5\times10^5$ cells/kg, no more than at or about $6\times10^5$ cells/kg, no more than at or about $7\times10^5$ cells/kg, no more than at or about $8\times10^5$ cells/kg, no more than at or about $9\times10^5$ cells/kg, no more than at or about $1\times10^6$ cells/kg, or no more than at or about $2\times10^6$ cells/kg. In some embodiments, the dose of cells comprises at least or at least about or at or about $2\times10^5$ of the cells (e.g. antigen-expressing, such as CAR-expressing cells) per kilogram body weight of the subject (cells/kg), such as at least or at least about or at or about $3\times10^5$ cells/kg, at least or at least about or at or about $4\times10^5$ cells/kg, at least or at least about or at or about $5\times10^5$ cells/kg, at least or at least about or at or about $6\times10^5$ cells/kg, at least or at least about or at or about $7\times10^5$ cells/kg, at least or at least about or at or about $8\times10^5$ cells/kg, at least or at least about or at or about $9\times10^5$ cells/kg, at least or at least about or at or about $1\times10^6$ cells/kg, or at least or at least about or at or about $2\times10^6$ cells/kg.

In certain embodiments, the cells, or individual populations of sub-types of cells, are administered to the subject at a range of about one million to about 100 billion cells and/or that amount of cells per kilogram of body weight, such as, e.g., 1 million to about 50 billion cells (e.g., about 5 million cells, 10 million cells, about 15 million cells, about 20 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges and/or per kilogram of body weight. Dosages may vary depending on attributes particular to the disease or disorder and/or patient and/or other treatments.

In some embodiments, the dose of cells is a flat dose of cells or fixed dose of cells such that the dose of cells is not tied to or based on the body surface area or weight of a subject.

In some embodiments, for example, where the subject is a human, the dose includes fewer than about $5\times10^8$ total recombinant receptor (e.g., CAR)-expressing cells, T cells, or peripheral blood mononuclear cells (PBMCs), e.g., in the range of about $1\times10^6$ to $5\times10^8$ such cells, such as $2\times10^6$, $5\times10^6$, $1\times10^7$, $5\times10^7$, $1\times10^8$, or $5\times10^8$ total such cells, or the range between any two of the foregoing values.

In some embodiments, the dose of genetically engineered cells comprises from or from about $1\times10^5$ to $5\times10^8$ total CAR-expressing T cells, $1\times10^5$ to $2.5\times10^8$ total CAR-expressing T cells, $1\times10^5$ to $1\times10^8$ total CAR-expressing T cells, $1\times10^5$ to $5\times10^7$ total CAR-expressing T cells, $1\times10^5$ to $2.5\times10^7$ total CAR-expressing T cells, $1\times10^5$ to $1\times10^7$ total CAR-expressing T cells, $1\times10^5$ to $5\times10^6$ total CAR-expressing T cells, $1\times10^5$ to $2.5\times10^6$ total CAR-expressing T cells, $1\times10^5$ to $1\times10^6$ total CAR-expressing T cells, $1\times10^6$ to $5\times10^8$ total CAR-expressing T cells, $1\times10^6$ to $2.5\times10^8$ total CAR-expressing T cells, $1\times10^6$ to $1\times10^8$ total CAR-expressing T cells, $1\times10^6$ to $5\times10^7$ total CAR-expressing T cells, $1\times10^6$ to $2.5\times10^7$ total CAR-expressing T cells, $1\times10^6$ to $1\times10^7$ total CAR-expressing T cells, $1\times10^6$ to $5\times10^6$ total CAR-expressing T cells, $1\times10^6$ to $2.5\times10^6$ total CAR-expressing T cells, $2.5\times10^6$ to $5\times10^8$ total CAR-expressing T cells, $2.5\times10^6$ to $2.5\times10^8$ total CAR-expressing T cells, $2.5\times10^6$ to $1\times10^8$ total CAR-expressing T cells, $2.5\times10^6$ to $5\times10^7$ total CAR-expressing T cells, $2.5\times10^6$ to $2.5\times10^7$ total CAR-expressing T cells, $2.5\times10^6$ to $1\times10^7$ total CAR-expressing T cells, $2.5\times10^6$ to $5\times10^6$ total CAR-expressing T cells, $5\times10^6$ to $5\times10^8$ total CAR-expressing T cells, $5\times10^6$ to $2.5\times10^8$ total CAR-expressing T cells, $5\times10^6$ to $1\times10^8$ total CAR-expressing T cells, $5\times10^6$ to $5\times10^7$ total CAR-expressing T cells, $5\times10^6$ to $2.5\times10^7$ total CAR-expressing T cells, $5\times10^6$ to $1\times10^7$ total CAR-expressing T cells, $1\times10^7$ to $5\times10^8$ total CAR-expressing T cells, $1\times10^7$ to $2.5\times10^8$ total CAR-expressing T cells, $1\times10^7$ to $1\times10^8$ total CAR-expressing T cells, $1\times10^7$ to $5\times10^7$ total CAR-expressing T cells, $1\times10^7$ to $2.5\times10^7$ total CAR-expressing T cells, $2.5\times10^7$ to $5\times10^8$ total CAR-expressing T cells, $2.5\times10^7$ to $2.5\times10^8$ total CAR-expressing T cells, $2.5\times10^7$ to $1\times10^8$ total CAR-expressing T cells, $2.5\times10^7$ to $5\times10^7$ total CAR-expressing T cells, $5\times10^7$ to $5\times10^8$ total CAR-expressing T cells, $5\times10^7$ to $2.5\times10^8$ total CAR-expressing T cells, $5\times10^7$ to $1\times10^8$ total CAR-expressing T cells, $1\times10^8$ to $5\times10^8$ total CAR-expressing T cells, $1\times10^8$ to $2.5\times10^8$ total CAR-expressing T cells, or $2.5\times10^8$ to $5\times10^8$ total CAR-expressing T cells.

In some embodiments, the dose of genetically engineered cells comprises at least or at least about $1\times10^5$ CAR-expressing cells, at least or at least about $2.5\times10^5$ CAR-expressing cells, at least or at least about $5\times10^5$ CAR-expressing cells, at least or at least about $1\times10^6$ CAR-expressing cells, at least or at least about $2.5\times10^6$ CAR-expressing cells, at least or at least about $5\times10^6$ CAR-expressing cells, at least or at least about $1\times10^7$ CAR-expressing cells, at least or at least about $2.5\times10^7$ CAR-expressing cells, at least or at least about $5\times10^7$ CAR-expressing cells, at least or at least about $1\times10^8$ CAR-expressing cells, at least or at least about $2.5\times10^8$ CAR-expressing cells, or at least or at least about $5\times10^8$ CAR-expressing cells.

In some embodiments, the cell therapy comprises administration of a dose comprising a number of cell from or from about $1\times10^5$ to $5\times10^8$ total recombinant receptor-expressing cells, total T cells, or total peripheral blood mononuclear cells (PBMCs), from or from about $5\times10^5$ to $1\times10^7$ total recombinant receptor-expressing cells, total T cells, or total peripheral blood mononuclear cells (PBMCs) or from or from about $1\times10^6$ to $1\times10^7$ total recombinant receptor-expressing cells, total T cells, or total peripheral blood mononuclear cells (PBMCs), each inclusive. In some embodiments, the cell therapy comprises administration of a dose of cells comprising a number of cells at least or at least about $1\times10^5$ total recombinant receptor-expressing cells, total T cells, or total peripheral blood mononuclear cells (PBMCs), such at least or at least $1\times10^6$, at least or at least about $1\times10^7$, at least or at least about $1\times10^8$ of such cells. In some embodiments, the number is with reference to the total number of CD3+ or CD8+, in some cases also recombinant receptor-expressing (e.g. CAR+) cells. In some embodiments, the cell therapy comprises administration of a dose comprising a number of cell from or from about $1\times10^5$ to $5\times10^8$ CD3+ or CD8+ total T cells or CD3+ or CD8+ recombinant receptor-expressing cells, from or from about $5\times10^5$ to $1\times10^7$ CD3+ or CD8+ total T cells or CD3+ or CD8+ recombinant receptor-expressing cells, or from or from about $1\times10^6$ to $1\times10^7$ CD3+ or CD8+ total T cells or CD3+ or CD8+ recombinant receptor-expressing cells, each inclusive. In some embodiments, the cell therapy comprises administration of a dose comprising a number of cell from or from about $1\times10^5$ to $5\times10^8$ total CD3+/CAR+ or CD8+/CAR+ cells, from or from about $5\times10^5$ to $1\times10^7$ total CD3+/CAR+ or CD8+/CAR+ cells, or from or from about $1\times10^6$ to $1\times10^7$ total CD3+/CAR+ or CD8+/CAR+ cells, each inclusive.

In some embodiments, the T cells of the dose include CD4+ T cells, CD8+ T cells or CD4+ and CD8+ T cells.

In some embodiments, for example, where the subject is human, the CD8+ T cells of the dose, including in a dose including CD4+ and CD8+ T cells, includes between about $1\times10^6$ and $5\times10^8$ total recombinant receptor (e.g., CAR)-expressing CD8+ cells, e.g., in the range of about $5\times10^6$ to $1\times10^8$ such cells, such cells $1\times10^7$, $2.5\times10^7$, $5\times10^7$, $7.5\times10^7$, $1\times10^8$, or $5\times10^8$ total such cells, or the range between any two of the foregoing values. In some embodiments, the patient is administered multiple doses, and each of the doses or the total dose can be within any of the foregoing values. In some embodiments, the dose of cells comprises the administration of from or from about $1\times10^7$ to $0.75\times10^8$ total recombinant receptor-expressing CD8+ T cells, $1\times10^7$ to $2.5\times10^7$ total recombinant receptor-expressing CD8+ T cells, from or from about $1\times10^7$ to $0.75\times10^8$ total recombinant receptor-expressing CD8+ T cells, each inclusive. In some embodiments, the dose of cells comprises the administration of or about $1\times10^7$, $2.5\times10^7$, $5\times10^7$ $7.5\times10^7$, $1\times10^8$, or $5\times10^8$ total recombinant receptor-expressing CD8+ T cells.

In some embodiments, the dose of cells, e.g., recombinant receptor-expressing T cells, is administered to the subject as a single dose or is administered only one time within a period of two weeks, one month, three months, six months, 1 year or more.

In the context of adoptive cell therapy, administration of a given "dose" encompasses administration of the given amount or number of cells as a single composition and/or single uninterrupted administration, e.g., as a single injection or continuous infusion, and also encompasses administration of the given amount or number of cells as a split dose or as a plurality of compositions, provided in multiple individual compositions or infusions, over a specified period of time, such as over no more than 3 days. Thus, in some contexts, the dose is a single or continuous administration of the specified number of cells, given or initiated at a single point in time. In some contexts, however, the dose is administered in multiple injections or infusions over a period of no more than three days, such as once a day for three days or for two days or by multiple infusions over a single day period.

Thus, in some aspects, the cells of the dose are administered in a single pharmaceutical composition. In some embodiments, the cells of the dose are administered in a plurality of compositions, collectively containing the cells of the dose.

In some embodiments, the term "split dose" refers to a dose that is split so that it is administered over more than one day. This type of dosing is encompassed by the present methods and is considered to be a single dose.

Thus, the dose of cells may be administered as a split dose, e.g., a split dose administered over time. For example, in some embodiments, the dose may be administered to the subject over 2 days or over 3 days. Exemplary methods for split dosing include administering 25% of the dose on the first day and administering the remaining 75% of the dose on the second day. In other embodiments, 33% of the dose may be administered on the first day and the remaining 67% administered on the second day. In some aspects, 10% of the dose is administered on the first day, 30% of the dose is administered on the second day, and 60% of the dose is administered on the third day. In some embodiments, the split dose is not spread over more than 3 days.

In some embodiments, cells of the dose may be administered by administration of a plurality of compositions or solutions, such as a first and a second, optionally more, each containing some cells of the dose. In some aspects, the plurality of compositions, each containing a different population and/or sub-types of cells, are administered separately or independently, optionally within a certain period of time. For example, the populations or sub-types of cells can include CD8+ and CD4+ T cells, respectively, and/or CD8+- and CD4+-enriched populations, respectively, e.g., CD4+ and/or CD8+ T cells each individually including cells genetically engineered to express the recombinant receptor. In some embodiments, the administration of the dose comprises administration of a first composition comprising a dose of CD8+ T cells or a dose of CD4+ T cells and administration of a second composition comprising the other of the dose of CD4+ T cells and the CD8+ T cells.

In some embodiments, the administration of the composition or dose, e.g., administration of the plurality of cell compositions, involves administration of the cell compositions separately. In some aspects, the separate administrations are carried out simultaneously, or sequentially, in any order. In some embodiments, the dose comprises a first composition and a second composition, and the first composition and second composition are administered 0 to 12 hours apart, 0 to 6 hours apart or 0 to 2 hours apart. In some embodiments, the initiation of administration of the first composition and the initiation of administration of the second composition are carried out no more than 2 hours, no more than 1 hour, or no more than 30 minutes apart, no more than 15 minutes, no more than 10 minutes or no more than 5 minutes apart. In some embodiments, the initiation and/or completion of administration of the first composition and the completion and/or initiation of administration of the second composition are carried out no more than 2 hours, no more than 1 hour, or no more than 30 minutes apart, no more than 15 minutes, no more than 10 minutes or no more than 5 minutes apart.

In some composition, the first composition, e.g., first composition of the dose, comprises CD4+ T cells. In some composition, the first composition, e.g., first composition of the dose, comprises CD8+ T cells. In some embodiments, the first composition is administered prior to the second composition.

In some embodiments, the dose or composition of cells includes a defined or target ratio of CD4+ cells expressing a recombinant receptor to CD8+ cells expressing a recombinant receptor and/or of CD4+ cells to CD8+ cells, which ratio optionally is approximately 1:1 or is between approximately 1:3 and approximately 3:1, such as approximately 1:1. In some aspects, the administration of a composition or dose with the target or desired ratio of different cell populations (such as CD4+:CD8+ ratio or CAR+ CD4+:CAR+ CD8+ ratio, e.g., 1:1) involves the administration of a cell composition containing one of the populations and then administration of a separate cell composition comprising the other of the populations, where the administration is at or approximately at the target or desired ratio. In some aspects, administration of a dose or composition of cells at a defined ratio leads to improved expansion, persistence and/or antitumor activity of the T cell therapy.

In some embodiments, the subject receives multiple doses, e.g., two or more doses or multiple consecutive doses, of the cells. In some embodiments, two doses are administered to a subject. In some embodiments, the subject receives the consecutive dose, e.g., second dose, is administered approximately 4, 5, 6, 7, 8, 9, 10, 11, 12, 13, 14, 15, 16, 17, 18, 19, 20 or 21 days after the first dose. In some embodiments, multiple consecutive doses are administered following the first dose, such that an additional dose or doses are administered following administration of the consecutive dose. In some aspects, the number of cells administered to the subject in the additional dose is the same as or similar to the first dose and/or consecutive dose. In some embodiments, the additional dose or doses are larger than prior doses.

In some aspects, the size of the first and/or consecutive dose is determined based on one or more criteria such as response of the subject to prior treatment, e.g. chemotherapy, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

In some aspects, the time between the administration of the first dose and the administration of the consecutive dose is about 9 to about 35 days, about 14 to about 28 days, or 15 to 27 days. In some embodiments, the administration of the consecutive dose is at a time point more than about 14 days after and less than about 28 days after the administration of the first dose. In some aspects, the time between the first and consecutive dose is about 21 days. In some embodiments, an additional dose or doses, e.g. consecutive doses, are administered following administration of the consecutive dose. In some aspects, the additional consecutive dose or doses are administered at least about 14 and less than about 28 days following administration of a prior dose. In some embodiments, the additional dose is administered less than about 14 days following the prior dose, for example, 4, 5, 6, 7, 8, 9, 10, 11, 12, or 13 days after the prior dose. In some embodiments, no dose is administered less than about 14 days following the prior dose and/or no dose is administered more than about 28 days after the prior dose.

In some embodiments, the dose of cells, e.g., recombinant receptor-expressing cells, comprises two doses (e.g., a double dose), comprising a first dose of the T cells and a consecutive dose of the T cells, wherein one or both of the first dose and the second dose comprises administration of the split dose of T cells.

In some embodiments, the dose of cells is generally large enough to be effective in reducing disease burden.

In some embodiments, the cells are administered at a desired dosage, which in some aspects includes a desired dose or number of cells or cell type(s) and/or a desired ratio of cell types. Thus, the dosage of cells in some embodiments is based on a total number of cells (or number per kg body weight) and a desired ratio of the individual populations or sub-types, such as the CD4+ to CD8+ ratio. In some embodiments, the dosage of cells is based on a desired total number (or number per kg of body weight) of cells in the individual populations or of individual cell types. In some embodiments, the dosage is based on a combination of such features, such as a desired number of total cells, desired ratio, and desired total number of cells in the individual populations.

In some embodiments, the populations or sub-types of cells, such as CD8+ and CD4+ T cells, are administered at or within a tolerated difference of a desired dose of total cells, such as a desired dose of T cells. In some aspects, the desired dose is a desired number of cells or a desired number of cells per unit of body weight of the subject to whom the cells are administered, e.g., cells/kg. In some aspects, the desired dose is at or above a minimum number of cells or minimum number of cells per unit of body weight. In some aspects, among the total cells, administered at the desired dose, the individual populations or sub-types are present at or near a desired output ratio (such as $CD4^+$ to $CD8^+$ ratio), e.g., within a certain tolerated difference or error of such a ratio.

In some embodiments, the cells are administered at or within a tolerated difference of a desired dose of one or more of the individual populations or sub-types of cells, such as a desired dose of CD4+ cells and/or a desired dose of CD8+ cells. In some aspects, the desired dose is a desired number of cells of the sub-type or population, or a desired number of such cells per unit of body weight of the subject to whom the cells are administered, e.g., cells/kg. In some aspects, the desired dose is at or above a minimum number of cells of the population or sub-type, or minimum number of cells of the population or sub-type per unit of body weight.

Thus, in some embodiments, the dosage is based on a desired fixed dose of total cells and a desired ratio, and/or based on a desired fixed dose of one or more, e.g., each, of the individual sub-types or sub-populations. Thus, in some embodiments, the dosage is based on a desired fixed or minimum dose of T cells and a desired ratio of $CD4^+$ to $CD8^+$ cells, and/or is based on a desired fixed or minimum dose of $CD4^+$ and/or $CD8^+$ cells.

In some embodiments, the cells are administered at or within a tolerated range of a desired output ratio of multiple cell populations or sub-types, such as CD4+ and CD8+ cells or sub-types. In some aspects, the desired ratio can be a specific ratio or can be a range of ratios. for example, in some embodiments, the desired ratio (e.g., ratio of $CD4^+$ to $CD8^+$ cells) is between at or about 5:1 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, such as at or about 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9: 1:2, 1:2.5, 1:3, 1:3.5, 1:4, 1:4.5, or 1:5. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

In particular embodiments, the numbers and/or concentrations of cells refer to the number of recombinant receptor (e.g., CAR)-expressing cells. In other embodiments, the numbers and/or concentrations of cells refer to the number or concentration of all cells, T cells, or peripheral blood mononuclear cells (PBMCs) administered.

In some aspects, the size of the dose is determined based on one or more criteria such as response of the subject to prior treatment, e.g. chemotherapy, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

In some embodiments, the methods also include administering one or more additional doses of cells expressing a chimeric antigen receptor (CAR) and/or lymphodepleting therapy, and/or one or more steps of the methods are repeated. In some embodiments, the one or more additional dose is the same as the initial dose. In some embodiments, the one or more additional dose is different from the initial dose, e.g., higher, such as 2-fold, 3-fold, 4-fold, 5-fold, 6-fold, 7-fold, 8-fold, 9-fold or 10-fold or more higher than the initial dose, or lower, such as e.g., higher, such as 2-fold, 3-fold, 4-fold, 5-fold, 6-fold, 7-fold, 8-fold, 9-fold or 10-fold or more lower than the initial dose. In some embodiments, administration of one or more additional doses is determined based on response of the subject to the initial treatment or any prior treatment, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

VI. Articles of Manufacture and Kits

Also provided are articles of manufacture, systems, apparatuses, and kits useful in performing the provided methods. Also provided are articles of manufacture, including: (i) one or more reagents for immunoaffinity-based selection of cells specific for CD57, CD3, CD4 and/or CD8; and (ii) instructions for use of the one or more reagents for performing any methods described herein.

Also provided are articles of manufacture, including: (i) one or more reagents for immunoaffinity-based selection of cells specific for CD57, CD3, CD4 and/or CD8; (ii) one or more stimulatory reagents capable of activating one or more intracellular signaling domains of one or more components of a TCR complex and one or more intracellular signaling domains of one or more costimulatory molecules; and (iii) instructions for use of the one or more reagents for performing any methods described herein.

In some of any such embodiments, the reagent for immunoaffinity-based selection is or includes an antibody capable of specifically binding to CD57, CD3, CD4 or CD8. In some of any such embodiments, the reagent for immunoaffinity-based selection is or includes an antibody capable of specifically binding to CD57. In some of any such embodiments, the antibody is immobilized on a magnetic particle or is immobilized on or attached to an affinity chromatography matrix.

Also provided are articles of manufacture, including: (i) one or more reagents for immunoaffinity-based selection of cells specific for CD27, CD3, CD4 and/or CD8; and (ii) instructions for use of the one or more reagents for performing any methods described herein.

Also provided are articles of manufacture, including: (i) one or more reagents for immunoaffinity-based selection of cells specific for CD27, CD3, CD4 and/or CD8; (ii) one or more stimulatory reagents capable of activating one or more intracellular signaling domains of one or more components of a TCR complex and one or more intracellular signaling domains of one or more costimulatory molecules; and (iii) instructions for use of the one or more reagents for performing any methods described herein.

In some of any such embodiments, the reagent for immunoaffinity-based selection is or includes an antibody capable of specifically binding to CD27, CD3, CD4 or CD8. In some of any such embodiments, the reagent for immunoaffinity-based selection is or includes an antibody capable of specifically binding to CD27. In some of any such embodiments, the antibody is immobilized on a magnetic particle or is immobilized on or attached to an affinity chromatography matrix.

In some of any such embodiments, the stimulatory reagent includes (i) a primary agent that specifically binds to a member of a TCR complex, optionally that specifically binds to CD3 and (ii) a secondary agent that specifically binds to a T cell costimulatory molecule, optionally wherein the costimulatory molecule is selected from CD28, CD137 (4-1-BB), OX40, or ICOS. In some of any such embodiments, the one or both of the primary and secondary agents include an antibody or an antigen-binding fragment thereof. In some of any such embodiments, the primary and secondary agents include an antibody, optionally wherein the stimulatory reagent includes incubation with an anti-CD3 antibody and an anti-CD28 antibody, or an antigen-binding fragment thereof. In some of any such embodiments, the primary agent and secondary agent are present or attached on the surface of a solid support. In some of any such embodiments, the solid support is or includes a bead, optionally a paramagnetic bead. In some of any such embodiments, the primary agent and secondary agent are reversibly bound on the surface of an oligomeric particle reagent including a plurality of streptavidin or streptavidin mutein molecules.

Also provided are articles of manufacture, including (i) any composition described herein; and (ii) instructions for administering the composition to a subject.

In some embodiments, the articles of manufacture or kits include one or more containers, typically a plurality of containers, packaging material, and a label or package insert on or associated with the container or containers and/or packaging, generally including instructions for use, e.g., instructions for reagents for immunoaffinity-based selection of particular cells, e.g., positive or negative selection of cells expressing CD57, CD3, CD4 and/or CD8, and instructions to carry out any of the methods provided herein, such as for engineering T cells to generate a composition, such as a therapeutic composition, for cell therapy. In some embodiments, the articles of manufacture or kits include one or more containers, typically a plurality of containers, packaging material, and a label or package insert on or associated with the container or containers and/or packaging, generally including instructions for use, e.g., instructions for reagents for immunoaffinity-based selection of particular cells, e.g., positive or negative selection of cells expressing CD27, CD3, CD4 and/or CD8, and instructions to carry out any of the methods provided herein, such as for engineering T cells to generate a composition, such as a therapeutic composition, for cell therapy. In some aspects, the provided articles of manufacture contain reagents for stimulation and/or cultivation of cells, for example, at one or more steps of the manufacturing process, such as any reagents described in any steps of Section II and Section III.

Also provided are articles of manufacture and kits containing engineered cells expressing a recombinant receptor or compositions thereof, such as those generated using the methods provided herein, and optionally instructions for use, for example, instructions for administering. In some embodiments, the instructions provide directions or specify methods for assessing if a subject, prior to receiving a cell therapy, is likely or suspected of being likely to respond and/or the degree or level of response following administration of engineered cells expressing a recombinant receptor for treating a disease or disorder. In some aspects, the articles of manufacture can contain a dose or a composition of engineered cells.

The articles of manufacture provided herein contain packaging materials. Packaging materials for use in packaging the provided materials are well known to those of skill in the art. See, for example, U.S. Pat. Nos. 5,323,907, 5,052,558 and 5,033,252, each of which is incorporated herein in its entirety. Examples of packaging materials include, but are not limited to, blister packs, bottles, tubes, inhalers, pumps, bags, vials, containers, syringes, disposable laboratory supplies, e.g., pipette tips and/or plastic plates, or bottles. The articles of manufacture or kits can include a device so as to facilitate dispensing of the materials or to facilitate use in a high-throughput or large-scale manner, e.g., to facilitate use in robotic equipment. Typically, the packaging is non-reactive with the compositions contained therein.

In some embodiments, the reagents and/or cell compositions are packaged separately. In some embodiments, each container can have a single compartment. In some embodiments, other components of the articles of manufacture or kits are packaged separately, or together in a single compartment.

VII. Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the singular forms “a,” “an,” and “the” include plural referents unless the context clearly dictates otherwise. For example, “a” or “an” means “at least one” or “one or more.” It is understood that aspects and variations described herein include “consisting” and/or “consisting essentially of” aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term “about” as used herein refers to the usual error range for the respective value readily known. Reference to “about” a value or parameter herein includes (and describes) embodiments that are directed to that value or parameter per se. For example, description referring to “about X” includes description of “X”. In certain embodiments, “about X” refers to a value of ±25%, ±10%, ±5%, ±2%, ±1%, ±0.1%, or ±0.01% of X.

As used herein, recitation that nucleotides or amino acid positions “correspond to” nucleotides or amino acid positions in a disclosed sequence, such as set forth in the Sequence listing, refers to nucleotides or amino acid positions identified upon alignment with the disclosed sequence to maximize identity using a standard alignment algorithm, such as the GAP algorithm. By aligning the sequences, corresponding residues can be identified, for example, using conserved and identical amino acid residues as guides. In general, to identify corresponding positions, the sequences of amino acids are aligned so that the highest order match is obtained (see, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; Carrillo et al. (1988) SIAM J Applied Math 48: 1073).

The term “vector,” as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as “expression vectors.” Among the vectors are viral vectors, such as retroviral, e.g., gammaretroviral and lentiviral vectors.

The terms “host cell,” “host cell line,” and “host cell culture” are used interchangeably and refer to cells into which exogenous nucleic acid has been introduced, including the progeny of such cells. Host cells include “transformants” and “transformed cells,” which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

As used herein, "percent (%) amino acid sequence identity" and "percent identity" when used with respect to an amino acid sequence (reference polypeptide sequence) is defined as the percentage of amino acid residues in a candidate sequence (e.g., the subject antibody or fragment) that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various known ways, for instance, using publicly available computer software such as BLAST, BLAST-2, ALIGN or Megalign (DNASTAR) software. Appropriate parameters for aligning sequences can be determined, including any algorithms needed to achieve maximal alignment over the full length of the sequences being compared.

An amino acid substitution may include replacement of one amino acid in a polypeptide with another amino acid. The substitution may be a conservative amino acid substitution or a non-conservative amino acid substitution. Amino acid substitutions may be introduced into a binding molecule, e.g., antibody, of interest and the products screened for a desired activity, e.g., retained/improved antigen binding, decreased immunogenicity, or improved ADCC or CDC.

Amino acids generally can be grouped according to the following common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

In some embodiments, conservative substitutions can involve the exchange of a member of one of these classes for another member of the same class. In some embodiments, non-conservative amino acid substitutions can involve exchanging a member of one of these classes for another class.

As used herein, a composition refers to any mixture of two or more products, substances, or compounds, including cells. It may be a solution, a suspension, liquid, powder, a paste, aqueous, non-aqueous or any combination thereof.

As used herein, a "subject" is a mammal, such as a human or other animal, and typically is human.

VIII. Exemplary Embodiments

Among the provided embodiments are:

1. A method of preparing a T cell composition from a donor pool, the method comprising:
   - (a) obtaining a plurality of engineered T cell compositions from a plurality of different donors, each engineered T cell composition comprising T cells enriched for T cells surface negative for CD57 (CD57−) from a donor sample from an individual donor of the plurality of different donors, wherein the T cells comprise T cells genetically engineered with a recombinant receptor; and
   - (b) combining the plurality of engineered T cell compositions to produce a donor pooled engineered T cell composition.
2. The method of embodiment 1, wherein each of the plurality of engineered T cell compositions is generated by a process comprising:
   - (i) selecting T cells enriched for T cells surface negative for CD57 (CD57−) from a donor sample from the individual donor, thereby generating a CD57 depleted T cell population; and
   - (ii) introducing a heterologous nucleic acid encoding the recombinant receptor into the CD57 depleted cell population, thereby generating the engineered T cell composition.
3. The method of embodiment 2, wherein prior to step (ii) the method comprises stimulating the CD57 depleted T cell population under conditions to activate T cells in the population.
4. The method of embodiment 2 or embodiment 3, wherein the method further comprises (iii) incubating the cells of the engineered T cell composition for up to 96 hours subsequent to the introducing, optionally at a temperature of at or about 37°±2° C.
5. The method of embodiment 4, wherein the incubating is carried out under conditions in which the cells are not expanded or not substantially expanded compared to the number of cells at the initiation of the incubating.
6. The method of embodiment 2 or embodiment 3, wherein the method further comprises (iii) cultivating the cells of the engineered T cell composition under conditions for expansion of T cells in the composition.
7. The method of any of embodiments 2-6, wherein the selecting T cells enriched for T cells surface negative for CD57 (CD57−) comprises:
   - (1) selecting one of (a) cells surface positive for a T cell marker(s) and (b) cells surface negative for CD57 (CD57−) from the donor sample from the individual donor, thereby generating an enriched population of cells; and (2) selecting, from the enriched population of cells, for the other of (a) cells surface positive for the T cell marker(s) and (b) CD57− cells, thereby generating the CD57 depleted T cell population.

8. The method of embodiment 7, wherein the T cell marker(s) is CD3.

9. The method of embodiment 7 or embodiment 8, wherein the T cell marker(s) is CD4.

10. The method of any of embodiments 7-9, wherein the T cell marker(s) is CD8.

11. The method of any of embodiments 7-10, wherein the T cell surface marker(s) is CD4 and CD8.

12. The method of any of embodiments 1-11, wherein the method further comprises knocking out expression of (i) an endogenous major histocompatibility complex (MEW) or a component thereof, optionally beta-2-microglobulin 032M); and/or (ii) an endogenous T cell receptor (TCR) or a component thereof, optionally T cell receptor alpha constant (TRAC), in the T cells of the CD57 depleted population and/or the engineered T cell composition prior to or during one or more of the steps of the method.

13. The method of any of embodiments 1-12, wherein T cells of the plurality of engineered T cell compositions are knocked out (KO) for expression of (i) an endogenous major histocompatibility complex (MHC) or a component thereof, optionally beta-2-microglobulin (132M) and/or (ii) an endogenous T cell receptor (TCR) or a component thereof, optionally T cell receptor alpha constant (TRAC).

14. A method of preparing a T cell composition from a donor pool, the method comprising:

(a) selecting T cells enriched for T cells surface negative for CD57 (CD57−) from a donor sample from an individual donor, thereby generating a CD57 depleted T cell population;

(b) genetically engineering the CD57 depleted T cell population, thereby producing an engineered T cell composition, the genetic engineering comprising:

(1) knocking out expression of (i) an endogenous major histocompatibility complex (MHC) or a component thereof, optionally beta-2-microglobulin (β2M); and/or (ii) an endogenous T cell receptor (TCR) or a component thereof, optionally T cell receptor alpha constant (TRAC), in cells of the CD57 depleted T cell population; and (2) introducing a heterologous nucleic acid encoding a recombinant receptor into the cells of the CD57 depleted T cell population, optionally wherein the heterologous nucleic acid is inserted into a locus of a gene encoding for the endogenous MHC or a component thereof and/or the endogenous TCR or a component thereof;

wherein the knocking out in (1) and the introducing in (2) are carried out concurrently or successively in either order;

(c) repeating steps (a) and (b) for a plurality of different donors to produce a plurality of donor engineered T cell compositions, wherein each donor engineered T cell composition is generated from cells from an individual donor of the plurality of different donors; and (d) combining the plurality of donor engineered T cell compositions from the plurality of different individual donors to produce a donor pooled engineered T cell composition.

15. The method of any of embodiments 1-14, wherein the method is repeated for each of the individual donors of the plurality of different donors.

16. The method of any of embodiments 1-15, wherein each of the plurality of engineered T cell compositions has been cryopreserved and thawed prior to the combining.

17. The method of any of embodiments 1-16, wherein the CD57 depleted T cell population comprises greater than or greater than at or about 75% CD3+/CD57− cells, greater than at or about 80% CD3+/CD57− cells, greater than at or about 85% CD3+/CD57− cells, greater than at or about 90% CD3+/CD57− cells, or greater than at or about 95% CD3+/CD57− cells.

18. The method of any of embodiments 1-17, wherein each of the plurality of engineered T cell compositions independently comprises greater than or greater than at or about 40% CD57−/recombinant receptor+ cells, greater than at or about 45% CD57−/recombinant receptor+ cells, greater than at or about 50% CD57−/recombinant receptor+ cells, greater than at or about 55% CD57−/recombinant receptor+ cells, greater than at or about 55% CD57−/recombinant receptor+ cells, greater than at or about 60% CD57−/recombinant receptor+ cells, greater than at or about 65% CD57−/recombinant receptor+ cells or greater than at or about 70% CD57−/recombinant receptor+ cells, optionally greater than or greater than at or about 40% CD3+/CD57−/recombinant receptor+ cells, greater than at or about 45% CD3+/CD57−/recombinant receptor+ cells, greater than at or about 50% CD3+/CD57−/recombinant receptor+ cells, greater than at or about 55% CD3+/CD57−/recombinant receptor+ cells, greater than at or about 55% CD3+/CD57−/recombinant receptor+ cells, greater than at or about 60% CD3+/CD57−/recombinant receptor+ cells, greater than at or about 65% CD3+/CD57−/recombinant receptor+ cells or greater than at or about 70% CD3+/CD57−/recombinant receptor+ cells.

19. The method of any of embodiments 1-18, wherein each of the plurality of engineered T cell compositions comprise CD4+ and CD8+ T cells.

20. The method of embodiment 19, wherein each of the plurality of engineered T cell compositions comprises a ratio of CD4+ to CD8+ T cells of between at or about 1:5 and at or about 5:1.

21. The method of embodiment 19, wherein each of the plurality of engineered T cell compositions comprises a ratio of CD4+ to CD8+ T cells of between at or about 1:3 and at or about 3:1.

22. The method of any of embodiments 12-21, further comprising, prior to the knocking out, stimulating the CD57 depleted T cell population under conditions to activate T cells in the population.

23. The method of any of embodiments 12-22, wherein the knocking out and the introducing the heterologous nucleic acid are carried out concurrently.

24. The method of any of embodiments 12-22, wherein the knocking out and the introducing the heterologous nucleic acid are carried out successively in either order.

25. A method of preparing a T cell composition from a donor pool, the method comprising:

(1) selecting for one of (a) cells surface positive for a T cell marker(s) and (b) cells surface negative for CD57 (CD57−) from a donor sample from a plurality of different donors, thereby generating an enriched population of cells; and (2) selecting, from the enriched population of cells, the other of (a) cells surface positive for the T cell marker (s) and (b) CD57− cells, thereby generating a CD57 depleted T cell population.

26. The method of embodiment 25, wherein the donor sample is a pooled sample comprising cells from the plurality of different donors, whereby the method produces a pooled CD57 depleted T cell population.

27. The method of embodiment 25, wherein the donor sample is a sample from an individual donor, and steps (1) and (2) are repeated separately for each donor sample from the plurality of different donors, whereby the method produces a CD57 depleted T cell population for each individual donor.

28. The method of embodiment 27, wherein the method further comprises combining the CD57 depleted T cell populations for each individual donor together to produce a pooled CD57 depleted T cell population.

29. The method of any of embodiments 25-28, wherein the T cell marker(s) is CD3.

30. The method of any of embodiments 25-29, wherein the T cell marker(s) is CD4.

31. The method of any of embodiments 25-30, wherein the T cell marker(s) is CD8.

32. The method of any of embodiments 25-31, wherein the T cell surface marker(s) is CD4 and CD8.

33. A method of preparing a T cell composition from a donor pool, the method comprising selecting for T cells that are surface negative for CD57 (CD57−) from a donor sample, wherein the donor sample is a pooled cell population enriched for human T cells from a plurality of different donors, thereby generating a pooled CD57 depleted T cell population.

34. A method of preparing a T cell composition from a donor pool, the method comprising:

(a) selecting for T cells that are surface negative for CD57 (CD57−) from a donor sample, wherein the donor sample is enriched for human T cells from an individual donor, thereby generating a CD57 depleted T cell population;

(b) repeating step (a) for a plurality of different individual donors; and (c) combining each of the CD57 depleted T cell populations from each of the individual donors, thereby generating a pooled CD57 depleted T cell population.

35. A method of preparing a T cell composition from a donor pool, the method comprising selecting for T cells from a donor sample, wherein the donor sample is a pooled cell population enriched for human T cells that are surface negative for CD57 (CD57−) from a plurality of different donors, thereby generating a pooled CD57 depleted T cell population.

36. A method of preparing a T cell composition from a donor pool, the method comprising:

(a) selecting for T cells from a donor sample, wherein the sample is enriched for human T cells that are surface negative for CD57 (CD57−) from an individual donor, thereby generating a CD57 depleted T cell population;

(b) repeating step (a) for a plurality of different donors; and (c) combining each of the CD57 depleted T cell populations from each of the individual donors, thereby generating a pooled CD57 depleted T cell population.

37. The method of any of embodiments 33-36, wherein the donor sample enriched for human T cells is obtained by selecting for CD3+ T cells.

38. The method of any of embodiments 33-37, wherein the donor sample enriched for human T cells is obtained by selecting for CD4+ T cells and/or CD8+ T cells.

39. The method of any of embodiments 33-38, wherein the donor sample enriched for human T cells comprises greater than at or about 85% CD3+ T cells.

40. The method of any of embodiments 33-39, wherein the donor sample enriched for human T cells comprises greater than at or about 90% CD3+ T cells.

41. The method of any of embodiments 33-40, wherein the donor sample enriched for human T cells comprises greater than at or about 95% CD3+ T cells.

42. The method of any of embodiments 33-41, wherein the donor sample enriched for human T cells comprises CD4+ and CD8+ T cells.

43. The method of embodiment 42, wherein the donor sample enriched for human T cells comprises a ratio of CD4+ to CD8+ T cells of between at or about 1:5 and at or about 5:1.

44. The method of embodiment 42, wherein the donor sample enriched for human T cells comprises a ratio of CD4+ to CD8+ T cells of between at or about 1:3 and at or about 3:1.

45. The method of any of embodiments 33-44, wherein the selecting for T cells comprises selecting for CD3+ T cells.

46. The method of any of embodiments 33-45, wherein the selecting for T cells comprises selecting for CD4+ and/or CD8+ T cells.

47. The method of any of embodiments 35-46, wherein the donor sample enriched for CD57− human T cells is obtained by selecting for CD57− T cells.

48. The method of any of embodiments 27-32, 34, and 36-47, wherein:

(a) cells of the CD57 depleted T cell population are knocked out (KO) for expression of (i) an endogenous major histocompatibility complex (MHC) or a component thereof, optionally beta-2-microglobulin (β2M); and/or (ii) an endogenous T cell receptor (TCR) or a component thereof, optionally T cell receptor alpha constant (TRAC); and/or (b) the method further comprises knocking out expression of (i) an endogenous major histocompatibility complex (MHC) or a component thereof, optionally beta-2-microglobulin (β2M); and/or (ii) an endogenous T cell receptor (TCR) or a component thereof, optionally TRAC, in cells of the CD57 depleted T cell population.

49. The method of any of embodiments 26 and 28-47, wherein:

(a) cells of the pooled CD57 depleted T cell population are knocked out (KO) for expression of (i) an endogenous major histocompatibility complex (MHC) or a component thereof, optionally beta-2-microglobulin (β2M); and/or (ii) an endogenous T cell receptor (TCR) or a component thereof, optionally T cell receptor alpha constant (TRAC); and/or (b) the method further comprises knocking out expression of (i) an endogenous major histocompatibility complex (MHC) or a component thereof, optionally beta-2-microglobulin (β2M); and/or (ii) an endogenous T cell receptor (TCR) or a component thereof, optionally T cell receptor alpha constant (TRAC), in cells of the pooled CD57 depleted T cell population.

50. The method of any of embodiments 27-32, 34, and 36-48, wherein:

(a) a heterologous polynucleotide encoding a recombinant receptor is introduced into cells of the CD57 depleted T cell population; and/or (b) the method further comprises introducing into cells of the CD57 depleted T cell population a heterologous polynucleotide encoding a recombinant receptor, the method thereby generating an engineered T cell composition.

51. The method of any of embodiments 26, 28-47, and 49, wherein:

(a) a heterologous polynucleotide encoding a recombinant receptor is introduced into cells of the pooled CD57 depleted T cell population; and/or (b) the method further comprises introducing into cells of the pooled CD57 depleted T cell population a heterologous polynucleotide encoding a recombinant receptor, the method thereby generating an engineered T cell composition.

52. The method of embodiment 50 or embodiment 51, wherein the knocking out and the introducing the heterologous nucleic acid are carried out concurrently.

53. The method of embodiment 50 or embodiment 51, wherein the knocking out and the introducing the heterologous nucleic acid are carried out successively in either order.

54. The method of any of embodiments 48-53, wherein the combining is performed prior to the cells of the CD57 depleted T cell population being knocked out and/or introduced to the heterologous nucleic acid.

55. The method of any of embodiments 48-53, wherein the combining is performed after the cells of the CD57 depleted T cell are knocked out and/or introduced to the heterologous nucleic acid.

56. A method of preparing a T cell composition from a donor pool, the method comprising:

(i) selecting for one of (a) cells surface positive for CD3 (CD3+), or surface positive for CD4 (CD4+) and/or CD8 (CD8+) and (b) cells surface negative for CD57 (CD57−) from a donor sample, thereby generating an enriched population of cells;

(ii) selecting, from the enriched population of cells, the other of (a) CD3+, or CD4+ and/or CD8+ cells and (b) CD57− cells, thereby generating a CD57 depleted T cell population;

(iii) stimulating cells of the CD57 depleted T cell population under conditions to activate T cells in the population;

(iv) genetically engineering the stimulated cells, thereby producing an engineered T cell composition, the genetic engineering comprising:

(1) knocking out expression of (a) an endogenous major histocompatibility complex (MHC) or a component thereof, optionally beta-2-microglobulin 032M); and/or (b) an endogenous T cell receptor (TCR) or a component thereof, optionally T cell receptor alpha constant (TRAC), in the stimulated cells; and (2) introducing a heterologous polynucleotide encoding a recombinant receptor into the stimulated cells, optionally into a locus of a gene encoding for TRAC;

wherein the knocking out in (1) and the introducing in (2) can be carried out concurrently or successively in either order;

(v) incubating the engineered T cell composition for up to 96 hours, optionally at a temperature of at or about 37°±2° C., optionally wherein the incubating further comprises cultivating the cells under conditions to promote proliferation or expansion; and (vi) repeating steps (i) through (v) for a plurality of different donors to produce a plurality of donor engineered T cell compositions, wherein each donor engineered T cell composition is generated from cells from an individual donor of the plurality of different donors; and (vii) combining the plurality of donor engineered T cell compositions from the plurality of different donors.

57. The method of any of embodiments 2-56, wherein the frequency of CD57+ T cells in the CD57 depleted T cell population and/or the pooled CD57 depleted T cell population is less than about or about 35%, 30%, 20%, 10%, 5%, 1% or 0.1% of the frequency of CD57+ T cells in the donor sample.

58. The method of any of embodiments 2-57, wherein the frequency of CD57+ T cells in the CD57 depleted T cell population and/or the pooled CD57 depleted T cell population is less than about 20% of the frequency of CD57+ T cells in the donor sample.

59. The method of any of embodiments 2-58, wherein the CD57 depleted T cell population and/or the pooled CD57 depleted T cell population comprises less than about 20% CD57+ T cells, less than about 15% CD57+ T cells, less than about 10% CD57+ T cells, less than about 5% CD57+ T cells, less than about 1% CD57+ T cells, or less than about 0.1% CD57+ T cells.

60. The method of any of embodiments 2-59, wherein the CD57 depleted T cell population and/or the pooled CD57 depleted T cell population comprises less than about 5% CD57+ T cells.

61. The method of any of embodiments 2-60, wherein the CD57 depleted T cell population and/or the pooled CD57 depleted T cell population is free or is essentially free of CD57+ T cells.

62. The method of any of embodiments 2-61, wherein the cells of the CD57 depleted T cell population and/or the pooled CD57 depleted T cell population exhibit a lower coefficient of variation (CV) in expression of one or more molecules, compared to that of the cells of the donor sample.

63. The method of embodiment 62, wherein the one or more molecules comprises a marker of naïve T cells, optionally CD27, Ki67, CD25, CD28, CCR7, and/or CD45RA.

64. The method of any of embodiments 2-63, wherein the cells of the CD57 depleted T cell population and/or the pooled CD57 depleted T cell population exhibit a lower CV in expression of CD27 and/or Ki67, compared to that of the cells of the donor sample.

65. A method of preparing a T cell composition from a donor pool, the method comprising:

(a) obtaining a plurality of engineered T cell compositions from a plurality of different donors, each engineered T cell composition comprising T cells enriched for T cells surface positive for CD27 (CD27+) from a donor sample from an individual donor of the plurality of different donors, wherein the T cells comprise T cells genetically engineered with a recombinant receptor; and (b) combining the plurality of engineered T cell compositions to produce a donor pooled engineered T cell composition.

66. The method of embodiment 65, wherein each of the plurality of engineered T cell compositions is generated by a process comprising:

(i) selecting T cells enriched for T cells surface positive for CD27 (CD27+) from a donor sample from the individual donor, thereby generating a CD27 enriched T cell population; and (ii) introducing a heterologous nucleic acid encoding the recombinant receptor into the CD27 enriched T cell population, thereby generating the engineered T cell composition.

67. The method of embodiment 66, wherein prior to step (ii) the method comprises stimulating the CD27 enriched T cell population under conditions to activate T cells in the population.
68. The method of embodiment 66 or embodiment 67, wherein the method further comprises (iii) incubating the cells of the engineered T cell composition for up to 96 hours subsequent to the introducing, optionally at a temperature of at or about 37°±2° C.
69. The method of embodiment 68, wherein the incubating is carried out under conditions in which the cells are not expanded or not substantially expanded compared to the number of cells at the initiation of the incubating.
70. The method of embodiment 66 or embodiment 67, wherein the method further comprises (iii) cultivating the cells of the engineered T cell composition under conditions for expansion of T cells in the composition.
71. The method of any of embodiments 66-70, wherein the selecting T cells enriched for T cells surface positive for CD27 (CD27+) comprises:
(1) selecting one of (a) cells surface positive for a T cell marker(s) and (b) cells surface positive for CD27 (CD27+) from the donor sample from the individual donor, thereby generating an enriched population of cells; and
(2) selecting, from the enriched population of cells, for the other of (a) cells surface positive for the T cell marker (s) and (b) CD27+ cells, thereby generating the CD27 enriched T cell population.
72. The method of embodiment 71, wherein the T cell marker(s) is CD3.
73. The method of embodiment 71 or embodiment 72, wherein the T cell marker(s) is CD4.
74. The method of any of embodiments 71-73, wherein the T cell marker(s) is CD8.
75. The method of any of embodiments 71-74, wherein the T cell surface marker(s) is CD4 and CD8.
76. The method of any of embodiments 65-75, wherein the method further comprises knocking out expression of (i) an endogenous major histocompatibility complex (MEW) or a component thereof, optionally beta-2-microglobulin (β2M); and/or (ii) an endogenous T cell receptor (TCR) or a component thereof, optionally T cell receptor alpha constant (TRAC), in the T cells of the CD27 enriched population and/or the engineered T cell composition prior to or during one or more of the steps of the method.
77. The method of any of embodiments 65-76, wherein T cells of the plurality of engineered T cell compositions are knocked out (KO) for expression of (i) an endogenous major histocompatibility complex (MHC) or a component thereof, optionally beta-2-microglobulin (132M) and/or (ii) an endogenous T cell receptor (TCR) or a component thereof, optionally T cell receptor alpha constant (TRAC).
78. A method of preparing a T cell composition from a donor pool, the method comprising:
(a) selecting T cells enriched for T cells surface positive for CD27 (CD27+) from a donor sample from an individual donor, thereby generating a CD27 enriched T cell population;
(b) genetically engineering the CD27 enriched T cell population, thereby producing an engineered T cell composition, the genetic engineering comprising:
(1) knocking out expression of (i) an endogenous major histocompatibility complex (MHC) or a component thereof, optionally beta-2-microglobulin (β2M); and/or (ii) an endogenous T cell receptor (TCR) or a component thereof, optionally T cell receptor alpha constant (TRAC), in cells of the CD27 enriched T cell population; and
(2) introducing a heterologous nucleic acid encoding a recombinant receptor into the cells of the CD27 enriched T cell population, optionally wherein the heterologous nucleic acid is inserted into a locus of a gene encoding for the endogenous MHC or a component thereof and/or the endogenous TCR or a component thereof;
wherein the knocking out in (1) and the introducing in (2) are carried out concurrently or successively in either order;
(c) repeating steps (a) and (b) for a plurality of different donors to produce a plurality of donor engineered T cell compositions, wherein each donor engineered T cell composition is generated from cells from an individual donor of the plurality of different donors; and
(d) combining the plurality of donor engineered T cell compositions from the plurality of different individual donors to produce a donor pooled engineered T cell composition.
79. The method of any of embodiments 65-78, wherein the method is repeated for each of the individual donors of the plurality of different donors.
80. The method of any of embodiments 65-79, wherein each of the plurality of engineered T cell compositions has been cryopreserved and thawed prior to the combining.
81. The method of any of embodiments 65-80, wherein the CD27 enriched T cell population comprises greater than or greater than at or about 75% CD3+/CD27+ cells, greater than at or about 80% CD3+/CD27+ cells, greater than at or about 85% CD3+/CD27+ cells, greater than at or about 90% CD3+/CD27+ cells, or greater than at or about 95% CD3+/CD27+ cells.
82. The method of any of embodiments 65-81, wherein each of the plurality of engineered T cell compositions independently comprises greater than or greater than at or about 40% CD27+ recombinant receptor+ cells, greater than at or about 45% CD27+/recombinant receptor+ cells, greater than at or about 50% CD27+/recombinant receptor+ cells, greater than at or about 55% CD27+/recombinant receptor+ cells, greater than at or about 55% CD27+/recombinant receptor+ cells, greater than at or about 60% CD27+/recombinant receptor+ cells, greater than at or about 65% CD27+/recombinant receptor+ cells or greater than at or about 70% CD27+/recombinant receptor+ cells, optionally greater than or greater than at or about 40% CD3+/CD27+/recombinant receptor+ cells, greater than at or about 45% CD3+/CD27+/recombinant receptor+ cells, greater than at or about 50% CD3+/CD27+/recombinant receptor+ cells, greater than at or about 55% CD3+/CD27+/recombinant receptor+ cells, greater than at or about 55% CD3+/CD27+/recombinant receptor+ cells, greater than at or about 60% CD3+/CD27+/recombinant receptor+ cells, greater than at or about 65% CD3+/CD27+/recombinant receptor+ cells or greater than at or about 70% CD3+/CD27+/recombinant receptor+ cells.
83. The method of any of embodiments 65-82, wherein each of the plurality of engineered T cell compositions comprise CD4+ and CD8+ T cells.
84. The method of embodiment 83, wherein each of the plurality of engineered T cell compositions comprises a ratio of CD4+ to CD8+ T cells of between at or about 1:5 and at or about 5:1.
85. The method of embodiment 83 or embodiment 84, wherein each of the plurality of engineered T cell compositions comprises a ratio of CD4+ to CD8+ T cells of between at or about 1:3 and at or about 3:1.

86. The method of any of embodiments 76-85, further comprising, prior to the knocking out, stimulating the CD27 enriched T cell population under conditions to activate T cells in the population.

87. The method of any of embodiments 76-86, wherein the knocking out and the introducing the heterologous nucleic acid are carried out concurrently.

88. The method of any of embodiments 76-86, wherein the knocking out and the introducing the heterologous nucleic acid are carried out successively in either order.

89. A method of preparing a T cell composition from a donor pool, the method comprising:

(i) selecting for one of (a) cells surface positive for a T cell marker(s) and (b) cells surface positive for CD27 (CD27+) from a donor sample from a plurality of different donors, thereby generating an enriched population of cells; and (ii) selecting, from the enriched population of cells, the other of (a) cells surface positive for the T cell marker (s) and (b) CD27+-cells, thereby generating a CD27 enriched T cell population.

90. The method of embodiment 89, wherein the donor sample is a pooled sample comprising cells from the plurality of different donors, whereby the method produces a pooled CD27 enriched T cell population.

91. The method of embodiment 89, wherein the donor sample is a sample from an individual donor, and steps (a) and (b) are repeated separately for each donor sample from the plurality of different donors, whereby the method produces a CD27 enriched T cell population for each individual donor.

92. The method of embodiment 91, wherein the method further comprises combining the CD27 enriched T cell populations for each individual donor together to produce a pooled CD27 enriched T cell population.

93. The method of any of embodiments 89-92, wherein the T cell marker(s) is CD3.

94. The method of any of embodiments 89-93, wherein the T cell marker(s) is CD4.

95. The method of any of embodiments 89-94, wherein the T cell marker(s) is CD8.

96. The method of any of embodiments 89-95, wherein the T cell surface marker(s) is CD4 and CD8.

97. A method of preparing a T cell composition from a donor pool, the method comprising selecting for T cells that are surface positive for CD27 (CD27+) from a donor sample, wherein the donor sample is a pooled cell population enriched for human T cells from a plurality of different donors, thereby generating a pooled CD27 enriched T cell population.

98. A method of preparing a T cell composition from a donor pool, the method comprising:

(a) selecting for T cells that are surface positive for CD27 (CD27+) from a donor sample, wherein the donor sample is enriched for human T cells from an individual donor, thereby generating a CD27 enriched T cell population;

(b) repeating step (a) for a plurality of different individual donors; and (c) combining each of the CD27 enriched T cell populations from each of the individual donors, thereby generating a pooled CD27 enriched T cell population.

99. A method of preparing a T cell composition from a donor pool, the method comprising selecting for T cells from a donor sample, wherein the donor sample is a pooled cell population enriched for human T cells that are surface positive for CD27 (CD27+) from a plurality of different donors, thereby generating a pooled CD27 enriched T cell population.

100. A method of preparing a T cell composition from a donor pool, the method comprising:

(a) selecting for T cells from a donor sample, wherein the sample is enriched for human T cells that are surface positive for CD27 (CD27+) from an individual donor, thereby generating a CD27 enriched T cell population;

(b) repeating step (a) for a plurality of different donors; and (c) combining each of the CD27 enriched T cell populations from each of the individual donors, thereby generating a pooled CD27 enriched T cell population.

101. The method of any of embodiments 97-100, wherein the donor sample enriched for human T cells is obtained by selecting for CD3+ T cells.

102. The method of any of embodiments 97-101, wherein the donor sample enriched for human T cells is obtained by selecting for CD4+ T cells and/or CD8+ T cells.

103. The method of any of embodiments 97-102, wherein the donor sample enriched for human T cells comprises greater than at or about 85% CD3+ T cells.

104. The method of any of embodiments 97-103, wherein the donor sample enriched for human T cells comprises greater than at or about 90% CD3+ T cells.

105. The method of any of embodiments 97-104, wherein the donor sample enriched for human T cells comprises greater than at or about 95% CD3+ T cells.

106. The method of any of embodiments 97-105, wherein the donor sample enriched for human T cells comprises CD4+ and CD8+ T cells.

107. The method of embodiment 106, wherein the donor sample enriched for human T cells comprises a ratio of CD4+ to CD8+ T cells of between at or about 1:5 and at or about 5:1.

108. The method of embodiment 106 or embodiment 107, wherein the donor sample enriched for human T cells comprises a ratio of CD4+ to CD8+ T cells of between at or about 1:3 and at or about 3:1.

109. The method of any of embodiments 97-108, wherein the selecting for T cells comprises selecting for CD3+ T cells.

110. The method of any of embodiments 97-109, wherein the selecting for T cells comprises selecting for CD4+ and/or CD8+ T cells.

111. The method of any of embodiments 97-110, wherein the donor sample enriched for CD27+ human T cells is obtained by selecting for CD27+ T cells.

112. The method of any of embodiments 91-96, 98, and 100-111, wherein:

(a) cells of the CD27 enriched T cell population are knocked out (KO) for expression of (i) an endogenous major histocompatibility complex (MHC) or a component thereof, optionally beta-2-microglobulin (β2M); and/or (ii) an endogenous T cell receptor (TCR) or a component thereof, optionally T cell receptor alpha constant (TRAC); and/or (b) the method further comprises knocking out expression of (i) an endogenous major histocompatibility complex (MHC) or a component thereof, optionally beta-2-microglobulin (β2M); and/or (ii) an endogenous T cell receptor (TCR) or a component thereof, optionally TRAC, in cells of the CD27 enriched T cell population.

113. The method of any of embodiments 90 and 92-111, wherein:

(a) cells of the pooled CD27 enriched T cell population are knocked out (KO) for expression of (i) an endogenous major histocompatibility complex (MHC) or a component thereof, optionally beta-2-microglobulin (β2M); and/or (ii) an endogenous T cell receptor (TCR) or a component thereof, optionally T cell receptor alpha constant (TRAC); and/or (b) the method further comprises knocking out expression of (i) an endogenous major histocompatibility complex (MHC) or a component thereof, optionally beta-2-microglobulin (β2M); and/or (ii) an endogenous T cell receptor (TCR) or a component thereof, optionally T cell receptor alpha constant (TRAC), in cells of the pooled CD27 enriched T cell population.

114. The method of any of embodiments 91-96, 98, and 100-112, wherein:

(a) a heterologous polynucleotide encoding a recombinant receptor is introduced into cells of the CD27 enriched T cell population; and/or (b) the method further comprises introducing into cells of the CD27 enriched T cell population a heterologous polynucleotide encoding a recombinant receptor, the method thereby generating an engineered T cell composition.

115. The method of any of embodiments 90, 92-111, and 113, wherein:

(a) a heterologous polynucleotide encoding a recombinant receptor is introduced into cells of the pooled CD27 enriched T cell population; and/or (b) the method further comprises introducing into cells of the pooled CD27 enriched T cell population a heterologous polynucleotide encoding a recombinant receptor, the method thereby generating an engineered T cell composition.

116. The method of embodiment 114 or embodiment 115, wherein the knocking out and the introducing the heterologous nucleic acid are carried out concurrently.

117. The method of embodient 114 or embodiment 115, wherein the knocking out and the introducing the heterologous nucleic acid are carried out successively in either order.

118. The method of any of embodiments 112-117, wherein the combining is performed prior to the cells of the CD27 enriched T cell population being knocked out and/or introduced to the heterologous nucleic acid.

119. The method of any of embodiments 112-117, wherein the combining is performed after the cells of the CD27 enriched T cell are knocked out and/or introduced to the heterologous nucleic acid.

120. A method of preparing a T cell composition from a donor pool, the method comprising:

(i) selecting for one of (a) cells surface positive for CD3 (CD3+), or surface positive for CD4 (CD4+) and/or CD8 (CD8+) and (b) cells surface positive for CD27 (CD27+) from a donor sample, thereby generating an enriched population of cells;

(ii) selecting, from the enriched population of cells, the other of (a) CD3+, or CD4+ and/or CD8+ cells and (b) CD27+ cells, thereby generating a CD27 enriched T cell population;

(iii) stimulating cells of the CD27 enriched T cell population under conditions to activate T cells in the population;

(iv) genetically engineering the stimulated cells, thereby producing an engineered T cell composition, the genetic engineering comprising:

(1) knocking out expression of (a) an endogenous major histocompatibility complex (MHC) or a component thereof, optionally beta-2-microglobulin 032M); and/or (b) an endogenous T cell receptor (TCR) or a component thereof, optionally T cell receptor alpha constant (TRAC), in the stimulated cells; and (2) introducing a heterologous polynucleotide encoding a recombinant receptor into the stimulated cells, optionally into a locus of a gene encoding for TRAC;

wherein the knocking out in (1) and the introducing in (2) can be carried out concurrently or successively in either order;

(v) incubating the engineered T cell composition for up to 96 hours, optionally at a temperature of at or about 37°±2° C., optionally wherein the incubating further comprises cultivating the cells under conditions to promote proliferation or expansion; and (vi) repeating steps (i) through (v) for a plurality of different donors to produce a plurality of donor engineered T cell compositions, wherein each donor engineered T cell composition is generated from cells from an individual donor of the plurality of different donors; and (vii) combining the plurality of donor engineered T cell compositions from the plurality of different donors.

121. The method of any of embodiments 66-120, wherein the frequency of CD27− T cells in the CD27 enriched T cell population and/or the pooled CD27 enriched T cell population is less than about or about 35%, 30%, 20%, 10%, 5%, 1% or 0.1% of the frequency of CD27− T cells in the donor sample.

122. The method of any of embodiments 66-121, wherein the frequency of CD27− T cells in the CD27 enriched T cell population and/or the pooled CD27 enriched T cell population is less than about 20% of the frequency of CD27− T cells in the donor sample.

123. The method of any of embodiments 66-122, wherein the CD27 enriched T cell population and/or the pooled CD27 enriched T cell population comprises less than about 20% CD27− T cells, less than about 15% CD27− T cells, less than about 10% CD27− T cells, less than about 5% CD27− T cells, less than about 1% CD27− T cells, or less than about 0.1% CD27-T cells.

124. The method of any of embodiments 66-123, wherein the CD27 enriched T cell population and/or the pooled CD27 enriched T cell population comprises less than about 5% CD27− T cells.

125. The method of any of embodiments 66-124, wherein the CD27 enriched T cell population and/or the pooled CD27 enriched T cell population is free or is essentially free of CD27− T cells.

126. The method of any of embodiments 66-125, wherein the cells of the CD27 enriched T cell population and/or the pooled CD27 enriched T cell population exhibit a lower coefficient of variation (CV) in expression of one or more molecules, compared to that of the cells of the donor sample.

127. The method of embodiment 126, wherein the one or more molecules comprises a marker of naïve T cells, optionally CD57, Ki67, CD25, CD28, CCR7, and/or CD45RA.

128. The method of any of embodiments 66-127, wherein the cells of the CD27 enriched T cell population and/or the pooled CD27 enriched T cell population exhibit a lower CV in expression of CD57 and/or Ki67, compared to that of the cells of the donor sample.

129. The method of any of embodiments 1-128, wherein the donor sample comprises an apheresis product or a leukapheresis product.

130. The method of any of embodiments 1-129, wherein the plurality of different donors comprises at least about or about 2 different donors, at least about or about 5 different donors, at least about or about 10 different donors, at least about or about 15 different donors, at least about or about 20 different donors, at least about or about 25 different donors, at least about or about 50 different donors, or at least about or about 100 different donors, or any range between any of the foregoing.

131. The method of any of embodiments 1-130, wherein the plurality of different donors comprises between 5 and 25 donors.

132. The method of any of embodiments 1-131, wherein the plurality of different donors comprises two or more donors that are less than 100% human leukocyte antigen (HLA) matched, less than about 90% HLA matched, less than about 80% HLA matched, less than about 70% HLA matched, less than about 60% HLA matched, or less than about 50% HLA matched.

133. The method of any of embodiments 1-132, wherein the plurality of different donors comprises at least two donors that are not 100% HLA matched.

134. The method of any of embodiments 1-24, 27-34, 36-88, 91-98, and 100-133, wherein the individual donor is healthy or is not suspected of having a disease or condition at the time the donor sample is obtained from the individual donor.

135. The method of any of embodiments 1-24, 27-34, 36-88, 91-98, and 100-133, wherein the individual donor has a disease or condition at the time the donor sample is obtained from the individual donor.

136. The method of any of embodiments 1-135, wherein the plurality of different donors comprises at least one donor that is healthy or is not suspected of having a disease or condition at the time the donor sample is obtained from the at least one donor.

137. The method of any of embodiments 1-136, wherein the plurality of different donors comprises at least one donor that has a disease or condition at the time the donor sample is obtained from the at least one donor.

138. The method of any of embodiments 1-136, wherein each of the donors of the plurality of different donors is healthy or is not suspected of having a disease or condition at the time the donor sample is obtained from each of the different donors.

139. The method of any of embodiments 2-64 and 66-138, wherein the selecting comprises immunoaffinity-based selection.

140. The method of embodiment 139, wherein the immununoaffinity-based selection comprises contacting T cells with an antibody capable of specifically binding to CD57 and recovering cells not bound to the antibody, thereby effecting negative selection.

141. The method of embodiment 139 or embodiment 140, wherein the immununoaffinity-based selection comprises contacting T cells with an antibody capable of specifically binding to CD3, CD4, or CD8, and recovering cells bound to the antibody, thereby effecting positive selection.

142. The method of embodiment 140 or embodiment 141, wherein the antibody is immobilized on a solid surface, optionally wherein the solid surface is a magnetic particle.

143. The method of embodiment 140 or embodiment 141, wherein the antibody is immobilized on or attached to an affinity chromatography matrix.

144. The method of embodiment 143, wherein the antibody further comprises one or more binding partners capable of forming a reversible bond with a binding reagent immobilized on the matrix, whereby the antibody is reversibly bound to said chromatography matrix during said contacting.

145. The method of embodiment 144, wherein the binding reagent is a streptavidin mutein that reversibly binds to the binding partner.

146. The method of any of embodiments 2-64 and 129-145, wherein:

(a) the method further comprises cryopreserving the CD57 depleted T cell population and/or the pooled CD57 depleted T cell population, optionally wherein the CD57 depleted T cell population and/or the pooled CD57 depleted T cell population is thawed before the subsequent step; and/or (b) the CD57 depleted T cell population and/or the pooled CD57 depleted T cell population is formulated with a cryoprotectant, and optionally is thawed prior to the subsequent step.

147. The method of any of embodiments 66-145, wherein:

(a) the method further comprises cryopreserving the CD27 enriched T cell population and/or the pooled CD27 enriched T cell population, optionally wherein the CD27 enriched T cell population and/or the pooled CD27 enriched T cell population is thawed before the subsequent step; and/or (b) the CD27 enriched T cell population and/or the pooled CD27 enriched T cell population is formulated with a cryoprotectant, and optionally is thawed prior to the subsequent step.

148. The method of any of embodiments 12-24, 48-64, 76-88, and 112-147, wherein the endogenous MHC or a component thereof comprises MHC class I protein or a component thereof.

149. The method of any of embodiments 12-24, 48-64, 76-88, and 112-148, wherein the endogenous MHC or a component thereof comprises β2M.

150. The method of embodiment any of embodiments 12-24, 48-64, 76-88, and 112-149, wherein the endogenous TCR or a component thereof comprises TRAC and/or T cell receptor beta constant (TRBC).

151. The method of any of embodiments 12-24, 48-64, 76-88, and 112-150, wherein the endogenous TCR or a component thereof comprises TRAC.

152. The method of any of embodiments 12-24, 48-64, 76-88, and 112-151, wherein the knocking out comprises introducing into the cells an agent that reduces expression of a product encoded by, or disrupts, the endogenous β2M gene and/or the endogenous TRAC gene.

153. The method of any of embodiments 12-24, 48-64, 76-88, and 112-152, wherein the knocking out comprises introducing into the cells an agent that reduces expression and/or activity of β2M and/or TRAC.

154. The method of any of embodiments 12-24, 48-64, 76-88, and 112-153, wherein the knocking out comprises introducing into the cells a zinc finger nuclease (ZFN), a TAL-effector nuclease (TALEN), or a CRISPR-Cas9 combination.

155. A method of genetically engineering a CD57 depleted T cell population, further comprising introducing a heterologous polynucleotide encoding a recombinant receptor into the cells of any of embodiments 24-49, 57-64, and 129-146, thereby generating an engineered T cell composition.

156. The method of any of embodiments 2-24, 50-64, and 121-155, wherein the genetic engineering is performed prior to one or more of the steps of selecting the cells.

157. The method of any of embodiments 1-24, 50-64, and 121-156, wherein the engineered T cells exhibit a lower CV in the expression of the recombinant receptor, compared to a method in which the engineered T cells are not depleted of CD57+ T cells.

158. A method of genetically engineering a CD27 enriched T cell population, further comprising introducing a heterologous polynucleotide encoding a recombinant receptor into the cells of any of embodiments 88-113, 121-145, and 147, thereby generating an engineered T cell composition.

159. The method of any of embodiments 66-88 and 114-158, wherein the genetic engineering is performed prior to one or more of the steps of selecting the cells.

160. The method of any of embodiments 65-88, 114-154, 158, and 159, wherein the engineered T cells exhibit a lower CV in the expression of the recombinant receptor, compared to a method in which the engineered T cells are not depleted of CD27− T cells.

161. The method of any of embodiments 2-24, 50-64, and 66-160, wherein the introducing comprises targeted insertion of the heterologous polynucleotide with a viral vector comprising the heterologous polynucleotide.

162. The method of embodiment 161, wherein the viral vector is an adeno-associated viral (AAV) vector.

163. The method of any of embodiments 2-24, 50-64, and 66-162, wherein the heterologous polynucleotide is inserted into the genetic locus of the β2M gene or the TRAC gene.

164. The method of any of embodiments 2-24 and 50-95, wherein the heterologous polynucleotide is inserted into the genetic locus of the TRAC gene.

165. The method of any of embodiments 2, 3, 6-24, 50-55, 57-64, 66, 67, 70-88, 114-119, and 121-164, further comprising incubating the engineered cells for up to 96 hours subsequent to the introducing, optionally at a temperature of at or about 37°±2° C.

166. The method of embodiment 56, 120, or 165, wherein the incubating is carried out for up to 72 hours subsequent to the introducing.

167. The method of embodiment 56, 120, or 165, wherein the incubating is carried out for up to 48 hours subsequent to the introducing.

168. The method of embodiment 56, 120, or 165, wherein the incubating is carried out for up to 24 hours subsequent to the introducing.

169. The method of any of embodiments 4-13, 56-64, 121-154, and 165-168, wherein the incubating results in integration of the viral vector into the genome of the CD57 depleted T cells and/or the pooled CD57 depleted T cells.

170. The method of any of embodiments 68-77, 120-154, and 165-169, wherein the incubating results in integration of the viral vector into the genome of the CD27 enriched T cells and/or the pooled CD27 enriched T cells.

171. The method of any of embodiments 14-24, 50-56, 57-64, 68-88, and 121-171, further comprising cultivating the cells under conditions to promote proliferation or expansion.

172. The method of embodiment 171, wherein the cultivating is carried out in the presence of one or more recombinant cytokines, optionally comprising one or more of IL-2, IL-7 and IL-15.

173. The method of any of embodiments 2-172, further comprising harvesting or collecting cells produced by the method.

174. The method of embodiment 173, wherein the harvesting or collecting is carried out at a time when the a threshold number of cells have been produced by the method.

175. The method of embodiment 174, wherein the time to reach the threshold number is less time than a method that does not include depleting CD57+ T cells.

176. The method of any of embodiments 173-175, wherein:

(a) the method further comprises formulating the harvested or collected cells for cryopreservation in the presence of a cryoprotectant; and/or (b) the harvested or collected cells are formulated in the presence of a pharmaceutically acceptable excipient.

177. The method of any of embodiments 1-24, 50-88, and 114-176, wherein the recombinant receptor is capable of binding to a target antigen that is associated with, specific to and/or expressed on a cell or tissue of a disease or a condition.

178. The method of embodiment 177, wherein the disease or the condition is an infectious disease or disorder, an autoimmune disease, an inflammatory disease or a tumor or a cancer.

179. The method of embodiment 177 or embodiment 178, wherein the target antigen is a tumor antigen.

180. The method of any of embodiments 177-179, wherein the target antigen is selected from among αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrin receptor A2 (EPHa2), estrogen receptor, Fc receptor like 5 (FCRLS; also known as Fc receptor homolog 5 or FCRHS), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPRCSD), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha(IL-22Rα), IL-13 receptor alpha 2 (IL-13Rα2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen or an antigen associated with a universal tag and/or biotinylated molecules and/or molecules expressed by HIV, HCV, HBV or other pathogens.

181. The method of any of embodiments 1-24, 50-88, and 114-180, wherein the recombinant receptor is or comprises a functional non-TCR antigen receptor or a TCR or antigen-binding fragment thereof.

182. The method of any of embodiments 1-24, 50-88, and 114-181, wherein the recombinant receptor is a chimeric antigen receptor (CAR).

183. The method of any of embodiments 1-24, 50-88, and 114-182, wherein the recombinant receptor comprises an extracellular domain comprising an antigen-binding domain, a spacer and/or a hinge region, a transmembrane domain and an intracellular signaling domain comprising a costimulatory signaling region.

184. The method of embodiment 183, wherein the extracellular domain comprises an antigen-binding domain comprising an scFv.

185. The method of embodiment 183 or 184, wherein the intracellular signaling domain is or comprises a primary signaling domain, a signaling domain that is capable of inducing a primary activation signal in a T cell, a signaling domain of a T cell receptor (TCR) component and/or a signaling domain comprising an immunoreceptor tyrosine-based activation motif (ITAM).

186. The method of any of embodiments 183-185, wherein the intracellular signaling domain is or comprises an intracellular signaling domain of a CD3 chain, optionally a CD3-zeta (CD3ζ) chain or a signaling portion thereof.

187. The method of any of embodiments 183-186, wherein the costimulatory signaling region comprises an intracellular signaling domain of a CD28, a 4-1BB or an ICOS or a signaling portion thereof.

188. The method of any of embodiments 1-187, wherein the T cells produced by the method are for administration to at least one subject having a disease or condition, optionally wherein at least a portion of the T cells are allogeneic to the at least one subject.

189. The method of embodiment 188, wherein the disease or condition is an infectious disease or disorder, an autoimmune disease, an inflammatory disease or a tumor or a cancer.

190. The method of embodiment 188 or embodiment 189, wherein the disease or condition is a tumor or a cancer.

191. The method of any of embodiments 188-190, wherein the T cells produced by the method are formulated for administration as one or more unit doses and the cells comprise at least about 100 unit doses of the cells, at least about 200 unit doses of the cells, at least about 300 unit doses of the cells, at least about 400 unit doses of the cells, at least about 500 unit doses of the cells, at least about 600 unit doses, at least about or at least about 1,000 unit doses of the cells.

192. The method of any of embodiments 188-191, wherein the T cells produced by the method are for administration to at least 2 subjects, at least 5 subjects, at least 10 subjects, at least 25 subjects, at least 50 subjects, at least 100 subjects, at least 200 subjects, at least 500 subjects, or at least 1,000 subjects.

193. The method of any of embodiment 191 or embodiment 192, wherein the unit dose comprises between about 10 and 75 million cells per milliliter number of cells/concentration of cells.

194. The method of any of embodiments 191-193, wherein the unit dose comprises between and between about $5.0\times10^6$ and $1\times10^9$, $5.0\times10^6$ and $5.0\times10^8$, $5.0\times10^6$ and $2.5\times10^8$, $5.0\times10^6$ and $1.0\times10^8$, $5.0\times10^6$ and $7.5\times10^7$, $1\times10^7$ and $1\times10^9$, $1\times10^7$ and $5.0\times10^8$, $1\times10^7$ and $2.5\times10^8$, $1\times10^7$ and $1.0\times10^8$, $1.0\times10^7$ and $7.5\times10^7$, $1.0\times10^7$ and $5.0\times10^7$, $1.0\times10^7$ and $2.5\times10^7$, $1.5\times10^7$ and $2.25\times10^7$, $2.5\times10^7$ and $1.0\times10^9$, or $2.5\times10^7$ and $7.5\times10^8$ cells, optionally between and between about $5.0\times10^6$ and $1\times10^9$, $1.0\times10^7$ and $1.0\times10^9$, $2.5\times10^7$ and $1\times10^9$, $5.0\times10^7$ and $1.0\times10^9$, $7.5\times10^7$ and $1.0\times10^9$, $1.0\times10^8$ and $1.0\times10^9$, $5.0\times10^7$ and $7.5\times10^8$, $5\times10^7$ and $5.0\times10^8$, $5\times10^7$ and $2.5\times10^8$, $5.0\times10^7$ and $1.0\times10^8$, or $5.0\times10^7$ and $7.5\times10^7$ recombinant receptor-expressing cells.

195. The method of any of embodiments 2, 4-21, 23-55, 57-64, and 121-194, further comprising stimulating cells of the CD57 depleted T cell population and/or the pooled CD57 depleted T cell population under conditions to activate T cells in the population, thereby generating a stimulated T cell population.

197. The method of any of embodiments 66, 68-85, 87-119, and 121-194, further comprising stimulating cells of the CD27 enriched T cell population and/or the pooled CD27 enriched T cell population under conditions to activate T cells in the population, thereby generating a stimulated T cell population.

198. The method of embodiment 3-13, 22-24, 56-64, 67-77, 86-88, and 120-196, wherein the stimulating conditions comprise the presence of a stimulatory reagent, said stimulatory reagent being capable of activating one or more intracellular signaling domains of one or more components of a TCR complex and one or more intracellular signaling domains of one or more costimulatory molecules.

199. The method of any of embodiment 198, wherein the stimulatory reagent comprises (i) a primary agent that specifically binds to a member of a TCR complex, optionally that specifically binds to CD3 and (ii) a secondary agent that specifically binds to a T cell costimulatory molecule, optionally wherein the costimulatory molecule is selected from CD28, CD137 (4-1-BB), OX40 or ICOS.

200. The method of embodiment 199, wherein at least one of the primary and secondary agents comprises an antibody or an antigen-binding fragment thereof.

201. The method of embodiment 199 or embodiment 200, wherein the primary agent is an anti-CD3 antibody or an antigen-binding fragment thereof and the secondary agent is an anti-CD28 antibody or an antigen-binding fragment thereof.

202. The method of embodiment 200 or embodiment 201, wherein the antigen binding fragment is a monovalent antibody fragment selected from the group consisting of a Fab fragment, an Fv fragment, and a single-chain Fv fragment (scFv).

203. The method of any of embodiments 199-202, wherein the primary agent and the secondary agent are reversibly bound on the surface of an oligomeric particle reagent comprising a plurality of streptavidin molecules or streptavidin mutein molecules.

204. The method of embodiment 203, wherein the streptavidin molecules or the streptavidin mutein molecules bind to or are capable of binding to biotin, avidin, a biotin analog or a biotin mutein, an avidin analog or an avidin mutein and/or a biologically active fragment thereof.

205. The method of any of embodiments 199-204, wherein the primary agent comprises an anti-CD3 Fab and the secondary agent comprises an anti-CD28 Fab.
206. The method of any of embodiments 198-205, further comprising separating the stimulatory reagent from the T cells, said separating comprising contacting the T cells with a substance, said substance being capable of reversing bonds between the primary and secondary agents and the oligomeric particle reagent.
207. The method of embodiment 206, wherein the substance is a free binding partner and/or is a competition agent.
208. The method of embodiment 206 or embodiment 207, wherein the substance is or comprises a streptavidin-binding peptide, biotin or a biologically active fragment thereof, or a biotin analog or biologically active fragment thereof.
209. The method of embodiment 208, wherein the substance is or comprises biotin or a biotin analog.
210. The method of any of embodiments 195-209, wherein the stimulating conditions comprise the presence of one or more recombinant cytokines.
211. The method of any of embodiments 195-210, wherein the stimulating conditions comprise the presence of one or more of recombinant IL-2, IL-7 and IL-15.
212. The method of any of embodiments 195-244, wherein:
(a) the method further comprises formulating the stimulated T cells for cryopreservation in the presence of a cryoprotectant; and/or
(b) the stimulated T cells are formulated in the presence of a cryoprotectant.
213. A composition comprising the T cell population produced by the method of any of embodiments 1-212.
214. A composition comprising T cells from a donor pool, comprising a population of T cells enriched in human T cells that are surface negative for CD57 (CD57−), wherein the population of cells is from a plurality of different donors, and wherein the plurality of different donors comprises at least two donors that are not 100% human leukocyte antigen (HLA) matched.
215. The composition of embodiment 214, wherein the T cells comprise T cells genetically engineered with a recombinant receptor.
216. The composition of any of embodiments 213-215, wherein the frequency of CD57+ T cells in the composition is less than about or about 35%, 30%, 20%, 10%, 5%, 1% or 0.1% of the total T cells in the composition.
217. The composition of any of embodiments 213-216, wherein the frequency of CD57+ T cells in the composition is less than about 20% of the total T cells in the composition.
218. The composition of any of embodiments 213-217, wherein the composition comprises less than about 20% CD57+ T cells, less than about 15% CD57+ T cells, less than about 10% CD57+ T cells, less than about 5% CD57+ T cells, less than about 1% CD57+ T cells, or less than about 0.1% CD57+ T cells.
219. The composition of any of embodiments 213-218, wherein the composition comprises less than about 5% CD57+ T cells.
220. The composition of any of embodiments 213-219, wherein the composition is free or is essentially free of CD57+ T cells.
221. The composition of any of embodiments 213-220, wherein the composition comprises greater than or greater than at or about 75% CD3+/CD57− cells.
222. The composition of any of embodiments 213-220, wherein the composition comprises greater than at or about 80% CD3+/CD57− cells.
223. The composition of any of embodiments 213-220, wherein the composition comprises greater than at or about 85% CD3+/CD57− cells.
224. The composition of any of embodiments 213-220, wherein the composition comprises greater than at or about 90% CD3+/CD57− cells.
225. The composition of any of embodiments 213-220, wherein the composition comprises greater than at or about 95% CD3+/CD57− cells.
226. The composition of any of embodiments 213-225, wherein the composition comprises greater than or greater than at or about 40% CD3+/CD57−/recombinant receptor+ cells.
227. The composition of any of embodiments 213-225, wherein the composition comprises greater than at or about 45% CD3+/CD57−/recombinant receptor+ cells.
228. The composition of any of embodiments 213-225, wherein the composition comprises greater than at or about 50% CD3+/CD57−/recombinant receptor+ cells.
229. The composition of any of embodiments 213-225, wherein the composition comprises greater than at or about 55% CD3+/CD57−/recombinant receptor+ cells.
230. The composition of any of embodiments 213-225, wherein the composition comprises greater than at or about 55% CD3+/CD57−/recombinant receptor+ cells.
231. The composition of any of embodiment 213-225, wherein the composition comprises greater than at or about 60% CD3+/CD57−/recombinant receptor+ cells.
232. The composition of any of embodiments 213-225, wherein the composition comprises greater than at or about 65% CD3+/CD57−/recombinant receptor+ cells.
233. The composition of any of embodiments 213-225, wherein the composition comprises greater than at or about 70% CD3+/CD57−/recombinant receptor+ cells.
234. The composition of any of embodiments 213-233, wherein each of the plurality of engineered T cell compositions comprise CD4+ and CD8+ T cells.
235. The composition of embodiment 234, wherein each of the plurality of engineered T cell compositions comprises a ratio of CD4+ to CD8+ T cells of between at or about 1:5 and at or about 5:1.
236. The composition of embodiment 234, wherein each of the plurality of engineered T cell compositions comprises a ratio of CD4+ to CD8+ T cells of between at or about 1:3 and at or about 3:1.
237. The composition of any of embodiments 213-236, wherein the cells of the composition exhibit a lower coefficient of variation (CV) in expression of one or more molecules, compared to that of a population of cells not enriched in human T cells that are surface negative for CD57 (CD57−).
238. The composition of embodiment 237, wherein the coefficient of variation (CV) of the cells of the composition is at least 20% lower, at least 40% lower, at least 60% lower, or at least 80% lower than that of a population of cells not enriched in human T cells that are surface negative for CD57 (CD57−).
239. The composition of embodiment 237 or embodiment 238, wherein the one or more molecules comprises a marker of naïve T cells, optionally CD27, Ki67, CD25, CD28, CCR7, and/or CD45RA.
240. The composition of any of embodiments 213-239, wherein the cells of the composition exhibit a lower coefficient of variation (CV) in expression of CD27 and/or Ki67, compared to that of a population of cells not enriched in human T cells that are surface negative for CD57 (CD57−).

241. The composition of embodiment 240, wherein the coefficient of variation (CV) of the cells of the composition is at least 20% lower, at least 40% lower, at least 60% lower, or at least 80% lower than that of a population of cells not enriched in human T cells that are surface negative for CD57 (CD57−).

242. A composition comprising T cells from a donor pool, comprising a population of T cells enriched in human T cells that are surface positive for CD27 (CD27+), wherein the population of cells is from a plurality of different donors, and wherein the plurality of different donors comprises at least two donors that are not 100% human leukocyte antigen (HLA) matched.

243. The composition of embodiment 242, wherein the T cells comprise T cells genetically engineered with a recombinant receptor.

244. The composition of any of embodiments 213, 242, and 243, wherein the frequency of CD27− T cells in the composition is less than about or about 35%, 30%, 20%, 10%, 5%, 1% or 0.1% of the total T cells in the composition.

245. The composition of any of embodiments 213 and 242-244, wherein the frequency of CD27− T cells in the composition is less than about 20% of the total T cells in the composition.

246. The composition of any of embodiments 213 and 242-245, wherein the composition comprises less than about 20% CD27− T cells, less than about 15% CD27− T cells, less than about 10% CD27− T cells, less than about 5% CD27− T cells, less than about 1% CD27− T cells, or less than about 0.1% CD27− T cells.

247. The composition of any of embodiments 213 and 242-246, wherein the composition comprises less than about 5% CD27− T cells.

248. The composition of any of embodiments 213 and 242-247, wherein the composition is free or is essentially free of CD27− T cells.

249. The composition of any of embodiments 213 and 242-248, wherein the composition comprises greater than or greater than at or about 75% CD3+/CD27+ cells.

250. The composition of any of embodiments 213 and 242-248, wherein the composition comprises greater than at or about 80% CD3+/CD27+ cells.

251. The composition of any of embodiments 213 and 242-248, wherein the composition comprises greater than at or about 85% CD3+/CD27+ cells.

252. The composition of any of embodiments 213 and 242-248, wherein the composition comprises greater than at or about 90% CD3+/CD27+ cells.

253. The composition of any of embodiments 213 and 242-248, wherein the composition comprises greater than at or about 95% CD3+/CD27+ cells.

254. The composition of any of embodiments 213 and 242-253, wherein the composition comprises greater than or greater than at or about 40% CD3+/CD27+/recombinant receptor+ cells.

255. The composition of any of embodiments 213 and 242-253, wherein the composition comprises greater than at or about 45% CD3+/CD27+/recombinant receptor+ cells.

256. The composition of any of embodiments 213 and 242-253, wherein the composition comprises greater than at or about 50% CD3+/CD27+/recombinant receptor+ cells.

257. The composition of any of embodiments 213 and 242-253, wherein the composition comprises greater than at or about 55% CD3+/CD27+/recombinant receptor+ cells.

258. The composition of any of embodiments 213 and 242-253, wherein the composition comprises greater than at or about 55% CD3+/CD27+/recombinant receptor+ cells.

259. The composition of any of embodiment 213 and 242-253, wherein the composition comprises greater than at or about 60% CD3+/CD27+/recombinant receptor+ cells.

260. The composition of any of embodiments 213 and 242-253, wherein the composition comprises greater than at or about 65% CD3+/CD27+/recombinant receptor+ cells.

261. The composition of any of embodiments 213 and 242-253, wherein the composition comprises greater than at or about 70% CD3+/CD27+/recombinant receptor+ cells.

262. The composition of any of embodiments 213 and 242-261, wherein each of the plurality of engineered T cell compositions comprise CD4+ and CD8+ T cells.

263. The composition of embodiment 262, wherein each of the plurality of engineered T cell compositions comprises a ratio of CD4+ to CD8+ T cells of between at or about 1:5 and at or about 5:1.

264. The composition of embodiment 262, wherein each of the plurality of engineered T cell compositions comprises a ratio of CD4+ to CD8+ T cells of between at or about 1:3 and at or about 3:1.

265. The composition of any of embodiments 213 and 242-264, wherein the cells of the composition exhibit a lower coefficient of variation (CV) in expression of one or more molecules, compared to that of a population of cells not enriched in human T cells that are surface positive for CD27 (CD27+).

266. The composition of embodiment 265, wherein the coefficient of variation (CV) of the cells of the composition is at least 20% lower, at least 40% lower, at least 60% lower, or at least 80% lower than that of a population of cells not enriched in human T cells that are surface positive for CD27 (CD27+).

267. The composition of embodiment 265 or embodiment 266, wherein the one or more molecules comprises a marker of naïve T cells, optionally Ki67, CD25, CD28, CCR7, and/or CD45RA.

268. The composition of any of embodiments 213 and 242-267, wherein the cells of the composition exhibit a lower coefficient of variation (CV) in expression of Ki67, compared to that of a population of cells not enriched in human T cells that are surface positive for CD27 (CD27+).

269. The composition of embodiment 268, wherein the coefficient of variation (CV) of the cells of the composition is at least 20% lower, at least 40% lower, at least 60% lower, or at least 80% lower than that of a population of cells not enriched in human T cells that are surface positive for CD27 (CD27+).

270. The composition of any of embodiments 214-269, wherein the plurality of different donors comprises at least about or about 2 different donors, at least about or about 5 different donors, at least about or about 10 different donors, at least about or about 15 different donors, at least about or about 20 different donors, at least about or about 25 different donors, at least about or about 50 different donors, or at least about or about 100 different donors.

271. The composition of any of embodiments 214-270, wherein the plurality of different donors comprises fewer than or fewer than about 25 donors.

272. The composition of any of embodiments 214-271, wherein the plurality of different donors comprises two or more donors that are less than 100% human leukocyte antigen (HLA) matched, less than about 90% HLA matched, less than about 80% HLA matched, less than about 70% HLA matched, less than about 60% HLA matched, or less than about 50% HLA matched.

273. The composition of any of embodiments 214-272, wherein the plurality of different donors comprises at least two donors that are not 100% HLA matched.

274. The composition of any of embodiments 214-273, wherein the plurality of different donors comprises at least one donor that is healthy or is not suspected of having a disease or condition at the time the cells are obtained from the at least one donor.

275. The composition of any of embodiments 214-274, wherein the plurality of different donors comprises at least one donor that has a disease or condition at the time the cells are obtained from the at least one donor.

276. The composition of any of embodiments 214-274, wherein each of the donors of the plurality of different donors is healthy or is not suspected of having a disease or condition at the time the cells are obtained from each of the different donors.

277. The composition of any of embodiments 214-276, wherein the T cells comprise T cells knocked out for expression of (i) an endogenous major histocompatibility complex (MHC) or a component thereof, optionally beta-2-microglobulin (β2M); and/or (ii) an endogenous T cell receptor (TCR) or a component thereof, optionally T cell receptor alpha constant (TRAC).

278. The composition of embodiment 277, wherein the endogenous MHC is comprises MHC class I protein or a component thereof.

279. The composition of embodiment 277 or embodiment 278, wherein the endogenous MHC comprises beta-2-microglobulin (β2M).

280. The composition of any of embodiments 277-279, wherein the endogenous TCR or a component thereof comprises T cell receptor alpha constant (TRAC) and/or T cell receptor beta constant (TRBC).

281. The composition of any of embodiments 277-280, wherein the endogenous TCR or a component thereof comprises T-cell receptor alpha constant (TRAC).

282. The composition of any of embodiments 277-281, wherein the heterologous polynucleotide is inserted into the genetic locus of the β2M gene or the TRAC gene.

283. The composition of any of embodiments 277-282, wherein the heterologous polynucleotide is inserted into the genetic locus of the TRAC gene.

284. The composition of any of embodiments 213-283, wherein the composition comprises a cryprotectant.

285. The composition of any of embodiments 213-284, wherein the composition comprises a pharmaceutically acceptable excipient.

286. The composition of any of embodiments 214-241 and 243-285, wherein the recombinant receptor is capable of binding to a target antigen that is associated with, specific to and/or expressed on a cell or tissue of a disease or a condition.

287. The composition of embodiment 286, wherein the disease or the condition is an infectious disease or disorder, an autoimmune disease, an inflammatory disease or a tumor or a cancer.

288. The composition of embodiment 286 or embodiment 287, wherein the target antigen is a tumor antigen.

289. The composition of any of embodiments 286-288, wherein the target antigen is selected from among αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrin receptor A2 (EPHa2), estrogen receptor, Fc receptor like 5 (FCRLS; also known as Fc receptor homolog 5 or FCRHS), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha(IL-22Rα), IL-13 receptor alpha 2 (IL-13Rα2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen or an antigen associated with a universal tag and/or biotinylated molecules and/or molecules expressed by HW, HCV, HBV or other pathogens.

290. The composition of any of embodiments 214-241 and 243-289, wherein the recombinant receptor is or comprises a functional non-TCR antigen receptor or a TCR or antigen-binding fragment thereof.

291. The composition of any of embodiments 214-241 and 243-290, wherein the recombinant receptor is a chimeric antigen receptor (CAR).

292. The composition of any of embodiments 214-241 and 243-291, wherein the recombinant receptor comprises an extracellular domain comprising an antigen-binding domain, a spacer and/or a hinge region, a transmembrane domain and an intracellular signaling domain comprising a costimulatory signaling region.

293. The composition of embodiment 292, wherein the extracellular domain comprises an antigen-binding domain comprising an scFv.

294. The composition of embodiment 292 or embodiment 293, wherein the intracellular signaling domain is or comprises a primary signaling domain, a signaling domain that is capable of inducing a primary activation signal in a T cell, a signaling domain of a T cell receptor (TCR) component and/or a signaling domain comprising an immunoreceptor tyrosine-based activation motif (ITAM).

295 The composition of any of embodiments 292-294, wherein the intracellular signaling domain is or comprises an intracellular signaling domain of a CD3 chain, optionally a CD3-zeta (CD3ζ) chain or a signaling portion thereof.

296. The composition of any of embodiments 292-295, wherein the costimulatory signaling region comprises an intracellular signaling domain of a CD28, a 4-1BB or an ICOS or a signaling portion thereof.

297. The composition of any of embodiments 212-296, for treatment of a subject having a disease or condition.

298. The composition of embodiment 297, wherein the disease or condition is a cancer or a tumor.

299. The composition of any of embodiments 212-298, wherein the cells of the composition are formulated for administration as one or more unit doses and the cells comprise at least about 100 unit doses of the cells, at least about 200 unit doses of the cells, at least about 300 unit doses of the cells, at least about 400 unit doses of the cells, at least about 500 unit doses of the cells, at least about 600 unit doses, at least about or at least about 1,000 unit doses of the cells.

300. The composition of any of embodiments 212-299, wherein the cells of the composition are for administration to at least 2 subjects, at least 5 subjects, at least 10 subjects, at least 25 subjects, at least 50 subjects, at least 100 subjects, at least 200 subjects, at least 500 subjects, or at least 1,000 subjects.

301. The composition of embodiment 299 or embodiment 300, wherein the unit dose comprises between about 10 and 75 million cells per milliliter.

302. The composition of any of embodiments 299-301, wherein the unit dose comprises between and between about $5.0\times10^6$ and $1\times10^9$, $5.0\times10^6$ and $5.0\times10^8$, $5.0\times10^6$ and $2.5\times10^8$, $5.0\times10^6$ and $1.0\times10^8$, $5.0\times10^6$ and $7.5\times10^7$, $1\times10^7$ and $1\times10^9$, $1\times10^7$ and $5.0\times10^8$, $1\times10^7$ and $2.5\times10^8$, $1\times10^7$ and $1.0\times10^8$, $1.0\times10^7$ and $7.5\times10^7$, $1.0\times10^7$ and $5.0\times10^7$, $1.0\times10^7$ and $2.5\times10^7$, $1.5\times10^7$ and $2.25\times10^7$, $2.5\times10^7$ and $1.0\times10^9$, or $2.5\times10^7$ and $7.5\times10^8$ cells, optionally between and between about $5.0\times10^6$ and $1\times10^9$, $1.0\times10^7$ and $1.0\times10^9$, $2.5\times10^7$ and $1\times10^9$, $5.0\times10^7$ and $1.0\times10^9$, $7.5\times10^7$ and $1.0\times10^9$, $1.0\times10^8$ and $1.0\times10^9$, $5.0\times10^7$ and $7.5\times10^8$, $5\times10^7$ and $5.0\times10^8$, $5\times10^7$ and $2.5\times10^8$, $5.0\times10^7$ and $1.0\times10^8$, or $5.0\times10^7$ and $7.5\times10^7$ recombinant receptor-expressing cells.

303. A container comprising the composition of any of embodiments 212-302.

304. The container of embodiment 303, wherein the container is a bag, optionally a freezing bag, and the container is filled with the composition to a volume that is:

between or between about 15 mL and 150 mL, 20 mL and 100 mL, 20 mL and 80 mL, 20 mL and 60 mL, 20 mL and 40 mL, 40 mL and 100 mL, 40 mL and 80 mL, 40 mL and 60 mL, 60 mL and 100 mL, 60 mL and 80 mL or 80 mL and 100 mL, each inclusive; or at least or at least about 15 mL, at least or at least about 20 mL, at least or at least about 30 mL, at least or at least about 40 mL, at least or at least about 50 mL, at least or at least about 60 mL, at least or at least about 70 mL, at least or at least about 80 mL or at least or at least about 90 mL; and/or no more than 100 mL.

305. The container of embodiment 303 or embodiment 304, wherein the container is filled with the composition to a surface area to volume ratio that:

is between or between about 0.1 $cm^{-1}$ and 100 $cm^{-1}$; 1 $cm^{-1}$ and 50 $cm^{-1}$, 1 $cm^{-1}$ and 20 $cm^{-1}$, 1 $cm^{-1}$ and 10 $cm^{-1}$, 1 $cm^{-1}$ and 7 $cm^{-1}$, 1 $cm^{-1}$ and 6 $cm^{-1}$, 1 $cm^{-1}$ and 3 $cm^{-1}$, 1 $cm^{-1}$ and 2 $cm^{-1}$, 2 $cm^{-1}$ and 20 $cm^{-1}$, 2 $cm^{-1}$ and 10 $cm^{-1}$, 2 $cm^{-1}$ and 7 $cm^{-1}$, 2 $cm^{-1}$ and 6 $cm^{-1}$, 2 $cm^{-1}$ and 3 $cm^{-1}$, 3 $cm^{-1}$ and 20 $cm^{-1}$, 3 $cm^{-1}$ and 10 $cm^{-1}$, 3 $cm^{-1}$ and 7 $cm^{-1}$, 3 $cm^{-1}$ and 6 $cm^{-1}$, 6 $cm^{-1}$ and 20 $cm^{-1}$, 6 $cm^{-1}$ and 10 $cm^{-1}$, 6 $cm^{-1}$ and 7 $cm^{-1}$, 7 $cm^{-1}$ and 20 $cm^{-1}$, 7 $cm^{-1}$ and 10 $cm^{-1}$, or 7 $cm^{-1}$ and 20 $cm^{-1}$, each inclusive; or is, is about, or is at least 3 $cm^{-1}$, 4 $cm^{-1}$, 5 $cm^{-1}$, 6 $cm^{-1}$, 7 $cm^{-1}$, 10 $cm^{-1}$, 15 $cm^{-1}$, or 20 $cm^{-1}$.

306. A method of treatment, comprising administering the composition of any of embodiments 212-302 to a subject having or suspected of having a disease or a condition, wherein the T cells of the composition are not derived from the subject.

307. A method of treatment, comprising administering the composition of any of embodiments 212-302 to a subject having or suspected of having a disease or a condition, wherein at least a portion of the T cells of the composition are not derived from the subject.

308. The method of embodiment 306 or embodiment 307, wherein less than 100% of the T cells of the composition are HLA-identical to the T cells of the subject.

309. The method of any of embodiments 306-308, wherein the disease or condition is an infectious disease or disorder, an autoimmune disease, an inflammatory disease or a tumor or a cancer.

310. The method of any of embodiments 306-309, wherein the disease or condition is a cancer.

311. Use of the composition of any of embodiments 212-302 for manufacture of a medicament for treating a disease or disorder in a subject having or suspected of having a disease or a condition, wherein the T cells of the composition are not derived from the subject or at least a portion of the T cells are not derived from the subject.

312. The use of embodiment 311, wherein the disease or condition is an infectious disease or disorder, an autoimmune disease, an inflammatory disease or a tumor or a cancer.

313. The use of embodiment 311 or embodiment 312, wherein the disease or condition is a cancer or a tumor.

314. A composition of any of embodiments 112-302 for use in treating a disease or disorder in a subject having or suspected of having a disease or a condition, wherein the T cells of the composition are not derived from the subject or at least a portion of the T cells are not derived from the subject.

315. The composition for use of embodiment 314, wherein the disease or condition is an infectious disease or disorder, an autoimmune disease, an inflammatory disease or a tumor or a cancer.

316. The composition for use of embodiment 314 or embodiment 315, wherein the disease or condition is a cancer or a tumor.

IX. Examples

The following examples are included for illustrative purposes only and are not intended to limit the scope of the invention.

Example 1: Assessment of Variability in T Cell Expansion, Cell Viability and Cell Cycle Entry Among Cell Populations Derived from Different Donors During a Process for Engineering T Cells CD8+ T cells were obtained from seven different exemplary donors (Donors A-G) and were engineered to express a chimeric antigen receptor (CAR) by a manufacturing process involving stimulation, transduction with a lentiviral vector encoding the CAR construct and cultivation for expansion, or were subjected to a similar process for stimulation and cultivation. Cell expansion, cell viability, and cell cycle entry in the stimulated and cultivated cells were assessed.

To generate the engineered cell compositions, CD8+ cells were isolated from human donor leukapheresis samples by immunoaffinity-based enrichment and cryopreserved. The cryopreserved cell compositions were subsequently thawed and stimulated by incubating the cells under stimulatory conditions in the presence of anti-CD3/anti-CD28 antibody-conjugated paramagnetic beads and recombinant cytokines (e.g. IL-2, IL-7 and IL-15) for approximately 24 hours. Cells from four of the donors (Donors D-G) were then transduced with a viral preparation containing nucleic acid encoding a chimeric antigen receptor (CAR). After transduction, the cells were cultivated in the presence of recombinant cytokines (e.g. IL-2, IL-7 and IL-15) in an incubator at 37 degrees Celsius and media was replenished daily. Cells from three of the donors (Donors A-C) were not subjected to transduction and were cultivated in the presence of recombinant cytokines after stimulation.

Donor cells were monitored for total cell number for up to approximately 240 hours after the start of the stimulation, and fold expansion over time was determined. Viability was assessed and cells were stained for a marker indicative of cell division (Ki67) and analyzed by flow cytometry at 72 hours after the start of stimulation.

Figure 1D:
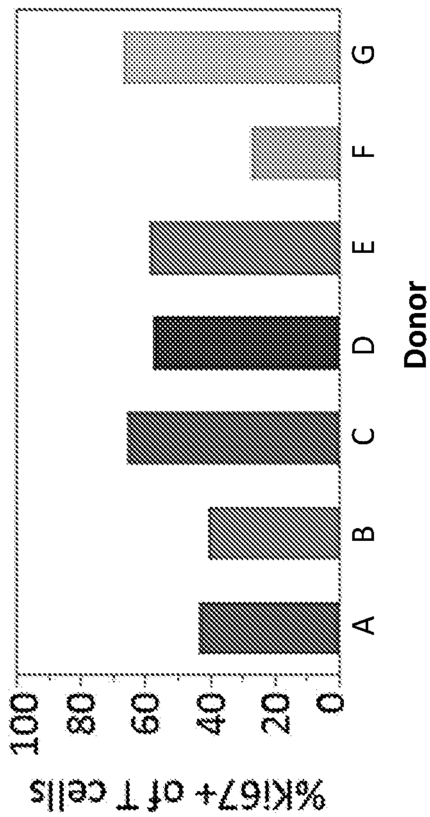

As shown in FIGS. 1A-1D, variability in T cell expansion (FIGS. 1A and 1B), cell viability (FIG. 1C) and Ki67 expression (marker associated with cell cycle entry; FIG. 1D) were observed among CD8+ T cells from different donors.

Example 2: Characterization of CD57+ and CD57− Populations Following Stimulation of Donor-Derived Cells During Cell Manufacturing The phenotypes of CD57+ and CD57− cells were characterized during an exemplary cell manufacturing process to engineer the cells to express a chimeric antigen receptor (CAR).

CD8+ and CD4+ T cells from three different exemplary donors (Donors A-C) were subjected to an exemplary process similar to as described in Example 1, but without transduction of the cells. Samples of the cells were collected immediately prior to the start of, and at various time points during stimulation, for up to approximately 216 hours after the start of the stimulation. The cells were stained for various markers, including markers associated with activation (CD25 and CD69), proliferative capacity (CD57), cell division (Ki67), and various surface markers associated with T cell differentiation phenotypes (e.g., naïve-like T cells, effector T ($T_{EFF}$) cells, memory T cells, central memory T cells ($T_{CM}$), effector memory T ($T_{EM}$) cells, effector memory RA T ($T_{EMRA}$) cells), for analysis by flow cytometry. Hierarchical clustering analysis was performed to assess the association between CD57 expression, Ki67 expression, and T cell differentiation phenotypes.

Figure 2A:
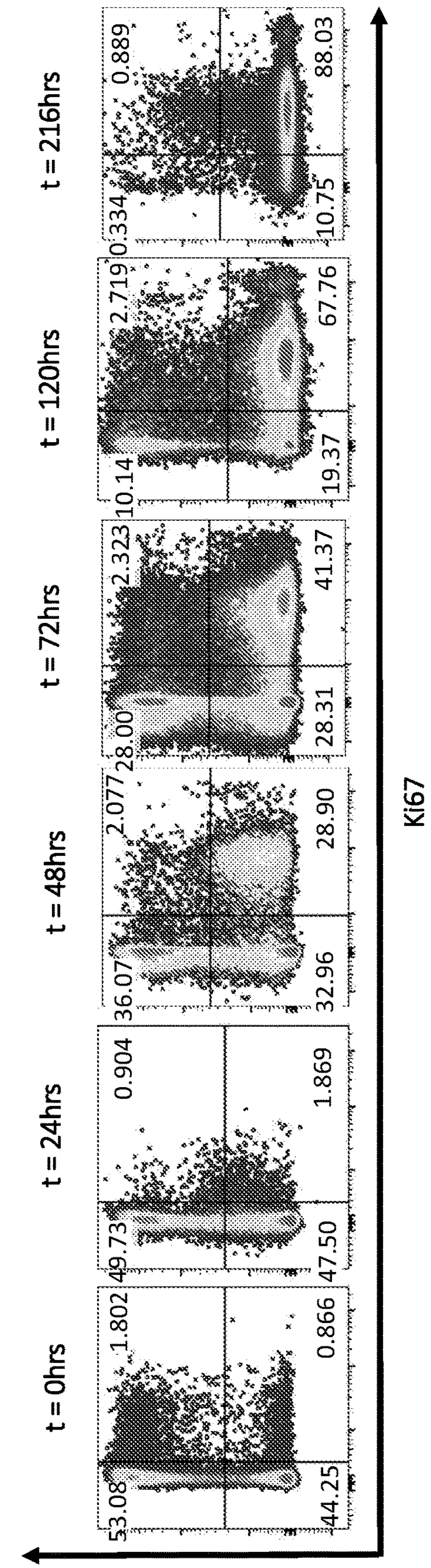
FIG. 2A shows a flow cytometry analysis for CD57 and Ki67 expression at various time points over approximately 216 hours after the start of stimulation in an exemplary process for primary human T cells.
Figure 2B:
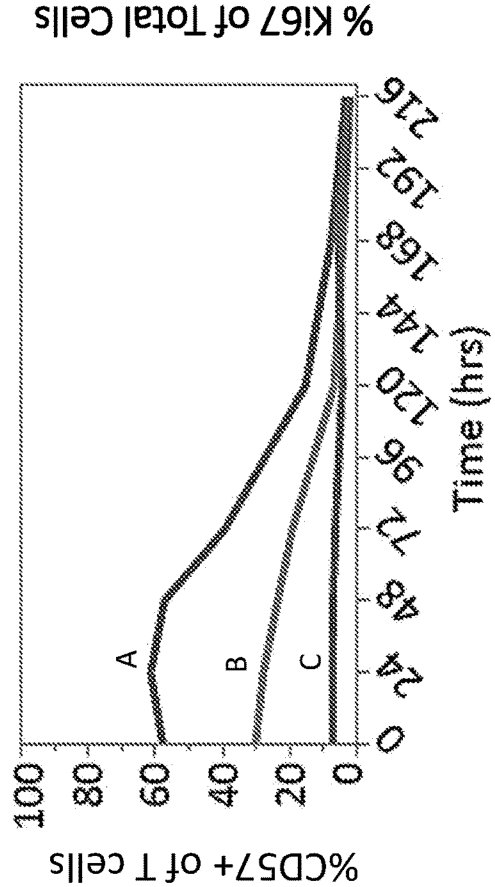
FIG. 2B shows the percentage of CD57+ cells in the cell population during stimulation and cultivation, in three different donors (Donors A-C).
Figure 2C:
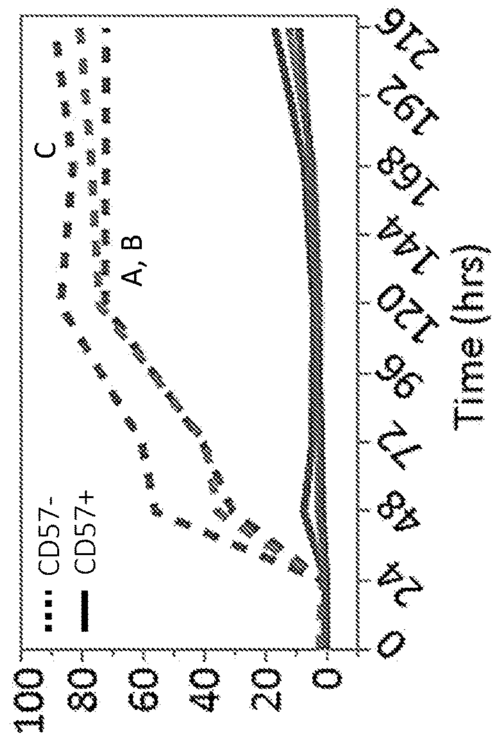
FIG. 2C shows the percentage of Ki67+ cells among CD57+ cells or CD57− cells in the cell population during stimulation and cultivation.
Figure 2D:
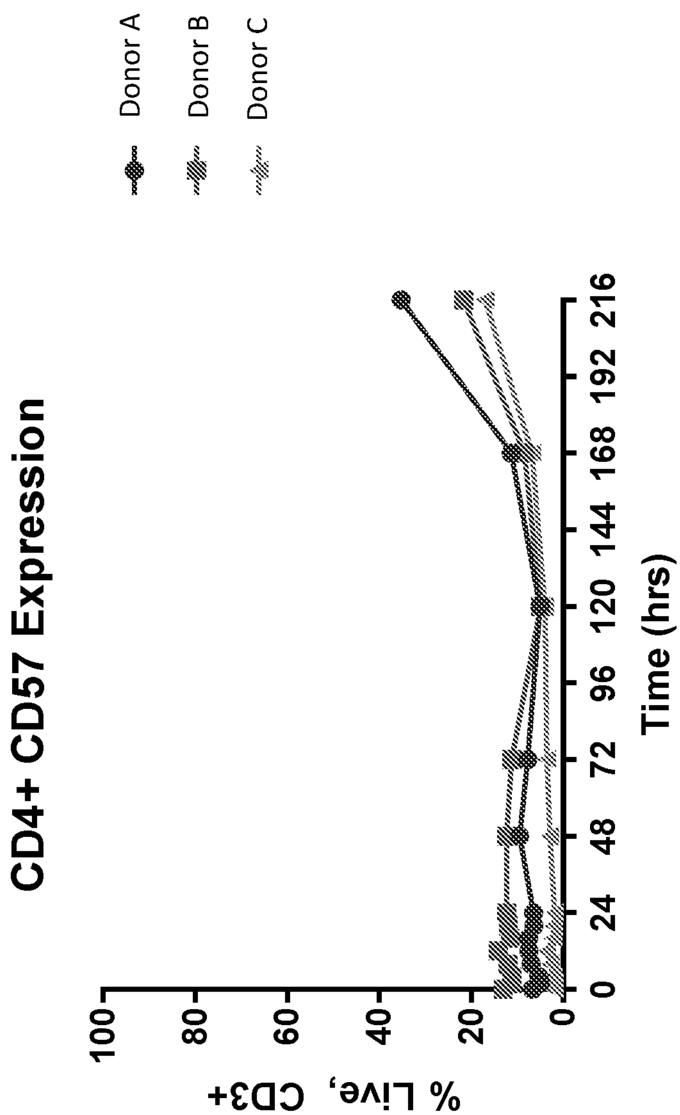
FIG. 2D shows the percentage of CD57+ cells in the CD4+ cell population during stimulation and cultivation, in three different donors (Donors A-C).

As shown in FIGS. 2A-2C, CD57+ T cells were present in the donor cell populations at the start of stimulation, and the percentage of CD57+ cells was reduced in the populations during stimulation and cultivation (see FIGS. 2A and 2B). The frequency of CD57+ T cells decreased approximately 48 hours after the start of stimulation, which coincided generally with T cell expansion and increased viability. Following stimulation, only a subset of CD8+ T cells entered the cell cycle, based on the expression of Ki67. Expression of Ki67 did not increase substantially among CD57+ cells following stimulation. In comparison, the percentage of Ki67+ cells increased substantially among CD57− cells (see FIGS. 2A and 2C). In contrast with the CD8+ cell compartment, among CD4+ cells, CD57+ cells were present at low levels at the start of stimulation, and the percentage of CD57+ cells increased toward the end of the stimulation and cultivation process (FIG. 2D). This results are consistent with an observation that the CD8+ cell compartment may be more homogenous than the CD4+ cell compartment.

Figure 2E:
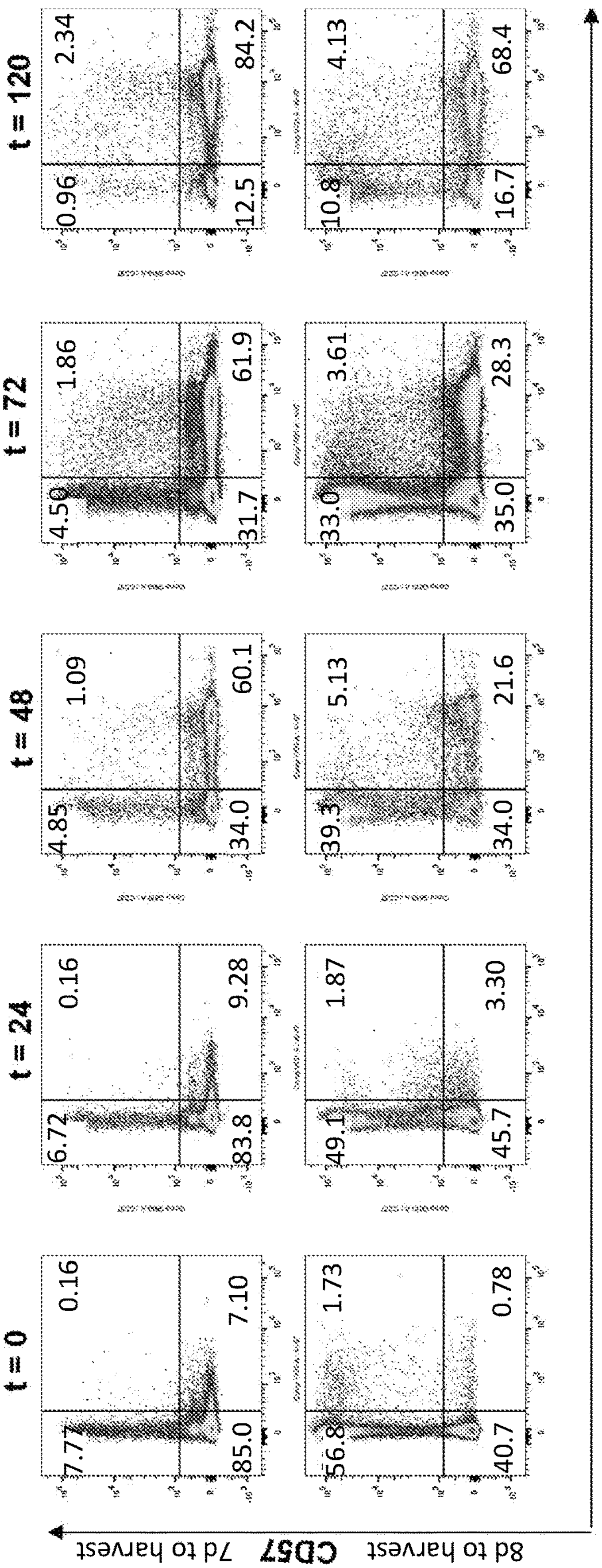
FIG. 2E shows CD57 and Ki67 expression on cells from donor cell compositions, over time, following stimulation. The cells of one donor cell composition required 8 days to reach harvest criterion ("8d to harvest"), while the cells of another donor cell composition required only 7 days to reach harvest criterion ("7d to harvest").
Figure 2F:
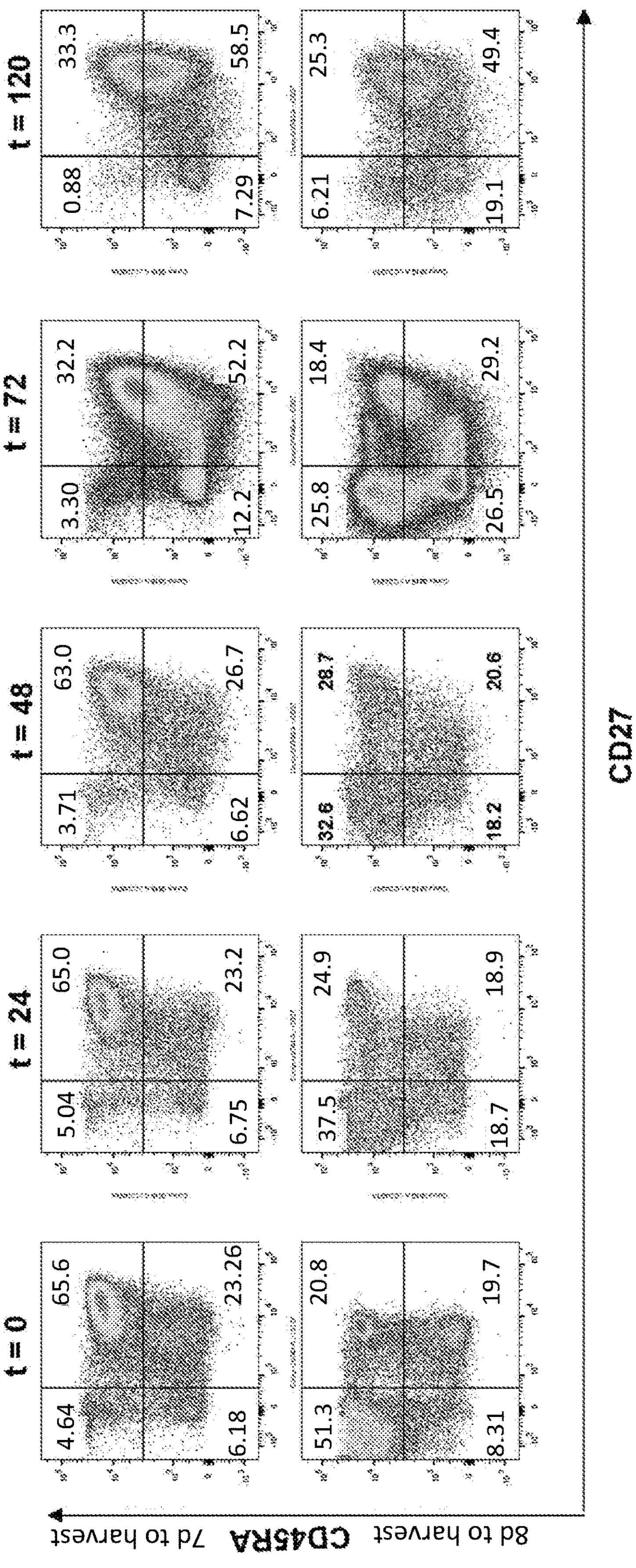
FIG. 2F shows CD45RA and CD27 expression on cells from the donor cell compositions described in FIG. 2E.

Notably, the donor-derived compositions exhibited variability in the time required to reach an exemplary threshold cell number for harvest (harvest criterion), which corresponded with variability in expression of various immunophenotype markers. One donor-derived composition required only 7 days of cultivation time to reach harvest criterion. By contrast, another donor-derived composition required 8 days of cultivation time to reach harvest criterion. Analysis of CD57, Ki67, CD45RA, and CD27 expression (as determined by flow cytometry) between the two donor compositions is shown in FIGS. 2E and 2F. Expression was analyzed beginning at time point t=0, which represented the time just prior to stimulation. As shown in FIG. 2E, at all assessed time points, substantially higher CD57 expression was observed in the donor cell composition that required 8 days to reach harvest criterion ("8d to harvest," shown by bottom row), compared to the donor cell composition that required 7 days to reach harvest criterion ("7d to harvest," shown by top row). As shown in FIG. 2F, at all time points assessed, cells from the composition requiring 7 days exhibited a higher frequency of CD27+ CD45RA+, compared to cells from the composition requiring 8 days. Cells from the composition requiring 8 days exhibited a substantially lower frequency of CD27+ cells at all assessed time points. These observations are consistent with a finding that cell compositions exhibiting a higher frequency of CD27+ cells in the starting material exhibit better expansion and a higher frequency of such cells at the end of the cultivation process.

Figure 3A:
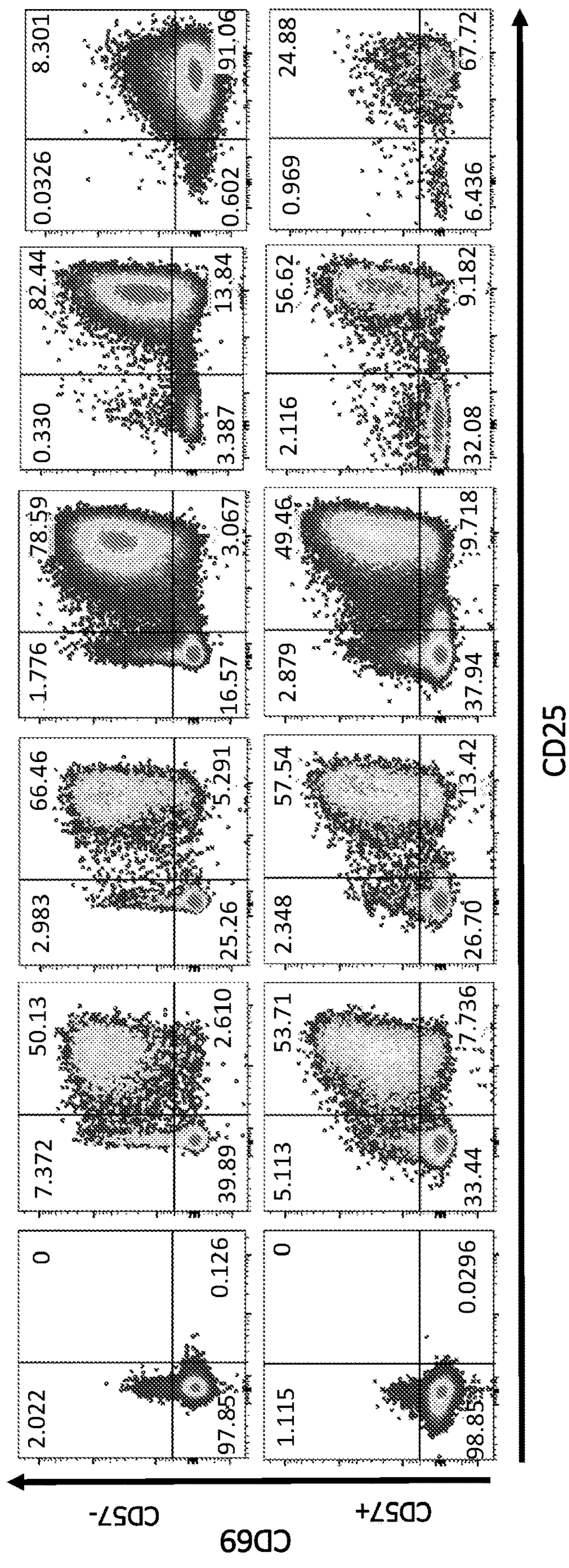
FIG. 3A shows a flow cytometry analysis for CD69 and CD25 expression (markers associated with activation) among CD57+ cells and CD57− cells in a cell population during stimulation and cultivation in an exemplary manufacturing process for primary human T cells.
Figure 3B:
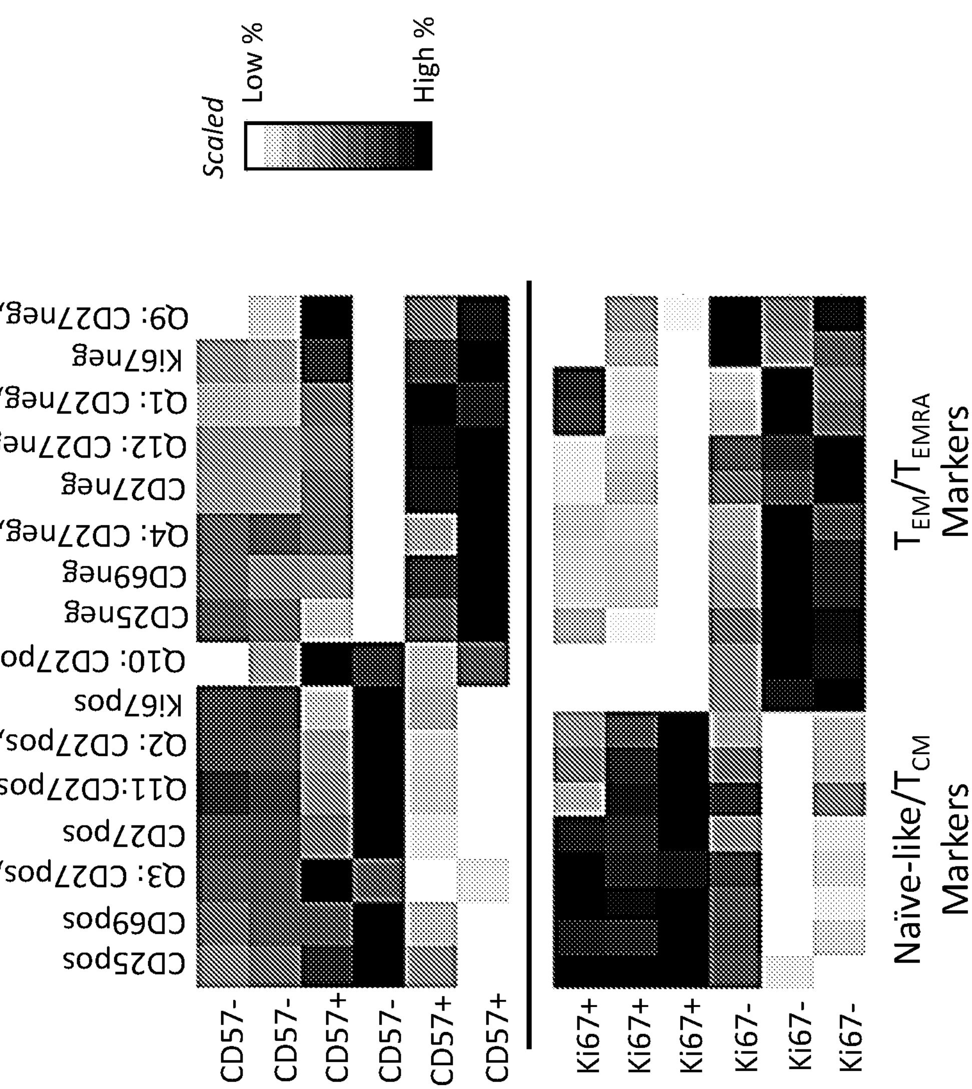
FIG. 3B shows hierarchical clustering analysis for expression of various surface markers associated with T cell differentiation phenotypes (e.g., naïve-like T cells, effector T ($T_{EFF}$) cells, memory T cells, central memory T cells ($T_{CM}$), effector memory T ($T_{EM}$) cells, effector memory RA T ($T_{EMRA}$) cells), and the expression of CD57 or Ki67. Each row represents a cell population from an individual donor, columns represent markers or combinations of markers that are associated with T cell differentiation phenotypes.

As shown in FIG. 3A, CD57+ T cells were observed to express markers indicative of activation (CD69 and CD25) following stimulation. CD57+ cells exhibited phenotypes associated with activation, and persisted throughout early process stages. Hierarchical clustering analysis showed that CD57+ and Ki67− T cells exhibited phenotypic features associated with more differentiated effector cell populations (FIG. 3B), compared to CD57− and Ki67+ cells (FIG. 3C). Ki67+ populations primarily included cells that were CD27+ CD28+, and Ki67− populations were enriched for CD57+ cells and corresponded with CD27−CD28− phenotypes.

The results were consistent with an observation that CD57+ T cells, while capable of being stimulated, exhibited phenotypes associated with more terminally differentiated cells and a reduced proliferative capacity. In some aspects, CD27+ T cells were observed to contribute to the majority of expanded cells during the CAR T cell manufacturing process. In comparison, CD57+ T cells did not expand, and contributed minimally to the cells in the final manufactured CART cell compositions. In some aspects, the presence of CD57+ cells in a cell population, which may exhibit reduced proliferative capacity, can contribute to variations and heterogeneity in cell populations undergoing the T cell manufacturing process.

Example 3: Frequency of CD57+ Cells in Donor Input Compositions and Effect on Cell Expansion, Viability, Stimulation Reagents and Cytokines Input compositions containing donor-matched CD57+ and CD57− cells were mixed at specific ratios and subjected to an exemplary manufacturing process. Cell expansion and viability of the cell compositions were assessed.

CD57+ CD8+ T cells and CD57−CD8+ T cells were isolated from a composition of CD8+ T cells obtained from a donor subject by positive selection of CD57+ cells by immunoaffinity-based enrichment. Purity of the isolated populations was determined by flow cytometry. To assess the impact of different frequencies of CD57+ T cells on the manufacturing process, input compositions containing the following frequency of CD57+ cells were generated by mixing the isolated CD57+ and CD57− populations, prior to stimulation: (1) 100% CD57+ cells; (2) 75% CD57+ cells; (3) 25% CD57+ cells; and (4) 0% CD57+ cells. The different titrated input compositions were subjected to an exemplary manufacturing process for CAR-expressing cells, similar to as described in Example 1, including stimulation by incubation with anti-CD3/anti-CD28 antibody-conjugated beads and recombinant cytokines, and transduction with a viral preparation containing nucleic acid encoding a CAR. Cells were monitored for total cell number and viability over time for up to approximately 288 hours after the start of the stimulation. Images of the wells of the cell culture plates were obtained at 48 hours after the start of stimulation, and assessed for cell clustering in the presence of the stimulation reagent. The concentration of IL-2 in the culture medium was assessed at 24 and 48 hours after the start of stimulation.

Figure 4A:
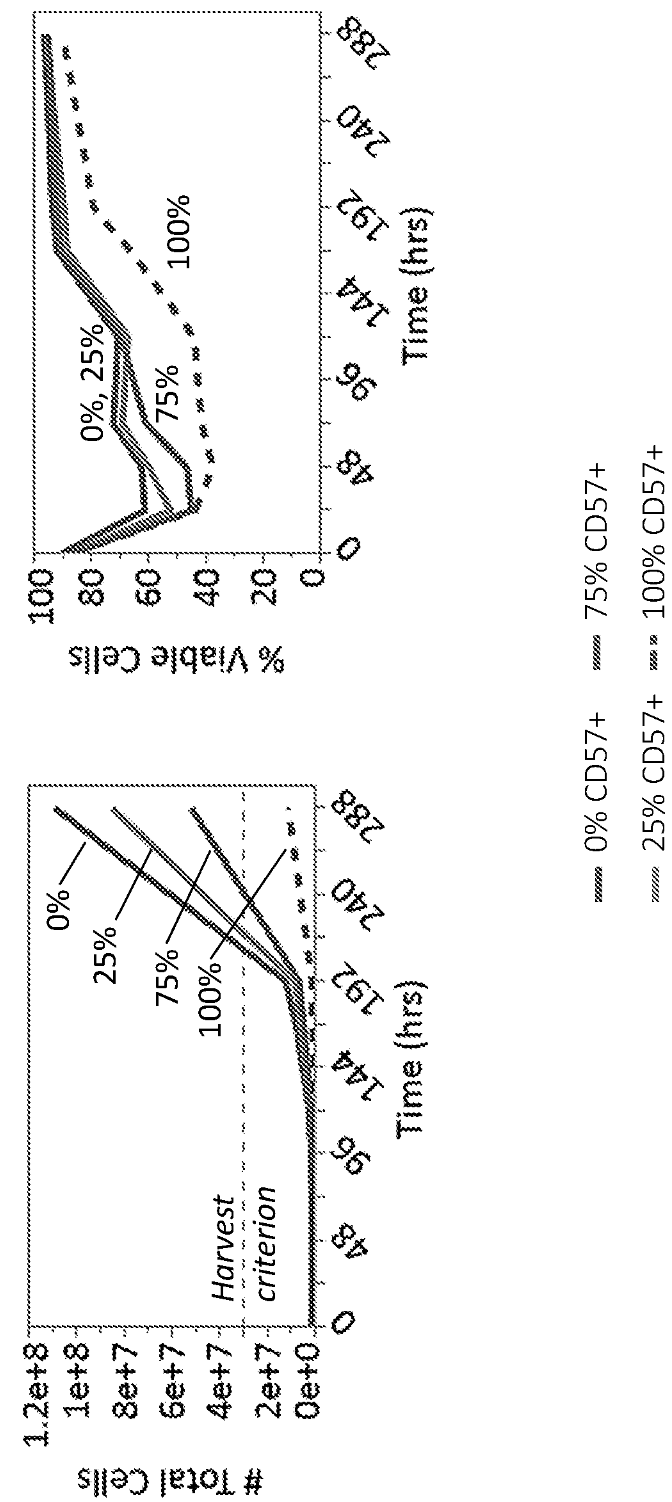
FIG. 4A shows the number of total cells (left panel) and the percentage of viable cells (right panel) over approximately 240 hours after the start of stimulation in an exemplary manufacturing process, for titrated cell compositions containing a mixture of CD57+ and CD57− cells at the following frequency: (1) 100% CD57+ cells; (2) 75% CD57+ cells; (3) 25% CD57+ cells; and (4) 0% CD57+ cells. An exemplary harvest criterion is indicated by the dashed line in the left panel.
Figure 4B:
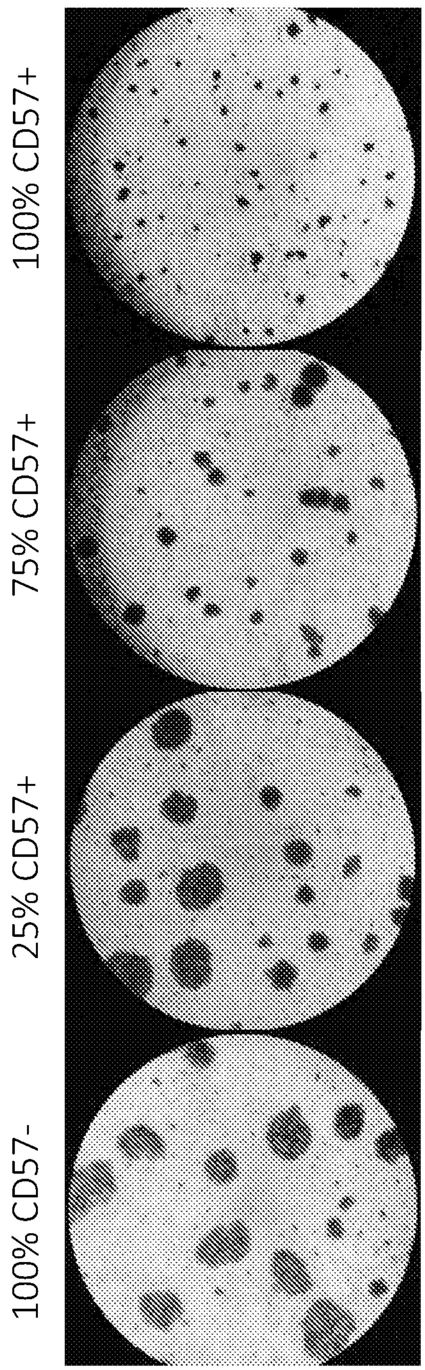
FIG. 4B shows images of cell culture wells at 48 hours after the start of stimulation, showing cell clustering in the presence of a stimulating reagent, in the stimulation and cultivation of the titrated cell compositions.
Figure 4C:
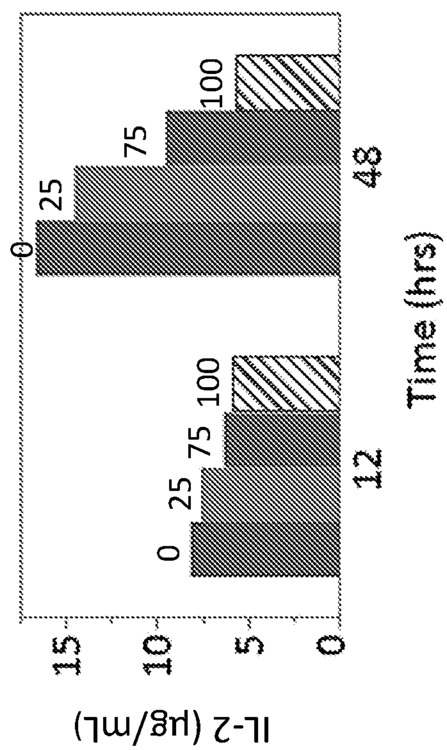
FIG. 4C shows the amount of IL-2 (μg/mL) present in the culture media at 12 hours and 48 hours after the start of stimulation, in the stimulation and cultivation of the titrated cell compositions.

As shown in FIG. 4A, input compositions containing higher frequencies of CD57+ cells exhibited slower cell expansion, required longer cultivation time to reach an exemplary threshold cell number for harvest (harvest criterion, shown by line on left panel), and exhibited lower cell viability, compared to input compositions containing lower frequencies of CD57+ cells. Very low or no expansion was observed in the composition containing 100% CD57+ cells. In general, the frequency of CD57+ cells in the input composition was observed to be associated with the duration of culture required to achieve the harvest criterion. As shown in FIG. 4B, input compositions containing higher frequencies of CD57+ cells also formed cell clusters in the presence of the stimulation reagent (anti-CD3/anti-CD28 antibody conjugated paramagnetic beads) at 48 hours, demonstrating the cells were responsive to the stimulation. It was observed that, 24 and 48 hours after the start of stimulation, the concentration of IL-2 in the culture media was lower in cultures of input compositions containing higher frequencies of CD57+ cells, compared to cultures of input compositions containing lower frequencies of CD57+ cells (FIG. 4C).

The results were consistent with an observation that the frequency of CD57+ cells in the input composition can affect total cell expansion and cell viability. Input compositions with higher frequencies of CD57+ cells required longer cultivation times to reach harvest criterion. In some aspects, CD57+ cells, which were capable of being stimulated and occupying or using stimulation reagents, were observed to consume the IL-2 present in the cultivation conditions and contribute to cell count numbers in the culture. This indicated that the presence of CD57+ cells may affect other cells in the population during the manufacturing process, such that depleting CD57+ cells in cell populations derived from different donors may reduce, and reduce the variance of, the cultivation time required within and among cell populations from different donors.

Example 4: Depletion of CD57+ Cells from Donor Cell Compositions and Effect on Culture Duration Input compositions that were depleted of CD57+ cells were subjected to an exemplary manufacturing process, and cell phenotypes and duration of cultivation before reaching harvest criterion were assessed.

CD8+ cells were obtained from four different subjects and each separated into two arms. In one arm, CD57+ cells were depleted from the cell composition to generate an input composition (depleted), and purity was assessed by flow cytometry. In the other arm, the CD8+ cells were used as input composition without depletion of CD57+ cells (undepleted). The depleted and undepleted input compositions were subjected to an exemplary manufacturing process for CAR-expressing cells by viral transduction, similar to as described in Example 1, including stimulation by incubation with anti-CD3/anti-CD28 antibody-conjugated beads and recombinant cytokines, transduction with a viral preparation containing nucleic acid encoding a CAR, and cultivation under conditions for expansion. Immediately prior to the start of the stimulation, samples of the cell compositions were stained for Ki67, CD3, CD57, CD27 and CD28. The duration for the depleted and undepleted cultures to reach an exemplary harvest criterion was assessed. The harvest criterion represented an approximately 10-fold expansion of cells.

Figures 5A, 5B, 5C:
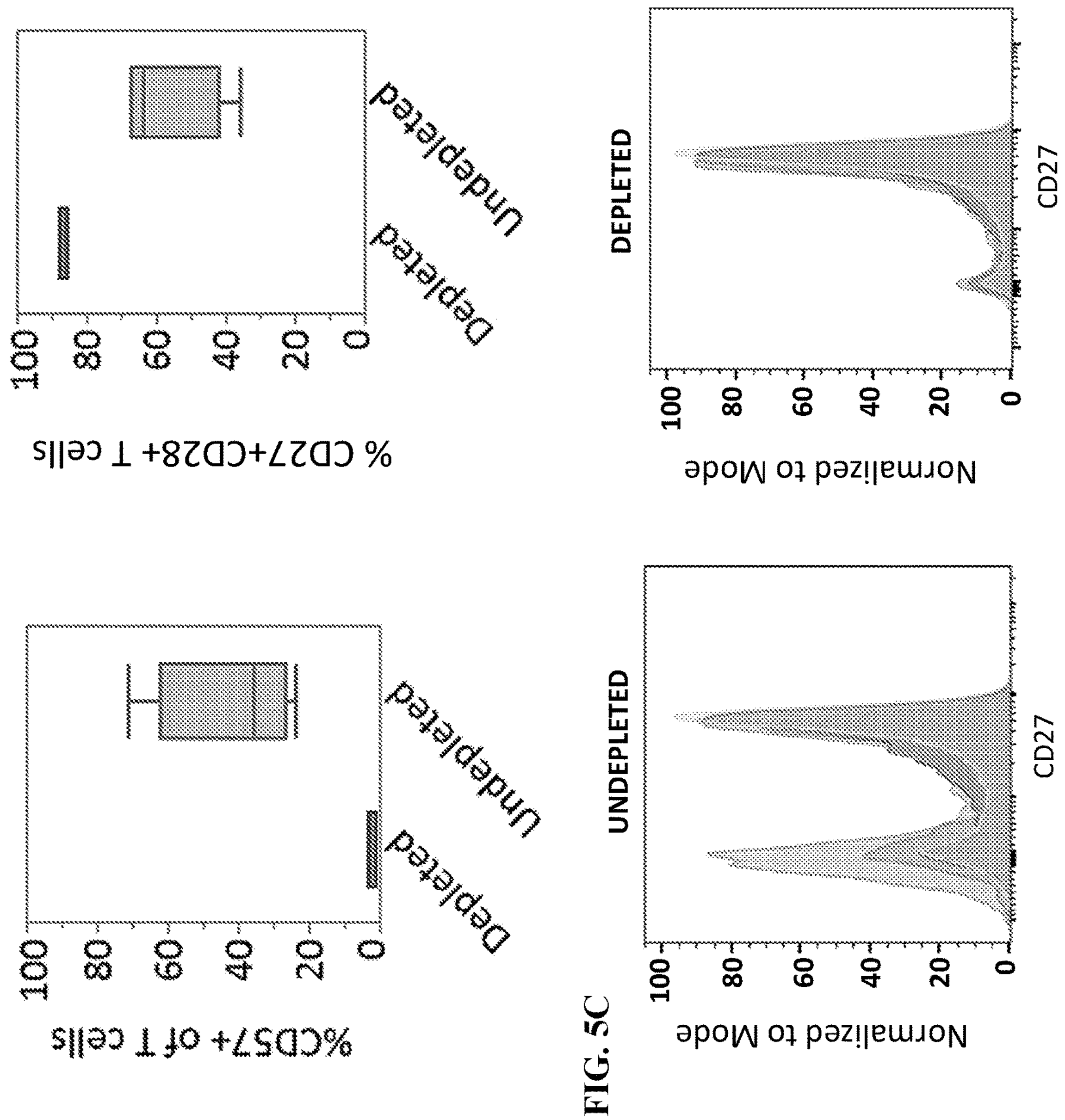
FIGS. 5A and 5B show the percentage of CD57+ T cells (FIG. 5A), CD27+ CD28+ T cells (FIG. 5B).
FIG. 5C shows the expression of CD27 for four different donor cell compositions that were not depleted of CD57+ cells (non-depleted) or that were depleted of CD57+ cells (depleted).

As shown in FIG. 5A, the undepleted input compositions exhibited varying frequencies of CD57 cells. As shown in FIG. 5B, the frequency of CD27+ CD28+ cells was higher and more consistent among the depleted input compositions, compared to the undepleted input compositions. Flow plots for CD27 expression among the four different donor undepleted and depleted input compositions is shown in FIG. 5C. The left panel of FIG. 5C shows that CD8+ T cells from the undepleted samples from the four donors exhibited varying degrees of CD27 expression. By contrast, as shown in the right panel of FIG. 5C, depletion of CD8+ CD57+ cells from the input compositions improved the starting material consistency across the donors, as evidenced by the similarly consistent CD27 expression. Together, these results demonstrate that variability in naïve-like or central memory cells within and among different donor cell populations in starting donor leukapheresis samples can be improved by depleting CD57+ cells.

Figure 5D:
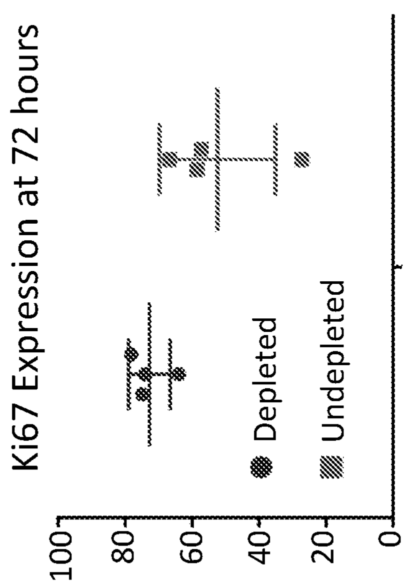
FIG. 5D shows Ki67 expression in depleted and undepleted CD3+ donor cell compositions.

Expression of Ki67, a marker of T cell proliferation and growth, was assessed among total CD3+ T cells in the donor input compositions 72 hours after the start of stimulation. As shown in FIG. 5D, Ki67 expression was higher and less variable among depleted donor input compositions, as compared to undepleted donor input compositions.

Figure 5E:
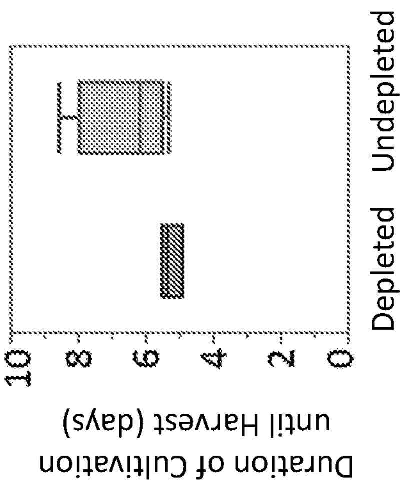
FIG. 5E shows the duration of cultivation to harvest (from the start of stimulation to the time at which harvest criterion was reached) for primary CD8+ cells obtained from donors that were depleted of CD57+ cells (depleted) or that were not depleted of CD57+ cells (undepleted).
Figure 5F:
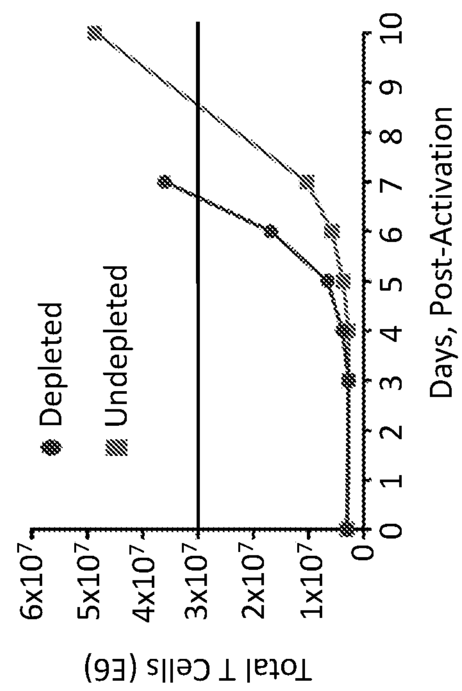
FIG. 5F shows the total number of T cells over time in depleted and undepleted donor cell compositions, following stimulation.

As shown in FIG. 5E, the duration of cultivation to harvest (from the start of stimulation to the time at which harvest criterion was reached) was generally shorter and more consistent among the depleted donor input compositions, compared to the undepleted donor input compositions. Expansion of cells from one exemplary donor, as assessed by total T cells at various days following stimulation, is shown in FIG. 5F. The results show that the total number of cells expanded from depleted donor input compositions was observed to be higher than the total number of cells expanded from undepleted donor input compositions, at multiple time points following stimulation (FIG. 5F). These findings are consistent with an observation that depleted donor populations may exhibit shorter duration to harvest criterion due to a greater number of dividing and total cells.

Figure 5G:
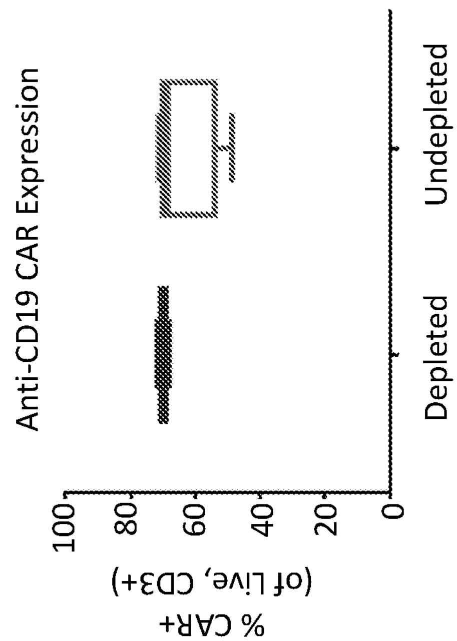
FIG. 5G shows the percentage of cells expressing a chimeric antigen receptor (CAR) following transduction, in donor cell compositions depleted of CD57+ cells (depleted) or not depleted of CD57+ cells (undepleted).

Following transduction of the depleted and undepleted donor cells with an exemplary chimeric antigen receptor (CAR), the percentage of cells expressing the CAR was assessed. As shown in FIG. 5G, the percentage of cells expressing the CAR among the depleted donor compositions was more consistent than the percentage of cells expressing the anti-CD19 CAR among the undepleted donor compositions. This result is consistent with an observation that depletion of CD57+ cells may improve the consistency of CAR expression by T cells, including those derived from different donors.

Together, the results were consistent with an observation that selected depletion of CD57+ cells improved expansion of donor cell populations and reduced the duration of cultivation required to reach the harvest criterion. Further, the findings indicate that depletion of CD57+ cells may reduce variability in the phenotype of cells among starting material (e.g. CD27+ cells) from different donors. In some aspects, the variability in the presence and frequency of CD57+ T cells among input compositions from multiple donors can impact the CAR T cell manufacturing process, and can result in variability in duration of cultivation and cell composition attributes. In some aspects, depletion of CD57+ T cells in input compositions derived from multiple donors can improve process control and consistency of the manufactured CART cell compositions.

Example 5: CD57+ CD8+ T Cell Frequency in Peripheral Blood of Non-Hodgkin Lymphoma (NHL) Patients Cells from the peripheral blood of non-Hodgkin lymphoma (NHL) patients were assessed for CD57+ expression and various surface markers associated with T cell differentiation phenotypes.

Separate compositions of CD4+ and CD8+ cells from leukapheresis samples from NHL patients in a clinical study were isolated by immunoaffinity-based enrichment and cryopreserved. The cells from each isolated cell composition were subsequently thawed and stimulated by separately incubating the cells under stimulatory conditions in the presence of anti-CD3/anti-CD28 antibody-conjugated paramagnetic beads and recombinant cytokines (e.g. IL-2, IL-7 and IL-15) for 48 hours. 48 hours after the start of the stimulation, samples from the cell compositions were stained for various markers for analysis by flow cytometry, including markers associated with lineage (CD4 and CD8), proliferative capacity (CD57), cell division (Ki67), and T cell differentiation phenotypes (e.g., naïve-like T cells, effector T ($T_{EFF}$) cells, memory T cells, central memory T ($T_{CM}$) cells). Hierarchical clustering was performed to assess association between CD57+ expression and a variety of the markers associated with T cell differentiation phenotypes.

Figure 6A:
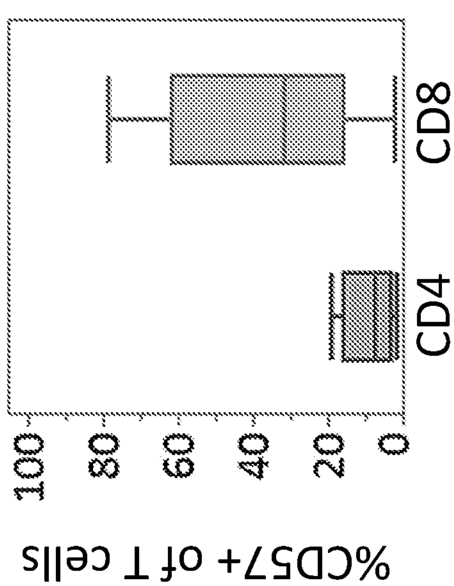
FIG. 6A shows a whisker plot indicating the percentage of CD57+ T cells in CD4+ and CD8+ T cells obtained from non-Hodgkins lymphoma (NHL) patients for engineering the cells to express a chimeric antigen receptor (CAR) using an exemplary manufacturing process. Boxes represent interquartile range and whiskers represent full range of the data set.
Figure 6B:
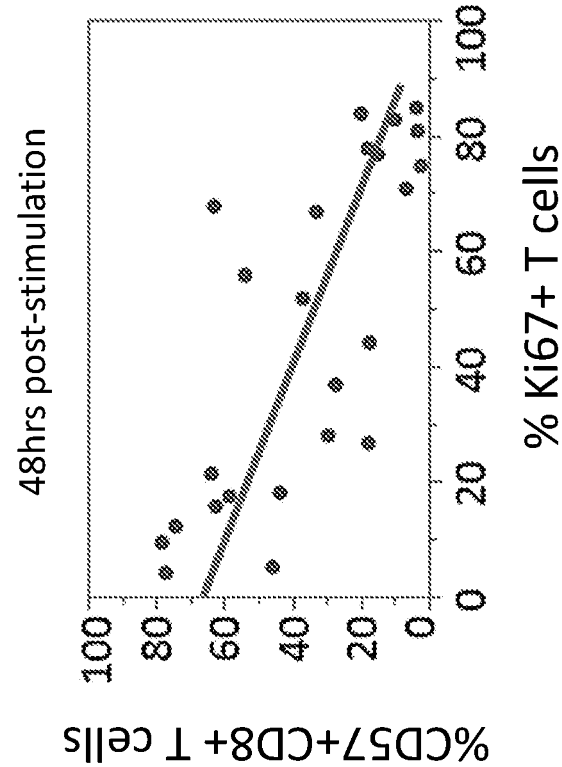
FIG. 6B shows the relationship between the percentage of CD57+ CD8+ cells and the percentage of Ki67+ cells in the various cell populations obtained from NHL patients.
Figure 6C:
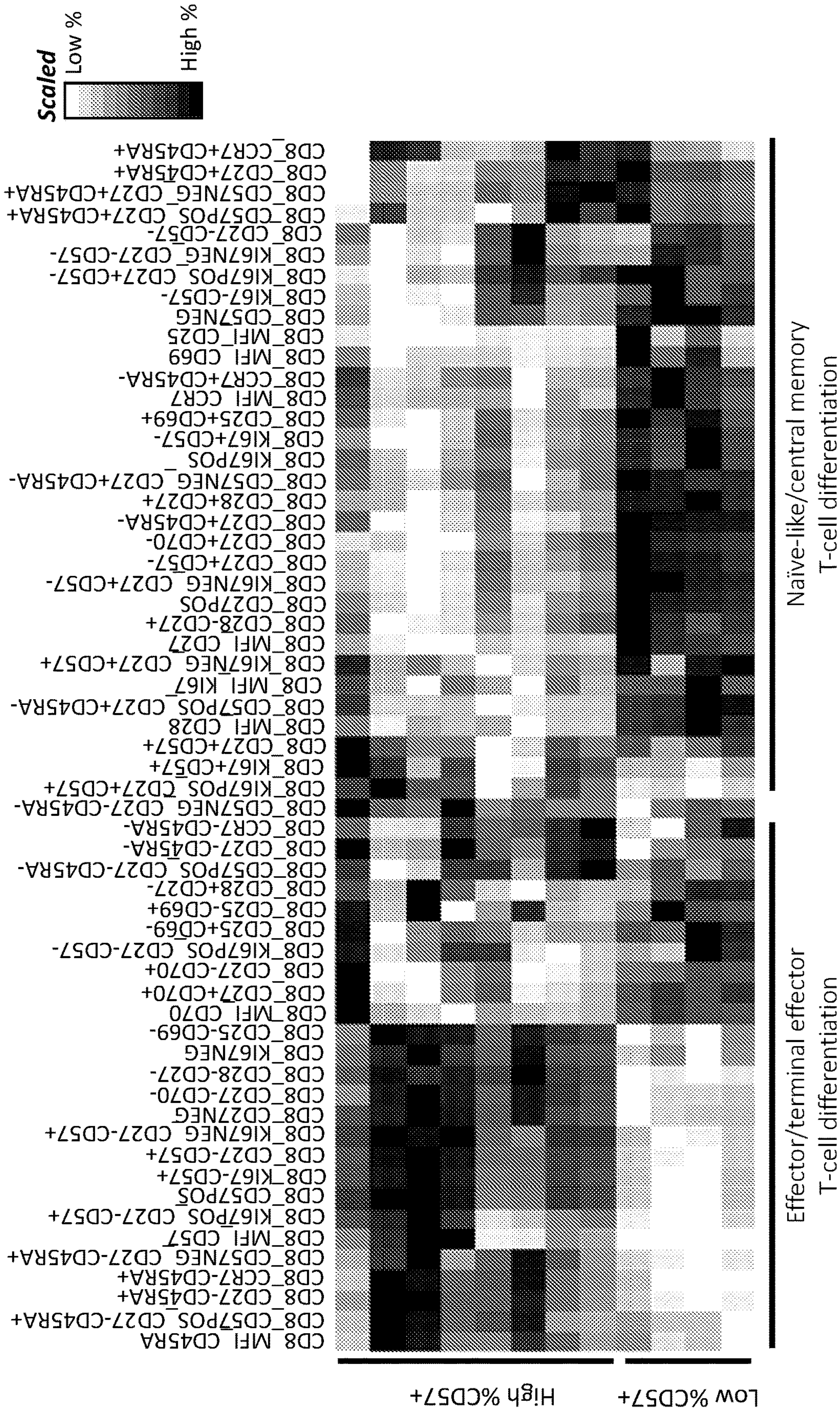
FIG. 6C shows a hierarchical clustering analysis for expression of various surface markers associated with T cell differentiation phenotypes (e.g., naïve-like T cells, effector T ($T_{EFF}$) cells, memory T cells, central memory T cells ($T_{CM}$), terminal effector cells), and the expression of CD57 in the cell populations obtained from NHL patients. Each row represents an individual patient, columns represent markers or combinations of markers that are associated with T cell differentiation phenotypes.

As shown in FIG. 6A, the frequency of CD57+ cells in the input composition varied among the CD8+ cell populations from different NHL patients. As shown in FIG. 6B, a general inverse relationship between the percentage of CD57+ CD8+ cells and the percentage of Ki67+ cells was observed at 48 hours after the start of stimulation. As shown in FIG. 6C, hierarchical clustering showed clusters that were distinguished by memory and effector T cell differentiation phenotypes, and these phenotype clusters further clustered samples with either high or low frequencies of CD57+ T cells.

Figure 6D:
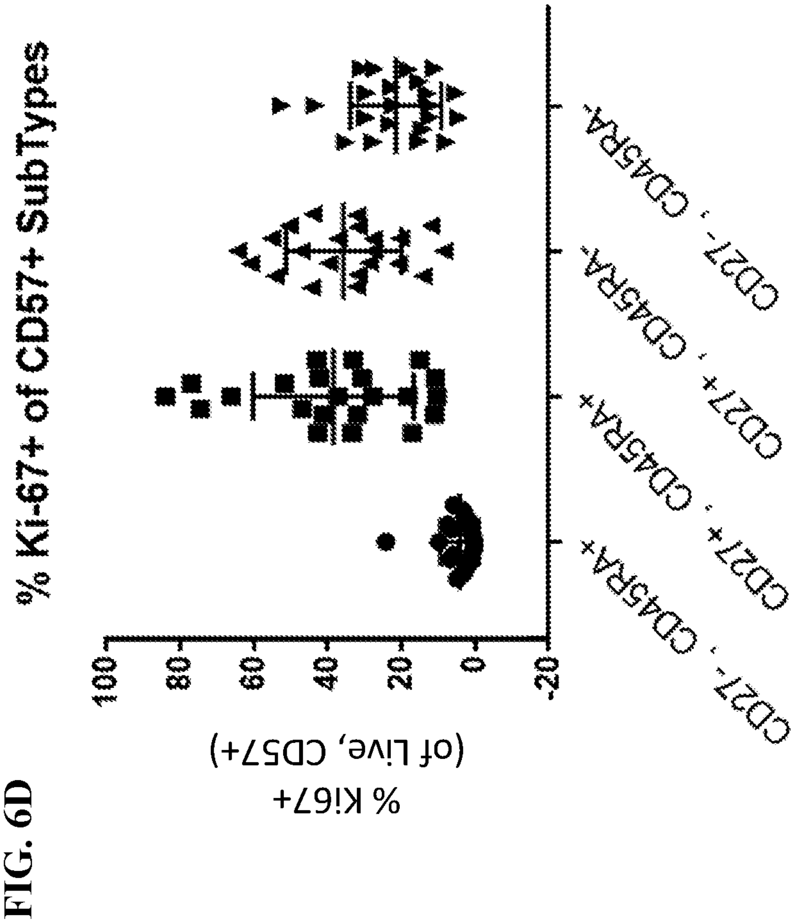
FIG. 6D shows the percentage of live, CD57+ cells expressing Ki67 in subsets of cell poulations, grouped by CD27 and CD45RA expression status.

Analysis of CD57+ cells from different donor input compositions revealed that Ki67 expression varied among cells with different T cell differentiation immunophenotypes. As shown in FIG. 6D, the percentage of live, CD57+ cells expressing Ki67 was lowest in CD27-CD45RA+ cells, and was higher in CD27-CD45RA− cells, CD27+ CD45RA+ and CD27+ CD45RA− cells.

Figure 6E:
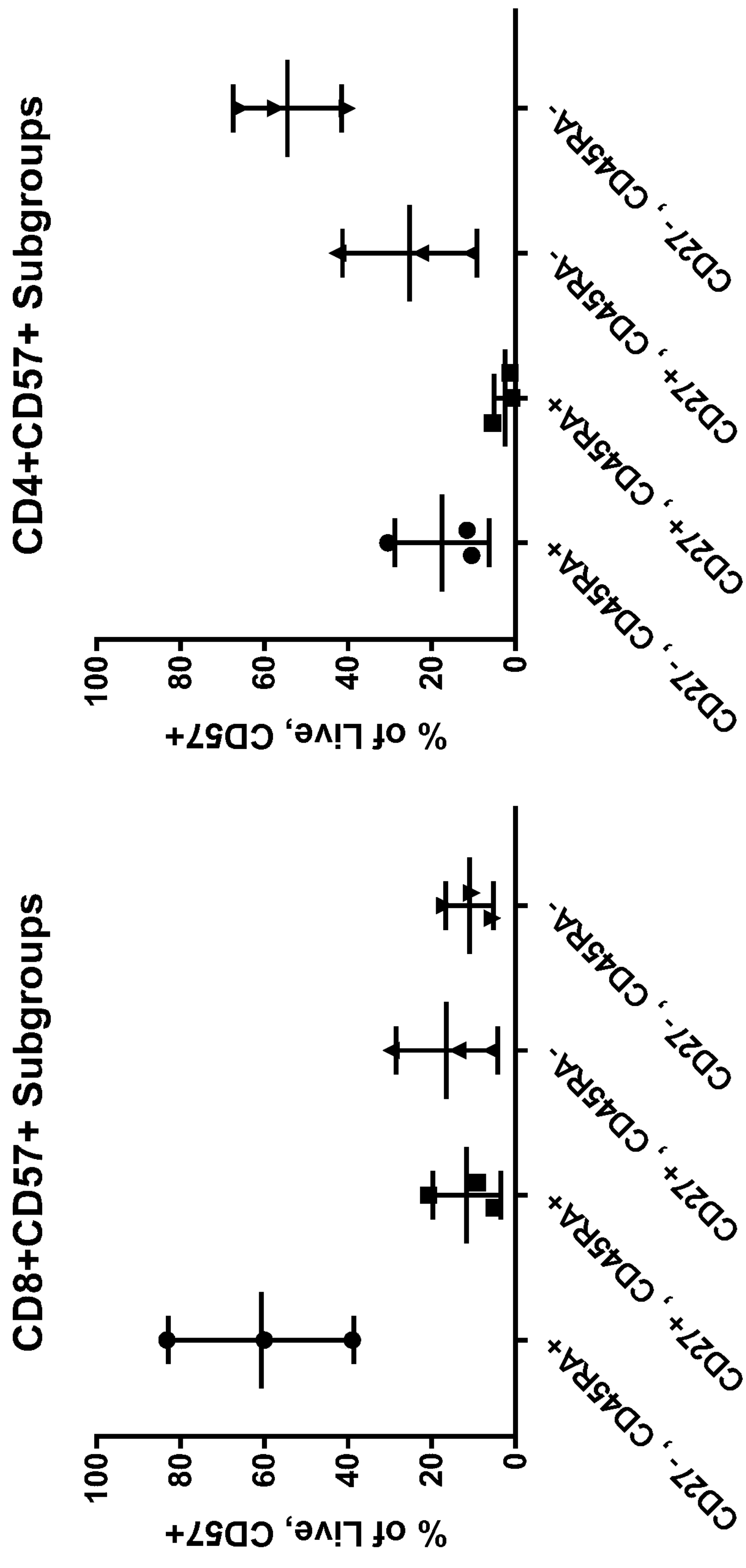
FIG. 6E shows the percentage of live, CD8+ CD57+ cells in subsets of cells populations, sorted by CD27 and CD45RA expression (left panel), and the percentage of live, CD4+ CD57+ cells in subsets of cell populations, sorted by CD27 and CD45RA expression (right panel).

The separate CD4+ and CD8+ donor cell compositions were analyzed for expression of Ki67, CD27, CD45RA, and CD57. As shown in FIG. 6E, a large percentage of CD8+ CD57+ cells were CD27-CD45RA+, indicating that these T cells were terminally differentiated effector memory RA (TEMRA) T cells. A high percentage of CD4+ CD57+ cells were CD27−CD45RA−, consistent with these cells being effector memory (EM) T cells. These findings demonstrate that CD57+ T cells are differentiated effector T cells of various immunophenotypes.

The results were consistent with an observation of variable frequencies of CD57+ T cells in peripheral circulation among NHL subjects. Similar to the findings with cell compositions generated from different donors (as described in previous examples), high CD57 expression was observed to be associated with phenotypes indicative of more differentiated cells with reduced proliferative capacity.

Example 6: Relationship of Number of Doublings and Cell Differentiation to Patient Response Exemplary therapeutic T cell compositions containing autologous T cells expressing a chimeric antigen-receptor (CAR) specific for CD19 were generated. The anti-CD19 CAR contained an anti-CD19 scFv derived from a murine antibody (variable region derived from FMC63), an immunoglobulin-derived spacer, a transmembrane domain derived from CD28, a costimulatory region derived from 4-1BB, and a CD3-zeta intracellular signaling domain.

For generation of cell compositions for administration to subjects with Relapsed and Refractory Non-Hodgkin's Lymphoma (NHL), autologous cells were isolated from the subjects via leukapheresis. Leukapheresis samples were subjected to a process for generation of CAR-expressing cells. The process involved washing of cells using an automated wash and immunoaffinity based selection for purification of CD4+ and CD8+ T cells, resulting in two compositions, enriched for CD8+(in which a median of 99%, Inter Quartile Range (IQR) 98-100%, of cells were CD8±) and CD4+(in which a median of 99%, IQR 99-100%, cells were CD4±) cells, respectively.

Cells of the enriched CD4+ and CD8+ compositions were activated with anti-CD3/anti-CD28 antibody-conjugated paramagnetic beads and then were separately subjected to lentiviral transduction with a vector encoding an anti-CD19 CAR with a 4-1BB costimulatory domain. The CAR contained an anti-CD19 scFv derived from a murine antibody, an immunoglobulin spacer, a transmembrane domain derived from CD28, a costimulatory region derived from 4-1BB, and a CD3-zeta intracellular signaling domain. Transduced populations then were separately incubated in the presence of recombinant IL-2 and IL-15 cytokines (and additionally recombinant IL-7 for the CD4+ T cell composition) for cell expansion. The incubation under conditions for expansion was carried out in a rocking motion bioreactor until reaching a threshold of about 4-fold expansion. Expanded CD8+ and CD4+ cells were formulated and cryopreserved separately and stored prior to administration. To minimize variations between lots and/or cell compositions derived from different patients, such as those having different patient attributes, in parameters indicative of cell health, cells were held at constant volumes across lots. Cell products exhibited a tight range of viable cell concentrations (based on an assessment of cell compositions for one group of subjects, CD8+: median $31\times10^6$ cells/mL, IQR 28-$40\times10^6$ cells/mL, N=38; CD4+: median $35\times10^6$ cells/mL, IQR 31-$40\times10^6$, N=36).

The generated T cell compositions were used for administration in subjects with Relapsed and Refractory Non-Hodgkin's Lymphoma (NHL) as described below.

A. Exemplary Attributes of Therapeutic T Cell Compositions

The generated therapeutic T cell compositions, used for administration in subjects with Relapsed and Refractory Non-Hodgkin's Lymphoma (NHL) described below, were assessed for CCR7 and CD27 using flow cytometry. Surface expression levels of CD4 and a truncated receptor used as a surrogate marker, also were assessed.

For each generated therapeutic composition, the number of doublings of the generated cell compositions also was determined based on total nuclear count (TNC) of cells, by dual-fluorescence staining with acridine orange (AO) and either propridum iodide (PI) or DAPI, using the following formula:

$$\text{Cell doublings} = \frac{\ln\left(\frac{TNC \text{ at harvest}}{TNC \text{ 3 days post-activation}}\right)}{\ln 2} \quad 1)$$

Figure 7:
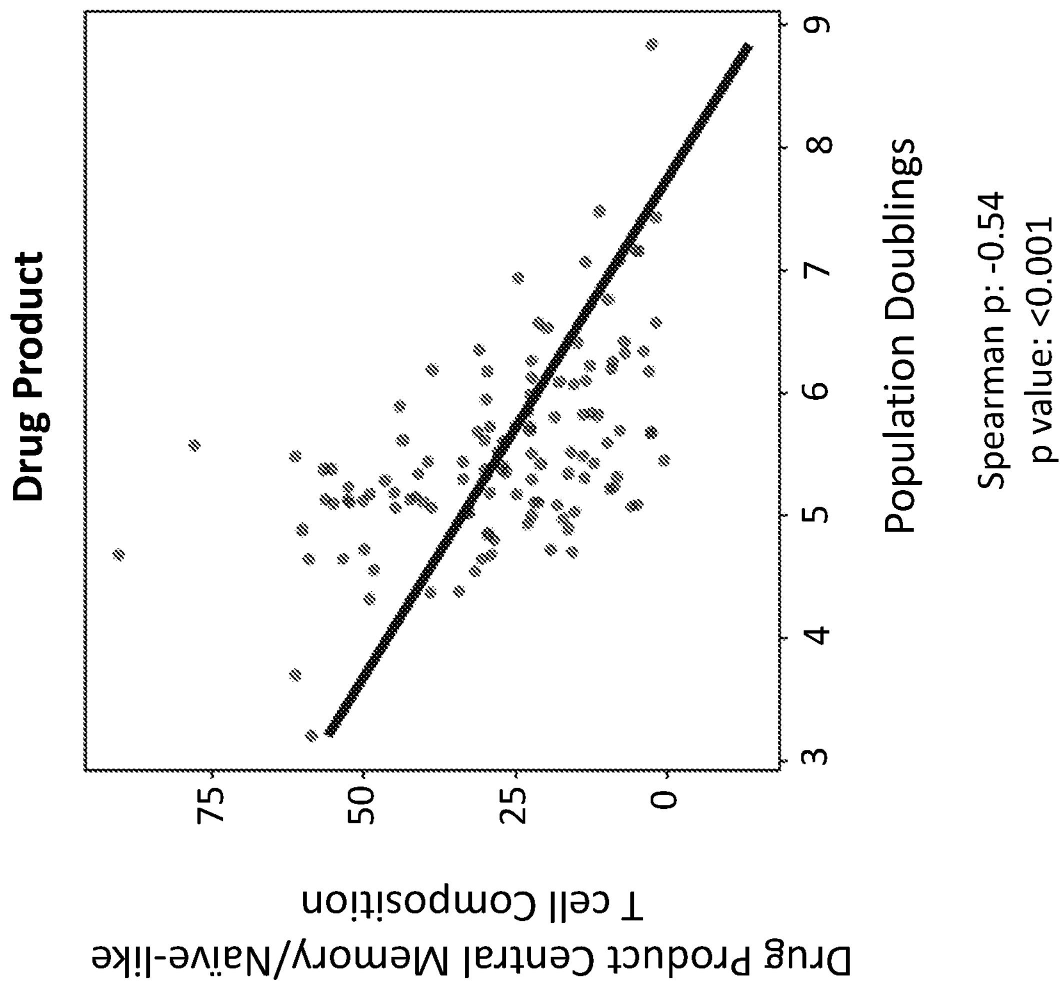
FIG. 7 shows the relationship between the percentage of central memory/naïve-like CD4+ T cells in the therapeutic output T cell composition (e.g., drug product) and the number of population doublings to achieve harvest criterion (Spearman p: −0.54; p-value: <0.001). A similar result was observed for CD8+ T cells in the therapeutic output T cell composition (e.g., drug product).

FIG. 7 shows the correlation between the number of doublings in the process for producing the therapeutic composition and the percentage of CD27+ cells of CD4+ CAR+ cells. Similar results were observed for CD8+ T cells. The results show that, in general, a lower number of doublings during the process to generate therapeutic T cell compositions is associated with increased levels of CD27+ cells. Without wishing to be bound by theory, the results are consistent with an observation that an increased percentage of CD27+ cells in a process for producing engineered T cells may be influenced by the limited doublings in the processes.

Figure 8A:
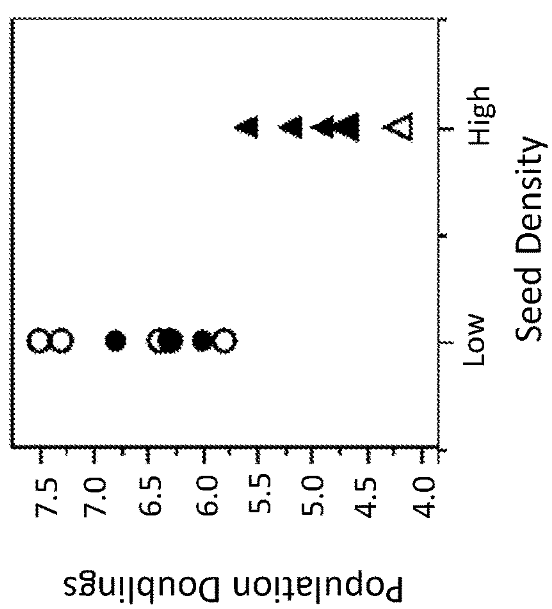
FIG. 8A shows the number of population doublings to reach harvest criterion for high ($0.35\times10^6$ cells/mL) and low ($0.05\times10^6$ cells/mL) seed density during the expansion step of the production process.
Figure 8B:
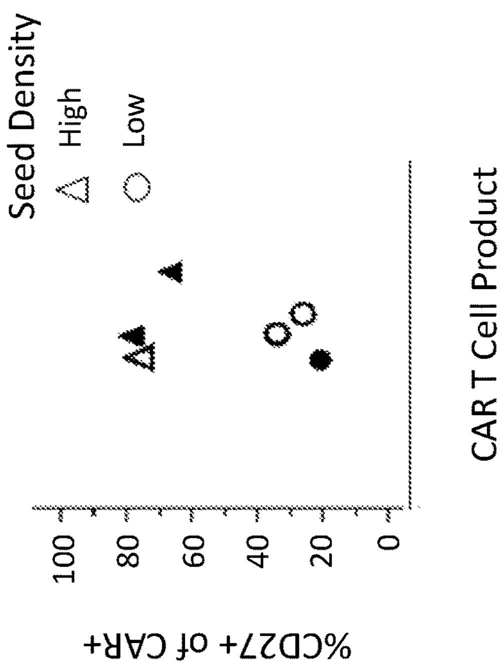
FIG. 8B shows the percentage of CD27+ CAR+ CD8+ T cells in the output therapeutic composition as a function of seed density during the expansion step of the production process.
Figure 8C:
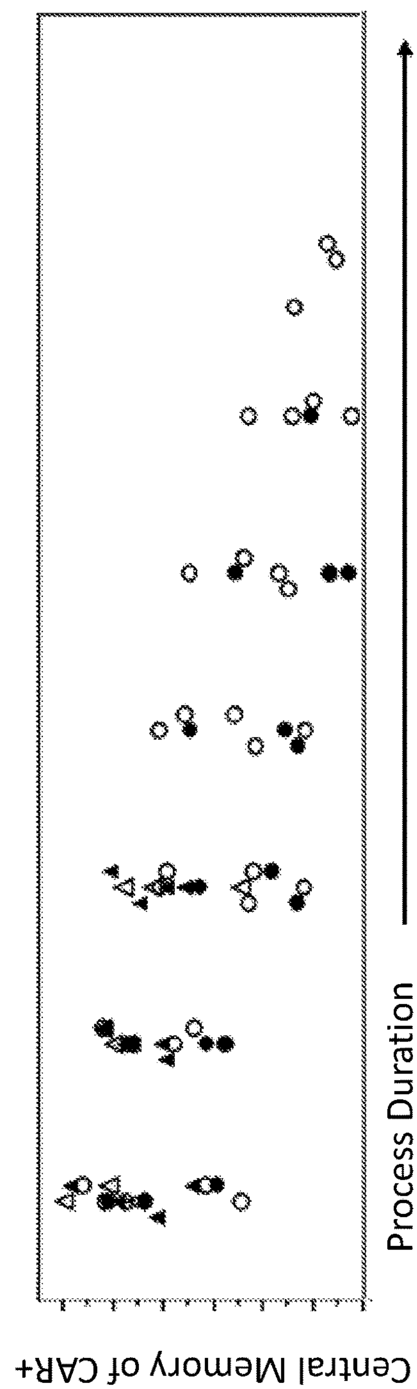
FIG. 8C shows the impact of processing duration on the amount of central memory T cells in the output T cell composition.
Figure 9A:
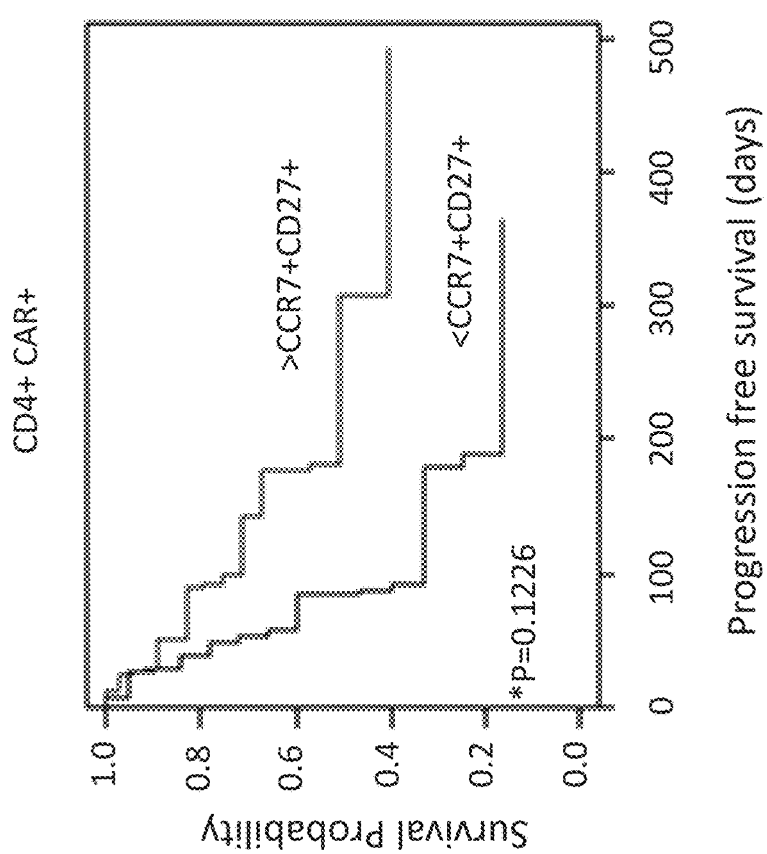
FIGS. 9A-9D show Kaplan-Meier survival curves for subjects who were administered CAR+ T cell compositions, divided into groups that were administered compositions containing a percentage of CCR7+ CD27+ CAR+ T cells among CD4+ CAR+ T cells (FIG. 9A for progression free survival, FIG. 9C for duration of response) and among CD8+ CAR+ T cells (FIG. 9B for progression free survival, FIG. 9D for duration of response) that is above or below a certain threshold level.
Figure 9B:
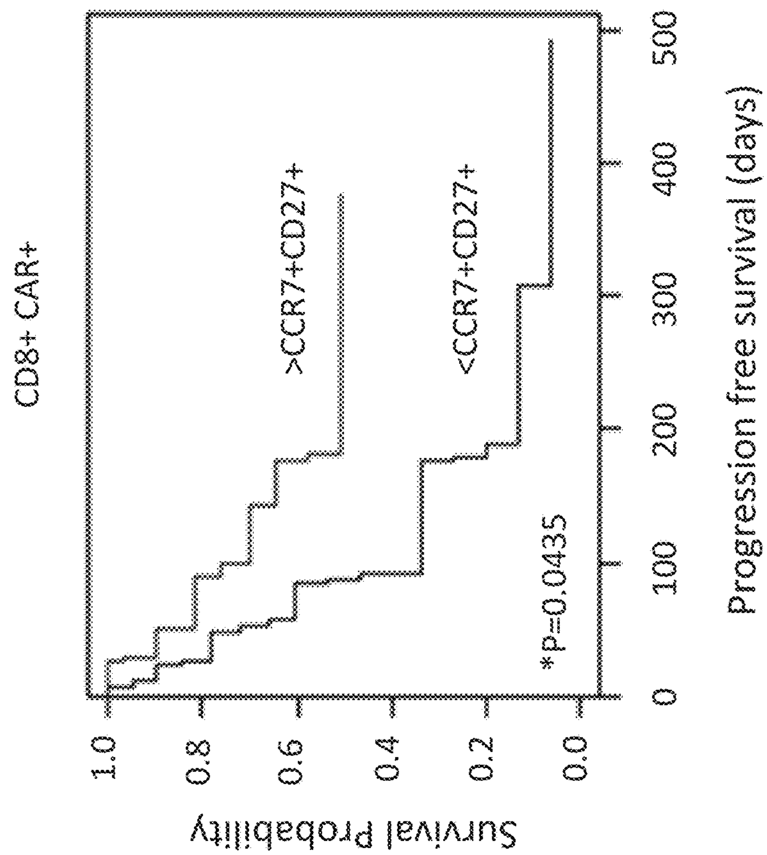
Figure 9D:
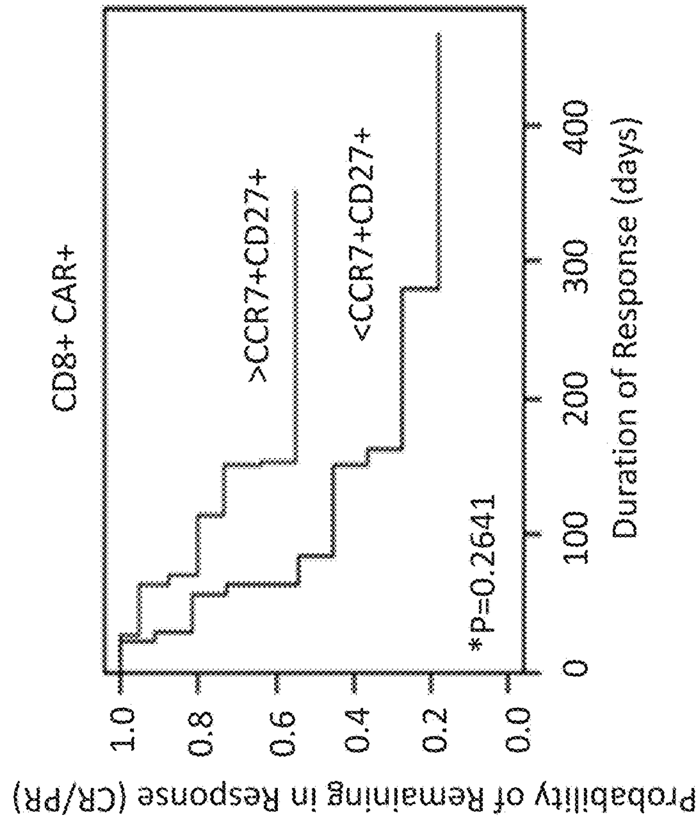
Figure 9C:
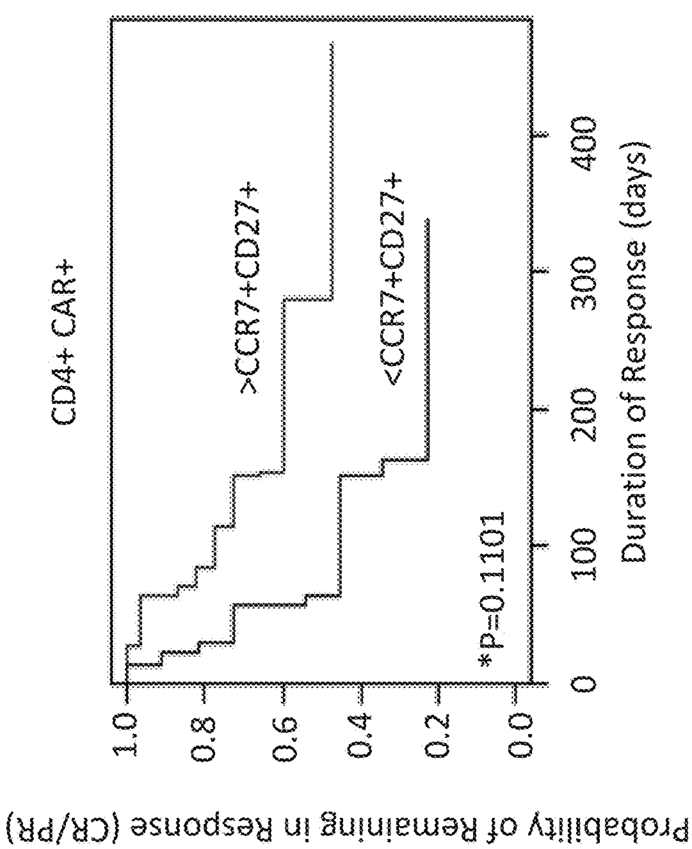

Studies modeling in-process seed density during the expansion step in a process substantially the same as described above demonstrated that a relatively higher seed density (e.g., $0.35\times10^6$ cells/mL or greater) was expected to reduce the number of population doublings to achieve harvest criterion compared to a lower seed density (e.g., $0.05\times10^6$ cells/mL or lower (FIG. 8A). Modeling also revealed that a relatively higher seed density (FIG. 8B) or a shorter process duration (FIG. 8C) also are expected to result in an increased percentage of CD8+ CAR+ T cells positive for CD27 in the output therapeutic T cell composition (e.g., drug product) compared to a lower seed density or longer process duration, respectively. These data are consistent with a finding that a higher seed density of cells at the initiation of the expansion step or a shorter process duration can result in an increase in the proportion of central memory cells in the engineered therapeutic T cell composition.

B. Administration of Anti-CD19 CAR+ T Cell Composition

The therapeutic CAR+ T cell compositions described above were administered to subjects with relapsed or refractory (R/R) aggressive non-Hodgkin's lymphoma (NHL) in a clinical study. Specifically, a cohort of adult human subjects with R/R NHL, including diffuse large B-cell lymphoma (DLBCL), de novo or transformed from indolent lymphoma (NOS), high-grade B-cell lymphoma (including double/triple hit), DLBCL transformed from chronic lymphocytic leukemia (CLL) or marginal zone lymphomas (MZL), primary mediastinal large b-cell lymphoma (PMBCL), and follicular lymphoma grade 3b (FLG3B), were administered with anti-CD19 CAR-expressing T cell compositions. Outcomes were separately assessed for a core subset of subjects within the full cohort (excluding those subjects with a poor performance status (ECOG 2), DLBCL transformed from marginal zone lymphomas (MZL) and/or chronic lymphocytic leukemia (CLL, Richter's), and excluding those subjects with primary mediastinal large b-cell lymphoma (PMBCL), and follicular lymphoma grade 3b (FLG3B) (core cohort)). The core cohort included subjects with DLBCL, NOS and transformed follicular lymphoma (tFL), or high grade B-cell lymphoma (double/triple hit) or high-grade B-cell lymphoma with MYC and BCL2 and/or BCL6 rearrangements with DLBCL histology (double/triple hit) and with Eastern Cooperative Oncology Group performance status (ECOG PS) of 0 or 1. The analysis at the time point presented in this example was based on assessment of a total of 91 subjects in the full cohort (88 (65 from the CORE cohort) assessed for response and 91 (67 from the CORE cohort) assessed for safety) that had been administered the anti-CD19 CAR-expressing cells.

The cryopreserved cell compositions containing anti-CD19 CAR-expressing cells were thawed prior to intravenous administration. The therapeutic T cell dose was administered as a defined cell composition by administering the formulated $CD4^+$ $CAR^+$ cell population and the formulated $CD8^+$ $CAR^+$ population separately administered at a target ratio of approximately 1:1. Subjects were administered a single or double dose of CAR-expressing T cells (each single dose via separate infusions of CD4+ CAR-expressing T cells and CD8+ CAR-expressing T cells, respectively) as follows: a single dose of dose level 1 (DL1) containing $5\times10^7$ total CAR-expressing T cells, or a single dose of dose level 2 (DL2) containing $1\times10^8$ total CAR-expressing T cells. In some cases, the subjects were administered a double dose of DL1 in which each dose was administered approximately fourteen (14) days apart, administered on day 1 and day 14, including one subject that inadvertently received two DL2 doses via the two-dose schedule, due to a dosing error. The dose level and the target numbers of T cell subsets for the administered composition at DL1 and DL2 are set forth in Table E1. In the core cohort, 34 subjects were administered DL1, and 27 subjects were administered DL2.

TABLE E1

Target dose level and number of T cell subsets for cell compositions containing anti-CD19 CAR T cells

| Dose level | Helper T cell ($T_H$) Dose ($CD4^+$ $CAR^+$) | Cytotoxic T Cell ($T_C$) Dose ($CD8^+$ $CAR^+$) | Total T Cell Dose ($CD3^+$ $CAR^+$) |
|---|---|---|---|
| 1 | $25 \times 10^6$ | $25 \times 10^6$ | $50 \times 10^6$ |
| 2 | $50 \times 10^6$ | $50 \times 10^6$ | $100 \times 10^6$ |

Table E2 shows the overall response and safety outcomes for the full cohort and the core cohort at the two dose levels. The objective response rate (ORR) was 74%, including 52% subjects who showed a complete response (CR). The incidence of any grade of cytokine release syndrome (CRS) was 35%, with 1% severe CRS; and the incidence of any grade of neurotoxicity (NT) was 19%, with 1% severe NT.

TABLE E2

| Response and Safety After CAR$^+$ Cell Administration | FULL | CORE | | |
|---|---|---|---|---|
| | All Dose Levels | All Dose Levels[a] | DL1 | DL2 |
| Best Overall Response (BOR), n[b] | 88 | 65 | 34 | 27 |
| ORR, % (95% CI) | 74 (63, 83) | 80 (68, 89) | 77 (59, 89) | 82 (62, 94) |
| CR, % (95% CI) | 52 (41, 63) | 55 (43, 68) | 47 (30, 65) | 63 (42, 81) |
| Safety, n[c] | 91 | 67 | 34 | 29 |
| Any CRS, % (95% CI) | 35 (25, 46) | 36 (24, 48) | 41 (25, 59) | 24 (10, 44) |
| sCRS (grade 3-4), % (95% CI) | 1 (0, 6) | 1 (0, 8) | 38 (0, 15) | 0 |
| Any NT, % (95% CI) | 19 (11, 28) | 21 (12, 33) | 24 (11, 41) | 17 (6, 36) |
| sNT (grade 3-4), % (95% CI) | 12 (6, 21) | 15 (7, 26) | 21 (9, 38) | 7 (1, 23) |

[a]Four patients treated on DL1D (dose level 1, two-dose schedule) with similar outcomes.
[b]Includes patients with event of PD, death, or 28-day restaging scans. One patient did not have restaging scans available.
[c]Includes all subjects who have received at least one dose of conforming CAR-expressing cell product 28 days prior to data snapshot date or died.

C. Association between Cell Attributes of Anti-CD19 CAR-Expressing T Cells and Response The relationship between certain phenotypic attributes of the CAR' T cells in the therapeutic compositions and parameters associated with clinical response outcomes were assessed. The correlations between memory phenotype in the composition and function translated to a positive correlation between central memory subset composition and peak in vivo expansion of CARP cells ($\rho$=0.42, P=0.002), and progression-free survival (PFS) (Kaplan-Meier survival estimate, P=0.0164) that were observed. FIGS. 9A-9D show the Kaplan-Meier survival curves for subjects who were administered CAR$^+$ T cell compositions, divided into groups that were administered compositions containing a frequency of CCR7$^+$ CD27$^+$ CAR$^+$ T cells among CD4$^+$ CARP T cells (FIG. 9A for progression free survival, FIG. 9C for duration of response) and among CD8$^+$ CAR$^+$ T cells (FIG. 9B for progression free survival, FIG. 9D for duration of response) that is above or below a certain threshold level. Higher frequency of CCR7$^+$ CD27$^+$ memory cells in the composition was observed to be correlated with longer progression free survival.

Figure 10:
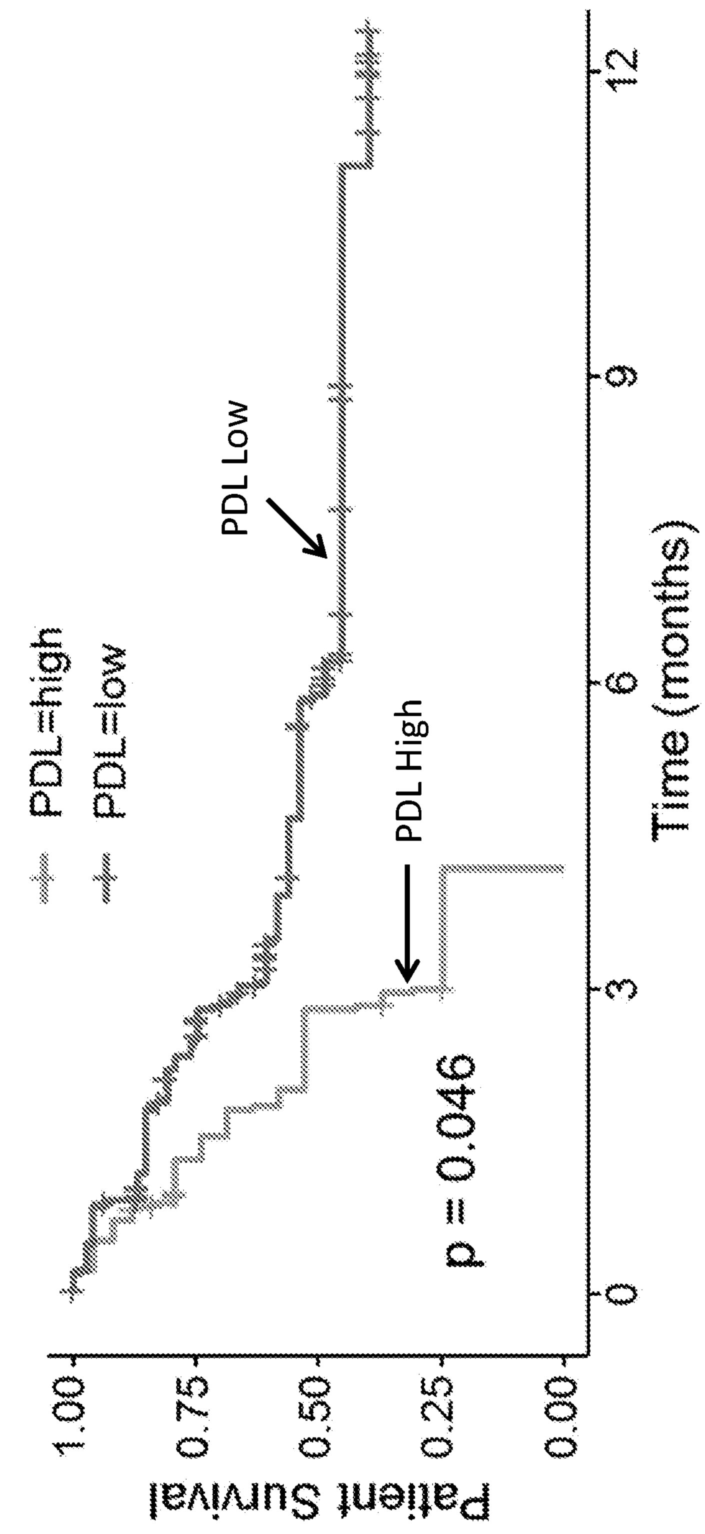
FIG. 10 shows a PFS curve based on an optimal-split log-rank test for patients with "high" or "low" numbers of population doublings (PDL) in CD8+/CAR+ T cells. Low PDL refers to <6 PDL and >6 PDL refers to high PDL.

Univariate analysis revealed an inverse correlation between T cell population doublings (PDL) during the process for producing the therapeutic T cell composition and the probability of progression free survival (PFS) in Non-Hodgkin Lymphoma (NHL) patients. FIG. 10 shows a PFS curve based on an optimal-split log-rank test for patients with "high" (>6 PDL) or "low" (<6 PDL) numbers of PDL in CD8+ CAR+ T cells. This result is consistent with a finding that factors that may limit the number of population doublings of T cells in a process for producing a therapeutic T cell composition may improve the likelihood of subjects exhibiting progression free survival that is durable.

Example 7: Assessment of Features of Selected (Input) Cell Compositions in a Process for Producing a Therapeutic Cell Composition Phenotypic attributes of T cells selected from subjects with Relapsed and Refractory Non-Hodgkin's Lymphoma (NHL), prior to engineering with an anti-CD19 CAR by the process described in Example 6, were assessed. CD4+ and CD8+ T cells were selected by immunoaffinity-based enrichment from leukapheresis of human peripheral blood mononuclear cells (PBMC) from a plurality of subjects. A composition of such selected T cells (before genetic engineering, designated "pre-engineering composition") were assessed for expression of cell surface markers indicative of certain T cell subtypes, such as effector memory or central memory cell subtypes, including C—C chemokine receptor type 7 (CCR7), CD27 and CD45RA. Surface expression of CD4 or CD8 was also assessed.

Figure 11:
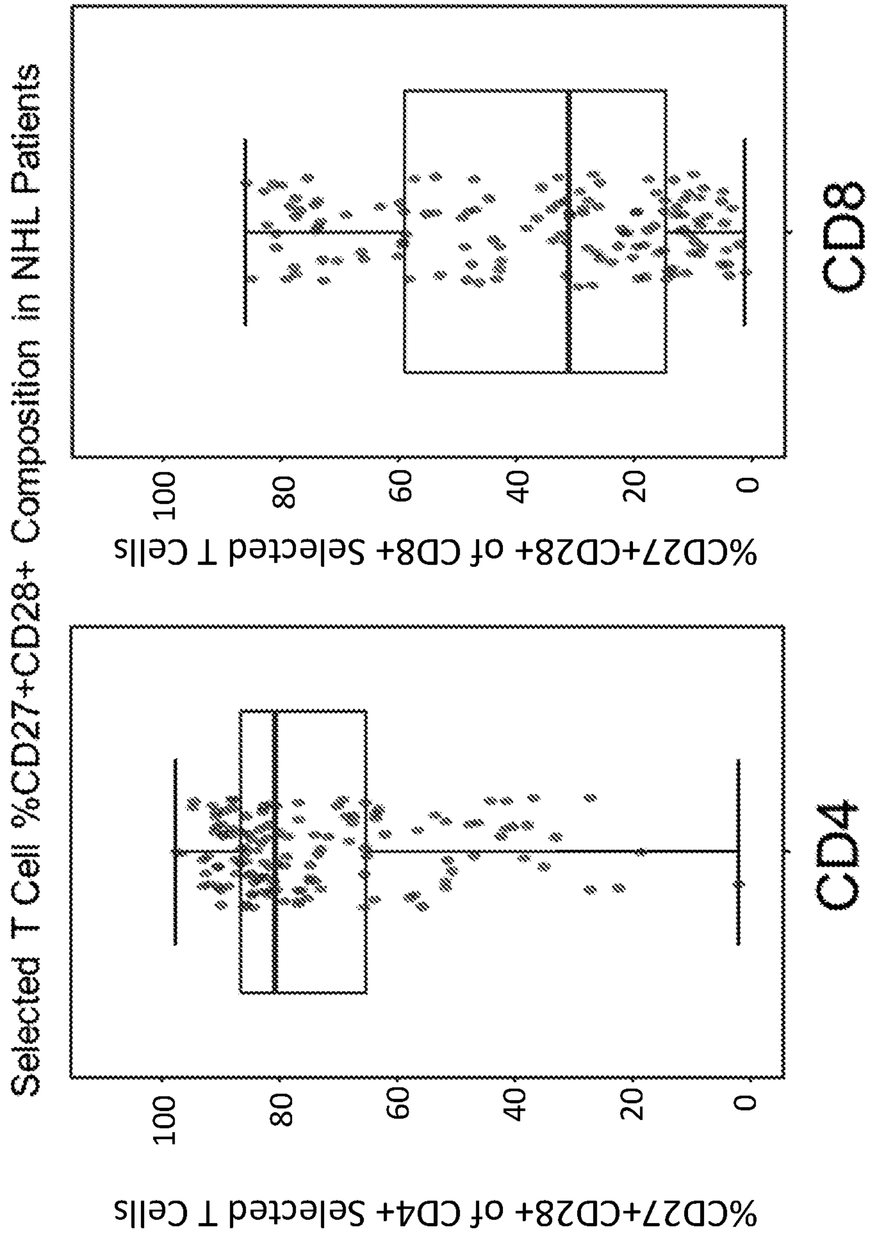
FIG. 11 shows the percentage of CD27+ CD28+ T cells in enriched CD4+(left panel) and CD8+(right panel) input compositions derived from NHL patients.

Assessment of the enriched CD4+ and CD8+ compositions (e.g., input compositions) revealed that the percentage of T cells positive for naïve-like markers (e.g. CD27+ CD28+ T cells), such as present on central memory T cell subsets, was highly variable among NHL patients (FIG. 11). These data indicate that interpatient T cell heterogeneity of central memory T cell subsets exists in selected (input) T cell compositions used to generate CAR+ T cell therapeutic T cell compositions.

Figure 12:
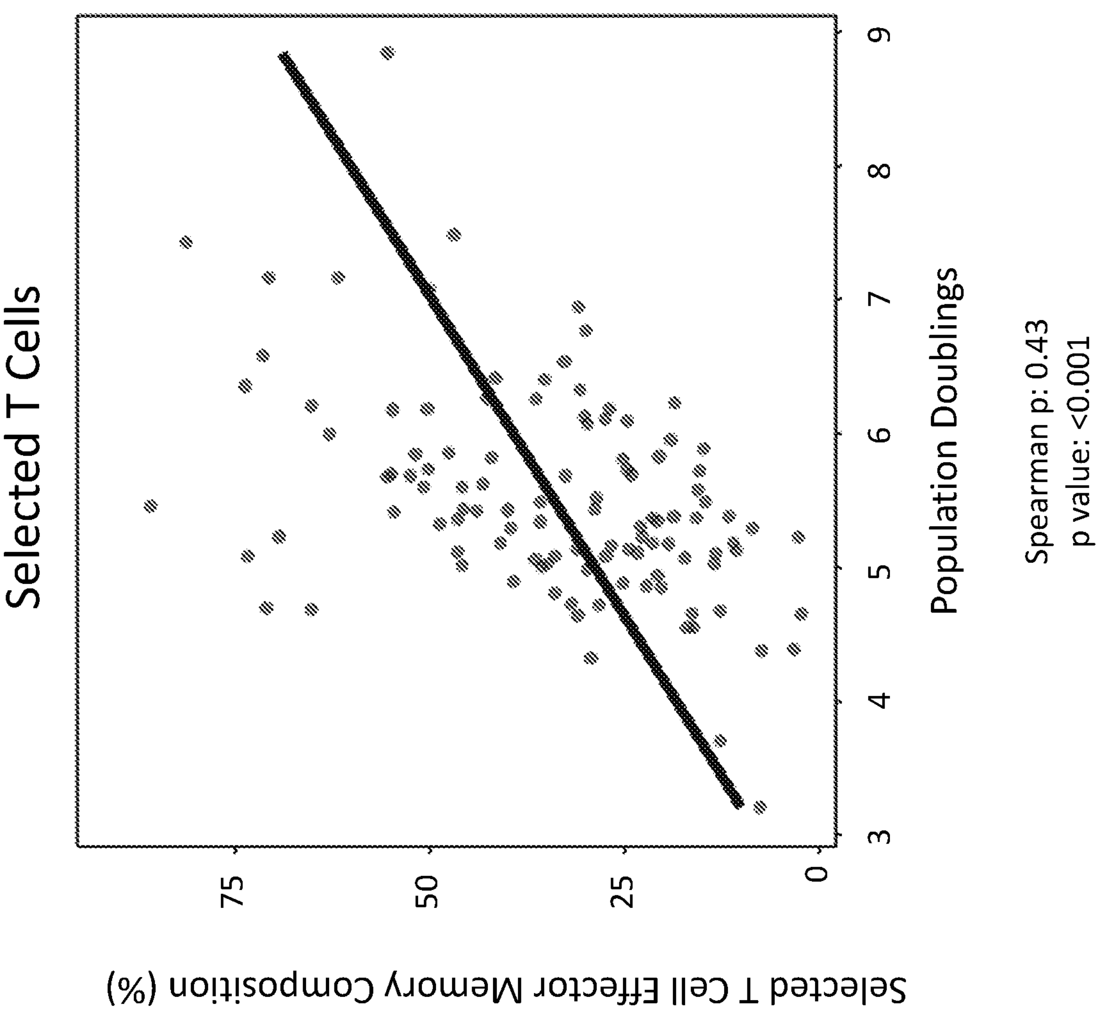
FIG. 12 shows the relationship between the percentage of effector memory T cells in enriched CD4+ input compositions and the number of population doublings needed to achieve harvest criterion (Spearman p: 0.43; p-value: <0.001). A similar result was observed for enriched CD8+ input compositions.

The selected (input) T cell compositions were used to generate CD4+ and CD8+ therapeutic T cell compositions substantially as described in Example 6. The number of doublings of the generated cell compositions also was determined based on total nuclear count (TNC) of cells as described in Example 6. The correlation between phenotypic attributes of cells in the selected (input) T cell compositions and the number of doublings in the process for producing the therapeutic composition was determined. As shown in FIG. 12, a higher percentage of effector memory CD4+ T cells identified by negative staining for CD45RA and CCR7 (CD45RA-CCR7−) in the enriched CD4+(input) compositions correlated positively with the number of population doublings during production of the therapeutic T cell composition. A similar result was observed for CD8+ T cells.

The above results are supportive of an approach that includes reducing the percentage of effector memory T cells and/or enriching for T cells positive for markers of naïve-like or central memory cell subsets in an input composition used in a process for producing an engineered T cell composition. Consistent with the results above, such an approach may improve one or more features of an engineered therapeutic T cell composition, such as reducing patient-to-patient variability, lowering the number of population doublings in a process for producing an engineered therapeutic T cell composition and/or increasing the likelihood a subject may exhibit PFS that is durable.

Example 8: Kinetics of Non-Expanded and Expanded Engineering Processes

Human T cells (CD4+ and CD8+) were engineered with a chimeric antigen receptor (CAR) by a variety of manufacturing process, including processes that did not include a cultivation step for expansion (non-expansion cohort) and processes that did include a cultivation step for expansion (expansion cohort). A composite analysis of cells produced during and after manufacturing runs by the various processes was carried out. The manufacturing runs for producing engineered T cell compositions included at-scale runs as described in Example 8 as well as processes as described below. The manufacturing runs also included scale-down models (SDMs) that were carried out substantially the same as the manufacturing runs but in which a lower number of T cells were used in the process for engineering cells. In general, the scale-down manufacturing runs shared the process activities described in Table E3.

In the analyzed processes, the T cells were engineered with either an anti-CD19 CAR or an anti-BCMA CAR. The exemplary anti-CD19 CAR contained an anti-CD19 scFv derived from a murine antibody FMC63, an immunoglobulin spacer, a transmembrane domain derived from CD28, a costimulatory region derived from 4-1BB, and a CD3-zeta intracellular signaling domain. The vector also encoded a truncated receptor molecule that served as a surrogate marker for CAR expression that was separated from the CAR construct by a T2A sequence. The exemplary anti-BCMA CAR contained an scFv antigen-binding domain specific for BCMA, a CD28 transmembrane region, a 4-1BB costimulatory signaling region, and a CD3-zeta derived intracellular signaling domain. The vector also encoded a truncated receptor molecule that served as a surrogate marker for CAR expression that was separated from the CAR construct by a T2A sequence.

The processes included stimulation of the T cells either with anti-CD3/anti-CD28 paramagnetic beads or with anti-CD3/anti-CD28 Fab-conjugated oligomeric streptavidin mutein reagents. The oligomeric reagent contained a polymer of a streptavidin mutein designated STREP-TACTIN® M2 (a streptavidin homo-tetramer containing the mutein sequence of amino acids set forth in SEQ ID NO:73 (International published app. No. WO2018/197949). The streptavidin mutein is also described in U.S. Pat. No. 6,103,493 and Voss and Skerra (1997) Protein Eng., 1:975-982, and Argarana et al. (1986) Nucleic Acids Research, 1871-1882). Stimulatory agents (anti-CD3 and anti-CD28 Fab fragments) were multimerized by reversible binding to oligomeric streptavidin mutein reagent. Anti-CD3 and anti-CD28 Fab fragments were reversibly bound to the streptavidin mutein oligomer via a streptavidin peptide-binding partner fused to each Fab fragment. The anti-CD3 Fab fragment was derived from the CD3 binding monoclonal antibody produced by the hybridoma cell line OKT3 (ATCC® CRL-8001™; see also U.S. Pat. No. 4,361,549), and contained the heavy chain variable domain and light chain variable domain of the anti-CD3 antibody OKT3 described in Arakawa et al J. Biochem. 120, 657-662 (1996). These sequences are set forth in SEQ ID NOs: 93 and 94, respectively. The anti-CD28 Fab fragment was derived from antibody CD28.3 (deposited as a synthetic single chain Fv construct under GenBank Accession No. AF451974.1; see also Vanhove et al., BLOOD, 15 Jul. 2003, Vol. 102, No. 2, pages 564-570) and contained the heavy and light chain variable domains of the anti-CD28 antibody CD28.3 set forth in SEQ ID NOS: 91 and 92, respectively. The Fab fragments were individually fused at the carboxy-terminus of their heavy chain to a streptavidin peptide-binding sequence containing a sequential arrangement of two streptavidin binding modules having the sequence of amino acids SAWSHPQFEK(GGGS)2GGSAWSHPQFEK (SEQ ID NO: 79). The peptide tagged Fab fragments were recombinantly produced (see International Patent App. Pub. Nos. WO 2013/011011 and WO 2013/124474). Binding of the peptide-tagged anti-CD3 and anti-CD28 to the oligomeric strepaviding mutein reagent can be disrupted, or reversed, by addition of D-biotin. D-biotin competes with the strep-tag on the agents for binding to the binding partner on the streptavidin mutein, thereby disrupting binding.

Cells were collected at various times during and at the end of the manufacturing runs, and were counted, and assessed for viability and by flow cytometry following staining with antibodies recognizing surface markers including CD4, CD8, CCR7, CD27, and CD45RA.

TABLE E3

| Day of Process | Summary of Activity |
|---|---|
| Day 1 | Cells are stimulated with stimulatory reagent (e.g. anti-CD3/anti-CD28 paramagnetic beads or anti-CD3/anti-CD28 Fab-conjugated oligomeric streptavidin mutein reagents) |
| Day 2 | Cells are transduced by spinoculation with lentivirus encoding a CAR (e.g. anti-CD19 CAR or anti-BCMA CAR) |
| Day 3 | For non-expansion cohort, biotin is added for cells stimulated with anti-CD3/anti-CD28 Fab-conjugated oligomeric streptavidin mutein reagents |
| Day 4 | Cells are in recovery |
| Day 5 | For non-expansion cohort, cells activated with anti-CD3/anti-CD28 paramagnetic beads, cells are debeaded<br>Cells are harvested as a non-expanded cohort; cells are washed in formulation buffer and cryopreserved |
| Day 5 | For expansion cohort, cells are transferred to a shaking incubator |
| Day 7 | For cells in expansion cohort activated with anti-CD3/anti-CD28 Fab conjugated oligomeric streptavidin mutein reagents, biotin is added |
| Day 9 | For expansion cohort, cells activated with anti-CD3/anti-CD28 paramagnetic beads, cells are debeaded<br>Cells are harvested as an expanded cohort; cells are washed in formulation buffer and cryopreserved |

A. T cell Engineering Processes

T cell compositions produced using different non-expanded processes that differed in various features, including the starting source of cells (cryopreserved apheresis or fresh apheresis), concentration of oligomeric stimulatory reagent, and number of cells used for stimulation, were compared. T cell compositions also were produced in which cells were further cultivated for expansion. The processes were carried out on healthy donors or on patient donors.

1. Non-Expanded Processes

Leukapheresis samples were collected from human donors and washed. CD4+ and CD8+ cells were selected directly by immunoaffinity-based selection from the leukapheresis samples which had not been cryopreserved. After selection, the separate CD4+ and CD8+ T cell compositions were cryopreserved and then were thawed, and then the selected CD4+ and CD8+ T cells were mixed at a ratio of 1:1 of viable CD4+ T cells to viable CD8+ T cells to produce an input composition. About $600\times10^6$ cells from the mixed input cell composition (about $300\times10^6$ CD4+ and $300\times10^6$ CD8+) were stimulated by incubation with 0.8 μg per $1\times10^6$ cells anti-CD3/anti-CD28 Fab conjugated oligomeric streptavidin mutein reagents generated as described above in this Example. The stimulation was carried out for between 18-30 hours (24±6 hours) in serum-free complete media containing basal media (e.g., CTS™ OpTmizer basal media, Thermo Fisher), a T cell supplement (e.g., 2.6% OpTmizer® T-cell Expansion Supplement, Thermo Fisher), an immune cell serum replacement (e.g., 2.5% CTS™ Immune Cell Serum Replacement), 2 mM L-glutamine, a dipeptide form of L-glutamine (e.g., 1.0% Glutamax™ Thermo Fisher), recombinant 100 IU/mL IL-2, recombinant 600 IU/mL IL-7, and recombinant 100 IU/mL IL-15. After stimulation, up to $300\times10^6$ cells were transduced by spinoculation with a lentiviral vector encoding either the exemplary anti-BCMA CAR or the exemplary anti-CD19 CAR.

After spinoculation, the cells were washed and resuspended at a density of up to about $0.75\times10^6$ cells/mL in basal media (e.g., CTS™ OpTmizer basal media, Thermo Fisher) with 2 mM glutamine but without the addition of recombinant cytokines, and incubated at about 37.0° C. in an incubator. After about 48 hours±6 hours after initiation of the stimulation (about 24 hours after beginning the incubation), 1.0 mM D-biotin was added and mixed with the cells to dissociate anti-CD3 and anti-CD28 Fab reagents from the oligomeric streptavidin reagent. The cells were further incubated for an additional about 48 hours (about 96 hours±6 hours after initiation of stimulation or until day 5 of the process), and then were formulated with a cryoprotectant.

In another process, leukapheresis samples were collected from human donors, washed and cryopreserved. The cryopreserved leukapheresis samples were thawed, and separate compositions of CD4+ and CD8+ cells were selected from each sample by immunoaffinity-based selection, and then the CD4+ and CD8+ T cells were mixed with the goal to produce an input composition of up to about $900\times10^6$ viable CD4+ and CD8+ T cells, in which the ratio of viable CD4+ T cells to viable CD8+ T cells varied. The mixed input cell composition were stimulated by incubation with 1.2 μg per $1\times10^6$ cells anti-CD3/anti-CD28 Fab conjugated oligomeric streptavidin mutein reagents generated as described above in this Example (where 1.2 μg of the oligomeric stimulatory reagent includes 0.9 μg of oligomeric particles and 0.15 μg of anti-CD3 Fabs and 0.15 μg of anti-CD28 Fabs). The stimulation was carried out for between 16-24 hours (20±4 hours) in the same serum-fee complete media described above. After stimulation, up to about $600\times10^6$ cells were transduced by spinoculation with a lentiviral vector encoding a CAR, in this case the same exemplary anti-BCMA CAR or exemplary anti-CD19 CAR described above. In this study, the cells that were incubated with the higher concentration of the oligomeric streptavidin mutein reagents exhibited an improved transduction efficiency (data not shown). After the spinoculation in this process, the cells were washed and resuspended at a density of $0.75\times10^6$ cells/mL in basal media ((e.g., CTS™ OpTmizer basal media, Thermo Fisher) with 2 mM glutamine and 2.6% T cell supplement (e.g. 2.6% OpTmizer® supplement, ThermoFisher) without the addition of recombinant cytokines, and incubated at about 37.0° C. in an incubator. After about 48 hours±6 hours after initiation of the stimulation (about 24 hours after beginning the incubation), 1.0 mM D-biotin was added and mixed with the cells to dissociate anti-CD3 and anti-CD28 Fab reagents from oligomeric streptavidin reagent. The cells were further incubated for an additional about 48 hours (about 96 hours±6 hours after initiation of stimulation or until day 5 of the process), and then were formulated with a cryoprotectant.

2. Expanded Process

In one process, anti-CD19 CART cells were engineered by the non-expanded process described above.

In another process, separate compositions of CD4+ and CD8+ cells were selected from human leukapheresis samples and were cryofrozen. The selected cell compositions were subsequently thawed and mixed at a ratio of 1:1 of viable CD4+ T cells to viable CD8+ T cells. Approximately $300\times10^6$ T cells ($150\times10^6$ CD4 and $150\times10^6$ CD8+ T cells) of the mixed composition were stimulated in the presence of paramagnetic polystyrene-coated beads with attached anti-CD3 and anti-CD28 antibodies at a 1:1 bead to cell ratio in serum free media containing recombinant IL-2, IL-7 and IL-15 for between 18 to 30 hours. Following the incubation, approximately $100\times10^6$ viable cells from the stimulated cell composition were concentrated in the serum free media containing recombinant IL-2, IL-7 and IL-15 The cells were transduced, by spinoculation at approximately 1600 g for 60 minutes, with a lentiviral vector encoding an exemplary CAR, in this case the exemplary anti-BCMA CAR described above. After spinoculation, the cells were resuspended in the serum free media containing recombinant IL-2, IL-7 and IL-15, and incubated for about 18 to 30 hours at about 37° C. The cells were then cultivated for expansion by transfer to a bioreactor (e.g. a rocking motion bioreactor) in about 500 mL of the exemplary serum free media containing twice the concentration of IL-2, IL-7 and IL-15 as used during the incubation and transduction steps. When a set viable cell density was achieved, perfusion was initiated, where media was replaced by semi-continuous perfusion with continual mixing. The cells were cultivated the next day in the bioreactor until a threshold cell density of about $3\times10^6$ cells/mL was achieved, which typically occurred in a process involving 6-7 days of expansion. The anti-CD3 and anti-CD28 antibody conjugated paramagnetic beads were removed from the cell composition by exposure to a magnetic field. The cells where then collected, formulated and cryopreserved.

B. Process Metrics

Figure 13A:
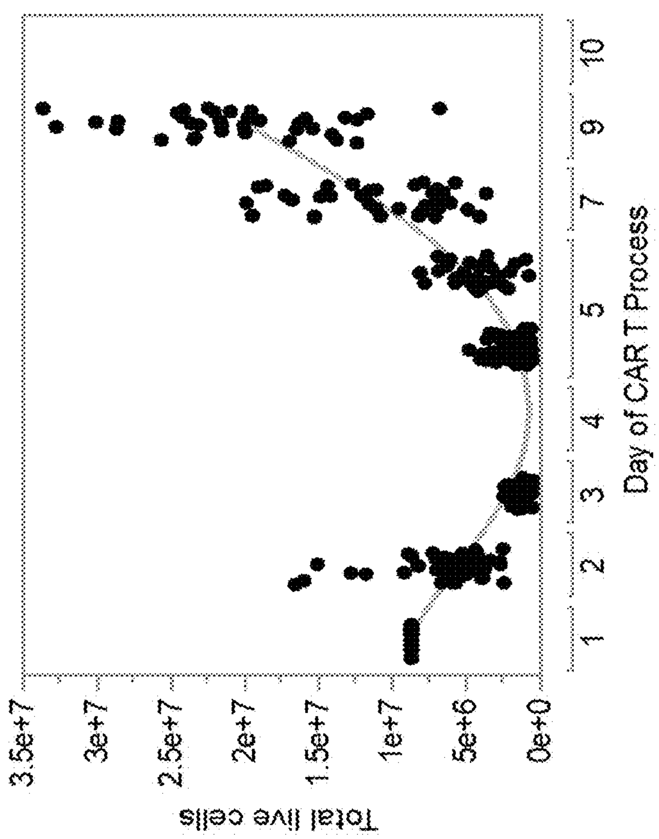
FIGS. 13A-D show total live cells (FIG. 13A), viability (FIG. 13B), and phenotype (FIGS. 13C and 13D) during and after manufacturing runs, including a variety of non-expanded and expanded engineering processes.
Figure 13B:
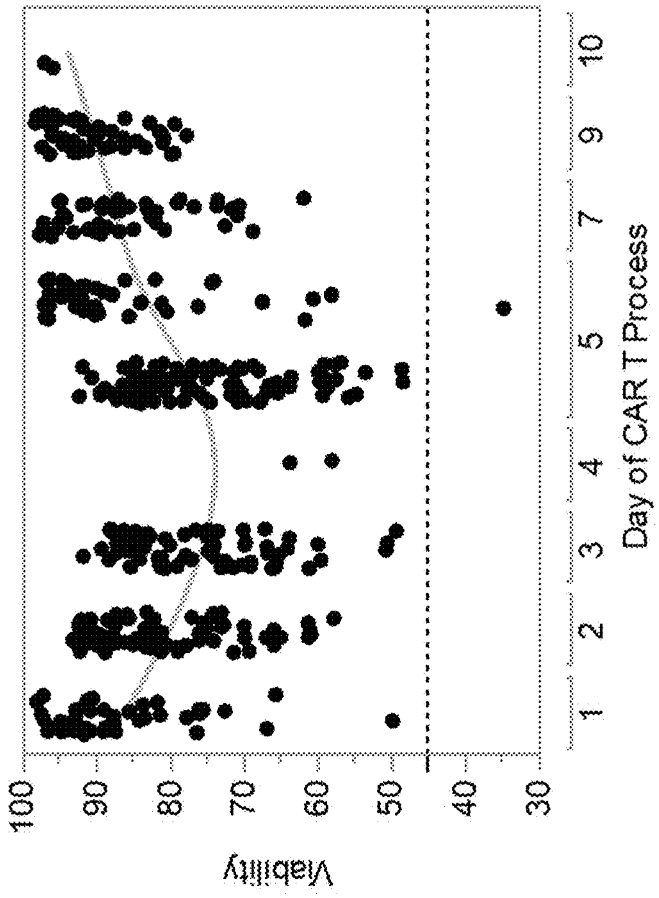

Process metrics such as total live cells (FIG. 13A) and viability (FIG. 13B) were monitored during the manufacturing runs. As shown in FIG. 13A, minimal expansion of cells was observed at the day 5 time point, with robust expansion beginning after Day 5. FIG. 13B shows an initial decrease in viability of cells in the manufacturing runs which began to increase as the cells started to expand after Day 5 of the processes.

Figure 13C:
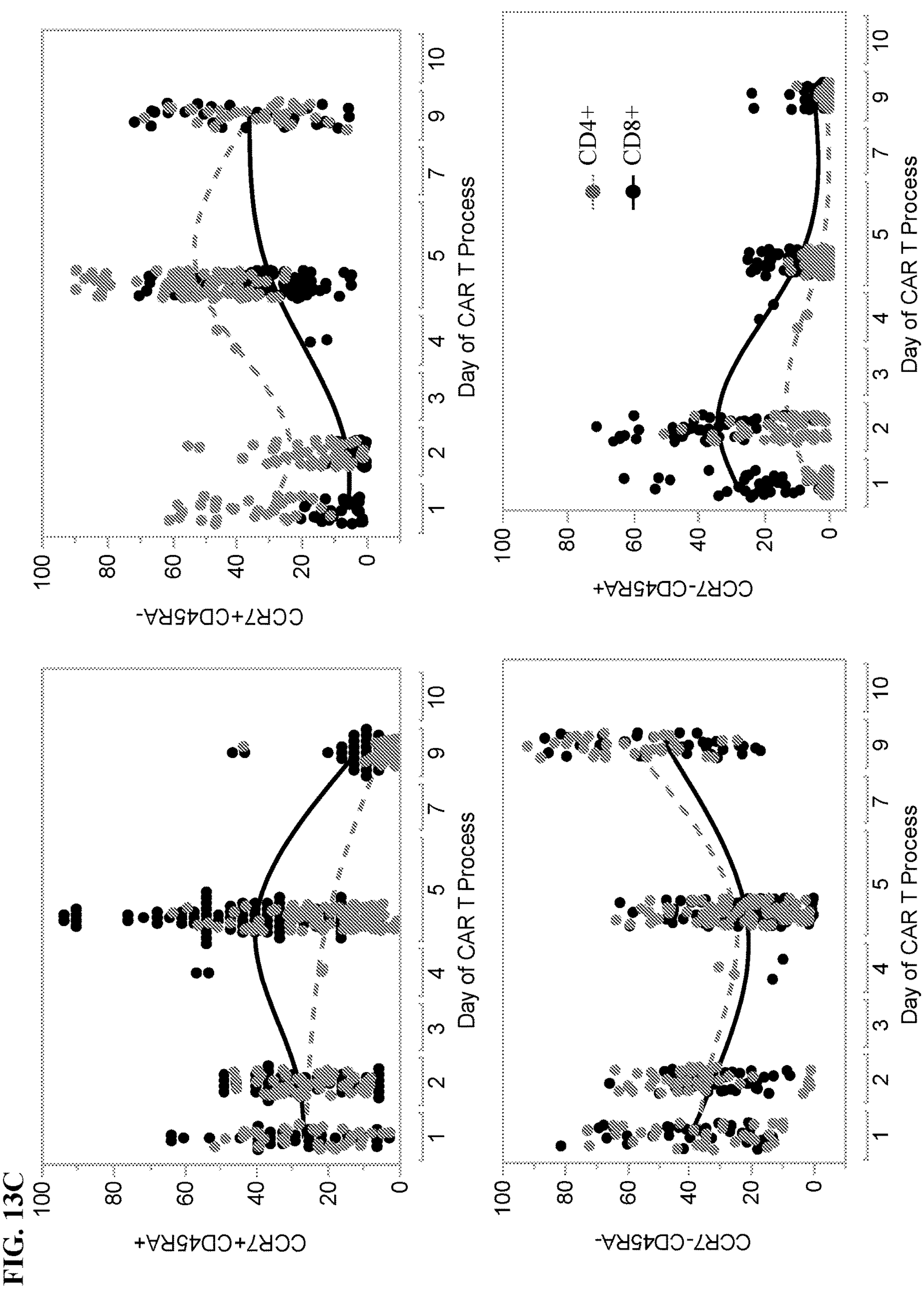
Figure 13D:
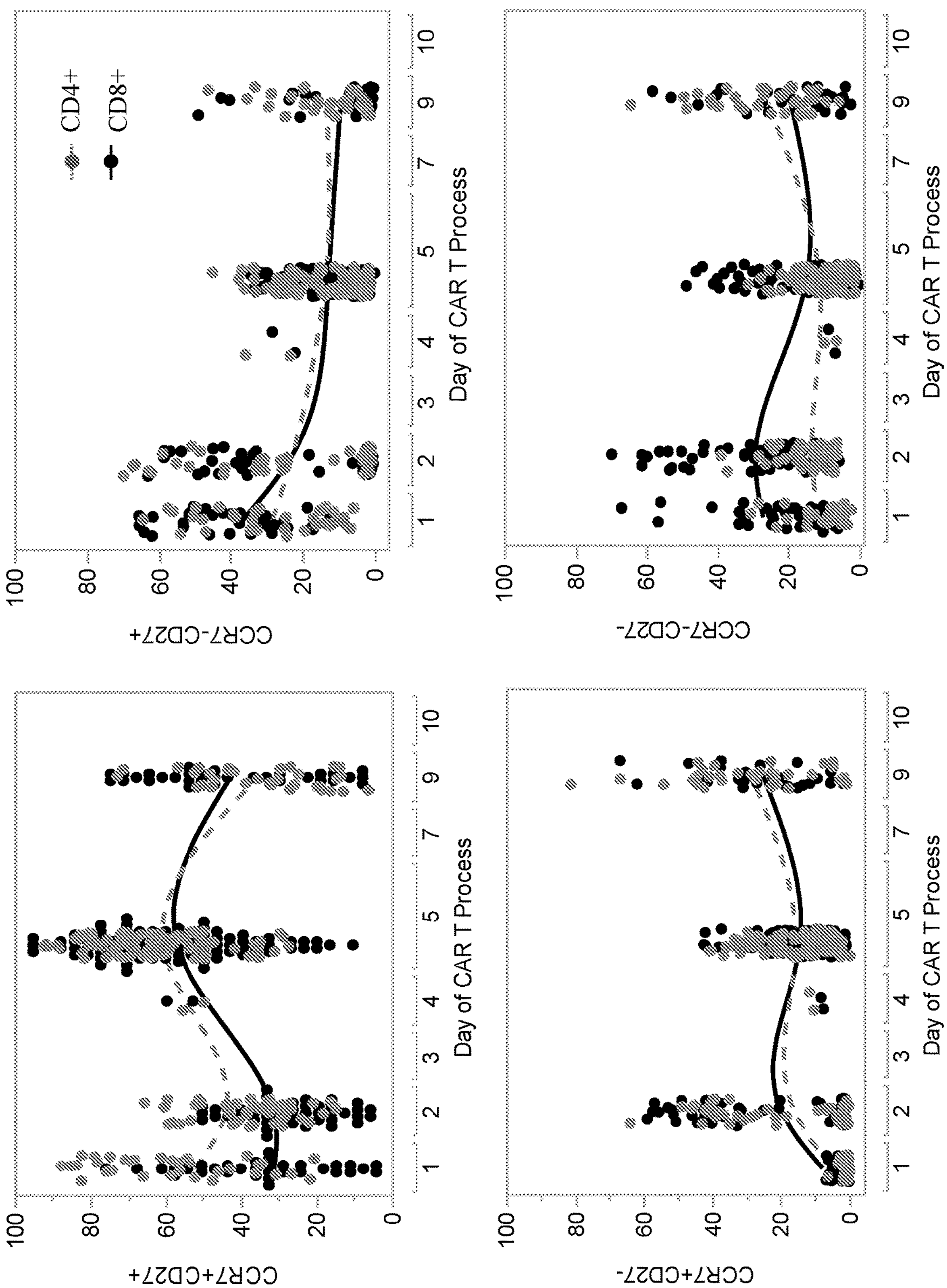
Figure 14:
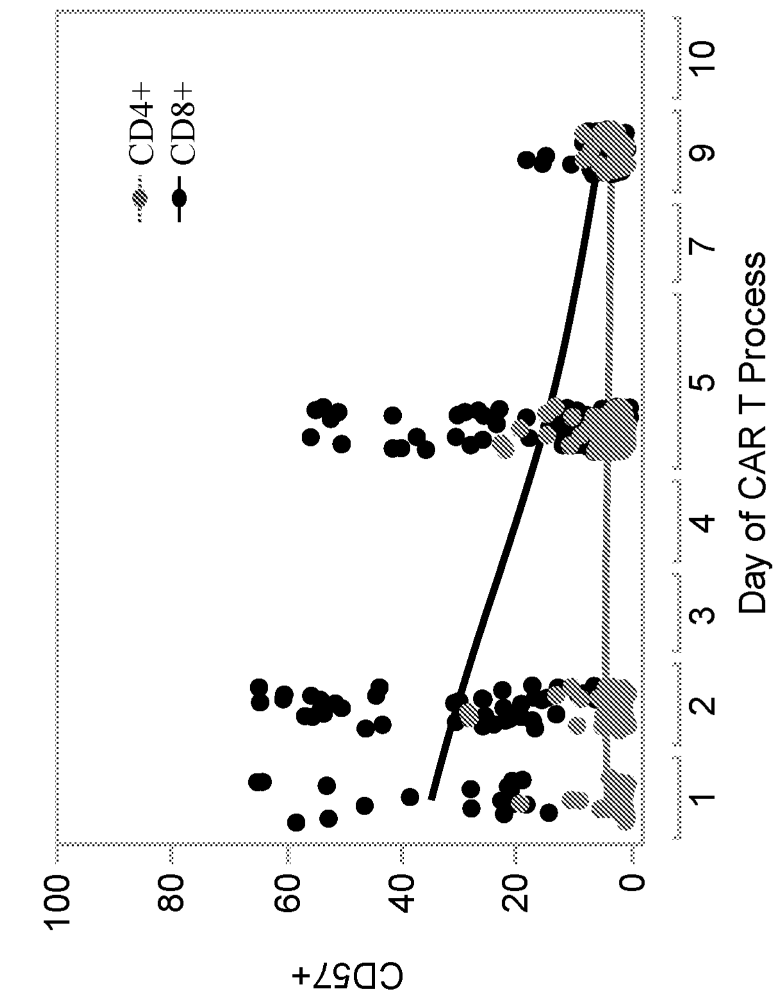
FIG. 14 shows the percentage of CD57+ cells in CD4+ and CD8+ cell populations during and after manufacturing runs, including a variety of non-expanded and expanded engineering processes.

Results of comparison of memory/differentiation phenotype at different time points in the manufacturing runs are shown in FIG. 13C (by CD5RA and CCR7 expression) and FIG. 13D (by CD27 and CCR7 expression). As shown, assessment of cells early during the manufacturing runs showed that cells at about day 5 were substantially more enriched for less differentiated cell types, such as CCR7+ CD45RA− or CCR7+ CD27+ cells, compared to cells both at earlier times in the process (e.g. Day 1 or Day 2) or later times in the process (e.g. Day 9). The number of CD57+ cells was analyzed over the duration of the manufacturing process. As shown in FIG. 14, the number of CD8+ CD57+ cells decreased over the course of the manufacturing process, while the number of CD4+ CD57+ cells remained low throughout.

Without wishing to be bound by theory, the results indicate that the exemplary manufacturing process may reduce the number of CD57+ cells in donor cell compositions, thereby reducing variability within and among cell compositions derived from different donors.

Example 9: Titration of CD57+ or CD27+ Frequency Cells in Donor Input Compositions and Effect on Transduction, Immunophenotype, and Gene Editing Leukapheresis samples obtained from healthy human donors were subjected to immunoaffinity-based selection for cells surface positive for CD4 (CD4+) or CD8 (CD8+) to generate T cell compositions containing CD4+ and CD8+ cells. In some cases, the selected CD4+ and/or CD8+ T cell compositions were subjected to a further immunoaffinity-based selection for cells surface positive for CD57 (CD57+) or CD27 (CD27+) by ligand-bound beads to obtain enriched populations of CD57+ or CD27+ cells. T cell compositions containing CD4+ and CD8+ cells were then titrated with an enriched population of the CD57+ or CD27+ cells to obtain final input compositions containing defined percentages of CD57+ or CD27+ cells, and the effects of CD57+ or CD27+ frequency on transduction, immunophenotype, and gene editing were assessed. Input compositions having only undergone CD4+ and CD8+ selection (No titration; NT) served as controls.

A. Titration of CD57+ Frequency

Selected CD8+ T cell compositions from two healthy human donors (Donor 1 and Donor 2) were titrated with varying amounts of an enriched population of CD57+ cells, as described above, to produce donor CD8+ T cell compositions wherein 0%, 25%, 50%, 75%, or 100% of the CD8+ T cells were CD57+. Selected CD4+ T cell compositions from each donor were fully depleted of CD57+ cells. Each of the CD57 titrated CD8+ T cell compositions from a donor was then combined with a CD57 depleted CD4+ T cell composition from the same donor to produce input compositions for each donor comprising CD4+ and CD8+ T cells, wherein 0%, 25%, 50%, 75%, or 100% of the CD8+ T cells were CD57+. Titrations of CD57+ cells were confirmed by flow cytometry. As described above, input compositions generated to contain CD4+ and CD8+ cells, wherein neither of the CD4+ or CD8+ T cell compositions were subjected to CD57+ selection or titration ("NT"), served as controls.

The input compositions containing CD4+ and CD8+ cells were stimulated with an anti-CD3/anti-CD28 reagent and transduced with a viral preparation containing nucleic acid encoding an anti-CD19 CAR. In some cases, following stimulation (activation) with anti-CD3/anti-CD28 reagents, cells were also subjected to gene editing. After further incubation with recombinant IL-2, IL-7 and IL-15 cytokines for expansion of cells, donor compositions were assessed for immunophenotype, CD4:CD8 ratio, CAR expression, and gene editing efficiency at stimulation and/or following transduction.

Figure 15:
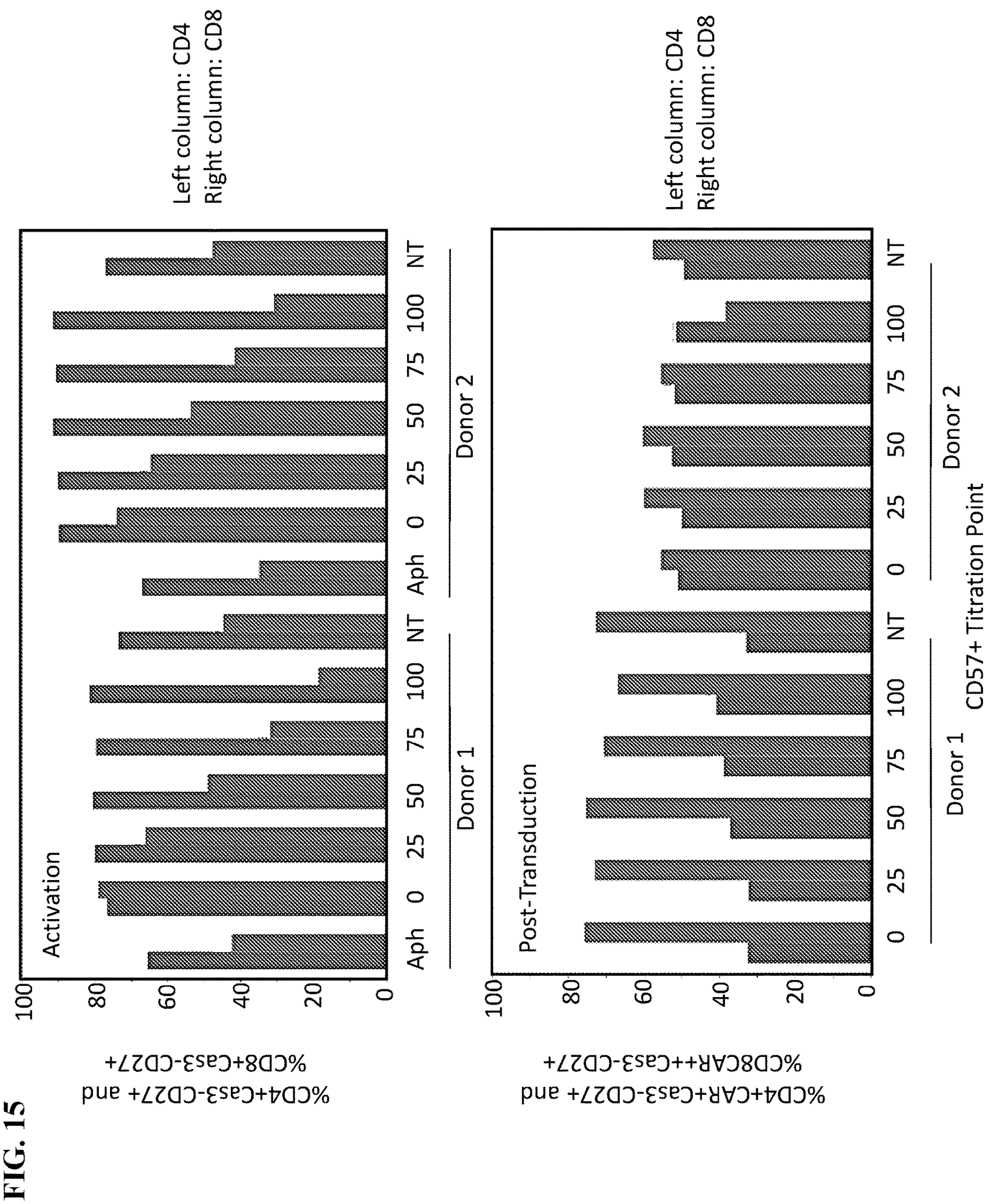
FIG. 15 shows the frequency of Caspase 3-negative, CD27-positive (Cas3−CD27+) cells in the CD4+ and CD8+ cellular compartments at activation (top panel) and following transduction (bottom panel) in CD57+ titrated compositions from Donor 1 and Donor 2. Left column: CD4+ cells; right column: CD8+ cells. NT: No CD57 titration.
Figure 16A:
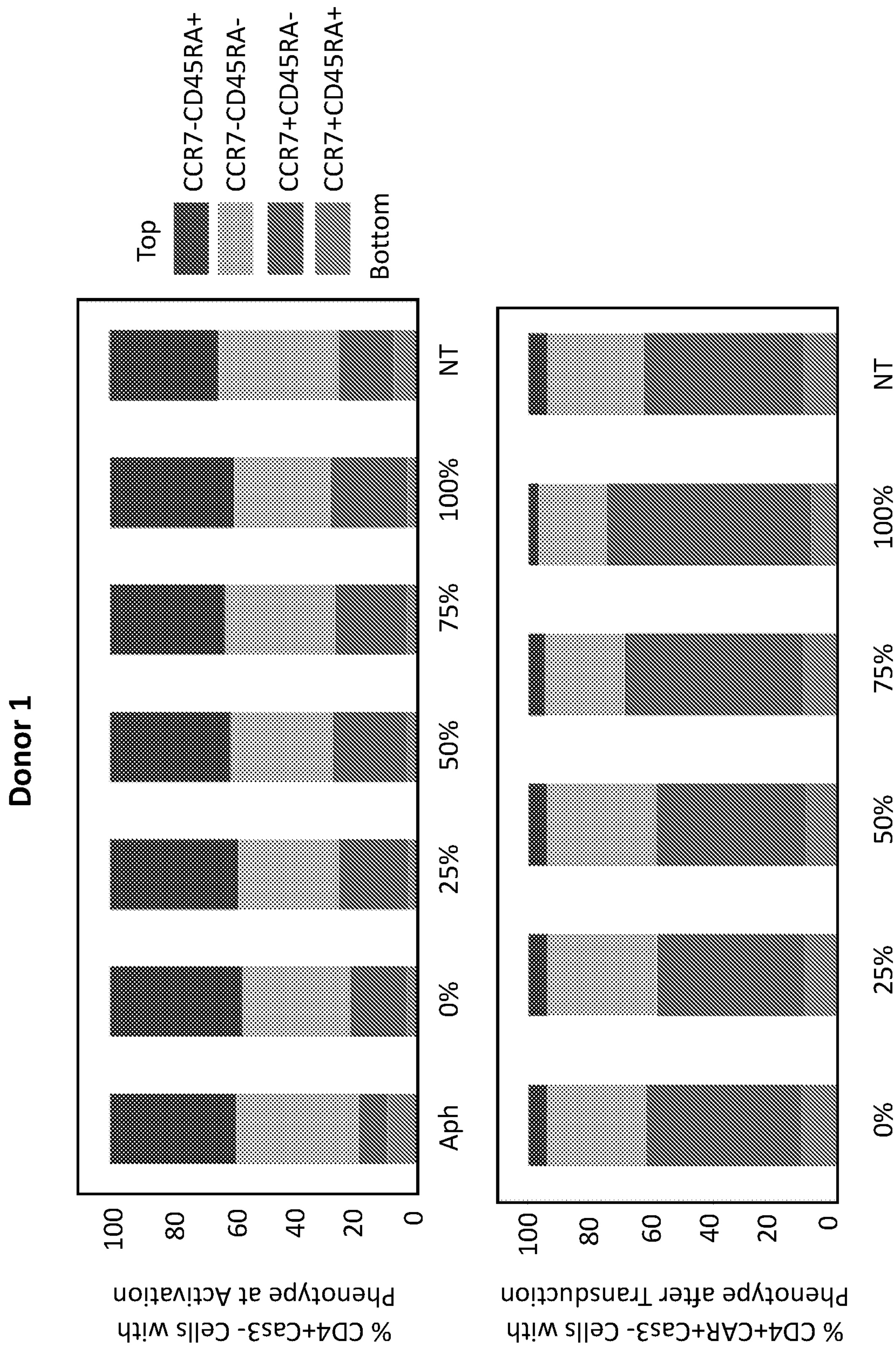
FIGS. 16 and 17 show the frequency of CCR7/CD45RA phenotypes of CD4+(FIGS. 16A and 17A) and CD8+(FIGS. 16B and 17B) cells from Donor 1 and Donor 2 CD57+ titrated compositions, respectively, at activation (top panels) and following transduction (bottom panels). Aph: apheresis sample; %: % CD57+ titrated cells; NT: No CD57 titration.
Figure 16B:
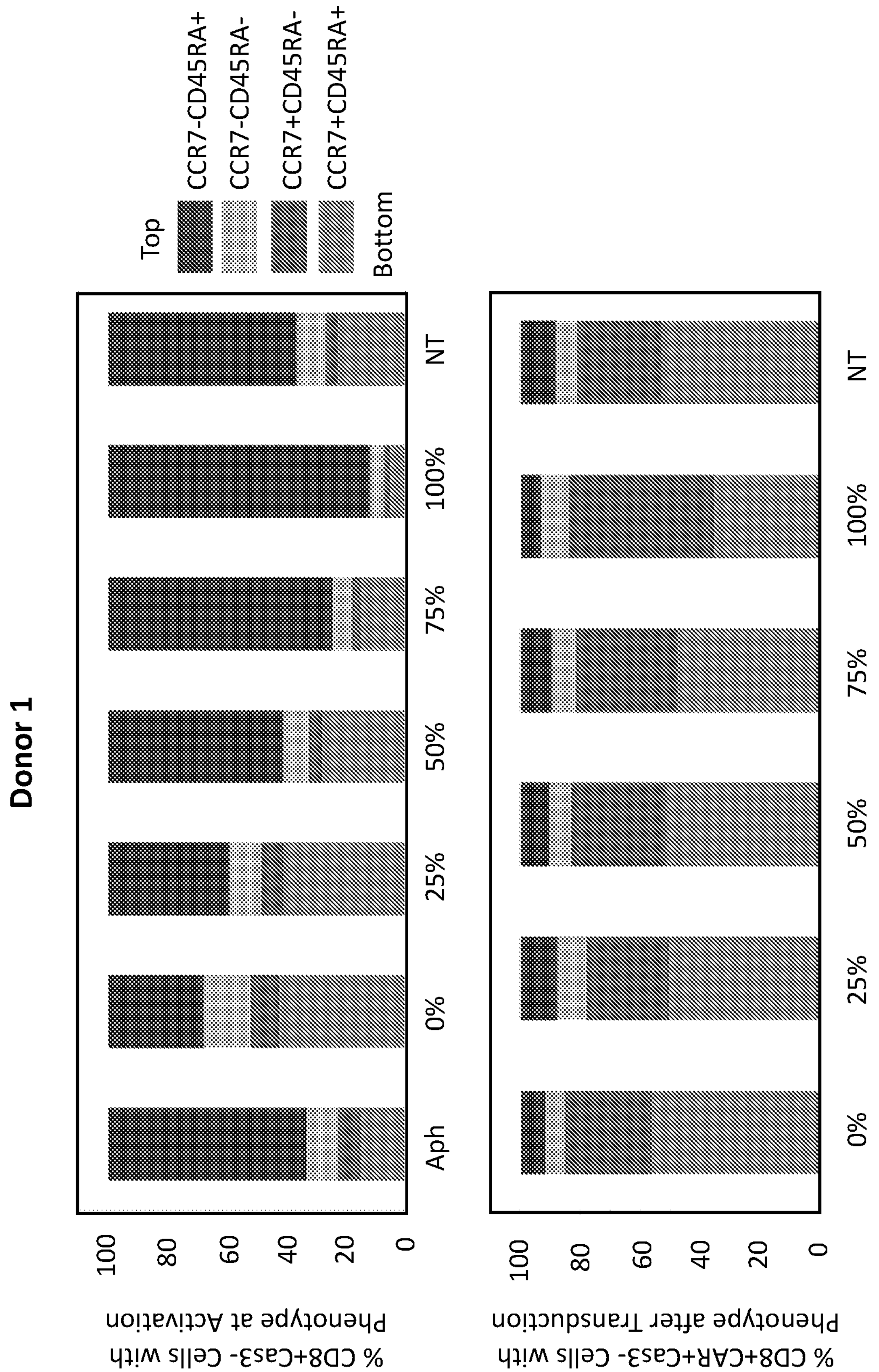
Figure 17A:
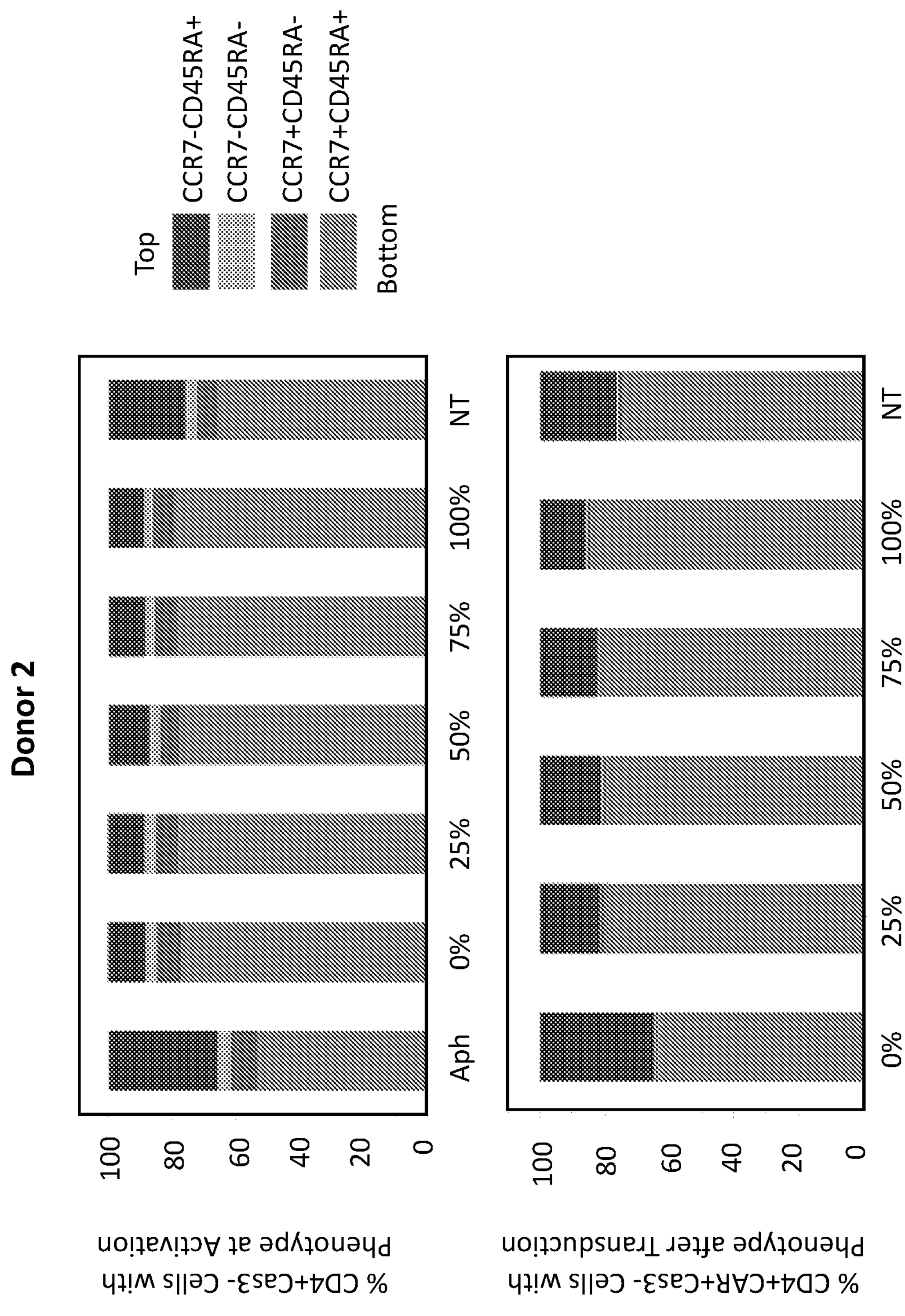
Figure 17B:
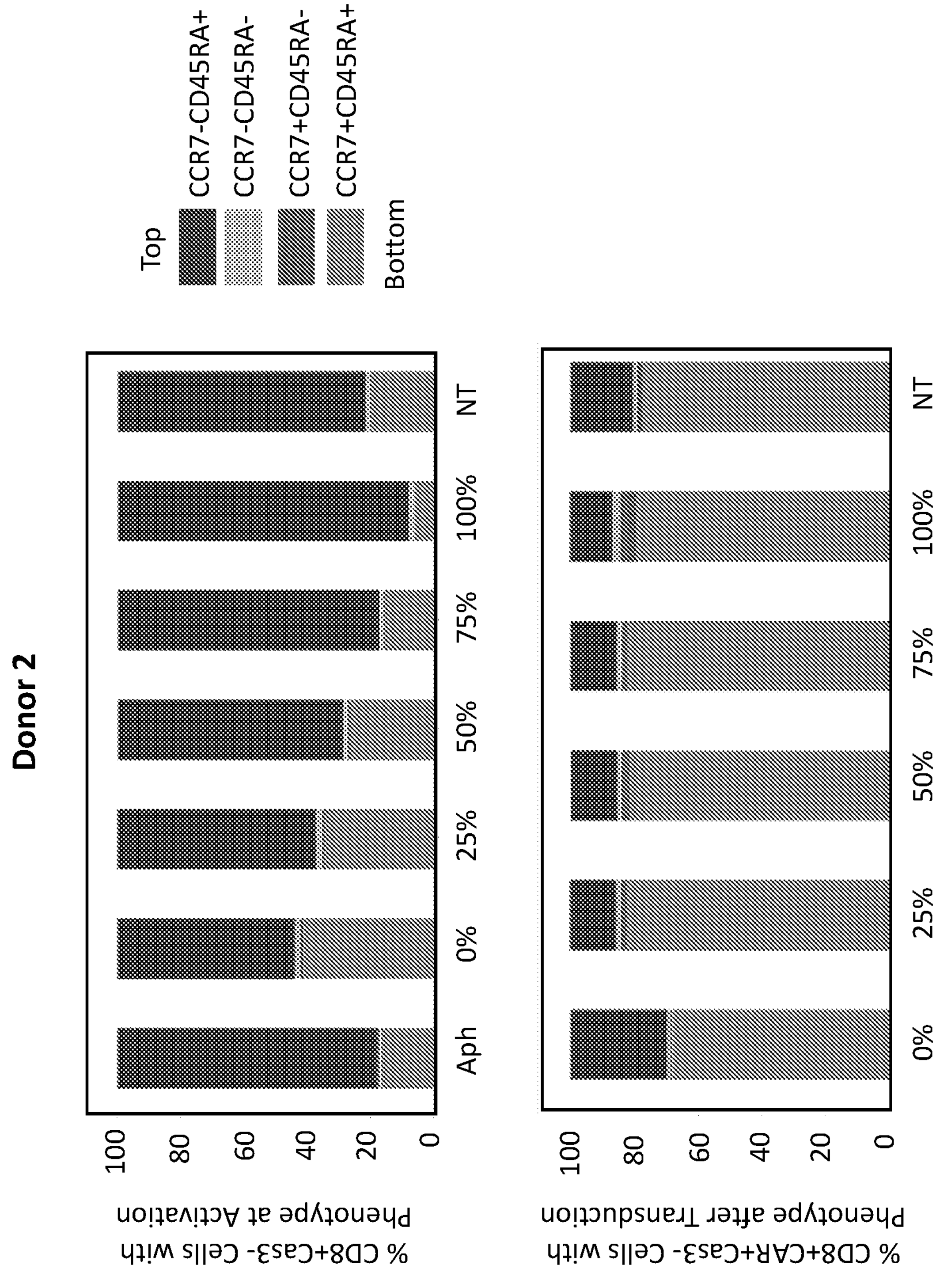
Figure 18A:
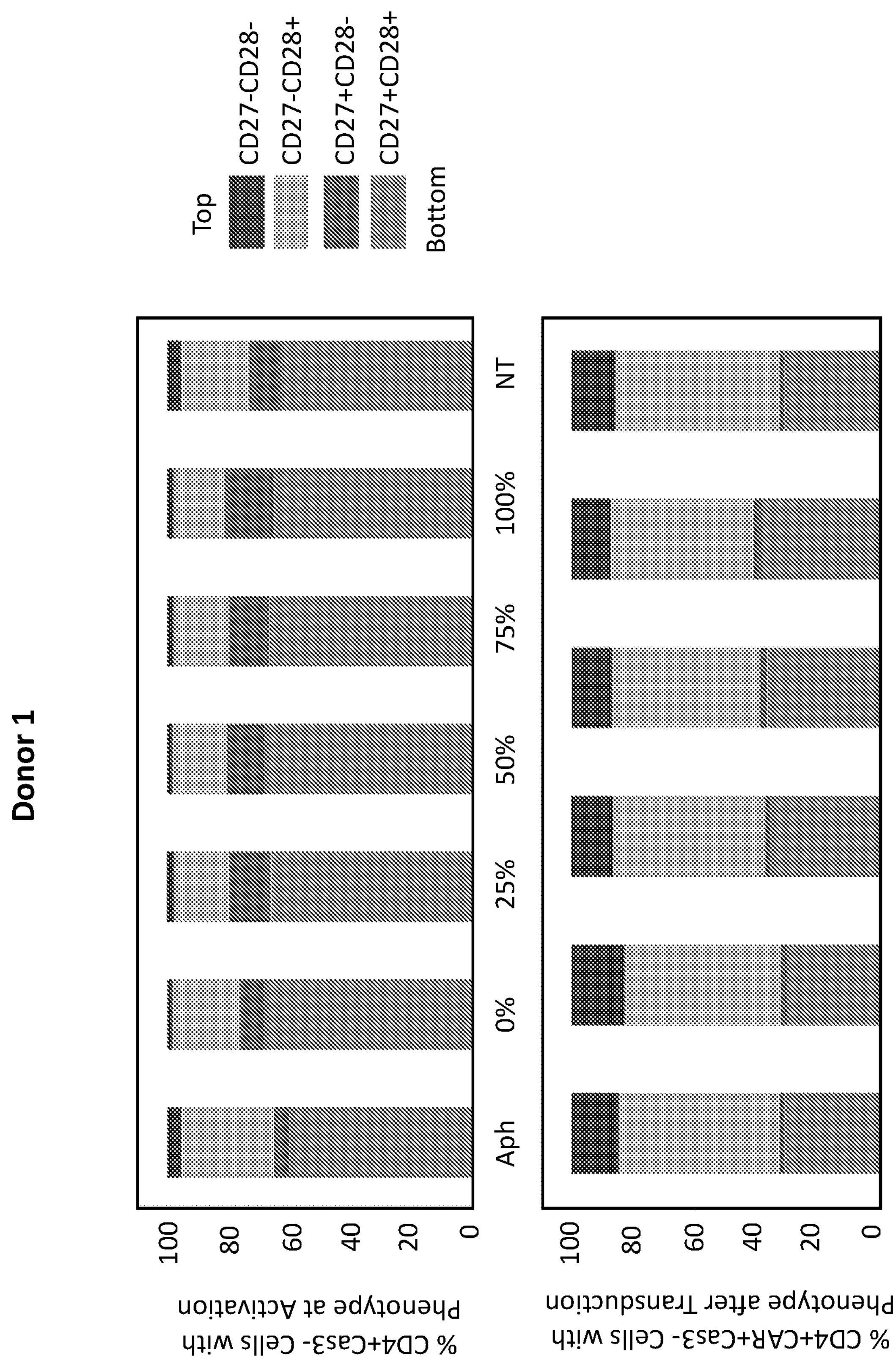
FIGS. 18 and 19 show the frequency of CD27/CD28 phenotypes of CD4+(FIGS. 18A and 19A) and CD8+(FIGS. 18B and 19B) cells from Donor 1 and Donor 2 CD57+ titrated compositions, respectively, at activation (top panels) and following transduction (bottom panels). Aph: apheresis sample; %: % CD57+ titrated cells; NT: No CD57 titration.
Figure 18B:
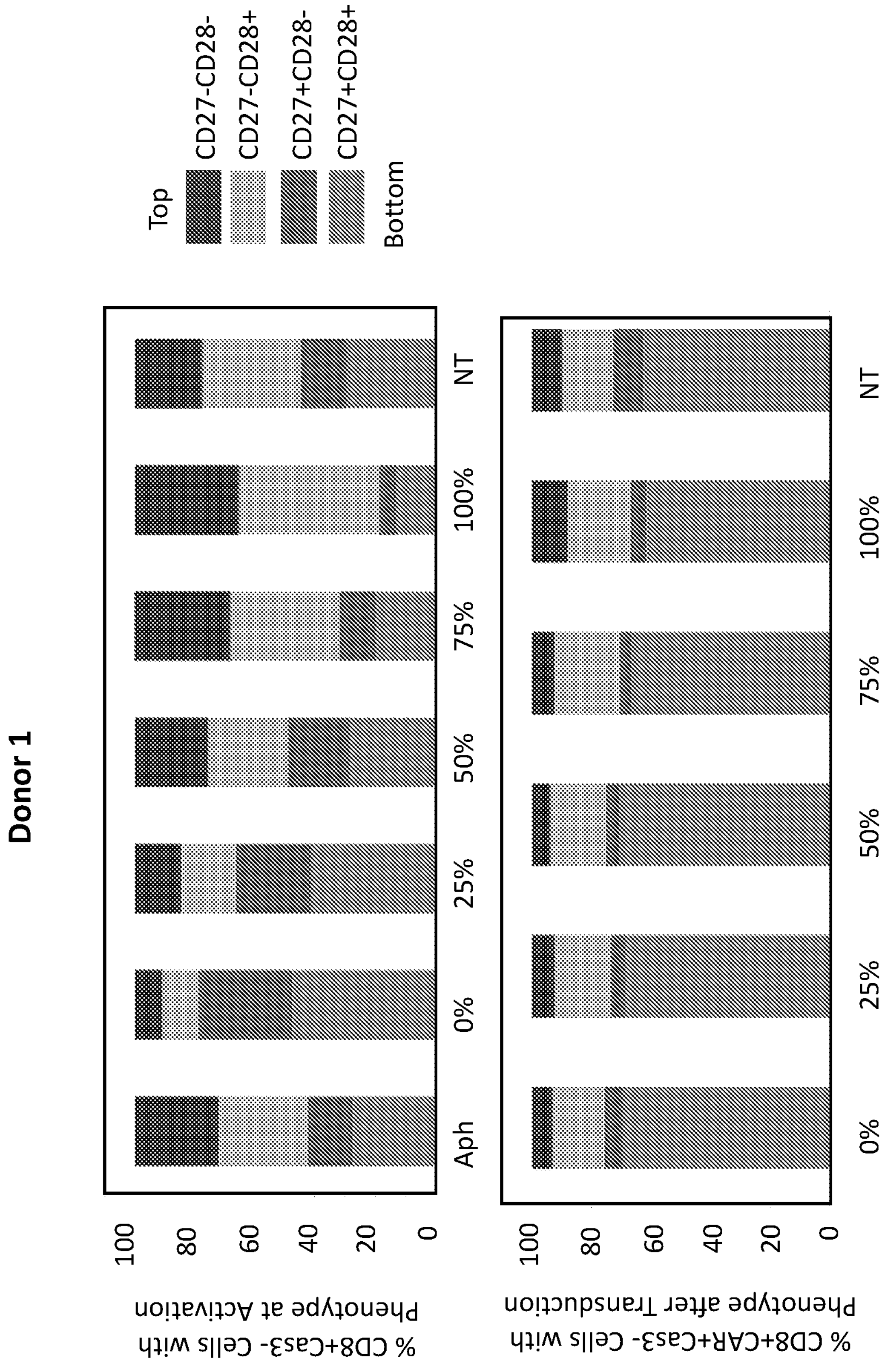
Figure 19A:
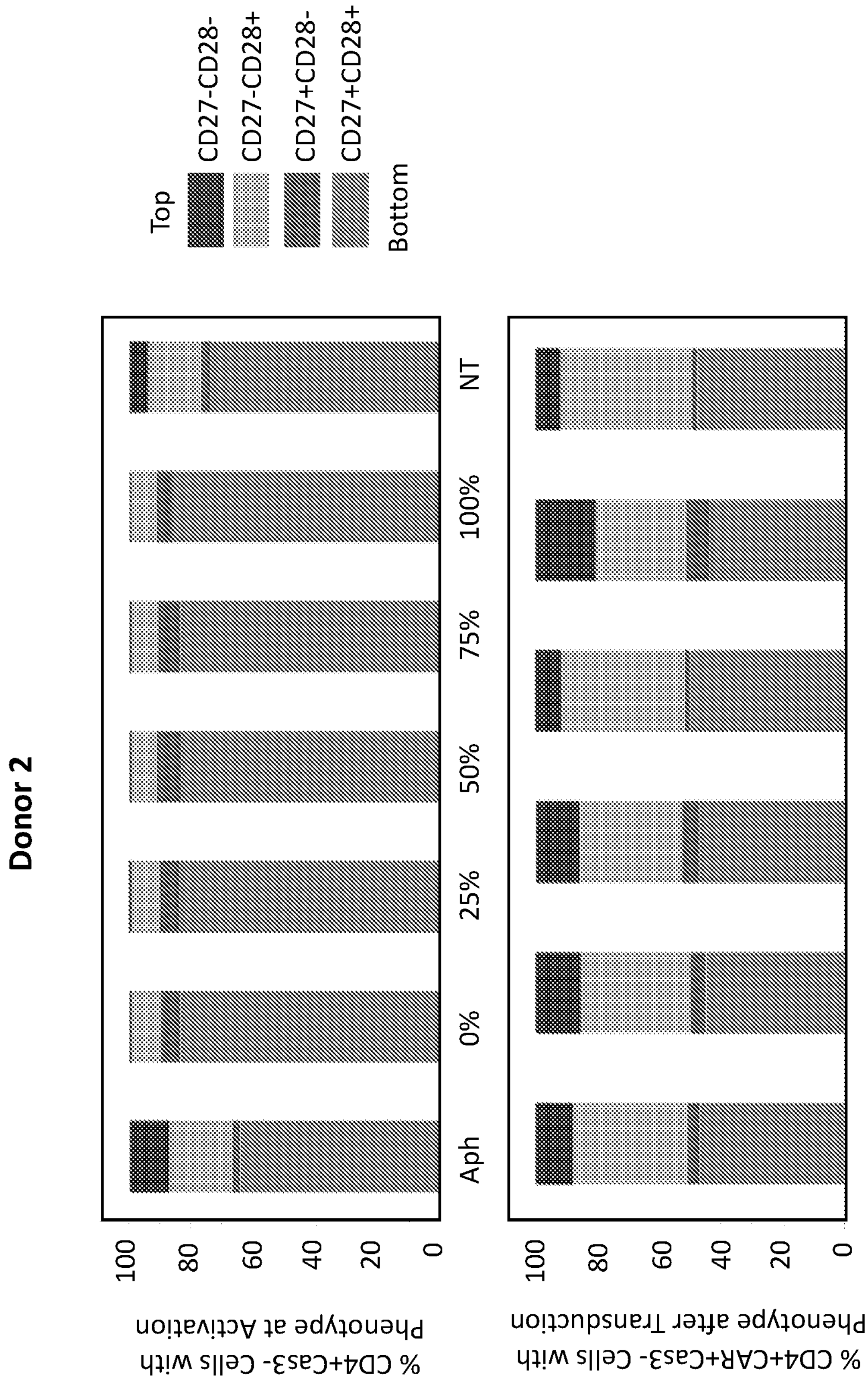
Figure 19B:
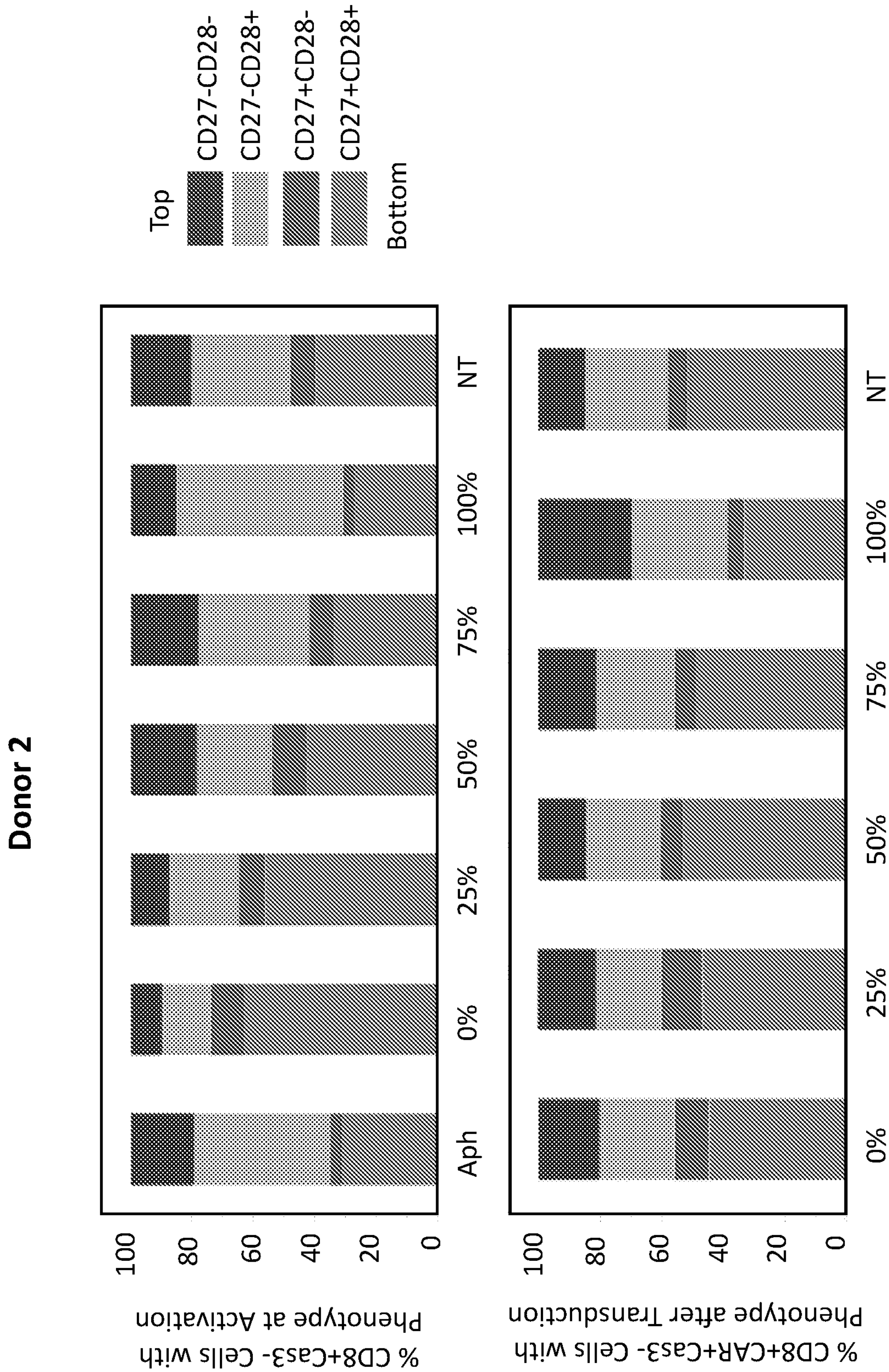
Figure 20A:
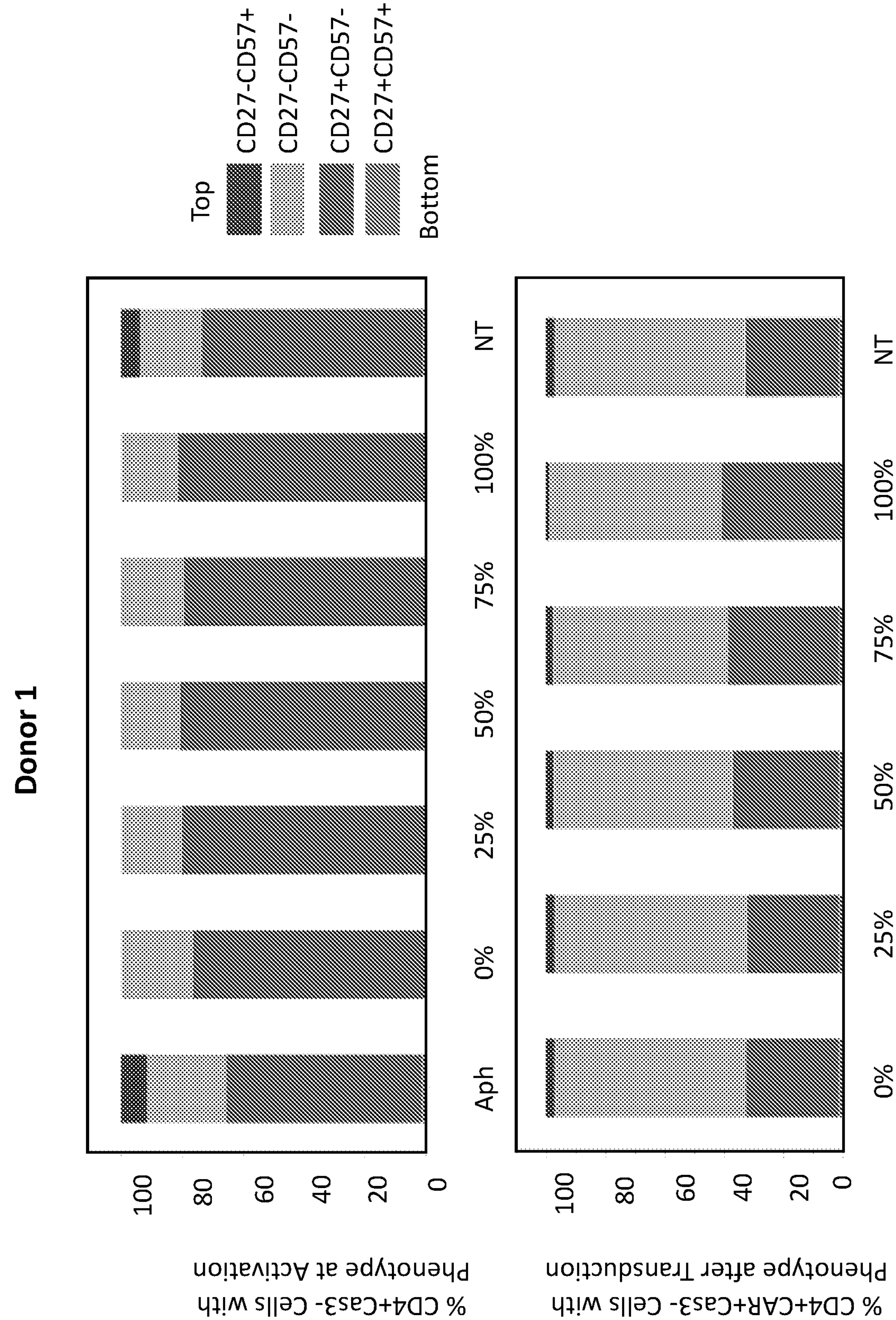
FIGS. 20 and 21 show the frequency of CD27/CD57 phenotypes of CD4+(FIGS. 20A and 21A) and CD8+(FIGS. 20B and 21B) cells from Donor 1 and Donor 2 CD57+ titrated compositions, respectively, at activation (top panels) and following transduction (bottom panels). Aph: apheresis sample; %: % CD57+ titrated cells; NT: No CD57 titration.
Figure 20B:
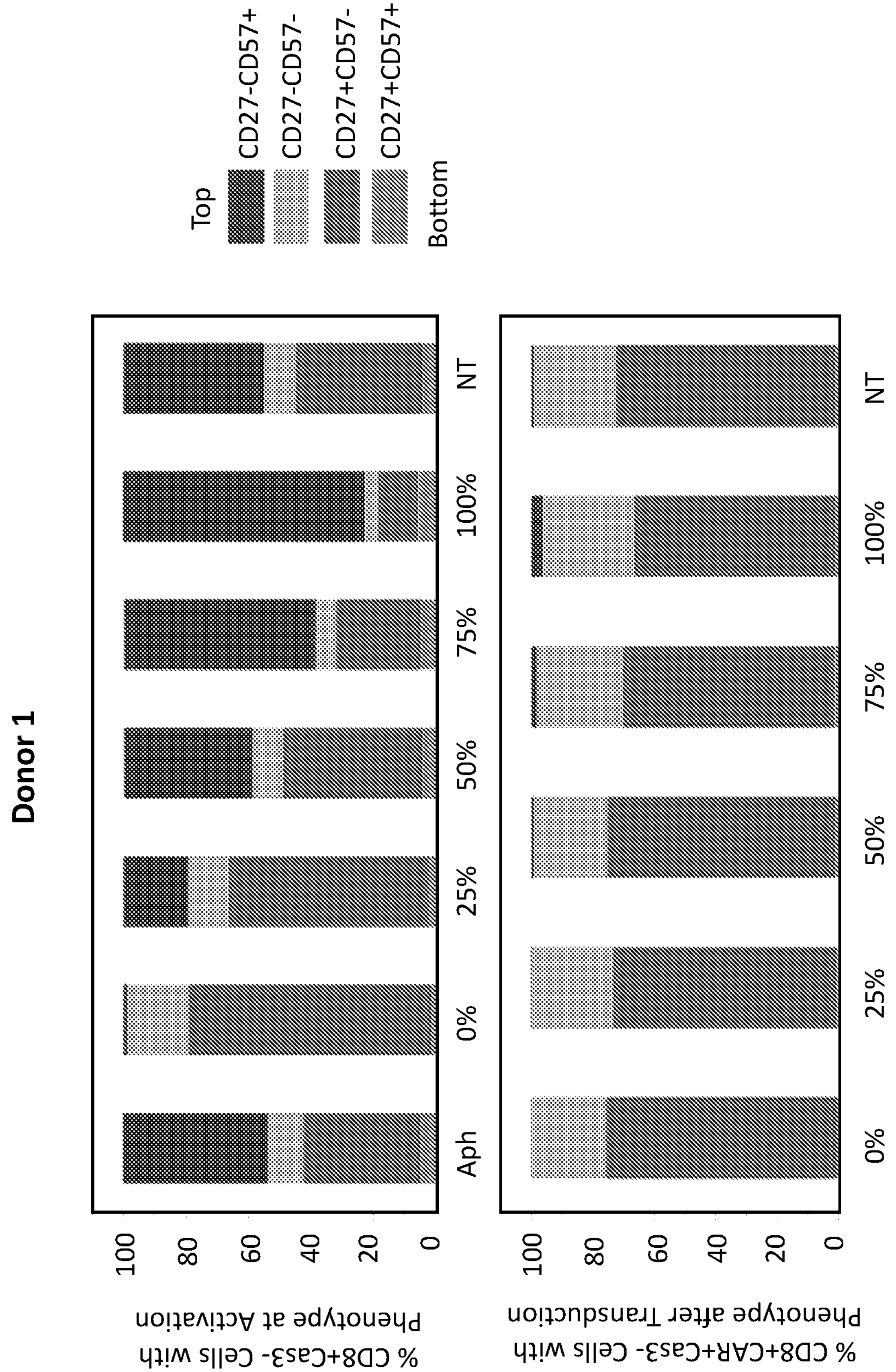
Figure 21A:
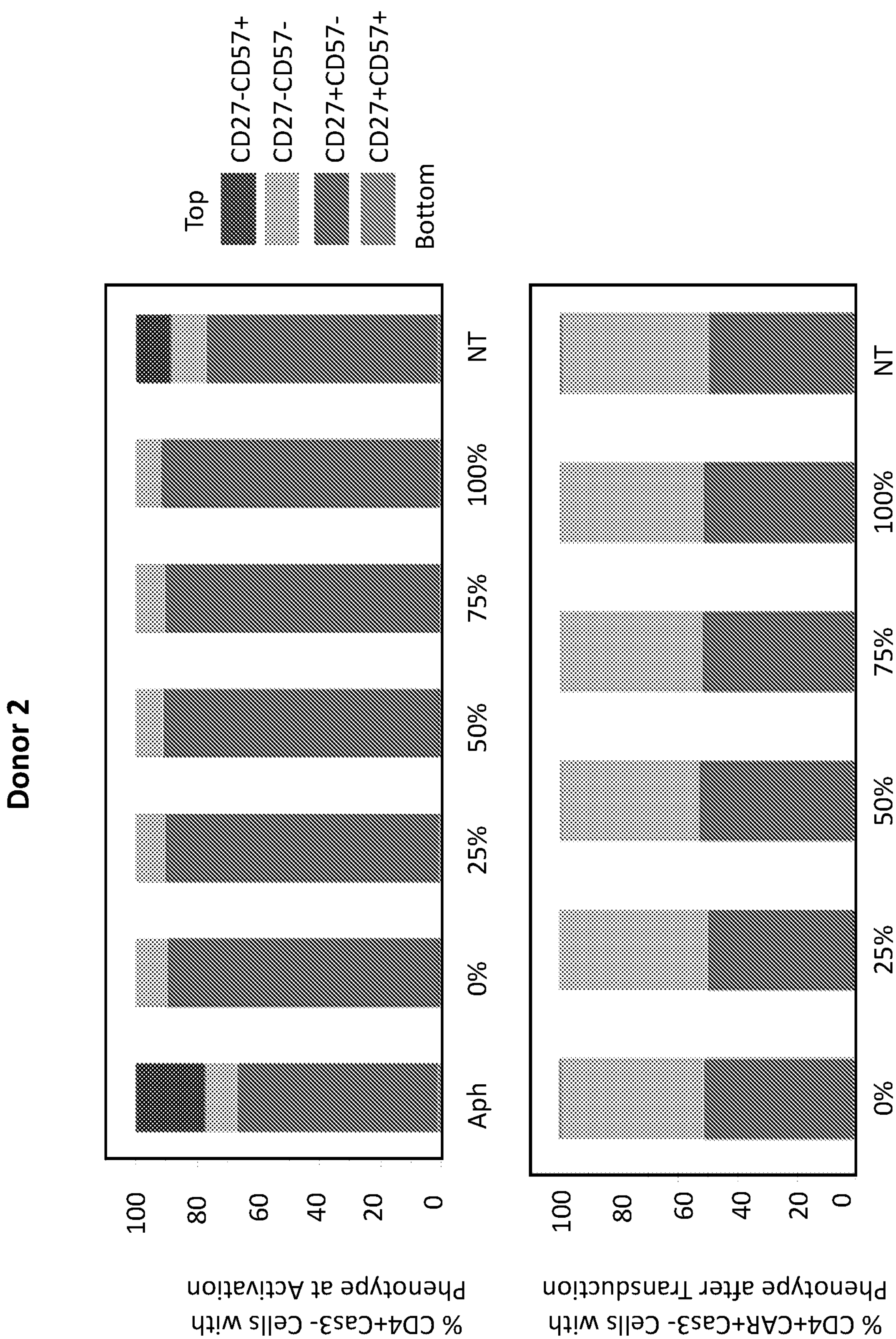
Figure 21B:
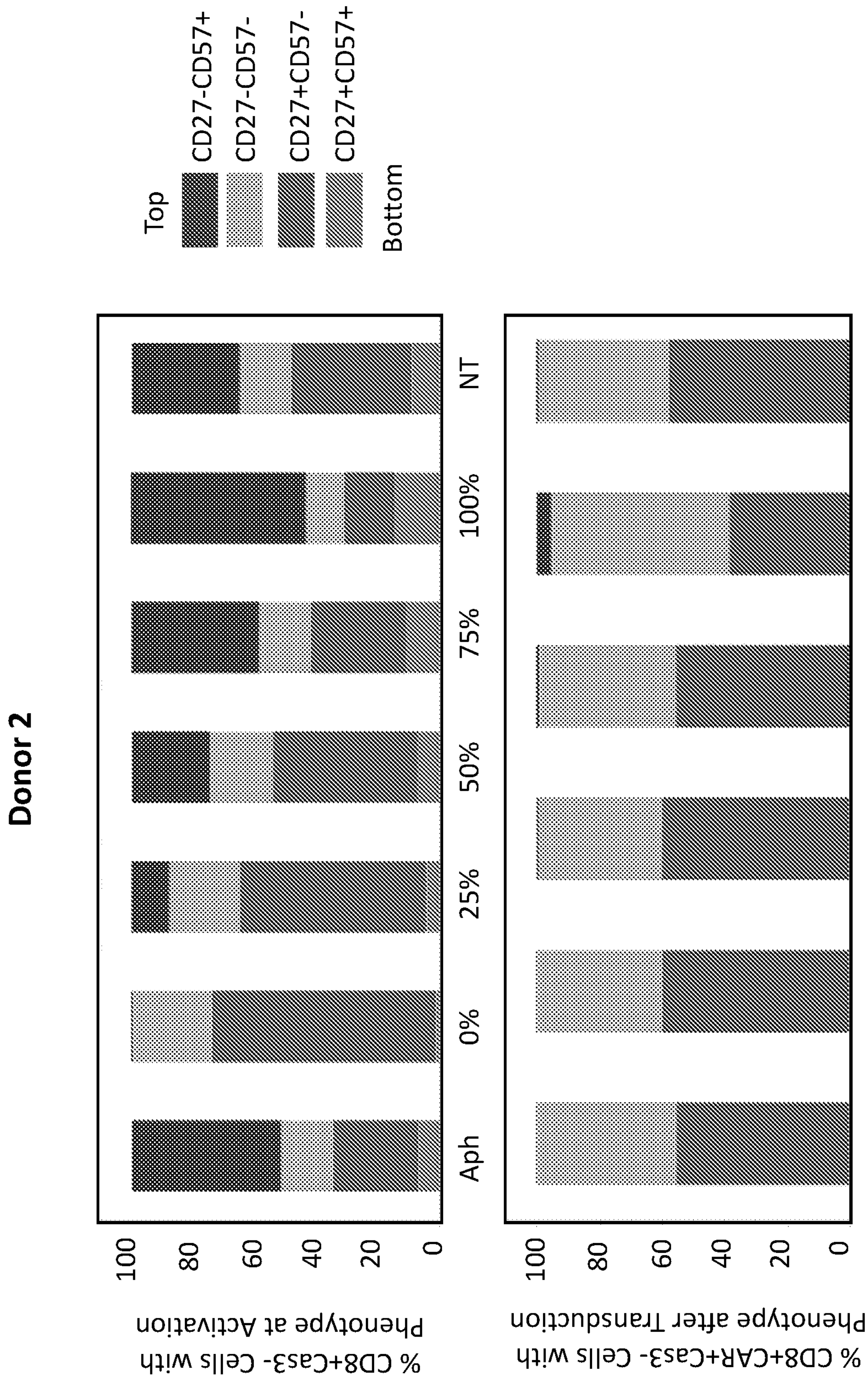

Immunophenotypes of compositions from both donors were assessed immediately prior to stimulation ("at activation") and following transduction with the CAR ("following transduction"). The percent of CD8+ CD27+ cells in donor compositions immediately prior to stimulation was found to inversely correlate with the percent of titrated CD57+ cells at the same time point, though this effect was normalized in transduced compositions (FIG. 15; NT: No CD57 titration; left column shows CD4+ cells and right column shows CD8+ cells). In addition, the frequencies of CD45RA/CCR7, CD27/CD28, and CD57/CD27 immunophenotypes in the CD4+ and CD8+ cellular compartments was assessed in both donors immediately prior to stimulation and following transduction (FIGS. 16-21; Aph: Apheresis sample; %: percent CD57+ titrated cells; NT: No CD57 titration). It was observed that immunophenotypes associated with memory T cells were normalized with increasing CD57+ cell depletion in transduced cell compositions, despite variations in input compositions. Further, the CD57 frequency in the CD57 titrated compositions did not impact the percentage of CD3+ transduced with the CAR.

Figure 22:
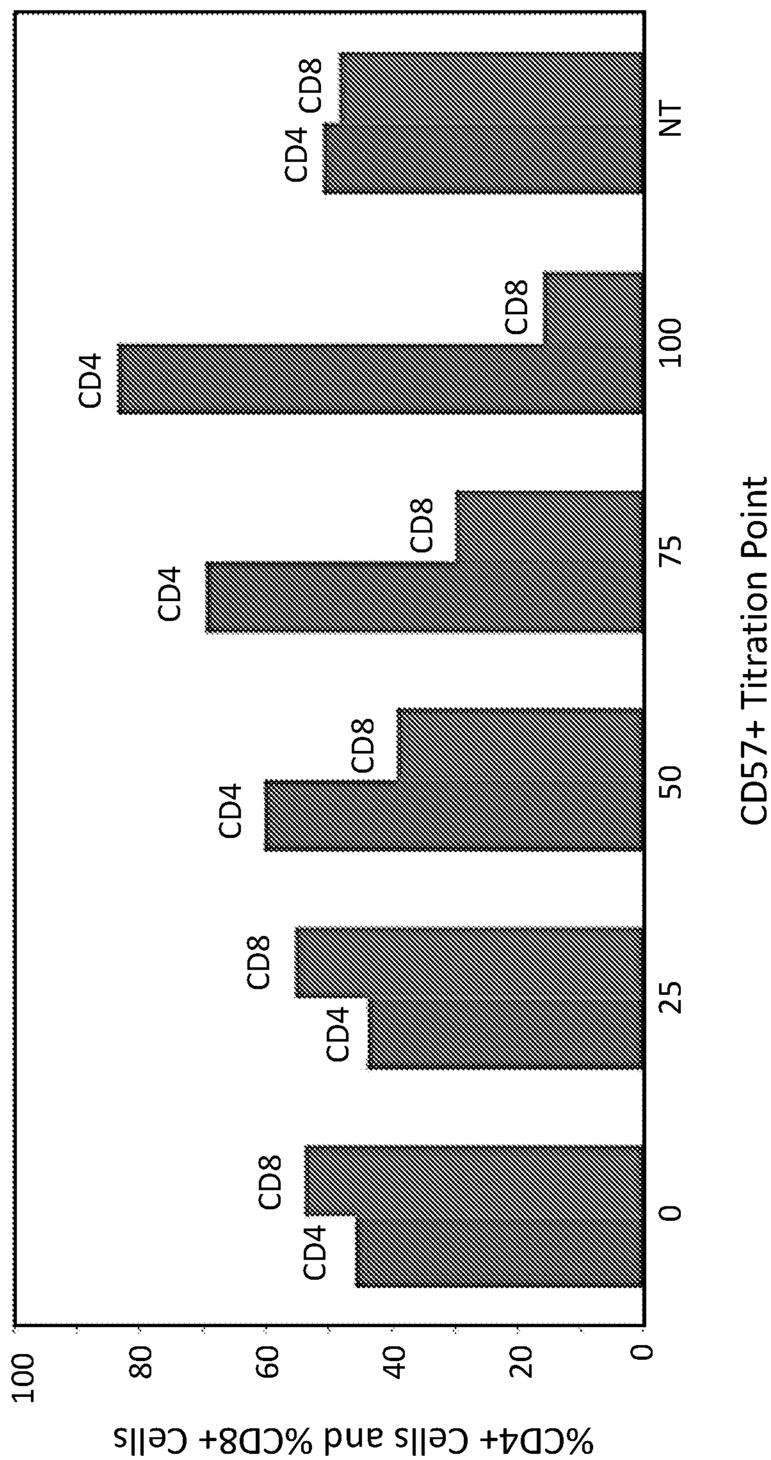
FIG. 22 shows the CD4+:CD8+ ratio in transduced cell compositions derived from CD57+ titrated input compositions from Donor 1 and Donor 2. NT: No CD57 titration.

The ratio of CD4+ to CD8+ cells in transduced cell compositions from Donor 1 were analyzed. As shown in FIG. 22 (NT: No CD57 titration), transduced populations with lower percentages of CD57+ cells in the input compositions were observed to maintain a ratio of CD4+ and CD8+ cells closer to 1:1, whereas the CD4:CD8 ratio skewed with increasing frequency of CD57+ cells.

Results also showed no substantial difference in the percentage of CD3+ cells that were successfully gene edited following stimulation between the healthy donors or among the CD57 titrated compositions.

The findings described herein indicate that reductions in the CD57+ frequency of donor cells compositions, such as either by enriching for CD57− cells in donor input compositions or by selecting for donors with lower CD57+ frequencies, improves the immunophenotype and 1:1 target ratio of CD4+ to CD8+ T cells of transduced CAR T cell compositions, without compromising the efficiency of transduction or genetic editing.

B. Titration of CD27+ Frequency

Selected CD8+ and CD4+ T cell compositions from two healthy donors (Donor 1 and Donor 2) were separately titrated with varying amounts of an enriched population of CD27+ cells, as described above, to produce separate donor CD8+ and CD4+ T cell compositions wherein 0%, 25%, 50%, 75%, or 100% of the CD8+ or CD4+ T cells were CD27+. CD27 titrated CD8+ T cell compositions and CD27 titrated CD4+ T cell compositions from the same donor were then combined to produce input compositions for each donor comprising CD4+ and CD8+ T cells, wherein 30%, 80%, or 100% (Donor 1), or 25%, 50%, 75%, or 100% (Donor 2) of the total CD4+ and CD8+ T cells were CD27+. Titrations were confirmed by flow cytometry. As described above, input compositions generated to contain CD4+ and CD8+ cells, wherein neither of the CD4+ or CD8+ T cell compositions were subjected to CD27+ selection or titration ("NT"), served as controls.

The input compositions containing CD4+ and CD8+ cells were stimulated with an anti-CD3/anti-CD28 reagent and transduced with a viral preparation containing nucleic acid encoding an anti-CD19 CAR. In some cases, following stimulation (activation) with anti-CD3/anti-CD28 reagents, cells were also subjected to genetic editing. After further incubation with recombinant IL-2, IL-7 and IL-15 cytokines for expansion of cells, donor compositions were assessed for immunophenotype, CD4:CD8 ratio, CAR expression, and gene editing efficiency at stimulation and/or following transduction.

Figure 23:
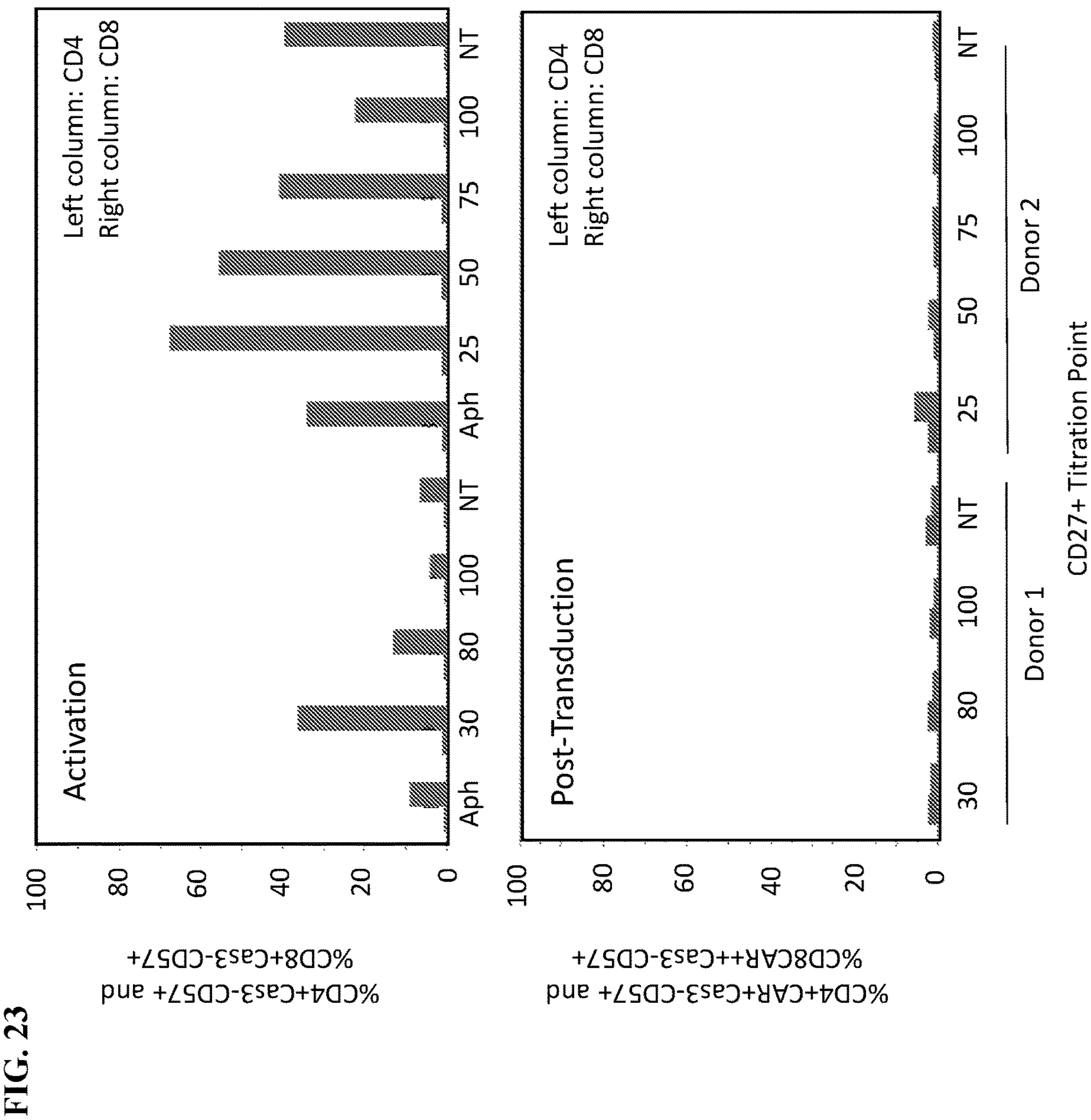
FIG. 23 shows the frequency of Caspase 3-negative, CD57-positive (Cas3-CD57+) cells in the CD4+ and CD8+ cellular compartments at activation (top panel) and following transduction (bottom panel) in CD27+ titrated compositions from Donor 1 and Donor 2. Left column: CD4+ cells; right column: CD8+ cells. NT: No CD27 titration.
Figure 24A:
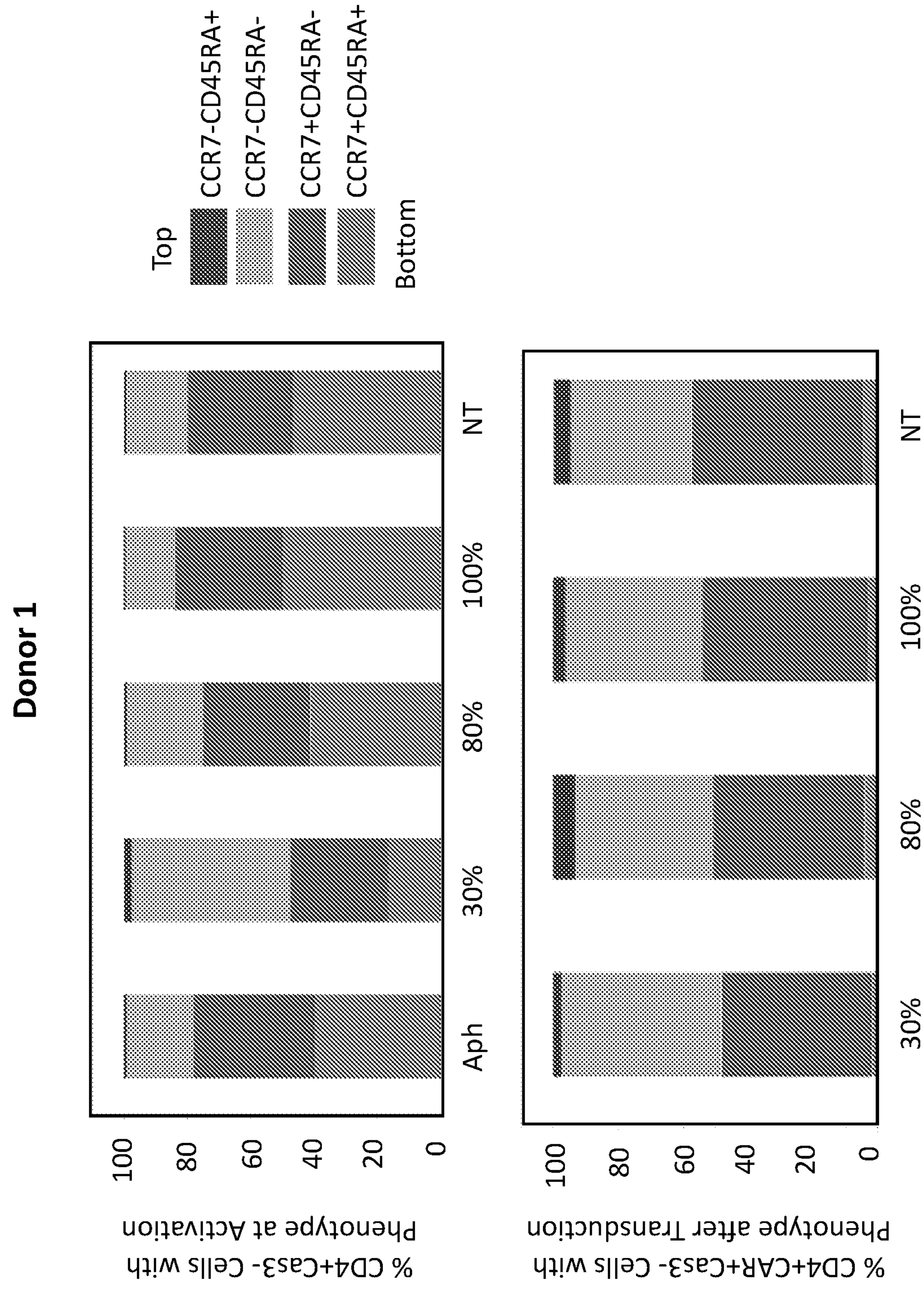
FIGS. 24 and 25 show the frequency of CCR7/CD45RA phenotypes of CD4+(FIGS. 24A and 25A) and CD8+(FIGS. 24B and 25B) cells from Donor 1 and Donor 2 CD27+ titrated compositions, respectively, at activation (top panels) and following transduction (bottom panels). Aph: apheresis sample; %: % CD27+ titrated cells; NT: No CD27 titration.
Figure 24B:
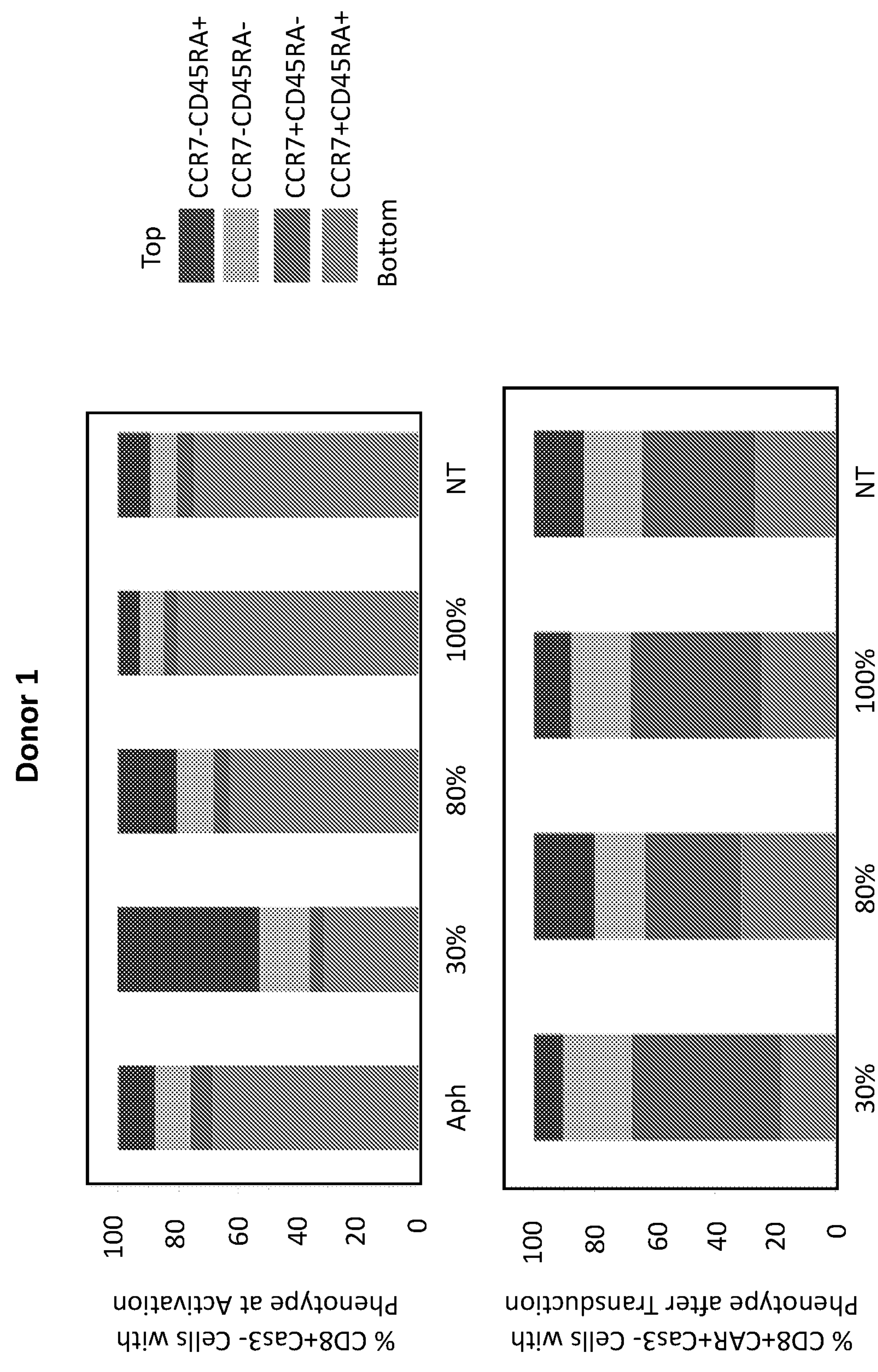
Figure 25A:
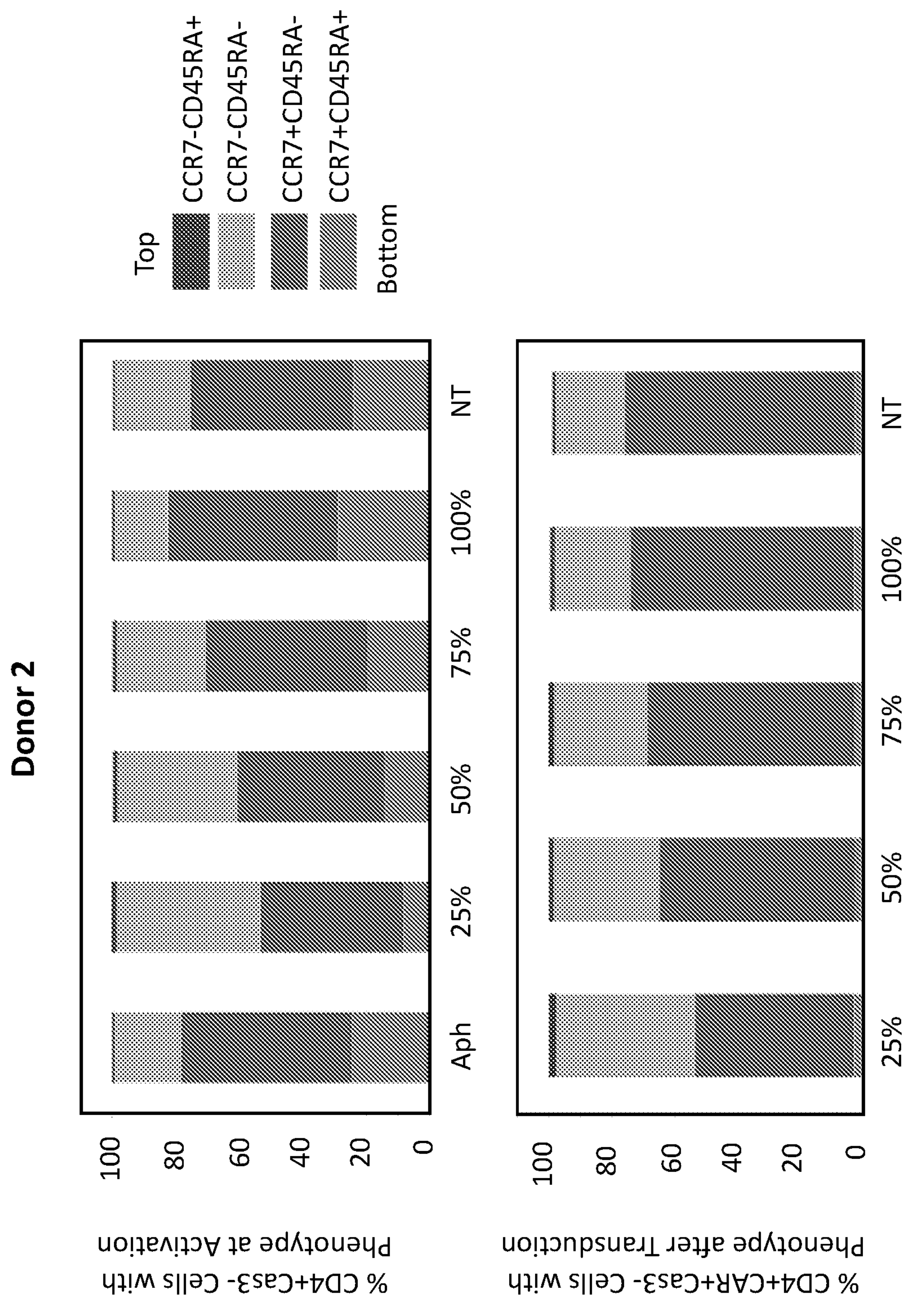
Figure 25B:
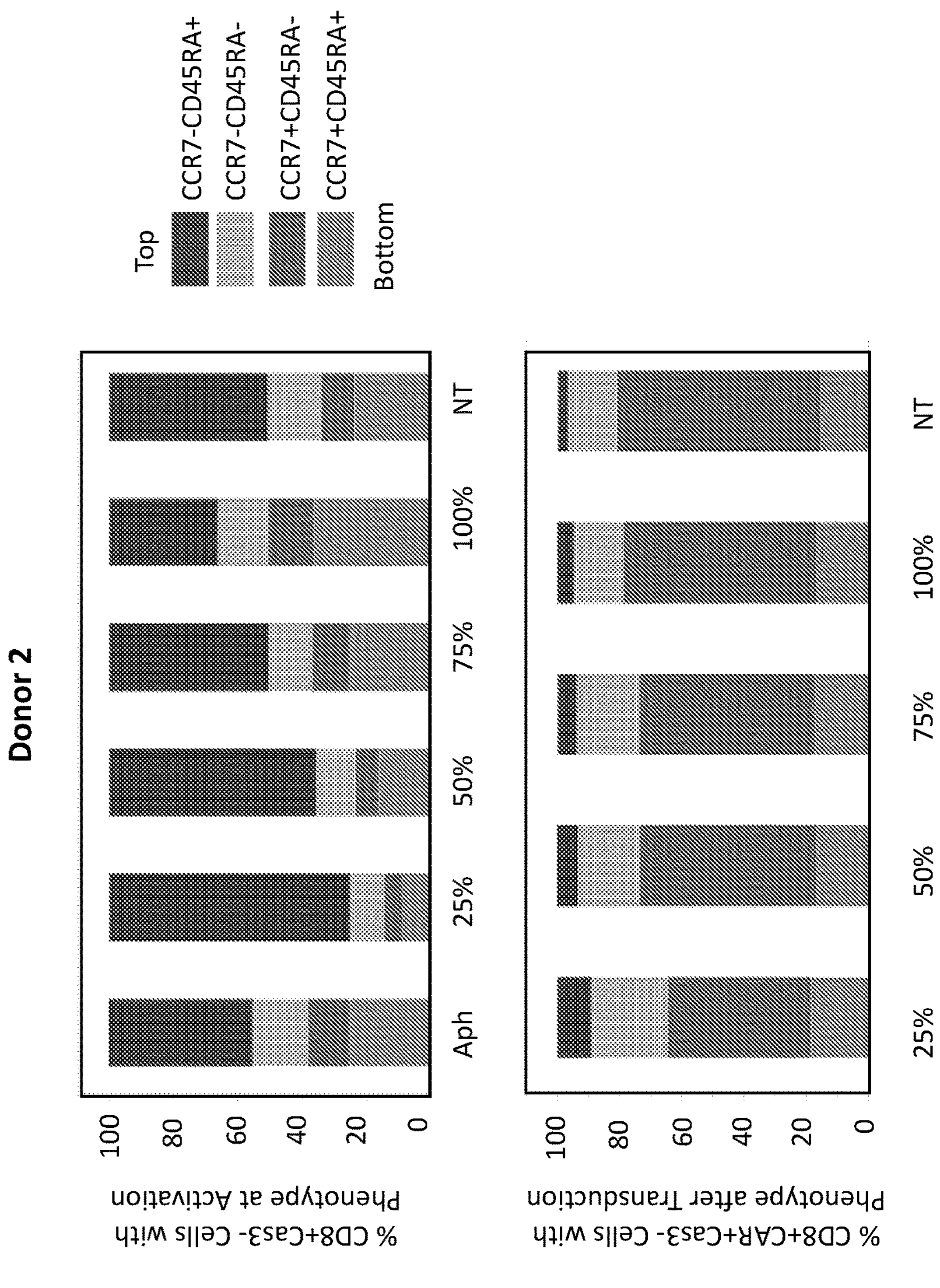
Figure 26A:
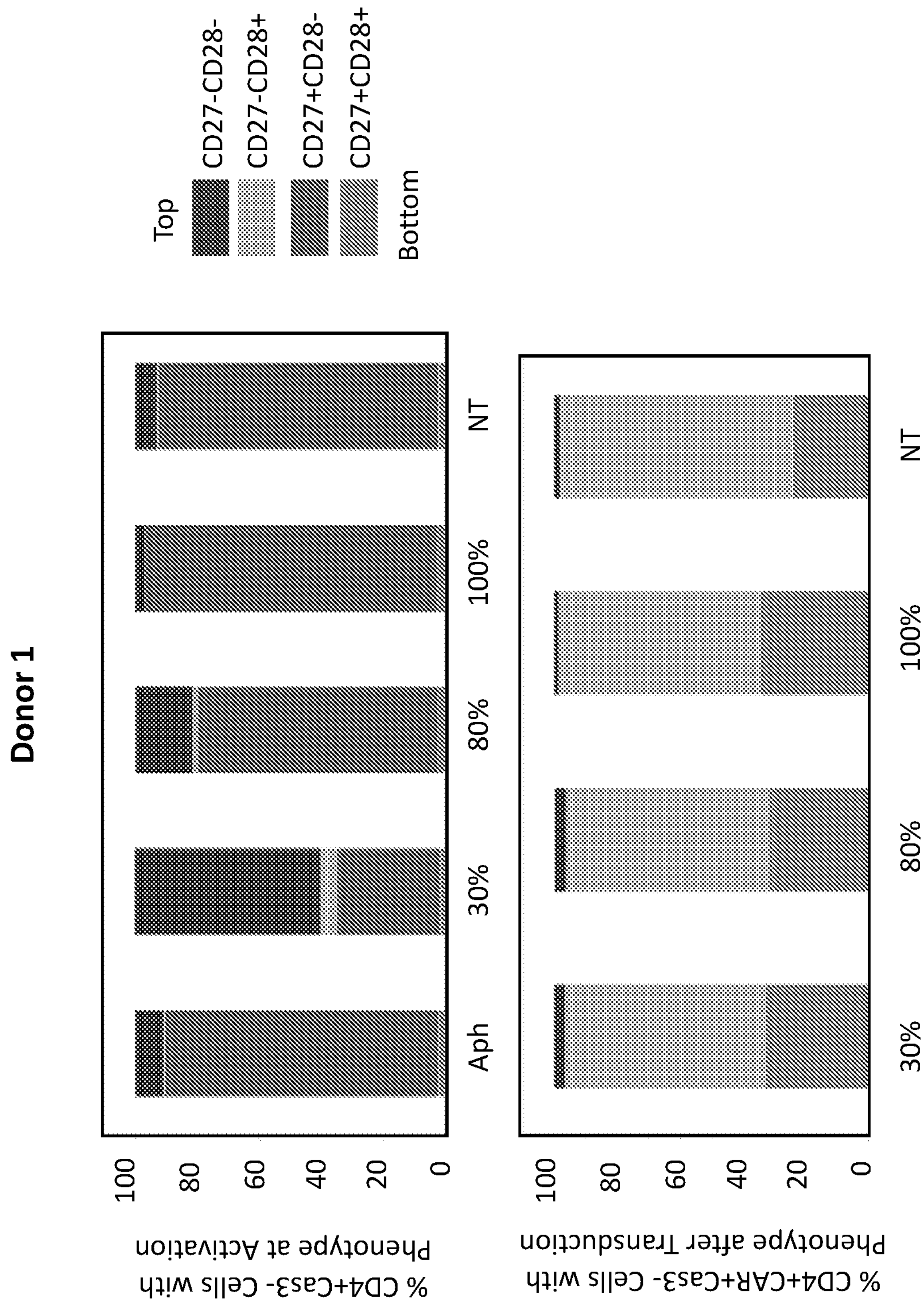
FIGS. 26 and 27 show the frequency of CD27/CD28 phenotypes of CD4+(FIGS. 26A and 27A) and CD8+(FIGS. 26B and 27B) cells from Donor 1 and Donor 2 CD27+ titrated compositions, respectively, at activation (top panels) and following transduction (bottom panels). Aph: apheresis sample; %: % CD27+ titrated cells; NT: No CD27 titration.
Figure 26B:
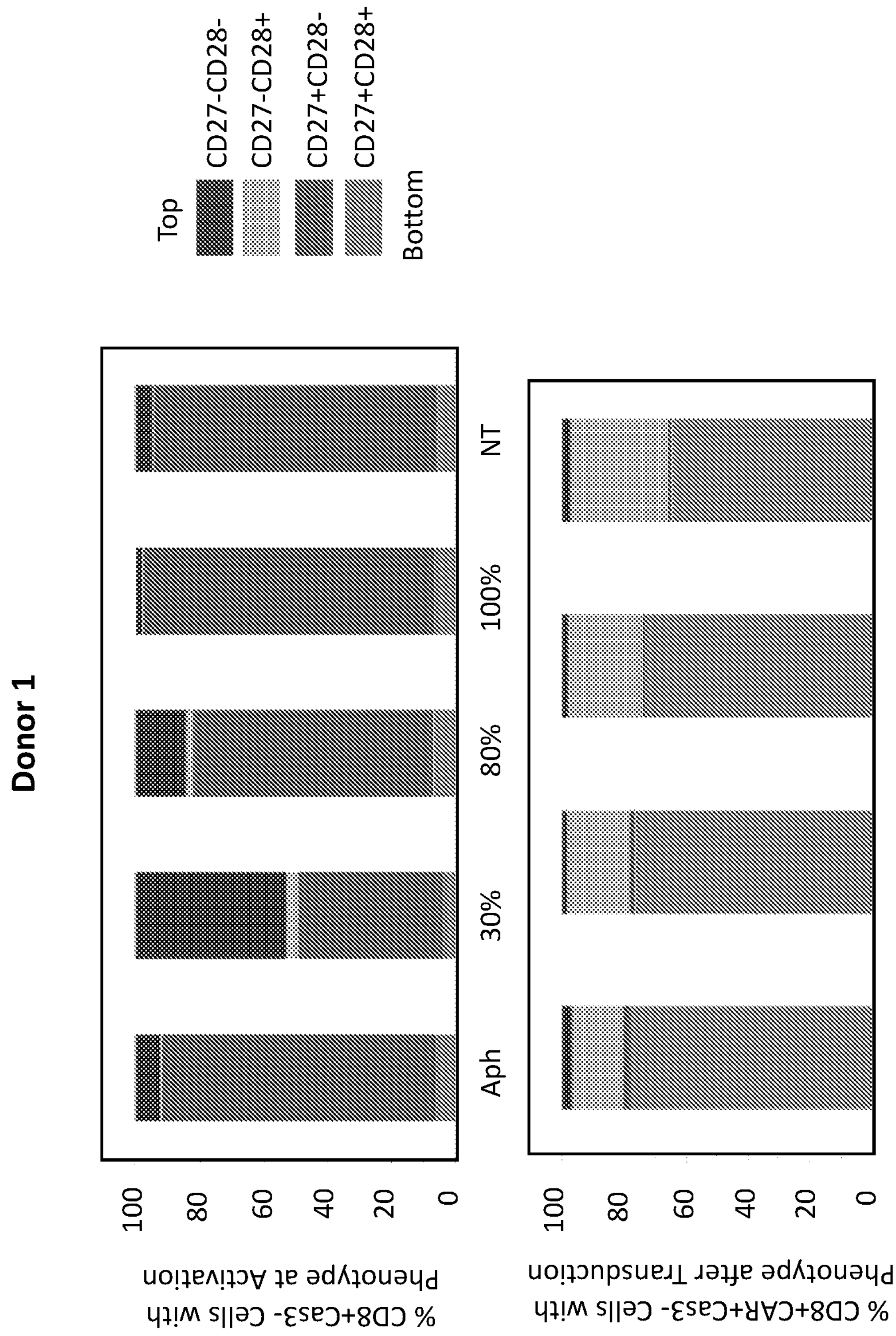
Figure 27A:
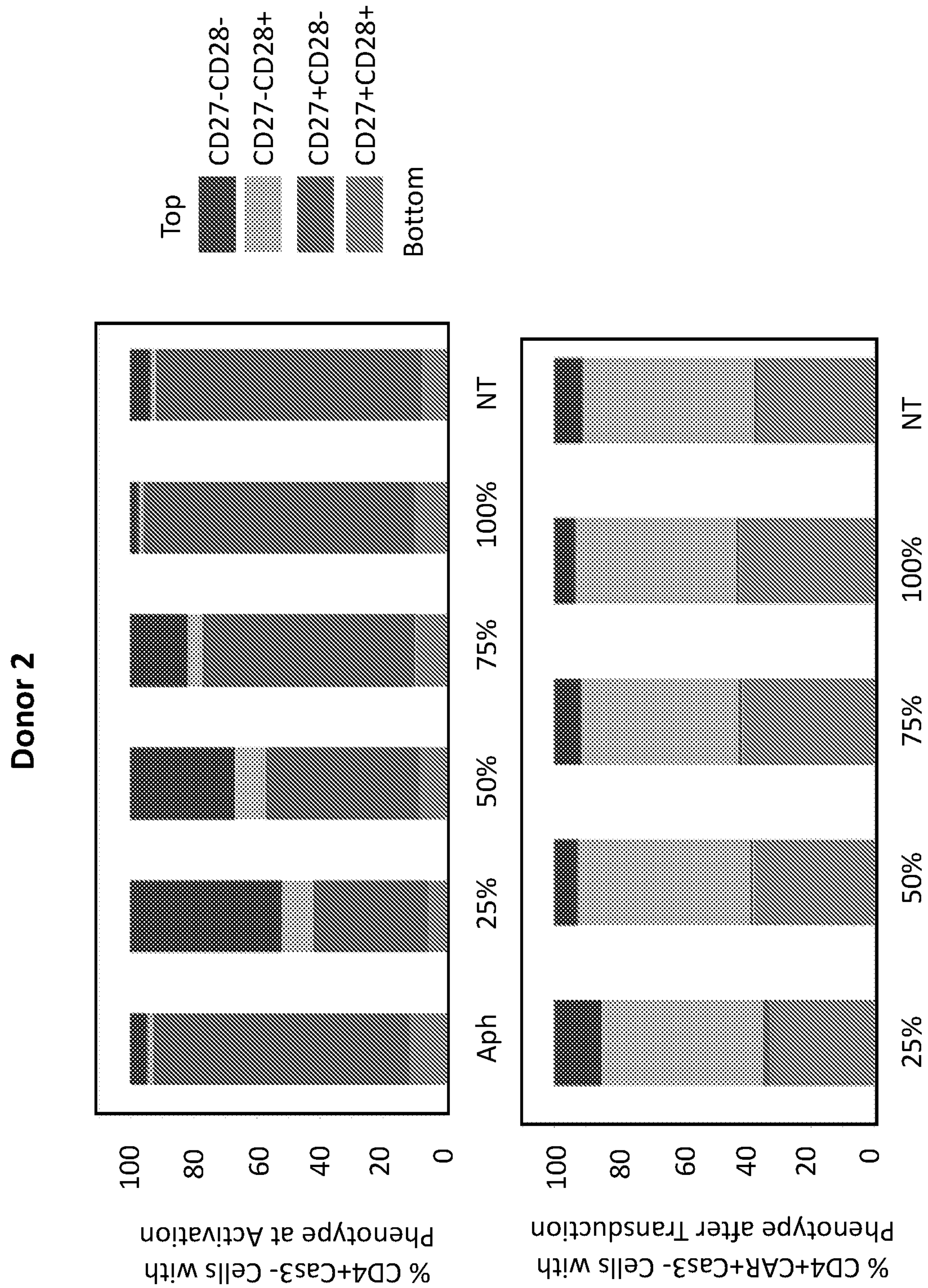
Figure 27B:
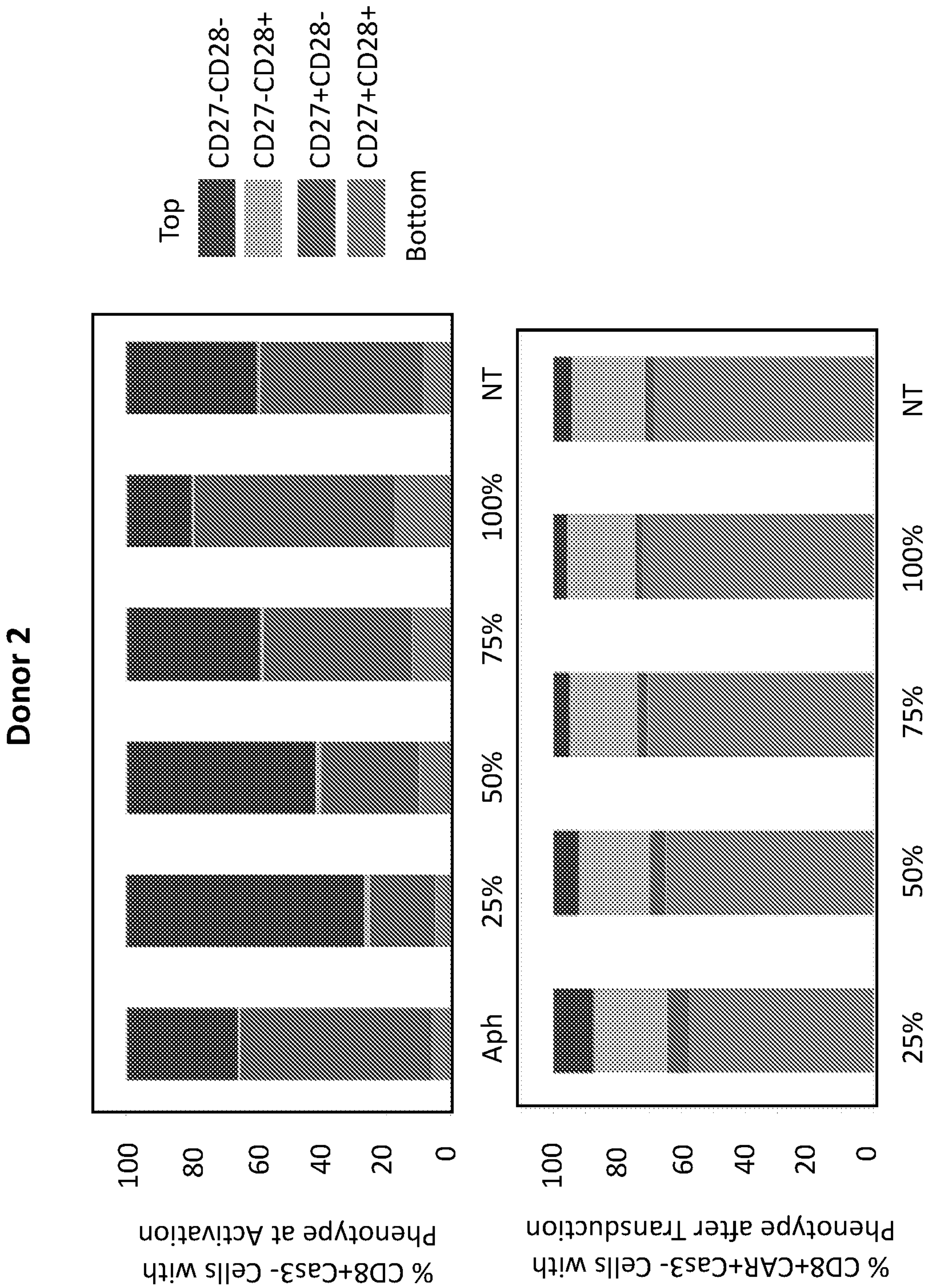
Figure 28A:
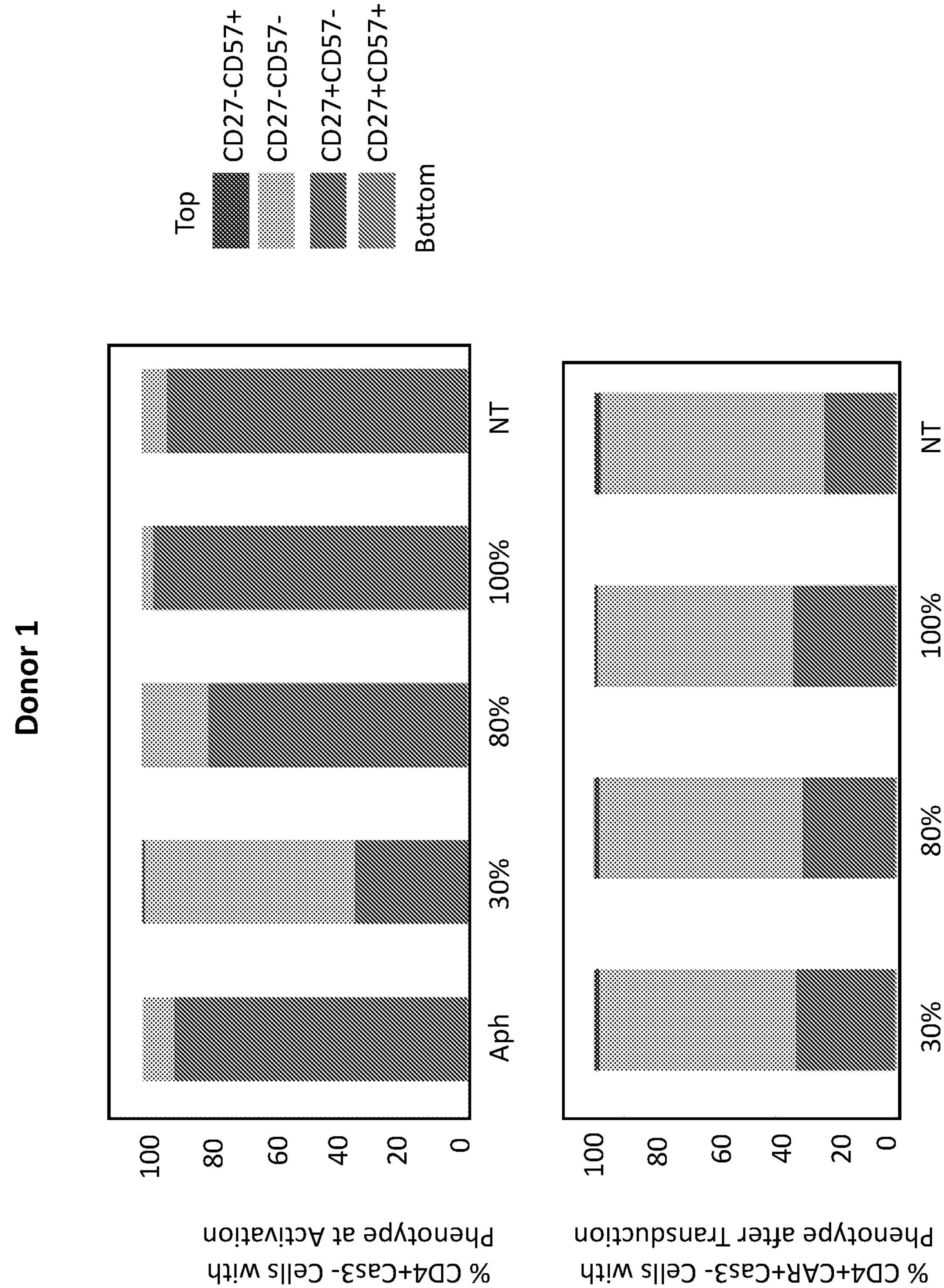
FIGS. 28 and 29 show the frequency of CD27/CD57 phenotypes of CD4+(FIGS. 28A and 29A) and CD8+(FIGS. 28B and 29B) cells from Donor 1 and Donor 2 CD27+ titrated compositions, respectively, at activation (top panels) and following transduction (bottom panels). Aph: apheresis sample; %: % CD27+ titrated cells; NT: No CD27 titration.
Figure 28B:
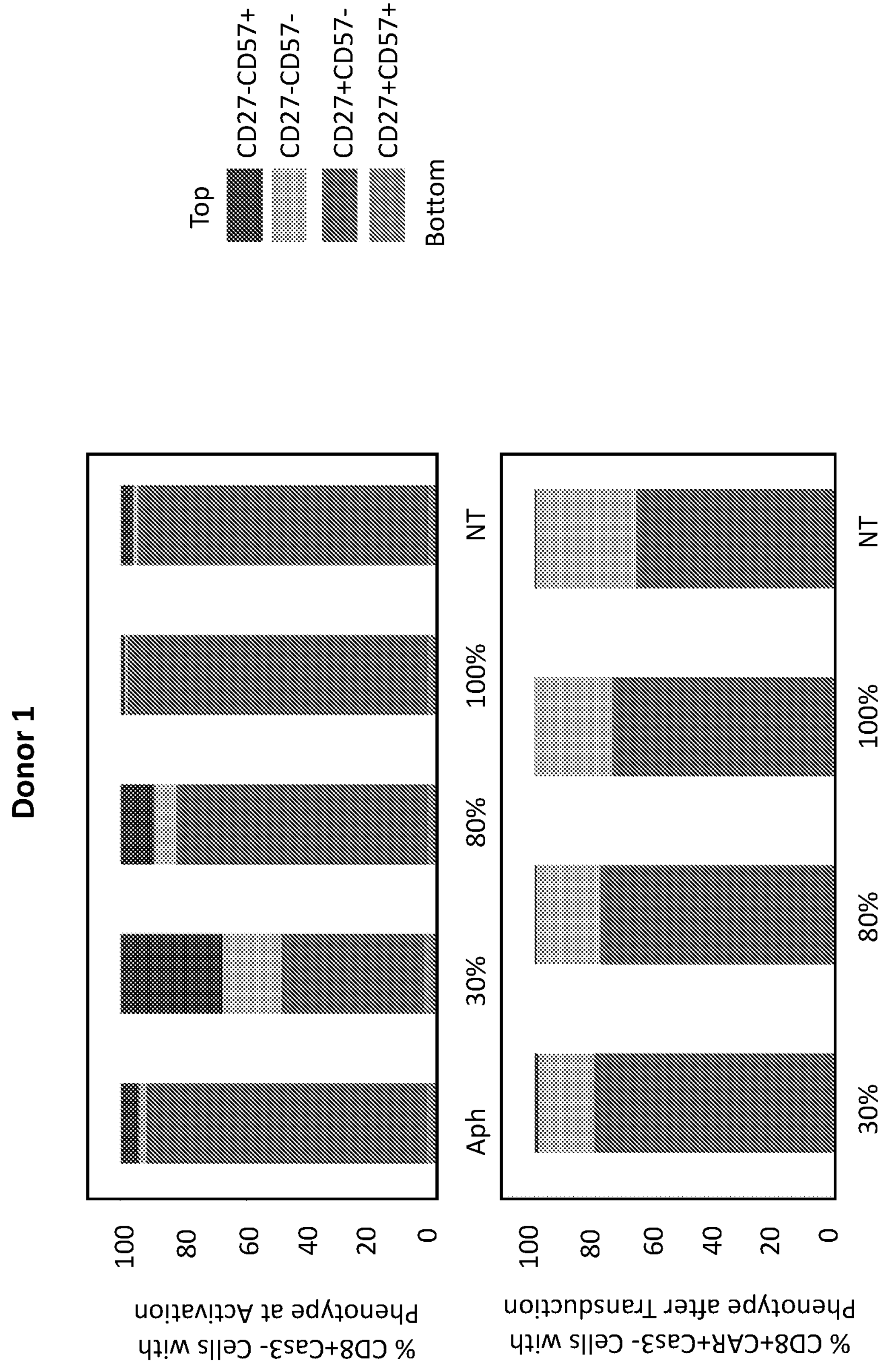
Figure 29A:
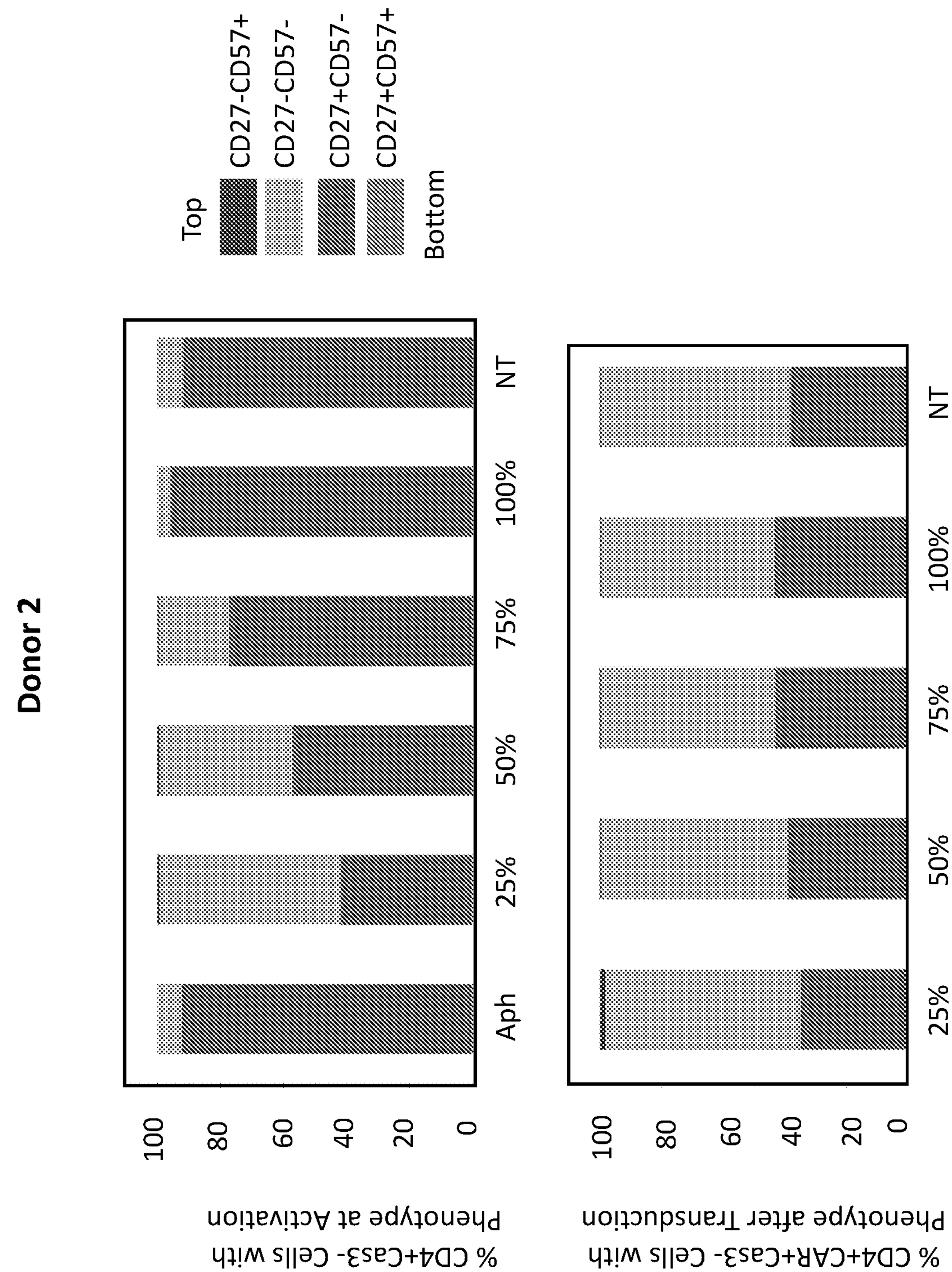
Figure 29B:
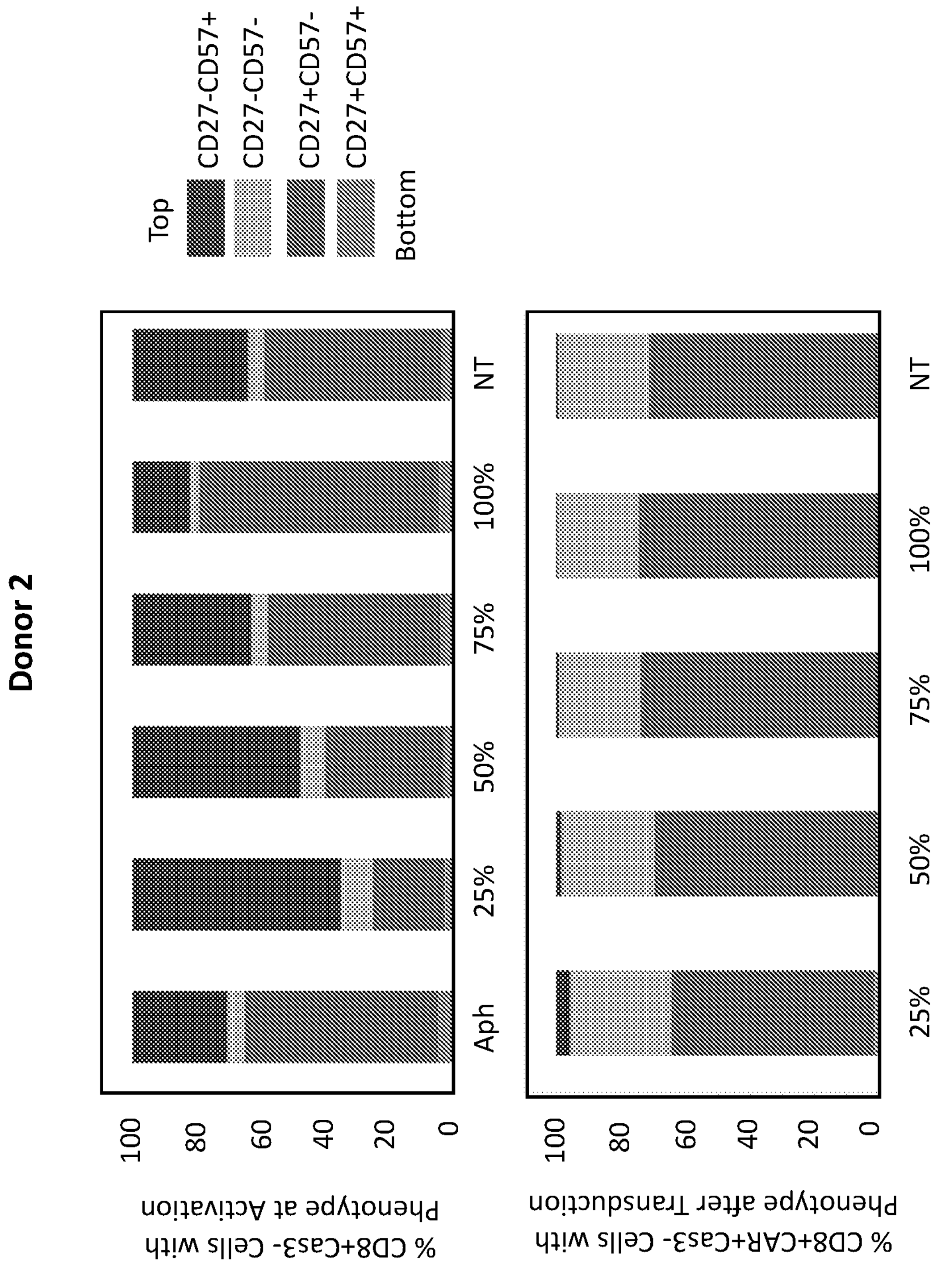
Figure 30:
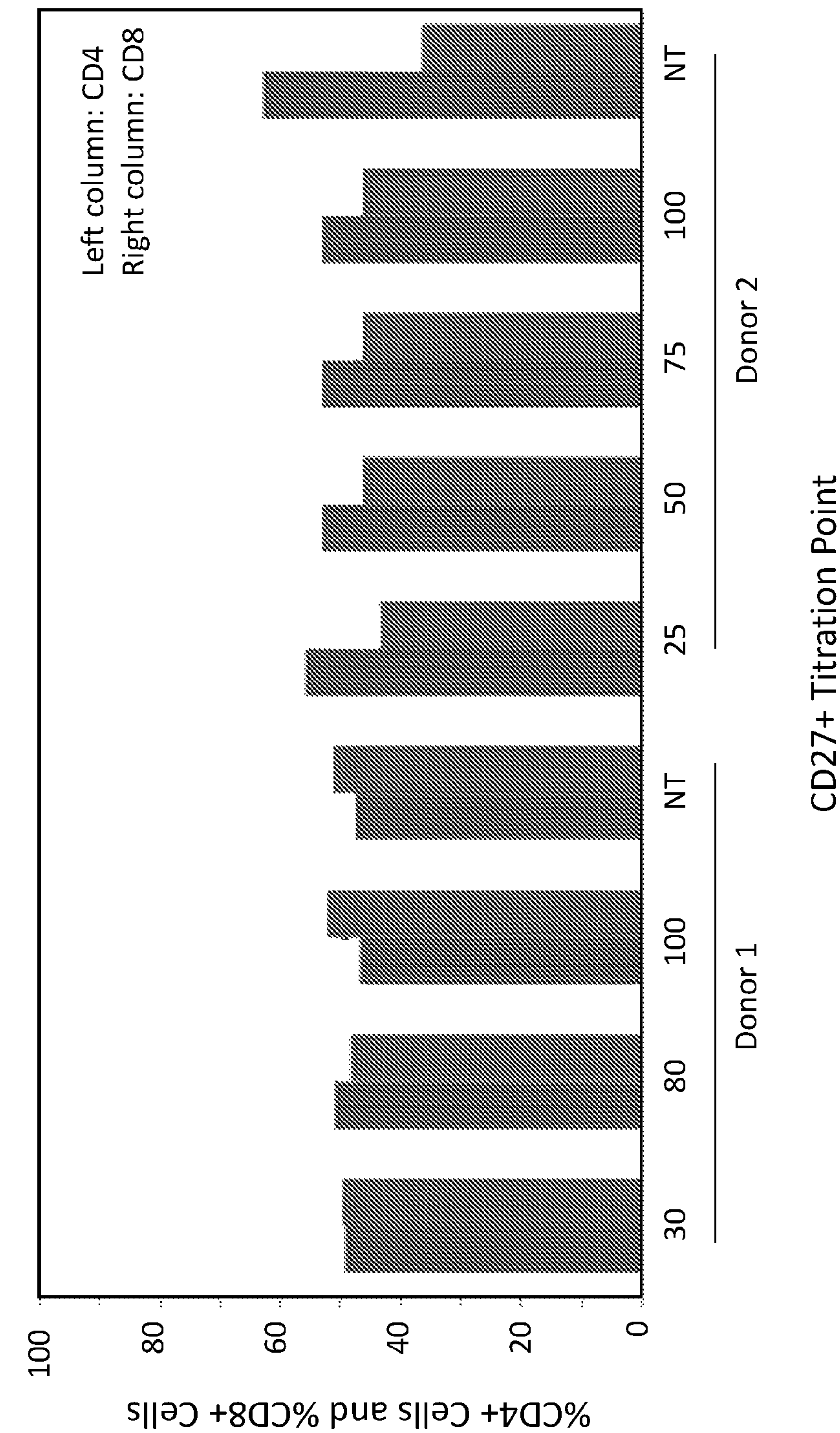
FIG. 30 shows the CD4+:CD8+ ratio in transduced cell compositions derived from CD27+ titrated input compositions from Donor 1 and Donor 2. NT: No CD27 titration.

Immunophenotypes of compositions from both donors were assessed immediately prior to stimulation ("at activation") and following transduction with the CAR. The percent of CD27+ cells in donor compositions immediately prior to stimulation was found to inversely correlate with the percent of CD57+ cells at the same time point, though this effect was normalized in transduced compositions (FIG. 23; NT: No CD27 titration; left column shows CD4+ cells and right column shows CD8+ cells). In addition, the frequencies of CD45RA/CCR7, CD27/CD28, and CD57/CD27 immunophenotypes in the CD4+ and CD8+ cellular compartments was assessed in both donors immediately prior to stimulation and following transduction (FIGS. 24-29; Aph: Apheresis sample; %: percent CD27+ titrated cells; NT: No CD27 titration). It was observed that immunophenotypes associated with memory T cells were normalized with increasing CD27+ frequency in transduced cell compositions, despite variations in input compositions. Further, the CD27 frequency in the CD27 titrated compositions did not impact the percentage of CD3+ transduced with the CAR. The ratio of CD4+ to CD8+ cells in transduced cell compositions from both donors was also analyzed (FIG. 30; C: Control).

Results also showed no substantial difference in the percentage of CD3+ cells that were successfully gene editing following stimulation between donors or among the CD27 titrated compositions.

The findings described herein indicate that increases in the CD27+ frequency of donor cell compositions, such as either by enriching for CD27+ cells in donor input compositions or by selecting for donors with higher CD27+ frequencies, improves the immunophenotype of transduced CAR T cell compositions, without compromising the efficiency of transduction or downstream genetic editing.

Example 10: Comparison of CD57+ Cell Depletion vs. CD27+ Cell Selection

Leukapheresis samples obtained from healthy human donors were subjected to immunoaffinity-based selection for cells surface positive for CD4 (CD4+) or CD8 (CD8+) to generate T cell compositions containing CD4+ and CD8+ cells. The separately selected CD4+ and CD8+ T cell compositions were subjected to a further immunoaffinity-based selection to deplete cells surface positive for CD57 (CD57+; via negative selection) or to enrich for cells surface positive CD27 (CD27+). The effects of CD57 depletion or CD27 enrichment on transduction, immunophenotype, and gene editing were assessed. Input compositions having only undergone CD4+ and CD8+ selections (No selection; NS) served as controls.

The endogenous CD27+ and CD57+ frequency of CD4+ and CD8+ T cells in leukapheresis samples from three different healthy human donors was analyzed prior to CD57 depletion or CD27 enrichment (Table E4).

TABLE E4

CD27+ and CD57+ Frequency in Donor Leukapheresis Samples

| Donor | CD4+ CD27+ (%) | CD8+ CD27+ (%) | CD4+ CD57+ (%) | CD8+ CD57+ (%) |
|---|---|---|---|---|
| Donor 1 | 76.5 | 58.1 | 9.62 | 41.8 |
| Donor 2 | 81.6 | 50.5 | 12.9 | 46.9 |
| Donor 3 | 92.0 | 97.2 | 1.55 | 4.24 |

Following CD57 depletion or CD27 enrichment of the separate CD4+ and CD8+ T cell compositions from each donor, CD4+ and CD8+ compositions derived from the same donor were combined and stimulated with an anti-CD3/anti-CD28 reagent and transduced with a viral preparation containing nucleic acid encoding an anti-CD19 CAR. After further incubation with recombinant IL-2, IL-7 and IL-15 cytokines for expansion of cells, donor compositions were assessed for immunophenotype, CD4:CD8 ratio, CAR expression, and gene editing efficiency at stimulation and/or following transduction.

Figure 31A:
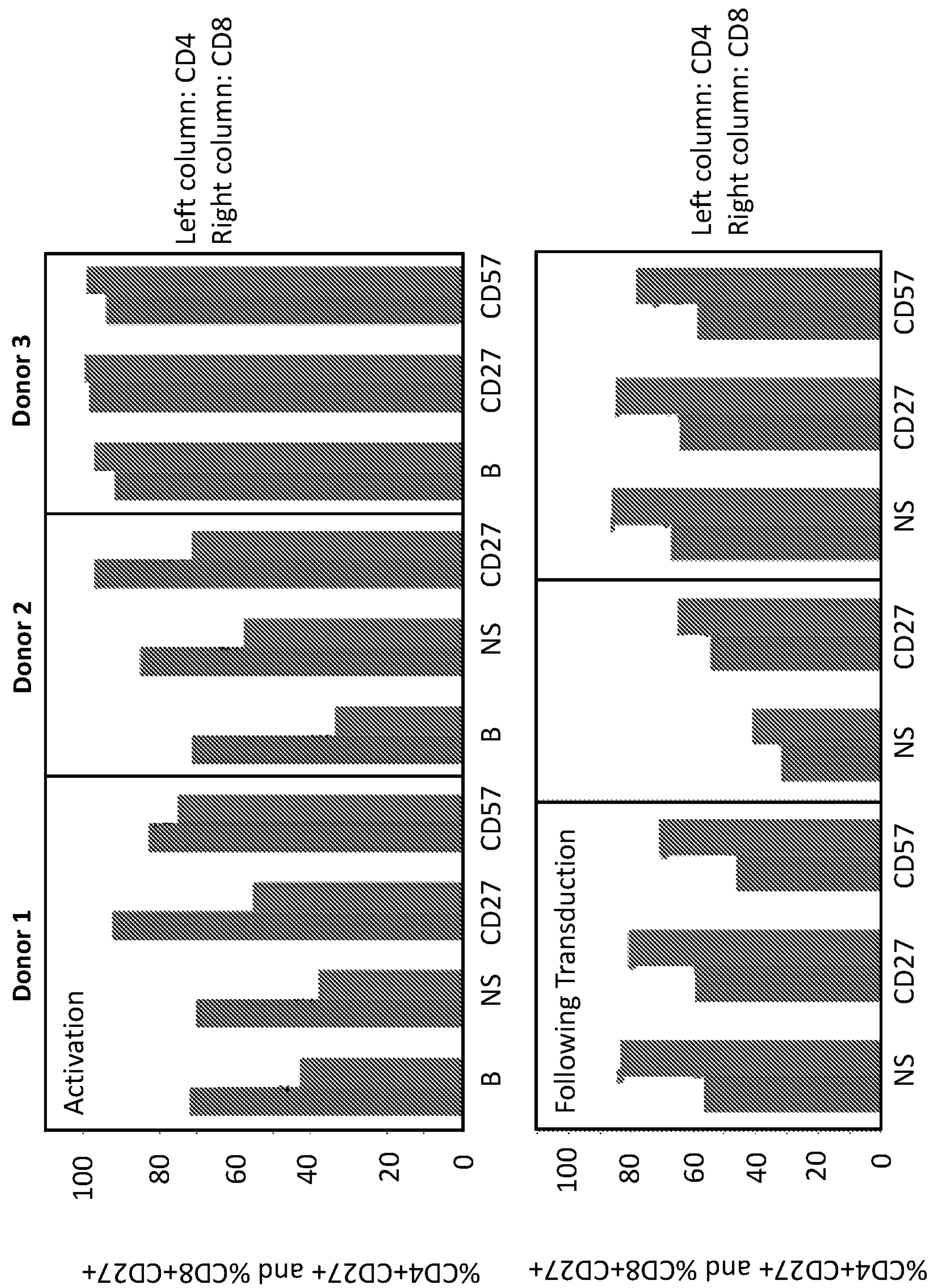
FIGS. 31A and 31B show the frequency of CD27-positive (CD27+) or CD57-positive (CD57+) cells, respectively in the CD4+ and CD8+ cellular compartments at activation (top panel) and following transduction (bottom panel) in compositions before selection (B), without CD27 or CD57 selection (NS), enriched for CD27+ cells (CD27), or depleted of CD57+ cells (CD57). Left column: CD4+ cells; right column: CD8+ cells.
Figure 31B:
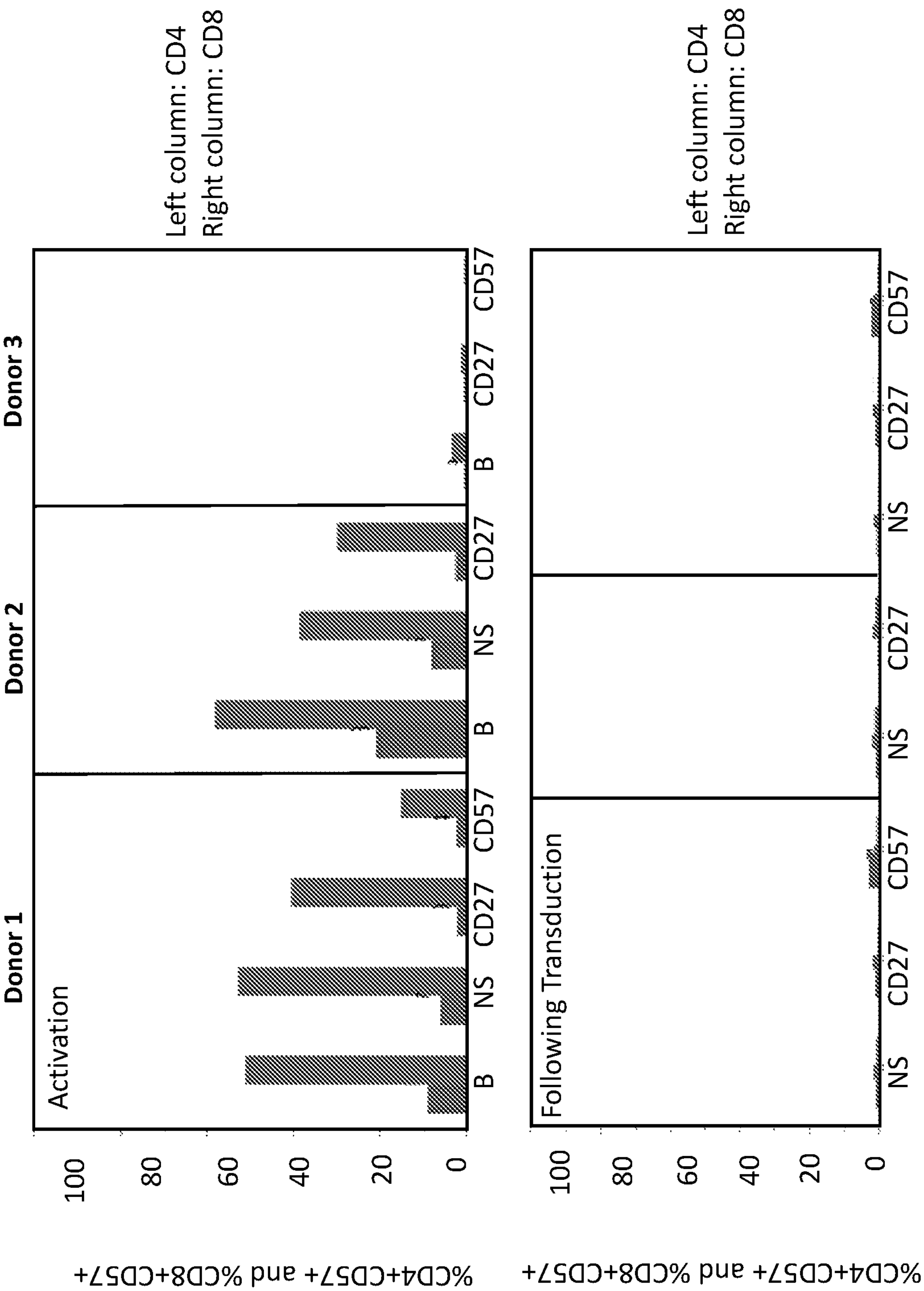
Figure 32A:
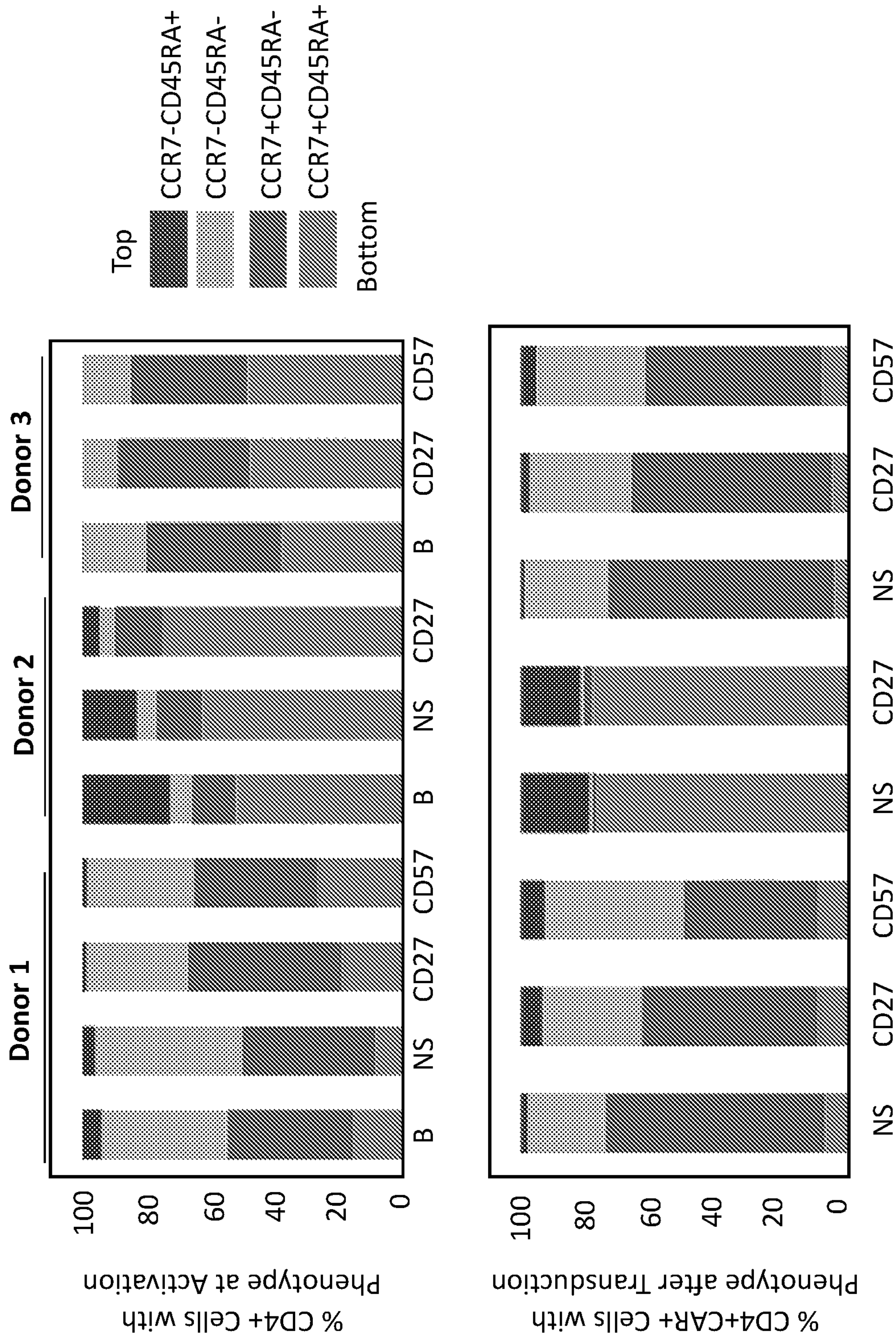
FIGS. 32A and 32B show the frequency of CCR7/CD45RA phenotypes of CD4+(FIG. 32A) and CD8+(FIG. 32B) cells at activation (top panels) and following transduction (bottom panels). B: Before selection; NS: No CD27 or CD57 selection; CD27: Enriched for CD27+ cells; CD57: Depleted of CD57+ cells.
Figure 32B:
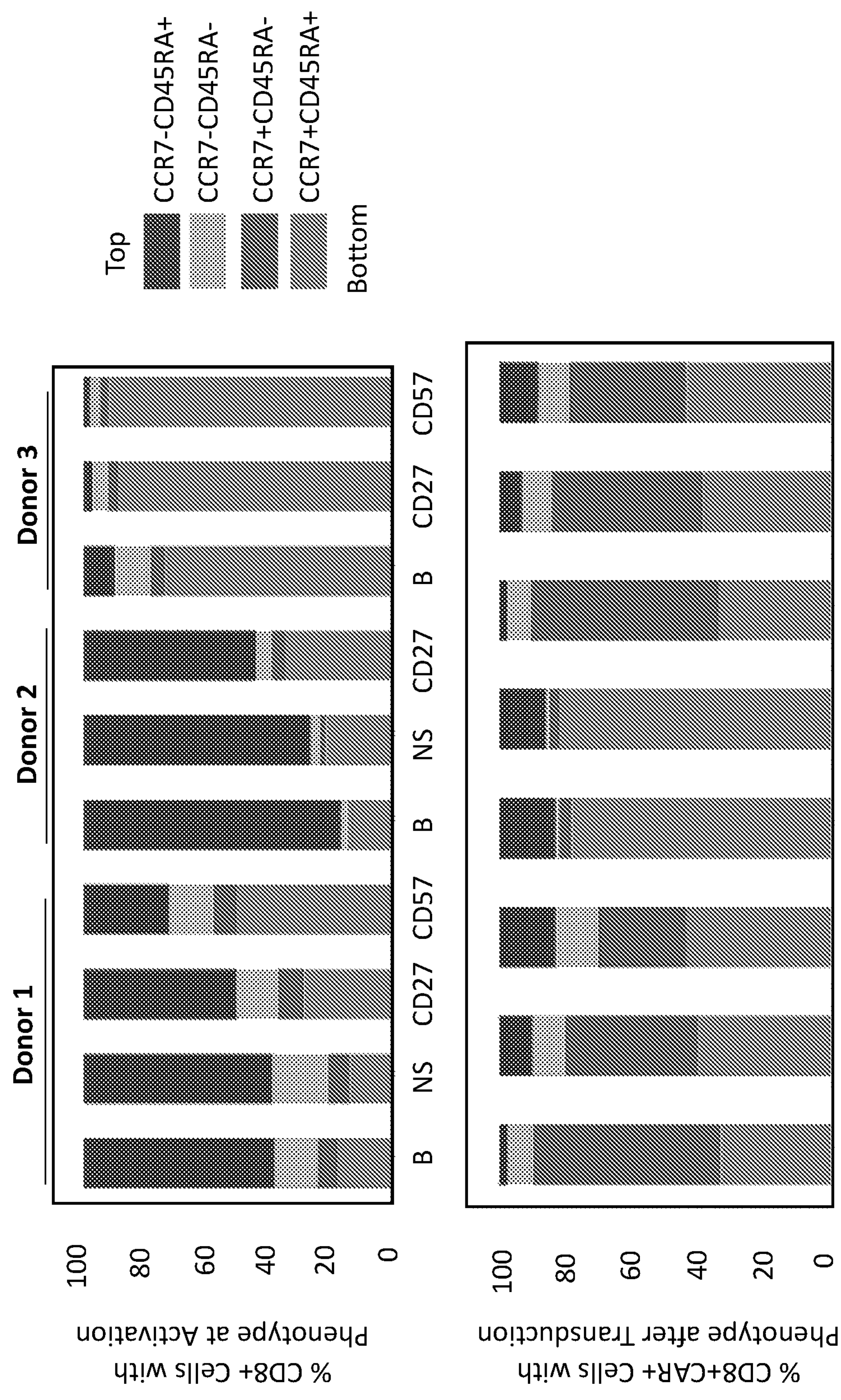

Immunophenotypes of compositions from both donors were assessed immediately prior to stimulation ("at activation") and following transduction with the CAR. Both CD27 enrichment (FIG. 31A) and CD57 depletion (FIG. 31B) were observed to increase the frequency of CD27+ cells and decrease the frequency of CD57+ cells in input compositions immediately prior to stimulation, and in some cases, appeared to also increase the frequency of CD27+ cells following transduction. In addition, the frequency of CD45RA/CCR7 immunophenotypes in the CD4+ and CD8+ cellular compartments was assessed in all three donors immediately prior to stimulation and following transduction (FIGS. 32A and 32B; B: Before selection; NS: No CD27 or CD57 selection). It was observed that CD57 depletion and/or CD27 enrichment increased the percentage of cells exhibiting a memory T cell immunophenotype (CCR7+ and CCR7+ CD45RA+) in transduced cell compositions, particularly in Donors 1 and 2, whose leukapheresis samples had lower frequencies of CD27+ cells and higher frequencies of CD57+ cells. Further, neither CD27 enrichment nor CD57 depletion was observed to affect the percentage of CD3+ cells transduced with the anti-CD19 CAR.

In some cases, CD57 depleted and CD27 enriched compositions were also subjected to gene editing. Results also showed no substantial difference in the percentage of CD3+ cells genetically edited among donors or between the CD27 enriched and CD57 depleted compositions.

The findings described herein indicate that both enrichment for CD27+ cells and depletion of CD27+ cells were observed to be compatible with CAR transduction and genetic editing.

Example 11: Non-Magnetic Immunoaffinity Column Chromatography-Based Cell Selection Leukapheresis samples obtained from healthy human donors were subjected to depletion of CD57+ cells, or enrichment of CD27+ and/or CD3+ cells by affinity chromatography, and the purity, depletion, and yield of resulting compositions were assessed.

A. Selection of CD57−, CD27+, and/or CD3+ Cells from a Leukapheresis Sample

An affinity chromatography system was employed to select for CD57− cells (via negative selection), CD27+ cells (via positive selection), and/or CD3+ cells (via positive selection). The system included streptavidin mutein multimer backbone molecules (Strep-Tactin® M2; SEQ ID NO:73) covalently immobilized on size-defined polystyrene beads (the "selection matrix"). Fab fragments targeting CD57, CD27, or CD3 were individually fused at the carboxy-terminus of their heavy chain to a Twin Strep-Tag® (SEQ ID NO:79). The peptide-tagged Fab fragments were bound to a selection matrix via the peptide tag. For each selection, a sample from a human donor was loaded onto the column filled with the selection matrix, and unbound cells (i.e. cells not expressing the target molecule) passed through without binding. The selection matrix was washed to remove residual trapped non-target cells. The cell population bound to the selection matrix (i.e. cells expressing the target molecule) was eluted by flushing the column with D-biotin-containing buffer, which outcompeted the Fab fragments for binding to biotin binding sites on the streptavidin mutein multimer, such that the bound cells were released. Residual Fab fragments remaining on the surface of the eluted cells were removed with washing.

Figure 33A:
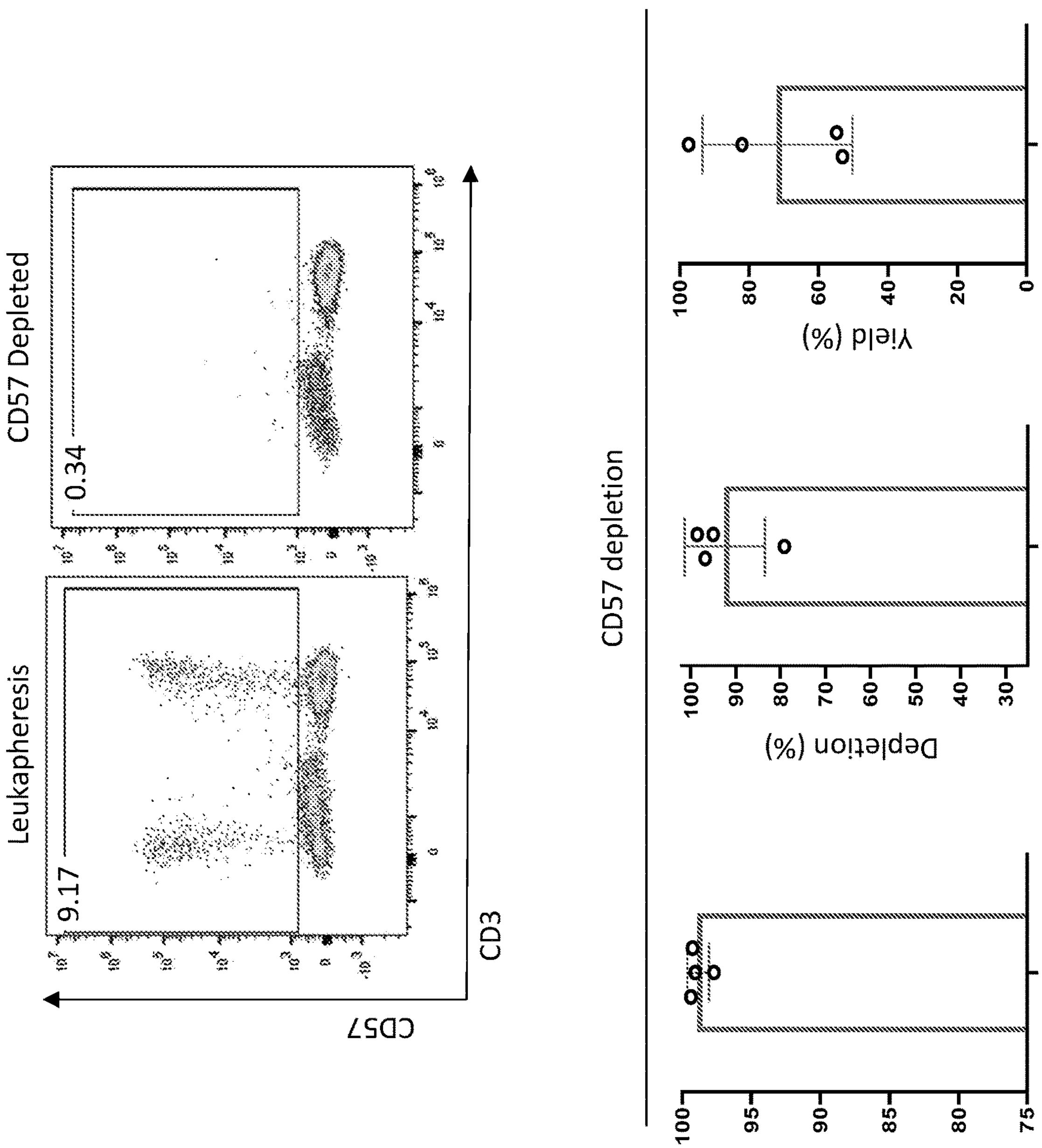
FIG. 33A shows CD57 and CD3 expression (top panel), and purity, depletion, and yield (bottom panel) in a CD57 depleted cell population.

A CD57 depleted cell population was obtained by negative selection by loading a leukapheresis sample onto a column containing a selection matrix with CD57-targeting peptide-tagged Fab fragments and collecting the unbound cells (i.e. CD57− cells) that flowed through the column. As shown in FIG. 33A, approximately 90% of CD57+ from the leukapheresis sample were captured in the resulting CD57 depleted cell population, which contained approximately 0.5-1% CD57+ cells.

Figure 33B:
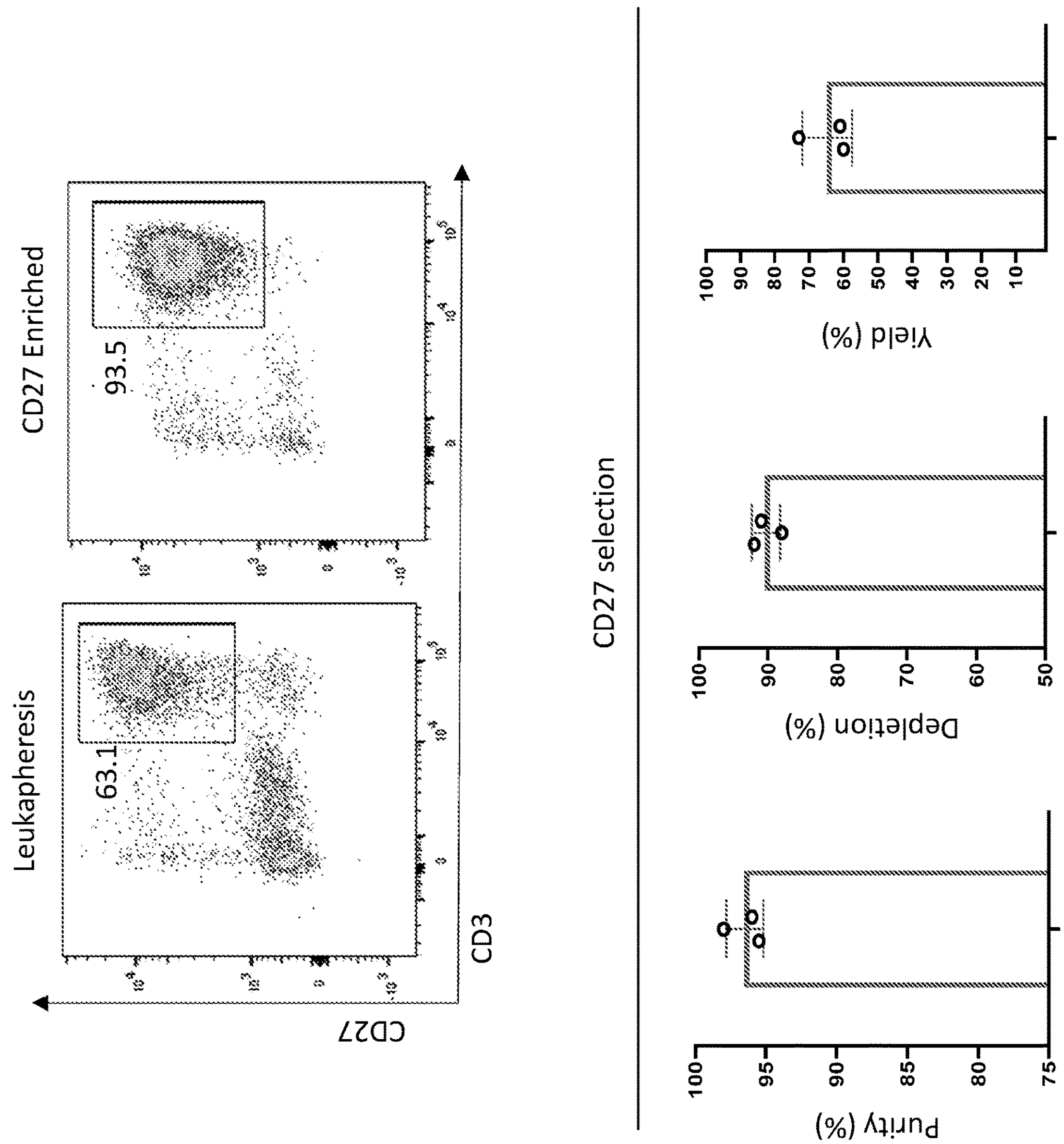
FIG. 33B shows CD27 and CD3 expression (top panel), and purity, depletion, and yield (bottom panel) in a CD27 enriched cell population.

Similarly, a CD27 enriched cell population was obtained by positive selection by loading a leukapheresis sample onto a column containing a selection matrix with CD27-targeting peptide-tagged Fab fragments. The cells that flowed through the column was discarded as waste, and the bound cells (i.e. CD27+ cells) were eluted with a D-biotin-containing buffer. The eluted CD27 enriched cell population resulted in purity of 95%, depletion of 90%, and yield of 65% (FIG. 33B).

Figure 33C:
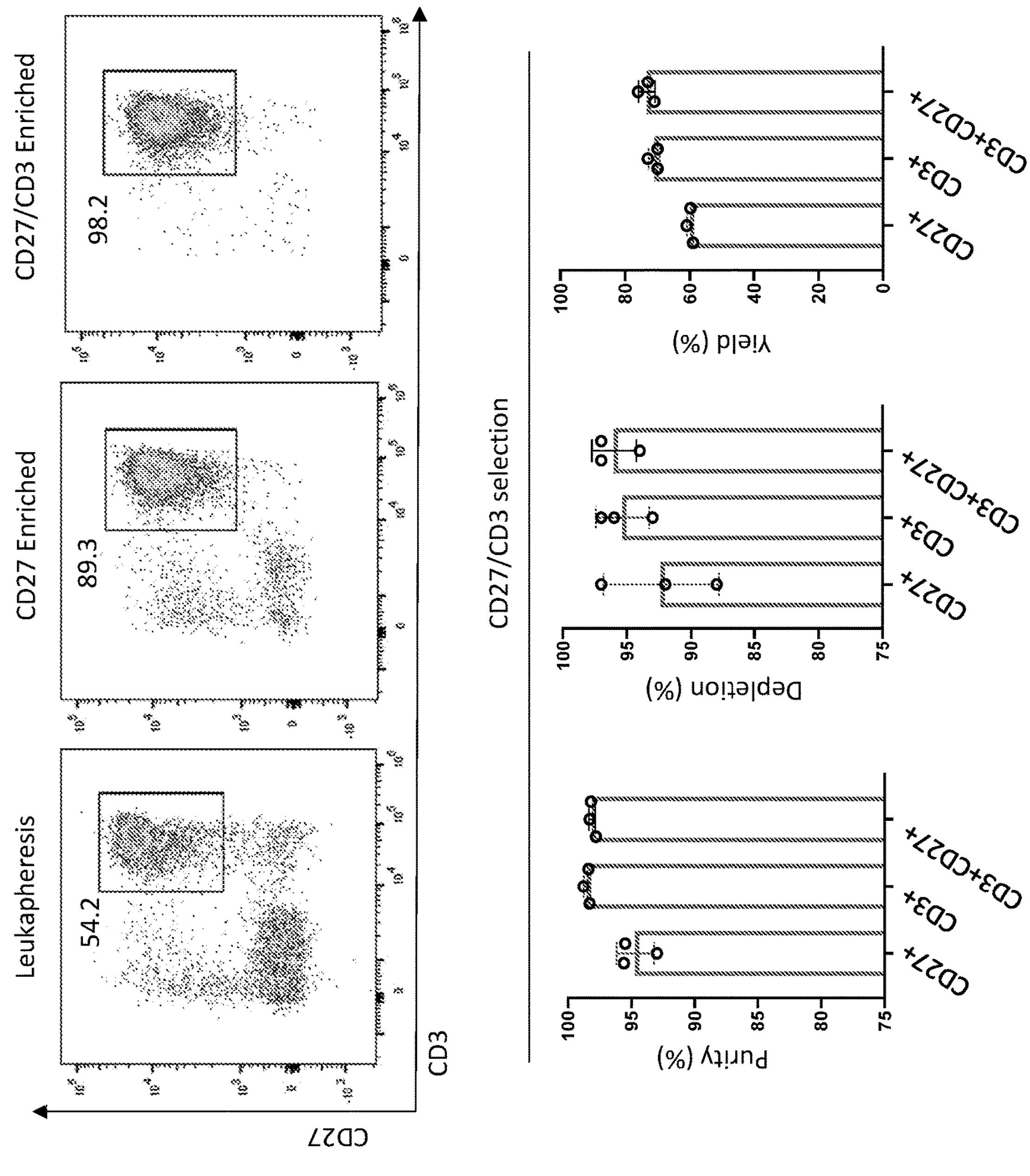
FIG. 33C shows CD27 and CD3 expression in cell populations enriched for either CD27 or CD27 and CD3 (top panel), and purity, depletion, and yield (bottom panel) in a cell population enriched for CD27 and CD3.

The immunoaffinity-based selection was also assessed for serial selection of cells positive for two different markers. A leukapheresis sample was loaded onto a first column containing a selection matrix with CD27-targeting peptide-tagged Fab fragments, and CD27+ cells were collected as a CD27 enriched population by positive selection. The CD27 enriched population was then loaded onto a second column containing a selection matrix with CD3-targeting peptide-tagged Fab fragments, and CD27+ CD3+ cells were collected by positive selection. The collected CD27+ CD3+ population was found to have 95% purity (FIG. 33C).

Example 12: CD3 Depletion of Genetically Edited Cells

T cells were isolated from a leukapheresis sample from a human donor and genetically edited using a CRISPR/CAR approach to disrupt the endogenous TCR receptor at the cell surface (e.g. by knockout of the T cell receptor alpha constant (TRAC) region). In cells that have undergone complete knockout, TCR complex formation and cell surface expression of CD3 are disrupted. To remove any cells that did not undergo complete knockout, the genetically edited cell population was subjected to CD3 depletion using the affinity chromatography system described in Example 11.

Figure 34:
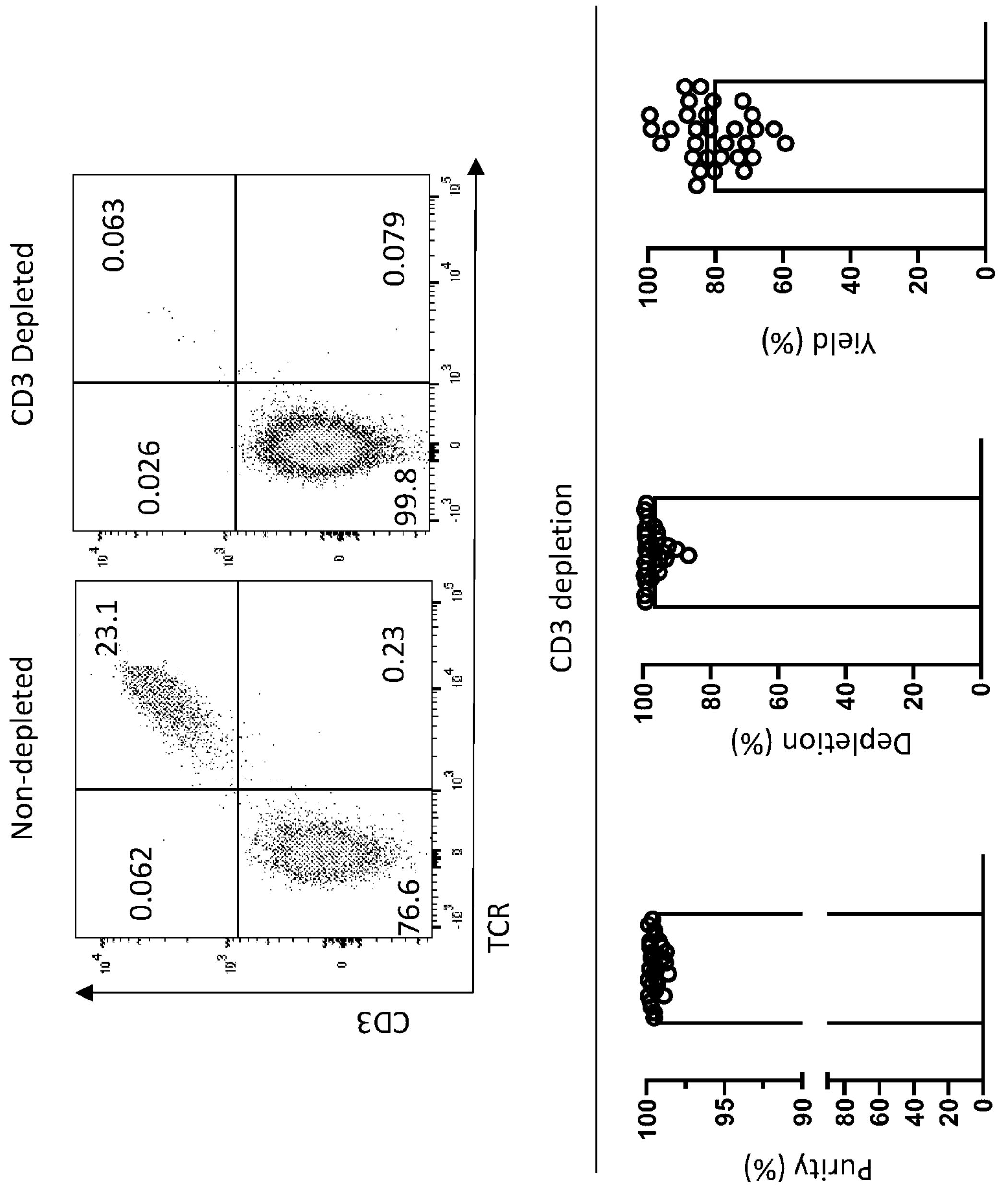
FIG. 34 shows TCR and CD3 expression (top panel), and purity, depletion, and yield (bottom panel) in a CD3 depleted cell population.

TCR-CD3− cells were isolated by negatively selecting for CD3. The genetically edited cells were loaded onto a column containing a selection matrix with CD3-targeting peptide-tagged Fab fragments, and the unbound cells (i.e. TCR-CD3− cells) that flowed through the column were collected as the population of cells completely knocked out for the TCR. As shown in FIG. 34 the collected cells were observed to reach purities of >99% TCR-CD3− cells. In some aspects, CD3 depletion in carried out in a process in which cells from allogeneic donors are provided to subjects, such as for therapeutic purposes, including cells in which expression of the endogenous TCR receptor at the cell surface has been disrupted.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

Sequences

| # | SEQUENCE | ANNOTATION |
|---|---|---|
| 1 | ESKYGPPCPPCP | spacer (IgG4hinge) (aa) |
| 2 | GAATCTAAGTACGGACCGCCCTGCCCCCCTTGCCCT | spacer (IgG4hinge) (nt) |
| 3 | ESKYGPPCPPCPGQPREPQVYTLPPSQEEMTKNQVSLTCLVKGFYPSDIAV<br>EWESNGQPENNYKTTPPVLDSDGSFFLYSRLTVDKSRWQEGNVFSCSVMHE<br>ALHNHYTQKSLSLSLGK | Hinge-CH3 spacer |
| 4 | ESKYGPPCPPCPAPEFLGGPSVFLFPPKPKDTLMISRTPEVTCVVVDVSQE<br>DPEVQFNWYVDGVEVHNAKTKPREEQFNSTYRVVSVLTVLHQDWLNGKEYK<br>CKVSNKGLPSSIEKTISKAKGQPREPQVYTLPPSQEEMTKNQVSLTCLVKG<br>FYPSDIAVEWESNGQPENNYKTTPPVLDSDGSFFLYSRLTVDKSRWQEGNV<br>FSCSVMHEALHNHYTQKSLSLSLGK | Hinge-CH2-CH3 spacer |
| 5 | RWPESPKAQASSVPTAQPQAEGSLAKATTAPATTRNTGRGGEEKKKEKEKE<br>EQEERETKTPECPSHTQPLGVYLLTPAVQDLWLRDKATFTCFVVGSDLKDA<br>HLTWEVAGKVPTGGVEEGLLERHSNGSQSQHSRLTLPRSLWNAGTSVTCTL<br>NHPSLPPQRLMALREPAAQAPVKLSLNLLASSDPPEAASWLLCEVSGFSPP<br>NILLMWLEDQREVNTSGFAPARPPPQPGSTTFWAWSVLRVPAPPSPQPATY<br>TCVVSHEDSRTLLNASRSLEVSYVTDH | IgD-hinge-Fc |
| 6 | LEGGGEGRGSLLTCGDVEENPGPR | T2A |
| 7 | MLLLVTSLLLCELPHPAFLLIPRKVCNGIGIGEFKDSLSINATNIKHFKNC<br>TSISGDLHILPVAFRGDSFTHTPPLDPQELDILKTVKEITGFLLIQAWPEN<br>RTDLHAFENLEIIRGRTKQHGQFSLAWSLNITSLGLRSLKEISDGDVIIS<br>GNKNLCYANTINWKKLFGTSGQKTKIISNRGENSCKATGQVCHALCSPEGC<br>WGPEPRDCVSCRNVSRGRECVDKCNLLEGEPREFVENSECIQCHPECLPQA<br>MNITCTGRGPDNCIQCAHYIDGPHCVKTCPAGVMGENNTLVWKYADAGHVC<br>HLCHPNCTYGCTGPGLEGCPTNGPKIPSIATGMVGALLLLLWALGIGLFM | tEGFR |
| 8 | FWVLVVVGGVLACYSLLVTVAFIIFWV | CD28 (amino acids 153-179 of Accession No. P10747) |
| 9 | IEVMYPPPYLDNEKSNGTIIHVKGKHLCPSPLFPGPSKP<br>FWVLVVVGGVLACYSLLVTVAFIIFWV | CD28 (amino acids 114-179 of Accession No. P10747) |
| 10 | RSKRSRLLHSDYMNMTPRRPGPTRKHYQPYAPPRDFAAYRS | CD28 (amino acids 180-220 of P10747) |
| 11 | RSKRSRGGHSDYMNMTPRRPGPTRKHYQPYAPPRDFAAYRS | CD28 (LL to GG) |
| 12 | KRGRKKLLYIFKQPFMRPVQTTQEEDGCSCRFPEEEEGGCEL | 4-1BB (amino acids 214-255 of Q07011.1) |

-continued

| Sequences | | |
|---|---|---|
| # | SEQUENCE | ANNOTATION |
| 13 | RVKFSRSADAPAYQQGQNQLYNELNLGRREEYDVLDKRRGRDPEMGGKPRR KNPQEGLYNELQKDKMAEAYSEIGMKGERRRGKGHDGLYQGLSTATKDTYD ALHMQALPPR | CD3 zeta |
| 14 | RVKFSRSAEPPAYQQGQNQLYNELNLGRREEYDVLDKRRGRDPEMGGKPRR KNPQEGLYNELQKDKMAEAYSEIGMKGERRRGKGHDGLYQGLSTATKDTYD ALHMQALPPR | CD3 zeta |
| 15 | RVKFSRSADAPAYKQGQNQLYNELNLGRREEYDVLDKRRGRDPEMGGKPRR KNPQEGLYNELQKDKMAEAYSEIGMKGERRRGKGHDGLYQGLSTATKDTYD ALHMQALPPR | CD3 zeta |
| 16 | RKVCNGIGIGEFKDSLSINATNIKHFKNCTSISGDLHILPVAFRGDSFTHT PPLDPQELDILKTVKEITGFLLIQAWPENRTDLHAFENLEIIRGRTKQHGQ FSLAVVSLNITSLGLRSLKEISDGDVIISGNKNLCYANTINWKKLFGTSGQ KTKIISNRGENSCKATGQVCHALCSPEGCWGPEPRDCVSCRNVSRGRECVD KCNLLEGEPREFVENSECIQCHPECLPQAMNITCTGRGPDNCIQCAHYIDG PHCVKTCPAGVMGENNTLVWKYADAGHVCHLCHPNCTYGCTGPGLEGCPTN GPKIPSIATGMVGALLLLLVVALGIGLFM | tEGFR |
| 17 | EGRGSLLTCGDVEENPGP | T2A |
| 18 | GSGATNFSLLKQAGDVEENPGP | P2A |
| 19 | ATNFSLLKQAGDVEENPGP | P2A |
| 20 | QCTNYALLKLAGDVESNPGP | E2A |
| 21 | VKQTLNFDLLKLAGDVESNPGP | F2A |
| 22 | -PGGG-$(SGGGG)_5$-P- wherein P is proline, G is glycine and S is serine | Linker |
| 23 | GSADDAKKDAAKKDGKS | Linker |
| 24 | atgcttctcctggtgacaagccttctgctctgtgagttaccacacccagca ttcctcctgatccca | GMCSFR alpha chain signal sequence |
| 25 | MLLLVTSLLLCELPHPAFLLIP | GMCSFR alpha chain signal sequence |
| 26 | MALPVTALLLPLALLLHA | CD 8 alpha signal peptide |
| 27 | EPKSCDKTHTCPPCP | Hinge |
| 28 | ERKCCVECPPCP | Hinge |
| 29 | ELKTPLGDTHTCPRCPEPKSCDTPPPCPRCPEPKSCDTPPPCPRCPEPKSC DTPPPCPRCP | Hinge |
| 30 | ESKYGPPCPSCP | Hinge |
| 31 | $X_1PPX_2P$<br>$X_1$ is glycine, cysteine or arginine<br>$X_2$ is cysteine or threonine | Hinge |
| 32 | YGPPCPPCP | Hinge |
| 33 | KYGPPCPPCP | Hinge |
| 34 | EVVVKYGPPCPPCP | Hinge |
| 35 | RASQDISKYLN | CDR L1 |
| 36 | SRLHSGV | CDR L2 |
| 37 | GNTLPYTFG | CDR L3 |
| 38 | DYGVS | CDR H1 |
| 39 | VIWGSETTYYNSALKS | CDR H2 |
| 40 | YAMDYWG | CDR H3 |

-continued

| Sequences | | |
|---|---|---|
| # | SEQUENCE | ANNOTATION |
| 41 | EVKLQESGPGLVAPSQSLSVTCTVSGVSLPDYGVSWIRQPPRKGLEWLGVI WGSETTYYNSALKSRLTIIKDNSKSQVFLKMNSLQTDDTAIYYCAKHYYYG GSYAMDYWGQGTSVTVSS | VH |
| 42 | DIQMTQTTSSLSASLGDRVTISCRASQDISKYLNWYQQKPDGTVKLLIYHT SRLHSGVPSRFSGSGSGTDYSLTISNLEQEDIATYFCQQGNTLPYTFGGGT KLEIT | VL |
| 43 | DIQMTQTTSSLSASLGDRVTISCRASQDISKYLNWYQQKPDGTVKLLIYHT SRLHSGVPSRFSGSGSGTDYSLTISNLEQEDIATYFCQQGNTLPYTFGGGT KLEITGSTSGSGKPGSGEGSTKGEVKLQESGPGLVAPSQSLSVTCTVSGVS LPDYGVSWIRQPPRKGLEWLGVIWGSETTYYNSALKSRLTIIKDNSKSQVF LKMNSLQTDDTAIYYCAKHYYYGGSYAMDYWGQGTSVTVSS | scFv |
| 44 | KASQNVGTNVA | CDR L1 |
| 45 | SATYRNS | CDR L2 |
| 46 | QQYNRYPYT | CDR L3 |
| 47 | SYWMN | CDR H1 |
| 48 | QIYPGDGDTNYNGKFKG | CDR H2 |
| 49 | KTISSWDFYFDY | CDR H3 |
| 50 | EVKLQQSGAELVRPGSSVKISCKASGYAFSSYWMNWVKQRPGQGLEWIGQI YPGDGDTNYNGKFKGQATLTADKSSSTAYMQLSGLTSEDSAVYFCARKTIS SVVDFYFDYWGQGTTVTVSS | VH |
| 51 | DIELTQSPKFMSTSVGDRVSVTCKASQNVGTNVAWYQQKPGQSPKPLIYSA TYRNSGVPDRFTGSGSGTDFTLTITNVQSKDLADYFCQQYNRYPYTSGGGT KLEIKR | VL |
| 52 | GGGGSGGGGSGGGGS | Linker |
| 53 | EVKLQQSGAELVRPGSSVKISCKASGYAFSSYWMNWVKQRPGQGLEWIGQI YPGDGDTNYNGKFKGQATLTADKSSSTAYMQLSGLTSEDSAVYFCARKTIS SVVDFYFDYWGQGTTVTVSSGGGGSGGGGSGGGGSDIELTQSPKFMSTSVG DRVSVTCKASQNVGTNVAWYQQKPGQSPKPLIYSATYRNSGVPDRFTGSGS GTDFTLTITNVQSKDLADYFCQQYNRYPYTSGGGTKLEIKR | scFv |
| 54 | HYYYGGSYAMDY | HC-CDR3 |
| 55 | HTSRLHS | LC-CDR2 |
| 56 | QQGNTLPYT | LC-CDR3 |
| 57 | gacatccagatgacccagaccacctccagcctgagcgccagcctgggcgac cgggtgaccatcagctgccgggccagccaggacatcagcaagtacctgaac tggtatcagcagaagcccgacggcaccgtcaagctgctgatctaccacacc agccggctgcacagcggcgtgcccagccggtttagcggcagcggctccggc accgactacagcctgaccatctccaacctggaacaggaagatatcgccacc tacttttgccagcagggcaacacactgccctacacctttggcggcggaaca aagctggaaatcaccggcagcacctccggcagcggcaagcctggcagcggc gagggcagcaccaagggcgaggtgaagctgcaggaaagcggccctggcctg gtggcccccagccagagcctgagcgtgacctgcaccgtgagcggcgtgagc ctgcccgactacggcgtgagctggatccggcagcccccaggaagggcctg gaatggctgggcgtgatctggggcagcgagaccacctactacaacagcgcc ctgaagagccggctgaccatcatcaaggacaacagcaagagccaggtgttc ctgaagatgaacagcctgcagaccgacgacaccgccatctactactgcgcc aagcactactactacggcggcagctacgccatggactactggggccagggc accagcgtgaccgtgagcagc | Sequence encoding scFv |
| 58 | GSTSGSGKPGSGEGSTKG | Linker |
| 59 | ASTKGPSVFPLAPCSRSTSESTAALGCLVKDYFPEPVTVSWNSGALTSGVH TFPAVLQSSGLYSLSSVVTVPSSNFGTQTYTCNVDHKPSNTKVDKTVERKC CVECPPCPAPPVAGPSVFLFPPKPKDTLMISRTPEVTCVVVDVSHEDPEVQ FNWYVDGVEVHNAKTKPREEQFNSTFRWSVLTWHQDWLNGKEYKCKVSN KGLPAPIEKTISKTKGQPREPQVYTLPPSREEMTKNQVSLTCLVKGFYPSD ISVEWESNGQPENNYKTTPPMLDSDGSFFLYSKLTVDKSRWQQGNVFSCSV MHEALHNHYTQKSLSLSPGK | Human IgG2 Fc (Uniprot P01859) |

-continued

Sequences

| # | SEQUENCE | ANNOTATION |
|---|---|---|
| 60 | ASTKGPSVFPLAPCSRSTSESTAALGCLVKDYFPEPVTVSWNSGALTSGVH TFPAVLQSSGLYSLSSVVTVPSSSLGTKTYTCNVDHKPSNTKVDKRVESKY GPPCPSCPAPEFLGGPSVFLFPPKPKDTLMISRTPEVTCVVVDVSQEDPEV QFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPS DIAVEWESNGQPENNYKTTPPVLDSDGSFFLYSRLTVDKSRWQEGNVFSCS VMHEALHNHYTQKSLSLSLGK | Human IgG4 Fc (Uniprot P01861) |
| 61 | GVQVETISPGDGRTFPKRGQTCVVHYTGMLEDGKKMDSSRDRNKPFKFMLG KQEVIRGWEEGVAQMSVGQRAKLTISPDYAYGATGHPGIIPPHATLVFDVE LLKLE | FKBP |
| 62 | GVQVETISPGDGRTFPKRGQTCVVHYTGMLEDGKKVDSSRDRNKPFKFMLG KQEVIRGWEEGVAQMSVGQRAKLTISPDYAYGATGHPGIIPPHATLVFDVE LLKLE | FKBP12v36 |
| 63 | MGSNKSKPKDASQRRR | acylation motif |
| 64 | Met-Gly-Cys-Xaa-Cys | dual acylation region |
| 65 | Cys-Ala-Ala-Xaa | CAAX box |
| 66 | DPSKDSKAQVSAAEAGITGTWYNQLGSTFIVTAGADGALTGTYESAVGNAE SRYVLTGRYDSAPATDGSGTALGWTVAWKNNYRNAHSATTWSGQYVGGAEA RINTQWLLTSGTTEANAWKSTLVGHDTFTKVKPSAASIDAAKKAGVNNGNP LDAVQQ | Streptavidin Species: *Streptomyces avidinii* UniProtNo. P22629 |
| 67 | EAGITGTWYNQLGSTFIVTAGADGALTGTYESAVGNAESRYVLTGRYDSAP ATDGSGTALGWTVAWKNNYRNAHSATTWSGQYVGGAEARINTQWLLTSGTT EANAWKSTLVGHDTFTKVKPSAAS | Minimal streptavidin Species: *Streptomyces avidinii* |
| 68 | EAGITGTWYNQLGSTFIVTAGADGALTGTYIGARGNAESRYVLTGRYDSAP ATDGSGTALGWTVAWKNNYRNAHSATTWSGQYVGGAEARINTQWLLTSGTT EANAWKSTLVGHDTFTKVKPSAAS | Minimal mutein Streptavidin Ile44-Gly45-Ala46-Arg47 Species: *Streptomyces avidinii* |
| 69 | WSHPQFEK | Strep-tag ® II |
| 70 | WSHPQFEKGGGSGGGSGGGSWSHPQFEK | Twin-Strep-tag |
| 71 | WSHPQFEKGGGSGGGSWSHPQFEK | Twin-Strep-tag |
| 72 | WSHPQFEKGGGSGGGSGGSAWSHPQFEK | Twin-Strep-tag |
| 73 | MEAGITGTWYNQLGSTFIVTAGADGALTGTYIGARGNAESRYVLTGRYDSA PATDGSGTALGWTVAWKNNYRNAHSATTWSGQYVGGAEARINTQWLLTSGT TEANAWKSTLVGHDTFTKVKPSAAS | Minimal mutein Streptavidin Ile44-Gly45-Ala46-Arg47 Species: *Streptomyces avidinii* |
| 74 | Trp-Xaa-His-Pro-Gin-Phe-Yaa-Zaa | Streptavidin-binding peptide Xaa is any amino acid; Yaa is Gly or Glu Zaa is Gly, Lys or Arg |
| 75 | Trp-Arg-His-Pro-Gin-Phe-Gly-Gly | Streptavidin binding peptide, Strep-tag ® |
| 76 | Trp-Ser-His-Pro-Gln-Phe-Glu-Lys-(Xaa)n-Trp-Ser-His-Pro-Gln-Phe-Glu-Lys | Sequential modules of streptavidin-binding peptide Xaa is any amino acid; n is either 8 or 12 |

-continued

Sequences

| # | SEQUENCE | ANNOTATION |
|---|---|---|
| 77 | Trp-Ser-His-Pro-Gln-Phe-Glu-Lys-(GlyGlyGlySer)n-Trp-Ser-His-Pro-Gin-Phe-Glu-Lys | Sequential modules of streptavidin-binding peptide; n is 2 or 3 |
| 78 | SAWSHPQFEKGGGSGGGSGGGSWSHPQFEK | Twin-Strep-tag |
| 79 | SAWSHPQFEKGGGSGGGSGGSAWSHPQFEK | Twin-Strep-tag |
| 80 | DPSKDSKAQVSAAEAGITGTWYNQLGSTFIVTAGADGALTGTYVTARGNAE SRYVLTGRYDSAPATDGSGTALGWTVAWKNNYRNAHSATTWSGQYVGGAEA RINTQWLLTSGTTEANAWKSTLVGHDTFTKVKPSAASIDAAKKAGVNNGNP LDAVQQ | Mutein Streptavidin Val44-Thr45-Ala46-Arg47 *Streptomyces avidinii* |
| 81 | EAGITGTWYNQLGSTFIVTAGADGALTGTYVTARGNAESRYVLTGRYDSAP ATDGSGTALGWTVAWKNNYRNAHSATTWSGQYVGGAEARINTQWLLTSGTT EANAWKSTLVGHDTFTKVKPSAAS | Minimal mutein Streptavidin Val44-Thr45-Ala46-Arg47 *Streptomyces avidinii* |
| 82 | MEAGITGTWYNQLGSTFIVTAGADGALTGTYVTARGNAESRYVLTGRYDSA PATDGSGTALGWTVAWKNNYRNAHSATTWSGQYVGGAEARINTQWLLTSGT TEANAWKSTLVGHDTFTKVKPSAAS | Minimal mutein Streptavidin Val44-Thr45-Ala46-Arg47 *Streptomyces avidinii* |
| 83 | His-Pro-Gln-Phe | Streptavidin-binding peptide |
| 84 | Oaa-Xaa-His-Pro-Gln-Phe-Yaa-Zaa | Streptavidin-binding peptide Oaa is Trp, Lys or Arg; Xaa is any amino acid; Yaa is Gly or Glu Zaa is Gly, Lys or Arg |
| 85 | DPSKDSKAQVSAAEAGITGTWYNQLGSTFIVTAGADGALTGTYIGARGNAE SRYVLTGRYDSAPATDGSGTALGWTVAWKNNYRNAHSATTWSGQYVGGAEA RINTQWLLTSGTTEANAWKSTLVGHDTFTKVKPSAASIDAAKKAGVNNGNP LDAVQQ | Mutein Streptavidin Ile44-Gly45-Ala-46-Arg47 Species: *Streptomyces avidinii* |
| 86 | EAGITGTWYNQLGSTFIVTAGADGALTGTYVTARGNAESRYVLTGRYDSAP ATDGSGTALGWTVAWKNNYRNAHSATTWSGQYVGGAEARINTQWLLTSGTT EENAGYSTLVGHDTFTKVKPSAAS | Minimal mutein Streptavidin Val44-Thr45-Ala46-Arg47 and Glu 117, Gly 120, Tyrl21 (mutein ml - 9) Species: *Streptomyces avidinii* |
| 87 | DPSKDSKAQVSAAEAGITGTWYNQLGSTFIVTAGADGALTGTYVTARGNAE SRYVLTGRYDSAPATDGSGTALGWTVAWKNNYRNAHSATTWSGQYVGGAEA RINTQWLLTSGTTEENAGYSTLVGHDTFTKVKPSAAS | Mutein Streptavidin Val44-Thr45-Ala-46-Arg47 and Glu117, Gly120, Tyrl21 (mutein m1-9) Species: *Streptomyces avidinii* |
| 88 | MEAGITGTWYNQLGSTFIVTAGADGALTGTYESAVGNAESRYVLTGRYDSA PATDGSGTALGWTVAWKNNYRNAHSATTWSGQYVGGAEARINTQWLLTSGT TEANAWKSTLVGHDTFTKVKPSAAS | Minimal streptavidin Species: *Streptomyces avidinii* |
| 89 | Trp-Ser-His-Pro-Gln-Phe-Glu-Lys-$(GlyGlyGlySer)_2$Gly-Gly-Ser-Ala-Trp-Ser-His-Pro-Gin-Phe-Glu-Lys | Mutein Streptavidin |

-continued

Sequences

| # | SEQUENCE | ANNOTATION |
|---|---|---|
| 90 | Ala-Trp-Arg-His-Pro-Gln-Phe-Gly-Gly | Strep-tag ® |
| 91 | LQQSGAELVKPGASVRLSCKASGYTFTEYIIHWIKLRSGQGLEWIGW FYPGSNDIQYNAKFKGKATLTADKSSSTVYMELTGLTSEDSAVYFC ARRDDFSGYDALPYWGQGTMVTV | VH anti-CD28 antibody CD28.3 |
| 92 | DIQMTQSPASLSVSVGETVTITCRTNENIYSNLAWYQQKQGKSPQLL IYAATHLVEGVPSRFSGSGSGTQYSLKITSLQSEDFGNYYCQHFWGT PCTFGGGTKLEIKR | VL anti-CD28 antibody CD28.3 |
| 93 | QVQLQQSGAELARPGASVKMSCKASGYTFTRYTMHWVKQRPGQG LEWIGYINPSRGYTNYNQKFKDKATLTTDKSSSTAYMQLSSLTSEDS AVYYCARYYDDHYCLDYWGQGTTLTVSS | VH anti-CD3 antibody OKT3 |
| 94 | QIVLTQSPAIMSASPGEKVTMTCSASSSVSYMNWYQQKSGTSPKRWI YDTSKLASGVPAHFRGSGSGTSYSLTISGMEAEDAATYYCQQWSSN PFTFGSGTKLEIN | VL anti-CD3 antibody OKT3 |
| 95 | AMQVQLKQSGPGLVQPSQSLSITCTVSGFSLTTFGVHWVRQSPGKG LEWLGVIWASGITDYNVPFMSRLSITKDNSKSQVFFKLNSLQPDDTA IYYCAKNDPGTGFAYWQGTLVTVSSTKGPSVFPAPSSKSTSGGTAAL GCLVKDYFPEPVTVSWNSGALTSGVHTFPAVLQSSLYSLSSVVTVPS SSLGTQTYICNVNHKPSNTKVDKKVEPKSCGSAWSHPQFEKGGGSG GGSGGSAWSHPQFEK | Variable Heavy chain of Fab fragment m13B8.2 |
| 96 | AMDIQMTQSPASLSASVGETVTFTCRASEMIYSYLAWYQQKQGKSP QLLVHDAKTLAEGVPSRFSGGGSGTQFSLKINTLQPEDFGTYYCQAH YGNPPTFGGGTKLEIKRGIAAPSVFIFPPSDEQLKSGTASVVCLLNNF YPREAKVQWKVDNALQSGNSQESVTEQDSKDSTYSLSSTLTLSKAD YEKHKVYACEVTHQGLSSPVTKSFNRGECGS | Variable Light chain of Fab Fragment m13B8.2 |
| 97 | QVQLVQSGAEVKKPGATVKISCKVSGFNIKDTYIHWVQQAPGKGLE WMGRIDPANDNTLYASKFQGRVTITADTSTDTAYMELSSLRSEDTA VYYCARGYGYYVFDHWGQGTLVTVSS | Variable Heavy chain of huOKT8 |
| 98 | DVQITQSPSSLSASVGDRVTITCRTSRSISQYLAWYQQKPGKVPKLLI YSGSTLQSGVPSRFSGSGSGTDFTLTISSLQPEDVATYYCQQHNENPL TFGGGTKVEIK | Variable Light chain of huOKT8 |

The invention claimed is:

1. A method of preparing a T cell composition from a donor pool, the method comprising:

(a) obtaining a plurality of engineered T cell compositions from a plurality of different donors, wherein each engineered T cell composition is enriched for T cells surface negative for CD57 (CD57−) from a donor sample from an individual donor of the plurality of different donors, and each engineered T cell composition comprises T cells genetically engineered with a recombinant receptor that is a chimeric antigen receptor (CAR); and (b) combining the plurality of engineered T cell compositions to produce a donor pooled engineered T cell composition.

2. The method of claim 1, wherein each of the plurality of engineered T cell compositions is generated by a process comprising:

(i) selecting T cells surface negative for CD57 (CD57−) from the donor sample from the individual donor, thereby generating a CD57 depleted T cell population; and (ii) introducing a heterologous polynucleotide encoding the recombinant receptor into the CD57 depleted cell population, thereby generating the engineered T cell composition.

3. The method of claim 2, wherein prior to step (ii), the method comprises stimulating the CD57 depleted T cell population under conditions to activate T cells in the population.

4. The method of claim 2, wherein the method further comprises (iii) incubating the cells of the engineered T cell composition for up to 96 hours subsequent to the introducing.

5. The method of claim 4, wherein the incubating is carried out under conditions in which the cells of the engineered T cell composition are not expanded or are not substantially expanded, compared to the number of cells of the engineered T cell composition at the initiation of the incubating.

6. The method of claim 2, wherein the method further comprises (iii) cultivating the cells of the engineered T cell composition under conditions for expansion of T cells in the composition.

7. The method of claim 2, wherein the selecting T cells surface negative for CD57 (CD57−) comprises:

(1) selecting one of (a) cells surface positive for a T cell marker(s) and (b) cells surface negative for CD57 (CD57−) from the donor sample from the individual donor, thereby generating an enriched population of cells; and (2) selecting, from the enriched population of cells, for the other of (a) cells surface positive for the T cell marker (s) and (b) CD57− cells, thereby generating the CD57 depleted T cell population.

8. The method of claim 2, wherein the method further comprises knocking out expression of (i) an endogenous major histocompatibility complex (MHC) or a component thereof; and/or (ii) an endogenous T cell receptor (TCR) or a component thereof, in the T cells of the CD57 depleted T cell population and/or the engineered T cell composition prior to or during one or more of the steps of the method.

9. The method of claim 1, wherein the method is repeated for each of the individual donors of the plurality of different donors.

10. A method of preparing a T cell composition from a donor pool, the method comprising:

(a) selecting T cells surface negative for CD57 (CD57−) from a donor sample from an individual donor, thereby generating a CD57 depleted T cell population;

(b) genetically engineering the CD57 depleted T cell population, thereby producing an engineered T cell composition, the genetic engineering comprising:

(1) knocking out expression of (i) an endogenous major histocompatibility complex (MHC) or a component thereof; and/or (ii) an endogenous T cell receptor (TCR) or a component thereof, in cells of the CD57 depleted T cell population; and (2) introducing a heterologous polynucleotide encoding a recombinant receptor into the cells of the CD57 depleted T cell population, wherein the recombinant receptor is a chimeric antigen receptor (CAR);

wherein the knocking out in (1) and the introducing in (2) are carried out concurrently or successively in either order;

(c) repeating steps (a) and (b) for a plurality of different donors to produce a plurality of donor engineered T cell compositions, wherein each donor engineered T cell composition is generated from cells from the donor sample from the individual donor of the plurality of different donors; and (d) combining the plurality of donor engineered T cell compositions from the plurality of different individual donors to produce a donor pooled engineered T cell composition.

11. The method of claim 2, wherein the CD57 depleted T cell population comprises greater than or greater than at or about 75% CD3+/CD57− cells.

12. The method of claim 1, wherein each of the plurality of engineered T cell compositions independently comprises greater than or greater than at or about 40% CD57−/CAR+ cells.

13. The method of claim 1, wherein each of the plurality of engineered T cell compositions comprise CD4+ and CD8+ T cells.

14. A method of preparing a T cell composition from a donor pool, the method comprising:

(i) selecting for one of (a) cells surface positive for a T cell marker(s) and (b) cells surface negative for CD57 (CD57−) from a donor sample from a plurality of different donors, thereby generating an enriched population of cells; and (ii) selecting, from the enriched population of cells, the other of (a) cells surface positive for the T cell marker (s) and (b) CD57− cells, thereby generating a CD57 depleted T cell population, wherein:

(1) the donor sample is a pooled sample comprising cells from the plurality of different donors, whereby the method produces a pooled CD57 depleted T cell population; or (2) the donor sample is a sample from an individual donor, and steps (i) and (ii) are repeated separately for each donor sample from the plurality of different donors, whereby the method produces a CD57 depleted T cell population for each individual donor.

15. The method of claim 14, wherein the method of (2) further comprises combining the CD57 depleted T cell populations for each individual donor together to produce a pooled CD57 depleted T cell population.

16. The method of claim 7, wherein the T cell marker(s) is CD3, CD4, and/or CD8.

17. The method of claim 14, wherein:

(a) cells of the CD57 depleted T cell population or cells of the pooled CD57 depleted T cell population are knocked out (KO) for expression of (i) an endogenous major histocompatibility complex (MHC) or a component thereof; and/or (b) the method further comprises knocking out expression of (i) an endogenous major histocompatibility complex (MHC) or a component thereof.

18. The method of claim 14, wherein:

(a) a heterologous polynucleotide encoding a recombinant receptor is introduced into cells of the CD57 depleted T cell population or cells of the pooled CD57 depleted T cell population, wherein the recombinant receptor is a chimeric antigen receptor (CAR); and/or (b) the method further comprises introducing into cells of the CD57 depleted T cell population or cells of the pooled CD57 depleted T cell population a heterologous polynucleotide encoding a recombinant receptor that is a chimeric antigen receptor (CAR), the method thereby generating an engineered T cell composition.

19. The method of claim 14, wherein the frequency of CD57+ T cells in the CD57 depleted T cell population and/or the pooled CD57 depleted T cell population is less than about or about 35% of the frequency of CD57+ T cells in the donor sample.

20. The method of claim 1, wherein the donor sample comprises an apheresis product or a leukapheresis product.

21. The method of claim 1, wherein:

the individual donor is healthy or is not suspected of having a disease or condition at the time the donor sample is obtained from the individual donor; and/or each of the donors of the plurality of different donors is healthy or is not suspected of having a disease or condition at the time the donor sample is obtained from each of the different donors.

22. The method of claim 14, further comprising introducing a heterologous polynucleotide encoding a recombinant receptor into the CD57 depleted T cell population, thereby generating an engineered CD57 depleted T cell population, wherein the recombinant receptor is a chimeric antigen receptor (CAR).

23. The method of claim 2, wherein the introducing comprises targeted insertion of the heterologous polynucleotide with a viral vector comprising the heterologous polynucleotide.

24. The method of claim 2, wherein the heterologous polynucleotide is inserted into the β2M gene locus or the TRAC gene locus.

* * * * *